United States Patent
Manoharan et al.

(10) Patent No.: US 9,220,683 B2
(45) Date of Patent: Dec. 29, 2015

(54) LIPIDS AND COMPOSITIONS FOR THE DELIVERY OF THERAPEUTICS

(75) Inventors: Muthiah Manoharan, Cambridge, MA (US); Kallanthottathil G. Rajeev, Cambridge, MA (US); David Butler, Medford, MA (US); Jayaprakash K. Narayanannair, Cambridge, MA (US); Muthusamy Jayaraman, Cambridge, MA (US); Laxmab Eltepu, Cambridge, MA (US)

(73) Assignee: Tekmira Pharmaceuticals Corporation, Burnaby (CA)

( * ) Notice: Subject to any disclaimer, the term of this patent is extended or adjusted under 35 U.S.C. 154(b) by 342 days.

(21) Appl. No.: 13/128,253

(22) PCT Filed: Nov. 10, 2009

(86) PCT No.: PCT/US2009/063933
§ 371 (c)(1),
(2), (4) Date: Sep. 2, 2011

(87) PCT Pub. No.: WO2010/054406
PCT Pub. Date: May 14, 2010

(65) Prior Publication Data
US 2012/0027796 A1 Feb. 2, 2012

Related U.S. Application Data

(60) Provisional application No. 61/113,179, filed on Nov. 10, 2008, provisional application No. 61/154,350, filed on Feb. 20, 2009, provisional application No. 61/171,439, filed on Apr. 21, 2009, provisional application No. 61/185,438, filed on Jun. 9, 2009, provisional application No. 61/225,898, filed on Jul. 15, 2009, provisional application No. 61/234,098, filed on Aug. 14, 2009.

(51) Int. Cl.
| | | |
|---|---|---|
| *A61K 39/12* | (2006.01) | |
| *A61K 9/127* | (2006.01) | |
| *A61K 39/00* | (2006.01) | |
| *C12N 15/11* | (2006.01) | |

(52) U.S. Cl.
CPC .............. *A61K 9/1272* (2013.01); *A61K 39/00* (2013.01); *C12N 15/111* (2013.01); *A61K 2039/55555* (2013.01); *A61K 2039/55561* (2013.01); *C12N 2310/14* (2013.01); *C12N 2310/3515* (2013.01); *C12N 2320/32* (2013.01)

(58) Field of Classification Search
None
See application file for complete search history.

(56) References Cited

U.S. PATENT DOCUMENTS

| | | |
|---|---|---|
| 4,910,310 A | 3/1990 | Campbell et al. |
| 6,235,310 B1 | 5/2001 | Wang et al. |
| 7,799,565 B2 | 9/2010 | MacLachlan et al. |
| 2006/0240554 A1 | 10/2006 | Chen et al. |

FOREIGN PATENT DOCUMENTS

| | | |
|---|---|---|
| WO | WO 2009/086558 A1 | 7/2009 |
| WO | WO 2010/105209 A1 | 9/2010 |
| WO | WO 2010/148013 A2 | 12/2010 |
| WO | WO 2011/005793 A1 | 1/2011 |

OTHER PUBLICATIONS

Babudri et al., "Synthesis of C2-symmetric 1, 4-diketones from tartaric acid dichloride", *Journal of Organometallic Chemistry 689*, 326-331 (2004).
Prasad et al., "Enantiospecific synthesis of (−−)-muricatacin from L-(+)-tartaric acid", *Tetrahedron: Asymmetry 17*, 2465-2467 (2006).
Gissot et al., "Sensitive liposomes encoded with oligonucleotide amphiphiles: a biocompatible switch", *Chem. Commun.*, 5550-5552 (2008).
Moreau et al., "Real time imaging of supramolecular assembly formation via programmed nucleolipid recognition" *J. Am. Chem. Soc. 130*, 14454-14455 (2008).
Gurjar et al., "Total Syntheses of Schulzeines B and C", *Journal of Organic Chemistry*, 72(17), 6591-6594 (2007).
Patent Cooperation Treaty, International Searching Authority, Search Report and Written Opinion for PCT/US09/63933, 10 pages, dated Apr. 9, 2010.
Prasad et al., "Enantiodivergent Synthesis of Both Enantiomers of Gypsy Moth Pheromone Disparture", *Journal of Organic Chemistry*, 72(8), 3155-3157 (2007).
Raghavan et al., "A formal convergent synthesis of (+)trans-solarnin", *Tetrahedron Letters*, vol. 49, No. 10, 1601-1604 (2008).
Sinha et al., "Total Synthesis of Goniocin and Cyclogoniodenin T. Unique Biosynthetic Implications", *Journal of the American Chemical Society*, 120(16), 4017-4018 (1998).
Takada et al., "Schulzeines A-C, New α-Glucosidase Inhibitors from the Marine Sponge *Penares schulzei*", *Journal of the American Chemical Society*, 126(1), 187-193 (2004).

*Primary Examiner* — Snigdha Maewall
(74) *Attorney, Agent, or Firm* — Viksnins Harris & Padys PLLP

(57) ABSTRACT

The present invention provides lipids that are advantageously used in lipid particles for the in vivo delivery of therapeutic agents to cells. In particular, the invention provides lipids having the following structures: (Formula (I) or (XXXV)).

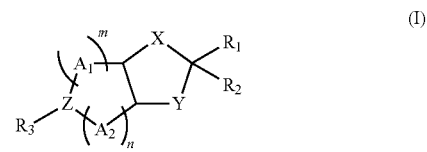

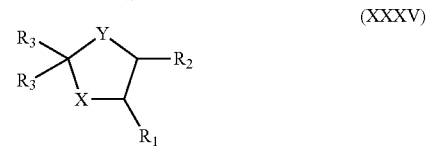

17 Claims, 4 Drawing Sheets

Figure 1.

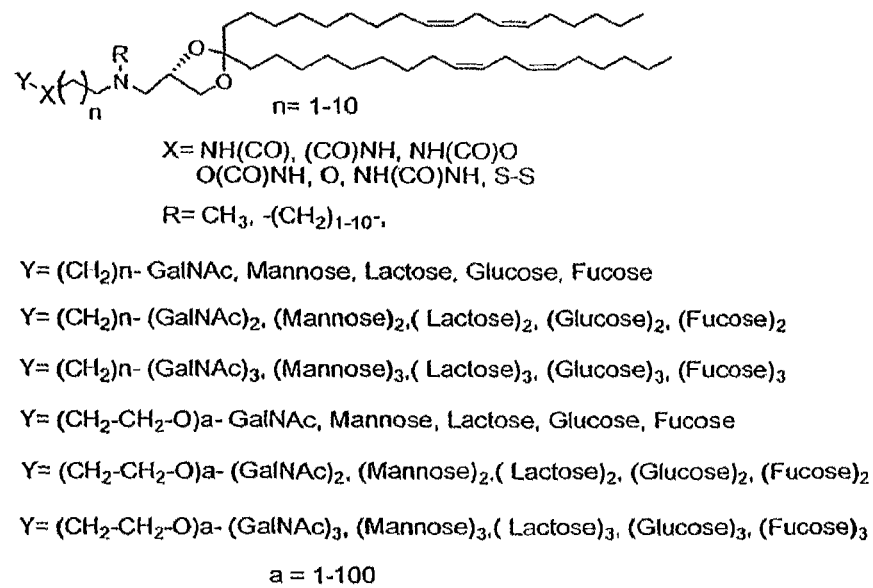

n= 1-10

X= NH(CO), (CO)NH, NH(CO)O
O(CO)NH, O, NH(CO)NH, S-S

R= $CH_3$, -$(CH_2)_{1-10}$-,

Y= $(CH_2)_n$- GalNAc, Mannose, Lactose, Glucose, Fucose

Y= $(CH_2)_n$- $(GalNAc)_2$, $(Mannose)_2$, $(Lactose)_2$, $(Glucose)_2$, $(Fucose)_2$ Y= $(CH_2)_n$- $(GalNAc)_3$, $(Mannose)_3$, $(Lactose)_3$, $(Glucose)_3$, $(Fucose)_3$ Y= $(CH_2-CH_2-O)_a$- GalNAc, Mannose, Lactose, Glucose, Fucose Y= $(CH_2-CH_2-O)_a$- $(GalNAc)_2$, $(Mannose)_2$, $(Lactose)_2$, $(Glucose)_2$, $(Fucose)_2$ Y= $(CH_2-CH_2-O)_a$- $(GalNAc)_3$, $(Mannose)_3$, $(Lactose)_3$, $(Glucose)_3$, $(Fucose)_3$ a = 1-100

Figure 2.

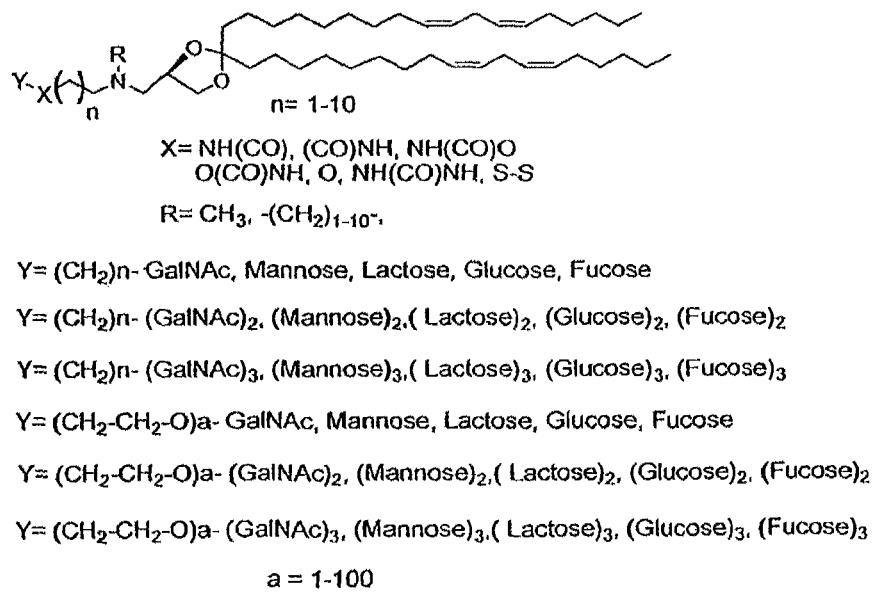

n= 1-10

X= NH(CO), (CO)NH, NH(CO)O
O(CO)NH, O, NH(CO)NH, S-S

R= $CH_3$, -$(CH_2)_{1-10}$-,

Y= $(CH_2)_n$- GalNAc, Mannose, Lactose, Glucose, Fucose

Y= $(CH_2)_n$- $(GalNAc)_2$, $(Mannose)_2$, $(Lactose)_2$, $(Glucose)_2$, $(Fucose)_2$ Y= $(CH_2)_n$- $(GalNAc)_3$, $(Mannose)_3$, $(Lactose)_3$, $(Glucose)_3$, $(Fucose)_3$ Y= $(CH_2-CH_2-O)_a$- GalNAc, Mannose, Lactose, Glucose, Fucose Y= $(CH_2-CH_2-O)_a$- $(GalNAc)_2$, $(Mannose)_2$, $(Lactose)_2$, $(Glucose)_2$, $(Fucose)_2$ Y= $(CH_2-CH_2-O)_a$- $(GalNAc)_3$, $(Mannose)_3$, $(Lactose)_3$, $(Glucose)_3$, $(Fucose)_3$ a = 1-100

Figure 3

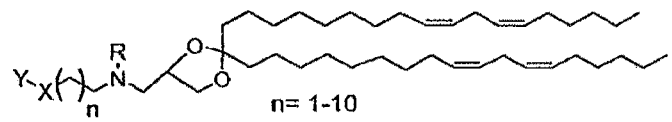

n= 1-10

X= NH(CO), (CO)NH, NH(CO)O
O(CO)NH, O, NH(CO)NH, S-S

R= $CH_3$, -$(CH_2)_{1-10}$-,

Y= $(CH_2)_n$- GalNAc, Mannose, Lactose, Glucose, Fucose

Y= $(CH_2)_n$- $(GalNAc)_2$, $(Mannose)_2$, $(Lactose)_2$, $(Glucose)_2$, $(Fucose)_2$ Y= $(CH_2)_n$- $(GalNAc)_3$, $(Mannose)_3$, $(Lactose)_3$, $(Glucose)_3$, $(Fucose)_3$ Y= $(CH_2-CH_2-O)_a$- GalNAc, Mannose, Lactose, Glucose, Fucose Y= $(CH_2-CH_2-O)_a$- $(GalNAc)_2$, $(Mannose)_2$, $(Lactose)_2$, $(Glucose)_2$, $(Fucose)_2$ Y= $(CH_2-CH_2-O)_a$- $(GalNAc)_3$, $(Mannose)_3$, $(Lactose)_3$, $(Glucose)_3$, $(Fucose)_3$ a = 1-100

Figure 4.

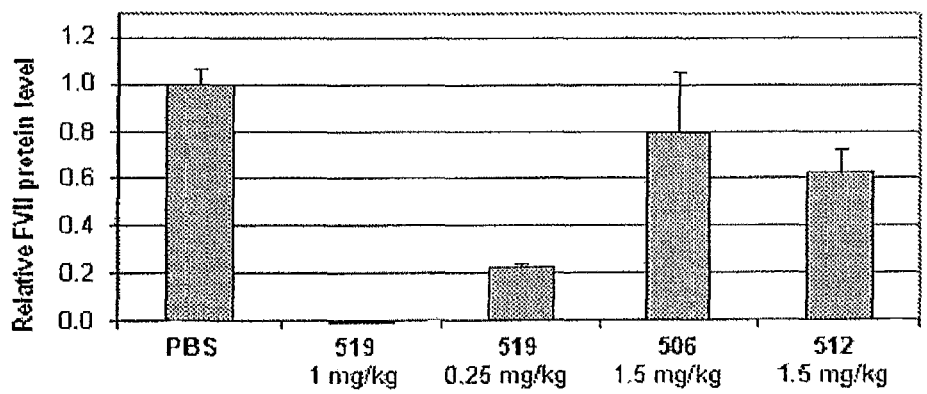

SEQUENCE LISTING

<160> NUMBER OF SEQ ID NOS: 68

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
taacgttgag gggcat                                                        16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4) .. (4)
<223> OTHER INFORMATION: methylated cytosine

<400> SEQUENCE: 2
taacgttgag gggcat                                                        16

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tccatgacgt tcctgacgtt                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8) .. (8)
<223> OTHER INFORMATION: methylated cytosine

<400> SEQUENCE: 4
tccatgacgt tcctgacgtt                                                    20

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
taagcatacg gggtgt                                                        16

<210> SEQ ID NO 6
<211> LENGTH: 24
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 6
gatgctgtgt cggggtctcc gggc                                              24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcgtcgtttt gtcgttttgt cgtt                                              24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: methylated cytosine
<220> FEATURE:
<221> NAME/KEY: modified_base
<222> LOCATION: (5)..(5)
<223> OTHER INFORMATION: methylated cytosine
<220> FEATURE:
<221> NAME/KEY: modified_base
<222> LOCATION: (13)..(13)
<223> OTHER INFORMATION: methylated cytosine
<220> FEATURE:
<221> NAME/KEY: modified_base
<222> LOCATION: (21)..(21)
<223> OTHER INFORMATION: methylated cytosine

<400> SEQUENCE: 8
tcgtcgtttt gtcgttttgt cgtt                                              24

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tccaggactt ctctcaggtt                                                   20

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tctcccagcg tgcgccat                                                     18

<210> SEQ ID NO 11
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgcatccccc aggccaccat                                                 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcccaagctg gcatccgtca                                                 20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gcccaagctg gcatccgtca                                                 20

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggtgctcact gcggc                                                      15

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aaccgttgag gggcat                                                     16

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tatgctgtgc cggggtcttc gggc                                            24

<210> SEQ ID NO 17
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtgccggggt cttcgggc                                                    18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggaccctcct ccggagcc                                                    18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tcctccggag ccagactt                                                    18

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aacgttgagg ggcat                                                       15

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ccgtggtcat gctcc                                                       15

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cagcctggct caccgccttg g                                                21

<210> SEQ ID NO 23
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 23
cagccatggt tccccccaac                                                   20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gttctcgctg gtgagtttca                                                   20

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tctcccagcg tgcgccat                                                     18

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gtgctccatt gatgc                                                        15

<210> SEQ ID NO 27
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
gaguucugau gaggccgaaa ggccgaaagu cug                                    33

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aacgttgagg ggcat                                                        15

<210> SEQ ID NO 29
<211> LENGTH: 16
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 29
caacgttatg gggaga                                                     16

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttccatgacg ttcctgacgt                                                 20

<210> SEQ ID NO 31
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Ala Leu Glu Ala Leu Ala Glu Ala Leu Glu Ala Leu Ala Glu Ala
1               5                   10                  15

Leu Glu Ala Leu Ala Glu Ala Ala Ala Ala Gly Gly Cys
            20                  25

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Ala Gly Gly Cys
            20                  25                  30

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ala Leu Glu Ala Leu Ala Glu Ala Leu Glu Ala Leu Ala Glu Ala
1               5                   10                  15

<210> SEQ ID NO 34
<211> LENGTH: 22
<212> TYPE: PRT
<213> ORGANISM: Influenza A virus

<400> SEQUENCE: 34

Gly Leu Phe Glu Ala Ile Glu Gly Phe Ile Glu Asn Gly Trp Glu Gly
1               5                   10                  15
```

```
Met Ile Trp Asp Tyr Gly
        20

<210> SEQ ID NO 35
<211> LENGTH: 23
<212> TYPE: PRT
<213> ORGANISM: Influenza A virus

<400> SEQUENCE: 35

Gly Leu Phe Gly Ala Ile Ala Gly Phe Ile Glu Asn Gly Trp Glu Gly
1               5                   10                  15

Met Ile Asp Gly Trp Tyr Gly
        20

<210> SEQ ID NO 36
<211> LENGTH: 24
<212> TYPE: PRT
<213> ORGANISM: Influenza A virus

<400> SEQUENCE: 36

Gly Leu Phe Glu Ala Ile Glu Gly Phe Ile Glu Asn Gly Trp Glu Gly
1               5                   10                  15

Met Ile Asp Gly Trp Tyr Gly Cys
        20

<210> SEQ ID NO 37
<211> LENGTH: 22
<212> TYPE: PRT
<213> ORGANISM: Influenza A virus

<400> SEQUENCE: 37

Gly Leu Phe Glu Ala Ile Glu Gly Phe Ile Glu Asn Gly Trp Glu Gly
1               5                   10                  15

Met Ile Asp Gly Gly Cys
        20

<210> SEQ ID NO 38
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gly Leu Phe Gly Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Gly
        20                  25                  30

Gly Ser Cys
        35

<210> SEQ ID NO 39
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gly Leu Phe Glu Ala Ile Glu Gly Phe Ile Glu Asn Gly Trp Glu Gly
1               5                   10                  15
```

Leu Ala Glu Ala Leu Ala Glu Ala Leu Glu Ala Leu Ala Ala Gly Gly
        20                  25                  30

Ser Cys

<210> SEQ ID NO 40
<211> LENGTH: 21
<212> TYPE: PRT
<213> ORGANISM: Influenza A virus
<220> FEATURE:
<221> NAME/KEY: MOD_RES
<222> LOCATION: (17)..(17)
<223> OTHER INFORMATION: Nle

<400> SEQUENCE: 40

Gly Leu Phe Glu Ala Ile Glu Gly Phe Ile Glu Asn Gly Trp Glu Gly
1               5                   10                  15

Leu Ile Asp Gly Lys
        20

<210> SEQ ID NO 41
<211> LENGTH: 20
<212> TYPE: PRT
<213> ORGANISM: Influenza A virus
<220> FEATURE:
<221> NAME/KEY: MOD_RES
<222> LOCATION: (17)..(17)
<223> OTHER INFORMATION: Nle

<400> SEQUENCE: 41

Gly Leu Phe Glu Ala Ile Glu Gly Phe Ile Glu Asn Gly Trp Glu Gly
1               5                   10                  15

Leu Ile Asp Gly
        20

<210> SEQ ID NO 42
<211> LENGTH: 16
<212> TYPE: PRT
<213> ORGANISM: Drosophila sp.

<400> SEQUENCE: 42

Arg Gln Ile Lys Ile Trp Phe Gln Asn Arg Arg Met Lys Trp Lys Lys
1               5                   10                  15

<210> SEQ ID NO 43
<211> LENGTH: 13
<212> TYPE: PRT
<213> ORGANISM: Human immunodeficiency virus 1

<400> SEQUENCE: 43

Gly Arg Lys Lys Arg Arg Gln Arg Arg Pro Pro Gln
1               5                   10

<210> SEQ ID NO 44
<211> LENGTH: 27
<212> TYPE: PRT
<213> ORGANISM: Human immunodeficiency virus 1

<400> SEQUENCE: 44

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
        20                  25

```
<210> SEQ ID NO 45
<211> LENGTH: 18
<212> TYPE: PRT
<213> ORGANISM: Mus sp.

<400> SEQUENCE: 45

Leu Leu Ile Ile Leu Arg Arg Arg Ile Arg Lys Gln Ala His Ala His
1               5                   10                  15

Ser Lys

<210> SEQ ID NO 46
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Lys Leu Ala Leu Lys Leu Ala Leu Lys Ala Leu Lys Ala Ala Leu Lys
1               5                   10                  15

Leu Ala

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Arg Arg Arg Arg Arg Arg Arg Arg
1               5

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Phe Phe Lys Phe Phe Lys Phe Phe Lys
1               5                   10

<210> SEQ ID NO 50
<211> LENGTH: 37
<212> TYPE: PRT
<213> ORGANISM: Homo sapiens
```

```
<400> SEQUENCE: 50

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
            35

<210> SEQ ID NO 51
<211> LENGTH: 31
<212> TYPE: PRT
<213> ORGANISM: Ascaris suum

<400> SEQUENCE: 51

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
                20                  25                  30

<210> SEQ ID NO 52
<211> LENGTH: 30
<212> TYPE: PRT
<213> ORGANISM: Homo sapiens

<400> SEQUENCE: 52

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
                20                  25                  30

<210> SEQ ID NO 53
<211> LENGTH: 36
<212> TYPE: PRT
<213> ORGANISM: Homo sapiens

<400> SEQUENCE: 53

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
                20                  25                  30

Lys Cys Cys Lys
            35

<210> SEQ ID NO 54
<211> LENGTH: 12
<212> TYPE: PRT
<213> ORGANISM: Unknown
<220> FEATURE:
<223> OTHER INFORMATION: Description of Unknown: Unknown bactenecin
      peptide

<400> SEQUENCE: 54

Arg Lys Cys Arg Ile Val Val Ile Arg Val Cys Arg
1               5                   10

<210> SEQ ID NO 55
<211> LENGTH: 42
<212> TYPE: PRT
<213> ORGANISM: Sus scrofa
<220> FEATURE:
<221> NAME/KEY: MOD_RES
<222> LOCATION: (42)..(42)
<223> OTHER INFORMATION: AMIDATION
```

```
<400> SEQUENCE: 55

Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
        35                  40

<210> SEQ ID NO 56
<211> LENGTH: 13
<212> TYPE: PRT
<213> ORGANISM: Unknown
<220> FEATURE:
<223> OTHER INFORMATION: Description of Unknown: Unknown indolicidin
      peptide
<220> FEATURE:
<221> NAME/KEY: MOD_RES
<222> LOCATION: (13)..(13)
<223> OTHER INFORMATION: AMIDATION

<400> SEQUENCE: 56

Ile Leu Pro Trp Lys Trp Pro Trp Trp Pro Trp Arg Arg
1               5                   10

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Ala Val Ala Leu Leu Pro Ala Val Leu Leu Ala Leu Leu Ala Pro
1               5                   10                  15

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Ala Leu Leu Pro Val Leu Leu Ala Ala Pro
1               5                   10

<210> SEQ ID NO 59
<211> LENGTH: 13
<212> TYPE: PRT
<213> ORGANISM: Human immunodeficiency virus

<400> SEQUENCE: 59

Gly Arg Lys Lys Arg Arg Gln Arg Arg Pro Pro Gln
1               5                   10

<210> SEQ ID NO 60
<211> LENGTH: 16
<212> TYPE: PRT
<213> ORGANISM: Drosophila sp.

<400> SEQUENCE: 60

Arg Gln Ile Lys Ile Trp Phe Gln Asn Arg Arg Met Lys Trp Lys Lys
1               5                   10                  15
```

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 2'deoxy nucleotide

<400> SEQUENCE: 61
cuuacgcuga guacuucgat t                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (7)..(7)
<223> OTHER INFORMATION: 2'-fluoro uracil
<220> FEATURE:
<221> NAME/KEY: modified_base
<222> LOCATION: (16)..(16)
<223> OTHER INFORMATION: 2'-fluoro uracil
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: modified_base
<222> LOCATION: (20)..(21)
<223> OTHER INFORMATION: 2'deoxy nucleotide

<400> SEQUENCE: 62
ucgaaguacu cagcguaagt t                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (3)..(3)
<223> OTHER INFORMATION: 2'-fluoro uracil
<220> FEATURE:
<221> NAME/KEY: modified_base
<222> LOCATION: (12)..(12)

```
<223> OTHER INFORMATION: 2'-fluoro uracil
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: modified_base
<222> LOCATION: (20)..(21)
<223> OTHER INFORMATION: 2'deoxy nucleotide

<400> SEQUENCE: 63
cuuacgcuga guacuucgat t                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 2'deoxy nucleotide

<400> SEQUENCE: 64
ucgaaguacu cagcguaagt t                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 2'deoxy nucleotide

<400> SEQUENCE: 65
ggaucaucuc aagucuuact t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 2'deoxy nucleotide

<400> SEQUENCE: 66
guaagacuug agaugaucct t                                              21

<210> SEQ ID NO 67
<211> LENGTH: 21
<212> TYPE: DNA
<213> ORGANISM: Artificial Sequence
```

<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: 2'-fluoro uracil
<220> FEATURE:
<221> NAME/KEY: modified_base
<222> LOCATION: (5)..(5)
<223> OTHER INFORMATION: 2'-fluoro cytosine
<220> FEATURE:
<221> NAME/KEY: modified_base
<222> LOCATION: (7)..(7)
<223> OTHER INFORMATION: 2'-fluoro uracil
<220> FEATURE:
<221> NAME/KEY: modified_base
<222> LOCATION: (8)..(8)
<223> OTHER INFORMATION: 2'-fluoro cytosine
<220> FEATURE:
<221> NAME/KEY: modified_base
<222> LOCATION: (9)..(9)
<223> OTHER INFORMATION: 2'-fluoro uracil
<220> FEATURE:
<221> NAME/KEY: modified_base
<222> LOCATION: (10)..(10)
<223> OTHER INFORMATION: 2'-fluoro cytosine
<220> FEATURE:
<221> NAME/KEY: modified_base
<222> LOCATION: (14)..(14)
<223> OTHER INFORMATION: 2'-fluoro uracil
<220> FEATURE:
<221> NAME/KEY: modified_base
<222> LOCATION: (15)..(15)
<223> OTHER INFORMATION: 2'-fluoro cytosine
<220> FEATURE:
<221> NAME/KEY: modified_base
<222> LOCATION: (16)..(17)
<223> OTHER INFORMATION: 2'-fluoro uracil
<220> FEATURE:
<221> NAME/KEY: modified_base
<222> LOCATION: (19)..(19)
<223> OTHER INFORMATION: 2'-fluoro cytosine
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: modified_base
<222> LOCATION: (20)..(21)
<223> OTHER INFORMATION: 2'deoxy nucleotide

<400> SEQUENCE: 67
ggaucaucuc aagucuuact t                                          21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-fluoro uracil
<220> FEATURE:
<221> NAME/KEY: modified_base
<222> LOCATION: (7)..(7)
<223> OTHER INFORMATION: 2'-fluoro cytosine
<220> FEATURE:

```
<221> NAME/KEY: modified_base
<222> LOCATION: (8)..(9)
<223> OTHER INFORMATION: 2'-fluoro uracil
<220> FEATURE:
<221> NAME/KEY: modified_base
<222> LOCATION: (14)..(14)
<223> OTHER INFORMATION: 2'-fluoro uracil
<220> FEATURE:
<221> NAME/KEY: modified_base
<222> LOCATION: (17)..(17)
<223> OTHER INFORMATION: 2'-fluoro uracil
<220> FEATURE:
<221> NAME/KEY: modified_base
<222> LOCATION: (18)..(19)
<223> OTHER INFORMATION: 2'-fluoro cytosine
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: modified_base
<222> LOCATION: (20)..(21)
<223> OTHER INFORMATION: 2'deoxy nucleotide

<400> SEQUENCE: 68
guaagacuug agaugaucct t                                    21
```

LIPIDS AND COMPOSITIONS FOR THE DELIVERY OF THERAPEUTICS

GOVERNMENT SUPPORT

The work described herein was carried out, at least in part, using funds from the U.S. Government under grant number HHSN266200600012C awarded by the National Institute of Allergy and Infectious Diseases. The government may therefore have certain rights in the invention.

PRIORITY

This application is a national phase of International Patent Application No. PCT/US09/63933, filed Nov. 10, 2009, which claims priority to U.S. Patent Application No. 61/113,179, filed Nov. 10, 2008; U.S. Patent Application No. 61/154,350, filed Feb. 20, 2009; U.S. Patent Application No. 61/171,439, filed Apr. 21, 2009; U.S. Patent Application No. 61/185,438, filed Jun. 9, 2009; U.S. Patent Application No. 61/225,898, filed Jul. 15, 2009; and U.S. Patent Application No. 61/234,098, filed Aug. 14, 2009, the contents of each of which is incorporated herein by reference in its entirety.

BACKGROUND

1. Technical Field

The present invention relates to the field of therapeutic agent delivery using lipid particles. In particular, the present invention provides cationic lipids and lipid particles comprising these lipids, which are advantageous for the in vivo delivery of nucleic acids, as well as nucleic acid-lipid particle compositions suitable for in vivo therapeutic use. Additionally, the present invention provides methods of making these compositions, as well as methods of introducing nucleic acids into cells using these compositions, e.g., for the treatment of various disease conditions.

2. Description of the Related Art

Therapeutic nucleic acids include, e.g., small interfering RNA (siRNA), micro RNA (miRNA), antisense oligonucleotides, ribozymes, plasmids, immune stimulating nucleic acids, antisense, antagomir, antimir, microRNA mimic, supermir, U1 adaptor, and aptamer. These nucleic acids act via a variety of mechanisms. In the case of siRNA or miRNA, these nucleic acids can down-regulate intracellular levels of specific proteins through a process termed RNA interference (RNAi). Following introduction of siRNA or miRNA into the cell cytoplasm, these double-stranded RNA constructs can bind to a protein termed RISC. The sense strand of the siRNA or miRNA is displaced from the RISC complex providing a template within RISC that can recognize and bind mRNA with a complementary sequence to that of the bound siRNA or miRNA. Having bound the complementary mRNA the RISC complex cleaves the mRNA and releases the cleaved strands. RNAi can provide down-regulation of specific proteins by targeting specific destruction of the corresponding mRNA that encodes for protein synthesis.

The therapeutic applications of RNAi are extremely broad, since siRNA and miRNA constructs can be synthesized with any nucleotide sequence directed against a target protein. To date, siRNA constructs have shown the ability to specifically down-regulate target proteins in both in vitro and in vivo models. In addition, siRNA constructs are currently being evaluated in clinical studies.

However, two problems currently faced by siRNA or miRNA constructs are, first, their susceptibility to nuclease digestion in plasma and, second, their limited ability to gain access to the intracellular compartment where they can bind RISC when administered systemically as the free siRNA or miRNA. These double-stranded constructs can be stabilized by incorporation of chemically modified nucleotide linkers within the molecule, for example, phosphothioate groups. However, these chemical modifications provide only limited protection from nuclease digestion and may decrease the activity of the construct. Intracellular delivery of siRNA or miRNA can be facilitated by use of carrier systems such as polymers, cationic liposomes or by chemical modification of the construct, for example by the covalent attachment of cholesterol molecules. However, improved delivery systems are required to increase the potency of siRNA and miRNA molecules and reduce or eliminate the requirement for chemical modification.

Antisense oligonucleotides and ribozymes can also inhibit mRNA translation into protein. In the case of antisense constructs, these single stranded deoxynucleic acids have a complementary sequence to that of the target protein mRNA and can bind to the mRNA by Watson-Crick base pairing. This binding either prevents translation of the target mRNA and/or triggers RNase H degradation of the mRNA transcripts. Consequently, antisense oligonucleotides have tremendous potential for specificity of action (i.e., down-regulation of a specific disease-related protein). To date, these compounds have shown promise in several in vitro and in vivo models, including models of inflammatory disease, cancer, and HIV (reviewed in Agrawal, *Trends in Biotech.* 14:376-387 (1996)). Antisense can also affect cellular activity by hybridizing specifically with chromosomal DNA. Advanced human clinical assessments of several antisense drugs are currently underway. Targets for these drugs include the bcl2 and apolipoprotein B genes and mRNA products.

Immune-stimulating nucleic acids include deoxyribonucleic acids and ribonucleic acids. In the case of deoxyribonucleic acids, certain sequences or motifs have been shown to illicit immune stimulation in mammals. These sequences or motifs include the CpG motif, pyrimidine-rich sequences and palindromic sequences. It is believed that the CpG motif in deoxyribonucleic acids is specifically recognized by an endosomal receptor, toll-like receptor 9 (TLR-9), which then triggers both the innate and acquired immune stimulation pathway. Certain immune stimulating ribonucleic acid sequences have also been reported. It is believed that these RNA sequences trigger immune activation by binding to toll-like receptors 6 and 7 (TLR-6 and TLR-7). In addition, double-stranded RNA is also reported to be immune stimulating and is believe to activate via binding to TLR-3.

One well known problem with the use of therapeutic nucleic acids relates to the stability of the phosphodiester internucleotide linkage and the susceptibility of this linker to nucleases. The presence of exonucleases and endonucleases in serum results in the rapid digestion of nucleic acids possessing phosphodiester linkers and, hence, therapeutic nucleic acids can have very short half-lives in the presence of serum or within cells. (Zelphati, O., et al., *Antisense. Res. Dev.* 3:323-338 (1993); and Thierry, A. R., et al., pp 147-161 in Gene Regulation: Biology of Antisense RNA and DNA (Eds. Erickson, R P and Izant, J G; Raven Press, NY (1992)). Therapeutic nucleic acid being currently being developed do not employ the basic phosphodiester chemistry found in natural nucleic acids, because of these and other known problems.

This problem has been partially overcome by chemical modifications that reduce serum or intracellular degradation. Modifications have been tested at the internucleotide phosphodiester bridge (e.g., using phosphorothioate, methylphosphonate or phosphoramidate linkages), at the nucleotide base (e.g., 5-propynyl-pyrimidines), or at the sugar (e.g., 2'-modified sugars) (Uhlmann E., et al. Antisense: Chemical Modifications. Encyclopedia of Cancer, Vol. X., pp 64-81 Academic Press Inc. (1997)). Others have attempted to improve stability using 2'-5' sugar linkages (see, e.g., U.S. Pat. No. 5,532,130). Other changes have been attempted. However, none of these solutions have proven entirely satisfactory, and in vivo free therapeutic nucleic acids still have only limited efficacy.

In addition, as noted above relating to siRNA and miRNA, problems remain with the limited ability of therapeutic nucleic acids to cross cellular membranes (see, Vlassov, et al., *Biochim. Biophys. Acta* 1197:95-1082 (1994)) and in the problems associated with systemic toxicity, such as complement-mediated anaphylaxis, altered coagulatory properties, and cytopenia (Galbraith, et al., *Antisense Nucl. Acid Drug Des.* 4:201-206 (1994)).

To attempt to improve efficacy, investigators have also employed lipid-based carrier systems to deliver chemically modified or unmodified therapeutic nucleic acids. In Zelphati, O. and Szoka, F. C., *J. Contr. Rel.* 41:99-119 (1996), the authors refer to the use of anionic (conventional) liposomes, pH sensitive liposomes, immunoliposomes, fusogenic liposomes, and cationic lipid/antisense aggregates. Similarly siRNA has been administered systemically in cationic liposomes, and these nucleic acid-lipid particles have been reported to provide improved down-regulation of target proteins in mammals including non-human primates (Zimmermann et al., *Nature* 441: 111-114 (2006)).

In spite of this progress, there remains a need in the art for improved lipid-therapeutic nucleic acid compositions that are suitable for general therapeutic use. Preferably, these compositions would encapsulate nucleic acids with high-efficiency, have high drug:lipid ratios, protect the encapsulated nucleic acid from degradation and clearance in serum, be suitable for systemic delivery, and provide intracellular delivery of the encapsulated nucleic acid. In addition, these lipid-nucleic acid particles should be well-tolerated and provide an adequate therapeutic index, such that patient treatment at an effective dose of the nucleic acid is not associated with significant toxicity and/or risk to the patient. The present invention provides such compositions, methods of making the compositions, and methods of using the compositions to introduce nucleic acids into cells, including for the treatment of diseases.

BRIEF SUMMARY

The present invention provides novel cationic lipids, as well as lipid particles comprising the same. These lipid particles may further comprise an active agent and be used according to related methods of the invention to deliver the active agent to a cell.

In one aspect, the invention provides lipids having the structure of formula I:

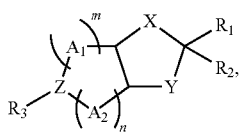

I salts or isomers thereof, wherein:

$R_1$ and $R_2$ are each independently for each occurrence optionally substituted $C_{10}$-$C_{30}$ alkyl, optionally substituted $C_{10}$-$C_{30}$ alkoxy, optionally substituted $C_{10}$-$C_{30}$ alkenyl, optionally substituted $C_{10}$-$C_{30}$ alkenyloxy, optionally substituted $C_{10}$-$C_{30}$ alkynyl, optionally substituted $C_{10}$-$C_{30}$ alkynyloxy, or optionally substituted $C_{10}$-$C_{30}$ acyl, or -linker-ligand;

$R_3$ is independently for each occurrence H, optionally substituted $C_1$-$C_{10}$ alkyl, optionally substituted $C_2$-$C_{10}$ alkenyl, optionally substituted $C_2$-$C_{10}$ alkynyl, optionally substituted alkylheterocycle, optionally substituted heterocyclealkyl, optionally substituted alkylphosphate, optionally substituted phosphoalkyl, optionally substituted alkylphosphorothioate, optionally substituted phosphorothioalkyl, optionally substituted alkylphosphorodithioate, optionally substituted phosphorodithioalkyl, optionally substituted alkylphosphonate, optionally substituted phosphonoalkyl, optionally substituted amino, optionally substituted alkylamino, optionally substituted di(alkyl)amino, optionally substituted aminoalkyl, optionally substituted alkylaminoalkyl, optionally substituted di(alkyl)aminoalkyl, optionally substituted hydroxyalkyl, optionally substituted polyethylene glycol (PEG, mw 100-40K), optionally substituted mPEG (mw 120-40K), optionally substituted heteroaryl, or optionally substituted heterocycle, or linker-ligand;

X and Y are each independently —O—, —S—, alkylene, —N(Q)-, —C(O)—, —O(CO), —OC(O)N(Q)-, —N(Q)C(O)O—, —C(O)O, —OC(O)O—, —OS(O)(Q$_2$)O—, or —OP(O)(Q$_2$)O—;

Q is H, alkyl, ω-aminoalkyl, ω-(substituted)aminoalkyl, ω-phosphoalkyl, or ω-thiophosphoalkyl;

$Q_1$ is independently for each occurrence O or S;

$Q_2$ is independently for each occurrence O, S, N(Q)(Q), alkyl or alkoxy;

$A_1$, and $A_2$ are each independently —O—, —S—, —CH$_2$—, —CHR$^5$—, —CR$^5$R$^5$—, —CHF— or —CF$_2$—;

Z is N, or C(R$_3$); and m and n are each independently 0 to 5, where m and n taken together result in a 3, 4, 5, 6, 7 or 8 member ring.

In another aspect, the invention provides a lipid having the structure of formula XXXV:

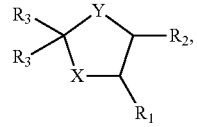

XXXV salts or isomers thereof, wherein:

$R_1$ and $R_2$ are each independently for each occurrence optionally substituted $C_{10}$-$C_{30}$ alkyl, optionally substituted $C_{10}$-$C_{30}$ alkoxy, optionally substituted $C_{10}$-$C_{30}$ alkenyl, optionally substituted $C_{10}$-$C_{30}$ alkenyloxy, optionally substituted $C_{10}$-$C_{30}$ alkynyl, optionally substituted $C_{10}$-$C_{30}$ alkynyloxy, or optionally substituted $C_{10}$-$C_{30}$ acyl, or -linker-ligand;

$R_3$ is independently for each occurrence H, optionally substituted $C_1$-$C_{10}$ alkyl, optionally substituted $C_2$-$C_{10}$ alkenyl, optionally substituted $C_2$-$C_{10}$ alkynyl, optionally substituted alkylheterocycle, optionally substituted heterocyclealkyl, optionally substituted alkylphosphate, optionally substituted phosphoalkyl, optionally substituted alkylphosphorothioate, optionally substituted phosphorothioalkyl, optionally substituted alkylphosphorodithioate, optionally substituted phosphorodithioalkyl, optionally substituted alkylphosphonate, optionally substituted phosphonoalkyl, optionally substituted amino, optionally substituted alkylamino, optionally substituted di(alkyl)amino, optionally substituted aminoalkyl, optionally substituted alkylaminoalkyl, optionally substituted di(alkyl)aminoalkyl, optionally substituted hydroxyalkyl, optionally substituted polyethylene glycol (PEG, mw 100-40K), optionally substituted mPEG (mw 120-40K), optionally substituted heteroaryl, or optionally substituted heterocycle, or linker-ligand; or, each $R_3$ taken together with the atom to which they are attached are a 3-8 membered optionally substituted cycloalkyl group or a 3-8 membered optionally substituted heterocycle group;

X and Y are each independently —O—, —S—, alkylene, —N(Q)-, —C(O)—, —O(CO)—, —OC(O)N(Q)-, —N(Q)C(O)O—, —C(O)O, —OC(O)O—, —OS(O)(Q$_2$)O—, or —OP(O)(Q$_2$)O—;

Q is H, alkyl, ω-aminoalkyl, ω-(substituted)aminoalkyl, ω-phosphoalkyl, or ω-thiophosphoalkyl;

$Q_1$ is independently for each occurrence O or S; and, $Q_2$ is independently for each occurrence O, S, N(Q)Q), alkyl or alkoxy;

In another aspect, the invention provides a lipid particle comprising the lipids of the present invention. In certain embodiments, the lipid particle further comprises a neutral lipid and a lipid capable of reducing particle aggregation. In one embodiment, the lipid particle consists essentially of (i) at least one lipid of the present invention; (ii) a neutral lipid selected from DSPC, DPPC, POPC, DOPE and SM; (iii) sterol, e.g. cholesterol; and (iv) peg-lipid, e.g. PEG-DMG or PEG-DMA, in a molar ratio of about 20-60% cationic lipid: 5-25% neutral lipid: 25-55% sterol; 0.5-15% PEG-lipid. In one embodiment, the lipid of the present invention is optically pure.

In one embodiment, the lipid particle comprises at least two lipids disclosed herein. For example, a mixture of cationic lipids can be used in a lipid particle, such that the mixture comprises 20-60% of the total lipid content on a molar basis.

In additional related embodiments, the present invention includes lipid particles of the invention that further comprise therapeutic agent. In one embodiment, the therapeutic agent is a nucleic acid. In one embodiment, the nucleic acid is a plasmid, an immunostimulatory oligonucleotide, a single stranded oligonucleotide, e.g. an antisense oligonucleotide, an antagomir; a double stranded oligonucleotide, e.g. a siRNA; an aptamer or a ribozyme.

In yet another related embodiment, the present invention includes a pharmaceutical composition comprising a lipid particle of the present invention and a pharmaceutically acceptable excipient, carrier of diluent.

The present invention further includes, in other related embodiments, a method of modulating the expression of a target gene in a cell, the method comprising providing to a cell a lipid particle or pharmaceutical composition of the present invention. The target gene can be a wild type gene. In another embodiment, the target gene contains one or more mutations. In a particular embodiment, the method comprises specifically modulating expression of a target gene containing one or more mutations. In particular embodiments, the lipid particle comprises a therapeutic agent selected from an immunostimulatory oligonucleotide, a single stranded oligonucleotide, e.g. an antisense oligonucleotide, an antagomir; a double stranded oligonucleotide, e.g. a siRNA, an aptamer, a ribozyme. In one embodiment, the nucleic acid is plasmid that encodes a siRNA, an antisense oligonucleotide, an aptamer or a ribozyme.

In one aspect of the invention, the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, SORT1 gene, XBP1 gene, topoisomerase I gene, topoisomerase II alpha gene, p73 gene, p21(WAF1/CIP1) gene, p27(KIP1) gene, PPM1D gene, RAS gene, caveolin I gene, MIB I gene, MTAI gene, M68 gene, mutations in tumor suppressor genes, p53 tumor suppressor gene, and combinations thereof.

In another embodiment, the nucleic acid is a plasmid that encodes a polypeptide or a functional variant or fragment thereof, such that expression of the polypeptide or the functional variant or fragment thereof is increased.

In yet a further related embodiment, the present invention includes a method of treating a disease or disorder characterized by overexpression of a polypeptide in a subject, comprising providing to the subject a lipid particle or pharmaceutical composition of the present invention, wherein the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

In another related embodiment, the present invention includes a method of treating a disease or disorder characterized by underexpression of a polypeptide in a subject, comprising providing to the subject the pharmaceutical composition of the present invention, wherein the therapeutic agent is a plasmid that encodes the polypeptide or a functional variant or fragment thereof.

In a further embodiment, the present invention includes a method of inducing an immune response in a subject, comprising providing to the subject a pharmaceutical composition of the present invention, wherein the therapeutic agent is an immunostimulatory oligonucleotide. In particular embodiments, the pharmaceutical composition is provided to the patient in combination with a vaccine or antigen.

In a related embodiment, the present invention includes a vaccine comprising the lipid particle of the present invention and an antigen associated with a disease or pathogen. In one embodiment, the lipid particle comprises an immunostimulatory nucleic acid or oligonucleotide. In a particular embodiment, the antigen is a tumor antigen. In another embodiment, the antigen is a viral antigen, a bacterial antigen, or a parasitic antigen.

The present invention further includes methods of preparing the lipid particles and pharmaceutical compositions of the present invention, as well as kits useful in the preparation of these lipid particle and pharmaceutical compositions.

In another aspect, the invention provides a method of evaluating a composition that includes an agent, e.g. a therapeutic agent or diagnostic agent, and a lipid of the present invention.

BRIEF DESCRIPTION OF THE SEVERAL VIEWS OF THE DRAWINGS

FIG. 1. Schematic representation of an optically pure lipid with conjugated targeting ligands.

FIG. 2. Schematic representation of an optically pure lipid with conjugated targeting ligands.

FIG. 3. Schematic representation of racemic lipids with conjugated targeting ligands.

FIG. 4. Shows the results of in vivo modulation of FVII gene using formulations comprising the lipids 506, 512 or 519.

DETAILED DESCRIPTION

The present invention is based, in part, upon the discovery of cationic lipids that provide advantages when used in lipid particles for the in vivo delivery of a therapeutic agent. In particular, as illustrated by the accompanying Examples, the present invention provides nucleic acid-lipid particle compositions comprising a cationic lipid according to the present invention. In some embodiments, a composition described herein provides increased activity of the nucleic acid and/or improved tolerability of the compositions in vivo, which can result in a significant increase in therapeutic index as compared to lipid-nucleic acid particle compositions previously described. Additionally compositions and methods of use are disclosed that can provide for amelioration of the toxicity observed with certain therapeutic nucleic acid-lipid particles.

In certain embodiments, the present invention specifically provides for improved compositions for the delivery of siRNA molecules. It is shown herein that these compositions are effective in down-regulating the protein levels and/or mRNA levels of target proteins. Furthermore, it is shown that the activity of these improved compositions is dependent on the presence of a certain cationic lipids and that the molar ratio of cationic lipid in the formulation can influence activity.

The lipid particles and compositions of the present invention may be used for a variety of purposes, including the delivery of associated or encapsulated therapeutic agents to cells, both in vitro and in vivo. Accordingly, the present invention provides methods of treating diseases or disorders in a subject in need thereof, by contacting the subject with a lipid particle of the present invention associated with a suitable therapeutic agent.

As described herein, the lipid particles of the present invention are particularly useful for the delivery of nucleic acids, including, e.g., siRNA molecules and plasmids. Therefore, the lipid particles and compositions of the present invention may be used to modulate the expression of target genes and proteins both in vitro and in vivo by contacting cells with a lipid particle of the present invention associated with a nucleic acid that reduces target gene expression (e.g., an siRNA) or a nucleic acid that may be used to increase expression of a desired protein (e.g., a plasmid encoding the desired protein).

Various exemplary embodiments of the cationic lipids of the present invention, as well as lipid particles and compositions comprising the same, and their use to deliver therapeutic agents and modulate gene and protein expression are described in further detail below.

Lipids

Figure 5:
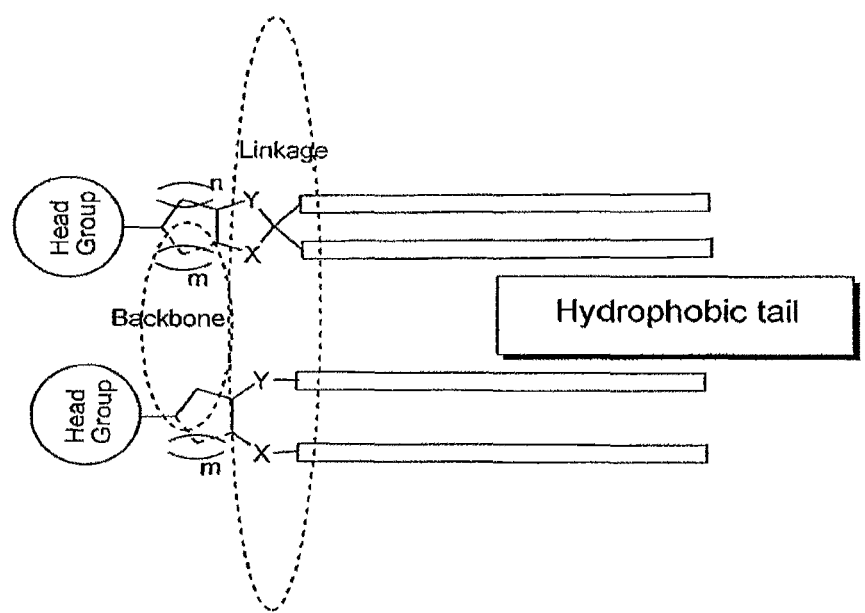
FIG. 5. Schematic representation of features of the lipids of the present invention.

The present invention provides novel lipids having certain design features. As shown in FIG. 5, the lipid design features include at least one of the following: a head group with varying pKa, a cationic, 1°, 2° and 3°, monoamine, Di and triamine, Oligoamine/polyamine, a low pKa head groups—imidazoles and pyridine, guanidinium, anionic, zwitterionic and hydrophobic tails can include symmetric and/or unsymmetric chains, long and shorter, saturated and unsaturated chain the back bone includes Backbone glyceride and other acyclic analogs, cyclic, spiro, bicyclic and polycyclic linkages with ethers, esters, phosphate and analogs, sulfonate and analogs, disulfides, pH sensitive linkages like acetals and ketals, imines and hydrazones, and oximes.

The present invention provides novel lipids that are advantageously used in lipid particles of the present invention for the in vivo delivery of therapeutic agents to cells, including lipids having the following structure

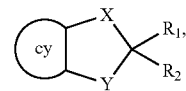

salts or isomers thereof wherein:
cy is optionally substituted cyclic, optionally substituted heterocyclic or heterocycle, optionally substituted aryl or optionally substituted heteroaryl;
$R_1$ and $R_2$ are each independently for each occurrence optionally substituted $C_{10}$-$C_{30}$ alkyl, optionally substituted $C_{10}$-$C_{30}$ alkenyl, optionally substituted $C_{10}$-$C_{30}$ alkynyl, optionally substituted $C_{10}$-$C_{30}$ acyl or -linker-ligand;
X and Y are each independently O or S, alkyl or N(Q); and
Q is H, alkyl, acyl, ω-aminoalkyl, ω-(substituted)aminoalky, ω-phosphoalkyl or ω-thiophosphoalkyl.

In one embodiment, the lipid has the structure

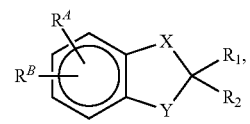

salts or isomers thereof, wherein:
$R_1$ and $R_2$ are each independently for each occurrence optionally substituted $C_{10}$-$C_{30}$ alkyl, optionally substituted $C_{10}$-$C_{30}$ alkenyl, optionally substituted $C_{10}$-$C_{30}$ alkynyl, optionally substituted $C_{10}$-$C_{30}$ acyl or -linker-ligand;
X and Y are each independently O or S, alkyl or N(Q);
Q is H, alkyl, acyl, alkylamino or alkylphosphate; and
$R^A$ and $R^B$ are each independently H, $R_3$, —Z'—$R_3$, -$(A_2)_j$-Z'—$R_3$, acyl, sulfonate or

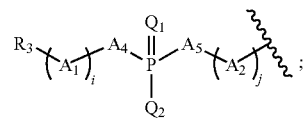

$Q_1$ is independently for each occurrence O or S;
$Q_2$ is independently for each occurrence O, S, N(Q), alkyl or alkoxy;
Q is H, alkyl, ω-aminoalkyl, ω-(substituted)aminoalky, ω-phosphoalkyl or ω-thiophosphoalkyl;
$A_1$, $A_4$, and $A_5$ are each independently O, S, $CH_2$, CHF or $CF_2$;
Z' is O, S, N(Q) or alkyl;
i and j are independently 0 to 10; and
$R_3$ is H, optionally substituted $C_1$-$C_{10}$ alkyl, optionally substituted $C_2$-$C_{10}$ alkenyl, optionally substituted $C_2$-$C_{10}$ alkenyl, alkylhetrocycle, alkylphosphate, alkylphosphorothioate, alkylphosphonates, alkylamines, hydroxyalkyls, ω-aminoalkyls, ω-(substituted)aminoalkyls, ω-phosphoalkyls, ω-thiophosphoalkyls, polyethylene glycol (PEG, mw 100-40K), mPEG (mw 120-40K), heteroaryl, heterocycle or linker-ligand.
In another aspect, the lipid has one of the following structures, salts or isomers thereof:
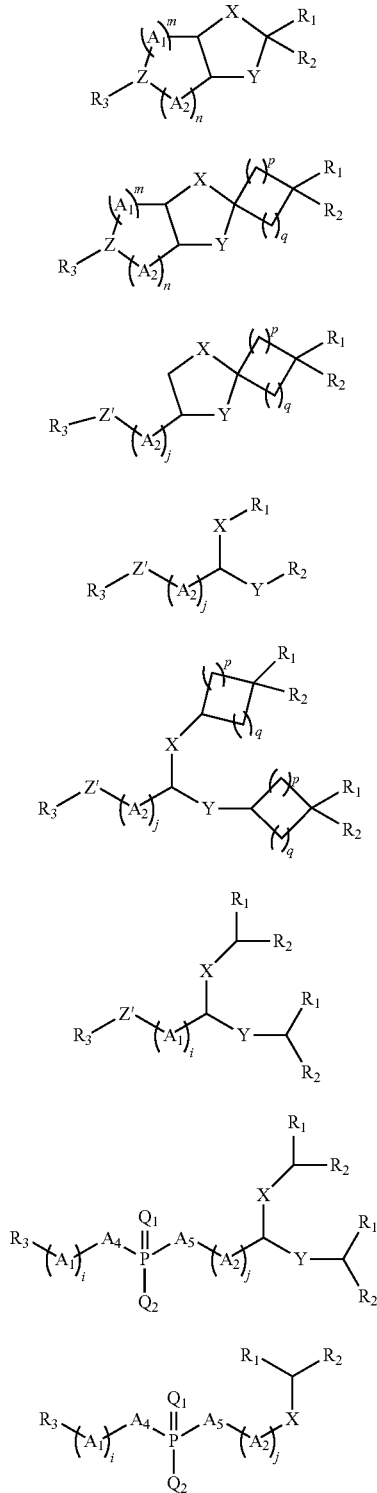
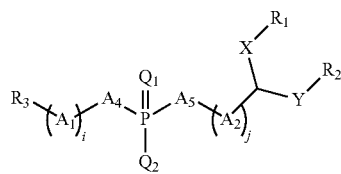
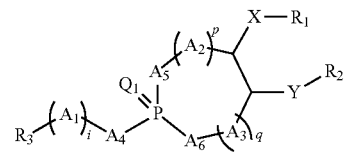
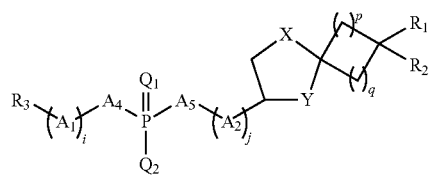
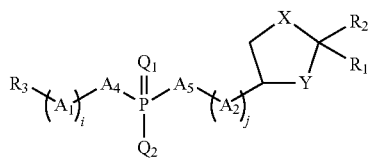
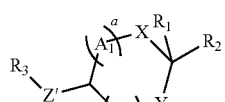
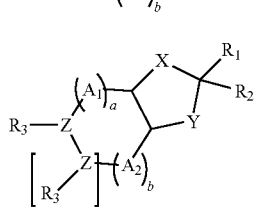
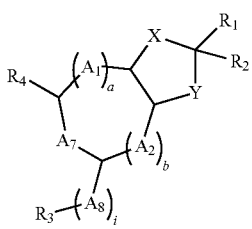
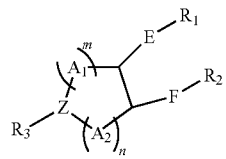
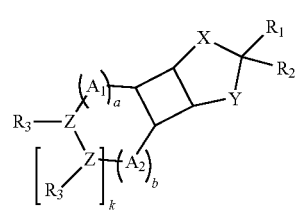

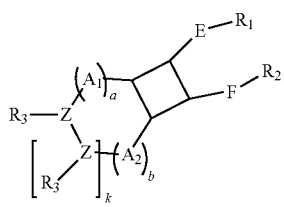 XIX
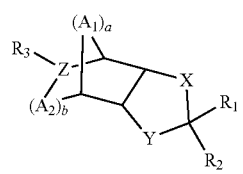 XX
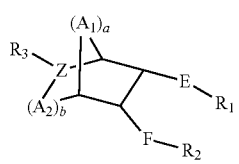 XXI
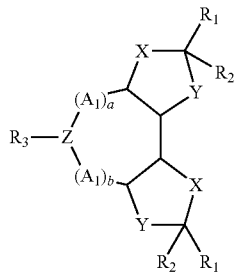 XXII
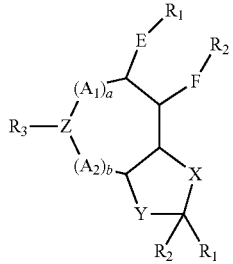 XXIII
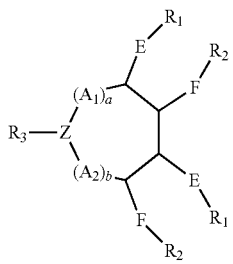 XXIV
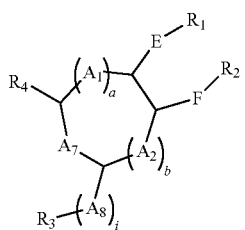 XXV
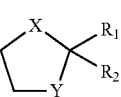 XXVI
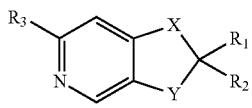 XXVII
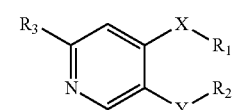 XXVIII
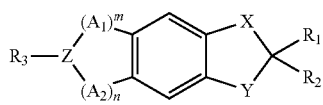 XXIX
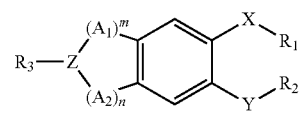 XXX
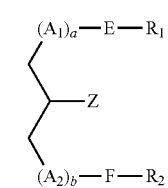 XXXI
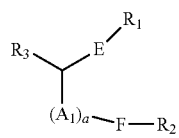 XXXII
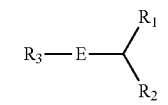 XXXIII
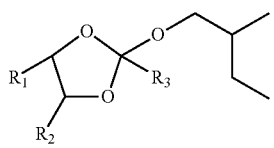 XXXIV
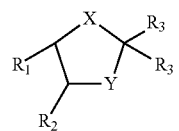 XXXV
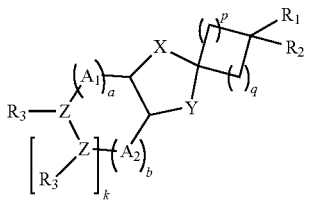 XXXVI

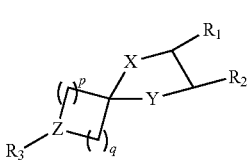

XXXVII wherein:

$R_1$ and $R_2$ are each independently for each occurrence optionally substituted $C_{10}$-$C_{30}$ alkyl, optionally substituted $C_{10}$-$C_{30}$ alkenyl, optionally substituted $C_{10}$-$C_{30}$ alkynyl, optionally substituted $C_{10}$-$C_{30}$ acyl, or -linker-ligand;

$R_3$ is independently for each occurrence H, optionally substituted $C_1$-$C_{10}$ alkyl, optionally substituted $C_2$-$C_{10}$ alkenyl, optionally substituted $C_2$-$C_{10}$ alkynyl, alkylhetrocycle, alkylphosphate, alkylphosphorothioate, alkylphosphorodithioate, alkylphosphonates, alkylamines, hydroxyalkyls, ω-aminoalkyls, ω-(substituted)aminoalkyls, ω-phosphoalkyls, ω-thiophosphoalkyls, optionally substituted polyethylene glycol (PEG, mw 100-40K), optionally substituted mPEG (mw 120-40K), heteroaryl, heterocycle, or linker-ligand;

$R^4$ is independently for each occurrence H, =O, $OR_3$ or $R_3$;

X and Y are each independently O, S, alkyl or N(Q);

Q is H, alkyl, ω-aminoalkyl, ω-(substituted)aminoalky, ω-phosphoalkyl or ω-thiophosphoalkyl;

$Q_1$ is independently for each occurrence O or S;

$Q_2$ is independently for each occurrence O, S, N(Q), alkyl or alkoxy;

$A_1$, $A_2$, $A_3$, $A_4$, $A_5$ and $A_6$ are each independently O, S, $CH_2$, CHF or $CF_2$;

$A_7$ is O, S or N(Q);

$A_8$ is independently for each occurrence $CH_2$, CHF or $CF_2$;

$A_9$ is —C(O)— or —C(H)($R_3$)—;

E and F are each independently for each occurrence O, S, N(Q), C(O), C(O)O, C(O)N, S(O), $S(O)_2$, SS, O=N, aryl, heteroaryl, cyclic or heterocycle Z is N, C($R_3$);

Z' is O, S, N(Q) or alkyl;

k is 0, 1 or 2;

m and n are 0 to 5, where m and n taken together result in a 3, 4, 5, 6, 7 or 8 member ring;

p is 1-5;

q is 0-5, where p and q taken together result in a 3, 4, 5, 6, 7 or 8 member ring i and j are 0-10; and a and b are 0-2.

In one embodiment, X and Y can be independently (CO), O(CO), O(CO)N, N(CO)O, (CO)O, O(CO)O, a sulfonate, or a phosphate.

In one embodiment, $R_1$ and $R_2$ are each independently for each occurrence optionally substituted $C_{10}$-$C_{30}$ alkyl, optionally substituted $C_{10}$-$C_{30}$ alkoxy, optionally substituted $C_{10}$-$C_{30}$ alkenyl, optionally substituted $C_{10}$-$C_{30}$ alkenyloxy, optionally substituted $C_{10}$-$C_{30}$ alkynyl, optionally substituted $C_{10}$-$C_{30}$ alkynyloxy, or optionally substituted $C_{10}$-$C_{30}$ acyl, or -linker-ligand.

In one embodiment, $R_3$ is independently for each occurrence H, optionally substituted $C_1$-$C_{10}$ alkyl, optionally substituted $C_2$-$C_{10}$ alkenyl, optionally substituted $C_2$-$C_{10}$ alkynyl, optionally substituted alkylheterocycle, optionally substituted heterocyclealkyl, optionally substituted alkylphosphate, optionally substituted phosphoalkyl, optionally substituted alkylphosphorothioate, optionally substituted phosphorothioalkyl, optionally substituted alkylphosphorodithioate, optionally substituted phosphorodithioalkyl, optionally substituted alkylphosphonate, optionally substituted phosphonoalkyl, optionally substituted amino, optionally substituted alkylamino, optionally substituted di(alkyl) amino, optionally substituted aminoalkyl, optionally substituted alkylaminoalkyl, optionally substituted di(alkyl) aminoalkyl, optionally substituted hydroxyalkyl, optionally substituted polyethylene glycol (PEG, mw 100-40K), optionally substituted mPEG (mw 120-40K), optionally substituted heteroaryl, or optionally substituted heterocycle, or linker-ligand.

In one embodiment, X and Y are each independently —O—, —S—, alkylene, —N(Q)-, —C(O)—, —O(CO)—, —OC(O)N(Q)-, —N(Q)C(O)O—, —C(O)O, —OC(O)O—, —OS(O)($Q_2$)O—, or —OP(O)($Q_2$)O—.

In one embodiment, Q is H, alkyl, ω-aminoalkyl, ω-(substituted)aminoalkyl, ω-phosphoalkyl, or ω-thiophosphoalkyl.

In one embodiment, $Q_2$ is independently for each occurrence O, S, N(Q)Q), alkyl or alkoxy, In one embodiment, $A_1$, $A_2$, $A_3$, $A_4$, $A_5$ and $A_6$ are each independently —O—, —S—, —$CH_2$—, —$CHR^5$—, —$CR^5R^5$—, —CHF— or —$CF_2$—.

In one embodiment, $A_8$ is independently for each occurrence —$CH_2$—, —$CHR^5$—, —$CR^5R^5$—, —CHF—, or —$CF_2$—.

In one embodiment, E and F are each independently for each occurrence —O—, —S—, —N(Q)-, —C(O)—, —C(O) O—, —OC(O)—, —C(O)N(Q)-, —N(Q)C(O)—, —S(O)—, —$S(O)_2$—, —SS—, —O—N=, =N—O—, arylene, heteroarylene, cycloalkylene, or heterocyclylene.

In one embodiment, Z is N, or C($R_3$).

In one embodiment, Z' is —O—, —S—, —N(Q)-, or alkylene.

In one embodiment, $R^5$ is H, halo, cyano, hydroxy, amino, optionally substituted alkyl, optionally substituted alkoxy, or optionally substituted cycloalkyl.

In one embodiment, i and j are each independently 0-10.

In one embodiment, a and b are each independently 0-2.

In some circumstances, $R_3$ is ω-aminoalkyl, ω-(substituted)aminoalkyl, ω-phosphoalkyl, or ω-thiophosphoalkyl; each of which is optionally substituted. Examples of ω-(substituted)aminoalkyl groups include 2-(dimethylamino)ethyl, 3-(diisopropylamino)propyl, or 3-(N-ethyl-N-isopropylamino)-1-methylpropyl.

In one embodiment, X and Y can be independently —O—, —S—, alkylene, or —N(Q)-.

It has been found that cationic lipids comprising unsaturated alkyl chains are particularly useful for forming lipid nucleic acid particles with increased membrane fluidity. In one embodiment, at least one of $R_1$ or $R_2$ comprises at least one, at least two or at least three sites of unsaturation, e.g. double bond or triple bond.

In one embodiment, only one of $R_1$ or $R_2$ comprises at least one, at least two or at least three sites of unsaturation.

In one embodiment, $R_1$ and $R_2$ both comprise at least one, at least two or at least three sites of unsaturation.

In one embodiment, $R_1$ and $R_2$ comprise different numbers of unsaturation, e.g., one of $R_1$ and $R_2$ has one site of unsaturation and the other has two or three sites of unsaturation.

In one embodiment, $R_1$ and $R_2$ both comprise the same number of unsaturation sites.

In one embodiment, $R_1$ and $R_2$ comprise different types of unsaturation, e.g. unsaturation in one of $R_1$ and $R_2$ is double bond and in the other unsaturation is triple bond.

In one embodiment, $R_1$ and $R_2$ both comprise the same type of unsaturation, e.g. double bond or triple bond.

In one embodiment, at least one of $R_1$ or $R_2$ comprises at least one double bond and at least one triple bond.

In one embodiment, only one of $R_1$ or $R_2$ comprises at least one double bond and at least one triple bond.

In one embodiment, $R_1$ and $R_2$ both comprise at least one double bond and at least one triple bond.

In one embodiment, $R_1$ and $R_2$ are both same, e.g. $R_1$ and $R_2$ are both linoleyl (C18) or $R_1$ and $R_2$ are both heptadeca-9-enyl.

In one embodiment, $R_1$ and $R_2$ are different from each other.

In one embodiment, at least one of $R_1$ and $R_2$ is cholesterol.

In one embodiment, one of $R_1$ and $R_2$ is -linker-ligand.

In one embodiment, one of $R_1$ and $R_2$ is -linker-ligand and ligand is a lipophile.

In one embodiment, at least one of $R_1$ or $R_2$ comprises at least one $CH_2$ group with one or both H replaced by F, e.g. CHF or $CF_2$. In one embodiment, both $R_1$ and $R_2$ comprise at least one $CH_2$ group with one or two H replaced by F, e.g. CHF or $CF_2$.

In one embodiment, only one of $R_1$ and $R_2$ comprises at least one $CH_2$ group with one or both H replaced by F.

In one embodiment, at least one of $R_1$ or $R_2$ terminates in $CH_2F$, $CHF_2$ or $CF_3$. In one embodiment, both $R_1$ and $R_2$ terminate in $CH_2F$, $CHF_2$ or $CF_3$.

In one embodiment, at least one of $R_1$ or $R_2$ is —$(CF_2)_y$—$Z''$—$(CH_2)_y$—$CH_3$, wherein each y is independently 1-10 and $Z''$ is O, S or N(Q).

In one embodiment, both of $R_1$ and $R_2$ are —$(CF_2)_y$—$Z''$—$(CH_2)_y$—$CH_3$, wherein each y is independently 1-10 and $Z''$ is O, S or N(Q).

In one embodiment, at least one of $R_1$ or $R_2$ is —$(CH_2)_y$—$Z''$—$(CF_2)_y$—$CF_3$, wherein each y is independently 1-10 and $Z''$ is O, S or N(Q).

In one embodiment, both of $R_1$ and $R_2$ are —$(CH_2)_y$—$Z''$—$(CF_2)_y$—$CF_3$, wherein each y is independently 1-10 and $Z''$ is O, S or N(Q).

In one embodiment, at least one of $R_1$ or $R_2$ is —$(CF_2)_y$—$(CF_2)_y$—$CF_3$, wherein each y is independently 1-10.

In one embodiment, both of $R_1$ and $R_2$ are —$(CF_2)_y$—$(CF_2)_y$—$CF_3$, wherein each y is independently 1-10.

In one embodiment,

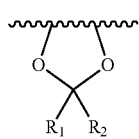

is selected from the group consisting of:

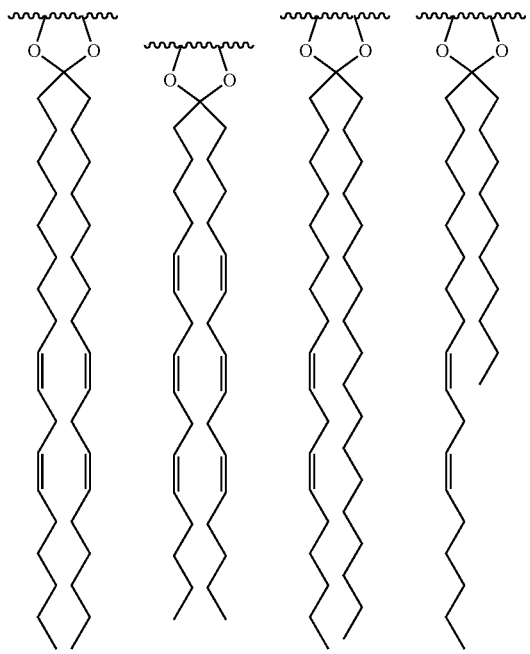

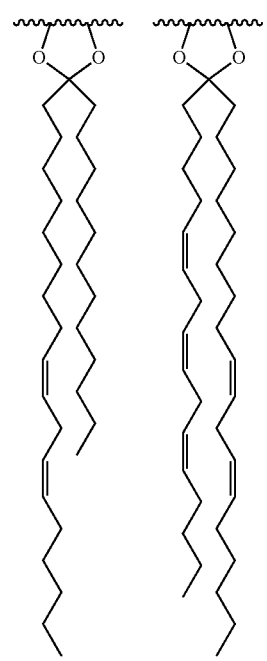

and

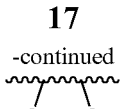

In one embodiment, $R_3$ is chosen from a group consisting of methyl, ethyl, polyamine, —$(CH_2)_h$-heteroaryl, —$(CH_2)_h$—$N(Q)_2$, —O—$N(Q)_2$, —$(CH_2)_h$—Z'—$(CH_2)_h$-heteroaryl, linker-ligand, —$(CH_2)_h$-heterocycle, and —$(CH_2)_h$—Z"—$(CH_2)_h$-heterocycle, wherein each h is independently 0-13 and Z" is O, S or N(Q).

In one embodiment, when Z is $C(R_3)$, at least one $R_3$ is ω-aminoalkyl or ω-(substituted)aminoalkyl.

In one embodiment, when Z' is O, S or alkyl, at least one $R_3$ is ω-aminoalkyl or ω-(substituted)aminoalkyl.

In one embodiment, Q is linker-ligand.

In one embodiment, ligand is fusogenic peptide.

In one embodiment, the lipid is a racemic mixture.

In one embodiment, the lipid is enriched in one diastereomer, e.g. the lipid has at least 95%, at least 90%, at least 80% or at least 70% diastereomeric excess.

In one embodiment, the lipid is enriched in one enantiomer, e.g. the lipid has at least 95%, at least 90%, at least 80% or at least 70% enantiomer excess.

In one embodiment, the lipid is chirally pure, e.g. is a single optical isomer.

In one embodiment, the lipid is enriched for one optical isomer.

Where a double bond is present (e.g., a carbon-carbon double bond or carbon-nitrogen double bond), there can be isomerism in the configuration about the double bond (i.e. cis/trans or E/Z isomerism). Where the configuration of a double bond is illustrated in a chemical structure, it is understood that the corresponding isomer can also be present. The amount of isomer present can vary, depending on the relative stabilities of the isomers and the energy required to convert between the isomers. Accordingly, some double bonds are, for practical purposes, present in only a single configuration, whereas others (e.g., where the relative stabilities are similar and the energy of conversion low) may be present as inseparable equilibrium mixture of configurations.

In another aspect, the invention features a compound of formula XXXIVa, XXXIVb, XXXIVc, XXXIVd, or XXXIVe, salts or isomers thereof:

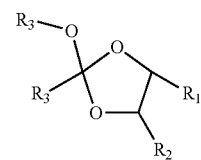
XXXIVa

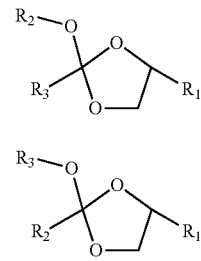
XXXIVb

XXXIVc

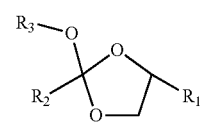
XXXIVd

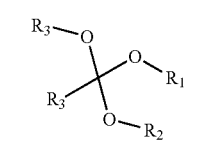
XXXIVe

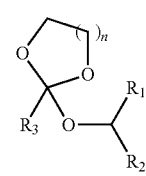

wherein:

$R_1$ and $R_2$ are each independently for each occurrence optionally substituted $C_{10}$-$C_{30}$ alkyl, optionally substituted $C_{10}$-$C_{30}$ alkenyl, or optionally substituted $C_{10}$-$C_{30}$ alkynyl;

$R_3$ is independently for each occurrence H, optionally substituted $C_1$-$C_{10}$ alkyl, optionally substituted $C_2$-$C_{10}$ alkenyl, optionally substituted $C_2$-$C_{10}$ alkynyl, optionally substituted alkylheterocycle, optionally substituted heterocyclealkyl, optionally substituted alkylphosphate, optionally substituted phosphoalkyl, optionally substituted alkylphosphorothioate, optionally substituted phosphorothioalkyl, optionally substituted alkylphosphorodithioate, optionally substituted phosphorodithioalkyl, optionally substituted alkylphosphonate, optionally substituted phosphonoalkyl, optionally substituted amino, optionally substituted alkylamino, optionally substituted di(alkyl)amino, optionally substituted aminoalkyl, optionally substituted alkylaminoalkyl, optionally substituted di(alkyl)aminoalkyl, optionally substituted hydroxyalkyl, optionally substituted polyethylene glycol (PEG, mw 100-40K), optionally substituted mPEG (mw 120-40K), optionally substituted heteroaryl, or optionally substituted heterocycle; and n is 1, 2, or 3.

In some embodiments, $R_3$ is optionally substituted heterocyclealkyl, optionally substituted amino, optionally substituted alkylamino, optionally substituted di(alkyl)amino, optionally substituted aminoalkyl, optionally substituted alkylaminoalkyl, optionally substituted di(alkyl)aminoalkyl, or optionally substituted heterocycle.

In one aspect, the lipid is a compound of formula XIIIa:

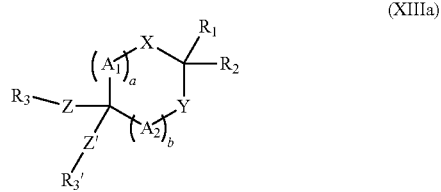

(XIIIa)

wherein:

$R_1$ and $R_2$ are each independently for each occurrence optionally substituted $C_{10}$-$C_{30}$ alkyl, optionally substituted $C_{10}$-$C_{30}$ alkenyl, or optionally substituted $C_{10}$-$C_{30}$ alkynyl;

$R_3$ and $R_{3'}$ are independently for each occurrence H, optionally substituted $C_1$-$C_{10}$ alkyl, optionally substituted $C_2$-$C_{10}$ alkenyl, optionally substituted $C_2$-$C_{10}$ alkynyl, optionally substituted alkylheterocycle, optionally substituted heterocyclealkyl, optionally substituted alkylphosphate, optionally substituted phosphoalkyl, optionally substituted alkylphosphorothioate, optionally substituted phosphorothioalkyl, optionally substituted alkylphosphorodithioate, optionally substituted phosphorodithioalkyl, optionally substituted alkylphosphonate, optionally substituted phosphonoalkyl, optionally substituted amino, optionally substituted alkylamino, optionally substituted di(alkyl)amino, optionally substituted aminoalkyl, optionally substituted alkylaminoalkyl, optionally substituted di(alkyl)aminoalkyl, optionally substituted hydroxyalkyl, optionally substituted polyethylene glycol (PEG, mw 100-40K), optionally substituted mPEG (mw 120-40K), optionally substituted heteroaryl, or optionally substituted heterocycle;

or $R_3$ and $R_{3'}$ can be taken together with the atoms to which they are attached to form an optionally substituted carbocyclyl, optionally substituted heterocyclyl, optionally substituted aryl or optionally substituted heteroaryl; each of which is substituted with 0-4 occurrences of $R_4$;

each $R_4$ is independently selected from optionally substituted $C_1$-$C_{10}$ alkyl, optionally substituted $C_2$-$C_{10}$ alkenyl, optionally substituted $C_2$-$C_{10}$ alkynyl, optionally substituted amino, optionally substituted alkylamino, optionally substituted di(alkyl)amino, optionally substituted aminoalkyl, optionally substituted alkylaminoalkyl, optionally substituted di(alkyl)aminoalkyl, optionally substituted hydroxyalkyl, optionally substituted aryl, optionally substituted heteroaryl, or optionally substituted heterocycle;

X and Y are each independently —O—, —S—, alkylene, or —N(Q)-;

Q is H, alkyl, ω-aminoalkyl, ω-(substituted)aminoalkyl, ω-phosphoalkyl, or ω-thiophosphoalkyl;

$A_1$ and $A_2$ are each independently —O—, —S—, or —$CR^5R^5$—; and $R^5$ is H, halo, cyano, hydroxy, amino, optionally substituted alkyl, optionally substituted alkoxy, or optionally substituted cycloalkyl; and Z and Z' are each independently selected from —O—, —S—, —N(Q)-, alkylene or absent; and a and b are each independently 0-2.

In some embodiments, X and Y are each independently O.

In some embodiments, the sum of a and b is 1, 2, or 3.

In some embodiments, $A_1$ and $A_2$ are each independently —$CR^5R^5$—.

In some embodiments, Z and Z' are each a bond.

In some embodiments, $R_3$ and $R_{3'}$ can be taken together with the atoms to which they are attached to form an optionally substituted carbocyclyl, optionally substituted heterocyclyl, optionally substituted aryl or optionally substituted heteroaryl.

In some embodiments, $R_3$ and $R_{3'}$ can be taken together with the atoms to which they are attached to form an optionally substituted carbocyclyl (e.g., optionally substituted with amino, alkylamino, or dialkylamino).

In some embodiments, $R_3$ and $R_{3'}$ can be taken together with the atoms to which they are attached to form an optionally substituted heterocyclyl (e.g., a nitrogen containing heterocyclyl).

In some embodiments, $R_3$ and $R_{3'}$ are taken together to form a carbocyclic ring (e.g., cyclohexyl) substituted with 0-3 occurrence of $R_4$.

In some embodiments, $R_3$ and $R_{3'}$ are taken together to form a heterocyclic ring (e.g., piperidine) substituted with 0-3 occurrences of $R_4$.

In some embodiments, each $R_4$ is independently selected from optionally optionally substituted amino, optionally substituted alkylamino, optionally substituted di(alkyl)amino, optionally substituted aminoalkyl, optionally substituted alkylaminoalkyl, optionally substituted di(alkyl)aminoalkyl, and optionally substituted hydroxyalkyl.

In one aspect, the lipid is a compound of formula XXXIX, salts or isomers thereof:

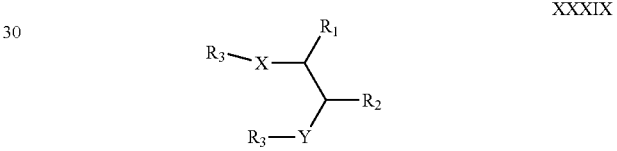

XXXIX wherein:

$R_1$ and $R_2$ are each independently for each occurrence optionally substituted $C_{10}$-$C_{30}$ alkyl, optionally substituted $C_{10}$-$C_{30}$ alkenyl, optionally substituted $C_{10}$-$C_{30}$ alkynyl, optionally substituted $C_{10}$-$C_{30}$ acyl, or -linker-ligand;

$R_3$ is independently for each occurrence H, optionally substituted $C_1$-$C_{10}$ alkyl, optionally substituted $C_2$-$C_{10}$ alkenyl, optionally substituted $C_2$-$C_{10}$ alkynyl, alkylhetrocycle, alkylphosphate, alkylphosphorothioate, alkylphosphorodithioate, alkylphosphonates, alkylamines, hydroxyalkyls, ω-aminoalkyls, ω-(substituted)aminoalkyls, ω-phosphoalkyls, ω-thiophosphoalkyls, optionally substituted polyethylene glycol (PEG, mw 100-40K), optionally substituted mPEG (mw 120-40K), heteroaryl, heterocycle, or linker-ligand;

X and Y are each independently O, C(O)O, S, alkyl or N(Q);

Q is H, alkyl, ω-aminoalkyl, ω-(substituted)aminoalky, ω-phosphoalkyl or ω-thiophosphoalkyl;

In one aspect, the lipid is a compound of formula XXXIII, salts or isomers thereof

XXXIII wherein:

$R_1$ and $R_2$ are each independently for each occurrence optionally substituted $C_{10}$-$C_{30}$ alkyl, optionally substituted $C_{10}$-$C_{30}$ alkenyl, optionally substituted $C_{10}$-$C_{30}$ alkynyl, optionally substituted $C_{10}$-$C_{30}$ acyl, or -linker-ligand;

$R_3$ is H, optionally substituted $C_1$-$C_{10}$ alkyl, optionally substituted $C_2$-$C_{10}$ alkenyl, optionally substituted $C_2$-$C_{10}$ alkynyl, alkylhetrocycle, alkylphosphate, alkylphosphorothioate, alkylphosphorodithioate, alkylphosphonates, alkylamines, hydroxyalkyls, ω-aminoalkyls, ω-(substituted)aminoalkyls, ω-phosphoalkyls, ω-thiophosphoalkyls, optionally substituted polyethylene glycol (PEG, mw 100-40K), optionally substituted mPEG (mw 120-40K), heteroaryl, heterocycle, or linker-ligand;

E is O, S, N(Q), C(O)O, C(O), N(Q)C(O), C(O)N(Q), (Q)N(CO)O, O(CO)N(Q), S(O), NS(O)2N(Q), S(O)2, N(Q)S(O)2, SS, O=N, aryl, heteroaryl, cyclic or heterocycle; and, Q is H, alkyl, ω-aminoalkyl, ω-(substituted)aminoalky, ω-phosphoalkyl or ω-thiophosphoalkyl.

In one embodiment, $R_1$ and $R_2$ are each independently for each occurrence optionally substituted $C_{10}$-$C_{30}$ alkyl, optionally substituted $C_{10}$-$C_{30}$ alkoxy, optionally substituted $C_{10}$-$C_{30}$ alkenyl, optionally substituted $C_{10}$-$C_{30}$ alkenyloxy, optionally substituted $C_{10}$-$C_{30}$ alkynyl, optionally substituted $C_{10}$-$C_{30}$ alkynyloxy, or optionally substituted $C_{10}$-$C_{30}$ acyl.

In another embodiment, $R_3$ is H, optionally substituted $C_1$-$C_{10}$ alkyl, optionally substituted $C_2$-$C_{10}$ alkenyl, optionally substituted $C_2$-$C_{10}$ alkynyl, optionally substituted alkylheterocycle, optionally substituted heterocyclealkyl, optionally substituted alkylphosphate, optionally substituted phosphoalkyl, optionally substituted alkylphosphorothioate, optionally substituted phosphorothioalkyl, optionally substituted alkylphosphorodithioate, optionally substituted phosphorodithioalkyl, optionally substituted alkylphosphonate, optionally substituted phosphonoalkyl, optionally substituted amino, optionally substituted alkylamino, optionally substituted di(alkyl)amino, optionally substituted aminoalkyl, optionally substituted alkylaminoalkyl, optionally substituted di(alkyl)aminoalkyl, optionally substituted hydroxyalkyl, optionally substituted polyethylene glycol (PEG, mw 100-40K), optionally substituted mPEG (mw 120-40K), optionally substituted heteroaryl, optionally substituted heterocycle, or linker-ligand.

In yet another embodiment, E is —O—, —S—, —N(Q)-, —C(O)O—, —OC(O)—, —C(O)—, —N(Q)C(O)—, —C(O)N(Q)-, —N(Q)C(O)O—, —OC(O)N(Q)-, S(O), —N(Q)S(O)$_2$N(Q)-, —S(O)$_2$—, —N(Q)S(O)$_2$—, —SS—, —O—N=, =N—O—, —C(O)—N(Q)-N=, —N(Q)-N=, —N(Q)-O—, —C(O)S—, arylene, heteroarylene, cyclalkylene, or heterocyclylene.

In another embodiment, Q is H, alkyl, ω-aminoalkyl, ω-(substituted)aminoalkyl, ω-phosphoalkyl or ω-thiophosphoalkyl.

In one embodiment, where the lipid is a compound of formula XXXIII, provided that when E is C(O)O and $R^3$ is

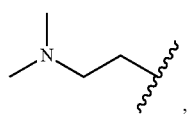 [SMILES: *CCN(C)C]

$R^1$ and $R^2$ are not both linoleyl.

In another embodiment, the lipid is a compound of formula XXXIII, wherein E is O, S, N(Q), C(O), N(Q)C(O), C(O)N(Q), (O)N(CO)O, O(CO)N(Q), S(O), NS(O)2N(Q), S(O)$_2$, N(Q)S(O)2, SS, O=N, aryl, heteroaryl, cyclic or heterocycle.

In one embodiment, the lipid is a compound of formula XXXIII, wherein $R_3$ is H, optionally substituted $C_2$-$C_{10}$ alkenyl, optionally substituted $C_2$-$C_{10}$ alkynyl, alkylhetrocycle, alkylphosphate, alkylphosphorothioate, alkylphosphorodithioate, alkylphosphonates, alkylamines, hydroxyalkyls, ω-aminoalkyls, ω-(substituted)aminoalkyls, ω-phosphoalkyls, ω-thiophosphoalkyls, optionally substituted polyethylene glycol (PEG, mw 100-40K), optionally substituted mPEG (mw 120-40K), heteroaryl, heterocycle, or linker-ligand.

In yet another embodiment, the lipid is a compound of formula XXXIII, wherein $R_1$ and $R_2$ are each independently for each occurrence optionally substituted $C_{10}$-$C_{30}$ alkyl, optionally substituted $C_{10}$-$C_{30}$ alkynyl, optionally substituted $C_{10}$-$C_{30}$ acyl, or -linker-ligand.

In one embodiment, the invention features a lipid of formula XXXVIII:

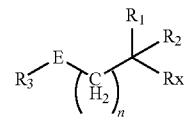

wherein

E is O, S, N(Q), C(O)O, C(O), N(Q)C(O), C(O)N(Q), (Q)N(CO)O, O(CO)N(Q), S(O), NS(O)2N(Q), S(O)2, N(Q)S(O)2, SS, O=N, aryl, heteroaryl, cyclic or heterocycle;

Q is H, alkyl, ω-aminoalkyl, ω-(substituted)aminoalky, ω-phosphoalkyl or ω-thiophosphoalkyl;

$R_1$ and $R_2$ and $R_x$ are each independently for each occurrence H, optionally substituted $C_1$-$C_{10}$ alkyl, optionally substituted $C_{10}$-$C_{30}$ alkyl, optionally substituted $C_{10}$-$C_{30}$ alkenyl, optionally substituted $C_{10}$-$C_{30}$ alkynyl, optionally substituted $C_{10}$-$C_{30}$ acyl, or linker-ligand, provided that at least one of $R_1$, $R_2$ and $R_x$ is not H;

$R_3$ is H, optionally substituted $C_1$-$C_{10}$ alkyl, optionally substituted $C_2$-$C_{10}$ alkenyl, optionally substituted $C_2$-$C_{10}$ alkynyl, alkylhetrocycle, alkylphosphate, alkylphosphorothioate, alkylphosphorodithioate, alkylphosphonates, alkylamines, hydroxyalkyls, ω-aminoalkyls, ω-(substituted)aminoalkyls, ω-phosphoalkyls, ω-thiophosphoalkyls, optionally substituted polyethylene glycol (PEG, mw 100-40K), optionally substituted mPEG (mw 120-40K), heteroaryl, heterocycle, or linker-ligand;

n is 0, 1, 2, or 3.

In one embodiment, where the lipid is a compound of formula XXXVIII, provided that when E is C(O)O, $R^3$ is

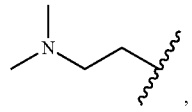 [SMILES: *CCN(C)C]

and one of $R_1$, $R_2$, or $R_x$ is H, then the remaining of $R_1$, $R_2$, or $R_x$ are not both linoleyl.

In some embodiments, each of $R_1$ and $R_2$ is independently for each occurrence optionally substituted $C_{10}$-$C_{30}$ alkyl, optionally substituted $C_{10}$-$C_{30}$ alkenyl, optionally substituted $C_{10}$-$C_{30}$ alkynyl, optionally substituted $C_{10}$-$C_{30}$ acyl, or linker-ligand.

In some embodiments, $R_x$ is H or optionally substituted $C_1$-$C_{10}$ alkyl.

In some embodiments, $R_x$ is optionally substituted $C_{10}$-$C_{30}$ alkyl, optionally substituted $C_{10}$-$C_{30}$ alkenyl, optionally substituted $C_{10}$-$C_{30}$ alkynyl, optionally substituted $C_{10}$-$C_{30}$ acyl, or linker-ligand.

In one aspect, the invention features a lipid of the following formula XL,

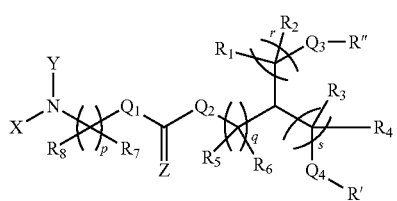

XL wherein:

$Q_1$ is O, S, $CH_2$, CHMe, $CMe_2$, N(R);

$Q_2$ is O, S, $CH_2$, CHMe, $CMe_2$, N(R), C(H)=N—N(R)—, N(R)—N=C(H), —C(H)=N—O—, —O—N=C(H), C(H)=N—N(R)—C(O)—, —C(O)—N(R)—N=C(H)

$Q_3$ and or $Q_4$ is O, S, N(R), $Q_1$-C(=Z)$Q_2$, C(H)=N—N(R)—, N(R)—N=C(H); —C(H)=N—O—, —O—N=C(H); C(H)=N—N(R)—C(O)—, —C(O)—N(R)—N=C(H);

Z=O, S, N(R) or absent and when Z is absent C(=Z) is $C(R_n)_2$ p is 0 to 20; q is 0 to 10; r is 0 to 6; s is 0 to 6.

R' and/or R' are: alkyl, substituted alkyls, alkenyls, substituted alkenyls, alkynyls, substituted alkynyls and combinations thereof with number of carbon atoms in the chain varying from 4 to 30. R' and/or R" with alkenyl chain has at least one C=C or substituted C=C moiety and when there is more than one C=C moiety is present they are separated by at least one methylene or substituted methylene group. R' and/or R" with alkynyl chain has at least one C≡C moiety and when there is more than one C≡C moiety is present they are separated by at least one methylene or substituted methylene group. One or more of methylene or substituted methylene is interrupted by hetero atoms such as O, S or N(R). The double bond or bonds in the alkyl chain are all with cis- or trans-configuration or combination of both. The stereochemistry of chiral center of formula XL is R, S or racemic.

R is H, R', ω-substituted amino-alkyls, ω-substituted amino-alkenyls, ω-substituted amino-alkynyls with number of carbon atoms in the chain varying from 1 to 30

$R_1$ to $R_n$ each occurrence is R;

X is: R, C(O)—NH(R), C(O)$NR_2$, C(=NR)NH(R), C(=NR)$NR_2$, N(R)—C(O)Y and Y is independently X.

In one aspect, the invention features a lipid of the following formula XLI,

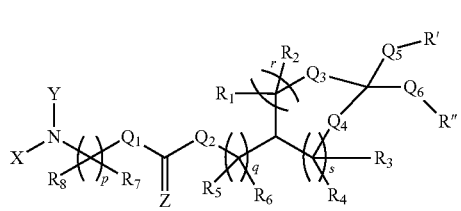

XLI wherein:

$Q_1$ is O, S, $CH_2$, CHMe, $CMe_2$, N(R);

$Q_2$ is O, S, $CH_2$, CHMe, $CMe_2$, N(R), C(H)=N—N(R)—, N(R)—N=C(H), —C(H)=N—O—, —O—N=C(H), C(H)=N—N(R)—C(O)—, —C(O)—N(R)—N=C(H)

$Q_3$ and or $Q_4$ is O, S, N(R), $CH_2$, substituted methylene;

$Q_5$ and or $Q_6$ is O, S, N(R), $CH_2$, substituted methylene

Z=O, S, N(R) or absent and when Z is absent C(=Z) is $C(R_n)_2$ p is 0 to 20; q is 0 to 10; r is 0 to 6; s is 0 to 6.

R' and/or R' are: alkyl, substituted alkyls, alkenyls, substituted alkenyls, alkynyls, substituted alkynyls and combinations thereof with number of carbon atoms in the chain varying from 4 to 30. R' and/or R" with alkenyl chain has at least one C=C or substituted C=C moiety and when there is more than one C=C moiety is present they are separated by at least one methylene or substituted methylene group. R' and/or R" with alkynyl chain has at least one C≡C moiety and when there is more than one C≡C moiety is present they are separated by at least one methylene or substituted methylene group. One or more of methylene or substituted methylene is interrupted by hetero atoms such as O, S or N(R). The double bond or bonds in the alkyl chain are all with cis- or trans-configuration or combination of both. The stereochemistry of chiral center of formula XLI is R, S or racemic.

R is H, R', ω-substituted amino-alkyls, ω-substituted amino-alkenyls, ω-substituted amino-alkynyls with number of carbon atoms in the chain varying from 1 to 30 $R_1$ to $R_n$ each occurrence is R;

X is: R, C(O)—NH(R), C(O)$NR_2$, C(=NR)NH(R), C(=NR)$NR_2$, N(R)—C(O)Y and Y is independently X.

In another aspect, the invention features a lipid of one of the following formula XLII, XLIII, XLIV, XLV, XLVI, XLVII, XLVIII, or XLIX

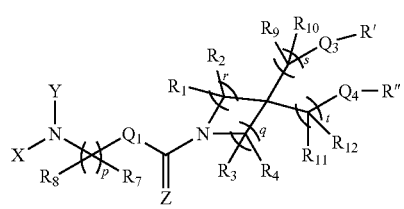

XLII

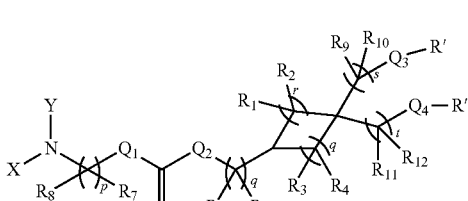

XLIII

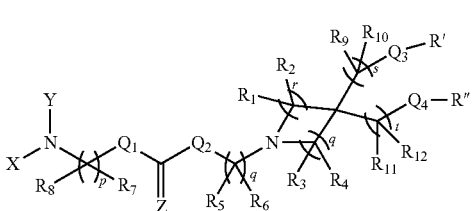

XLIV

XLV
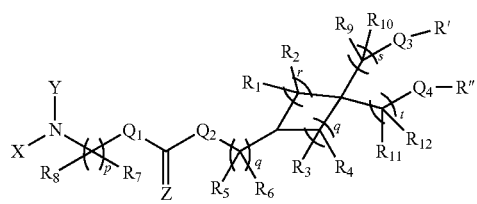

XLVI
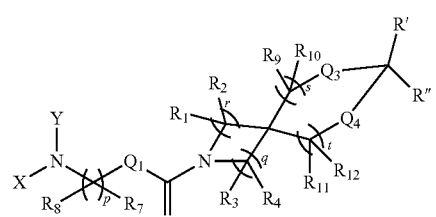

XLVII
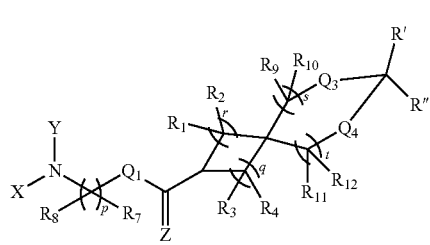

XLVIII
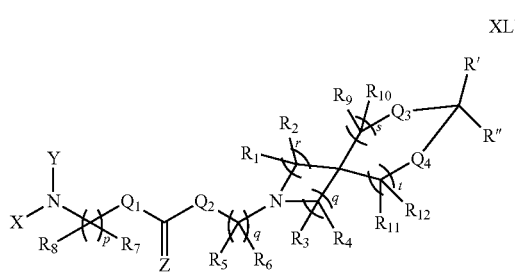

XLIX
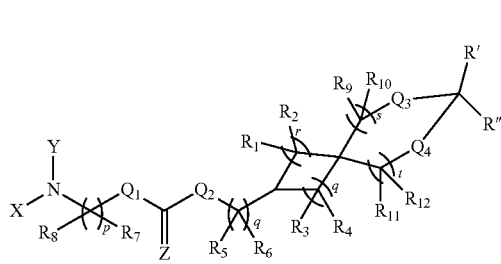

L
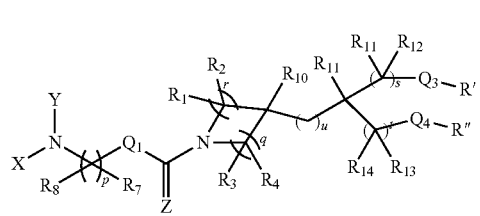

LI
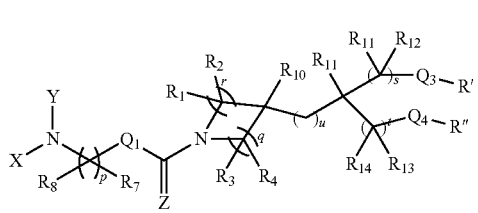

LII
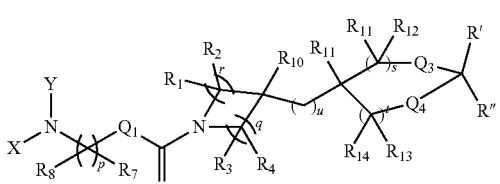

LIII
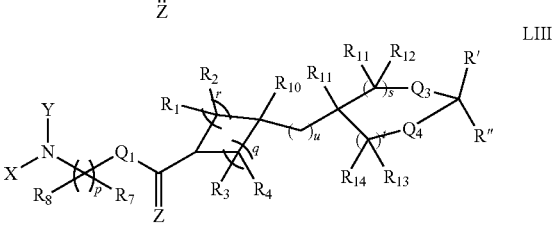

LIV
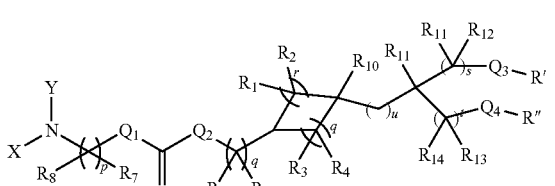

LV
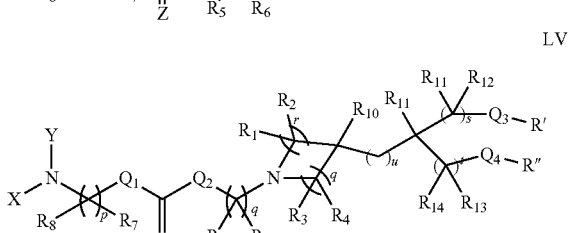

LVI
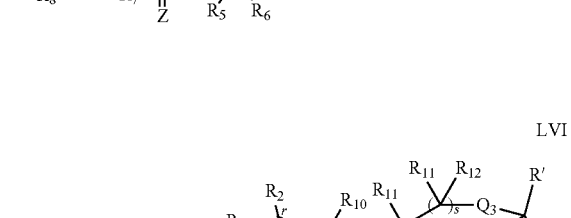

LVII
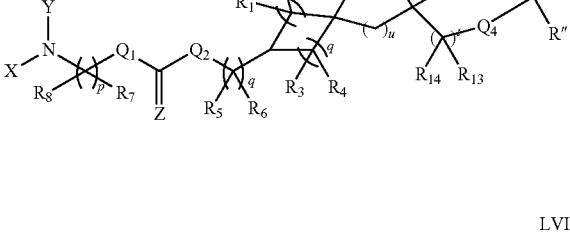

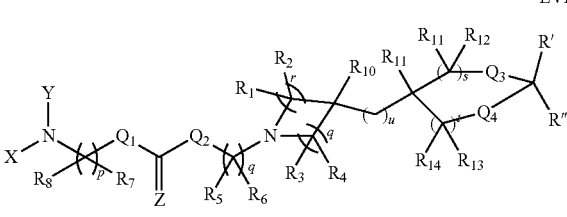

Wherein the variables recited above are as described herein and wherein for the compounds of formulae above: p is 0 to 20; q is 0 to 10; r is 0 to 6; s is 0 to 6, t is 0 to 6 and u is 0 to 10 and the other variables are as described above.

The present invention comprises of synthesis of lipids described herein in racemic as well as in optically pure form.

In one aspect, the invention features a lipid of the formula provided below:

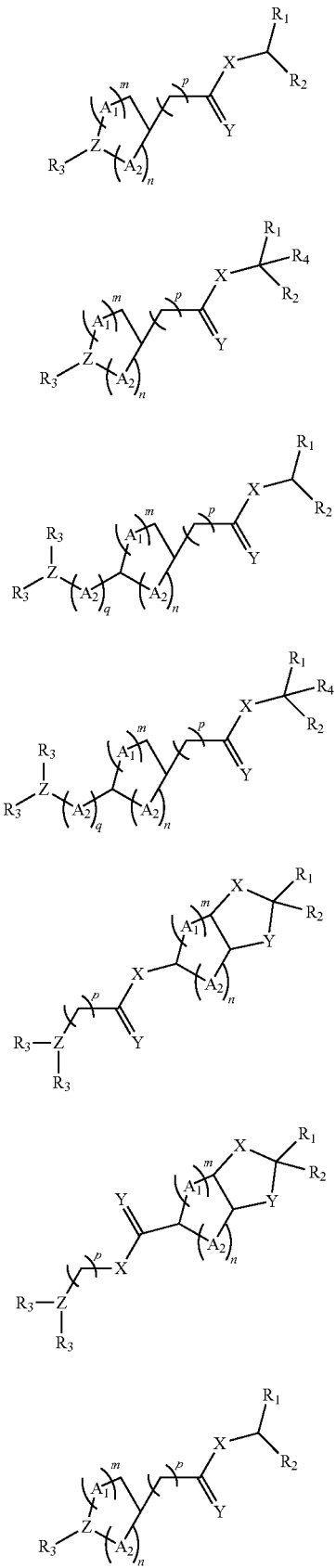

LX

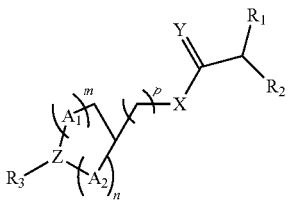

LXI

LXII

LXIII

LXIV

LXV

LXVI

LXVII

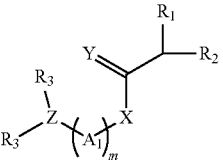

LXVIII

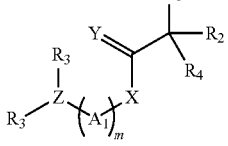

LXIX

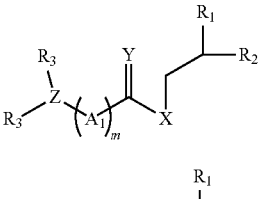

LXX

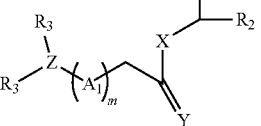

LXXI

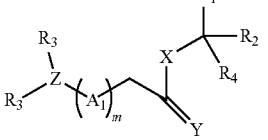

LXXII

LXXIII

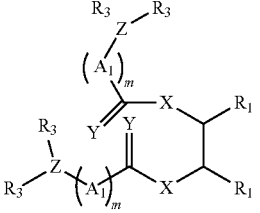

X=O, S, CH$_2$, N(Q$_3$) where Q is H, Me, Et, —(CH$_2$)$_r$—N(Q$_3$, Q$_4$), Y=O, S, CH$_2$, N(Q$_3$) where Q is H, Me, Et, —(CH$_2$)$_r$—N(Q$_3$, Q$_4$); Z=N, CH, C(Me), C(Et); Q$_1$=O or S; Q$_2$=O or S; A$_1$, A$_2$, =CH$_2$, CHF, CF$_2$; m, n, p and/or q is independently 0 to 5.

The present invention comprises of synthesis of cationic lipids of described above in racemic as well as in optically pure form.

R$_1$, R$_2$ and R$_4$ are each independently selected from the group consisting of alkyl groups having about 10 to 30 carbon atoms, wherein R$_1$, R$_2$ and R$_4$ independently comprises of: fully saturated alkyl chain, at least one double bond, at least one triple bond, at least one hetero atom, at least one CF$_2$, at least one CHF or at least one perfluoroalkylated chain. $CF_2$/CHF could be on the lipid anchor or on the core. $R_3$ is independently selected from the group consisting of: H and $C_1$-$C_{10}$ alkyls, $C_1$-$C_{10}$ alkenyls, $C_1$-$C_{10}$ alkynyls, alkylheterocycles, alkylphospates, alkylphosphorothioate, alkylphosphonates, alkylamines, hydroxyalkyls, ω-aminoalkyls, ω-(substituted)aminoalkyls, ω-phosphoalkyls, ω-thiophosphoalkyls, PEG with MW range from 100-40000, mPEG with MW range from 120-40000, heterocycles such as imidazoles, triazoles, pyridines, pyrimidines, purines, substituted pyridines, alkyl/PEG spacer containing receptor targeting ligands such as GalNAc, folic acid, mannose, Fucose, naproxen, ibuprofen and the ligands include small molecules that binds to chemokines, integrins, somatostatin, androgen and CNS receptors. $R_3$ also covers above ligands without spacer between the lipids core/anchor.

In one embodiment, the cationic lipid is chosen from a group consisting of lipids shown in Table 1 below.

TABLE 1

Some cationic lipids of the present invention.

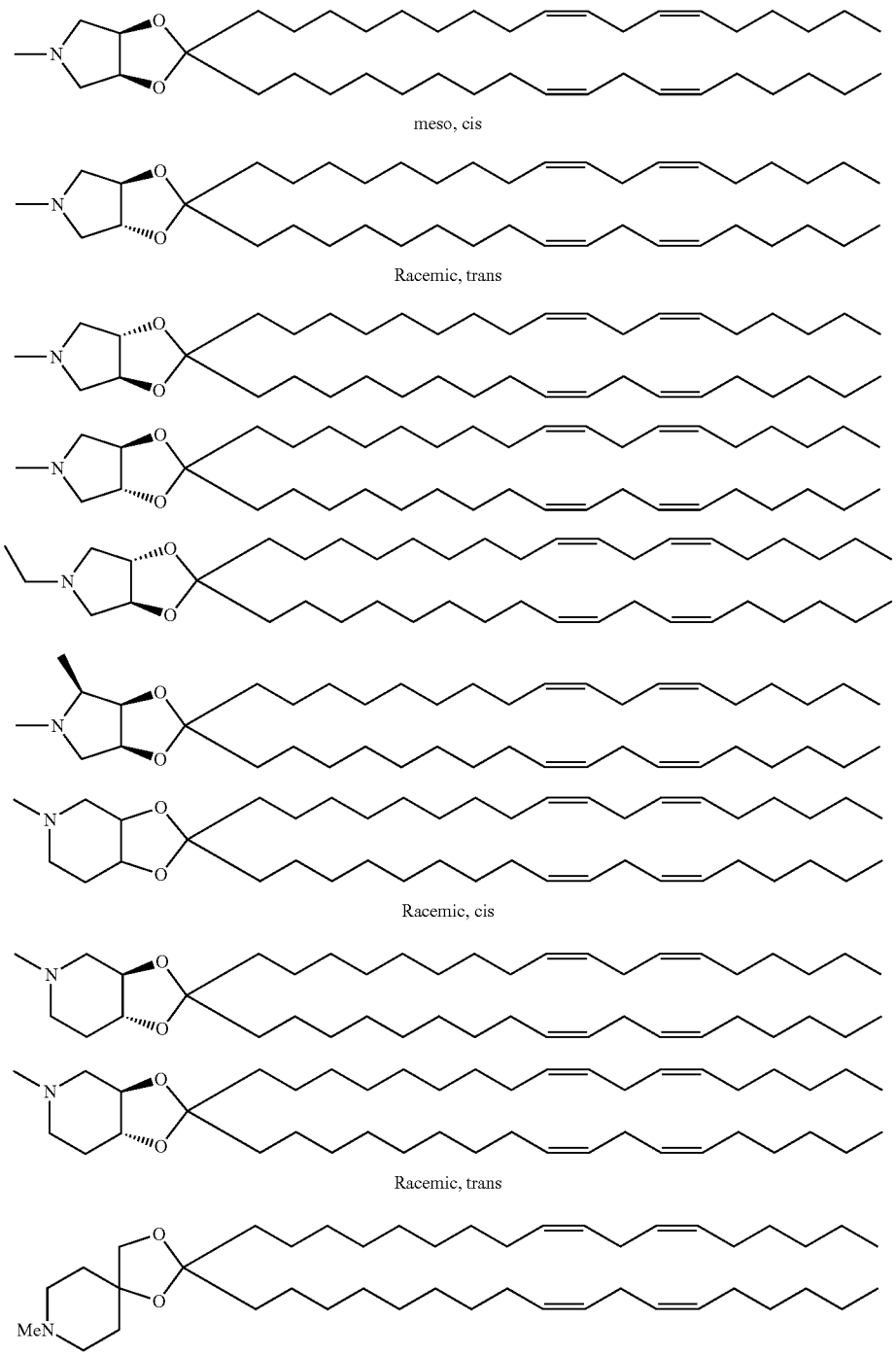

TABLE 1-continued
Some cationic lipids of the present invention.
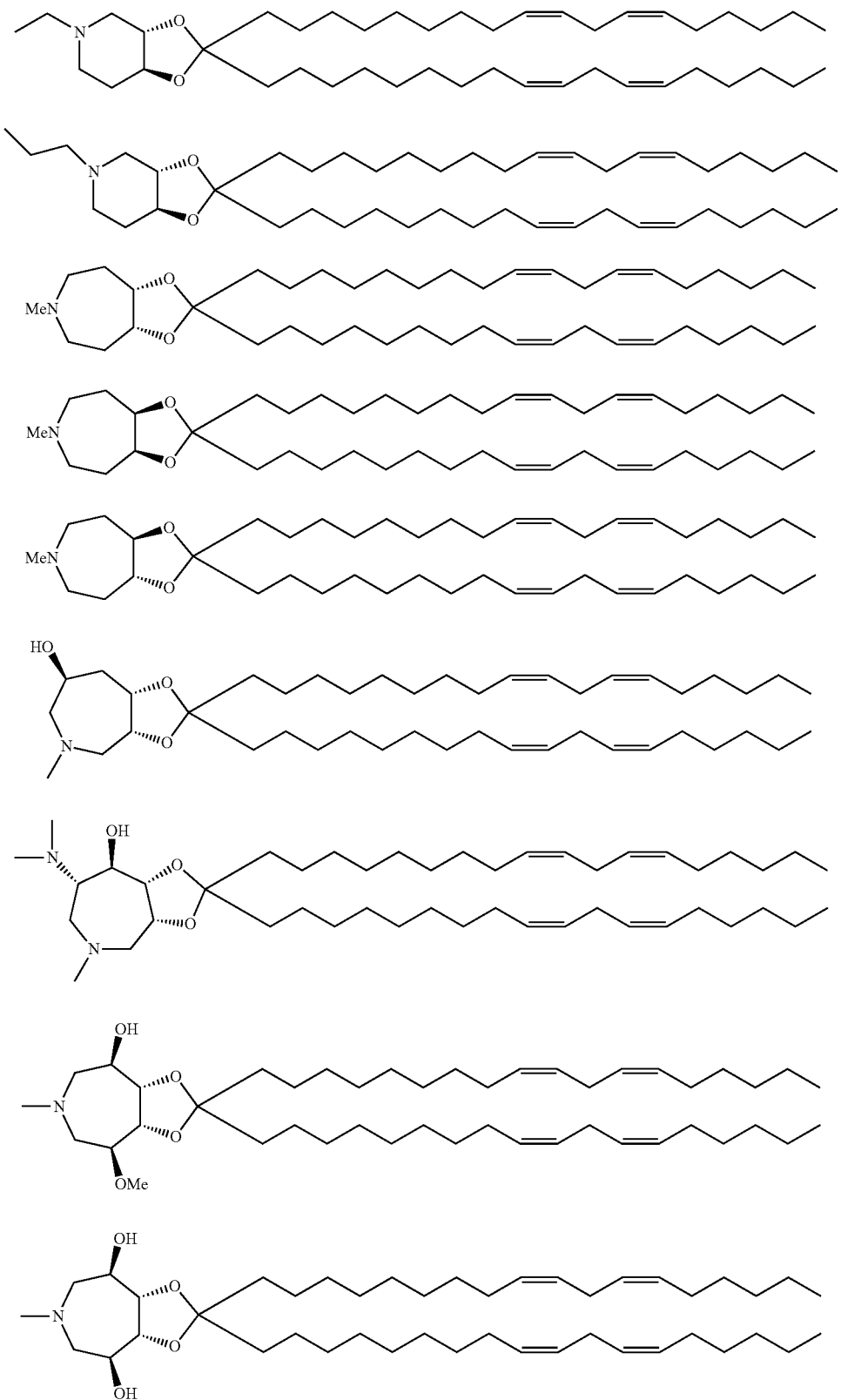

TABLE 1-continued
Some cationic lipids of the present invention.
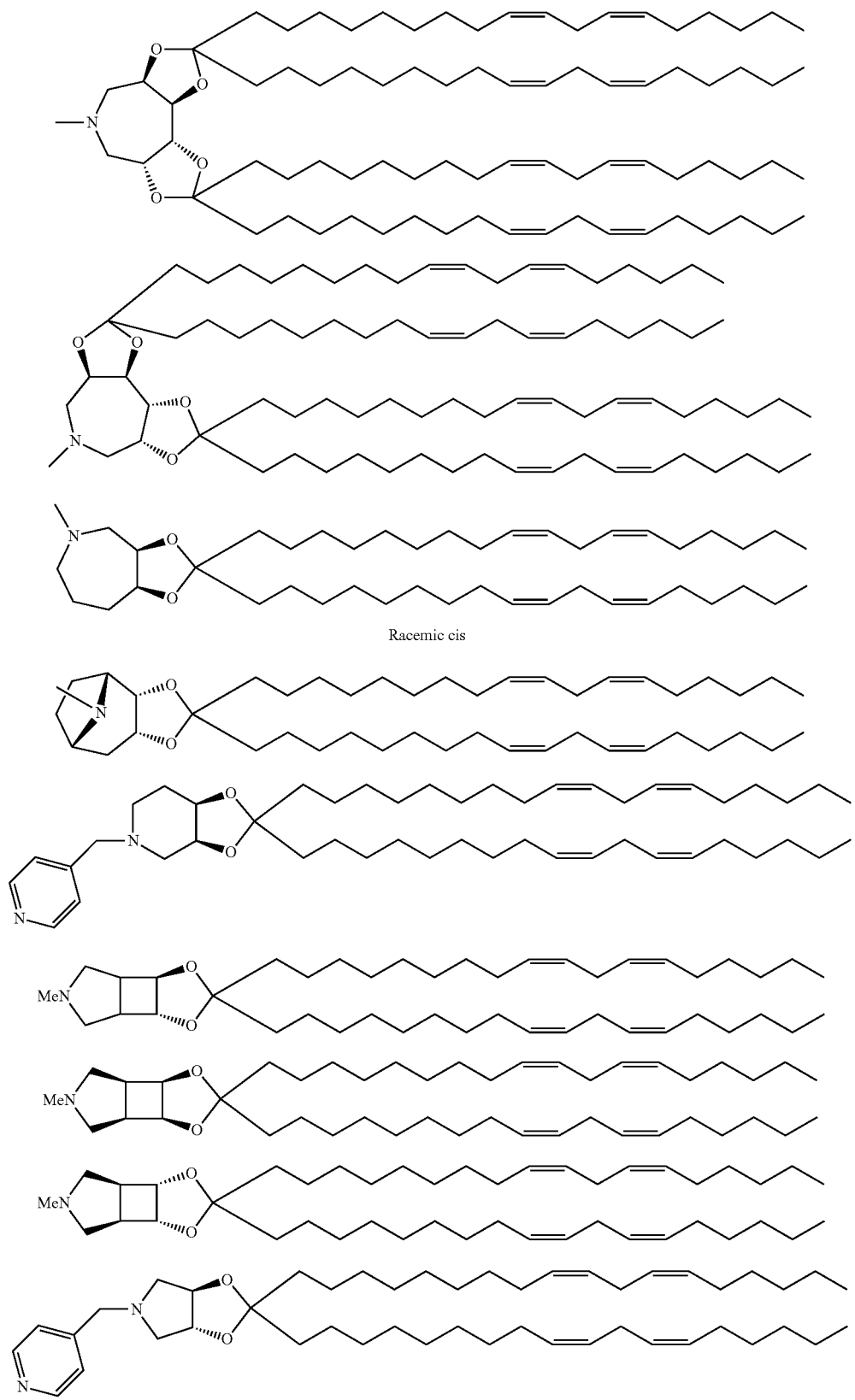
Racemic cis TABLE 1-continued
Some cationic lipids of the present invention.
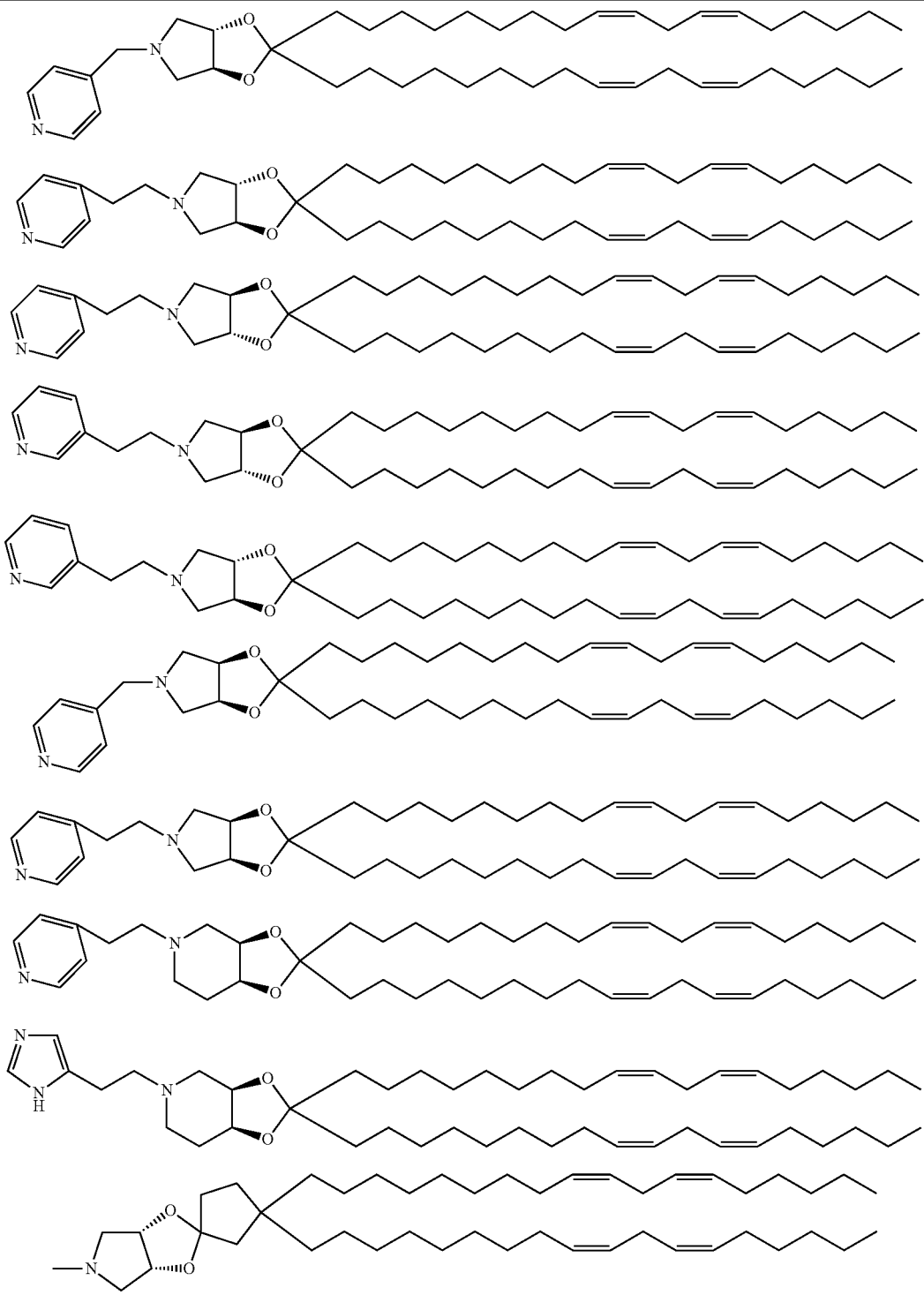
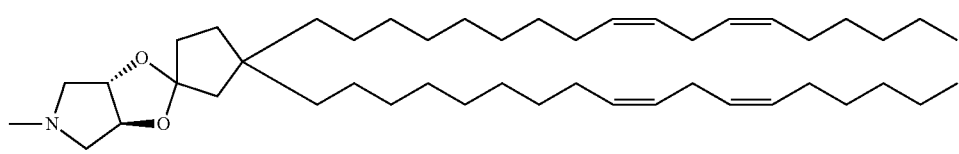 [SMILES: CCCCC/C=C\C/C=C\CCCCCCCCC1(CCCCCCCC/C=C\C/C=C\CCCCC)CCC2(C1)O[C@H]1CN(C)C[C@@H]1O2]
cis Racemic and optically pure TABLE 1-continued
Some cationic lipids of the present invention.
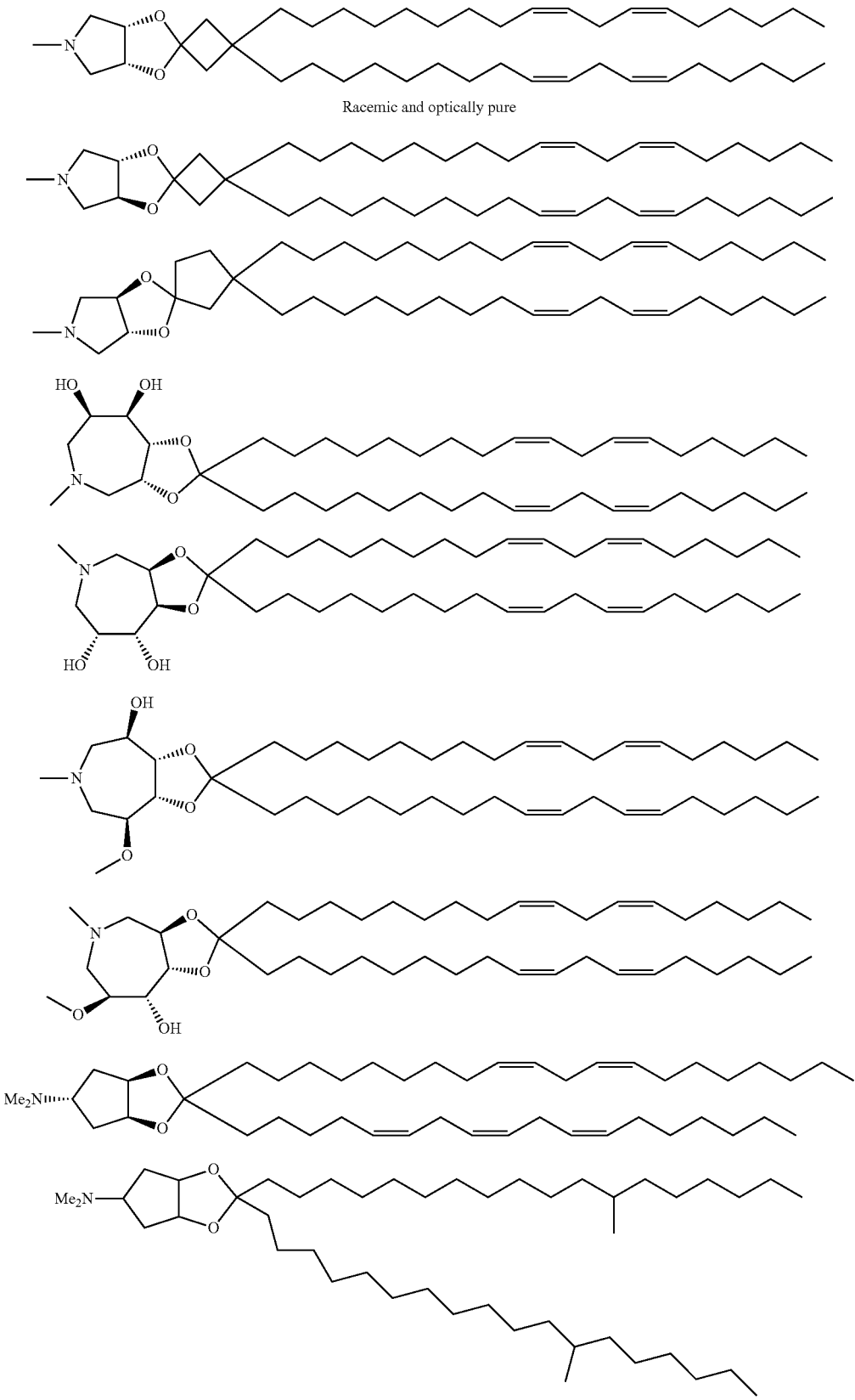
Racemic and optically pure TABLE 1-continued
Some cationic lipids of the present invention.
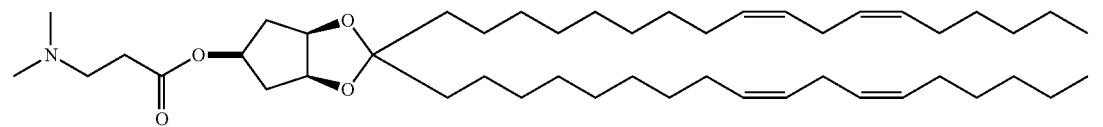 [SMILES: CCCCC/C=C\C/C=C\CCCCCCCCC1(CCCCCCCC/C=C\C/C=C\CCCCC)O[C@H]2C[C@@H](OC(=O)CCN(C)C)C[C@H]2O1]
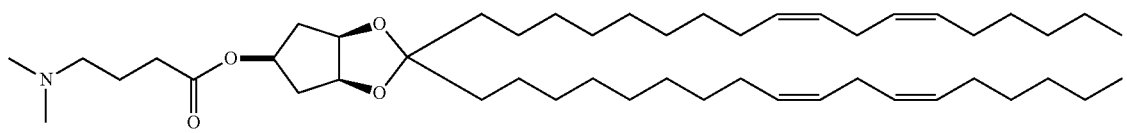 [SMILES: CCCCC/C=C\C/C=C\CCCCCCCCC1(CCCCCCCC/C=C\C/C=C\CCCCC)O[C@H]2C[C@@H](OC(=O)CCCN(C)C)C[C@H]2O1]
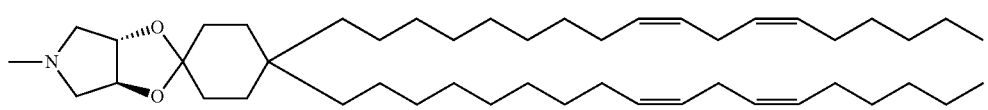
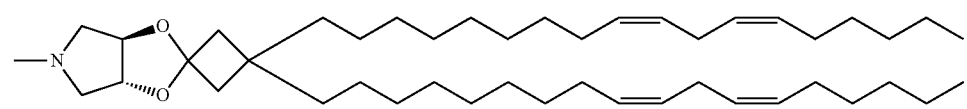 [SMILES: CCCCC/C=C\C/C=C\CCCCCCCCC1(CCCCCCCC/C=C\C/C=C\CCCCC)CC2(C1)O[C@@H]1CN(C)C[C@H]1O2]
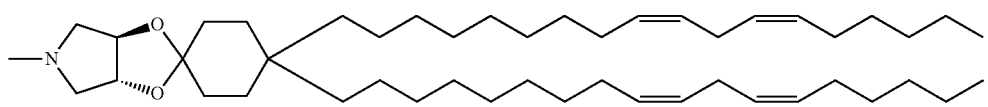 [SMILES: CCCCC/C=C\C/C=C\CCCCCCCCC1(CCCCCCCC/C=C\C/C=C\CCCCC)CCC2(CC1)O[C@@H]1CN(C)C[C@H]1O2]
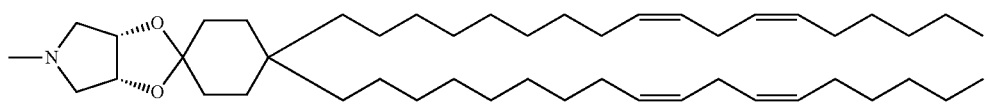
cis Racemic and optically pure
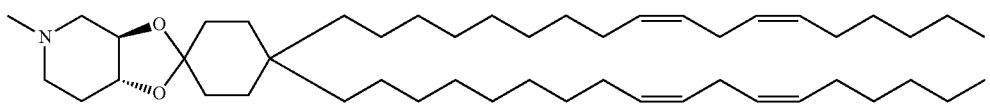
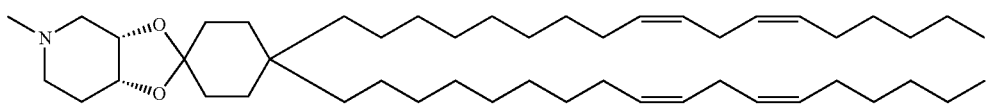
cis Racemic and optically pure
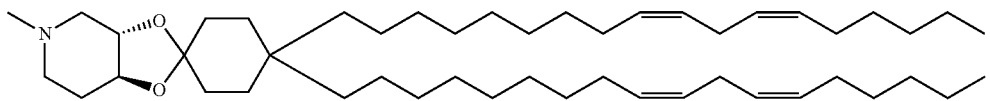 [SMILES: CCCCC/C=C\C/C=C\CCCCCCCCC1(CCCCCCCC/C=C\C/C=C\CCCCC)CCC2(CC1)O[C@H]1CCN(C)C[C@@H]1O2]
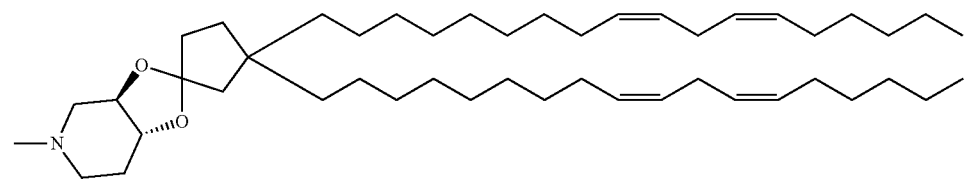
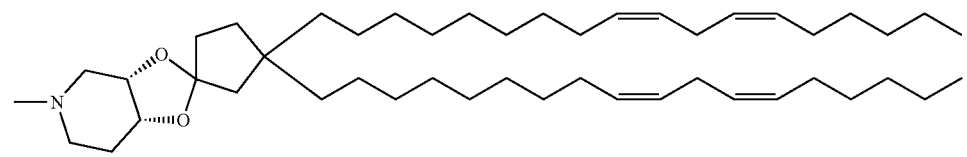
cis Racemic and optically pure TABLE 1-continued
Some cationic lipids of the present invention.
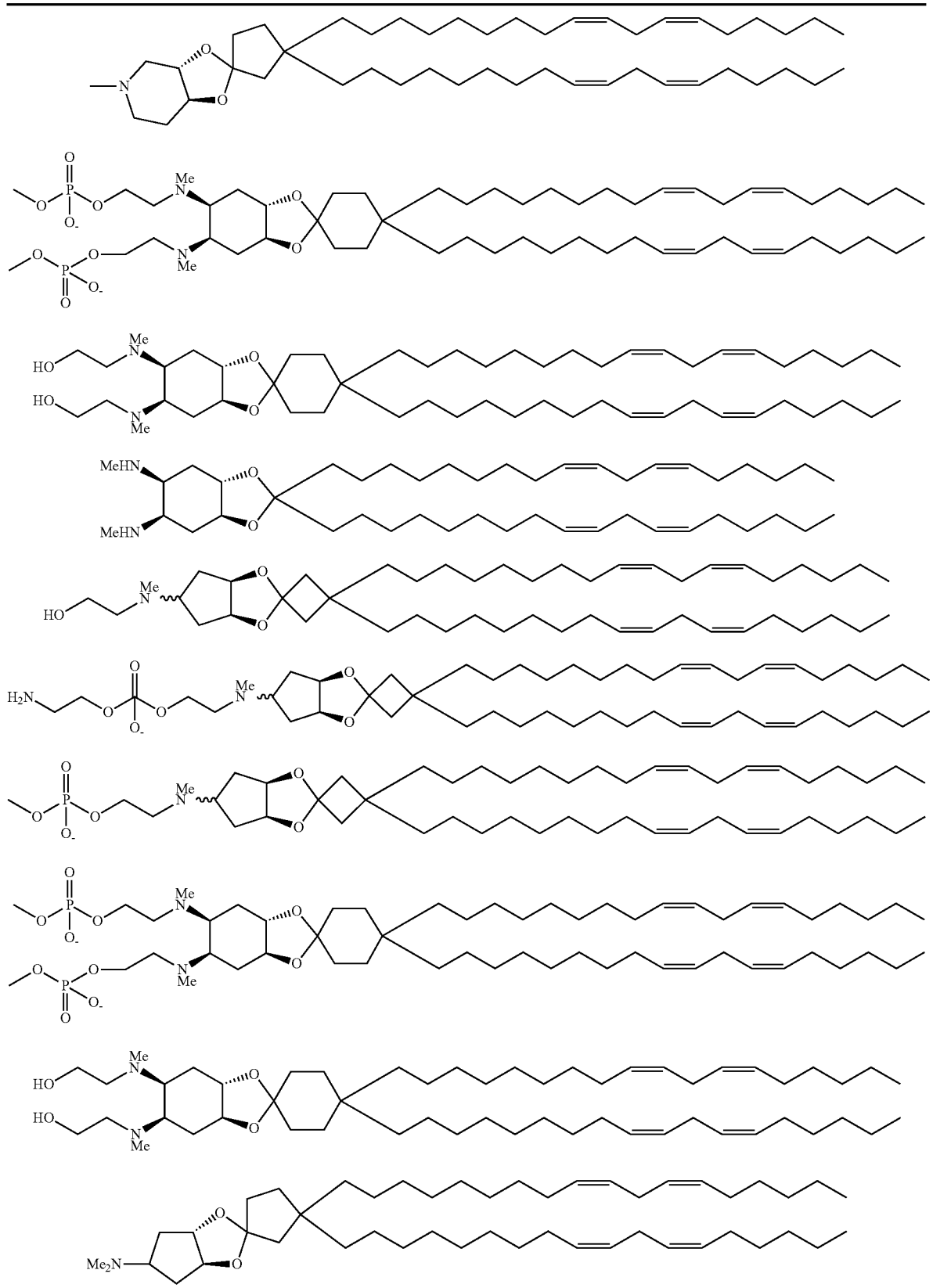

TABLE 1-continued
Some cationic lipids of the present invention.
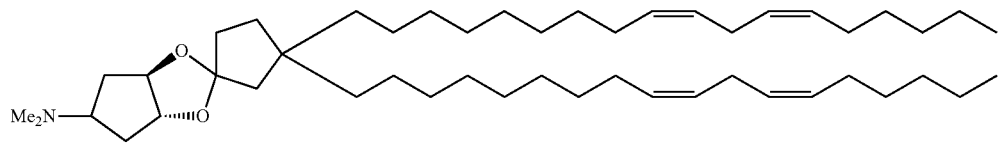 [SMILES: CCCCC/C=C\C/C=C\CCCCCCCCC1(CCCCCCCC/C=C\C/C=C\CCCCC)CCC2(C1)O[C@@H]1CC(N(C)C)C[C@H]1O2]
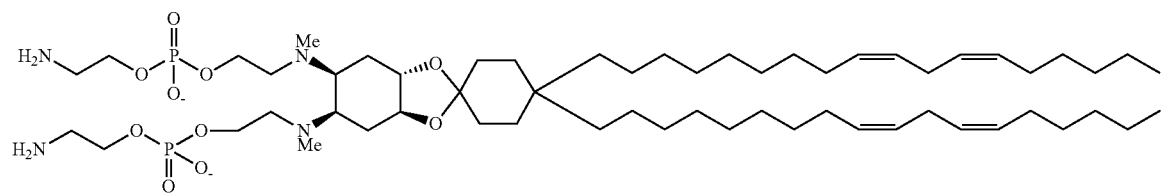
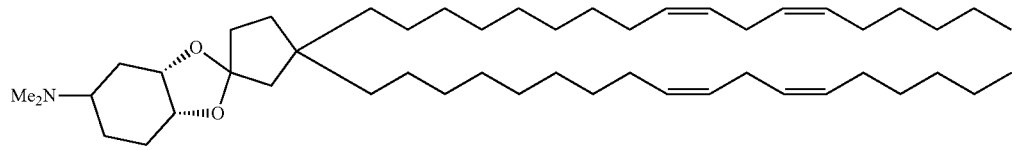
cis Racemic and optically pure
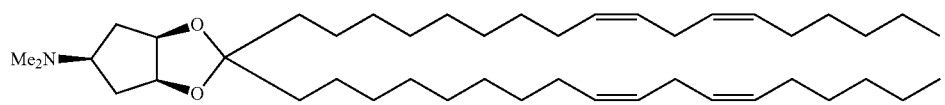
meso compound
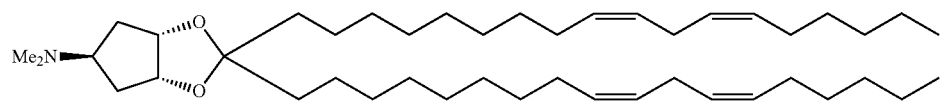
meso compound
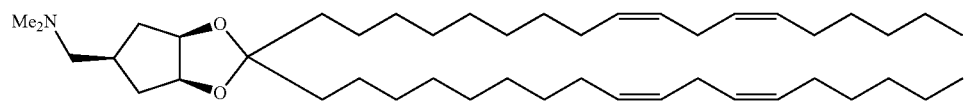 [SMILES: CCCCC/C=C\C/C=C\CCCCCCCCC1(CCCCCCCC/C=C\C/C=C\CCCCC)O[C@H]2C[C@@H](CN(C)C)C[C@H]2O1]
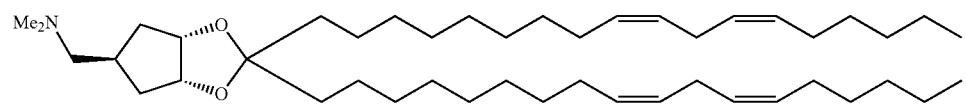 [SMILES: CCCCC/C=C\C/C=C\CCCCCCCCC1(CCCCCCCC/C=C\C/C=C\CCCCC)O[C@H]2C[C@H](CN(C)C)C[C@H]2O1]
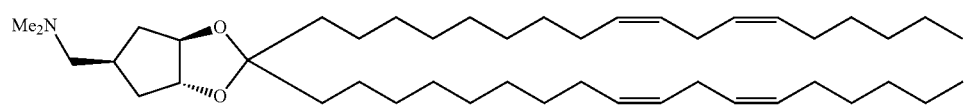
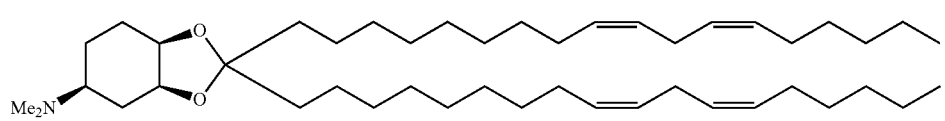
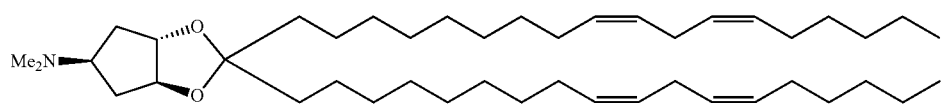
racemic compound TABLE 1-continued
Some cationic lipids of the present invention.
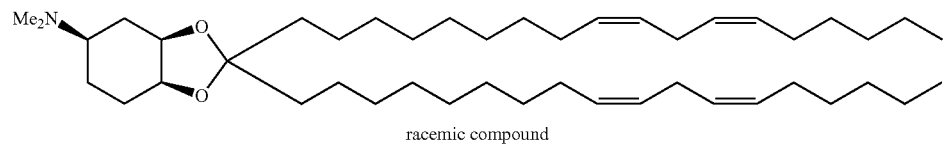 [SMILES: CCCCC/C=C\C/C=C\CCCCCCCCC1(CCCCCCCC/C=C\C/C=C\CCCCC)O[C@H]2CC[C@@H](N(C)C)C[C@H]2O1]
racemic compound
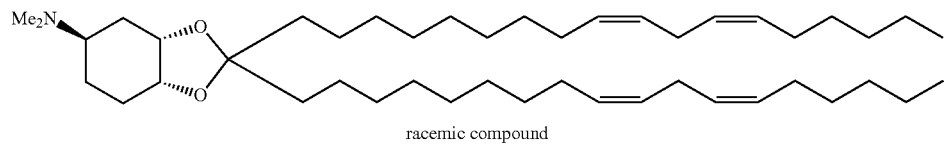 [SMILES: CCCCC/C=C\C/C=C\CCCCCCCCC1(CCCCCCCC/C=C\C/C=C\CCCCC)O[C@H]2C[C@H](N(C)C)CC[C@H]2O1]
racemic compound
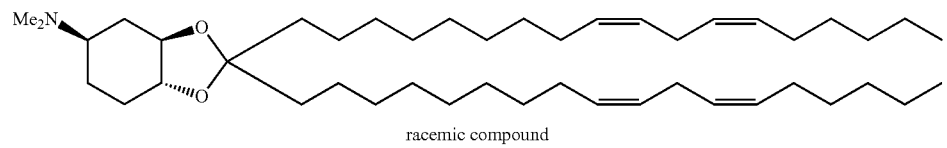 [SMILES: CCCCC/C=C\C/C=C\CCCCCCCCC1(CCCCCCCC/C=C\C/C=C\CCCCC)O[C@@H]2CC[C@@H](N(C)C)C[C@H]2O1]
racemic compound
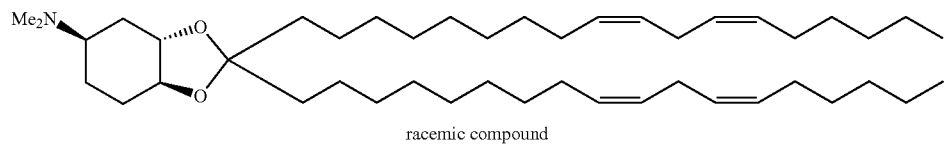 [SMILES: CCCCC/C=C\C/C=C\CCCCCCCCC1(CCCCCCCC/C=C\C/C=C\CCCCC)O[C@H]2CC[C@@H](N(C)C)C[C@@H]2O1]
racemic compound
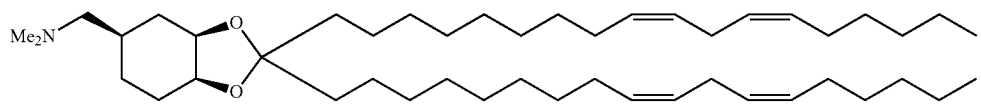 [SMILES: CCCCC/C=C\C/C=C\CCCCCCCCC1(CCCCCCCC/C=C\C/C=C\CCCCC)O[C@H]2CC[C@@H](CN(C)C)C[C@H]2O1]
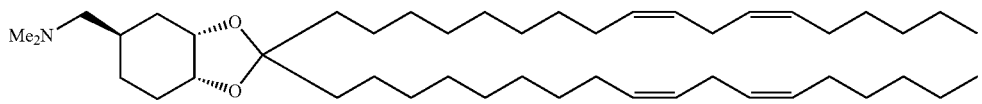 [SMILES: CCCCC/C=C\C/C=C\CCCCCCCCC1(CCCCCCCC/C=C\C/C=C\CCCCC)O[C@H]2C[C@H](CN(C)C)CC[C@H]2O1]
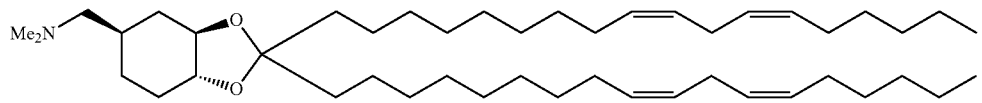 [SMILES: CCCCC/C=C\C/C=C\CCCCCCCCC1(CCCCCCCC/C=C\C/C=C\CCCCC)O[C@@H]2CC[C@@H](CN(C)C)C[C@H]2O1]
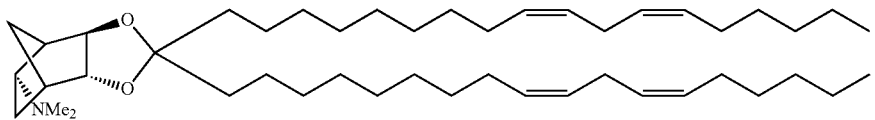 [SMILES: CCCCC/C=C\C/C=C\CCCCCCCCC1(CCCCCCCC/C=C\C/C=C\CCCCC)O[C@@H]2C3CC([C@H]2O1)[C@@H](N(C)C)C3]
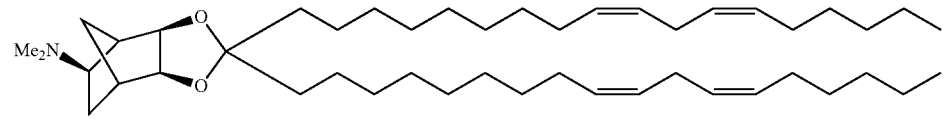 [SMILES: CCCCC/C=C\C/C=C\CCCCCCCCC1(CCCCCCCC/C=C\C/C=C\CCCCC)O[C@@H]2C3CC(C[C@H]3N(C)C)[C@@H]2O1]
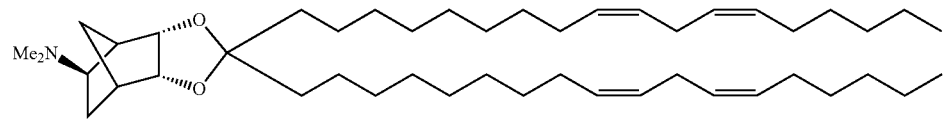 [SMILES: CCCCC/C=C\C/C=C\CCCCCCCCC1(CCCCCCCC/C=C\C/C=C\CCCCC)O[C@@H]2C3CC([C@H](N(C)C)C3)[C@@H]2O1]
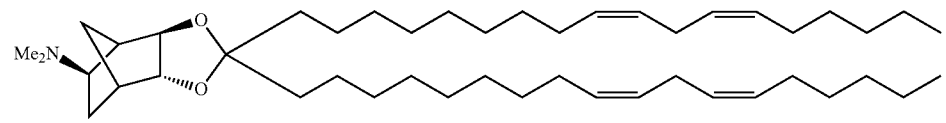

TABLE 1-continued
Some cationic lipids of the present invention.
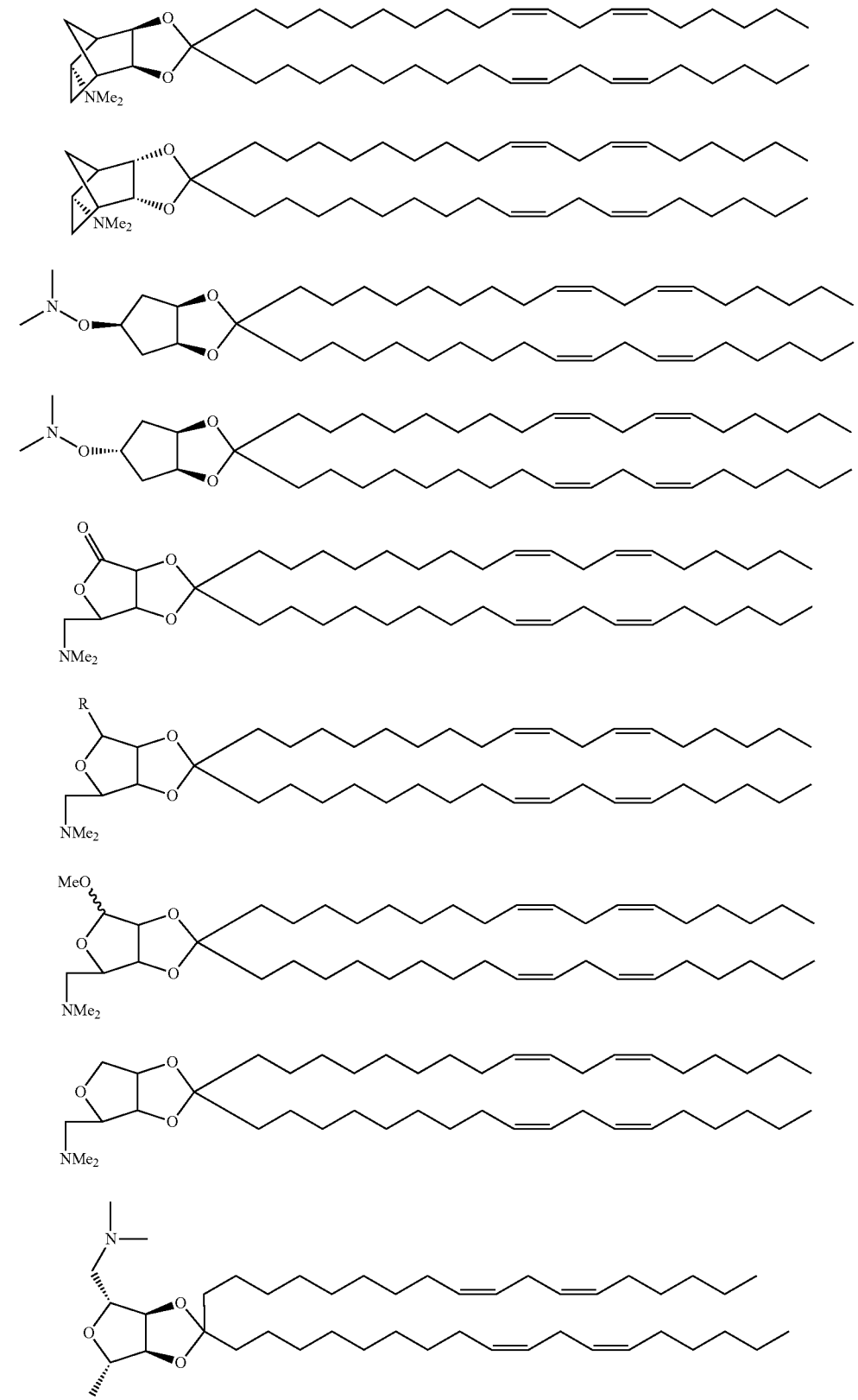

TABLE 1-continued
Some cationic lipids of the present invention.
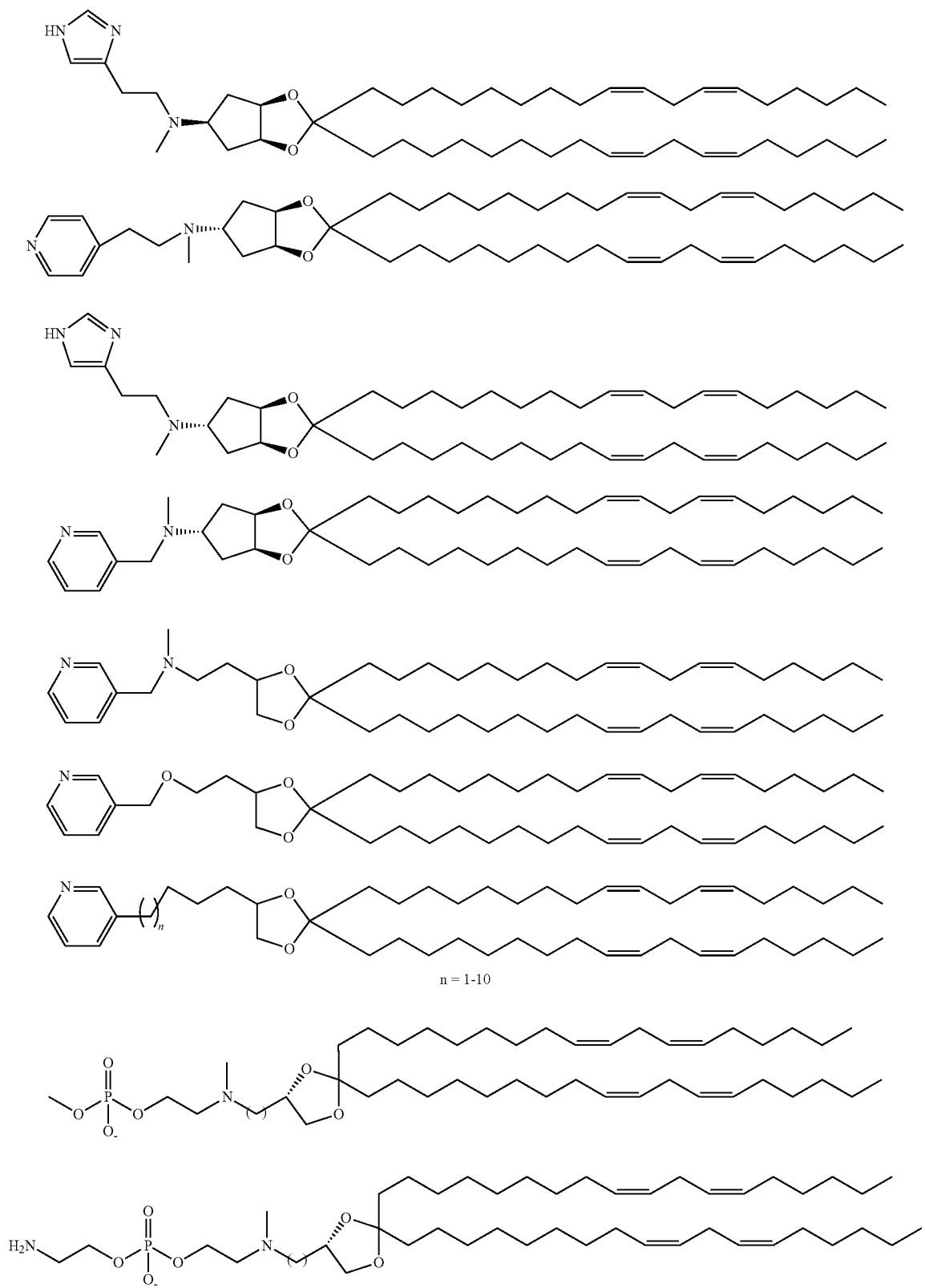

TABLE 1-continued
Some cationic lipids of the present invention.
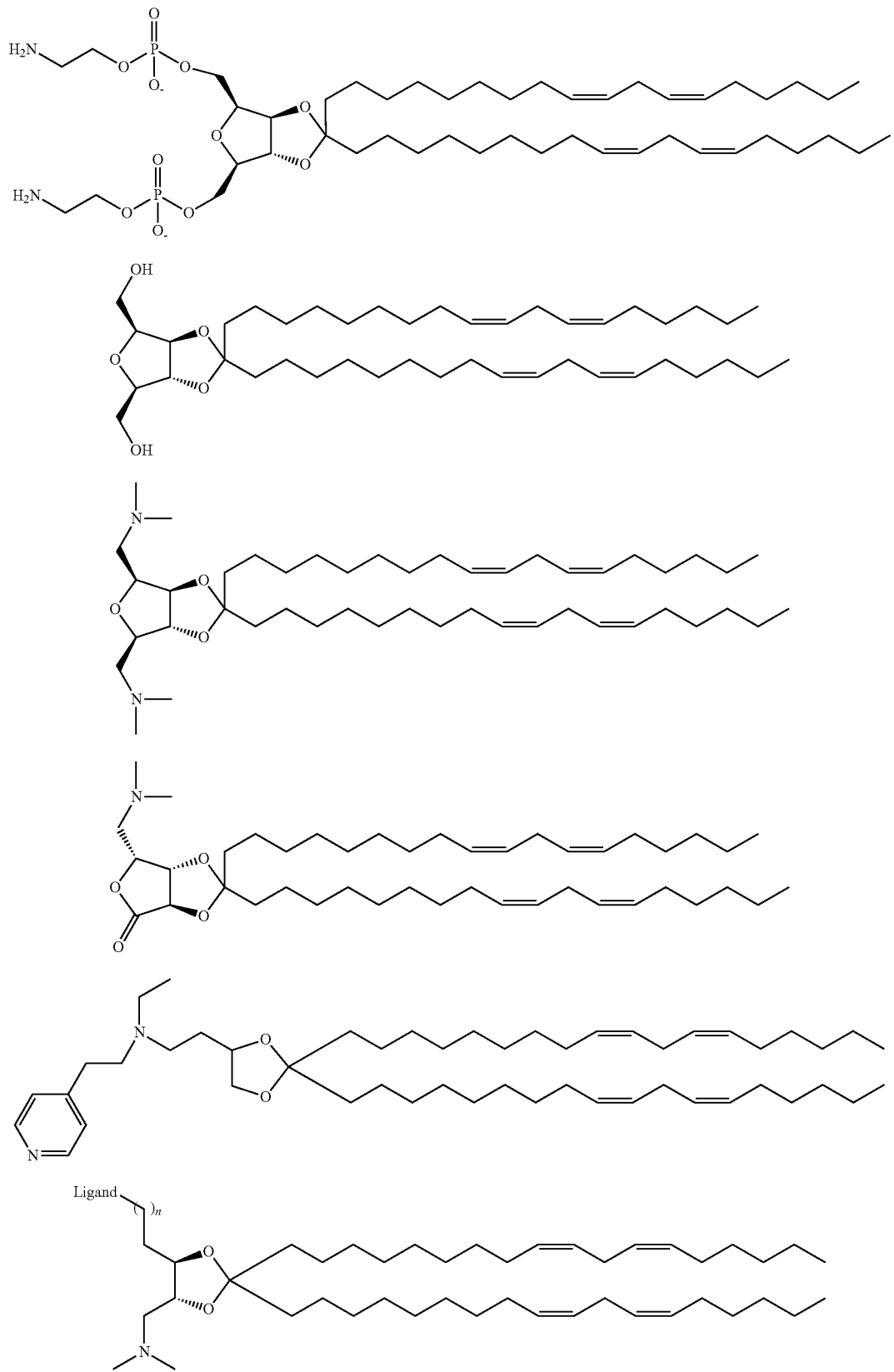

TABLE 1-continued
Some cationic lipids of the present invention.
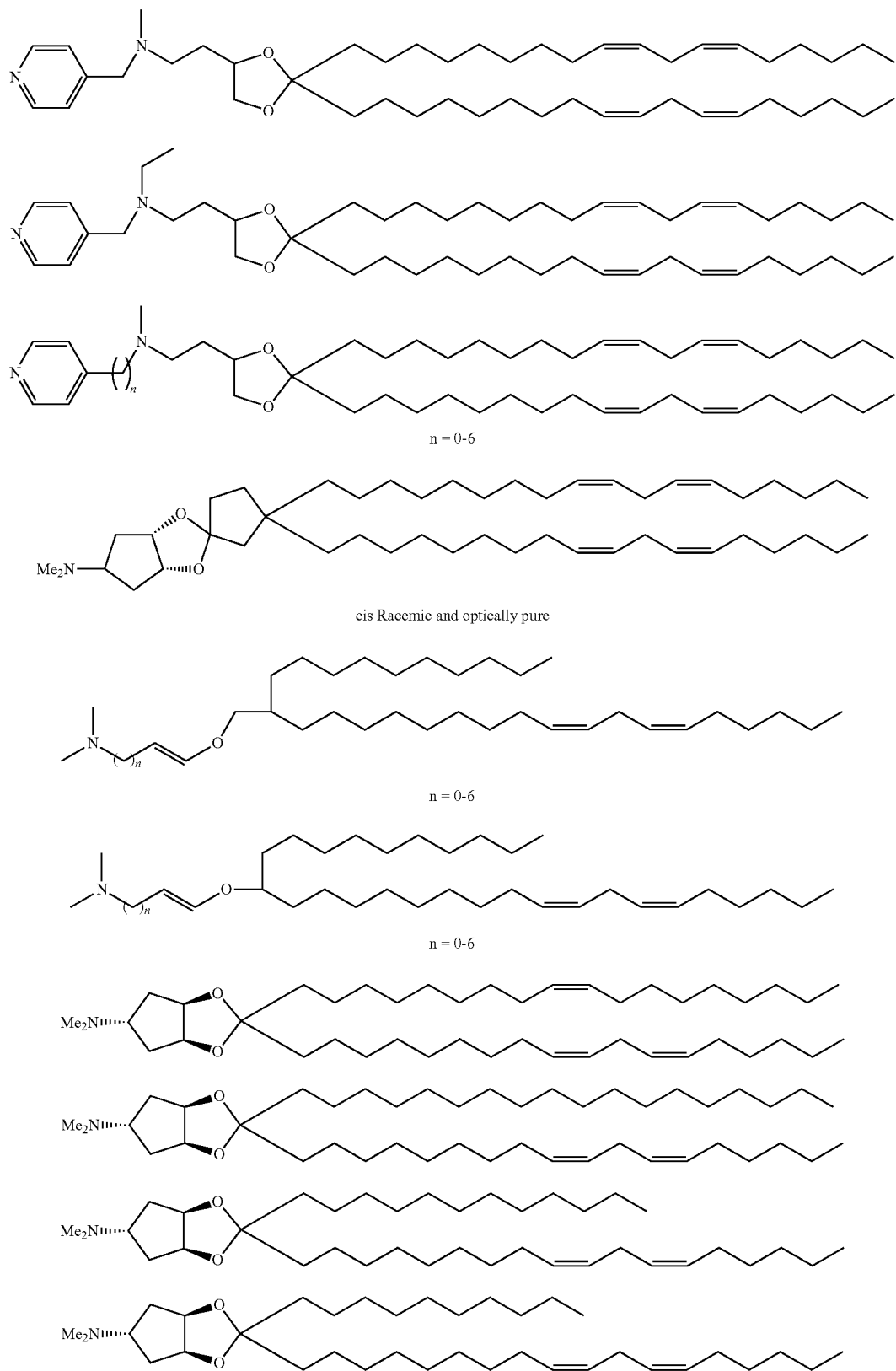
n = 0-6
cis Racemic and optically pure
n = 0-6
n = 0-6

TABLE 1-continued
Some cationic lipids of the present invention.
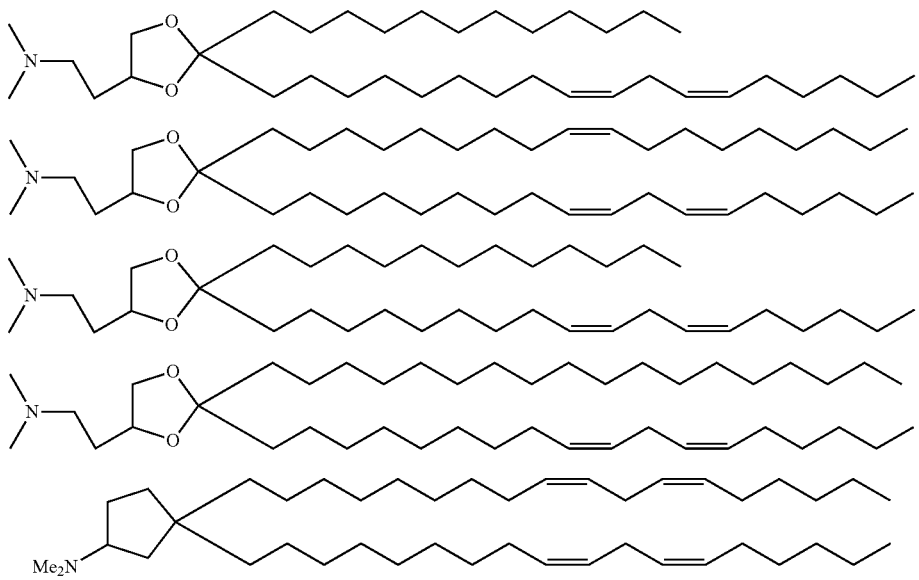
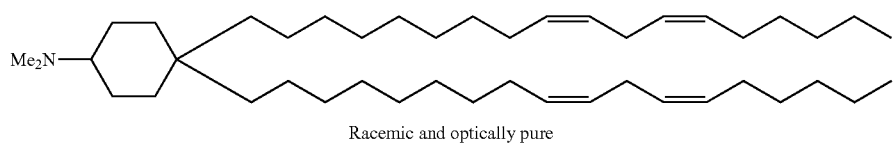 [SMILES: CCCCC/C=C\C/C=C\CCCCCCCCC1(CCCCCCCC/C=C\C/C=C\CCCCC)CCC(N(C)C)CC1]
Racemic and optically pure
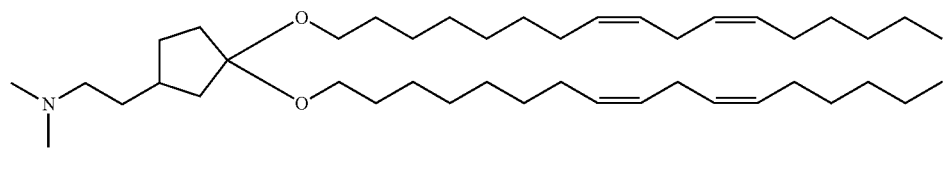 [SMILES: CCCCC/C=C\C/C=C\CCCCCCCOC1(OCCCCCCC/C=C\C/C=C\CCCCC)CCC(CCN(C)C)C1]
Racemic and optically pure
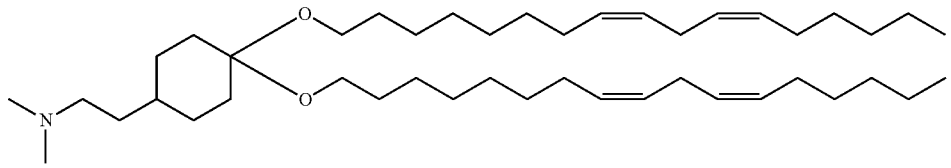 [SMILES: CCCCC/C=C\C/C=C\CCCCCCCOC1(OCCCCCCC/C=C\C/C=C\CCCCC)CCC(CCN(C)C)CC1]
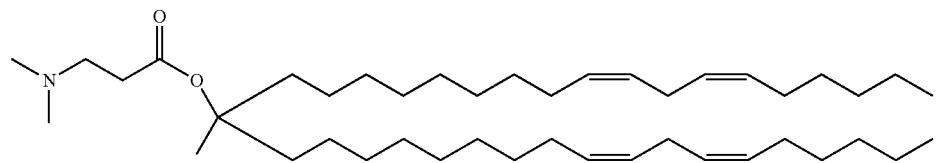 [SMILES: CCCCC/C=C\C/C=C\CCCCCCCCC(C)(CCCCCCCC/C=C\C/C=C\CCCCC)OC(=O)CCN(C)C]
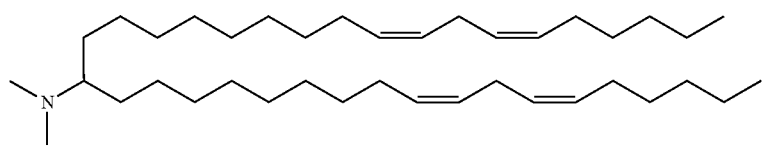
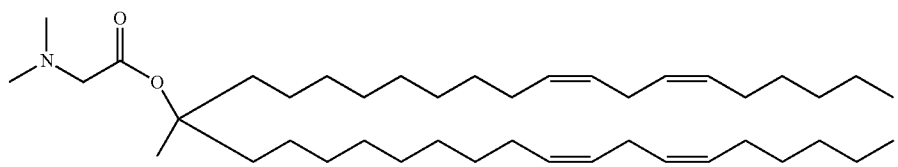 [SMILES: CCCCC/C=C\C/C=C\CCCCCCCCC(C)(CCCCCCCC/C=C\C/C=C\CCCCC)OC(=O)CN(C)C]

TABLE 1-continued
Some cationic lipids of the present invention.
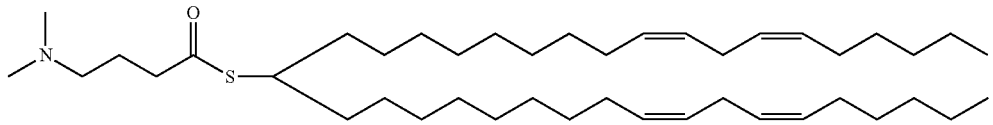
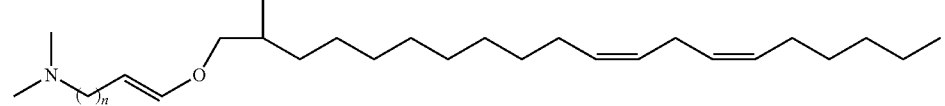
n = 0-6
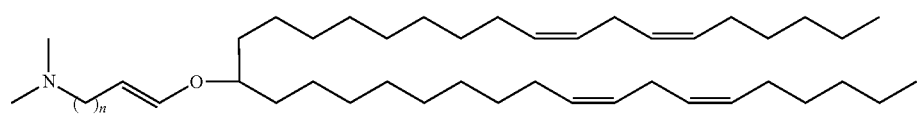
n = 0-6
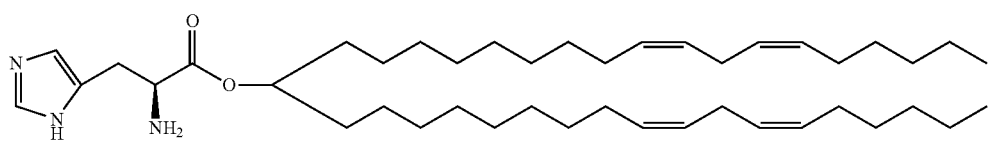 [SMILES: CCCCC/C=C\C/C=C\CCCCCCCCC(CCCCCCCC/C=C\C/C=C\CCCCC)OC(=O)[C@@H](N)Cc1cnc[nH]1]
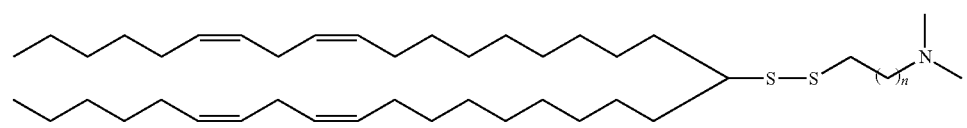
n = 0-6
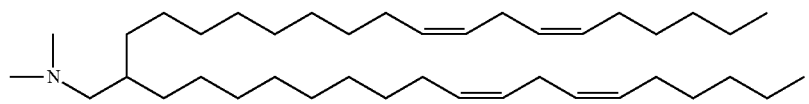
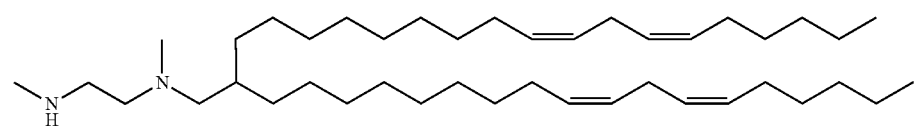 [SMILES: CCCCC/C=C\C/C=C\CCCCCCCCC(CCCCCCCC/C=C\C/C=C\CCCCC)CN(C)CCNC]
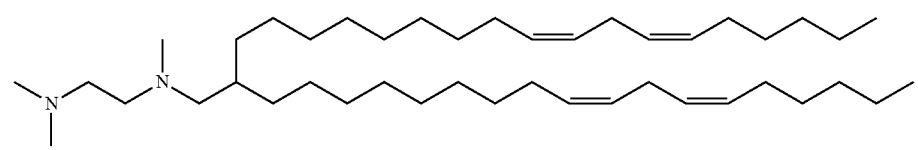
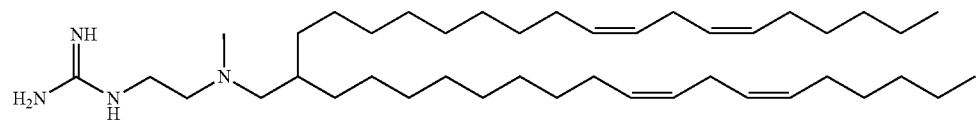 [SMILES: CCCCC/C=C\C/C=C\CCCCCCCCC(CCCCCCCC/C=C\C/C=C\CCCCC)CN(C)CCNC(=N)N]
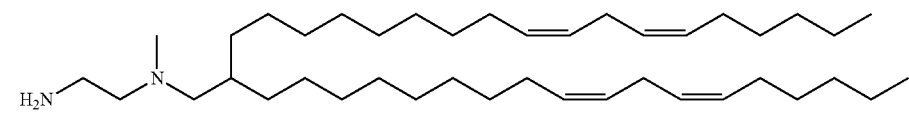

TABLE 1-continued
Some cationic lipids of the present invention.
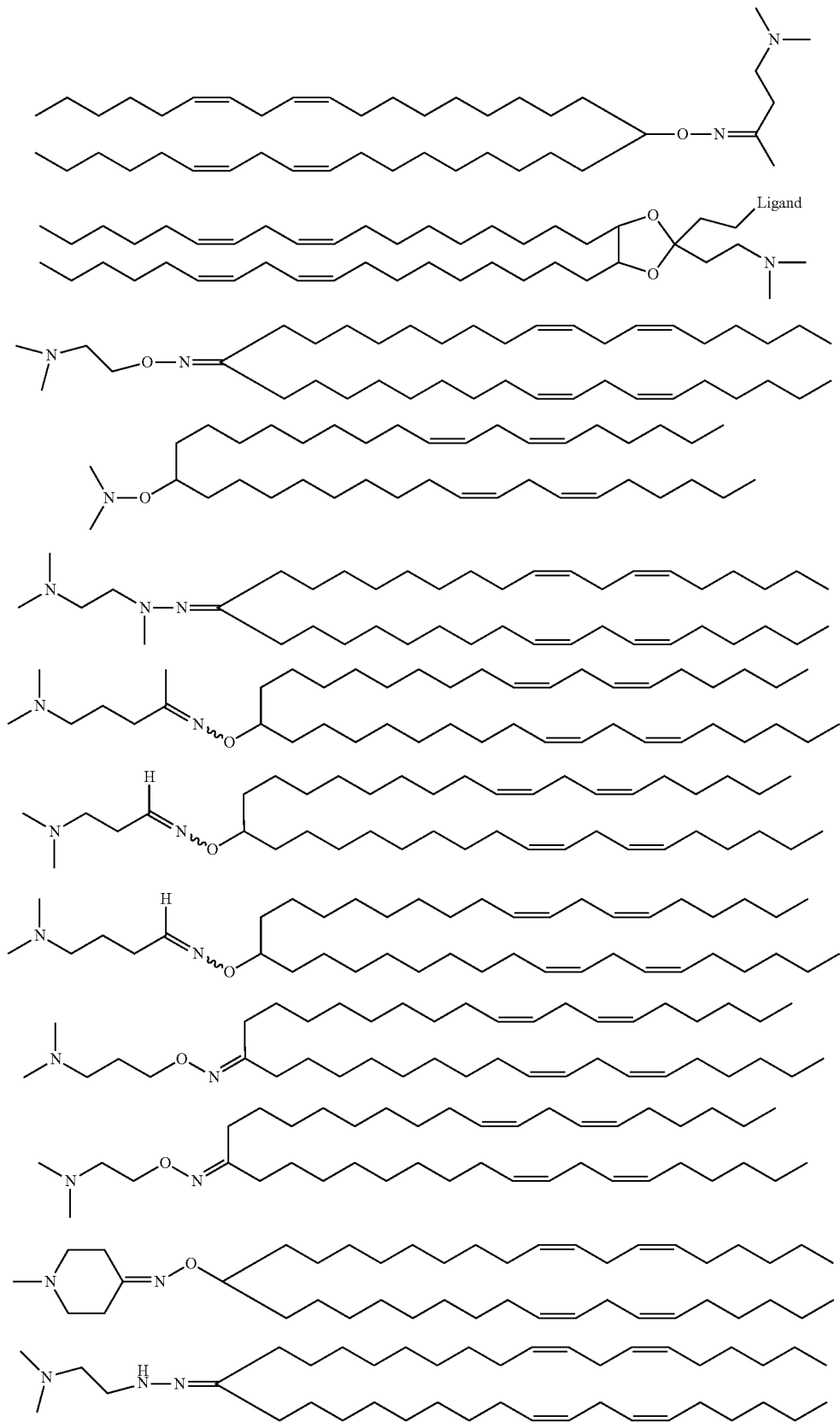

TABLE 1-continued
Some cationic lipids of the present invention.
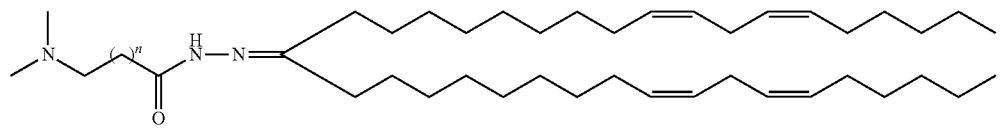
n = 0-6
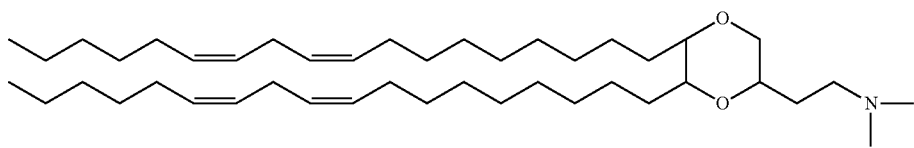 [SMILES: CCCCC/C=C\C/C=C\CCCCCCCCC1OCC(CCN(C)C)OC1CCCCCCCC/C=C\C/C=C\CCCCC]
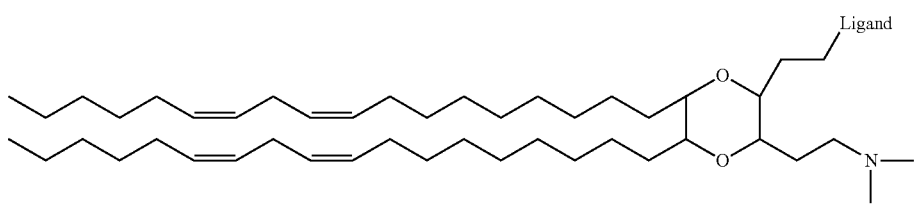
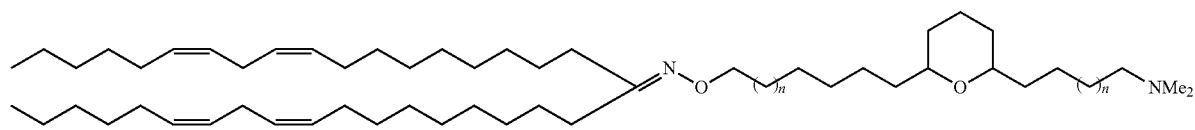
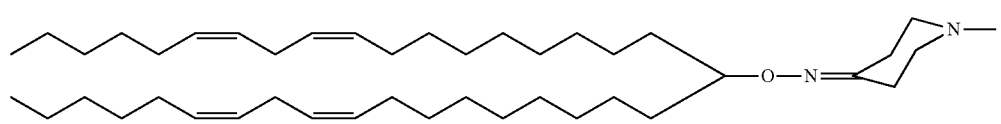 [SMILES: CCCCC/C=C\C/C=C\CCCCCCCCC(CCCCCCCC/C=C\C/C=C\CCCCC)ON=C1CCN(C)CC1]
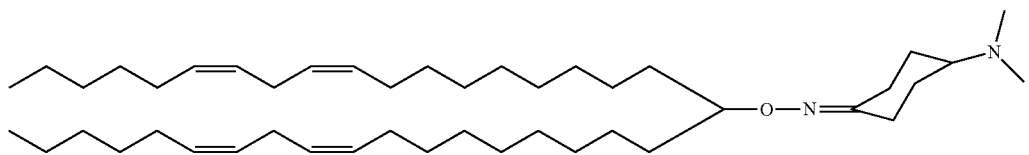 [SMILES: CCCCC/C=C\C/C=C\CCCCCCCCC(CCCCCCCC/C=C\C/C=C\CCCCC)ON=C1CCC(N(C)C)CC1]
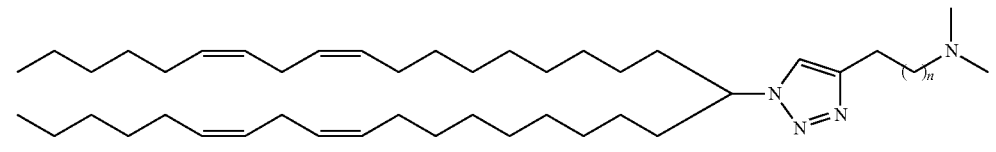
n = 0-6
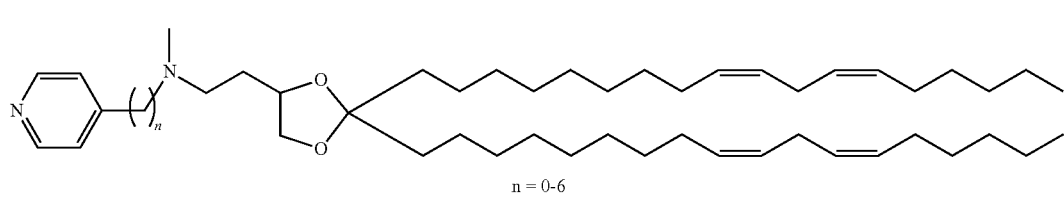
n = 0-6
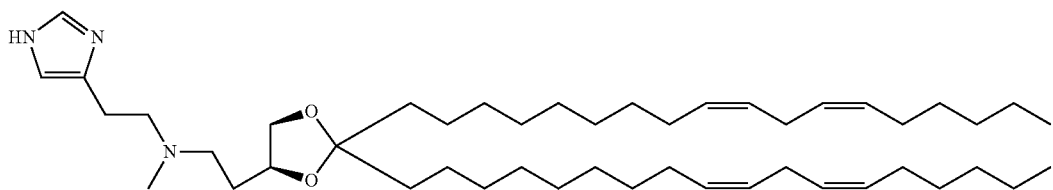

TABLE 1-continued
Some cationic lipids of the present invention.
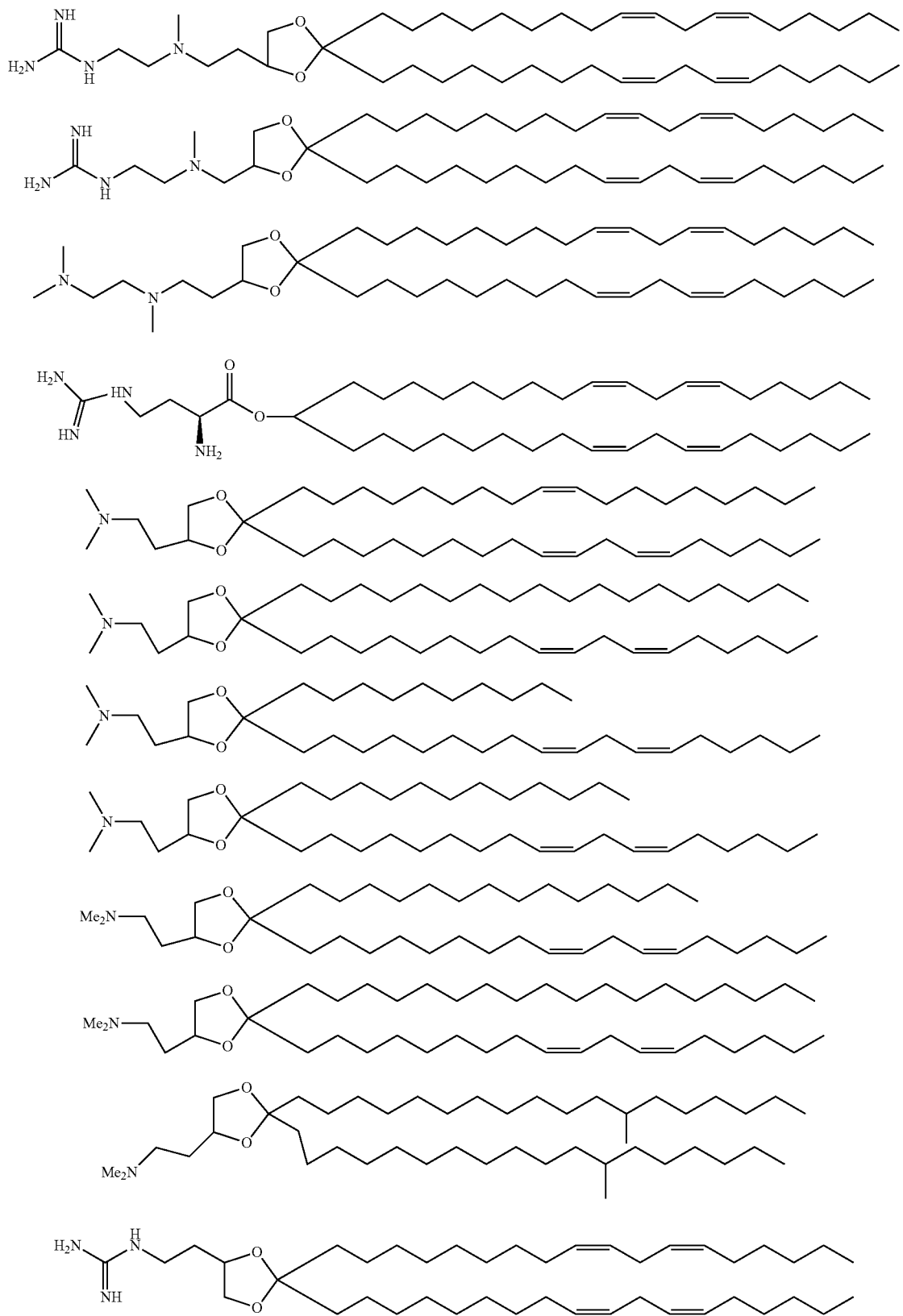

TABLE 1-continued
Some cationic lipids of the present invention.
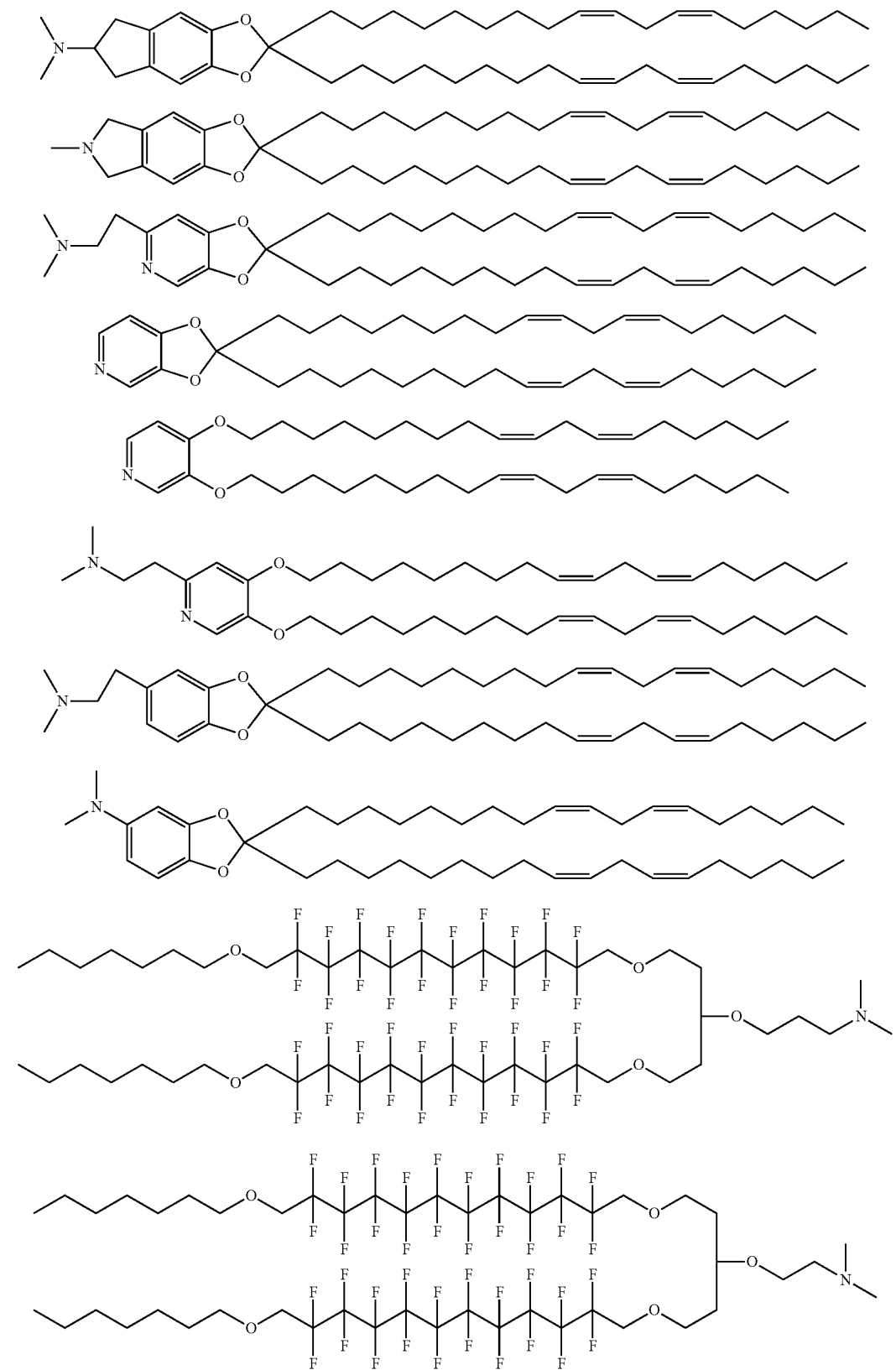

US 9,220,683 B2
TABLE 1-continued
Some cationic lipids of the present invention.
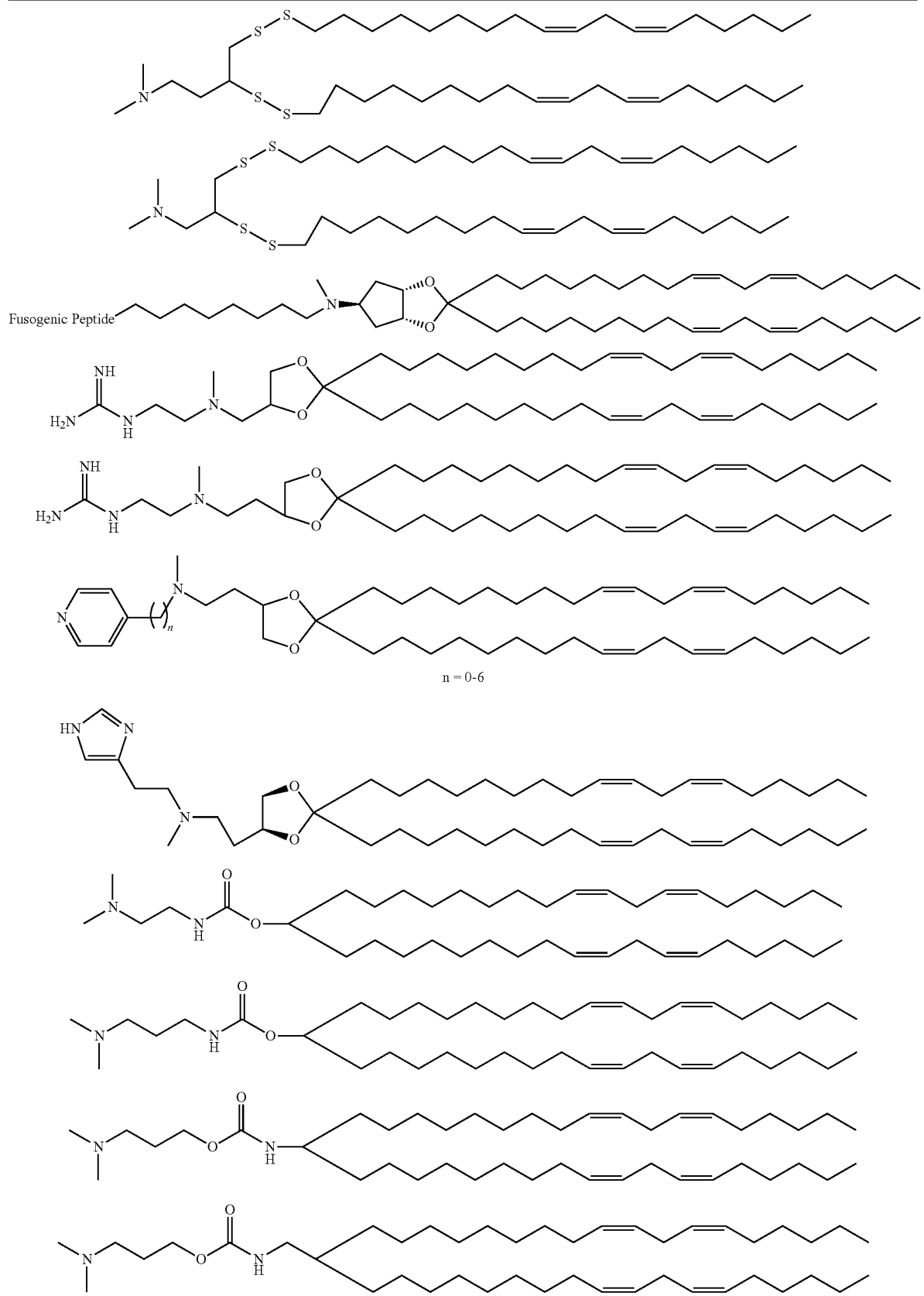

TABLE 1-continued
Some cationic lipids of the present invention.
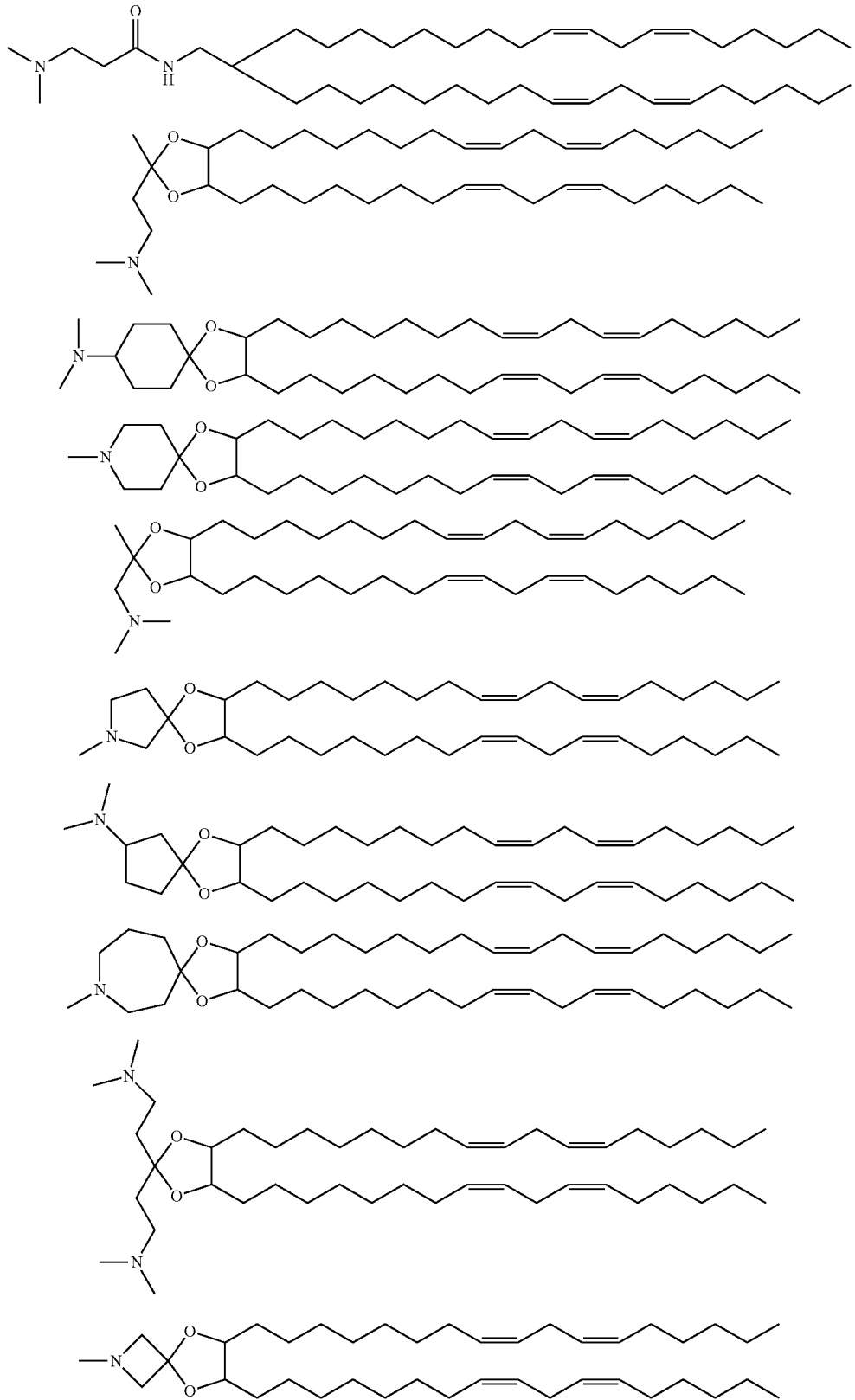

TABLE 1-continued
Some cationic lipids of the present invention.
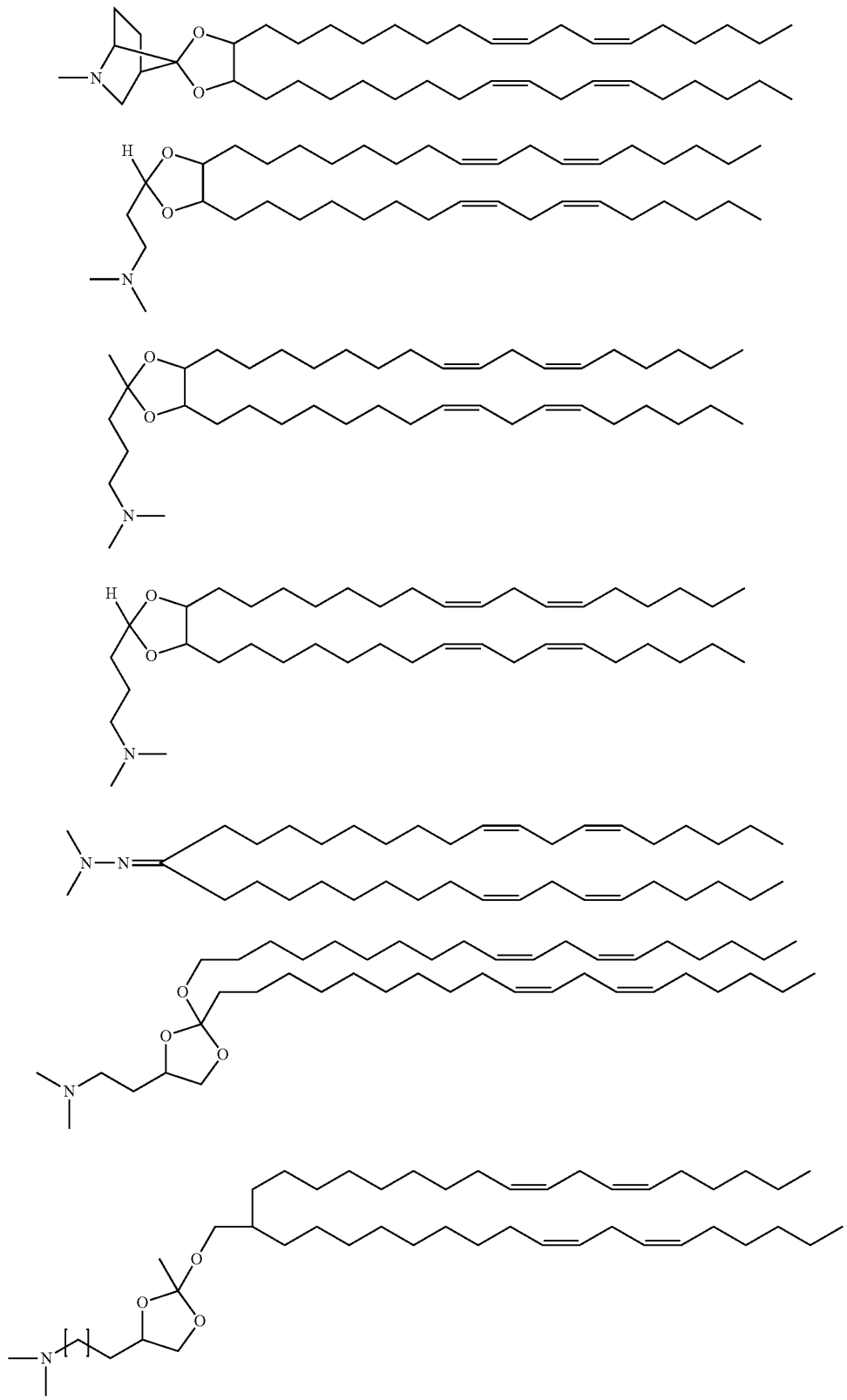

TABLE 1-continued
Some cationic lipids of the present invention.
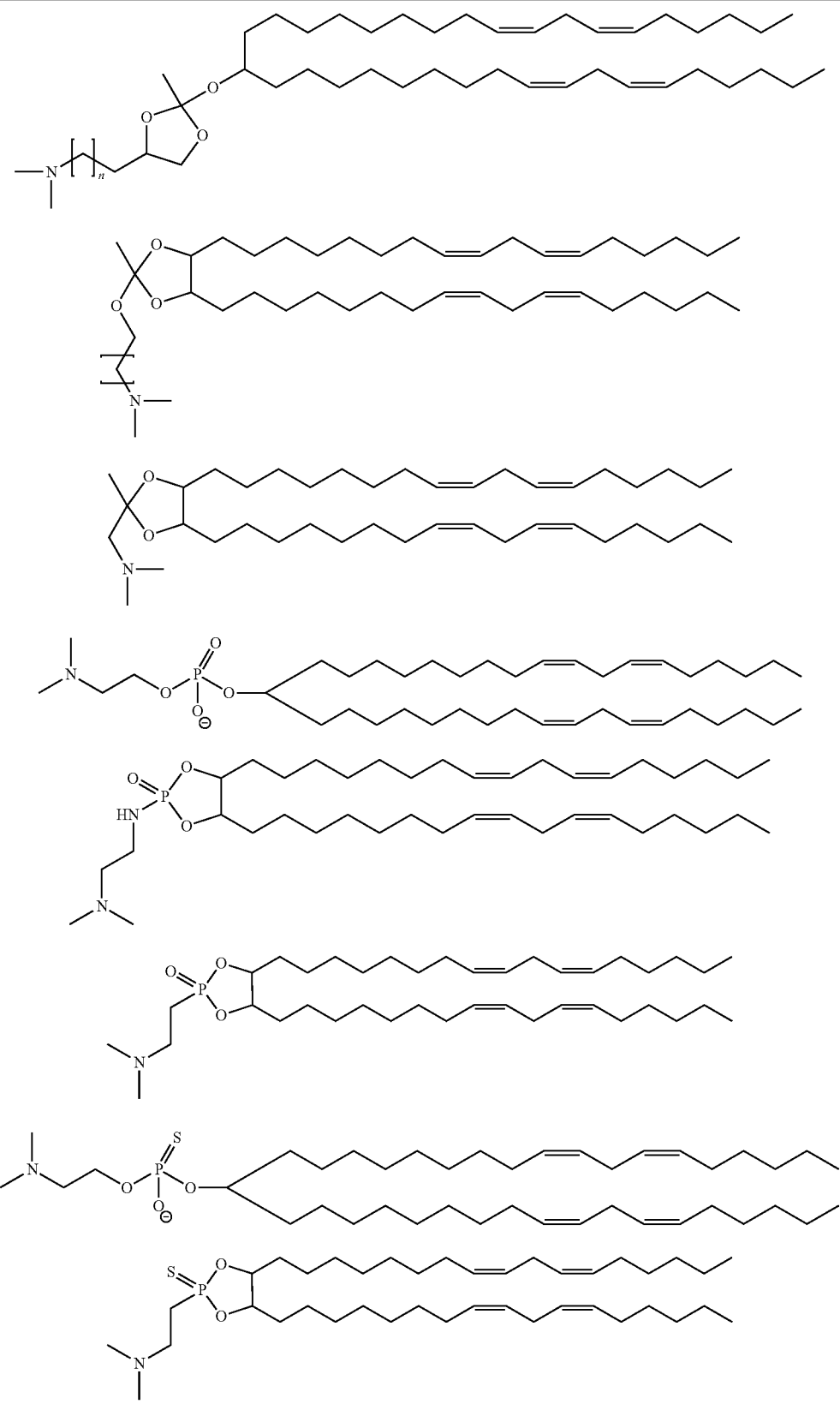

TABLE 1-continued
Some cationic lipids of the present invention.
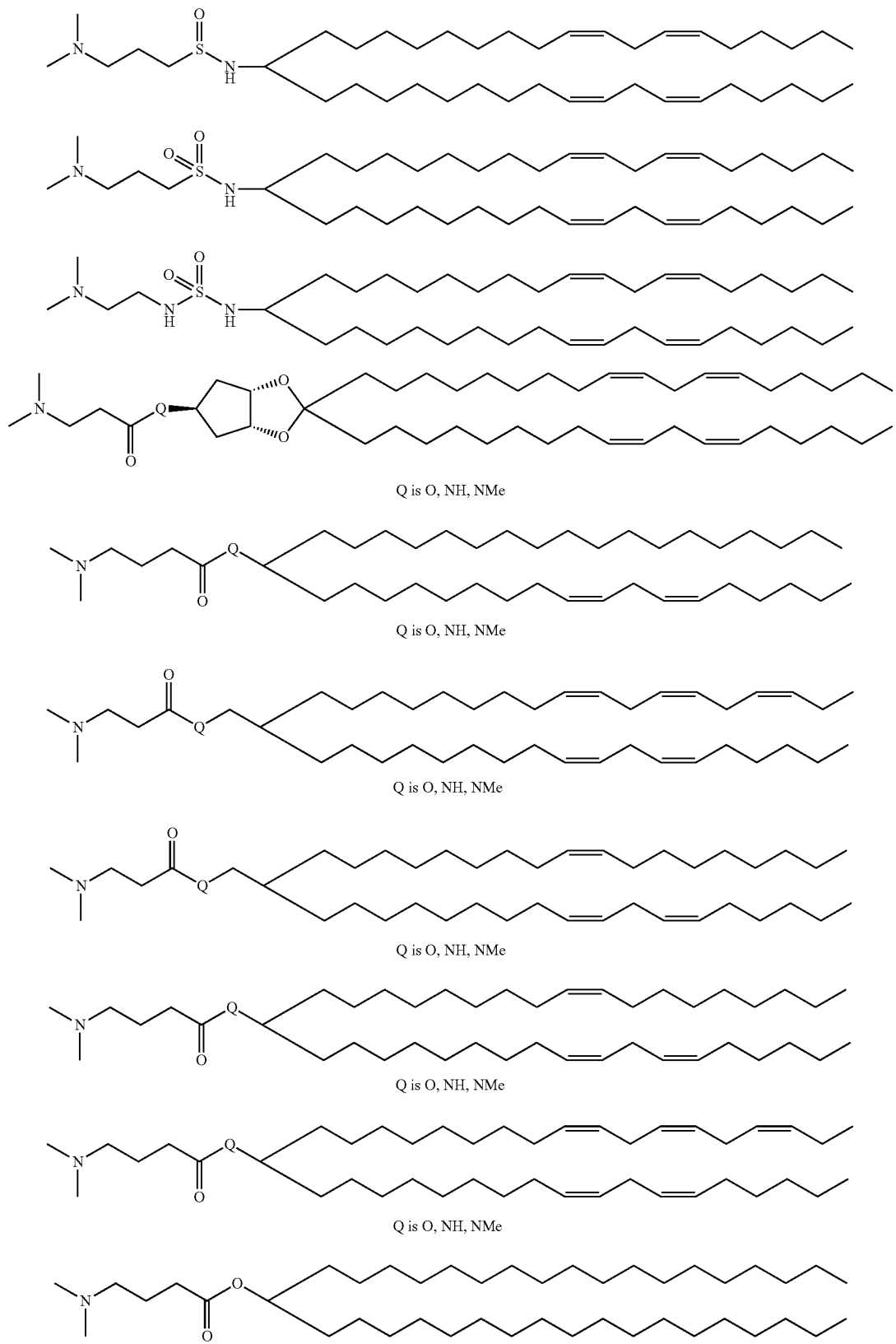

TABLE 1-continued
Some cationic lipids of the present invention.
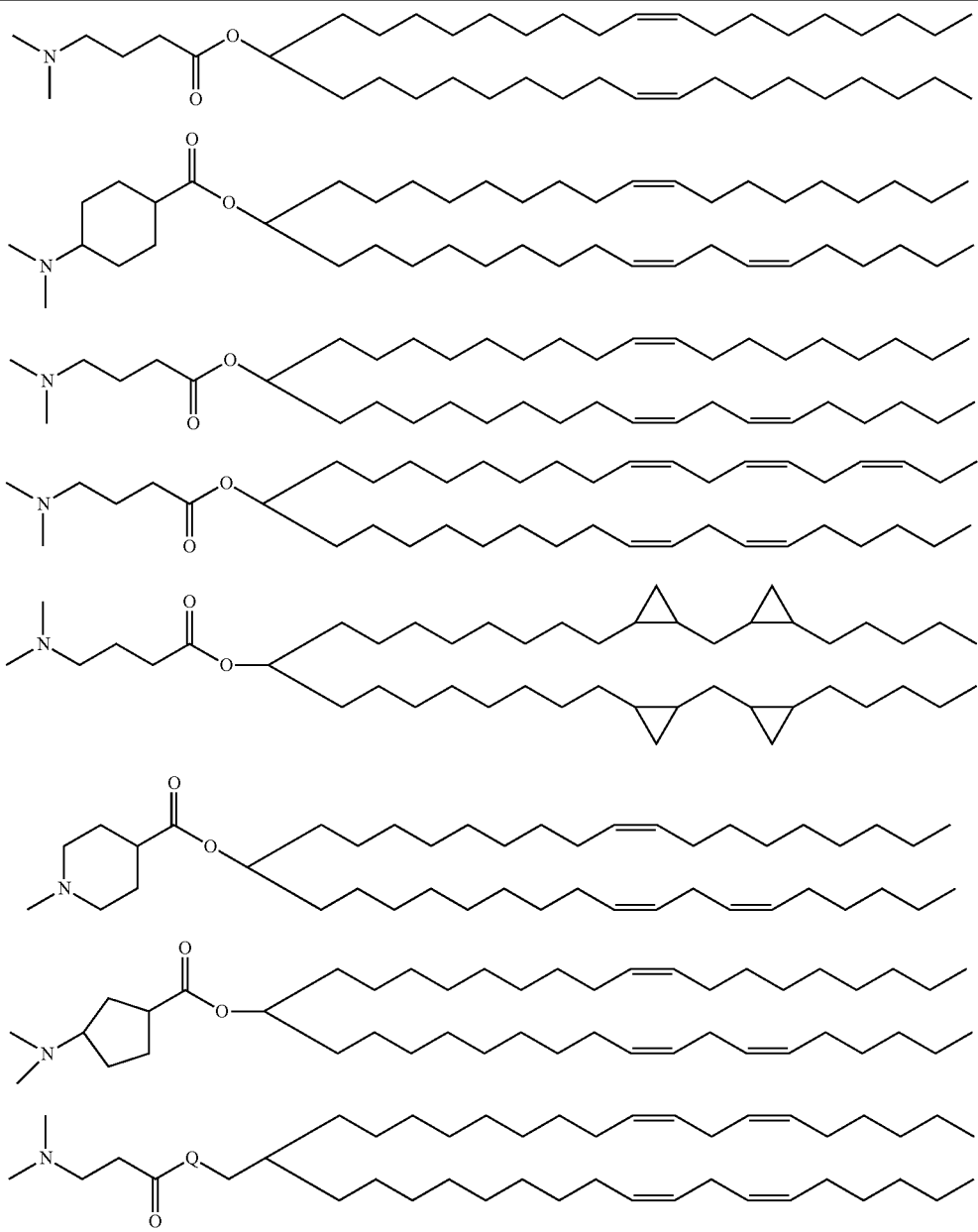
Q is O, NH, NMe
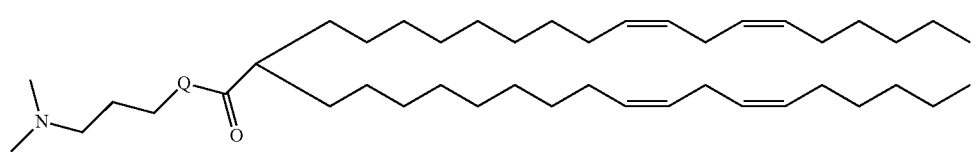
Q is O, NH, NMe
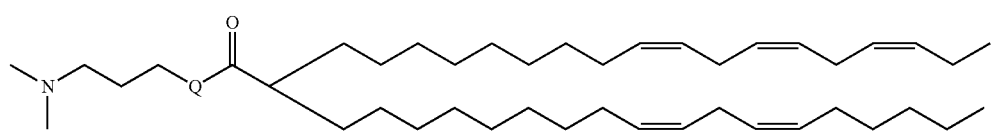
Q is O, NH, NMe TABLE 1-continued
Some cationic lipids of the present invention.
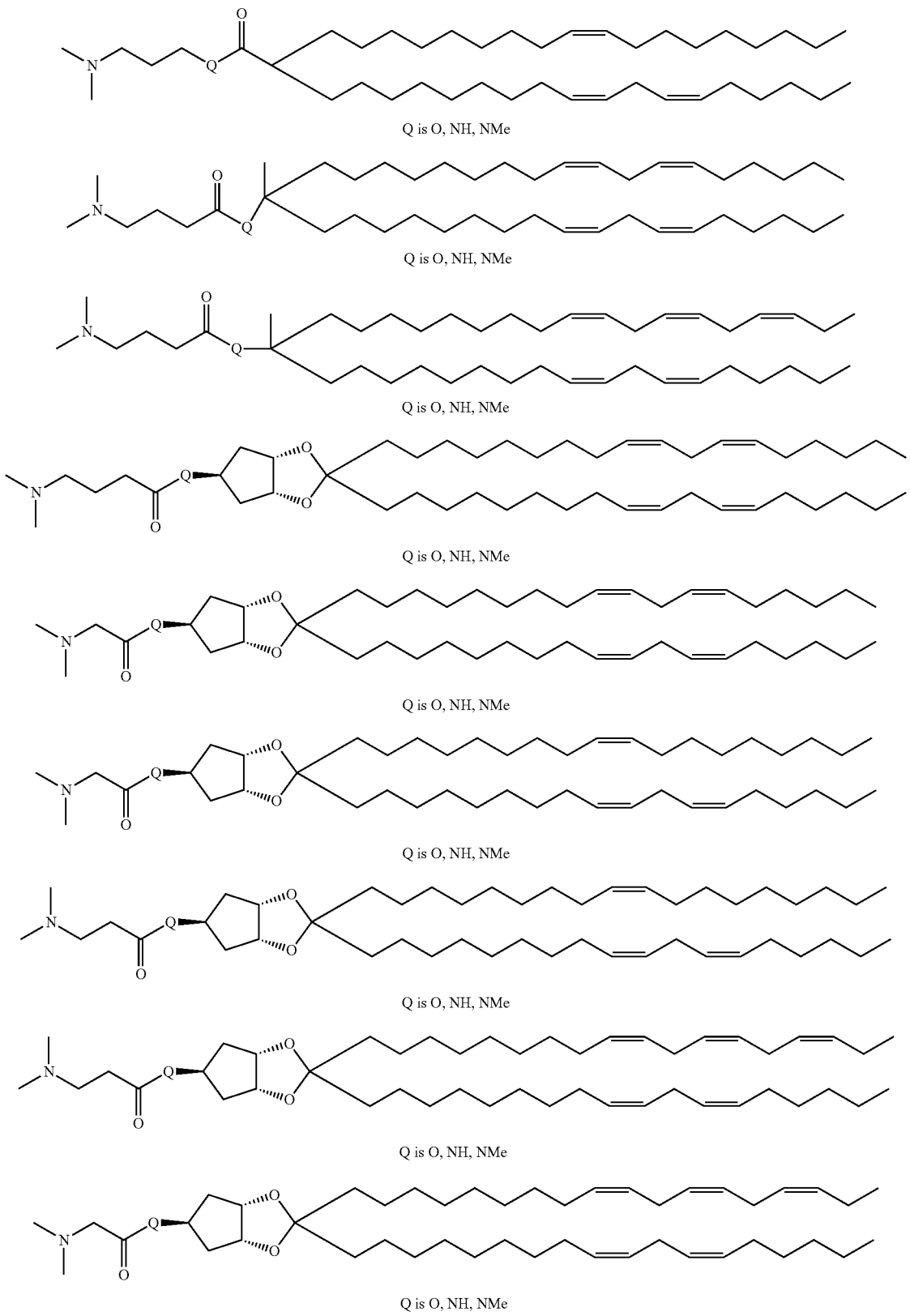
Q is O, NH, NMe
Q is O, NH, NMe
Q is O, NH, NMe
Q is O, NH, NMe
Q is O, NH, NMe
Q is O, NH, NMe
Q is O, NH, NMe
Q is O, NH, NMe
Q is O, NH, NMe TABLE 1-continued
Some cationic lipids of the present invention.
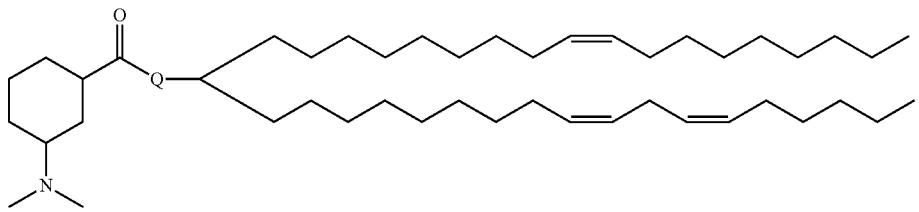
Q is O, NH, NMe
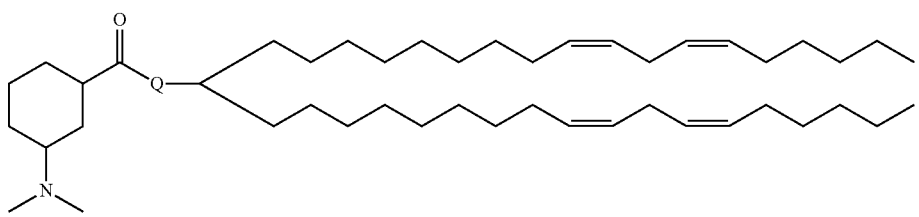
Q is O, NH, NMe
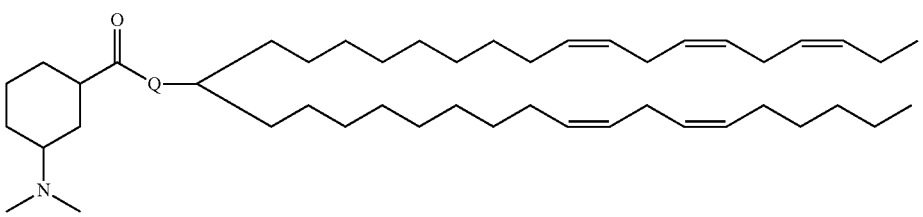
Q is O, NH, NMe
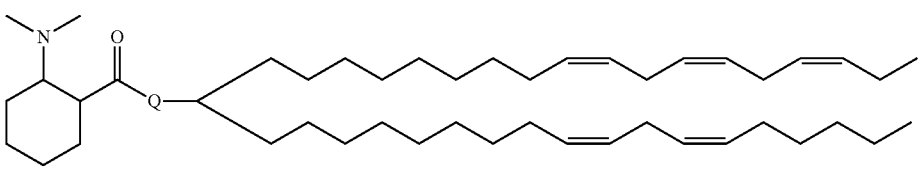
Q is O, NH, NMe
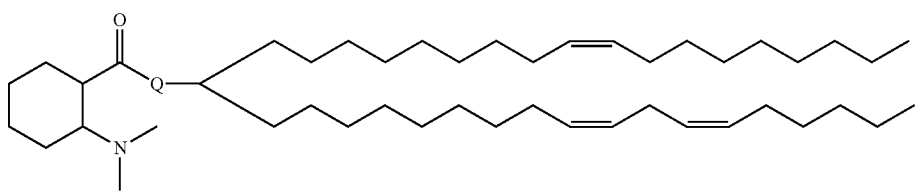
Q is O, NH, NMe
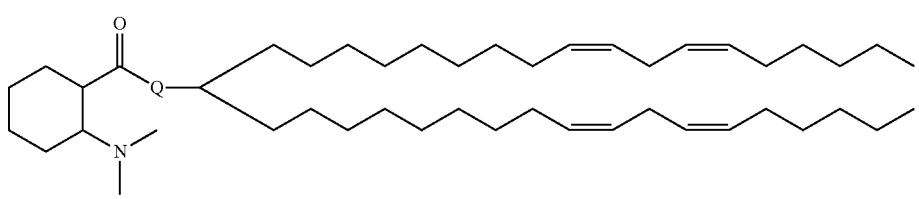
Q is O, NH, NMe TABLE 1-continued
Some cationic lipids of the present invention.
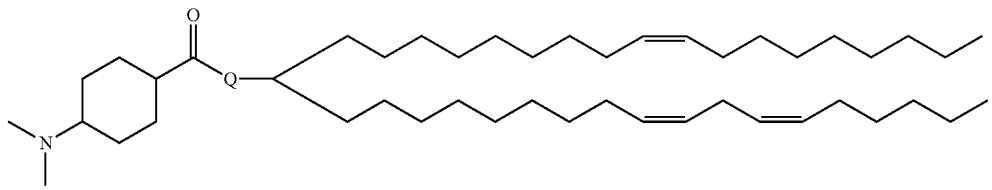
Q is O, NH, NMe
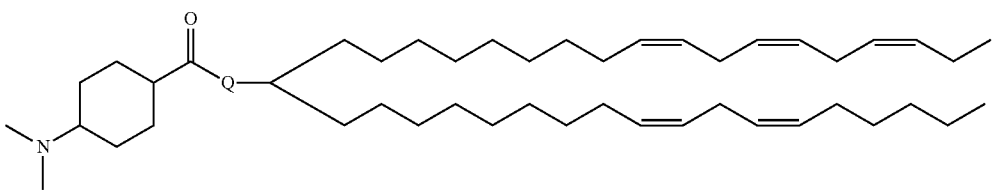
Q is O, NH, NMe
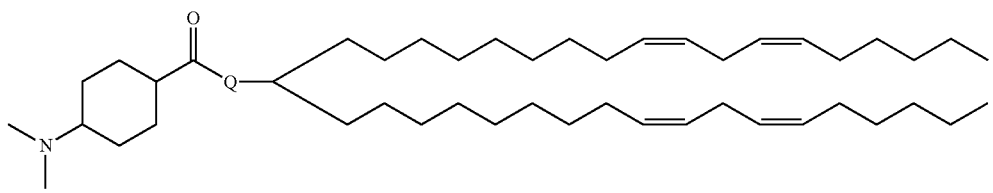
Q is O, NH, NMe
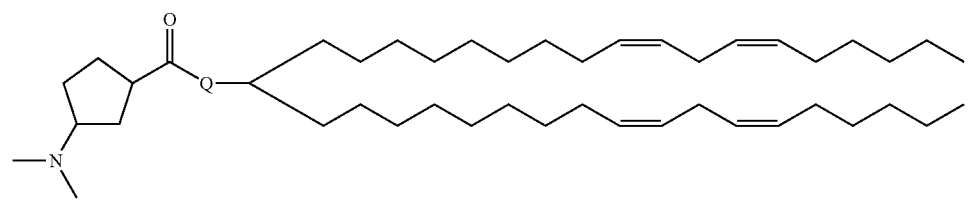
Q is O, NH, NMe
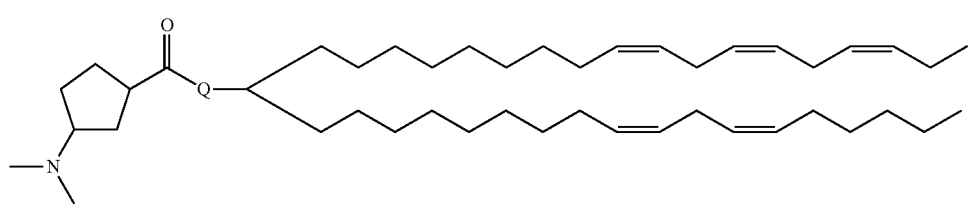
Q is O, NH, NMe
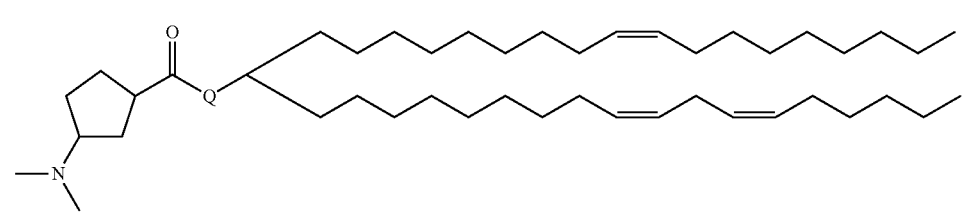
Q is O, NH, NMe TABLE 1-continued
Some cationic lipids of the present invention.
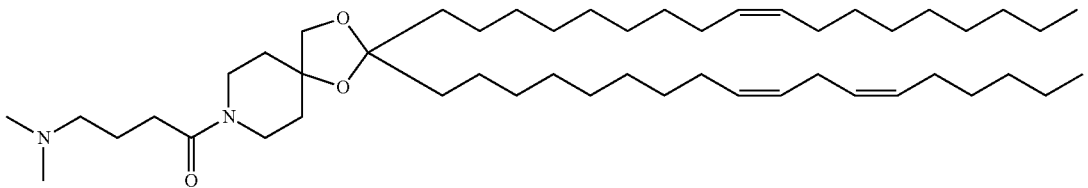 [SMILES: CCCCC/C=C\C/C=C\CCCCCCCCC1(CCCCCCCC/C=C\CCCCCCCC)OCC2(CCN(C(=O)CCCN(C)C)CC2)O1]
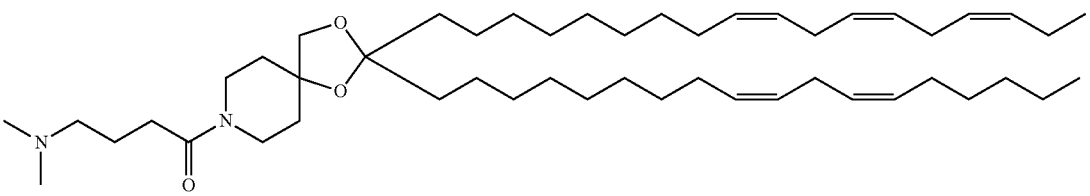
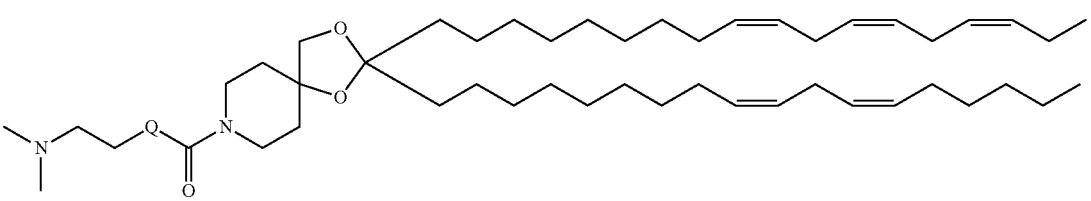
Q is O, NH, NMe
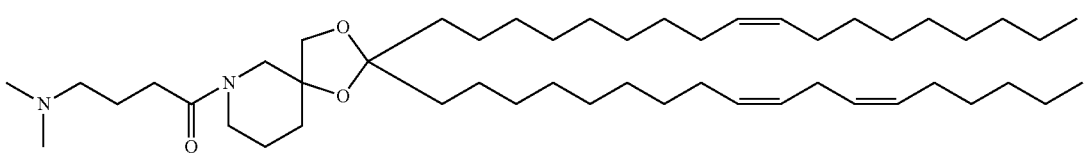 [SMILES: CCCCC/C=C\C/C=C\CCCCCCCCC1(CCCCCCCC/C=C\CCCCCCCC)OCC2(CCCN(C(=O)CCCN(C)C)C2)O1]
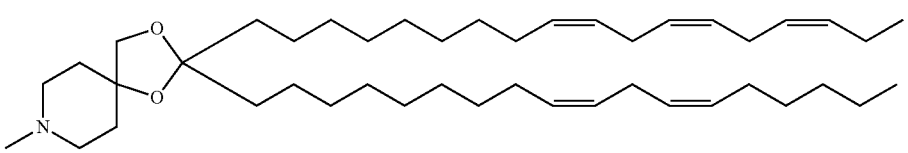 [SMILES: CC/C=C\C/C=C\C/C=C\CCCCCCCCC1(CCCCCCCC/C=C\C/C=C\CCCCC)OCC2(CCN(C)CC2)O1]
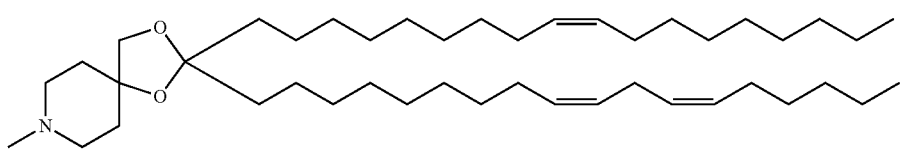 [SMILES: CCCCC/C=C\C/C=C\CCCCCCCCC1(CCCCCCCC/C=C\CCCCCCCC)OCC2(CCN(C)CC2)O1]
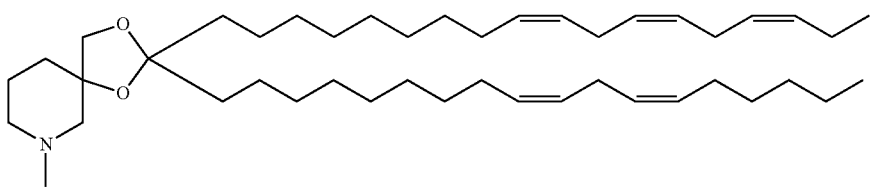 [SMILES: CC/C=C\C/C=C\C/C=C\CCCCCCCCC1(CCCCCCCC/C=C\C/C=C\CCCCC)OCC2(CCCN(C)C2)O1]
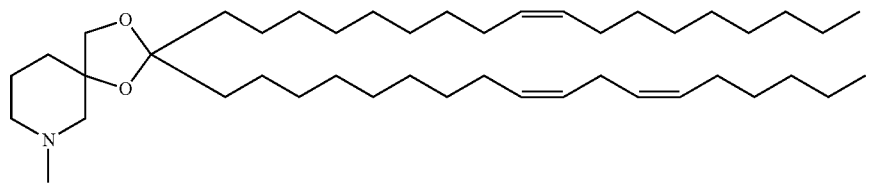 [SMILES: CCCCC/C=C\C/C=C\CCCCCCCCC1(CCCCCCCC/C=C\CCCCCCCC)OCC2(CCCN(C)C2)O1]

TABLE 1-continued
Some cationic lipids of the present invention.
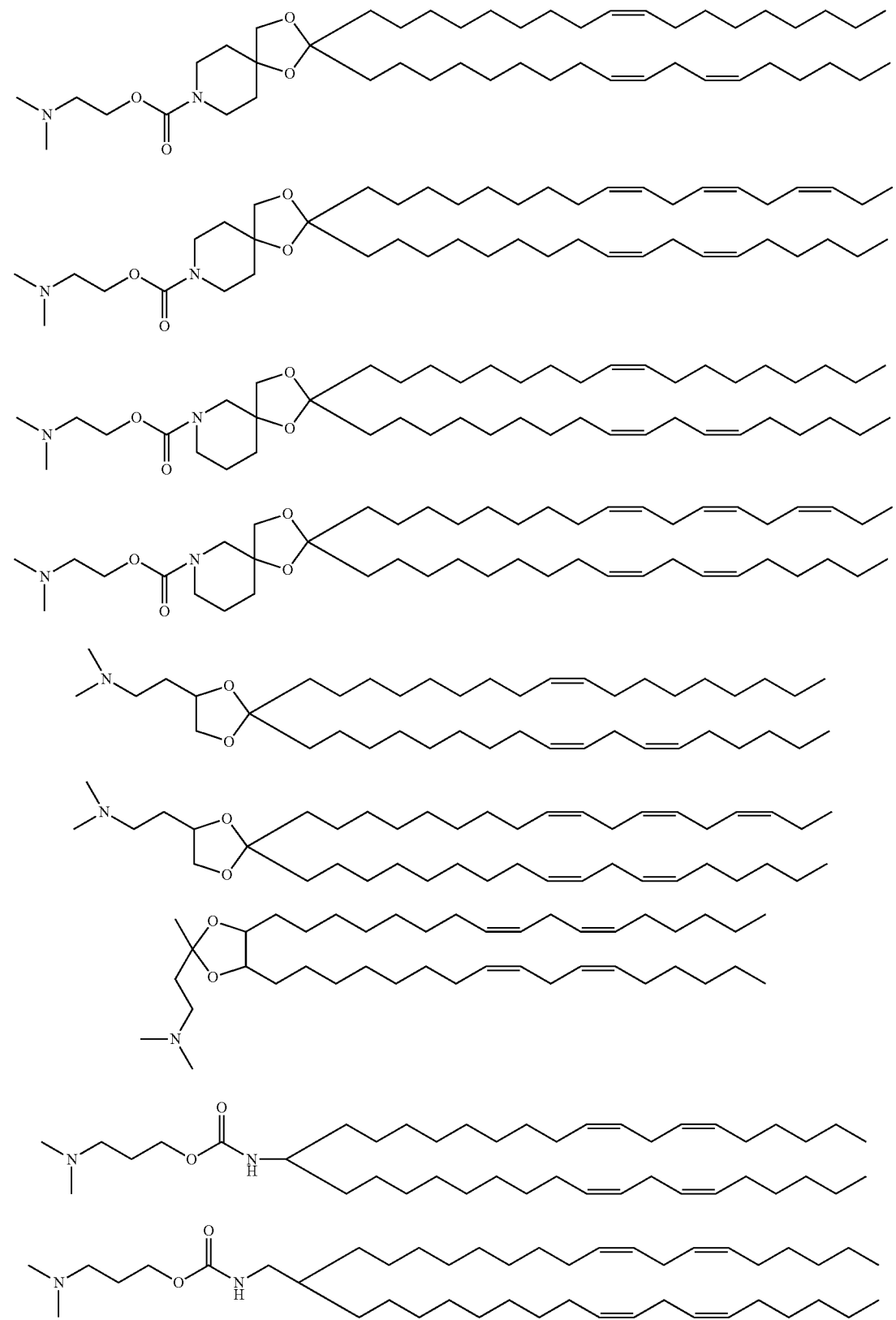

TABLE 1-continued
Some cationic lipids of the present invention.
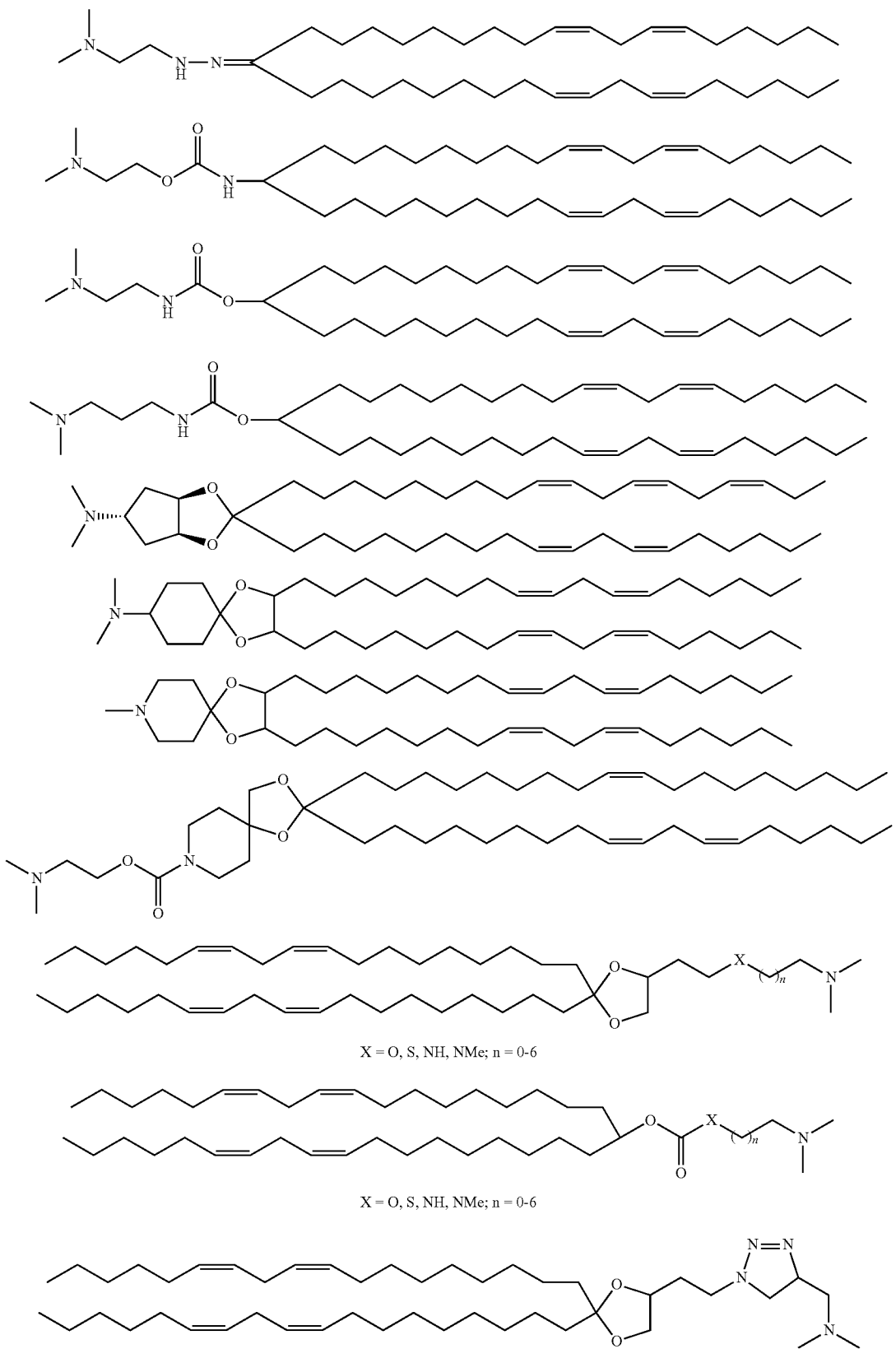
X = O, S, NH, NMe; n = 0-6
X = O, S, NH, NMe; n = 0-6

TABLE 1-continued
Some cationic lipids of the present invention.
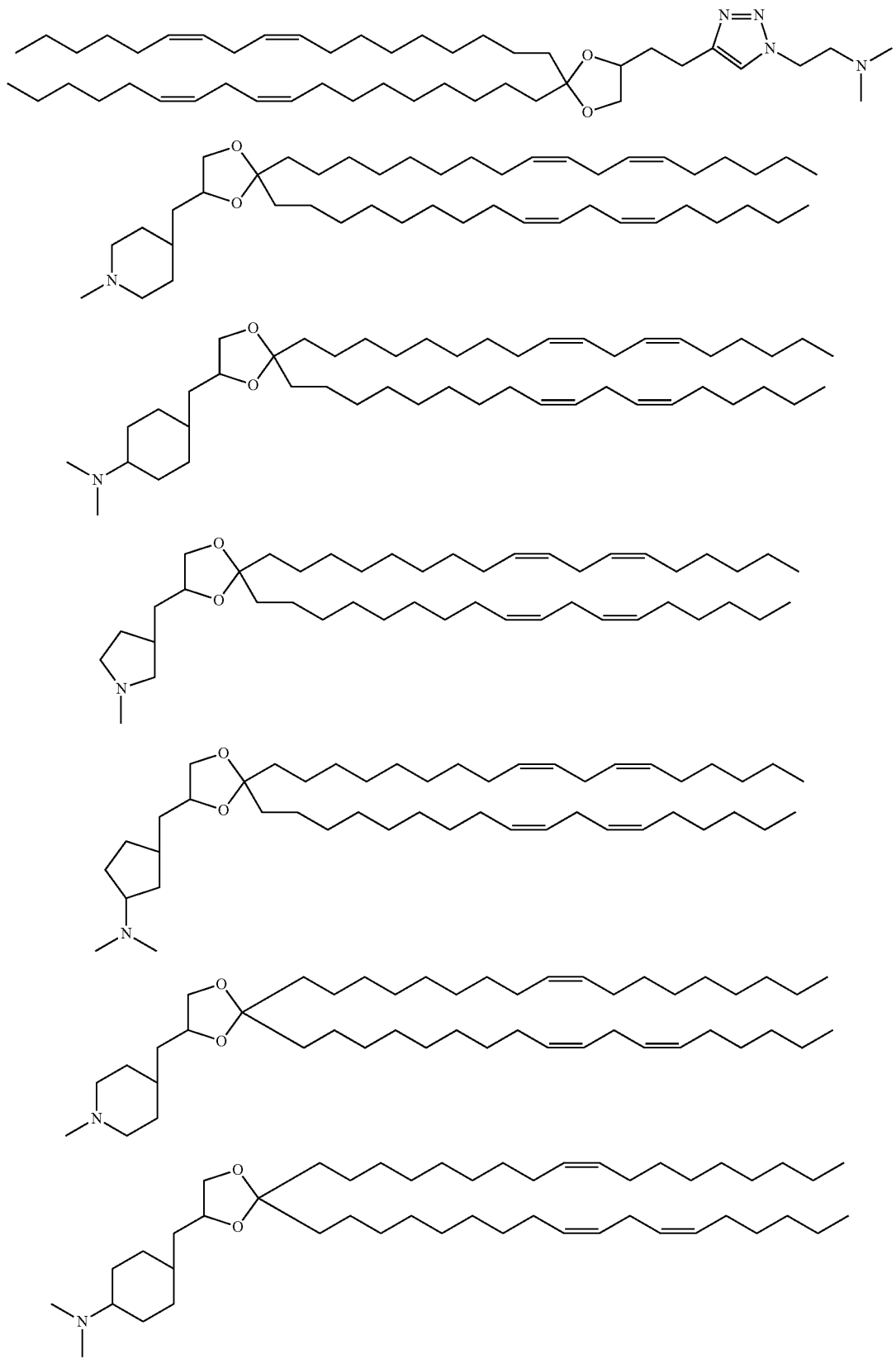

TABLE 1-continued
Some cationic lipids of the present invention.
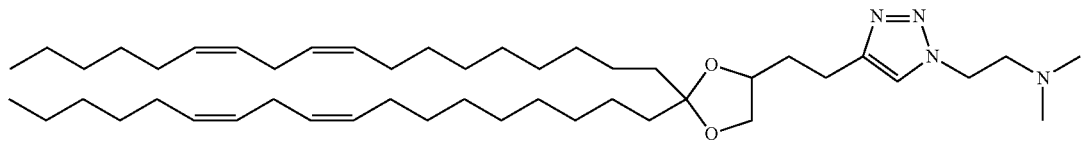 [SMILES: CCCCC/C=C\C/C=C\CCCCCCCCC1(CCCCCCCC/C=C\C/C=C\CCCCC)OCC(CCc2cn(CCN(C)C)nn2)O1]
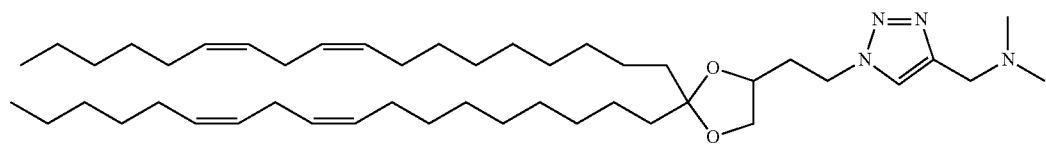 [SMILES: CCCCC/C=C\C/C=C\CCCCCCCCC1(CCCCCCCC/C=C\C/C=C\CCCCC)OCC(CCn2cc(CN(C)C)nn2)O1]
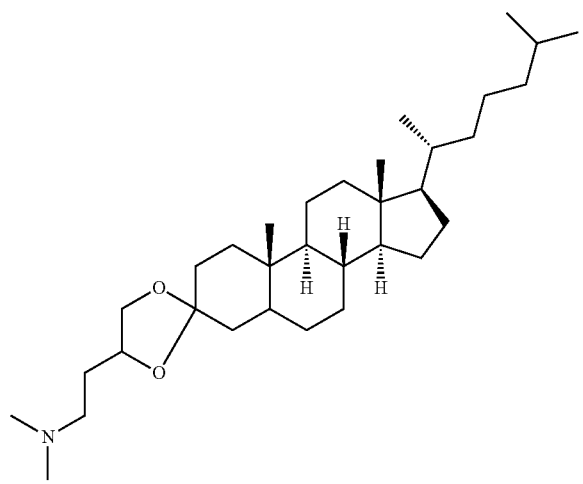
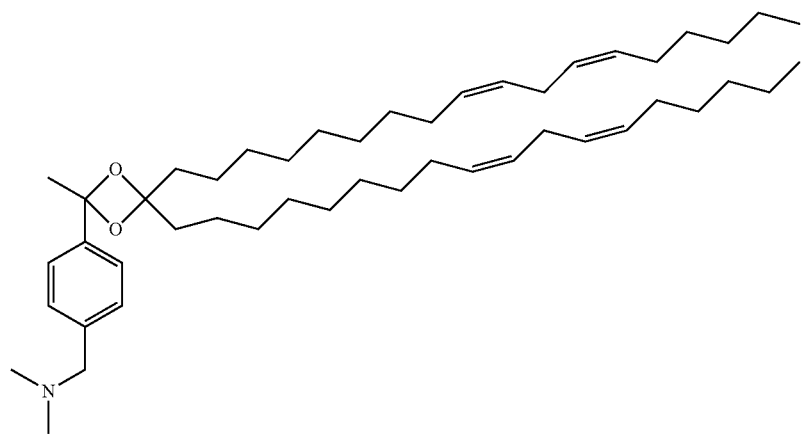 [SMILES: CCCCC/C=C\C/C=C\CCCCCCCCC1(CCCCCCCC/C=C\C/C=C\CCCCC)OC(C)(c2ccc(CN(C)C)cc2)O1]
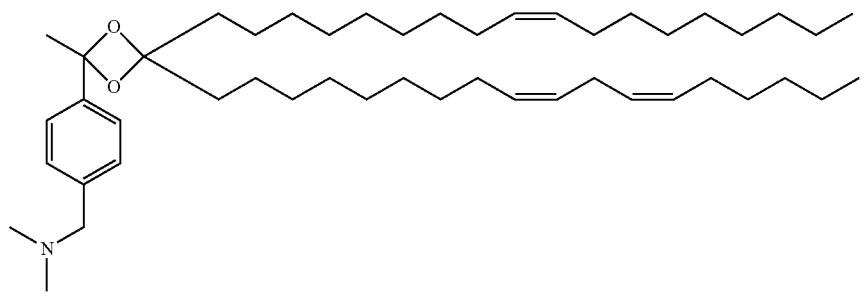 [SMILES: CCCCC/C=C\C/C=C\CCCCCCCCC1(CCCCCCCC/C=C\CCCCCCCC)OC(C)(c2ccc(CN(C)C)cc2)O1]

TABLE 1-continued

Some cationic lipids of the present invention.

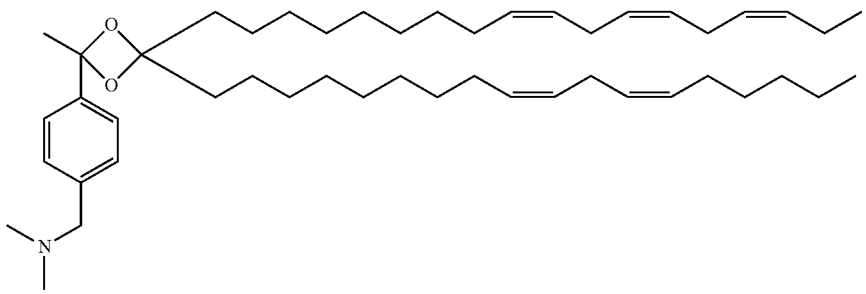 [SMILES: CC/C=C\C/C=C\C/C=C\CCCCCCCCC1(CCCCCCCC/C=C\C/C=C\CCCCC)OC(C)(c2ccc(CN(C)C)cc2)O1]

Although not all diasteromers for a lipid are shown, one aspect of the present invention is to provide all diastereomers and as such chirally pure and diastereomerically enriched lipids are also part of this invention.

In one embodiment, $R_3$ is -linker-ligand.

In one embodiment, the lipid is a targeting cationic lipid and chosen from a group consisting of lipids shown in Table 2 below.

TABLE 2

Targeting lipids.

| # | Structure |
|---|---|
| 1. | GalNAc-Mono |
| 2. | Mannose-Mono |

TABLE 2-continued
Targeting lipids.
| # | Structure |
|---|---|
| 3. | 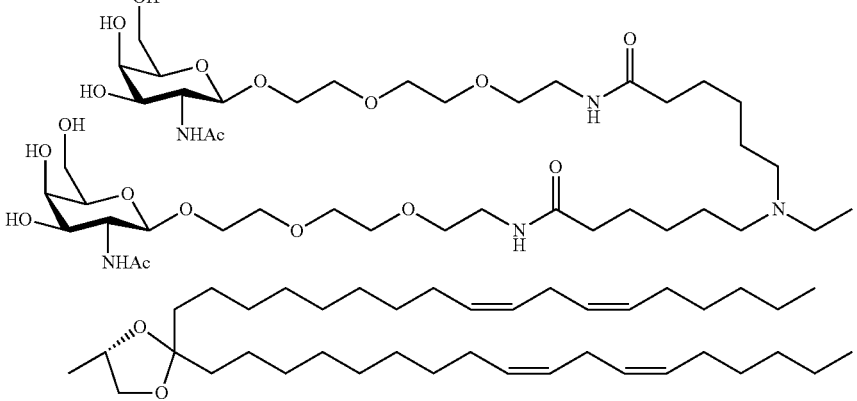<br>GalNAc-Biantineary |
| 4. | 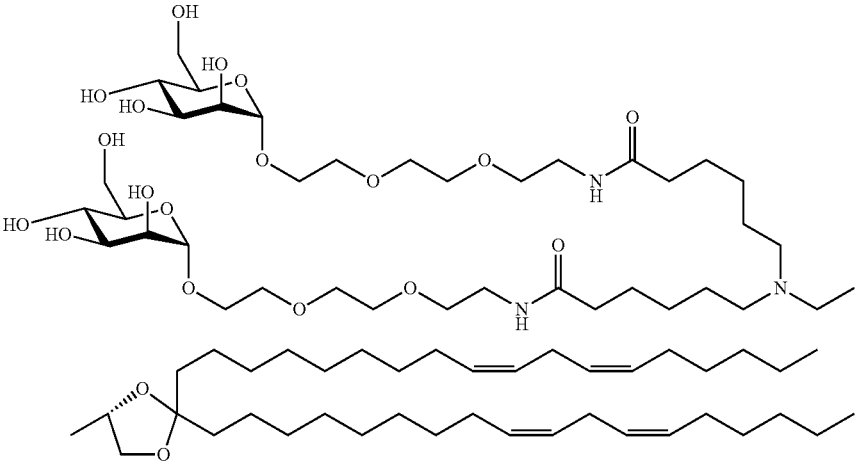<br>Mannose-Biantineary |
| 5. | 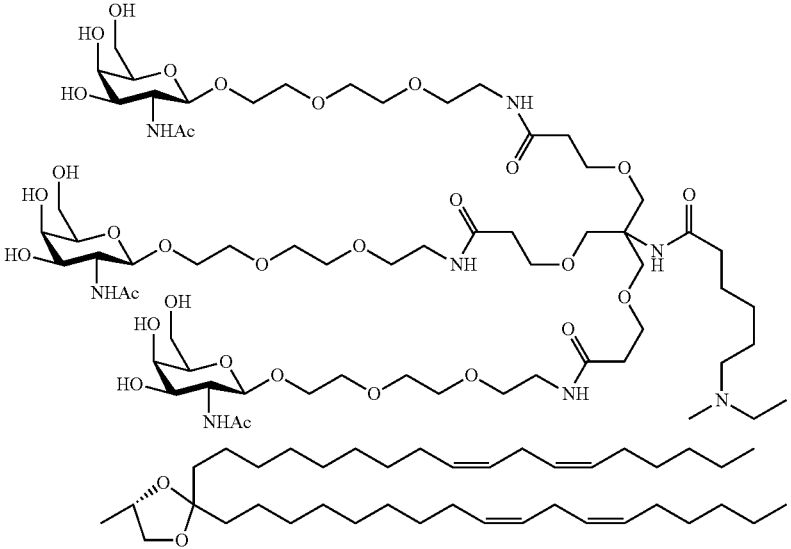<br>GalNAc-Triantineary |

TABLE 2-continued

Targeting lipids.

| # | Structure |
|---|---|
| 6. | Mannose-Triantineary |

Although not all diasteromers for a lipid are shown, one aspect of the present invention is to provide all diastereomers and as such chirally pure and diastereomerically enriched lipids are also part of this invention.

In particular embodiments, the lipids of the present invention are cationic lipids. As used herein, the term "cationic lipid" is meant to include those lipids having one or two fatty acid or fatty alkyl chains and an amino head group (including an alkylamino or dialkylamino group) that may be protonated to form a cationic lipid at physiological pH. In some embodiments, a cationic lipid is referred to as an "amino lipid."

Other cationic lipids would include those having alternative fatty acid groups and other dialkylamino groups, including those in which the alkyl substituents are different (e.g., N-ethyl-N-methylamino-, N-propyl-N-ethylamino- and the like). For those embodiments in which $R_1$ and $R_2$ are both long chain alkyl or acyl groups, they can be the same or different. In general, lipids (e.g., a cationic lipid) having less saturated acyl chains are more easily sized, particularly when the complexes are sized below about 0.3 microns, for purposes of filter sterilization. Cationic lipids containing unsaturated fatty acids with carbon chain lengths in the range of $C_{10}$ to $C_{20}$ are typical. Other scaffolds can also be used to separate the amino group (e.g., the amino group of the cationic lipid) and the fatty acid or fatty alkyl portion of the cationic lipid. Suitable scaffolds are known to those of skill in the art.

In certain embodiments, cationic lipids of the present invention have at least one protonatable or deprotonatable group, such that the lipid is positively charged at a pH at or below physiological pH (e.g. pH 7.4), and neutral at a second pH, preferably at or above physiological pH. Such lipids are also referred to as cationic lipids. It will, of course, be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterrionic, are not excluded from use in the invention.

In certain embodiments, protonatable lipids (i.e., cationic lipids) according to the invention have a pKa of the protonatable group in the range of about 4 to about 11. Typically, lipids will have a pKa of about 4 to about 7, e.g., between about 5 and 7, such as between about 5.5 and 6.8, when incorporated into lipid particles. Such lipids will be cationic at a lower pH formulation stage, while particles will be largely (though not completely) surface neutralized at physiological pH around pH 7.4. One of the benefits of a pKa in the range of between about 4 and 7 is that at least some nucleic acid associated with the outside surface of the particle will lose its electrostatic interaction at physiological pH and be removed by simple dialysis; thus greatly reducing the particle's susceptibility to clearance. pKa measurements of lipids within lipid particles can be performed, for example, by using the fluorescent probe 2-(p-toluidino)-6-napthalene sulfonic acid (TNS), using methods described in Cullis et al., (1986) Chem Phys Lipids 40, 127-144.

In one embodiment, the formulations of the invention are entrapped by at least 75%, at least 80% or at least 90%.

In one embodiment, the formulations of the invention further comprise an apolipoprotein. As used herein, the term "apolipoprotein" or "lipoprotein" refers to apolipoproteins known to those of skill in the art and variants and fragments thereof and to apolipoprotein agonists, analogues or fragments thereof described below. Suitable apolipoproteins include, but are not limited to, ApoA-I, ApoA-II, ApoA-IV, ApoA-V and ApoE, and active polymorphic forms, isoforms, variants and mutants as well as fragments or truncated forms thereof. In certain embodiments, the apolipoprotein is a thiol containing apolipoprotein. "Thiol containing apolipoprotein" refers to an apolipoprotein, variant, fragment or isoform that contains at least one cysteine residue. The most common thiol containing apolipoproteins are ApoA-I Milano (ApoA-$I_M$) and ApoA-I Paris (ApoA-$I_P$) which contain one cysteine residue (Jia et al., 2002, Biochem. Biophys. Res. Comm. 297:

206-13; Bielicki and Oda, 2002, Biochemistry 41: 2089-96). ApoA-II, ApoE2 and ApoE3 are also thiol containing apolipoproteins. Isolated ApoE and/or active fragments and polypeptide analogues thereof, including recombinantly produced forms thereof, are described in U.S. Pat. Nos. 5,672, 685; 5,525,472; 5,473,039; 5,182,364; 5,177,189; 5,168,045; 5,116,739; the disclosures of which are herein incorporated by reference. ApoE3 is disclosed in Weisgraber, et al., "Human E apoprotein heterogeneity: cysteine-arginine interchanges in the amino acid sequence of the apo-E isoforms," J. Biol. Chem. (1981) 256: 9077-9083; and Rall, et al., "Structural basis for receptor binding heterogeneity of apolipoprotein E from type III hyperlipoproteinemic subjects," Proc. Nat. Acad. Sci. (1982) 79: 4696-4700. See also GenBank accession number K00396.

In certain embodiments, the apolipoprotein can be in its mature form, in its preproapolipoprotein form or in its proapolipoprotein form. Homo- and heterodimers (where feasible) of pro- and mature ApoA-I (Duverger et al., 1996, Arterioscler. Thromb. Vasc. Biol. 16(12):1424-29), ApoA-I Milano (Klon et al., 2000, Biophys. J. 79:(3)1679-87; Franceschini et al., 1985, J. Biol. Chem. 260: 1632-35), ApoA-I Paris (Daum et al., 1999, J. Mol. Med. 77:614-22), ApoA-II (Shelness et al., 1985, J. Biol. Chem. 260(14):8637-46; Shelness et al., 1984, J. Biol. Chem. 259(15):9929-35), ApoA-IV (Duverger et al., 1991, Euro. J. Biochem. 201(2):373-83), and ApoE (McLean et al., 1983, J. Biol. Chem. 258(14):8993-9000) can also be utilized within the scope of the invention.

In certain embodiments, the apolipoprotein can be a fragment, variant or isoform of the apolipoprotein. The term "fragment" refers to any apolipoprotein having an amino acid sequence shorter than that of a native apolipoprotein and which fragment retains the activity of native apolipoprotein, including lipid binding properties. By "variant" is meant substitutions or alterations in the amino acid sequences of the apolipoprotein, which substitutions or alterations, e.g., additions and deletions of amino acid residues, do not abolish the activity of native apolipoprotein, including lipid binding properties. Thus, a variant can comprise a protein or peptide having a substantially identical amino acid sequence to a native apolipoprotein provided herein in which one or more amino acid residues have been conservatively substituted with chemically similar amino acids. Examples of conservative substitutions include the substitution of at least one hydrophobic residue such as isoleucine, valine, leucine or methionine for another. Likewise, the present invention contemplates, for example, the substitution of at least one hydrophilic residue such as, for example, between arginine and lysine, between glutamine and asparagine, and between glycine and serine (see U.S. Pat. Nos. 6,004,925, 6,037,323 and 6,046,166). The term "isoform" refers to a protein having the same, greater or partial function and similar, identical or partial sequence, and may or may not be the product of the same gene and usually tissue specific (see Weisgraber 1990, J. Lipid Res. 31(8):1503-11; Hixson and Powers 1991, J. Lipid Res. 32(9):1529-35; Lackner et al., 1985, J. Biol. Chem. 260(2):703-6; Hoeg et al., 1986, J. Biol. Chem. 261(9):3911-4; Gordon et al., 1984, J. Biol. Chem. 259(1):468-74; Powell et al., 1987, Cell 50(6):831-40; Aviram et al., 1998, Arterioscler. Thromb. Vasc. Biol. 18(10):1617-24; Aviram et al., 1998, J. Clin. Invest. 101(8):1581-90; Billecke et al., 2000, Drug Metab. Dispos. 28(11):1335-42; Draganov et al., 2000, J. Biol. Chem. 275(43):33435-42; Steinmetz and Utermann 1985, J. Biol. Chem. 260(4):2258-64; Widler et al., 1980, J. Biol. Chem. 255(21):10464-71; Dyer et al., 1995, J. Lipid Res. 36(1):80-8; Sacre et al., 2003, FEBS Lett. 540(1-3):181-7; Weers, et al., 2003, Biophys. Chem. 100(1-3):481-92; Gong et al., 2002, J. Biol. Chem. 277(33):29919-26; Ohta et al., 1984, J. Biol. Chem. 259(23):14888-93 and U.S. Pat. No. 6,372,886).

In certain embodiments, the methods and compositions of the present invention include the use of a chimeric construction of an apolipoprotein. For example, a chimeric construction of an apolipoprotein can be comprised of an apolipoprotein domain with high lipid binding capacity associated with an apolipoprotein domain containing ischemia reperfusion protective properties. A chimeric construction of an apolipoprotein can be a construction that includes separate regions within an apolipoprotein (i.e., homologous construction) or a chimeric construction can be a construction that includes separate regions between different apolipoproteins (i.e., heterologous constructions). Compositions comprising a chimeric construction can also include segments that are apolipoprotein variants or segments designed to have a specific character (e.g., lipid binding, receptor binding, enzymatic, enzyme activating, antioxidant or reduction-oxidation property) (see Weisgraber 1990, J. Lipid Res. 31(8):1503-11; Hixson and Powers 1991, J. Lipid Res. 32(9):1529-35; Lackner et al., 1985, J. Biol. Chem. 260(2):703-6; Hoeg et al, 1986, J. Biol. Chem. 261(9):3911-4; Gordon et al., 1984, J. Biol. Chem. 259(1):468-74; Powell et al., 1987, Cell 50(6):831-40; Aviram et al., 1998, Arterioscler. Thromb. Vasc. Biol. 18(10):1617-24; Aviram et al., 1998, J. Clin. Invest. 101(8):1581-90; Billecke et al., 2000, Drug Metab. Dispos. 28(11):1335-42; Draganov et al., 2000, J. Biol. Chem. 275(43):33435-42; Steinmetz and Utermann 1985, J. Biol. Chem. 260(4):2258-64; Widler et al., 1980, J. Biol. Chem. 255(21):10464-71; Dyer et al., 1995, J. Lipid Res. 36(1):80-8; Sorenson et al., 1999, Arterioscler. Thromb. Vasc. Biol. 19(9):2214-25; Palgunachari 1996, Arterioscler. Throb. Vasc. Biol. 16(2):328-38: Thurberg et al., J. Biol. Chem. 271(11):6062-70; Dyer 1991, J. Biol. Chem. 266(23):150009-15; Hill 1998, J. Biol. Chem. 273(47):30979-84).

Apolipoproteins utilized in the invention also include recombinant, synthetic, semi-synthetic or purified apolipoproteins. Methods for obtaining apolipoproteins or equivalents thereof, utilized by the invention are well-known in the art. For example, apolipoproteins can be separated from plasma or natural products by, for example, density gradient centrifugation or immunoaffinity chromatography, or produced synthetically, semi-synthetically or using recombinant DNA techniques known to those of the art (see, e.g., Mulugeta et al., 1998, J. Chromatogr. 798(1-2): 83-90; Chung et al., 1980, J. Lipid Res. 21(3):284-91; Cheung et al., 1987, J. Lipid Res. 28(8):913-29; Persson, et al., 1998, J. Chromatogr. 711: 97-109; U.S. Pat. Nos. 5,059,528, 5,834,596, 5,876,968 and 5,721,114; and PCT Publications WO 86/04920 and WO 87/02062).

Apolipoproteins utilized in the invention further include apolipoprotein agonists such as peptides and peptide analogues that mimic the activity of ApoA-I, ApoA-I Milano (ApoA-I$_M$), ApoA-I Paris (ApoA-I$_P$), ApoA-II, ApoA-IV, and ApoE. For example, the apolipoprotein can be any of those described in U.S. Pat. Nos. 6,004,925, 6,037,323, 6,046,166, and 5,840,688, the contents of which are incorporated herein by reference in their entireties.

Apolipoprotein agonist peptides or peptide analogues can be synthesized or manufactured using any technique for peptide synthesis known in the art including, e.g., the techniques described in U.S. Pat. Nos. 6,004,925, 6,037,323 and 6,046, 166. For example, the peptides may be prepared using the solid-phase synthetic technique initially described by Merrifield (1963, J. Am. Chem. Soc. 85:2149-2154). Other peptide synthesis techniques may be found in Bodanszky et al., Peptide Synthesis, John Wiley & Sons, 2d Ed., (1976) and other references readily available to those skilled in the art. A summary of polypeptide synthesis techniques can be found in Stuart and Young, Solid Phase Peptide. Synthesis, Pierce Chemical Company, Rockford, Ill., (1984). Peptides may also be synthesized by solution methods as described in The Proteins, Vol. II, 3d Ed., Neurath et. al., Eds., p. 105-237, Academic Press, New York, N.Y. (1976). Appropriate protective groups for use in different peptide syntheses are described in the above-mentioned texts as well as in McOmie, Protective Groups in Organic Chemistry, Plenum Press, New York, N.Y. (1973). The peptides of the present invention might also be prepared by chemical or enzymatic cleavage from larger portions of, for example, apolipoprotein A-I.

In certain embodiments, the apolipoprotein can be a mixture of apolipoproteins. In one embodiment, the apolipoprotein can be a homogeneous mixture, that is, a single type of apolipoprotein. In another embodiment, the apolipoprotein can be a heterogeneous mixture of apolipoproteins, that is, a mixture of two or more different apolipoproteins. Embodiments of heterogenous mixtures of apolipoproteins can comprise, for example, a mixture of an apolipoprotein from an animal source and an apolipoprotein from a semi-synthetic source. In certain embodiments, a heterogenous mixture can comprise, for example, a mixture of ApoA-I and ApoA-I Milano. In certain embodiments, a heterogeneous mixture can comprise, for example, a mixture of ApoA-I Milano and ApoA-I Paris. Suitable mixtures for use in the methods and compositions of the invention will be apparent to one of skill in the art.

If the apolipoprotein is obtained from natural sources, it can be obtained from a plant or animal source. If the apolipoprotein is obtained from an animal source, the apolipoprotein can be from any species. In certain embodiments, the apolipoprotien can be obtained from an animal source. In certain embodiments, the apolipoprotein can be obtained from a human source. In preferred embodiments of the invention, the apolipoprotein is derived from the same species as the individual to which the apolipoprotein is administered.

Lipid Particles

The present invention also provides lipid particles comprising one or more of the cationic lipids described above. Lipid particles include, but are not limited to, liposomes. As used herein, a liposome is a structure having lipid-containing membranes enclosing an aqueous interior. Liposomes may have one or more lipid membranes. The invention contemplates both single-layered liposomes, which are referred to as unilamellar, and multi-layered liposomes, which are referred to as multilamellar. When complexed with nucleic acids, lipid particles may also be lipoplexes, which are composed of cationic lipid bilayers sandwiched between DNA layers, as described, e.g., in Felgner, *Scientific American.*

The lipid particles of the present invention may further comprise one or more additional lipids and/or other components such as cholesterol. Other lipids may be included in the liposome compositions of the present invention for a variety of purposes, such as to prevent lipid oxidation or to attach ligands onto the liposome surface. Any of a number of lipids may be present in liposomes of the present invention, including amphipathic, neutral, cationic, and anionic lipids. Such lipids can be used alone or in combination. Specific examples of additional lipid components that may be present are described below.

Additional components that may be present in a lipid particle of the present invention include bilayer stabilizing components such as polyamide oligomers (see, e.g., U.S. Pat. No. 6,320,017), peptides, proteins, detergents, lipid-derivatives, such as PEG coupled to phosphatidylethanolamine and PEG conjugated to ceramides (see, U.S. Pat. No. 5,885,613).

In particular embodiments, the lipid particles include one or more of a second amino lipid or cationic lipid, a neutral lipid, a sterol, and a lipid selected to reduce aggregation of lipid particles during formation, which may result from steric stabilization of particles which prevents charge-induced aggregation during formation.

Examples of lipids that reduce aggregation of particles during formation include polyethylene glycol (PEG)-modified lipids, monosialoganglioside Gm1, and polyamide oligomers ("PAO") such as (described in U.S. Pat. No. 6,320, 017). Other compounds with uncharged, hydrophilic, steric-barrier moieties, which prevent aggregation during formulation, like PEG, Gm1 or ATTA, can also be coupled to lipids for use as in the methods and compositions of the invention. ATTA-lipids are described, e.g., in U.S. Pat. No. 6,320,017, and PEG-lipid conjugates are described, e.g., in U.S. Pat. Nos. 5,820,873, 5,534,499 and 5,885,613. Typically, the concentration of the lipid component selected to reduce aggregation is about 1 to 15% (by mole percent of lipids).

Specific examples of PEG-modified lipids (or lipid-polyoxyethylene conjugates) that are useful in the present invention can have a variety of "anchoring" lipid portions to secure the PEG portion to the surface of the lipid vesicle. Examples of suitable PEG-modified lipids include PEG-modified phosphatidylethanolamine and phosphatidic acid, PEG-ceramide conjugates (e.g., PEG-CerC14 or PEG-CerC20) which are described in co-pending U.S. Ser. No. 08/486,214, incorporated herein by reference, PEG-modified dialkylamines and PEG-modified 1,2-diacyloxypropan-3-amines. Particularly preferred are PEG-modified diacylglycerols and dialkylglycerols.

In embodiments where a sterically-large moiety such as PEG or ATTA are conjugated to a lipid anchor, the selection of the lipid anchor depends on what type of association the conjugate is to have with the lipid particle. It is well known that mPEG (mw2000)-diastearoylphosphatidylethanolamine (PEG-DSPE) will remain associated with a liposome until the particle is cleared from the circulation, possibly a matter of days. Other conjugates, such as PEG-CerC20 have similar staying capacity. PEG-CerC14, however, rapidly exchanges out of the formulation upon exposure to serum, with a $T_{1/2}$ less than 60 mins. in some assays. As illustrated in U.S. patent application Ser. No. 08/486,214, at least three characteristics influence the rate of exchange: length of acyl chain, saturation of acyl chain, and size of the steric-barrier head group. Compounds having suitable variations of these features may be useful for the invention. For some therapeutic applications it may be preferable for the PEG-modified lipid to be rapidly lost from the nucleic acid-lipid particle in vivo and hence the PEG-modified lipid will possess relatively short lipid anchors. In other therapeutic applications it may be preferable for the nucleic acid-lipid particle to exhibit a longer plasma circulation lifetime and hence the PEG-modified lipid will possess relatively longer lipid anchors.

It should be noted that aggregation preventing compounds do not necessarily require lipid conjugation to function properly. Free PEG or free ATTA in solution may be sufficient to prevent aggregation. If the particles are stable after formulation, the PEG or ATTA can be dialyzed away before administration to a subject.

Neutral lipids, when present in the lipid particle, can be any of a number of lipid species which exist either in an uncharged or neutral zwitterionic form at physiological pH. Such lipids include, for example diacylphosphatidylcholine, diacylphosphatidylethanolamine, ceramide, sphingomyelin, dihydrosphingomyelin, cephalin, and cerebrosides. The selection of neutral lipids for use in the particles described herein is generally guided by consideration of, e.g., liposome size and stability of the liposomes in the bloodstream. Preferably, the neutral lipid component is a lipid having two acyl groups, (i.e., diacylphosphatidylcholine and diacylphosphatidylethanolamine). Lipids having a variety of acyl chain groups of varying chain length and degree of saturation are available or may be isolated or synthesized by well-known techniques. In one group of embodiments, lipids containing saturated fatty acids with carbon chain lengths in the range of $C_{10}$ to $C_{20}$ are preferred. In another group of embodiments, lipids with mono or diunsaturated fatty acids with carbon chain lengths in the range of $C_{10}$ to $C_{20}$ are used. Additionally, lipids having mixtures of saturated and unsaturated fatty acid chains can be used. Preferably, the neutral lipids used in the present invention are DOPE, DSPC, POPC, DPPC or any related phosphatidylcholine. The neutral lipids useful in the present invention may also be composed of sphingomyelin, dihydrosphingomyeline, or phospholipids with other head groups, such as serine and inositol.

The sterol component of the lipid mixture, when present, can be any of those sterols conventionally used in the field of liposome, lipid vesicle or lipid particle preparation. A preferred sterol is cholesterol.

Other cationic lipids, which carry a net positive charge at about physiological pH, in addition to those specifically described above, may also be included in lipid particles of the present invention. Such cationic lipids include, but are not limited to, N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy) propyl)-N,N,N-trimethylammonium chloride ("DOTAP"); 1,2-Dioleyloxy-3-trimethylaminopropane chloride salt ("DOTAP.Cl"); 3-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl-2,3-dioleyloxy)propylamine ("DODMA"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). In particular embodiments, a cationic lipid is an amino lipid.

Anionic lipids suitable for use in lipid particles of the present invention include, but are not limited to, phosphatidylglycerol, cardiolipin, diacylphosphatidylserine, diacylphosphatidic acid, N-dodecanoyl phosphatidyletha noloamine, N-succinyl phosphatidylethanolamine, N-glutaryl phosphatidylethanolamine, lysylphosphatidylglycerol, and other anionic modifying groups joined to neutral lipids.

In numerous embodiments, amphipathic lipids are included in lipid particles of the present invention. "Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and -acyloxyacids, can also be used. Additionally, such amphipathic lipids can be readily mixed with other lipids, such as triglycerides and sterols.

Also suitable for inclusion in the lipid particles of the present invention are programmable fusion lipids. Such lipid particles have little tendency to fuse with cell membranes and deliver their payload until a given signal event occurs. This allows the lipid particle to distribute more evenly after injection into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the lipid particle membrane over time. By the time the lipid particle is suitably distributed in the body, it has lost sufficient cloaking agent so as to be fusogenic. With other signal events, it is desirable to choose a signal that is associated with the disease site or target cell, such as increased temperature at a site of inflammation.

In certain embodiments, it is desirable to target the lipid particles of this invention using targeting moieties that are specific to a cell type or tissue. Targeting of lipid particles using a variety of targeting moieties, such as ligands, cell surface receptors, glycoproteins, vitamins (e.g., riboflavin) and monoclonal antibodies, has been previously described (see, e.g., U.S. Pat. Nos. 4,957,773 and 4,603,044). The targeting moieties can comprise the entire protein or fragments thereof. Targeting mechanisms generally require that the targeting agents be positioned on the surface of the lipid particle in such a manner that the target moiety is available for interaction with the target, for example, a cell surface receptor. A variety of different targeting agents and methods are known and available in the art, including those described, e.g., in Sapra, P. and Allen, T M, *Prog. Lipid Res.* 42(5):439-62 (2003); and Abra, R M et al., *J. Liposome Res.* 12:1-3, (2002).

The use of lipid particles, i.e., liposomes, with a surface coating of hydrophilic polymer chains, such as polyethylene glycol (PEG) chains, for targeting has been proposed (Allen, et al., *Biochimica et Biophysica Acta* 1237: 99-108 (1995); DeFrees, et al., *Journal of the American Chemistry Society* 118: 6101-6104 (1996); Blume, et al., *Biochimica et Biophysica Acta* 1149: 180-184 (1993); Klibanov, et al., *Journal of Liposome Research* 2: 321-334 (1992); U.S. Pat. No. 5,013, 556; Zalipsky, *Bioconjugate Chemistry* 4: 296-299 (1993); Zalipsky, *FEBS Letters* 353: 71-74 (1994); Zalipsky, in Stealth Liposomes Chapter 9 (Lasic and Martin, Eds) CRC Press, Boca Raton Fl (1995). In one approach, a ligand, such as an antibody, for targeting the lipid particle is linked to the polar head group of lipids forming the lipid particle. In another approach, the targeting ligand is attached to the distal ends of the PEG chains forming the hydrophilic polymer coating (Klibanov, et al., *Journal of Liposome Research* 2: 321-334 (1992); Kirpotin et al., *FEBS Letters* 388: 115-118 (1996)).

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., *J. Bio. Chem.*, 265:16337-16342 (1990) and Leonetti, et al., *Proc. Natl. Acad. Sci. (USA)*, 87:2448-2451 (1990). Other examples of antibody conjugation are disclosed in U.S. Pat. No. 6,027,726, the teachings of which are incorporated herein by reference. Examples of targeting moieties can also include other proteins, specific to cellular components, including antigens associated with neoplasms or tumors. Proteins used as targeting moieties can be attached to the liposomes via covalent bonds (see, Heath, *Covalent Attachment of Proteins to Liposomes*, 149 *Methods in Enzymology* 111-119 (Academic Press, Inc. 1987)). Other targeting methods include the biotin-avidin system.

In one exemplary embodiment, the lipid particle comprises a mixture of a cationic lipid of the present invention, neutral lipids (other than a cationic lipid), a sterol (e.g., cholesterol) and a PEG-modified lipid (e.g., a PEG-DMG or PEG-DMA). In certain embodiments, the lipid mixture consists of or consists essentially of a cationic lipid of the present invention, a neutral lipid, cholesterol, and a PEG-modified lipid. In further preferred embodiments, the lipid particle consists of or consists essentially of the above lipid mixture in molar ratios of about 20-70% amino lipid: 5-45% neutral lipid:20-55% cholesterol:0.5-15% PEG-modified lipid.

In particular embodiments, the lipid particle consists of or consists essentially of a cationic lipid chosen from Table 1 or Table 2, DSPC, Chol, and either PEG-DMG or PEG-DMA, e.g., in a molar ratio of about 20-60% cationic lipid: 5-25% DSPC:25-55% Chol:0.5-15% PEG-DMG or PEG-DMA. In particular embodiments, the molar lipid ratio is approximately 40/10/40/10 (mol % cationic lipid/DSPC/Chol/PEG-DMG or PEG-DMA), 35/15/40/10 (mol % cationic lipid/DSPC/Chol/PEG-DMG or PEG-DMA) or 52/13/30/5 (mol % cationic lipid/DSPC/Chol/PEG-DMG or PEG-DMA). In one embodiment, the cationic lipid is agent. In particular embodiments, the active agent is encapsulated within an aqueous interior of the lipid particle. In other embodiments, the active agent is present within one or more lipid layers of the lipid particle. In other embodiments, the active agent is bound to the exterior or interior lipid surface of a lipid particle.

"Fully encapsulated" as used herein indicates that the nucleic acid in the particles is not significantly degraded after exposure to serum or a nuclease assay that would significantly degrade free nucleic acids. In a fully encapsulated system, preferably less than 25% of particle nucleic acid is degraded in a treatment that would normally degrade 100% of free nucleic acid, more preferably less than 10% and most preferably less than 5% of the particle nucleic acid is degraded. Alternatively, full encapsulation may be determined by an Oligreen® assay. Oligreen® is an ultra-sensitive fluorescent nucleic acid stain for quantitating oligonucleotides and single-stranded DNA in solution (available from Invitrogen Corporation, Carlsbad, Calif.). Fully encapsulated also suggests that the particles are serum stable, that is, that they do not rapidly decompose into their component parts upon in vivo administration.

Active agents, as used herein, include any molecule or compound capable of exerting a desired effect on a cell, tissue, organ, or subject. Such effects may be biological, physiological, or cosmetic, for example. Active agents may be any type of molecule or compound, including e.g., nucleic acids, peptides and polypeptides, including, e.g., antibodies, such as, e.g., polyclonal antibodies, monoclonal antibodies, antibody fragments; humanized antibodies, recombinant antibodies, recombinant human antibodies, and Primatized™ antibodies, cytokines, growth factors, apoptotic factors, differentiation-inducing factors, cell surface receptors and their ligands; hormones; and small molecules, including small organic molecules or compounds.

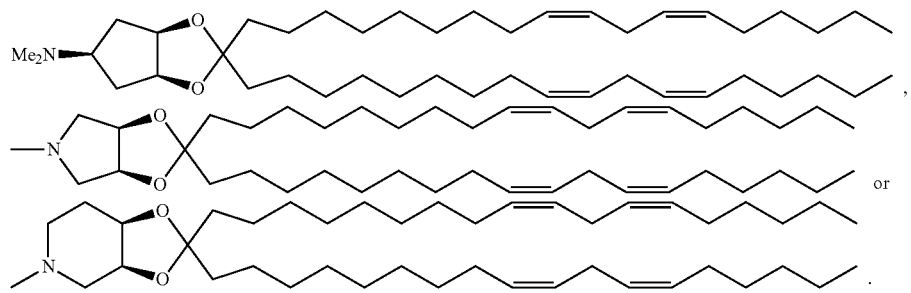

In one preferred embodiment, the cationic lipid is

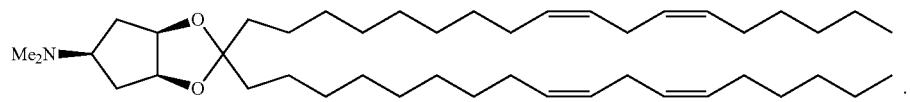

In another group of embodiments, the neutral lipid, DSPC, in these compositions is replaced with POPC, DPPC, DOPE or SM.

Therapeutic Agent-Lipid Particle Compositions and Formulations

The present invention includes compositions comprising a lipid particle of the present invention and an active agent, wherein the active agent is associated with the lipid particle. In particular embodiments, the active agent is a therapeutic In one embodiment, the active agent is a therapeutic agent, or a salt or derivative thereof. Therapeutic agent derivatives may be therapeutically active themselves or they may be prodrugs, which become active upon further modification. Thus, in one embodiment, a therapeutic agent derivative retains some or all of the therapeutic activity as compared to the unmodified agent, while in another embodiment, a therapeutic agent derivative lacks therapeutic activity.

In various embodiments, therapeutic agents include any therapeutically effective agent or drug, such as anti-inflammatory compounds, anti-depressants, stimulants, analgesics, antibiotics, birth control medication, antipyretics, vasodilators, anti-angiogenics, cytovascular agents, signal transduction inhibitors, cardiovascular drugs, e.g., anti-arrhythmic agents, vasoconstrictors, hormones, and steroids.

In certain embodiments, the therapeutic agent is an oncology drug, which may also be referred to as an anti-tumor drug, an anti-cancer drug, a tumor drug, an antineoplastic agent, or the like. Examples of oncology drugs that may be used according to the invention include, but are not limited to, adriamycin, alkeran, allopurinol, altretamine, amifostine, anastrozole, araC, arsenic trioxide, azathioprine, bexarotene, biCNU, bleomycin, busulfan intravenous, busulfan oral, capecitabine (Xeloda), carboplatin, carmustine, CCNU, celecoxib, chlorambucil, cisplatin, cladribine, cyclosporin A, cytarabine, cytosine arabinoside, daunorubicin, cytoxan, daunorubicin, dexamethasone, dexrazoxane, dodetaxel, doxorubicin, doxorubicin, DTIC, epirubicin, estramustine, etoposide phosphate, etoposide and VP-16, exemestane, FK506, fludarabine, fluorouracil, 5-FU, gemcitabine (Gemzar), gemtuzumab-ozogamicin, goserelin acetate, hydrea, hydroxyurea, idarubicin, ifosfamide, imatinib mesylate, interferon, irinotecan (Camptostar, CPT-111), letrozole, leucovorin, leustatin, leuprolide, levamisole, litretinoin, megastrol, melphalan, L-PAM, mesna, methotrexate, methoxsalen, mithramycin, mitomycin, mitoxantrone, nitrogen mustard, paclitaxel, pamidronate, Pegademase, pentostatin, porfimer sodium, prednisone, rituxan, streptozocin, STI-571, tamoxifen, taxotere, temozolamide, teniposide, VM-26, topotecan (Hycamtin), toremifene, tretinoin, ATRA, valrubicin, velban, vinblastine, vincristine, VP16, and vinorelbine. Other examples of oncology drugs that may be used according to the invention are ellipticin and ellipticin analogs or derivatives, epothilones, intracellular kinase inhibitors and camptothecins.

Nucleic Acid-Lipid Particles

In certain embodiments, lipid particles of the present invention are associated with a nucleic acid, resulting in a nucleic acid-lipid particle. In particular embodiments, the nucleic acid is fully encapsulated in the lipid particle. As used herein, the term "nucleic acid" is meant to include any oligonucleotide or polynucleotide. Fragments containing up to 50 nucleotides are generally termed oligonucleotides, and longer fragments are called polynucleotides. In particular embodiments, oligonucletoides of the present invention are 15-50 nucleotides in length.

In the context of this invention, the terms "polynucleotide" and "oligonucleotide" refer to a polymer or oligomer of nucleotide or nucleoside monomers consisting of naturally occurring bases, sugars and intersugar (backbone) linkages. The terms "polynucleotide" and "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

The nucleic acid that is present in a lipid-nucleic acid particle according to this invention includes any form of nucleic acid that is known. The nucleic acids used herein can be single-stranded DNA or RNA, or double-stranded DNA or RNA, or DNA-RNA hybrids. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include, e.g., antisense oligonucleotides, ribozymes, microRNA, and triplex-forming oligonucleotides. The nucleic acid that is present in a lipid-nucleic acid particle of this invention may include one or more of the oligonucleotide modifications described below.

Nucleic acids of the present invention may be of various lengths, generally dependent upon the particular form of nucleic acid. For example, in particular embodiments, plasmids or genes may be from about 1,000 to 100,000 nucleotide residues in length. In particular embodiments, oligonucleotides may range from about 10 to 100 nucleotides in length. In various related embodiments, oligonucleotides, single-stranded, double-stranded, and triple-stranded, may range in length from about 10 to about 50 nucleotides, from about 20 o about 50 nucleotides, from about 15 to about 30 nucleotides, from about 20 to about 30 nucleotides in length.

In particular embodiments, the oligonucleotide (or a strand thereof) of the present invention specifically hybridizes to or is complementary to a target polynucleotide. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility or expression therefrom, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, in other embodiments, this oligonucleotide includes 1, 2, or 3 base substitutions, e.g. mismatches, as compared to the region of a gene or mRNA sequence that it is targeting or to which it specifically hybridizes.

RNA Interference Nucleic Acids

In particular embodiments, nucleic acid-lipid particles of the present invention are associated with RNA interference (RNAi) molecules. RNA interference methods using RNAi molecules may be used to disrupt the expression of a gene or polynucleotide of interest. Small interfering RNA (siRNA) has essentially replaced antisense ODN and ribozymes as the next generation of targeted oligonucleotide drugs under development.

SiRNAs are RNA duplexes normally 16-30 nucleotides long that can associate with a cytoplasmic multi-protein complex known as RNAi-induced silencing complex (RISC). RISC loaded with siRNA mediates the degradation of homologous mRNA transcripts, therefore siRNA can be designed to knock down protein expression with high specificity. Unlike other antisense technologies, siRNA function through a natural mechanism evolved to control gene expression through non-coding RNA. This is generally considered to be the reason why their activity is more potent in vitro and in vivo than either antisense ODN or ribozymes. A variety of RNAi reagents, including siRNAs targeting clinically relevant targets, are currently under pharmaceutical development, as described, e.g., in de Fougerolles, A. et al., Nature Reviews 6:443-453 (2007).

While the first described RNAi molecules were RNA:RNA hybrids comprising both an RNA sense and an RNA antisense strand, it has now been demonstrated that DNA sense:RNA antisense hybrids, RNA sense:DNA antisense hybrids, and DNA:DNA hybrids are capable of mediating RNAi (Lamberton, J. S, and Christian, A. T., (2003) Molecular Biotechnology 24:111-119). Thus, the invention includes the use of RNAi molecules comprising any of these different types of double-stranded molecules. In addition, it is understood that RNAi molecules may be used and introduced to cells in a variety of forms. Accordingly, as used herein, RNAi molecules encompasses any and all molecules capable of inducing an RNAi response in cells, including, but not limited to, double-stranded oligonucleotides comprising two separate strands, i.e. a sense strand and an antisense strand, e.g., small interfering RNA (siRNA); double-stranded oligonucleotide comprising two separate strands that are linked together by non-nucleotidyl linker; oligonucleotides comprising a hairpin loop of complementary sequences, which forms a double-stranded region, e.g., shRNAi molecules, and expression vectors that express one or more polynucleotides capable of forming a double-stranded polynucleotide alone or in combination with another polynucleotide.

A "single strand siRNA compound" as used herein, is an siRNA compound which is made up of a single molecule. It may include a duplexed region, formed by intra-strand pairing, e.g., it may be, or include, a hairpin or pan-handle structure. Single strand siRNA compounds may be antisense with regard to the target molecule A single strand siRNA compound may be sufficiently long that it can enter the RISC and participate in RISC mediated cleavage of a target mRNA. A single strand siRNA compound is at least 14, and in other embodiments at least 15, 20, 25, 29, 35, 40, or 50 nucleotides in length. In certain embodiments, it is less than 200, 100, or 60 nucleotides in length.

Hairpin siRNA compounds will have a duplex region equal to or at least 17, 18, 19, 29, 21, 22, 23, 24, or 25 nucleotide pairs. The duplex region will may be equal to or less than 200, 100, or 50, in length. In certain embodiments, ranges for the duplex region are 15-30, 17 to 23, 19 to 23, and 19 to 21 nucleotides pairs in length. The hairpin may have a single strand overhang or terminal unpaired region. In certain embodiments, the overhangs are 2-3 nucleotides in length. In some embodiments, the overhang is at the sense side of the hairpin and in some embodiments on the antisense side of the hairpin.

A "double stranded siRNA compound" as used herein, is an siRNA compound which includes more than one, and in some cases two, strands in which interchain hybridization can form a region of duplex structure.

The antisense strand of a double stranded siRNA compound may be equal to or at least, 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length. As used herein, term "antisense strand" means the strand of an siRNA compound that is sufficiently complementary to a target molecule, e.g. a target RNA.

The sense strand of a double stranded siRNA compound may be equal to or at least 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length.

The double strand portion of a double stranded siRNA compound may be equal to or at least, 14, 15, 16 17, 18, 19, 20, 21, 22, 23, 24, 25, 29, 40, or 60 nucleotide pairs in length. It may be equal to or less than 200, 100, or 50, nucleotides pairs in length. Ranges may be 15-30, 17 to 23, 19 to 23, and 19 to 21 nucleotides pairs in length.

In many embodiments, the siRNA compound is sufficiently large that it can be cleaved by an endogenous molecule, e.g., by Dicer, to produce smaller siRNA compounds, e.g., siRNAs agents The sense and antisense strands may be chosen such that the double-stranded siRNA compound includes a single strand or unpaired region at one or both ends of the molecule. Thus, a double-stranded siRNA compound may contain sense and antisense strands, paired to contain an overhang, e.g., one or two 5' or 3' overhangs, or a 3' overhang of 1-3 nucleotides. The overhangs can be the result of one strand being longer than the other, or the result of two strands of the same length being staggered. Some embodiments will have at least one 3' overhang. In one embodiment, both ends of an siRNA molecule will have a 3' overhang. In some embodiments, the overhang is 2 nucleotides.

In certain embodiments, the length for the duplexed region is between 15 and 30, or 18, 19, 20, 21, 22, and 23 nucleotides in length, e.g., in the ssiRNA compound range discussed above. ssiRNA compounds can resemble in length and structure the natural Dicer processed products from long dsiRNAs. Embodiments in which the two strands of the ssiRNA compound are linked, e.g., covalently linked are also included. Hairpin, or other single strand structures which provide the required double stranded region, and a 3' overhang are also within the invention.

The siRNA compounds described herein, including double-stranded siRNA compounds and single-stranded siRNA compounds can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an ssiRNA compound of 21 to 23 nucleotides.

In one embodiment, an siRNA compound is "sufficiently complementary" to a target RNA, e.g., a target mRNA, such that the siRNA compound silences production of protein encoded by the target mRNA. In another embodiment, the siRNA compound is "exactly complementary" to a target RNA, e.g., the target RNA and the siRNA compound anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in certain embodiments, the siRNA compound specifically discriminates a single-nucleotide difference. In this case, the siRNA compound only mediates RNAi if exact complementary is found in the region (e.g., within 7 nucleotides of) the single-nucleotide difference.

MicroRNAs

Micro RNAs (miRNAs) are a highly conserved class of small RNA molecules that are transcribed from DNA in the genomes of plants and animals, but are not translated into protein. Processed miRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

The number of miRNA sequences identified to date is large and growing, illustrative examples of which can be found, for example, in: "*miRBase: microRNA sequences, targets and gene nomenclature*" Griffiths-Jones S, Grocock R J, van Dongen S, Bateman A, Enright A J. NAR, 2006, 34, Database Issue, D140-D144; "*The microRNA Registry*" Griffiths-Jones S, NAR, 2004, 32, Database Issue, D109-D111; and also at http://microrna.sanger.ac.uk/sequences/.

Antisense Oligonucleotides

In one embodiment, a nucleic acid is an antisense oligonucleotide directed to a target polynucleotide. The term "antisense oligonucleotide" or simply "antisense" is meant to include oligonucleotides that are complementary to a targeted polynucleotide sequence. Antisense oligonucleotides are single strands of DNA or RNA that are complementary to a chosen sequence, e.g. a target gene mRNA. Antisense oligonucleotides are thought to inhibit gene expression by binding to a complementary mRNA. Binding to the target mRNA can lead to inhibition of gene expression by through making the either by preventing translation of complementary mRNA strands by binding to it or by leading to degradation of the target mRNA Antisense DNA can be used to target a specific, complementary (coding or non-coding) RNA. If binding takes places this DNA/RNA hybrid can be degraded by the enzyme RNase H. In particular embodiment, antisense oligonucleotides contain from about 10 to about 50 nucleotides, more preferably about 15 to about 30 nucleotides. The term also encompasses antisense oligonucleotides that may not be exactly complementary to the desired target gene. Thus, the invention can be utilized in instances where non-target specific-activities are found with antisense, or where an antisense sequence containing one or more mismatches with the target sequence is the most preferred for a particular use.

Antisense oligonucleotides have been demonstrated to be effective and targeted inhibitors of protein synthesis, and, consequently, can be used to specifically inhibit protein synthesis by a targeted gene. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., Science. 1988 Jun. 10; 240(4858):1544-6; Vasanthakumar and Ahmed, Cancer Commun. 1989; 1(4):225-32; Penis et al., Brain Res Mol Brain Res. 1998 Jun. 15; 57(2):310-20; U.S. Pat. No. 5,801,154; U.S. Pat. No. 5,789,573; U.S. Pat. No. 5,718,709 and U.S. Pat. No. 5,610,288). Furthermore, antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683).

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, $T_m$, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., Nucleic Acids Res. 1997, 25(17):3389-402).

Antagomirs

Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate backbone and, for example, a cholesterol-moiety at 3'-end. Antagomirs may be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein in its entirety. Antagomir RNAs may be synthesized using standard solid phase oligonucleotide synthesis protocols. See U.S. patent application Ser. Nos. 11/502,158 and 11/657,341 (the disclosure of each of which are incorporated herein by reference).

An antagomir can include ligand-conjugated monomer subunits and monomers for oligonucleotide synthesis. Exemplary monomers are described in U.S. application Ser. No. 10/916,185, filed on Aug. 10, 2004. An antagomir can have a ZXY structure, such as is described in PCT Application No. PCT/US2004/07070 filed on Mar. 8, 2004. An antagomir can be complexed with an amphipathic moiety. Exemplary amphipathic moieties for use with oligonucleotide agents are described in PCT Application No. PCT/US2004/07070, filed on Mar. 8, 2004.

Aptamers

Aptamers are nucleic acid or peptide molecules that bind to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9 (1999), and Hermann and Patel, Science 287:820-5 (2000). Aptamers may be RNA or DNA based, and may include a riboswitch. A riboswitch is a part of an mRNA molecule that can directly bind a small target molecule, and whose binding of the target affects the gene's activity. Thus, an mRNA that contains a riboswitch is directly involved in regulating its own activity, depending on the presence or absence of its target molecule. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer may be prepared by any known method, including synthetic, recombinant, and purification methods, and may be used alone or in combination with other aptamers specific for the same target. Further, as described more fully herein, the term "aptamer" specifically includes "secondary aptamers" containing a consensus sequence derived from comparing two or more known aptamers to a given target.

Ribozymes

According to another embodiment of the invention, nucleic acid-lipid particles are associated with ribozymes. Ribozymes are RNA molecules complexes having specific catalytic domains that possess endonuclease activity (Kim and Cech, Proc Natl Acad Sci USA. 1987 December; 84(24): 8788-92; Forster and Symons, *Cell.* 1987 Apr. 24; 49(2):211-20). For example, a large number of ribozymes accelerate phosphoester transfer reactions with a high degree of specificity, often cleaving only one of several phosphoesters in an oligonucleotide substrate (Cech et al., Cell. 1981 December; 27(3 Pt 2):487-96; Michel and Westhof, J Mol. Biol. 1990 Dec. 5; 216(3):585-610; Reinhold-Hurek and Shub, Nature. 1992 May 14; 357(6374):173-6). This specificity has been attributed to the requirement that the substrate bind via specific base-pairing interactions to the internal guide sequence ("IGS") of the ribozyme prior to chemical reaction.

At least six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, a hepatitis δ virus, group I intron or RNaseP RNA (in association with an RNA guide sequence) or *Neurospora* VS RNA motif, for example. Specific examples of hammerhead motifs are described by Rossi et al. Nucleic Acids Res. 1992 Sep. 11; 20(17):4559-65. Examples of hairpin motifs are described by Hampel et al. (Eur. Pat. Appl. Publ. No. EP 0360257), Hampel and Tritz, Biochemistry 1989 Jun. 13; 28(12):4929-33; Hampel et al., Nucleic Acids Res. 1990 Jan. 25; 18(2):299-304 and U.S. Pat. No. 5,631,359. An example of the hepatitis virus motif is described by Perrotta and Been, Biochemistry. 1992 Dec. 1; 31(47):11843-52; an example of the RNaseP motif is described by Guerrier-Takada et al., Cell. 1983 December; 35(3 Pt 2):849-57; *Neurospora* VS RNA ribozyme motif is described by Collins (Saville and Collins, Cell. 1990 May 18; 61(4):685-96; Saville and Collins, Proc Natl Acad Sci USA. 1991 Oct. 1; 88(19):8826-30; Collins and Olive, Biochemistry. 1993 Mar. 23; 32(11):2795-9); and an example of the Group I intron is described in U.S. Pat. No. 4,987,071. Important characteristics of enzymatic nucleic acid molecules used according to the invention are that they have a specific substrate binding site which is complementary to one or more of the target gene DNA or RNA regions, and that they have nucleotide sequences within or surrounding that substrate binding site which impart an RNA cleaving activity to the molecule. Thus the ribozyme constructs need not be limited to specific motifs mentioned herein.

Methods of producing a ribozyme targeted to any polynucleotide sequence are known in the art. Ribozymes may be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

Ribozyme activity can be optimized by altering the length of the ribozyme binding arms or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Immunostimulatory Oligonucleotides

Nucleic acids associated with lipid particles of the present invention may be immunostimulatory, including immunostimulatory oligonucleotides (ISS; single- or double-stranded) capable of inducing an immune response when administered to a subject, which may be a mammal or other patient. ISS include, e.g., certain palindromes leading to hairpin secondary structures (see Yamamoto S., et al. (1992) J. Immunol. 148: 4072-4076), or CpG motifs, as well as other known ISS features (such as multi-G domains, see WO 96/11266).

The immune response may be an innate or an adaptive immune response. The immune system is divided into a more innate immune system, and acquired adaptive immune system of vertebrates, the latter of which is further divided into humoral cellular components. In particular embodiments, the immune response may be mucosal.

In particular embodiments, an immunostimulatory nucleic acid is only immunostimulatory when administered in combination with a lipid particle, and is not immunostimulatory when administered in its "free form." According to the present invention, such an oligonucleotide is considered to be immunostimulatory.

Immunostimulatory nucleic acids are considered to be non-sequence specific when it is not required that they specifically bind to and reduce the expression of a target polynucleotide in order to provoke an immune response. Thus, certain immunostimulatory nucleic acids may comprise a sequence corresponding to a region of a naturally occurring gene or mRNA, but they may still be considered non-sequence specific immunostimulatory nucleic acids.

In one embodiment, the immunostimulatory nucleic acid or oligonucleotide comprises at least one CpG dinucleotide. The oligonucleotide or CpG dinucleotide may be unmethylated or methylated. In another embodiment, the immunostimulatory nucleic acid comprises at least one CpG dinucleotide having a methylated cytosine. In one embodiment, the nucleic acid comprises a single CpG dinucleotide, wherein the cytosine in said CpG dinucleotide is methylated. In a specific embodiment, the nucleic acid comprises the sequence 5' TAACGTTGAGGGGCAT 3'. In an alternative embodiment, the nucleic acid comprises at least two CpG dinucleotides, wherein at least one cytosine in the CpG dinucleotides is methylated. In a further embodiment, each cytosine in the CpG dinucleotides present in the sequence is methylated. In another embodiment, the nucleic acid comprises a plurality of CpG dinucleotides, wherein at least one of said CpG dinucleotides comprises a methylated cytosine.

In one specific embodiment, the nucleic acid comprises the sequence 5' TTCCATGACGTTCCTGACGT 3'. In another specific embodiment, the nucleic acid sequence comprises the sequence 5' TCCATGACGTTCCTGACGT 3', wherein the two cytosines indicated in bold are methylated. In particular embodiments, the ODN is selected from a group of ODNs consisting of ODN #1, ODN #2, ODN #3, ODN #4, ODN #5, ODN #6, ODN #7, ODN #8, and ODN #9, as shown below.

TABLE 3

Exemplary Immunostimulatory Oligonucleotides (ODNs)

| ODN NAME | SEQ ID | ODN SEQUENCE (5'-3'). |
|---|---|---|
| ODN 1 human c-myc | NO:1. | 5'-TAACGTTGAGGGGCAT-3' |
| * ODN 1m | NO:2. | 5'-TAAZGTTGAGGGGCAT-3' |
| ODN 2 | NO:3. | 5'-TCCATGACGTTCCTGACGTT-3' |
| * ODN 2m | NO:4. | 5'-TCCATGAZGTTCCTGAZGTT-3' |
| ODN 3 | NO:5. | 5'-TAAGCATACGGGTGT-3' |
| ODN 5 | | 5'-AACGTT-3' |
| ODN 6 | NO:6. | 5'-GATGCTGTGTCGGGTCTCCGGGC-3' |
| ODN 7 | NO:7. | 5'-TCGTCGTTTTGTCGTTTTGTCGTT-3' |
| ODN 7m | NO:8. | 5'-TZGTZGTTTTGTZGTTTTGTZGTT-3' |
| ODN 8 | NO:9. | 5'-TCCAGGACTTCTCTCAGGTT-3' |
| ODN 9 | NO:10. | 5'-TCTCCCAGCGTGCGCCAT-3' |
| ODN 10 murine Intracellular Adhesion Molecule-1 | NO:11. | 5'-TGCATCCCCCAGGCCACCAT-3' |
| ODN 11 human Intracellular Adhesion Molecule-1 | NO:12. | 5'-GCCCAAGCTGGCATCCGTCA-3' |
| ODN 12 human Intracellular Adhesion Molecule-1 | NO:13. | 5'-GCCCAAGCTGGCATCCGTCA-3' |
| ODN 13 human erb-B-2 | NO:14. | 5'-GGT GCTCACTGC GGC-3' |
| ODN 14 human c-myc | NO:15. | 5'-AACC GTT GAG GGG CAT-3' |
| ODN 15 human c-myc | NO:16. | 5'-TAT GCT GTG CCG GGG TCT TCG GGC-3' |
| ODN 16 | NO:17. | 5'-GTGCCG GGGTCTTCGGGC-3' |
| ODN 17 human Insulin Growth Factor 1-Receptor | NO:18. | 5'-GGACCCTCCTCCGGAGCC-3' |
| ODN 18 human Insulin Growth Factor 1-Receptor | NO:19. | 5'-TCC TCC GGA GCC AGA CTT-3' |
| ODN 19 human Epidermal Growth Factor-Receptor | NO:20. | 5'-AAC GTT GAG GGG CAT-3' |
| ODN 20 Epidermal Growth Factor-Receptor | NO:21. | 5'-CCGTGGTCA TGCTCC-3' |

TABLE 3-continued

Exemplary Immunostimulatory Oligonucleotides (ODNs)

| ODN NAME | SEQ ID | ODN SEQUENCE (5'-3'). |
|---|---|---|
| ODN 21 human Vascular Endothelial Growth Factor | NO:22. | 5'-CAG CCTGGCTCACCG CCTTGG-3' |
| ODN 22 murine Phosphokinase C-alpha | NO:23. | 5'-CAG CCA TGG TTC CCC CCA AC-3' |
| ODN 23 | NO:24. | 5'-GTT CTC GCT GGT GAG TTT CA-3' |
| ODN 24 human Bcl-2 | NO:25. | 5'-TCT CCCAGCGTGCGCCAT-3' |
| ODN 25 human C-Raf-s | NO:26. | 5'-GTG CTC CAT TGA TGC-3' |
| ODN #26 human Vascular Endothelial Growth Factor Receptor-1 | NO:27. | 5'-GAGUUCUGAUGAGGCCGAAAGG-CCGAAAGUCUG-3' |
| ODN #27 | | 5'-RRCGYY-3' |
| ODN #28 | NO:28. | 5'-AACGTTGAGGGGCAT-3' |
| ODN #29 | NO:29. | 5'-CAACGTTATGGGAGA-3' |
| ODN #30 human c-myc | NO:30. | 5'-TAACGTTGAGGGGCAT-3' |

"Z" represents a methylated cytosine residue. ODN 14 is a 15-mer oligonucleotide and ODN 1 is the same oligonucleotide having a thymidine added onto the 5' end making ODN 1 into a 16-mer. No difference in biological activity between ODN 14 and ODN 1 has been detected and both exhibit similar immunostimulatory activity (Mui et al., 2001)

Additional specific nucleic acid sequences of oligonucleotides (ODNs) suitable for use in the compositions and methods of the invention are described in Raney et al., Journal of Pharmacology and Experimental Therapeutics, 298:1185-1192 (2001). In certain embodiments, ODNs used in the compositions and methods of the present invention have a phosphodiester ("PO") backbone or a phosphorothioate ("PS") backbone, and/or at least one methylated cytosine residue in a CpG motif.

Decoy Oligonucleotides

Because transcription factors recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to upregulate genes that are suppressed by the binding of a transcription factor. Examples of the utilization of decoy oligonucleotides may be found in Mann et al., J. Clin. Invest., 2000, 106: 1071-1075, which is expressly incorporated by reference herein, in its entirety Supermir A supermir refers to a single stranded, double stranded or partially double stranded oligomer or polymer of ribonucleic acid (RNA) or deoxyribonucleic acid (DNA) or both or modifications thereof, which has a nucleotide sequence that is substantially identical to an miRNA and that is antisense with respect to its target. This term includes oligonucleotides composed of naturally-occurring nucleobases, sugars and covalent internucleoside (backbone) linkages and which contain at least one non-naturally-occurring portion which functions similarly. Such modified or substituted oligonucleotides are preferred over native forms because of desirable properties such as, for example, enhanced cellular uptake, enhanced affinity for nucleic acid target and increased stability in the presence of nucleases. In a preferred embodiment, the supermir does not include a sense strand, and in another preferred embodiment, the supermir does not self-hybridize to a significant extent. An supermir featured in the invention can have secondary structure, but it is substantially single-stranded under physiological conditions. An supermir that is substantially single-stranded is single-stranded to the extent that less than about 50% (e.g., less than about 40%, 30%, 20%, 10%, or 5%) of the supermir is duplexed with itself. The supermir can include a hairpin segment, e.g., sequence, preferably at the 3' end can self hybridize and form a duplex region, e.g., a duplex region of at least 1, 2, 3, or 4 and preferably less than 8, 7, 6, or n nucleotides, e.g., 5 nucleotides. The duplexed region can be connected by a linker, e.g., a nucleotide linker, e.g., 3, 4, 5, or 6 dTs, e.g., modified dTs. In another embodiment the supermir is duplexed with a shorter oligo, e.g., of 5, 6, 7, 8, 9, or 10 nucleotides in length, e.g., at one or both of the 3' and 5' end or at one end and in the non-terminal or middle of the supermir.

miRNA Mimics miRNA mimics represent a class of molecules that can be used to imitate the gene silencing ability of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression. miRNA mimics can be designed as mature molecules (e.g. single stranded) or mimic precursors (e.g., pri- or pre-miRNAs) miRNA mimics can be comprised of nucleic acid (modified or modified nucleic acids) including oligonucleotides comprising, without limitation, RNA, modified RNA, DNA, modified DNA, locked nucleic acids, or 2'-O,4'-C-ethylene-bridged nucleic acids (ENA), or any combination of the above (including DNA-RNA hybrids). In addition, miRNA mimics can comprise conjugates that can affect delivery, intracellular compartmentalization, stability, specificity, functionality, strand usage, and/or potency. In one design, miRNA mimics are double stranded molecules (e.g., with a duplex region of between about 16 and about 31 nucleotides in length) and contain one or more sequences that have identity with the mature strand of a given miRNA. Modifications can comprise 2' modifications (including 2'-O methyl modifications and 2' F modifications) on one or both strands of the molecule and internucleotide modifications (e.g. phorphorthioate modifications) that enhance nucleic acid stability and/or specificity. In addition, miRNA mimics can include overhangs. The overhangs can consist of 1-6 nucleotides on either the 3' or 5' end of either strand and can be modified to enhance stability or functionality. In one embodiment, a miRNA mimic comprises a duplex region of between 16 and 31 nucleotides and one or more of the following chemical modification patterns: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3' overhang.

Antimir or miRNA Inhibitor.

The terms "antimir" "microRNA inhibitor", "miR inhibitor", or "inhibitor" are synonymous and refer to oligonucleotides or modified oligonucleotides that interfere with the ability of specific miRNAs. In general, the inhibitors are nucleic acid or modified nucleic acids in nature including oligonucleotides comprising RNA, modified RNA, DNA, modified DNA, locked nucleic acids (LNAs), or any combination of the above. Modifications include 2' modifications (including 2'-0 alkyl modifications and 2' F modifications) and internucleotide modifications (e.g. phosphorothioate modifications) that can affect delivery, stability, specificity, intracellular compartmentalization, or potency. In addition, miRNA inhibitors can comprise conjugates that can affect delivery, intracellular compartmentalization, stability, and/or potency. Inhibitors can adopt a variety of configurations including single stranded, double stranded (RNA/RNA or RNA/DNA duplexes), and hairpin designs, in general, microRNA inhibitors comprise contain one or more sequences or portions of sequences that are complementary or partially complementary with the mature strand (or strands) of the miRNA to be targeted, in addition, the miRNA inhibitor may also comprise additional sequences located 5' and 3' to the sequence that is the reverse complement of the mature miRNA. The additional sequences may be the reverse complements of the sequences that are adjacent to the mature miRNA in the pri-miRNA from which the mature miRNA is derived, or the additional sequences may be arbitrary sequences (having a mixture of A, G, C, or U). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. Micro-RNA inhibitors, when double stranded, may include mismatches between nucleotides on opposite strands. Furthermore, micro-RNA inhibitors may be linked to conjugate moieties in order to facilitate uptake of the inhibitor into a cell. For example, a micro-RNA inhibitor may be linked to cholesteryl 5-(bis(4-methoxyphenyl)(phenyl) methoxy)-3 hydroxypentylcarbamate) which allows passive uptake of a micro-RNA inhibitor into a cell. Micro-RNA inhibitors, including hairpin miRNA inhibitors, are described in detail in Vermeulen et al., "Double-Stranded Regions Are Essential Design Components Of Potent Inhibitors of RISC Function," RNA 13: 723-730 (2007) and in WO2007/095387 and WO 2008/036825 each of which is incorporated herein by reference in its entirety. A person of ordinary skill in the art can select a sequence from the database for a desired miRNA and design an inhibitor useful for the methods disclosed herein.

U1 Adaptor

U1 adaptor inhibit polyA sites and are bifunctional oligonucleotides with a target domain complementary to a site in the target gene's terminal exon and a 'U1 domain' that binds to the U1 smaller nuclear RNA component of the U1 snRNP (Goraczniak, et al., 2008, Nature Biotechnology, 27(3), 257-263, which is expressly incorporated by reference herein, in its entirety). U1 snRNP is a ribonucleoprotein complex that functions primarily to direct early steps in spliceosome formation by binding to the pre-mRNA exon-intron boundary (Brown and Simpson, 1998, Annu Rev Plant Physiol Plant Mol Biol 49:77-95). Nucleotides 2-11 of the 5'end of U1 snRNA base pair bind with the 5'ss of the pre mRNA. In one embodiment, oligonucleotides of the invention are U1 adaptors. In one embodiment, the U1 adaptor can be administered in combination with at least one other iRNA agent.

Oligonucleotide Modifications

Unmodified oligonucleotides may be less than optimal in some applications, e.g., unmodified oligonucleotides can be prone to degradation by e.g., cellular nucleases. Nucleases can hydrolyze nucleic acid phosphodiester bonds. However, chemical modifications of oligonucleotides can confer improved properties, and, e.g., can render oligonucleotides more stable to nucleases.

As oligonucleotides are polymers of subunits or monomers, many of the modifications described below occur at a position which is repeated within an oligonucleotide, e.g., a modification of a base, a sugar, a phosphate moiety, or the non-bridging oxygen of a phosphate moiety. It is not necessary for all positions in a given oligonucleotide to be uniformly modified, and in fact more than one of the aforementioned modifications may be incorporated in a single oligonucleotide or even at a single nucleoside within an oligonucleotide.

In some cases the modification will occur at all of the subject positions in the oligonucleotide but in many, and in fact in most cases it will not. By way of example, a modification may only occur at a 3' or 5' terminal position, may only occur in the internal region, may only occur in a terminal regions, e.g. at a position on a terminal nucleotide or in the last 2, 3, 4, 5, or 10 nucleotides of an oligonucleotide. A modification may occur in a double strand region, a single strand region, or in both. A modification may occur only in the double strand region of a double-stranded oligonucleotide or may only occur in a single strand region of a double-stranded oligonucleotide. E.g., a phosphorothioate modification at a non-bridging oxygen position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. The 5' end or ends can be phosphorylated.

A modification described herein may be the sole modification, or the sole type of modification included on multiple nucleotides, or a modification can be combined with one or more other modifications described herein. The modifications described herein can also be combined onto an oligonucleotide, e.g. different nucleotides of an oligonucleotide have different modifications described herein.

In some embodiments it is particularly preferred, e.g., to enhance stability, to include particular nucleobases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Specific modifications are discussed in more detail below.

The Phosphate Group

The phosphate group is a negatively charged species. The charge is distributed equally over the two non-bridging oxygen atoms. However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. In certain embodiments, one of the non-bridging phosphate oxygen atoms in the phosphate backbone moiety can be replaced by any of the following: S, Se, $BR_3$ (R is hydrogen, alkyl, aryl), C (i.e. an alkyl group, an aryl group, etc. . . . ), H, $NR_2$ (R is hydrogen, alkyl, aryl), or OR(R is alkyl or aryl). The phosphorous atom in an unmodified phosphate group is achiral. However, replacement of one of the non-bridging oxygens with one of the above atoms or groups of atoms renders the phosphorous atom chiral; in other words a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligoribonucleotides diastereomers. Thus, while not wishing to be bound by theory, modifications to both non-bridging oxygens, which eliminate the chiral center, e.g. phosphorodithioate formation, may be desirable in that they cannot produce diastereomer mixtures. Thus, the non-bridging oxygens can be independently any one of S, Se, B, C, H, N, or OR (R is alkyl or aryl).

The phosphate linker can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either linking oxygen or at both the linking oxygens. When the bridging oxygen is the 3'-oxygen of a nucleoside, replacement with carbon is preferred. When the bridging oxygen is the 5'-oxygen of a nucleoside, replacement with nitrogen is preferred.

Replacement of the Phosphate Group

The phosphate group can be replaced by non-phosphorus containing connectors. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Modified phosphate linkages where at least one of the oxygens linked to the phosphate has been replaced or the phosphate group has been replaced by a non-phosphorous group, are also referred to as "non phosphodiester backbone linkage."

Replacement of Ribophosphate Backbone

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the mophilino, cyclobutyl, pyrrolidine and peptide nucleic acid (PNA) nucleoside surrogates. A preferred surrogate is a PNA surrogate.

Sugar Modifications

A modified RNA can include modification of all or some of the sugar groups of the ribonucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O(CH$_2$CH$_2$O)$_n$CH$_2$CH$_2$OR; "locked" nucleic acids (LNA) in which the 2' hydroxyl is connected, e.g., by a methylene bridge, to the 4' carbon of the same ribose sugar; O-AMINE (AMINE=NH$_2$; alkylamino, dialkylamino, heterocyclyl, arylamino, diaryl amino, heteroaryl amino, or diheteroaryl amino, ethylene diamine, polyamino) and aminoalkoxy, O(CH$_2$)$_n$AMINE, (e.g., AMINE=NH$_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), (OCH$_2$CH$_2$OCH$_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. NH$_2$; alkylamino, dialkylamino, heterocyclyl, arylamino, diaryl amino, heteroaryl amino, diheteroaryl amino, or amino acid); NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino), —NHC(O) R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Preferred substitutents are 2'-methoxyethyl, 2'-OCH3, 2'-O-allyl, 2'-C-allyl, and 2'-fluoro.

The sugar group can also contain one or more carbons that possess the opposite stereochemical configuration than that of the corresponding carbon in ribose. Thus, an oligonucleotide can include nucleotides containing e.g., arabinose, as the sugar. The monomer can have an alpha linkage at the 1' position on the sugar, e.g., alpha-nucleosides. Oligonucleotides can also include "abasic" sugars, which lack a nucleobase at C-1'. These abasic sugars can also be further containing modifications at one or more of the constituent sugar atoms. Oligonucleotides can also contain one or more sugars that are in the L form, e.g. L-nucleosides.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

When a linker/phosphate-functional molecular entity-linker/phosphate array is interposed between two strands of a dsRNA, this array can substitute for a hairpin RNA loop in a hairpin-type RNA agent.

Terminal modifications useful for modulating activity include modification of the 5' end with phosphate or phosphate analogs. E.g., in preferred embodiments antisense strands of dsRNAs, are 5' phosphorylated or include a phosphoryl analog at the 5' prime terminus 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH) (O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-).

Terminal modifications can also be useful for monitoring distribution, and in such cases the preferred groups to be added include fluorophores, e.g., fluorscein or an Alexa dye, e.g., Alexa 488. Terminal modifications can also be useful for enhancing uptake, useful modifications for this include cholesterol. Terminal modifications can also be useful for cross-linking an RNA agent to another moiety; modifications useful for this include mitomycin C.

Nucleobases

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases", "modified bases", "non-natural bases" and "universal bases" described herein, can be employed. Examples include without limitation 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine,7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, $N^4$-acetyl cytosine, 2-thiocytosine, N6-methyladenine, N6-isopentyladenine, 2-methylthio-N-6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Cationic Groups

Modifications to oligonucleotides can also include attachment of one or more cationic groups to the sugar, base, and/or the phosphorus atom of a phosphate or modified phosphate backbone moiety. A cationic group can be attached to any atom capable of substitution on a natural, unusual or universal base. A preferred position is one that does not interfere with hybridization, i.e., does not interfere with the hydrogen bonding interactions needed for base pairing. A cationic group can be attached e.g., through the C2' position of a sugar or analogous position in a cyclic or acyclic sugar surrogate. Cationic groups can include e.g., protonated amino groups, derived from e.g., O-AMINE (AMINE=$NH_2$; alkylamino, dialkylamino, heterocyclyl, arylamino, diaryl amino, heteroaryl amino, or diheteroaryl amino, ethylene diamine, polyamino); aminoalkoxy, e.g., $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino); amino (e.g. $NH_2$; alkylamino, dialkylamino, heterocyclyl, arylamino, diaryl amino, heteroaryl amino, diheteroaryl amino, or amino acid); or $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino).

Placement within an Oligonucleotide

Some modifications may preferably be included on an oligonucleotide at a particular location, e.g., at an internal position of a strand, or on the 5' or 3' end of an oligonucleotide. A preferred location of a modification on an oligonucleotide, may confer preferred properties on the agent. For example, preferred locations of particular modifications may confer optimum gene silencing properties, or increased resistance to endonuclease or exonuclease activity.

One or more nucleotides of an oligonucleotide may have a 2'-5' linkage. One or more nucleotides of an oligonucleotide may have inverted linkages, e.g. 3'-3', 5'-5',2'-2' or 2'-3' linkages.

A double-stranded oligonucleotide may include at least one 5'-uridine-adenine-3' (5'-UA-3') dinucleotide wherein the uridine is a 2'-modified nucleotide, or a terminal 5'-uridine-guanine-3' (5'-UG-3') dinucleotide, wherein the 5'-uridine is a 2'-modified nucleotide, or a terminal 5'-cytidine-adenine-3' (5'-CA-3') dinucleotide, wherein the 5'-cytidine is a 2'-modified nucleotide, or a terminal 5'-uridine-uridine-3' (5'-UU-3') dinucleotide, wherein the 5'-uridine is a 2'-modified nucleotide, or a terminal 5'-cytidine-cytidine-3' (5'-CC-3') dinucleotide, wherein the 5'-cytidine is a 2'-modified nucleotide, or a terminal 5'-cytidine-uridine-3' (5'-CU-3') dinucleotide, wherein the 5'-cytidine is a 2'-modified nucleotide, or a terminal 5'-uridine-cytidine-3' (5'-UC-3') dinucleotide, wherein the 5'-uridine is a 2'-modified nucleotide. Double-stranded oligonucleotides including these modifications are particularly stabilized against endonuclease activity.

General References

The oligoribonucleotides and oligoribonucleosides used in accordance with this invention may be synthesized with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3,2'-O-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chian. Acta,* 1995, 78, 486-504; Beaucage, S. L. and Iyer, R. P., *Tetrahedron,* 1992, 48, 2223-2311 and Beaucage, S. L. and Iyer, R. P., *Tetrahedron,* 1993, 49, 6123-6194, or references referred to therein. Modification described in WO 00/44895, WO01/75164, or WO02/44321 can be used herein. The disclosure of all publications, patents, and published patent applications listed herein are hereby incorporated by reference.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. No. 5,256,775 or U.S. Pat. No. 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. *J. Org. Chem.* 2001, 66, 2789-2801. Preparation of sulfur bridged nucleotides is described in Sproat et al. *Nucleosides Nucleotides* 1988, 7,651 and Crosstick et al. *Tetrahedron Lett.* 1989, 30, 4693.

Sugar Group References

Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, *J. Acc. Chem. Res.* 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489,677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc. Perkin Trans.* 11972, 1991. Carbamate replacements are described in Stirchak, E. P. Nucleic Acids Res. 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. No. 5,539,083.

Terminal Modification References

Terminal modifications are described in Manoharan, M. et al. *Antisense and Nucleic Acid Drug Development* 12, 103-128 (2002) and references therein.

Nucleobases References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908.

Linkers

The term "linker" means an organic moiety that connects two parts of a compound. Linkers typically comprise a direct bond or an atom such as oxygen or sulfur, a unit such as $NR^1$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylherocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In one embodiment, the linker is —[(P-Q-R)$_q$—X—(P'-Q'-R')$_{q'}$]$_{q''}$-T-, wherein:

P, R, T, P', R' and T are each independently for each occurrence absent, CO, NH, O, S, OC(O), NHC(O), $CH_2$, $CH_2NH$, $CH_2O$; NHCH($R^a$)C(O), —C(O)—CH($R^a$)—NH—, CH=N—O,

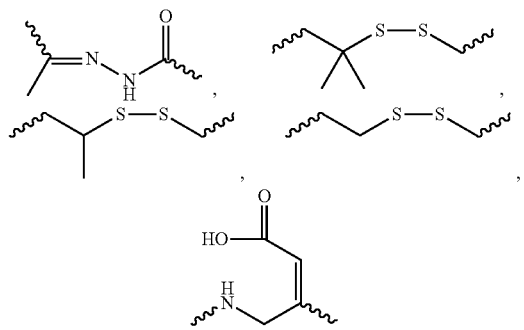

or heterocyclyl;

Q and Q' are each independently for each occurrence absent, —(CH$_2$)$_n$—, —C($R^1$)($R^2$)(CH$_2$)$_n$—, —(CH$_2$)$_n$C($R^1$)($R^2$)—, —(CH$_2$CH$_2$O)$_m$CH$_2$CH$_2$—, or —(CH$_2$CH$_2$O)$_m$CH$_2$CH$_2$NH—;

X is absent or a cleavable linking group;

$R^a$ is H or an amino acid side chain;

$R^1$ and $R^2$ are each independently for each occurrence H, $CH_3$, OH, SH or $N(R^N)_2$;

$R^N$ is independently for each occurrence H, methyl, ethyl, propyl, isopropyl, butyl or benzyl;

q, q' and q" are each independently for each occurrence 0-20 and wherein the repeating unit can be the same or different;

n is independently for each occurrence 1-20; and m is independently for each occurrence 0-50.

In one embodiment, the linker comprises at least one cleavable linking group.

In certain embodiments, the linker is a branched linker. The branchpoint of the branched linker may be at least trivalent, but may be a tetravalent, pentavalent or hexavalent atom, or a group presenting such multiple valencies. In certain embodiments, the branchpoint is, —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In other embodiment, the branchpoint is glycerol or glycerol derivative.

Cleavable Linking Groups

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum). Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NH-CHR$^B$C(O)—, where R$^A$ and R$^B$ are the R groups of the two adjacent amino acids. These candidates can be evaluated using methods analogous to those described above.

Ligands

A wide variety of entities can be coupled to the oligonucleotides and lipids of the present invention. Preferred moieties are ligands, which are coupled, preferably covalently, either directly or indirectly via an intervening tether.

In preferred embodiments, a ligand alters the distribution, targeting or lifetime of the molecule into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Ligands providing enhanced affinity for a selected target are also termed targeting ligands. Preferred ligands for conjugation to the lipids of the present invention are targeting ligands.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In certain embodiments, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In certain embodiments, the endosomolytic component may contain a chemical group (e.g., an amino acid) which will undergo a change in charge or protonation in response to a change in pH. The endosomolytic component may be linear or branched. Exemplary primary sequences of peptide based endosomolytic ligands are shown in Table 4.

TABLE 4

List of peptides with endosomolytic activity.

| Name | SEQ ID | Sequence (N to C) | Ref. |
|---|---|---|---|
| GALA | NO:31. | AALEALAEALEALAEALEALAEAAAAGGC | 1 |
| EALA | NO:32. | AALAEALAEALAEALAEALAEALAAAAGGC | 2 |
|  | NO:33. | ALEALAEALEALAEA | 3 |
| INF-7 | NO:34. | GLFEAIEGFIENGWEGMIWDYG | 4 |
| Inf HA-2 | NO:35. | GLFGAIAGFIENGWEGMIDGWYG | 5 |
| diINF-7 | NO:36. | GLF EAI EGFI ENGW EGMI DGWYGC GLF EAI EGFI ENGW EGMI DGWYGC | 5 |
| diINF3 | NO:37. | GLF EAI EGFI ENGW EGMI DGGC GLF EAI EGFI ENGW EGMI DGGC | 6 |
| GLF | NO:38. | GLFGALAEALAEALAEHLAEALAEALEALAAGGSC | 6 |
| GALA-INF3 | NO:39. | GLFEAIEGFIENGWEGLAEALAEALEALAAGGSC | 6 |
| INF-5 | NO:40. NO:41. | GLF EAI EGFI ENGW EGnI DG K GLF EAI EGFI ENGW EGnI DG | 4 | n, norleucine
References
1. Subbarao et al., Biochemistry, 1987, 26: 2964-2972.
2. Vogel et al., J. Am. Chem. Soc., 1996, 118: 1581-1586
3. Turk, M. J., Reddy, J. A. et al. (2002). Characterization of a novel pH-sensitive peptide that enhances drug release from folate-targeted liposomes at endosomal pHs. Biochim. Biophys. Acta 1559, 56-68.
4. Plank, C. Oberhauser, B. Mechtler, K. Koch, C. Wagner, E. (1994). The influence of endosome-disruptive peptides on gene transfer using synthetic virus-like gene transfer systems, J. Biol. Chem. 269 12918-12924.
5. Mastrobattista, E., Koning, G. A. et al. (2002). Functional characterization of an endosome-disruptive peptide and its application in cytosolic delivery of immunoliposome-entrapped proteins. J. Biol. Chem. 277, 27135-43.
6. Oberhauser, B., Plank, C. et al. (1995). Enhancing endosomal exit of nucleic acids using pH-sensitive viral fusion peptides. Deliv. Strategies Antisense Oligonucleotide Ther. 247-66.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics Ligands can include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer. Table 5 shows some examples of targeting ligands and their associated receptors.

TABLE 5

Targeting Ligands and their associated receptors

| Liver Cells | Ligand | Receptor |
|---|---|---|
| 1) Parenchymal Cell (PC) (Hepatocytes) | Galactose | ASGP-R (Asiologlycoprotein receptor) |
|  | Gal NAc (n-acetyl-galactosamine) | ASPG-R Gal NAc Receptor |
|  | Lactose | |
|  | Asialofetuin | ASPG-r |
| 2) Sinusoidal Endothelial Cell (SEC) | Hyaluronan | Hyaluronan receptor |
|  | Procollagen | Procollagen receptor |
|  | Negatively charged molecules | Scavenger receptors |
|  | Mannose | Mannose receptors |
|  | N-acetyl Glucosamine | Scavenger receptors |
|  | Immunoglobulins | Fc Receptor |
|  | LPS | CD14 Receptor |
|  | Insulin | Receptor mediated transcytosis |
|  | Transferrin | Receptor mediated transcytosis |
|  | Albumins | Non-specific |
|  | Sugar-Albumin conjugates | |
|  | Mannose-6-phosphate | Mannose-6-phosphate receptor |
| 3) Kupffer Cell (KC) | Mannose | Mannose receptors |
|  | Fucose | Fucose receptors |
|  | Albumins | Non-specific |
|  | Mannose-albumin conjugates | |

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the iRNA agent into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long (see Table 6, for example).

TABLE 6

Exemplary Cell Permeation Peptides.

| Cell Permeation Peptide | SEQ ID | Amino acid Sequence | Reference |
|---|---|---|---|
| Penetratin | NO:42. | RQIKIWFQNRRMKWKK | Derossi et al., J. Biol. Chem. 269: 10444, 1994 |
| Tat fragment (48-60) | NO:43. | GRKKRRQRRRPPQC | Vives et al., J. Biol. Chem., 272: 16010, 1997 |
| Signal Sequence-based peptide | NO:44. | GALFLGWLGAAGSTMGAWSQPKKKRKV | Chaloin et al., Biochem. Biophys. Res. Commun., 243: 601, 1998 |
| PVEC | NO:45. | LLIILRRRIRKQAHAHSK | Elmquist et al., Exp. Cell Res., 269: 237, 2001 |
| Transportan | NO:46. | GWTLNSAGYLLKINLKALAALAKKIL | Pooga et al., FASEB J., 12: 67, 1998 |
| Amphiphilic model peptide | NO:47. | KLALKLALKALKAALKLA | Oehlke et al., Mol. Ther., 2: 339, 2000 |
| Arg$_9$ | NO:48. | RRRRRRRRR | Mitchell et al., J. Pept. Res., 56: 318, 2000 |
| Bacterial cell wall permeating | NO:49. | KFFKFFKFFK | |
| LL-37 | NO:50. | LLGDFFRKSKEKIGKEFKRIVQRIKDFLRNLVPRTES | |
| Cecropin P1 | NO:51. | SWLSKTAKKLENSAKKRISEGIAIAIQGGPR | |
| α-defensin | NO:52. | ACYCRIPACIAGERRYGTCIYQGRLWAFCC | |
| b-defensin | NO:53. | DHYNCVSSGGQCLYSACPIFTKIQGTCYRGKAKCCK | |
| Bactenecin | NO:54. | RKCRIVVIRVCR | |
| PR-39 | NO:55. | RRRPRPPYLPRPRPPPFFPPRLPPRIPPGFPPRFPPRFPGKR-NH2 | |
| Indolicidin | NO:56. | ILPWKWPWWPWRR-NH2 | |

These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO:57.). An RFGF analogue (e.g., amino acid sequence AALLPVLLAAP (SEQ ID NO:57.)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO:57.)) and the *Droso-* phila Antennapedia protein (RQIKIWFQNRRMKWKK (SEQ ID NO:57.)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an iRNA agent to tumors of a variety of other tissues, including the lung, kidney, spleen, or liver (Aoki et al., Cancer Gene Therapy 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., Jour. Nucl. Med., 42:326-336, 2001).

Peptides that target markers enriched in proliferating cells can be used. E.g., RGD containing peptides and peptidomimetics can target cancer cells, in particular cells that exhibit an $\alpha v\beta 3$ integrin. Thus, one could use RGD peptides, cyclic peptides containing RGD, RGD peptides that include D-amino acids, as well as synthetic RGD mimics. In addition to RGD, one can use other moieties that target the $\alpha v\beta 3$ integrin ligand. Generally, such ligands can be used to control proliferating cells and angiogeneis. Preferred conjugates of this type ligands that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide tethered to an iRNA agent and/or the carrier oligomer can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, *S. clava* peptides, hagfish intestinal antimicrobial peptides (HFIAPs), magainines, brevinins-2, dermaseptins, melittins, pleurocidin, H$_2$A peptides, *Xenopus* peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an apatamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycarboxylates, polyacations, masked oligo or poly cations or anions, acetals, polyacetals, ketals/polyketyals, orthoesters, polymers with masked or unmasked cationic or anionic charges, dendrimers with masked or unmasked cationic or anionic charges.

PK modulator stands for pharmacokinetic modulator. PK modulator include lipophiles, bile acids, steroids, phospholipid analogues, peptides, protein binding agents, PEG, vitamins etc. Examplary PK modulator include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbone are also amenable to the present invention as ligands (e.g. as PK modulating ligands).

In addition, aptamers that bind serum components (e.g. serum proteins) are also amenable to the present invention as PK modulating ligands.

Other ligands amenable to the invention are described in copending applications U.S. Ser. No. 10/916,185, filed Aug. 10, 2004; U.S. Ser. No. 10/946,873, filed Sep. 21, 2004; U.S. Ser. No. 10/833,934, filed Aug. 3, 2007; U.S. Ser. No. 11/115, 989 filed Apr. 27, 2005 and U.S. Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the oligonucleotides various places, for example, 3'-end, 5'-end, and/or at an internal position. In preferred embodiments, the ligand is attached to the oligonucleotides via an intervening tether. The ligand or tethered ligand may be present on a monomer when said monomer is incorporated into the growing strand. In some embodiments, the ligand may be incorporated via coupling to a "precursor" monomer after said "precursor" monomer has been incorporated into the growing strand. For example, a monomer having, e.g., an amino-terminated tether (i.e., having no associated ligand), e.g., TAP-$(CH_2)_nNH_2$ may be incorporated into a growing sense or antisense strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

For double-stranded oligonucleotides, ligands can be attached to one or both strands. In some embodiments, a double-stranded iRNA agent contains a ligand conjugated to the sense strand. In other embodiments, a double-stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligomeric compounds. Generally, an oligomeric compound is attached to a conjugate moiety by contacting a reactive group (e.g., OH, SH, amine, carboxyl, aldehyde, and the like) on the oligomeric compound with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

Representative United States patents that teach the preparation of oligonucleotide conjugates include, but are not limited to, U.S. Pat. Nos. 4,828,979; 4,948,882; 5,218, 105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578, 718; 5,608,046; 4,587,044; 4,605,735; 4,667,025; 4,762,779; 4,789,737; 4,824,941; 4,835,263; 4,876,335; 4,904, 582; 4,958,013; 5,082,830; 5,112,963; 5,214,136; 5,082, 830; 5,112,963; 5,149,782; 5,214,136; 5,245,022; 5,254, 469; 5,258,506; 5,262,536; 5,272,250; 5,292,873; 5,317,098; 5,371,241, 5,391,723; 5,416,203, 5,451,463; 5,510, 475; 5,512,667; 5,514,785; 5,565,552; 5,567,810; 5,574, 142; 5,585,481; 5,587,371; 5,595,726; 5,597,696; 5,599,923; 5,599,928; 5,672,662; 5,688,941; 5,714,166; 6,153, 737; 6,172,208; 6,300,319; 6,335,434; 6,335,437; 6,395,437; 6,444,806; 6,486,308; 6,525,031; 6,528,631; 6,559,279; each of which is herein incorporated by reference.

Characteristic of Nucleic Acid-Lipid Particles

In certain embodiments, the present invention relates to methods and compositions for producing lipid-encapsulated nucleic acid particles in which nucleic acids are encapsulated within a lipid layer. Such nucleic acid-lipid particles, incorporating siRNA oligonucleotides, are characterized using a variety of biophysical parameters including: (1) drug to lipid ratio; (2) encapsulation efficiency; and (3) particle size. High drug to lipid rations, high encapsulation efficiency, good nuclease resistance and serum stability and controllable particle size, generally less than 200 nm in diameter are desirable. In addition, the nature of the nucleic acid polymer is of significance, since the modification of nucleic acids in an effort to impart nuclease resistance adds to the cost of therapeutics while in many cases providing only limited resistance. Unless stated otherwise, these criteria are calculated in this specification as follows:

Nucleic acid to lipid ratio is the amount of nucleic acid in a defined volume of preparation divided by the amount of lipid in the same volume. This may be on a mole per mole basis or on a weight per weight basis, or on a weight per mole basis. For final, administration-ready formulations, the nucleic acid:lipid ratio is calculated after dialysis, chromatography and/or enzyme (e.g., nuclease) digestion has been employed to remove as much of the external nucleic acid as possible;

Encapsulation efficiency refers to the drug to lipid ratio of the starting mixture divided by the drug to lipid ratio of the final, administration competent formulation. This is a measure of relative efficiency. For a measure of absolute efficiency, the total amount of nucleic acid added to the starting mixture that ends up in the administration competent formulation, can also be calculated. The amount of lipid lost during the formulation process may also be calculated. Efficiency is a measure of the wastage and expense of the formulation; and Size indicates the size (diameter) of the particles formed. Size distribution may be determined using quasi-elastic light scattering (QELS) on a Nicomp Model 370 sub-micron particle sizer. Particles under 200 nm are preferred for distribution to neo-vascularized (leaky) tissues, such as neoplasms and sites of inflammation.

Pharmaceutical Compositions

The lipid particles of present invention, particularly when associated with a therapeutic agent, may beformulated as a pharmaceutical composition, e.g., which further comprises a pharmaceutically acceptable diluent, excipient, or carrier, such as physiological saline or phosphate buffer, selected in accordance with the route of administration and standard pharmaceutical practice.

In particular embodiments, pharmaceutical compositions comprising the lipid-nucleic acid particles of the invention are prepared according to standard techniques and further comprise a pharmaceutically acceptable carrier. Generally, normal saline will be employed as the pharmaceutically acceptable carrier. Other suitable carriers include, e.g., water, buffered water, 0.9% saline, 0.3% glycine, and the like, including glycoproteins for enhanced stability, such as albumin, lipoprotein, globulin, etc. In compositions comprising saline or other salt containing carriers, the carrier is preferably added following lipid particle formation. Thus, after the lipid-nucleic acid compositions are formed, the compositions can be diluted into pharmaceutically acceptable carriers such as normal saline.

The resulting pharmaceutical preparations may be sterilized by conventional, well known sterilization techniques. The aqueous solutions can then be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the lipidic suspension may include lipid-protective agents which protect lipids against free-radical and lipid-peroxidative damages on storage. Lipophilic free-radical quenchers, such as α-tocopherol and water-soluble iron-specific chelators, such as ferrioxamine, are suitable.

The concentration of lipid particle or lipid-nucleic acid particle in the pharmaceutical formulations can vary widely, i.e., from less than about 0.01%, usually at or at least about 0.05-5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, complexes composed of irritating lipids may be diluted to low concentrations to lessen inflammation at the site of administration. In one group of embodiments, the nucleic acid will have an attached label and will be used for diagnosis (by indicating the presence of complementary nucleic acid). In this instance, the amount of complexes administered will depend upon the particular label used, the disease state being diagnosed and the judgement of the clinician but will generally be between about 0.01 and about 50 mg per kilogram of body weight, preferably between about 0.1 and about 5 mg/kg of body weight.

As noted above, the lipid-therapeutic agent (e.g., nucleic acid) particles of the invention may include polyethylene glycol (PEG)-modified phospholipids, PEG-ceramide, or ganglioside $G_{M1}$-modified lipids or other lipids effective to prevent or limit aggregation. Addition of such components does not merely prevent complex aggregation. Rather, it may also provide a means for increasing circulation lifetime and increasing the delivery of the lipid-nucleic acid composition to the target tissues.

The present invention also provides lipid-therapeutic agent compositions in kit form. The kit will typically be comprised of a container that is compartmentalized for holding the various elements of the kit. The kit will contain the particles or pharmaceutical compositions of the present invention, preferably in dehydrated or concentrated form, with instructions for their rehydration or dilution and administration. In certain embodiments, the particles comprise the active agent, while in other embodiments, they do not.

Methods of Manufacture

The methods and compositions of the invention make use of certain cationic lipids, the synthesis, preparation and characterization of which is described below and in the accompanying Examples. In addition, the present invention provides methods of preparing lipid particles, including those associated with a therapeutic agent, e.g., a nucleic acid. In the methods described herein, a mixture of lipids is combined with a buffered aqueous solution of nucleic acid to produce an intermediate mixture containing nucleic acid encapsulated in lipid particles wherein the encapsulated nucleic acids are present in a nucleic acid/lipid ratio of about 3 wt % to about 25 wt %, preferably 5 to 15 wt %. The intermediate mixture may optionally be sized to obtain lipid-encapsulated nucleic acid particles wherein the lipid portions are unilamellar vesicles, preferably having a diameter of 30 to 150 nm, more preferably about 40 to 90 nm. The pH is then raised to neutralize at least a portion of the surface charges on the lipid-nucleic acid particles, thus providing an at least partially surface-neutralized lipid-encapsulated nucleic acid composition.

As described above, several of these cationic lipids are amino lipids that are charged at a pH below the $pK_a$ of the amino group and substantially neutral at a pH above the $pK_a$. These cationic lipids are termed titratable cationic lipids and can be used in the formulations of the invention using a two-step process. First, lipid vesicles can be formed at the lower pH with titratable cationic lipids and other vesicle components in the presence of nucleic acids. In this manner, the vesicles will encapsulate and entrap the nucleic acids. Second, the surface charge of the newly formed vesicles can be neutralized by increasing the pH of the medium to a level above the $pK_a$ of the titratable cationic lipids present, i.e., to physiological pH or higher. Particularly advantageous aspects of this process include both the facile removal of any surface adsorbed nucleic acid and a resultant nucleic acid delivery vehicle which has a neutral surface. Liposomes or lipid particles having a neutral surface are expected to avoid rapid clearance from circulation and to avoid certain toxicities which are associated with cationic liposome preparations. Additional details concerning these uses of such titratable cationic lipids in the formulation of nucleic acid-lipid particles are provided in U.S. Pat. No. 6,287,591 and U.S. Pat. No. 6,858,225, incorporated herein by reference.

It is further noted that the vesicles formed in this manner provide formulations of uniform vesicle size with high content of nucleic acids. Additionally, the vesicles have a size range of from about 30 to about 150 nm, more preferably about 30 to about 90 nm.

Without intending to be bound by any particular theory, it is believed that the very high efficiency of nucleic acid encapsulation is a result of electrostatic interaction at low pH. At acidic pH (e.g. pH 4.0) the vesicle surface is charged and binds a portion of the nucleic acids through electrostatic interactions. When the external acidic buffer is exchanged for a more neutral buffer (e.g., pH 7.5) the surface of the lipid particle or liposome is neutralized, allowing any external nucleic acid to be removed. More detailed information on the formulation process is provided in various publications (e.g., U.S. Pat. No. 6,287,591 and U.S. Pat. No. 6,858,225).

In view of the above, the present invention provides methods of preparing lipid/nucleic acid formulations. In the methods described herein, a mixture of lipids is combined with a buffered aqueous solution of nucleic acid to produce an intermediate mixture containing nucleic acid encapsulated in lipid particles, e.g., wherein the encapsulated nucleic acids are present in a nucleic acid/lipid ratio of about 10 wt % to about 20 wt %. The intermediate mixture may optionally be sized to obtain lipid-encapsulated nucleic acid particles wherein the lipid portions are unilamellar vesicles, preferably having a diameter of 30 to 150 nm, more preferably about 40 to 90 nm. The pH is then raised to neutralize at least a portion of the surface charges on the lipid-nucleic acid particles, thus providing an at least partially surface-neutralized lipid-encapsulated nucleic acid composition.

In certain embodiments, the mixture of lipids includes at least two lipid components: a first lipid component of the present invention that is selected from among lipids which have a pKa such that the lipid is cationic at pH below the pKa and neutral at pH above the pKa, and a second lipid component that is selected from among lipids that prevent particle aggregation during lipid-nucleic acid particle formation. In particular embodiments, the amino lipid is a novel cationic lipid of the present invention.

In preparing the nucleic acid-lipid particles of the invention, the mixture of lipids is typically a solution of lipids in an organic solvent. This mixture of lipids can then be dried to form a thin film or lyophilized to form a powder before being hydrated with an aqueous buffer to form liposomes. Alternatively, in a preferred method, the lipid mixture can be solubilized in a water miscible alcohol, such as ethanol, and this ethanolic solution added to an aqueous buffer resulting in spontaneous liposome formation. In most embodiments, the alcohol is used in the form in which it is commercially available. For example, ethanol can be used as absolute ethanol (100%), or as 95% ethanol, the remainder being water. This method is described in more detail in U.S. Pat. No. 5,976,567).

In one exemplary embodiment, the mixture of lipids is a mixture of cationic lipids, neutral lipids (other than a cationic lipid), a sterol (e.g., cholesterol) and a PEG-modified lipid (e.g., a PEG-DMG or PEG-DMA) in an alcohol solvent. In preferred embodiments, the lipid mixture consists essentially of a cationic lipid, a neutral lipid, cholesterol and a PEG-modified lipid in alcohol, more preferably ethanol. In further preferred embodiments, the first solution consists of the above lipid mixture in molar ratios of about 20-70% cationic lipid: 5-45% neutral lipid:20-55% cholesterol:0.5-15% PEG-modified lipid. In still further preferred embodiments, the first solution consists essentially of a lipid chosen from Table 1 or Table 2, DSPC, Chol and PEG-DMG or PEG-DMA, more preferably in a molar ratio of about 20-60% cationic lipid: 5-25% DSPC:25-55% Chol:0.5-15% PEG-DMG or PEG-DMA. In particular embodiments, the molar lipid ratio is approximately 40/10/40/10 (mol % cationic lipid/DSPC/Chol/PEG-DMG or PEG-DMA), 35/15/40/10 (mol % cationic lipid/DSPC/Chol/PEG-DMG or PEG-DMA) or 52/13/30/5 (mol % cationic lipid/DSPC/Chol/PEG-DMG or PEG-DMA). In another group of preferred embodiments, the neutral lipid in these compositions is replaced with POPC, DPPC, DOPE or SM.

In accordance with the invention, the lipid mixture is combined with a buffered aqueous solution that may contain the nucleic acids. The buffered aqueous solution of is typically a solution in which the buffer has a pH of less than the $pK_a$ of the protonatable lipid in the lipid mixture. Examples of suitable buffers include citrate, phosphate, acetate, and MES. A particularly preferred buffer is citrate buffer. Preferred buffers will be in the range of 1-1000 mM of the anion, depending on the chemistry of the nucleic acid being encapsulated, and optimization of buffer concentration may be significant to achieving high loading levels (see, e.g., U.S. Pat. No. 6,287,591 and U.S. Pat. No. 6,858,225). Alternatively, pure water acidified to pH 5-6 with chloride, sulfate or the like may be useful. In this case, it may be suitable to add 5% glucose, or another non-ionic solute which will balance the osmotic potential across the particle membrane when the particles are dialyzed to remove ethanol, increase the pH, or mixed with a pharmaceutically acceptable carrier such as normal saline. The amount of nucleic acid in buffer can vary, but will typically be from about 0.01 mg/mL to about 200 mg/mL, more preferably from about 0.5 mg/mL to about 50 mg/mL.

The mixture of lipids and the buffered aqueous solution of therapeutic nucleic acids is combined to provide an intermediate mixture. The intermediate mixture is typically a mixture of lipid particles having encapsulated nucleic acids. Additionally, the intermediate mixture may also contain some portion of nucleic acids which are attached to the surface of the lipid particles (liposomes or lipid vesicles) due to the ionic attraction of the negatively-charged nucleic acids and positively-charged lipids on the lipid particle surface (the amino lipids or other lipid making up the protonatable first lipid component are positively charged in a buffer having a pH of less than the $pK_a$, of the protonatable group on the lipid). In one group of preferred embodiments, the mixture of lipids is an alcohol solution of lipids and the volumes of each of the solutions is adjusted so that upon combination, the resulting alcohol content is from about 20% by volume to about 45% by volume. The method of combining the mixtures can include any of a variety of processes, often depending upon the scale of formulation produced. For example, when the total volume is about 10-20 mL or less, the solutions can be combined in a test tube and stirred together using a vortex mixer. Large-scale processes can be carried out in suitable production scale glassware.

Optionally, the lipid-encapsulated therapeutic agent (e.g., nucleic acid) complexes which are produced by combining the lipid mixture and the buffered aqueous solution of therapeutic agents (nucleic acids) can be sized to achieve a desired size range and relatively narrow distribution of lipid particle sizes. Preferably, the compositions provided herein will be sized to a mean diameter of from about 70 to about 200 nm, more preferably about 90 to about 130 nm. Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles (SUVs) less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size determination. For certain methods herein, extrusion is used to obtain a uniform vesicle size.

Extrusion of liposome compositions through a small-pore polycarbonate membrane or an asymmetric ceramic membrane results in a relatively well-defined size distribution. Typically, the suspension is cycled through the membrane one or more times until the desired liposome complex size distribution is achieved. The liposomes may be extruded through successively smaller-pore membranes, to achieve a gradual reduction in liposome size. In some instances, the lipid-nucleic acid compositions which are formed can be used without any sizing.

In particular embodiments, methods of the present invention further comprise a step of neutralizing at least some of the surface charges on the lipid portions of the lipid-nucleic acid compositions. By at least partially neutralizing the surface charges, unencapsulated nucleic acid is freed from the lipid particle surface and can be removed from the composition using conventional techniques. Preferably, unencapsulated and surface adsorbed nucleic acids are removed from the resulting compositions through exchange of buffer solutions. For example, replacement of a citrate buffer (pH about 4.0, used for forming the compositions) with a HEPES-buffered saline (HBS pH about 7.5) solution, results in the neutralization of liposome surface and nucleic acid release from the surface. The released nucleic acid can then be removed via chromatography using standard methods, and then switched into a buffer with a pH above the pKa of the lipid used.

Optionally the lipid vesicles (i.e., lipid particles) can be formed by hydration in an aqueous buffer and sized using any of the methods described above prior to addition of the nucleic acid. As described above, the aqueous buffer should be of a pH below the pKa of the amino lipid. A solution of the nucleic acids can then be added to these sized, preformed vesicles. To allow encapsulation of nucleic acids into such "pre-formed" vesicles the mixture should contain an alcohol, such as ethanol. In the case of ethanol, it should be present at a concentration of about 20% (w/w) to about 45% (w/w). In addition, it may be necessary to warm the mixture of pre-formed vesicles and nucleic acid in the aqueous buffer-ethanol mixture to a temperature of about 25° C. to about 50° C. depending on the composition of the lipid vesicles and the nature of the nucleic acid. It will be apparent to one of ordinary skill in the art that optimization of the encapsulation process to achieve a desired level of nucleic acid in the lipid vesicles will require manipulation of variable such as ethanol concentration and temperature. Examples of suitable conditions for nucleic acid encapsulation are provided in the Examples. Once the nucleic acids are encapsulated within the preformed vesicles, the external pH can be increased to at least partially neutralize the surface charge. Unencapsulated and surface adsorbed nucleic acids can then be removed as described above.

Method of Use

The lipid particles of the present invention may be used to deliver a therapeutic agent to a cell, in vitro or in vivo. In particular embodiments, the therapeutic agent is a nucleic acid, which is delivered to a cell using a nucleic acid-lipid particles of the present invention. While the following description o various methods of using the lipid particles and related pharmaceutical compositions of the present invention are exemplified by description related to nucleic acid-lipid particles, it is understood that these methods and compositions may be readily adapted for the delivery of any therapeutic agent for the treatment of any disease or disorder that would benefit from such treatment.

In certain embodiments, the present invention provides methods for introducing a nucleic acid into a cell. Preferred nucleic acids for introduction into cells are siRNA, immunestimulating oligonucleotides, plasmids, antisense and ribozymes. These methods may be carried out by contacting the particles or compositions of the present invention with the cells for a period of time sufficient for intracellular delivery to occur.

The compositions of the present invention can be adsorbed to almost any cell type. Once adsorbed, the nucleic acid-lipid particles can either be endocytosed by a portion of the cells, exchange lipids with cell membranes, or fuse with the cells. Transfer or incorporation of the nucleic acid portion of the complex can take place via any one of these pathways. Without intending to be limited with respect to the scope of the invention, it is believed that in the case of particles taken up into the cell by endocytosis the particles then interact with the endosomal membrane, resulting in destabilization of the endosomal membrane, possibly by the formation of non-bilayer phases, resulting in introduction of the encapsulated nucleic acid into the cell cytoplasm. Similarly in the case of direct fusion of the particles with the cell plasma membrane, when fusion takes place, the liposome membrane is integrated into the cell membrane and the contents of the liposome combine with the intracellular fluid. Contact between the cells and the lipid-nucleic acid compositions, when carried out in vitro, will take place in a biologically compatible medium. The concentration of compositions can vary widely depending on the particular application, but is generally between about 1 μmol and about 10 mmol. In certain embodiments, treatment of the cells with the lipid-nucleic acid compositions will generally be carried out at physiological temperatures (about 37° C.) for periods of time from about 1 to 24 hours, preferably from about 2 to 8 hours. For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

In one group of embodiments, a lipid-nucleic acid particle suspension is added to 60-80% confluent plated cells having a cell density of from about $10^3$ to about $10^5$ cells/mL, more preferably about $2 \times 10^4$ cells/mL. The concentration of the suspension added to the cells is preferably of from about 0.01 to 20 μg/mL, more preferably about 1 μg/mL.

In another embodiment, the lipid particles of the invention can be may be used to deliver a nucleic acid to a cell or cell line (for example, a tumor cell line). Non-limiting examples of such cell lines include: HELA (ATCC Cat N: CCL-2), KB (ATCC Cat N: CCL-17), HEP3B (ATCC Cat N: HB-8064), SKOV-3 (ATCC Cat N: HTB-77), HCT-116 (ATCC Cat N: CCL-247), HT-29 (ATCC Cat N: HTB-38), PC-3 (ATCC Cat N: CRL-1435), A549 (ATCC Cat N: CCL-185), MDA-MB-231 (ATCC Cat N: HTB-26).

Typical applications include using well known procedures to provide intracellular delivery of siRNA to knock down or silence specific cellular targets. Alternatively applications include delivery of DNA or mRNA sequences that code for therapeutically useful polypeptides. In this manner, therapy is provided for genetic diseases by supplying deficient or absent gene products (i.e., for Duchenne's dystrophy, see Kunkel, et al., *Brit. Med. Bull.* 45(3):630-643 (1989), and for cystic fibrosis, see Goodfellow, *Nature* 341:102-103 (1989)). Other uses for the compositions of the present invention include introduction of antisense oligonucleotides in cells (see, Bennett, et al., *Mol. Pharm.* 41:1023-1033 (1992)).

Alternatively, the compositions of the present invention can also be used for deliver of nucleic acids to cells in vivo, using methods which are known to those of skill in the art. With respect to delivery of DNA or mRNA sequences, Zhu, et al., *Science* 261:209-211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature* 362:250-256 (1993), incorporated herein by reference, describes the delivery of the cystic fibrosis transmembrane conductance regulator (CFTR) gene to epithelia of the airway and to alveoli in the lung of mice, using liposomes. Brigham, et al., *Am. J. Med. Sci.* 298:278-281 (1989), incorporated herein by reference, describes the in vivo transfection of lungs of mice with a functioning prokaryotic gene encoding the intracellular enzyme, chloramphenicol acetyltransferase (CAT). Thus, the compositions of the invention can be used in the treatment of infectious diseases.

For in vivo administration, the pharmaceutical compositions are preferably administered parenterally, i.e., intraarticularly, intravenously, intraperitoneally, subcutaneously, or intramuscularly. In particular embodiments, the pharmaceutical compositions are administered intravenously or intraperitoneally by a bolus injection. For one example, see Stadler, et al., U.S. Pat. No. 5,286,634, which is incorporated herein by reference. Intracellular nucleic acid delivery has also been discussed in Straubringer, et al., METHODS IN ENZYMOLOGY, Academic Press, New York. 101:512-527 (1983); Mannino, et al., *Biotechniques* 6:682-690 (1988); Nicolau, et al., *Crit. Rev. Ther. Drug Carrier Syst.* 6:239-271 (1989), and Behr, *Acc. Chem. Res.* 26:274-278 (1993). Still other methods of administering lipid-based therapeutics are described in, for example, Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578.

In other methods, the pharmaceutical preparations may be contacted with the target tissue by direct application of the preparation to the tissue. The application may be made by topical, "open" or "closed" procedures. By "topical," it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The lipid-nucleic acid compositions can also be administered in an aerosol inhaled into the lungs (see, Brigham, et al., *Am. J. Sci.* 298(4):278-281 (1989)) or by direct injection at the site of disease (Culver, Human Gene Therapy, MaryAnn Liebert, Inc., Publishers, New York. pp. 70-71 (1994)).

The methods of the present invention may be practiced in a variety of hosts. Preferred hosts include mammalian species, such as humans, non-human primates, dogs, cats, cattle, horses, sheep, and the like.

Dosages for the lipid-therapeutic agent particles of the present invention will depend on the ratio of therapeutic agent to lipid and the administrating physician's opinion based on age, weight, and condition of the patient.

In one embodiment, the present invention provides a method of modulating the expression of a target polynucleotide or polypeptide. These methods generally comprise contacting a cell with a lipid particle of the present invention that is associated with a nucleic acid capable of modulating the expression of a target polynucleotide or polypeptide. As used herein, the term "modulating" refers to altering the expression of a target polynucleotide or polypeptide. In different embodiments, modulating can mean increasing or enhancing, or it can mean decreasing or reducing. Methods of measuring the level of expression of a target polynucleotide or polypeptide are known and available in the arts and include, e.g., methods employing reverse transcription-polymerase chain reaction (RT-PCR) and immunohistochemical techniques. In particular embodiments, the level of expression of a target polynucleotide or polypeptide is increased or reduced by at least 10%, 20%, 30%, 40%, 50%, or greater than 50% as compared to an appropriate control value.

For example, if increased expression of a polypeptide desired, the nucleic acid may be an expression vector that includes a polynucleotide that encodes the desired polypeptide. On the other hand, if reduced expression of a polynucleotide or polypeptide is desired, then the nucleic acid may be, e.g., an antisense oligonucleotide, siRNA, or microRNA that comprises a polynucleotide sequence that specifically hybridizes to a polnucleotide that encodes the target polypeptide, thereby disrupting expression of the target polynucleotide or polypeptide. Alternatively, the nucleic acid may be a plasmid that expresses such an antisense oligonucletoide, siRNA, or microRNA.

In one particular embodiment, the present invention provides a method of modulating the expression of a polypeptide by a cell, comprising providing to a cell a lipid particle that consists of or consists essentially of a lipid chosen from Table 1 or Table 2, DSPC, Chol and PEG-DMG or PEG-DMA, e.g., in a molar ratio of about 20-60% cationic lipid: 5-25% DSPC: 25-55% Chol:0.5-15% PEG-DMG or PEG-DMA, wherein the lipid particle is associated with a nucleic acid capable of modulating the expression of the polypeptide. In particular embodiments, the molar lipid ratio is approximately 40/10/40/10 (mol % cationic lipid/DSPC/Chol/PEG-DMG or PEG-DMA), 35/15/40/10 (mol % cationic lipid/DSPC/PEG-DMG or PEG-DMA) or 52/13/30/5 (mol % cationic lipid/DSPC/Chol/PEG-DMG or PEG-DMA). In another group of embodiments, the neutral lipid in these compositions is replaced with POPC, DPPC, DOPE or SM.

In particular embodiments, the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof, such that the expression of the polypeptide is reduced.

In other embodiments, the nucleic acid is a plasmid that encodes the polypeptide or a functional variant or fragment thereof, such that expression of the polypeptide or the functional variant or fragment thereof is increased.

In related embodiments, the present invention provides a method of treating a disease or disorder characterized by overexpression of a polypeptide in a subject, comprising providing to the subject a pharmaceutical composition of the present invention, wherein the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

In one embodiment, the pharmaceutical composition comprises a lipid particle that consists of or consists essentially of a lipid chosen from Table 1 or Table 2, DSPC, Chol and PEG-DMG or PEG-DMA, e.g., in a molar ratio of about 20-60% cationic lipid: 5-25% DSPC:25-55% Chol:0.5-15% PEG-DMG or PEG-DMA, wherein the lipid particle is associated with the therapeutic nucleic acid. In particular embodiments, the molar lipid ratio is approximately 40/10/40/10 (mol % cationic lipid/DSPC/Chol/PEG-DMG or PEG-DMA), 35/15/40/10 (mol % cationic lipid/DSPC/Chol/PEG-DMG or PEG-DMA) or 52/13/30/5 (mol % cationic lipid/DSPC/Chol/PEG-DMG or PEG-DMA). In another group of embodiments, the neutral lipid in these compositions is replaced with POPC, DPPC, DOPE or SM.

In another related embodiment, the present invention includes a method of treating a disease or disorder characterized by underexpression of a polypeptide in a subject, comprising providing to the subject a pharmaceutical composition of the present invention, wherein the therapeutic agent is a plasmid that encodes the polypeptide or a functional variant or fragment thereof.

In one embodiment, the pharmaceutical composition comprises a lipid particle that consists of or consists essentially of a lipid chosen from Table 1 or Table 2, DSPC, Chol and PEG-DMG or PEG-DMA, e.g., in a molar ratio of about 20-60% cationic lipid: 5-25% DSPC:25-55% Chol:0.5-15% PEG-DMG or PEG-DMA, wherein the lipid particle is associated with the therapeutic nucleic acid. In particular embodiments, the molar lipid ratio is approximately 40/10/40/10 (mol % cationic lipid/DSPC/Chol/PEG-DMG or PEG-DMA), 35/15/40/10 (mol % cationic lipid/DSPC/Chol/PEG-DMG or PEG-DMA) or 52/13/30/5 (mol % cationic lipid/DSPC/Chol/PEG-DMG or PEG-DMA). In another group of embodiments, the neutral lipid in these compositions is replaced with POPC, DPPC, DOPE or SM.

The present invention further provides a method of inducing an immune response in a subject, comprising providing to the subject the pharmaceutical composition of the present invention, wherein the therapeutic agent is an immunostimulatory oligonucleotide. In certain embodiments, the immune response is a humoral or mucosal immune response. In one embodiment, the pharmaceutical composition comprises a lipid particle that consists of or consists essentially of a lipid chosen from Table 1 or Table 2, DSPC, Chol and PEG-DMG or PEG-DMA, e.g., in a molar ratio of about 20-60% cationic lipid: 5-25% DSPC:25-55% Chol:0.5-15% PEG-DMG or PEG-DMA, wherein the lipid particle is associated with the therapeutic nucleic acid. In particular embodiments, the molar lipid ratio is approximately 40/10/40/10 (mol % cationic lipid/DSPC/Chol/PEG-DMG or PEG-DMA), 35/15/40/10 (mol % cationic lipid/DSPC/Chol/PEG-DMG or PEG-DMA) or 52/13/30/5 (mol % cationic lipid/DSPC/Chol/PEG-DMG or PEG-DMA). In another group of embodiments, the neutral lipid in these compositions is replaced with POPC, DPPC, DOPE or SM.

In further embodiments, the pharmaceutical composition is provided to the subject in combination with a vaccine or antigen. Thus, the present invention itself provides vaccines comprising a lipid particle of the present invention, which comprises an immunostimulatory oligonucleotide, and is also associated with an antigen to which an immune response is desired. In particular embodiments, the antigen is a tumor antigen or is associated with an infective agent, such as, e.g., a virus, bacteria, or parasite.

A variety of tumor antigens, infections agent antigens, and antigens associated with other disease are well known in the art and examples of these are described in references cited herein. Examples of antigens suitable for use in the present invention include, but are not limited to, polypeptide antigens and DNA antigens. Specific examples of antigens are Hepatitis A, Hepatitis B, small pox, polio, anthrax, influenza, typhus, tetanus, measles, rotavirus, diphtheria, pertussis, tuberculosis, and rubella antigens. In a preferred embodiment, the antigen is a Hepatitis B recombinant antigen. In other aspects, the antigen is a Hepatitis A recombinant antigen. In another aspect, the antigen is a tumor antigen. Examples of such tumor-associated antigens are MUC-1, EBV antigen and antigens associated with Burkitt's lymphoma. In a further aspect, the antigen is a tyrosinase-related protein tumor antigen recombinant antigen. Those of skill in the art will know of other antigens suitable for use in the present invention.

Tumor-associated antigens suitable for use in the subject invention include both mutated and non-mutated molecules that may be indicative of single tumor type, shared among several types of tumors, and/or exclusively expressed or overexpressed in tumor cells in comparison with normal cells. In addition to proteins and glycoproteins, tumor-specific patterns of expression of carbohydrates, gangliosides, glycolipids and mucins have also been documented. Exemplary tumor-associated antigens for use in the subject cancer vaccines include protein products of oncogenes, tumor suppressor genes and other genes with mutations or rearrangements unique to tumor cells, reactivated embryonic gene products, oncofetal antigens, tissue-specific (but not tumor-specific) differentiation antigens, growth factor receptors, cell surface carbohydrate residues, foreign viral proteins and a number of other self proteins.

Specific embodiments of tumor-associated antigens include, e.g., mutated antigens such as the protein products of the Ras p21 protooncogenes, tumor suppressor p53 and BCR-abl oncogenes, as well as CDK4, MUM1, Caspase 8, and Beta catenin; overexpressed antigens such as galectin 4, galectin 9, carbonic anhydrase, Aldolase A, PRAME, Her2/neu, ErbB-2 and KSA, oncofetal antigens such as alpha fetoprotein (AFP), human chorionic gonadotropin (hCG); self antigens such as carcinoembryonic antigen (CEA) and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESO1, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn. Also included as tumor-associated antigens herein are whole cell and tumor cell lysates as well as immunogenic portions thereof, as well as immunoglobulin idiotypes expressed on monoclonal proliferations of B lymphocytes for use against B cell lymphomas.

Pathogens include, but are not limited to, infectious agents, e.g., viruses, that infect mammals, and more particularly humans. Examples of infectious virus include, but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronoviridae (e.g., coronaviruses); Rhabdoviradae (e.g., vesicular stomatitis viruses, rabies viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxyiridae (variola viruses, vaccinia viruses, pox viruses); and Iridoviridae (e.g., African swine fever virus);

and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Also, gram negative and gram positive bacteria serve as antigens in vertebrate animals. Such gram positive bacteria include, but are not limited to *Pasteurella* species, Staphylococci species, and *Streptococcus* species. Gram negative bacteria include, but are not limited to, *Escherichia coli*, *Pseudomonas* species, and *Salmonella* species. Specific examples of infectious bacteria include but are not limited to: *Helicobacter pyloris*, *Borelia burgdorferi*, *Legionella pneumophilia*, *Mycobacteria* sps (e.g., *M. tuberculosis*, *M. avium*, *M. intracellulare*, *M. kansaii*, *M. gordonae*), *Staphylococcus aureus*, *Neisseria gonorrhoeae*, *Neisseria meningitidis*, *Listeria monocytogenes*, *Streptococcus pyogenes* (Group A *Streptococcus*), *Streptococcus agalactiae* (Group B *Streptococcus*), *Streptococcus* (viridans group), *Streptococcus faecalis*, *Streptococcus bovis*, *Streptococcus* (anaerobic sps.), *Streptococcus pneumoniae*, pathogenic *Campylobacter* sp., *Enterococcus* sp., *Haemophilus infuenzae*, *Bacillus antracis*, *corynebacterium diphtheriae*, *corynebacterium* sp., *Erysipelothrix rhusiopathiae*, *Clostridium perfringers*, *Clostridium tetani*, *Enterobacter aerogenes*, *Klebsiella pneumoniae*, *Pasturella multocida*, *Bacteroides* sp., *Fusobacterium nucleatum*, *Streptobacillus moniliformis*, *Treponema pallidium*, *Treponema pertenue*, *Leptospira*, *Rickettsia*, and *Actinomyces israelli*.

Additional examples of pathogens include, but are not limited to, infectious fungi that infect mammals, and more particularly humans. Examples of infectious fingi include, but are not limited to: *Cryptococcus neoformans*, *Histoplasma capsulatum*, *Coccidioides immitis*, *Blastomyces dermatitidis*, *Chlamydia trachomatis*, *Candida albicans*. Examples of infectious parasites include *Plasmodium* such as *Plasmodium falciparum*, *Plasmodium malariae*, *Plasmodium ovale*, and *Plasmodium vivax*. Other infectious organisms (i.e., protists) include *Toxoplasma gondii*.

In one embodiment, the formulations of the invention can be used to silence or modulate a target gene such as but not limited to FVII, Eg5, PCSK9, TPX2, apoB, SAA, TTR, RSV, PDGF beta gene, Erb-B gene, Src gene, CRK gene, GRB2 gene, RAS gene, MEKK gene, .INK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, SORT1 gene, XBP1 gene, topoisomerase I gene, topoisomerase II alpha gene, p73 gene, p21(WAF1/CIP1) gene, p27(KIP1) gene, PPM1D gene, RAS gene, caveolin I gene, MIB I gene, MTAI gene, M68 gene, tumor suppressor genes, p53 tumor suppressor gene, p53 family member DN-p63, pRb tumor suppressor gene, APC1 tumor suppressor gene, BRCA1 tumor suppressor gene, PTEN tumor suppressor gene, mLL fusion gene, BCR/ABL fusion gene, TEL/AML1 fusion gene, EWS/FLI1 fusion gene, TLS/FUS1 fusion gene, PAX3/FKHR fusion gene, AML1/ETO fusion gene, alpha v-integrin gene, Flt-1 receptor gene, tubulin gene, Human Papilloma Virus gene, a gene required for Human Papilloma Virus replication, Human Immunodeficiency Virus gene, a gene required for Human Immunodeficiency Virus replication, Hepatitis A Virus gene, a gene required for Hepatitis A Virus replication, Hepatitis B Virus gene, a gene required for Hepatitis B Virus replication, Hepatitis C Virus gene, a gene required for Hepatitis C Virus replication, Hepatitis D Virus gene, a gene required for Hepatitis D Virus replication, Hepatitis E Virus gene, a gene required for Hepatitis E Virus replication, Hepatitis F Virus gene, a gene required for Hepatitis F Virus replication, Hepatitis G Virus gene, a gene required for Hepatitis G Virus replication, Hepatitis H Virus gene, a gene required for Hepatitis H Virus replication, Respiratory Syncytial Virus gene, a gene that is required for Respiratory Syncytial Virus replication, Herpes Simplex Virus gene, a gene that is required for Herpes Simplex Virus replication, herpes Cytomegalovirus gene, a gene that is required for herpes Cytomegalovirus replication, herpes Epstein Barr Virus gene, a gene that is required for herpes Epstein Barr Virus replication, Kaposi's Sarcoma-associated Herpes Virus gene, a gene that is required for Kaposi's Sarcoma-associated Herpes Virus replication, JC Virus gene, human gene that is required for JC Virus replication, myxovirus gene, a gene that is required for myxovirus gene replication, rhinovirus gene, a gene that is required for rhinovirus replication, coronavirus gene, a gene that is required for coronavirus replication, West Nile Virus gene, a gene that is required for West Nile Virus replication, St. Louis Encephalitis gene, a gene that is required for St. Louis Encephalitis replication, Tick-borne encephalitis virus gene, a gene that is required for Tick-borne encephalitis virus replication, Murray Valley encephalitis virus gene, a gene that is required for Murray Valley encephalitis virus replication, dengue virus gene, a gene that is required for dengue virus gene replication, Simian Virus 40 gene, a gene that is required for Simian Virus 40 replication, Human T Cell Lymphotropic Virus gene, a gene that is required for Human T Cell Lymphotropic Virus replication, Moloney-Murine Leukemia Virus gene, a gene that is required for Moloney-Murine Leukemia Virus replication, encephalomyocarditis virus gene, a gene that is required for encephalomyocarditis virus replication, measles virus gene, a gene that is required for measles virus replication, Vericella zoster virus gene, a gene that is required for Vericella zoster virus replication, adenovirus gene, a gene that is required for adenovirus replication, yellow fever virus gene, a gene that is required for yellow fever virus replication, poliovirus gene, a gene that is required for poliovirus replication, poxvirus gene, a gene that is required for poxvirus replication, *plasmodium* gene, a gene that is required for *plasmodium* gene replication, *Mycobacterium ulcerans* gene, a gene that is required for *Mycobacterium ulcerans* replication, *Mycobacterium tuberculosis* gene, a gene that is required for *Mycobacterium tuberculosis* replication, *Mycobacterium leprae* gene, a gene that is required for *Mycobacterium leprae* replication, *Staphylococcus aureus* gene, a gene that is required for *Staphylococcus aureus* replication, *Streptococcus pneumoniae* gene, a gene that is required for *Streptococcus pneumoniae* replication, *Streptococcus pyogenes* gene, a gene that is required for *Streptococcus pyogenes* replication, *Chlamydia pneumoniae* gene, a gene that is required for *Chlamydia pneumoniae* replication, *Mycoplasma pneumoniae* gene, a gene that is required for *Mycoplasma pneumoniae* replication, an integrin gene, a selectin gene, complement system gene, chemokine gene, chemokine receptor gene, GCSF gene, Gro1 gene, Gro2 gene, Gro3 gene, PF4 gene, MIG gene, Pro-Platelet Basic Protein gene, MIP-1I gene, MIP-1J gene, RANTES gene, MCP-1 gene, MCP-2 gene, MCP-3 gene, CMBKR1 gene, CMBKR2 gene, CMBKR3 gene, CMBKR5v, AIF-1 gene, I-309 gene, a gene to a component of an ion channel, a gene to a neurotransmitter receptor, a gene to a neurotransmitter ligand, amyloid-family gene, presenilin gene, HD gene, DRPLA gene, SCA1 gene, SCA2 gene, MJD1 gene, CACNL1A4 gene, SCAT gene, SCA8 gene, allele gene found in LOH cells, or one allele gene of a polymorphic gene.

DEFINITIONS

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as (C1-C20)alkanoyl (e.g., formyl, acetyl, propionyl, butyryl, valeryl, caproyl, t-butylacetyl, etc.), (C3-C20)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.).

The term "aryl" refers to an aromatic monocyclic, bicyclic, or tricyclic hydrocarbon ring system, wherein any ring atom can be substituted. Examples of aryl moieties include, but are not limited to, phenyl, naphthyl, anthracenyl, and pyrenyl.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heteroaryl groups herein described may also contain fused rings that share a common carbon-carbon bond. The term "alkylheterocyle" refers to a heteroaryl wherein at least one of the ring atoms is substituted with alkyl, alkenyl or alkynyl The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, oxo, thioxy, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted. Exemplary substituents include amino, alkylamino, dialkylamino, and cyclic amino compounds.

"Halogen" means fluoro, chloro, bromo and iodo.

The terms "alkylamine" and "dialkylamine" refer to —NH(alkyl) and —N (alkyl)$_2$ radicals respectively.

The term "alkylphosphate" refers to —O—P(Q')(Q")-O—R, wherein Q' and Q" are each independently O, S, N(R)$_2$, optionally substituted alkyl or alkoxy; and R is optionally substituted alkyl, ω-aminoalkyl or ω-(substituted)aminoalkyl.

The term "alkylphosphorothioate" refers to an alkylphosphate wherein at least one of Q' or Q" is S.

The term "alkylphosphonate" refers to an alkylphosphate wherein at least one of Q' or Q" is alkyl.

The term "hydroxyalkyl" means —O-alkyl radical.

The term "alkylheterocycle" refers to an alkyl where at least one methylene has been replaced by a heterocycle.

The term "ω-aminoalkyl" refers to -alkyl-NH$_2$ radical. And the term "ω-(substituted)aminoalkyl refers to an ω-aminoalkyl wherein at least one of the H on N has been replaced with alkyl.

The term "ω-phosphoalkyl" refers to -alkyl-O—P(Q')(Q")—O—R, wherein Q' and Q" are each independently O or S and R optionally substituted alkyl.

The term "ω-thiophosphoalkyl refers to ω-phosphoalkyl wherein at least one of Q' or Q" is S.

In some embodiments, the methods of the invention may require the use of protecting groups. Protecting group methodology is well known to those skilled in the art (see, for example, PROTECTIVE GROUPS IN ORGANIC SYNTHESIS, Green, T. W. et. al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

The compounds of the present invention may be prepared by known organic synthesis techniques, including the methods described in more detail in the Examples.

EXAMPLES

Example 1

Synthesis of methanesulfonic acid octadeca-9,12-dienyl ester 2

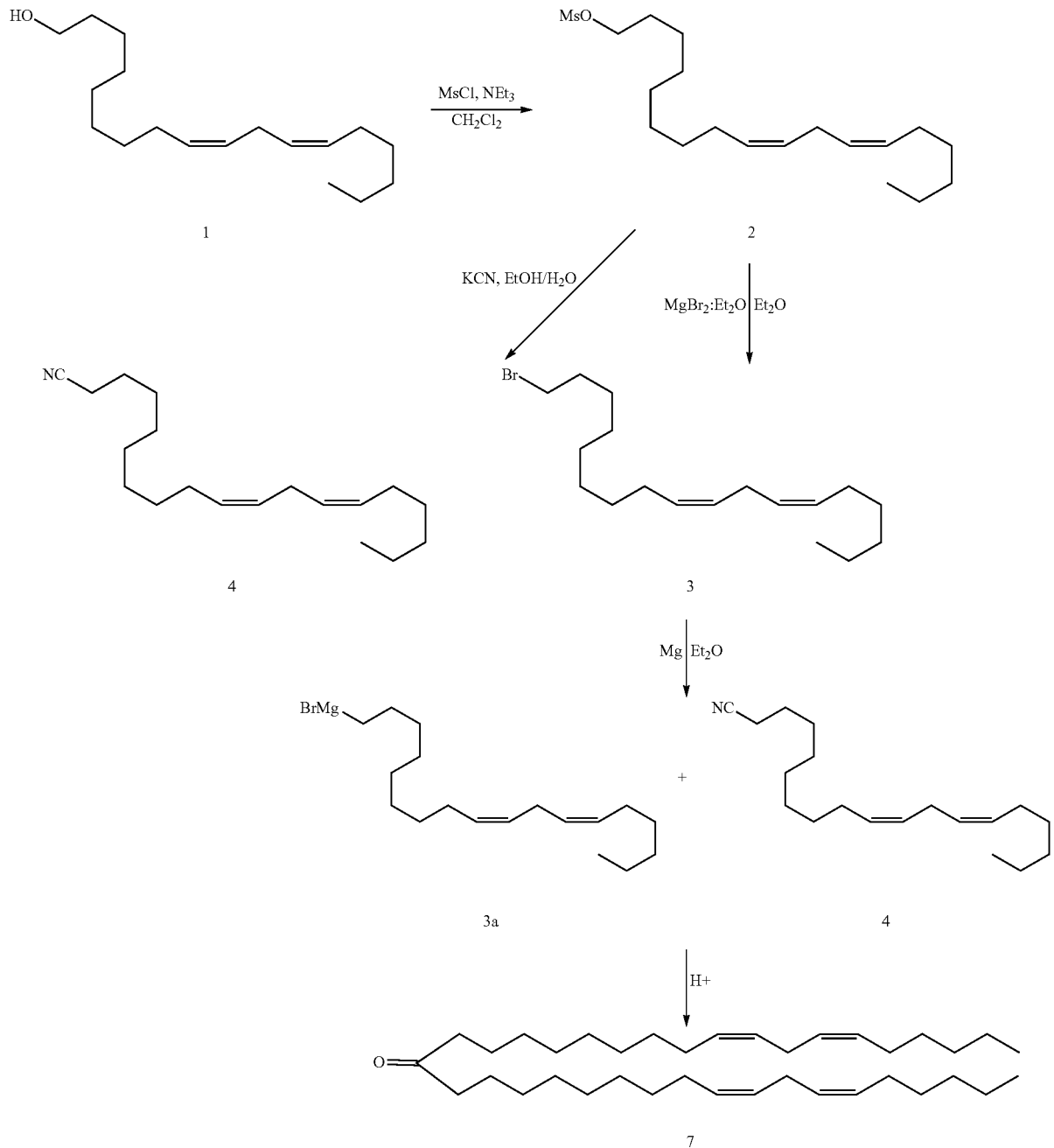

To a solution of the alcohol 1 (26.6 g, 100 mmol) in dichloromethane (100 mL), triethylamine (13.13 g, 130 mmol) was added and this solution was cooled in an ice-bath. To this cold solution, a solution of mesyl chloride (12.6 g, 110 mmol) in dichloromethane (60 mL) was added dropwise and after the completion of the addition, the reaction mixture was allowed to warm to ambient temperature and stirred overnight. The TLC of the reaction mixture showed the completion of the reaction. The reaction mixture was diluted with dichloromethane (200 mL), washed with water (200 mL), satd. NaHCO$_3$ (200 mL), brine (100 mL) and dried (NaSO$_4$). The organic layer was concentrated to get the crude product which was purified by column chromatography (silica gel) using 0-10% Et$_2$O in hexanes. The pure product fractions were combined and concentrated to obtain the pure product 2 as colorless oil (30.6 g, 89%). $^1$H NMR (CDCl$_3$, 400 MHz) δ=5.42-5.21 (m, 4H), 4.20 (t, 2H), 3.06 (s, 3H), 2.79 (t, 2H), 2.19-2.00 (m, 4H), 1.90-1.70 (m, 2H), 1.06-1.18 (m, 18H), 0.88 (t, 3H). $^{13}$C NMR (CDCl$_3$) δ=130.76, 130.54, 128.6, 128.4, 70.67, 37.9, 32.05, 30.12, 29.87, 29.85, 29.68, 29.65, 29.53, 27.72, 27.71, 26.15, 25.94, 23.09, 14.60. MS. Molecular weight calculated for C$_{19}$H$_{36}$O$_3$S, Cal. 344.53. Found 343.52 (M−H$^−$).

Synthesis of 18-Bromo-octadeca-6,9-diene 3

The mesylate 2 (13.44 g, 39 mmol) was dissolved in anhydrous ether (500 mL) and to it the MgBr.Et$_2$O complex (30.7 g, 118 mmol) was added under argon and the mixture was refluxed under argon for 26 h after which the TLC showed the completion of the reaction. The reaction mixture was diluted with ether (200 mL) and ice-cold water (200 mL) was added to this mixture and the layers were separated. The organic layer was washed with 1% aqueous K$_2$CO$_3$ (100 mL), brine (100 mL) and dried (Anhyd. Na$_2$SO$_4$). Concentration of the organic layer provided the crude product which was further purified by column chromatography (silica gel) using 0-1% Et$_2$O in hexanes to isolate the bromide 3 (12.6 g, 94%) as a colorless oil. $^1$H NMR (CDCl$_3$, 400 MHz) δ=5.41-5.29 (m, 4H), 4.20 (d, 2H), 3.40 (t, J=7 Hz, 2H), 2.77 (t, J=6.6 Hz, 2H), 2.09-2.02 (m, 4H), 1.88-1.00 (m, 2H), 1.46-1.27 (m, 18H), 0.88 (t, J=3.9 Hz, 3H). $^{13}$C NMR (CDCl$_3$) δ=130.41, 130.25, 128.26, 128.12, 34.17, 33.05, 31.75, 29.82, 29.57, 29.54, 29.39, 28.95, 28.38, 27.42, 27.40, 25.84, 22.79, 14.28.

Synthesis of 18-Cyano-octadeca-6,9-diene 4

To a solution of the mesylate (3.44 g, 10 mmol) in ethanol (90 mL), a solution of KCN (1.32 g, 20 mmol) in water (10 mL) was added and the mixture was refluxed for 30 min after which, the TLC of the reaction mixture showed the completion of the reaction after which, ether (200 mL) was added to the reaction mixture followed by the addition of water. The reaction mixture was extracted with ether and the combined organic layers was washed with water (100 mL), brine (200 mL) and dried. Concentration of the organic layer provided the crude product which was purified by column chromatography (0-10% Et$_2$O in hexanes). The pure product 4 was isolated as colorless oil (2 g, 74%). $^1$H NMR (CDCl$_3$, 400 MHz) δ=5.33-5.22 (m, 4H), 2.70 (t, 2H), 2.27-2.23 (m, 2H), 2.00-1.95 (m, 4H), 1.61-1.54 (m, 2H), 1.39-1.20 (m, 18H), 0.82 (t, 3H). $^{13}$C NMR (CDCl$_3$) δ=130.20, 129.96, 128.08, 127.87, 119.78, 70.76, 66.02, 32.52, 29.82, 29.57, 29.33, 29.24, 29.19, 29.12, 28.73, 28.65, 27.20, 27.16, 25.62, 25.37, 22.56, 17.10, 14.06. MS. Molecular weight calculated for C$_{19}$H$_{33}$N, Cal. 275.47. Found 276.6 (M−H$^−$).

Synthesis of Heptatriaconta-6,9,28,31-tetraen-19-one 7

To a flame dried 500 mL 2NRB flask, freshly activated Mg turnings (0.144 g, 6 mmol) were added and the flask was equipped with a magnetic stir bar and a reflux condenser. This set-up was degassed, flushed with argon and 10 mL of anhydrous ether was added to the flask via syringe. The bromide 3 (1.65 g, 5 mmol) was dissolved in anhydrous ether (10 mL) and added dropwise via syringe to the flask. An exothermic reaction was noticed (to confirm/accelerate the Grignard reagent formation, 2 mg of iodine was added and immediate decolorization was observed confirming the formation of the Grignard reagent) and the ether started refluxing. After the completion of the addition the reaction mixture was kept at 35° C. for 1 h and then cooled in ice bath. The cyanide 4 (1.38 g, 5 mmol) was dissolved in anhydrous ether (20 mL) and added dropwise to the reaction mixture with stirring. An exothermic reaction was observed and the reaction mixture was stirred overnight at ambient temperature. The reaction was quenched by adding 10 mL of acetone dropwise followed by ice cold water (60 mL). The reaction mixture was treated with aq. H$_2$SO$_4$ (10% by volume, 200 mL) until the solution became homogeneous and the layers were separated. The aq. phase was extracted with ether (2×100 mL). The combined ether layers were dried (Na$_2$SO$_4$) and concentrated to get the crude product which was purified by column (silica gel, 0-10% ether in hexanes) chromatography. The pure product fractions were evaporated to provide the pure ketone 7 as a colorless oil (2 g, 74%). $^1$H NMR (CDCl$_3$, 400 MHz) δ=5.33-5.21 (m, 8H), 2.69 (t, 4H), 2.30 (t, 4H), 2.05-1.95 (m, 8H), 1.55-1.45 (m, 2H), 1.35-1.15 (m, 18H), 0.82 (t, 3H). $^{13}$C NMR (CDCl$_3$) δ=211.90, 130.63, 130.54, 128.47, 128.41, 43.27, 33.04, 32.01, 30.93, 29.89, 29.86, 29.75, 29.74, 27.69, 26.11, 24.35, 23.06, 14.05. MS. Molecular weight calculated for C$_{37}$H$_{66}$O, Cal. 526.92. Found 528.02 (M+H$^+$).

Example 2

Alternative Synthesis of the Ketone 7

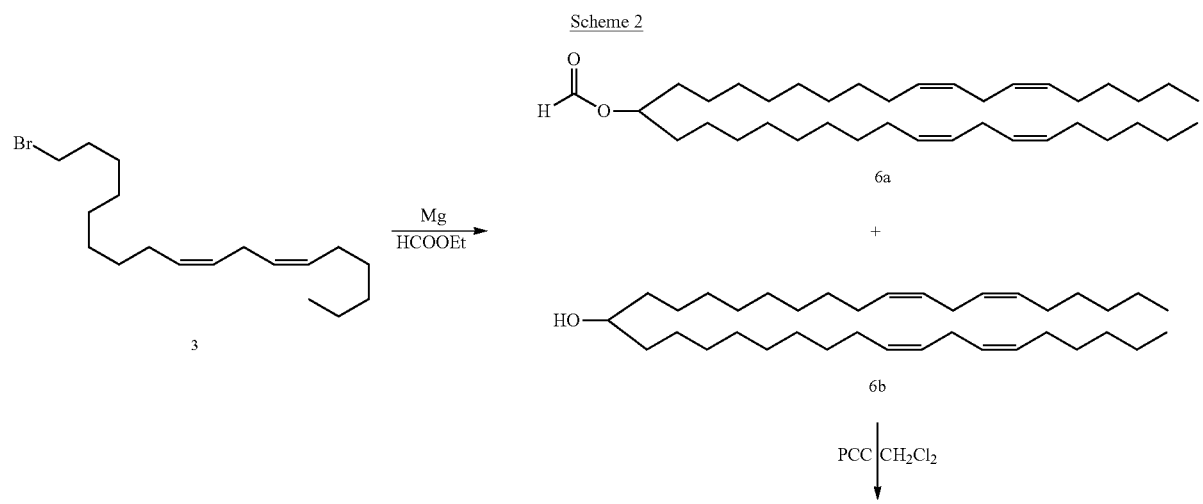

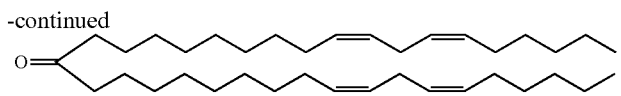

7

Synthesis of Compound 6b

To a flame dried 500 mL RB flask, freshly activated Mg turnings (2.4 g, 100 mmol) were added and the flask was equipped with a magnetic stir bar, an addition funnel and a reflux condenser. This set-up was degassed and flushed with argon and 10 mL of anhydrous ether was added to the flask via syringe. The bromide 3 (26.5 g, 80.47 mmol) was dissolved in anhydrous ether (50 mL) and added to the addition funnel. About 5 mL of this ether solution was added to the Mg turnings while stirring vigorously. An exothermic reaction was noticed (to confirm/accelerate the Grignard reagent formation, 5 mg of iodine was added and immediate decolorization was observed confirming the formation of the Grignard reagent) and the ether started refluxing. The rest of the solution of the bromide was added dropwise while keeping the reaction under gentle reflux by cooling the flask in water. After the completion of the addition the reaction mixture was kept at 35° C. for 1 h and then cooled in ice bath. Ethyl formate (2.68 g, 36.2 mmol) was dissolved in anhydrous ether (40 mL) and transferred to the addition funnel and added dropwise to the reaction mixture with stirring. An exothermic reaction was observed and the reaction mixture started refluxing. After the initiation of the reaction the rest of the ethereal solution of formate was quickly added as a stream and the reaction mixture was stirred for a further period of 1 h at ambient temperature. The reaction was quenched by adding 10 mL of acetone dropwise followed by ice cold water (60 mL). The reaction mixture was treated with aq. $H_2SO_4$ (10% by volume, 300 mL) until the solution became homogeneous and the layers were separated. The aq. phase was extracted with ether (2×100 mL). The combined ether layers were dried ($Na_2SO_4$) and concentrated to get the crude product which was purified by column (silica gel, 0-10% ether in hexanes) chromatography. The slightly less polar fractions were concentrated to get the formate 6a (1.9 g) and the pure product fractions were evaporated to provide the pure product 6b as a colorless oil (14.6 g, 78%).

Synthesis of Compound 7

To a solution of the alcohol 6b (3 g, 5.68 mmol) in $CH_2Cl_2$ (60 mL), freshly activated 4A molecular sieves (50 g) were added and to this solution powdered PCC (4.9 g, 22.7 mmol) was added portion wise over a period of 20 minutes and the mixture was further stirred for 1 hour (Note: careful monitoring of the reaction is necessary in order to get good yields since prolonged reaction times leads to lower yields) and the TLC of the reaction mixture was followed every 10 minutes (5% ether in hexanes) After completion of the reaction, the reaction mixture was filtered through a pad of silica gel and the residue was washed with $CH_2Cl_2$ (400 mL). The filtrate was concentrated and the thus obtained crude product was further purified by column chromatography (silica gel, 1% $Et_2O$ in hexanes) to isolate the pure product 7 (2.9 g, 97%) as a colorless oil. $^1H$ NMR (CDCl$_3$, 400 MHz) δ=5.33-5.21 (m, 8H), 2.69 (t, 4H), 2.30 (t, 4H), 2.05-1.95 (m, 8H), 1.55-1.45 (m, 2H), 1.35-1.15 (m, 18H), 0.82 (t, 3H). $^{13}C$ NMR (CDCl$_3$) δ=211.90, 130.63, 130.54, 128.47, 128.41, 43.27, 33.04, 32.01, 30.93, 29.89, 29.86, 29.75, 29.74, 27.69, 26.11, 24.35, 23.06, 14.05. MS. Molecular weight calculated for $C_{37}H_{66}O$, Cal. 526.92. Found 528.02 (M+H$^+$).

Example 3

Synthesis of Unsymmetric Ketones 25 and 27

Scheme 3

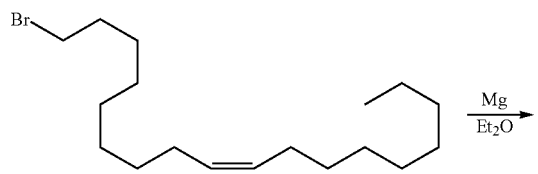

24

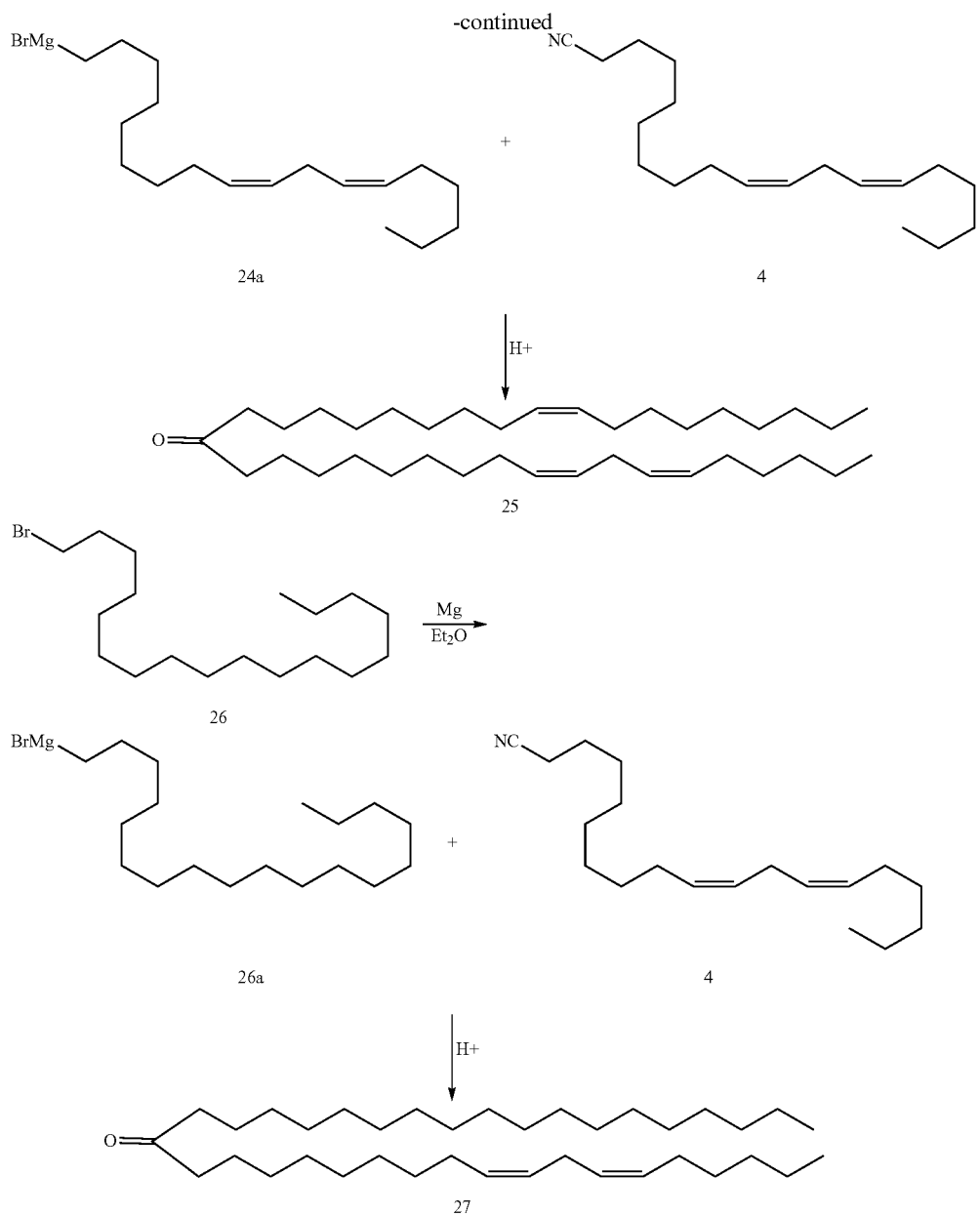

Synthesis of heptatriaconta-6,9,28-trien-19-one 25

To a dry 50 ml 2NRB flask, a freshly activated Mg turnings (132 mg, 0.0054 mol) was added and the flask was equipped with a magnetic stir bar and a reflux condenser. This setup was degassed and flushed with nitrogen and 10 mL of anhydrous ether was added to the flask via syringe. The bromide 24 (1.8 g, 0.0054 mol) was dissolved in anhydrous ether (10 mL) and added dropwise via syringe to the flask. An exothermic reaction was noticed (reaction initiated with dibromoethane) and the ether started refluxing. After completion of the addition the reaction mixture was kept at 35° C. for 1 h and then cooled in ice bath to 10-15° C. The cyanide 4 (0.5 g, 0.0018 mol) was dissolved in dry THF (5 mL) and added dropwise to the reaction with stirring. An exothermic reaction was observed and the reaction mixture was refluxed (at 70° C.) for 12 h and quenched with ammonium chloride solution. It was then treated with 25% HCl solution until the solution became homogenous and the layers were separated. The aqueous phase was extracted with ether. The combined ether layers were dried and concentrated to get the crude product which was purified by column chromatography. The pure product fractions were evaporated to provide the pure ketone 25 as colorless oil.

Yield: 0.230 g (24%). $^1$H-NMR (CDCl3, 400 MHz): δ=5.37-5.30 (m, 6H), 2.77-2.74 (t, 2H), 2.38-2.34 (t, 4H), 2.05-1.95 (m, 8H), 1.56-1.52 (m, 4H), 1.35-1.25 (m, aliphatic protons), 0.89-0.85 (t, 6H). IR (cm-1):2924, 2854,1717,1465, 1049,721.

Synthesis of heptatriaconta-6,9-dien-19-one 27

To a flame dried 500 mL 2NRB flask, a freshly activated Mg turnings (0.144 g, 6 mmol) is added and the flask is equipped with a magnetic stir bar and a reflux condenser. This set-up is degassed and flushed with argon and 10 mL of anhydrous ether is added to the flask via syringe. The commercially available bromide 26 (2.65 g, 5 mmol) is dissolved in anhydrous ether (10 mL) and added dropwise via syringe to the flask. After the completion of the addition the reaction mixture is kept at 35° C. for 1 h and then cooled in ice bath. The cyanide 4 (1.38 g, 5 mmol) is dissolved in anhydrous ether (20 mL) and added dropwise to the reaction mixture with stirring. An exothermic reaction is observed and the reaction mixture is stirred overnight at ambient temperature. The reaction is quenched by adding 10 mL of acetone dropwise followed by ice cold water (60 mL). The reaction mixture is treated with aq. $H_2SO_4$ (10% by volume, 200 mL) until the solution becomes homogeneous and the layers are separated. The aq. phase is extracted with ether (2×100 mL). The combined ether layers are dried ($Na_2SO_4$) and concentrated to get the crude product which is purified by column chromatography to provide the pure ketone 27 as a colorless oil. 1H-NMR (CDCl3, 400 MHz): δ=5.42-5.30 (m, 4H), 2.79-2.78 (t, 2H), 2.40-2.37 (t, 4H), 2.08-2.03 (m, 4H), 1.58-1.54 (m, 4H), 1.36-1.26 (br m, aliphatic protons), 0.91-0.87 (t, 6H). IR (cm-1):2924, 2854, 1716, 1465, 1375, 721.

Example 4

Synthesis of Unsymmetrical Ketones with $C_{12}$ Chain

To a dry 50 ml 2NRB flask, a freshly activated Mg turnings (175 mg, 0.0072 mol) was added and the flask was equipped with a magnetic stir bar and a reflux condenser. This setup was degassed and flushed with nitrogen and 10 mL of anhydrous ether was added to the flask via syringe. The bromide 28 (1.5 g, 0.006 mol) was dissolved in anhydrous ether (7 ml) and added dropwise via syringe to the flask. An exothermic reaction was noticed (reaction initiated with dibromoethane) and the ether started refluxing. After completion of the addition the reaction mixture was kept at 35° C. for 1 h and then cooled in ice bath to 10-15° C. The cyanide 4 (1 g, 0.0036 mol) was dissolved in anhydrous ether (7 mL) and added dropwise to the reaction with stirring. An exothermic reaction was observed and the reaction mixture was refluxed for 12 h and quenched with ammonium chloride solution. It was then treated with 25% HCl solution until the solution becomes homogenous and the layers were separated. The aq phase was extracted with ether. The combined ether layers were dried and concentrated to get the crude product which was purified by column chromatography. The pure product fractions were evaporated to provide the pure ketone 29 as colorless oil. Yield: 0.65 g (26%). $^1$H-NMR (δ ppm): 5.388-5.302 (m, 4H), 2.77-2.74 (t, 2H), 2.38-2.34 (t, 4H), 2.04-2.01 (m, 4H), 1.34-1.18 (m, 36H), 0.89-0.85 (m 6H). IR (cm$^{-1}$): 3009, 2920, 2851, 1711 (C=O), 1466, 1376, 1261.

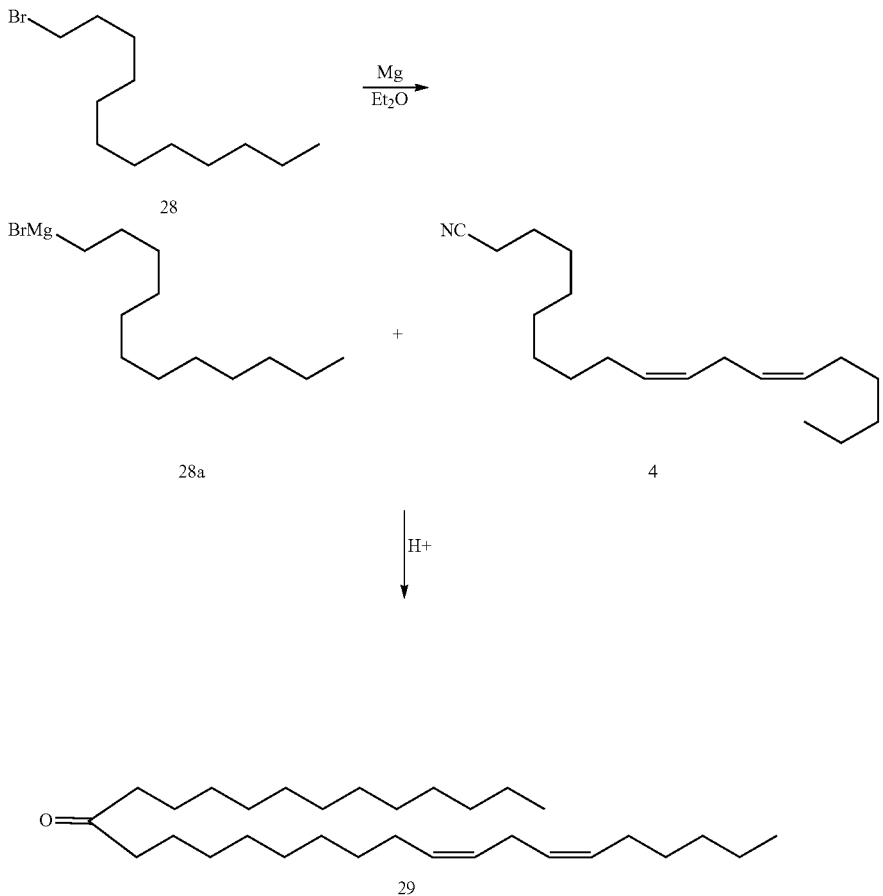

Scheme 4

Example 5

Synthesis of Unsymmetrical Ketones with $C_{10}$ Chain 31

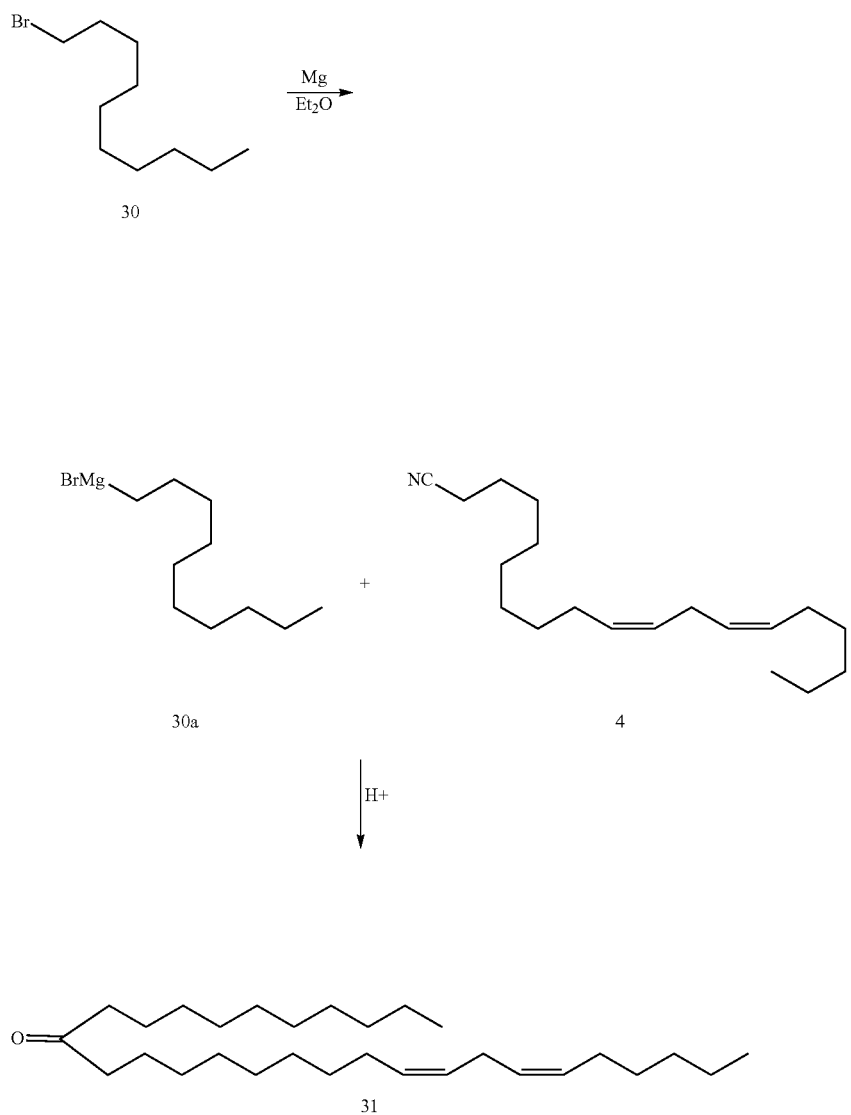

Scheme 5

To a dry 50 ml 2NRB flask, a freshly activated Mg turnings (266 mg, 0.0109 mol) was added and the flask was equipped with a magnetic stir bar and a reflux condenser. This setup was degassed and flushed with nitrogen and 10 mL of anhydrous ether was added to the flask via syringe. The bromide (2.43 g, 0.0109 mol) was dissolved in anhydrous ether (7 ml) and added dropwise via syringe to the flask. An exothermic reaction was noticed (reaction initiated with dibromoethane) and the ether started refluxing. After completion of the addition the reaction mixture was kept at 35° C. for 1 h and then cooled in ice bath to 10-15° C. The cyanide (1 g, 0.0036 mol) was dissolved in anhydrous ether (7 mL) and added dropwise to the reaction with stirring. An exothermic reaction was observed and the reaction mixture was stirred at ambient temperature for 2 hr. THF (4 ml) was added to the reaction mixture and it was warmed to 45-50° C. for 4 hr till the cyano derivative was complete consumed. The reaction was quenched by adding 3 mL of acetone dropwise followed by ice cold water. The reaction mixture was treated with 25% HCl solution until the solution becomes homogenous and the layers were separated. The aq. phase was extracted with ether. The combined ether layers were dried and concentrated to get the crude product which was purified by column chromatography. The pure product fractions were evaporated to provide the pure ketone as colorless oil. Yield: 0.93 gms (61%). $^1$H-NMR (δ ppm): 5.37-5.302 (m, 4H), 2.77-2.74 (t, 2H), 2.38-2.34 (t, 4H), 2.05-2.00 (m, 4H), 1.55-1.52 (m, 2H), 1.35-1.24 (m, 34H), 0.89-0.84 (m 6H). IR (cm$^{-1}$): 3009, 2925, 2854, 1717 (C=O), 1465, 1376.

Example 6
Synthesis of Unsymmetrical Ketones with Cholesterol 33
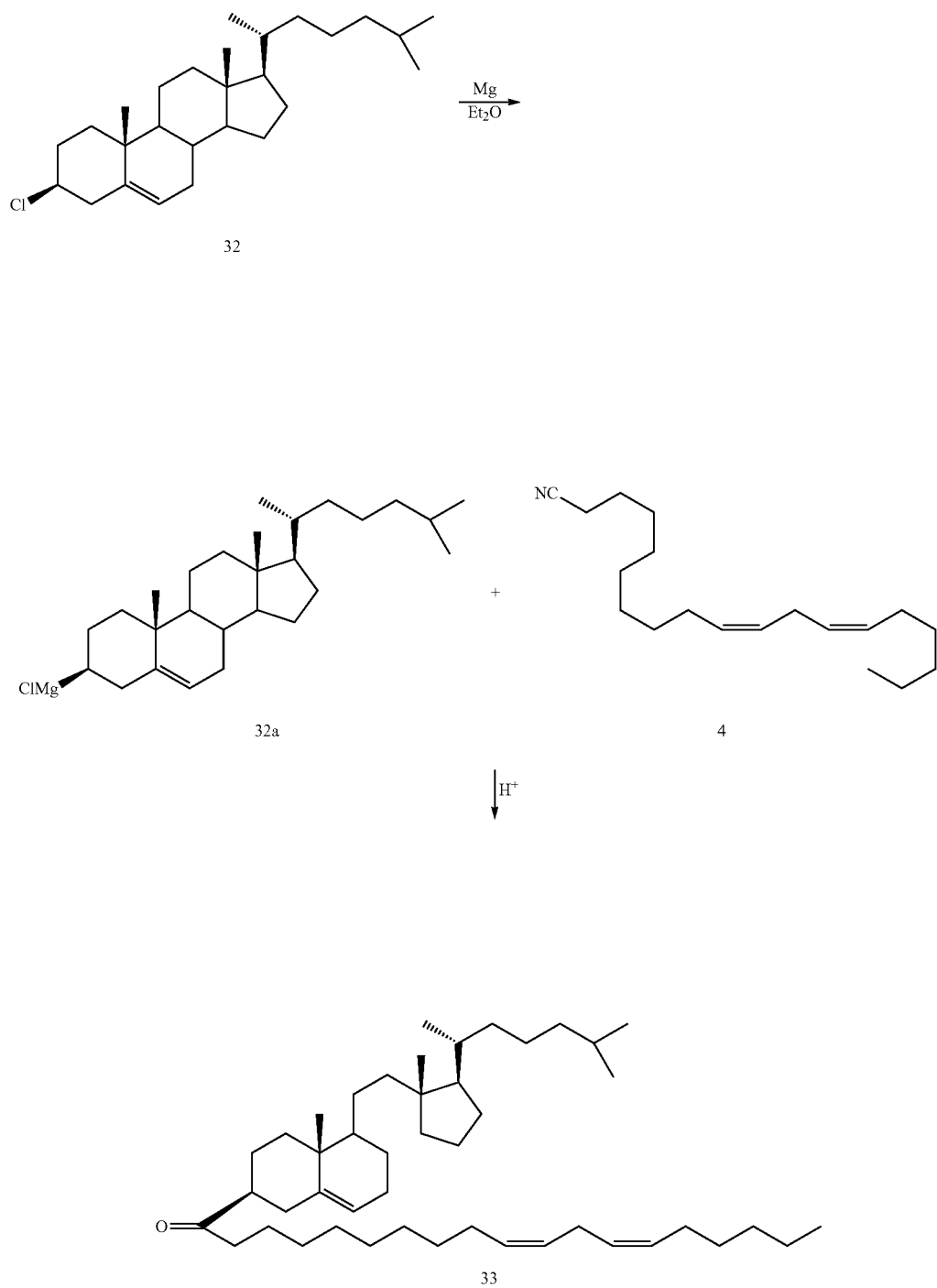
Scheme 6
Using a similar procedure to that used for the synthesis of ketone 31, the cholesteryl chloride on conversion to the corresponding magnesium chloride followed by addition to the linoleyl cyanide provided the ketone 33.

Example 7
Synthesis of Unsymmetrical Ketones with Cholesterol 35
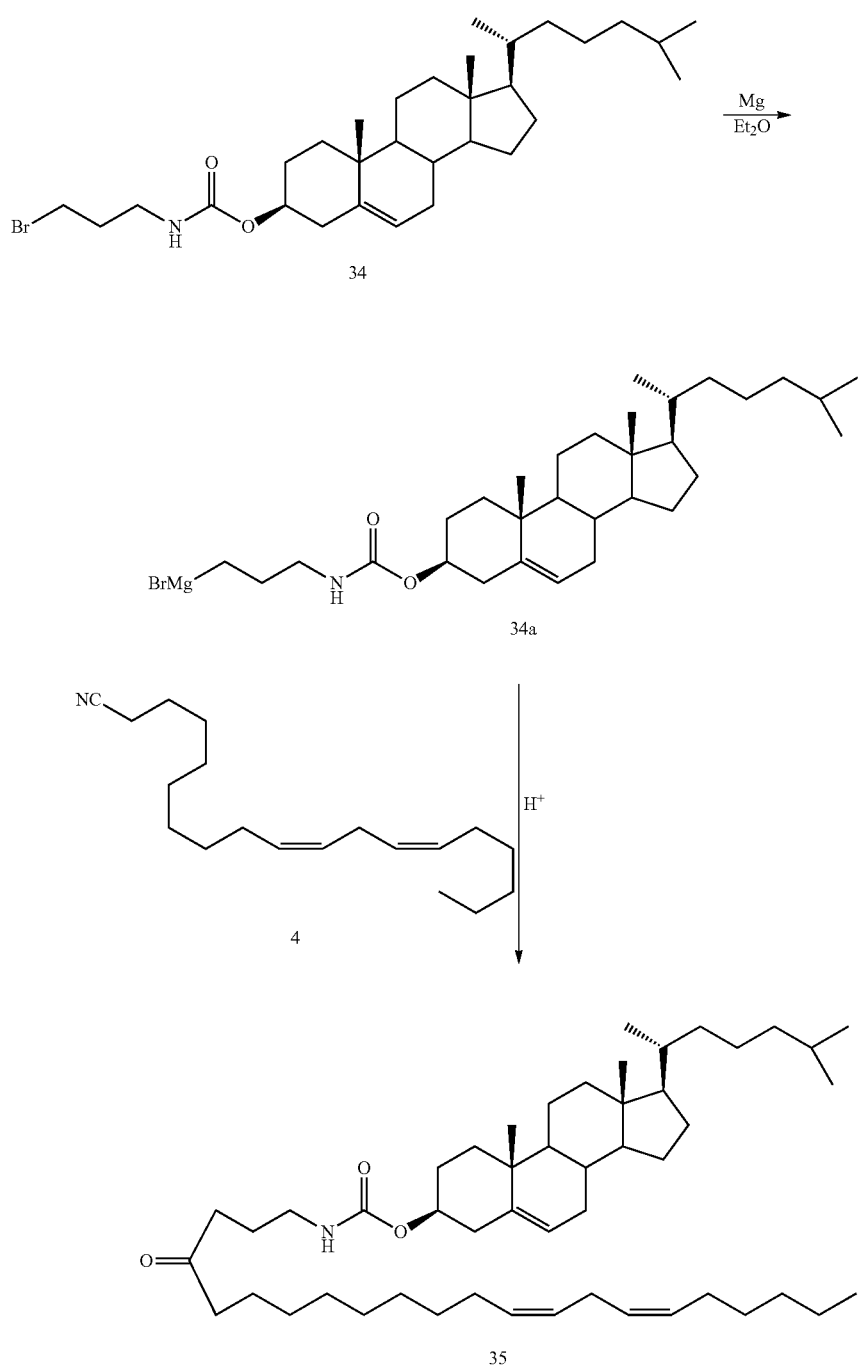
Scheme 7
The treatment of the cholesterolchloroformate with 3-bromopropylamine provided the bromide 34 which is converted to the corresponding Grignard reagent 34a which on treatment with the linoleyl cyanide provided the corresponding unsymmetrical ketone 35 in good yield.

Example 8

Synthesis of Unsymmetric Ketone 40

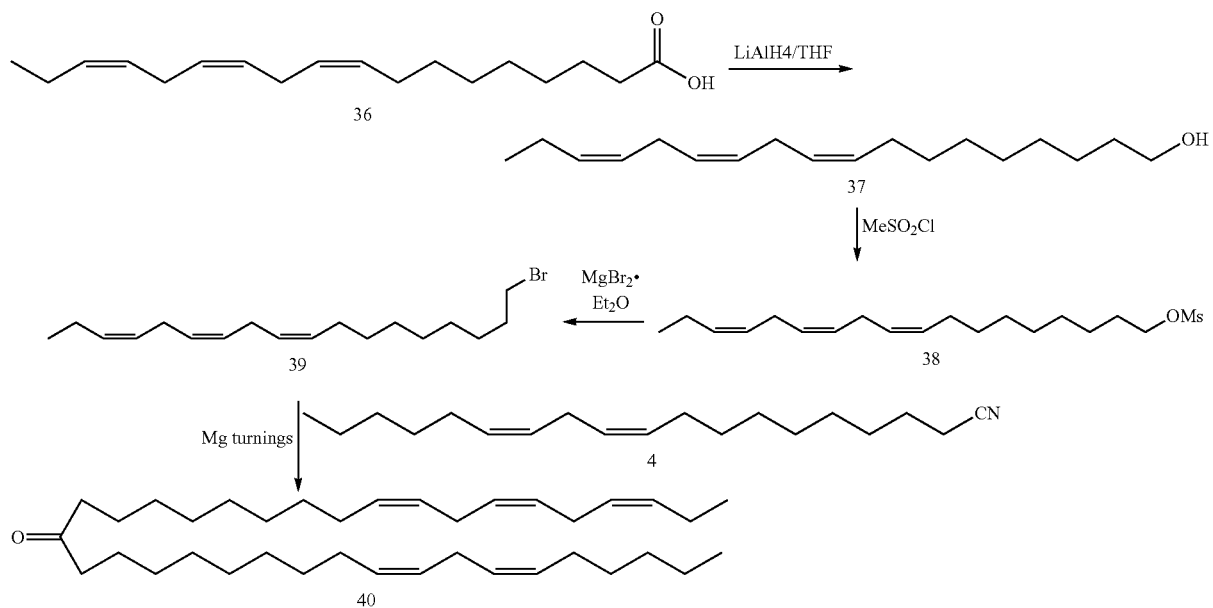

Scheme 8

Synthesis of Compound 37

To a 500 ml two neck RBF containing LiAlH$_4$ (1.02 g, 0.0269 mol) was added anhydrous THF (20 mL) at room temperature under nitrogen atmosphere. The suspension was stirred for 1 h at room temperature and then cooled to 0° C. To this mixture was added a solution of compound 1 (5 g, 0.01798 mol) in anhydrous THF (50 mL) slowly maintaining the inside temperature 0° C. After completion of the addition, reaction mixture was warmed to ambient temperature and stirred for 1 h. Progress of the reaction was monitored by TLC. Upon completion of the reaction, mixture was cooled to 0° C. and quenched with sat. solution of aq. Na$_2$SO$_4$. Reaction mixture was stirred for 30 minutes and solid formed was filtered through celite bed and washed with ethyl acetate (100 mL). Filtrate and washings were combined and evaporated on rotary evaporator to afford the compound 37 as colorless liquid, which was taken as such for the next stage without any purification. Yield: (4.5 g, 95%); $^1$H NMR (400 MHz, CDCl$_3$) δ=5.39-5.28 (m, 6H), 3.64-3.61 (t, 2H), 2.81-2.78 (t, 4H), 2.10-2.01 (m, 4H), 1.59-1.51 (m, 2H), 1.29-1.22 (m, aliphatic protons), 0.98-0.94 (t, 3H).

Synthesis of Compound 38

Compound 37 (14 g, 0.0530 mol) was dissolved in DCM (300 ml) in a 500 ml two neck RBF and cooled to 0° C. To this solution was added triethylamine (29.5 ml, 0.2121 mol) slowly under inert atmosphere. Reaction mixture was then stirred for 10-15 minutes and to it mesyl chloride (6.17 mL, 0.0795 mol)) was added slowly. After complete addition, the reaction mixture was allowed to warm to ambient temperature and stirred for 20 h. Reaction was monitored by TLC. Upon completion, the reaction mixture was diluted with water (200 mL) stirred for few minutes and organic layer was separated. Organic phase was further washed with brine (1×70 mL), dried over Na$_2$SO$_4$ and solvent was removed on rotary evaporator to get the crude compound 38 as brown oil which was used as such for next reaction. Yield: (17 g, 93%) $^1$H NMR (400 MHz, CDCl$_3$) δ=5.39-5.31 (m, 6H), 4.22-4.19 (t, 2H), 2.99 (s, 3H), 2.81-2.78 (m, 4H), 2.08-2.01 (m, 4H), 1.75. 1.69 (m, 2H), 1.39-1.29 (m, aliphatic protons), 0.98-0.94 (t, 3H).

Synthesis of Compound 39

The mesylate 38 (10 g, 0.2923 mol) was dissolved in (300 mL) anhydrous ether in a 1000 mL two neck RBF and MgBr$_2$.Et$_2$O complex (22.63 g, 0.0877 mol) was added into it under nitrogen atmosphere. Resulting mixture was then heated to reflux for 26 h. After completion of the reaction (by TLC), reaction mixture was diluted with ether (300 mL) and ice cold water (200 mL) and ether layer was separated out. Organic layer was then washed with 1% aq. K$_2$CO$_3$ (100 mL) followed by brine (80 mL). Organic phase was then dried over anhydrous Na$_2$SO$_4$ and solvent was evaporated off under vacuum to give the crude material which was chromatographed on silca gel (60-120 mesh) using 0-1% ethyl acetate in hexane as eluting system to yield the desired compound 39 as oil. Yield: (7 g, 73%) $^1$H NMR (400 MHz, CDCl$_3$) δ=5.39-5.31 (m, 6H), 3.41-3.37 (t, 2H), 2.81-2.78 (m, 4H), 2.08-2.02 (m, 4H), 1.86-1.80 (m, 2H), 1.42-1.29 (m, aliphatic protons), 0.98-0.94 (t, 3H).

Synthesis of Unsymetric Ketone 40

To a flame dried 500 mL two neck RBF, equipped with magnetic stir bar and a reflux condenser, freshly activated Mg turnings (0.88 g, 0.03636 mol) were added. This set up was degassed, flushed with argon and ether (150 mL) was added into it. Few drops of bromo compound 4 (11.89 g, 0.03636 mol) in 50 mL ether was added at the beginning to initiate the reaction (note: catalytic amount of 1,2-dibromo ethane was also added to accelerate formation of grignard reagent). Upon initiation, the remaining solution of bromo compound was added slowly to the refluxing ethereal solution. After complete addition, the reaction mixture was refluxed at 40° C. for 1.5 h. It was then cooled to 10° C. and the linoleyl cyanide 4 (5 g, 0.01818 mol) in 30 mL of dry ether was added drop wise and the resulting mixture was then heated to reflux for 20 h at 40° C. Progress of the reaction was monitored by TLC. After complete consumption of the cyano derivative 40 (by TLC), mixture was cooled to room temperature and quenched with 30 mL of acetone followed by (50 mL) ice water. This solution was further acidified with 10% HCl solution and ether layer was separated out. Aqueous phase was further extracted with diethyl ether (2×100 mL). Removal of the solvent after drying over anhydrous $Na_2SO_4$ afforded the crude ketone which was purified by silica gel column chromatography (100-200 mesh) using 0-5% ether in hexane as eluting system to give the title compound 40 as pale yellow oil. Yield: (4.8 g, 50.5%) $^1$H NMR (400 MHz, $CDCl_3$) δ=5.38-5.28 (m, 10H), 2.80-2.74 (m, 6H), 2.38-2.34 (t, 4H), 2.08-2.00 (m, 8H), 1.55-1.52 (m, 4H), 1.35-1.26 (m, aliphatic protons), 0.98-0.94 (t, 3H), 0.89-0.85 (t, 3H). HPLC-98.04%.

Example 9

Synthesis of Ketal 506

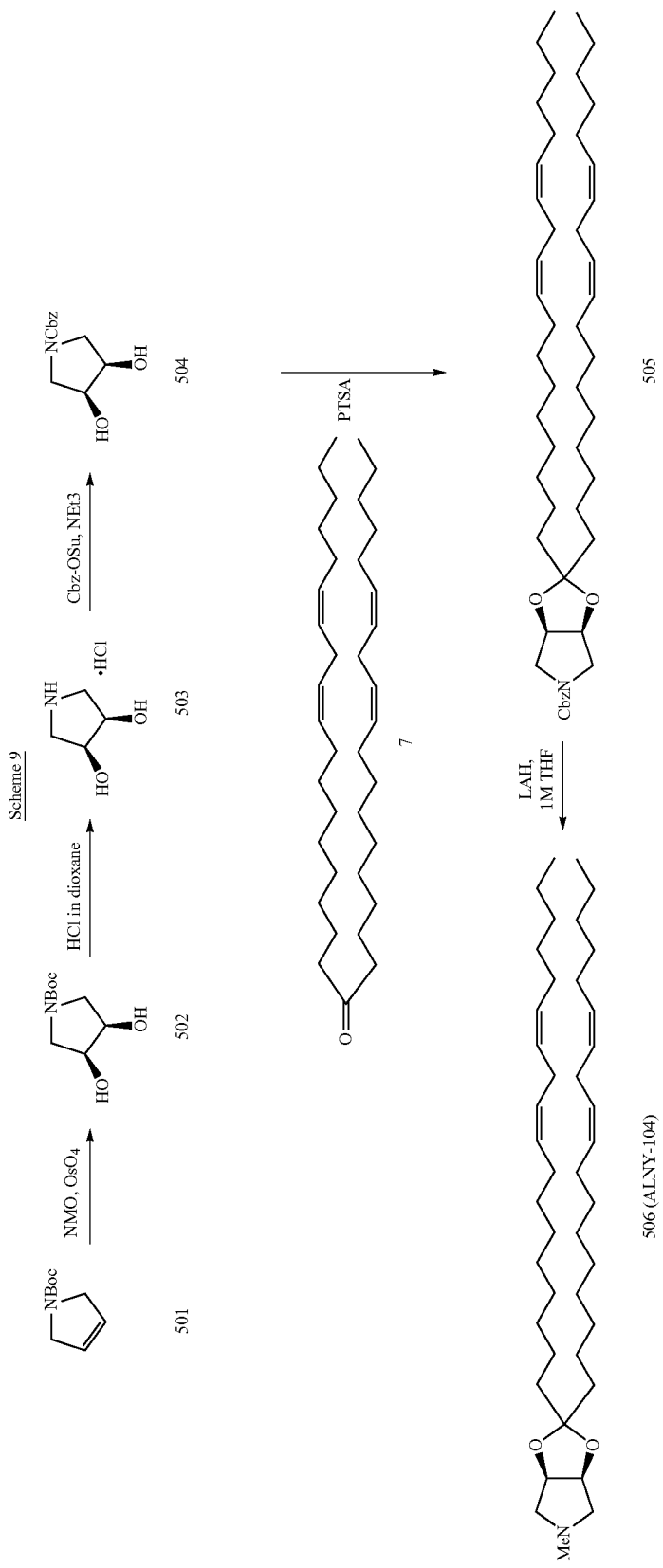

Dihydroxylation of Compound 501

A cooled (0° C.) solution of $OsO_4$ (0.01 eq) and NMO (1 eq) in water (100 mL) was treated dropwise with a solution of compound 501 (10.3 g, 61 mmol) in acetone (100 mL). After 5 h at r.t., the solvent was removed and the aqueous residue was partitioned with EtOAc. After aqueous workup, column chromatography gave compound 502 (9.2 g, 74%) as a colorless solid. $^1$H NMR (DMSO-$d_6$, 400 MHz) δ=4.86 (t, J=4.0 Hz, 2H), 3.96 (m, 2H), 3.36-3.26 (m, 2H), 3.05 (dd, J=9.8 and 3.8 Hz, 2H), 1.38 (s, 9H); Electrospray MS (+ve): Molecular weight for C9H18NO4 (M+H)$^+$ Calc. 204.0. Found 104.0 (M+H minus Boc).

Preparation of Compound 503

A DCM solution (20 mL) of compound 502 (2.5 g, 12.3 mmol) was treated with HCl in dioxane (4 M, 80 mL) over 18 h. $Et_2O$ (200 mL) was added and the resulting brown solid (compound 503) was collected by filtration (1.73 g, 100%). $^1$H NMR (DMSO-$d_6$, 400 MHz) δ=9.35 (br, 1H), 9.25 (br, 1H), 5.6-5.1 (br, 2H), 4.05 (t, J=4.1 Hz, 2H), 3.23-3.13 (m, 2H), 2.97-2.89 (m, 2H); Electrospray MS (+ve): Molecular weight for C4H10NO2 (M+H)$^+$ Calc. 104.0. Found 104.0.

Preparation of Compound 504

A DCM solution (20 mL) of $NEt_3$ (3 eq) and compound 503 (1.73 g, 12.3 mmol) was treated with Cbz-OSu (1.1 eq) over 18 h. Aqueous workup then column chromatography gave pure compound 7 (2.0 g, 68%). $^1$H NMR (CDCl$_3$, 400 MHz) δ=7.40-7.26 (m, 5H), 5.04 (s, 2H), 5.92 (d, J=4.5 Hz, 2H), 3.99 (m, 2H), 3.44 (dd, J=10.5 and 5.4 Hz, 1H), 3.37 (dd, J=10.9 and 5.3 Hz, 1H), 3.14 (dt, J=10.4 and 4.6 Hz, 2H).

Preparation of Compound 505

A mixture of compound 504 (1.85 g, 7.8 mmol), ketone 7 (2.74 g, 5.2 mmol) and p-TSA (0.1 eq) was heated under toluene reflux with Dean-Stark apparatus for 3 h. Removal of solvent then column chromatography gave compound 505 (3.6 g, 93%) as a colorless oil. $^1$H NMR (CDCl$_3$, 400 MHz) δ=7.40-7.26 (m, 5H), 5.43-5.29 (m, 8H), 5.13 (d, J=9.2 Hz, 2H), 4.71 (d, J=4.1 Hz, 2H), 3.88 (dd, J=22.4 and 12.9 Hz, 2H), 3.31 (d, J=12.9 Hz, 2H), 2.77 (t, J=6.4 Hz, 4H), 2.09-2.00 (m, 8H), 1.62 (m, 2H), 1.51 (br, 2H), 1.40-1.21 (m, 36H), 0.89 (t, J=6.8 Hz, 6H); Electrospray MS (+ve): Molecular weight for C49H80NO4 (M+H)$^+$ Calc. 746.6. Found 746.4.

Preparation of Compound 506 (ALNY-104)

A solution of compound 505 (2 g, 2.68 mmol) in hexane (20 mL) was added in a dropwise fashion to an ice-cold solution of LAH in THF (1 M, 5.4 mL). After complete addition, the mixture was heated at 40° C. over 0.5 h then cooled again on an ice bath. The mixture was carefully hydrolyzed with saturated aqueous $Na_2SO_4$ then filtered through celite and reduced to an oil. Column chromatography gave pure 506, 1.32 g, 79% as a colorless oil. $^1$H NMR (CDCl$_3$, 400 MHz) δ=5.43-5.29 (m, 8H), 4.61 (s, 2H), 2.97 (d, J=10.9 Hz, 2H), 2.77 (t, J=6.4 Hz, 4H), 2.28 (s, 3H), 2.12-2.01 (m, 10H), 1.72 (m, 2H), 1.52 (br, 2H), 1.44-1.23 (m, 36H), 0.89 (t, J=6.8 Hz, 6H); $^{13}$C NMR δ=130.2 (×3), 128.0, 127.9, 115.1, 80.2, 82.3, 41.9, 36.8, 35.9, 31.5, 30.0, 29.9, 29.7 (×2), 29.6, 29.5, 29.4, 29.3, 27.3, (×2), 27.2, 25.7, 24.3, 23.9, 22.6, 14.0; Electrospray MS (+ve): Molecular weight for C42H76NO2 (M+H)$^+$ Calc. 626.6. Found 626.6.

Example 10
Synthesis of Ketal 512

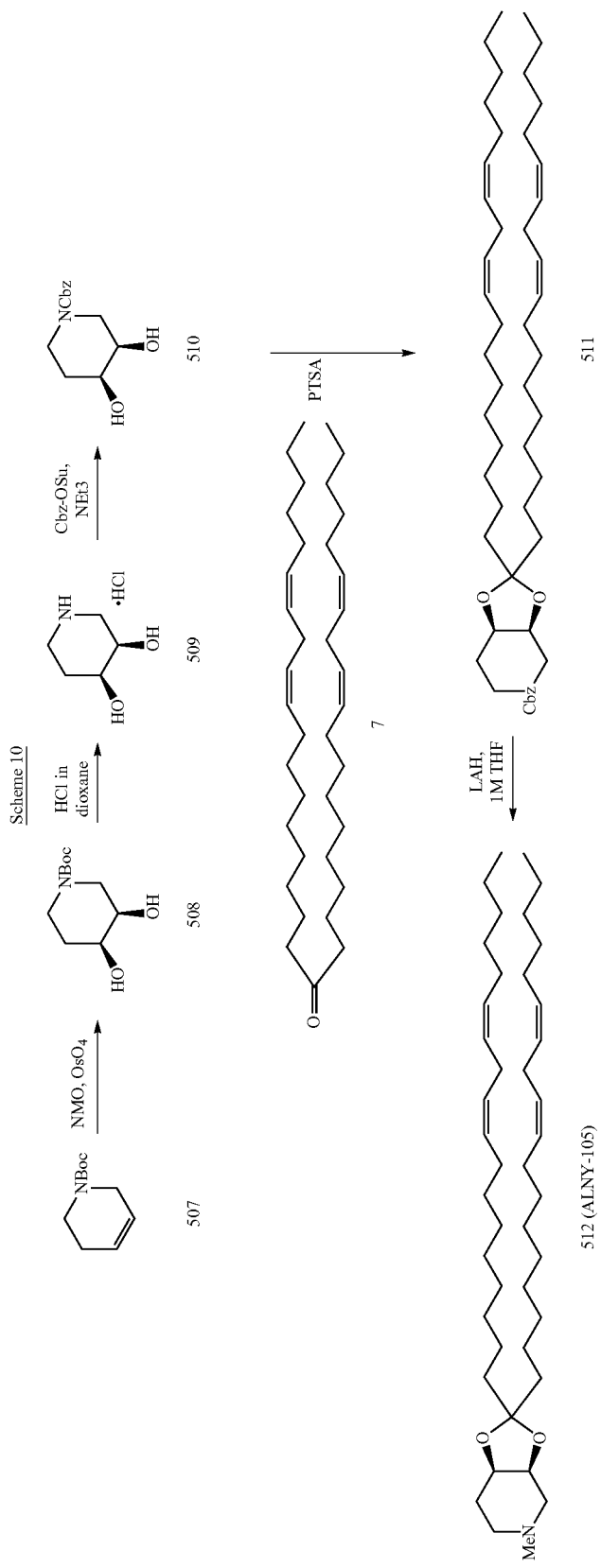

Preparation of Compound 508

Using a procedure analogous to that described for the synthesis of compound 502, compound 508 (10 g, 73%) was obtained as a colorless oil. $^1$H NMR (400 MHz, DMSO) δ 4.65-4.55 (br, 1H), 4.50 (d, J=4.1, 1H), 3.64 (m, 1H), 3.49-3.37 (m, 1H), 3.31-3.04 (m, 4H), 1.60 (m, 1H), 1.49-1.27 (m, 10H); Electrospray MS (+ve): Molecular weight for $C_{10}H_{20}NO_4$ (M+H)$^+$ Calc. 218.1. Found 118.0 (M+H minus Boc).

Preparation of Compound 509

Using a procedure analogous to that described for the synthesis of compound 503, compound 509 (7.33 g, 100%) was obtained as a colorless oil. $^1$H NMR (400 MHz, DMSO) δ 9.05 (s, 1H), 8.51 (s, 1H), 5.5-4.7 (br, 2H), 3.83-3.73 (m, 1H), 3.73-3.63 (m, 1H), 3.06-2.79 (m, 4H), 1.80 (m, 1H), 1.67 (m, 1H); Electrospray MS (+ve): Molecular weight for $C_5H_{12}NO_2$ (M+H)$^+$ Calc. 118.1. Found 118.0.

Preparation of Compound 510

Using a procedure analogous to that described for the synthesis of compound 504, compound 510 (2.68 g, 82%) was obtained as a colorless oil. $^1$H NMR (400 MHz, DMSO) δ 7.45-7.21 (m, 5H), 5.05 (s, 2H), 4.68 (s, 1H), 4.57 (s, 1H), 3.67 (d, J=3.0, 1H), 3.55-3.11 (m, 5H), 1.65 (m, 1H), 1.48 (m, 1H); Electrospray MS (+ve): Molecular weight for $C_{13}H_{18}NO_4$ (M+H)$^+$ Calc. 252.1. Found 252.0.

Preparation of Compound 511

Using a procedure analogous to that described for the synthesis of compound 505, compound 511 (4.7 g, 87%) was obtained as a colorless oil. $^1$H NMR (400 MHz, CDCl$_3$) δ 7.45-7.28 (m, 5H), 5.42-5.28 (m, 8H), 5.23-5.00 (m, 2H), 4.43-4.33 (m, 1H), 4.27 (d, J=26.5, 1H), 3.94-3.72 (m, 1H), 3.61-3.24 (m, 4H), 2.77 (t, J=6.3, 4H), 2.15-1.91 (m, 8H), 1.89-1.76 (br, 1H), 1.71-1.60 (m, 2H), 1.54 (m, 2H), 1.42-1.20 (m, 36H), 0.88 (t, J=6.7, 6H); Electrospray MS (+ve): Molecular weight for $C_{50}H_{82}NO_4$ (M+H)$^+$ Calc. 760.6. Found 760.4.

Preparation of Compound 512 (ALNY-105)

Using a procedure analogous to that described for the synthesis of compound 506, compound 512 (ALNY-105) (0.90 g, 69%) was obtained as a colorless oil. $^1$H NMR (400 MHz, CDCl$_3$) δ 5.49-5.23 (m, 8H), 4.16 (t, J=5.2, 2H), 2.77 (t, J=6.3, 4H), 2.70 (dd, J=11.6, 5.0, 1H), 2.44-2.33 (m, 1H), 2.31-2.14 (m, 5H), 2.04 (dd, J=13.6, 6.8, 8H), 1.99-1.88 (m, 1H), 1.78-1.63 (m, 2H), 1.56 (m, 2H), 1.48-1.15 (m, 37H), 0.88 (t, J=6.7, 6H). $^{13}$C NMR=130.2, 130.1 (×2), 127.9 (×2), 72.1, 70.6, 68.1, 51.1, 46.3, 38.5, 36.5, 31.5, 30.0, 29.7, 29.6, 29.5 (×2), 29.3 (×3), 27.7, 27.2 (×2), 25.6, 24.4, 22.6, 14.1; Electrospray MS (+ve): Molecular weight for $C_{43}H_{78}NO_2$ (M+H)$^+$ Calc. 640.6. Found 640.6.

Example 11
Synthesis of Ketal 519a-g [ALNY-100, 101, 107, 108, 109, 110 and 189]

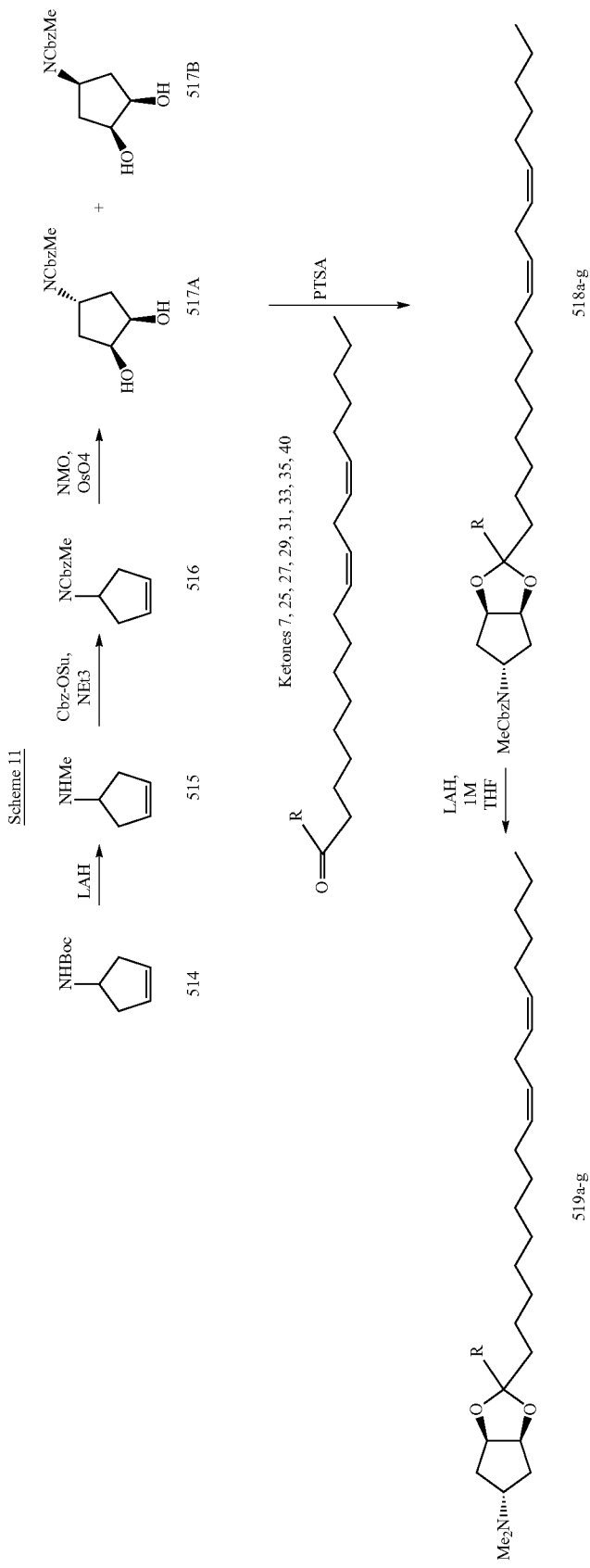

Synthesis of 515

To a stirred suspension of LiAlH4 (3.74 g, 0.09852 mol) in 200 ml anhydrous THF in a two neck RBF (1 L), was added a solution of 514 (10 g, 0.04926 mol) in 70 mL of THF slowly at 0° C. under nitrogen atmosphere. After complete addition, reaction mixture was warmed to room temperature and then heated to reflux for 4 h. Progress of the reaction was monitored by TLC. After completion of reaction (by TLC) the mixture was cooled to 0° C. and quenched with careful addition of saturated $Na_2SO_4$ solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g $^1$H-NMR (DMSO, 400 MHz): δ=9.34 (broad, 2H), 5.68 (s, 2H), 3.74 (m, 1H), 2.66-2.60 (m, 2H), 2.50-2.45 (m, 5H).

Synthesis of 516

To a stirred solution of compound 515 in 100 mL dry DCM in a 250 mL two neck RBF, was added $NEt_3$ (37.2 mL, 0.2669 mol) and cooled to 0° C. under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was washed successively with 1N HCl solution (1×100 mL) and saturated $NaHCO_3$ solution (1×50 mL). The organic layer was then dried over anhyd. $Na_2SO_4$ and the solvent was evaporated to give crude material which was purified by silica gel column chromatography to get 516 as sticky mass. Yield: 11 g (89%). 1H-NMR (CDCl3, 400 MHz): δ=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H]-232.3 (96.94%).

Synthesis of 517A and 517B

The cyclopentene 516 (5 g, 0.02164 mol) was dissolved in a solution of 220 mL acetone and water (10:1) in a single neck 500 mL RBF and to it was added N-methyl morpholine-N-oxide (7.6 g, 0.06492 mol) followed by 4.2 mL of 7.6% solution of OsO4 (0.275 g, 0.00108 mol) in tert-butanol at room temperature. After completion of the reaction (~3 h), the mixture was quenched with addition of solid $Na_2SO_3$ and resulting mixture was stirred for 1.5 h at room temperature. Reaction mixture was diluted with DCM (300 mL) and washed with water (2×100 mL) followed by saturated $NaHCO_3$ (1×50 mL) solution, water (1×30 mL) and finally with brine (1×50 mL). Organic phase was dried over an $Na_2SO_4$ and solvent was removed in vacuum. Silica gel column chromatographic purification of the crude material was afforded a mixture of diastereomers, which were separated by prep HPLC. Yield:-6 g crude 517A—Peak-1 (white solid), 5.13 g (96%). $^1$H-NMR (DMSO, 400 MHz): δ=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS—[M+H]-266.3, [M+NH4+]-283.5 present, HPLC-97.86%. Stereochemistry confirmed by X-ray.

Synthesis of 518a

Using a procedure analogous to that described for the synthesis of compound 505, compound 518a (1.2 g, 41%) was obtained as a colorless oil. 1H-NMR (CDCl3, 400 MHz): δ=7.35-7.33 (m, 4H), 7.30-7.27 (m, 1H), 5.37-5.27 (m, 8H), 5.12 (s, 2H), 4.75 (m, 1H), 4.58-4.57 (m, 2H), 2.78-2.74 (m, 7H), 2.06-2.00 (m, 8H), 1.96-1.91 (m, 2H), 1.62 (m, 4H), 1.48 (m, 2H), 1.37-1.25 (br m, 36H), 0.87 (m, 6H). HPLC-98.65%.

Synthesis of 518b

Using a procedure analogous to that described for the synthesis of compound 505, compound 518b (x g, y %) was obtained as a colorless oil.

Synthesis of 518c

Using a procedure analogous to that described for the synthesis of compound 505, compound 518c (1.2 g, 82%) was obtained as a colorless oil. 1H-NMR (CDCl3, 400 MHz): δ=7.34-7.33 (m, 4H), 7.30-7.29 (m, 1H), 5.35-5.32 (m, 6H), 5.12 (s, 2H), 4.76-4.73 (m, 1H), 4.58-4.57 (m, 2H), 2.78-2.75 (m, 5H), 2.04-1.92 (br m, 10H), 1.62 (m, 4H), 1.48 (m, 2H), 1.37-1.24 (br m, 38H), 0.87-0.81 (m, 6H). HPLC-88.72%.

Synthesis of 518d

Using a procedure analogous to that described for the synthesis of compound 505, compound 518d (1.8 g, 77%) was obtained as a colorless oil. 1H-NMR (CDCl3, 400 MHz): δ=7.34-7.33 (m, 4H), 7.30-7.28 (m, 1H), 5.36-5.32 (m, 4H), 5.12 (s, 2H), 4.77-4.70 (m, 1H), 4.58-4.57 (m, 2H), 2.78-2.75 (m, 5H), 2.04-2.00 (m, 4H), 1.95-1.92 (m, 2H), 1.62 (m, 4H), 1.56-1.53 (m, 2H), 1.35-1.23 (br m, 40H), 0.87-0.84 (m, 6H). HPLC-98.34%.

Synthesis of 518e

Using a procedure analogous to that described for the synthesis of compound 505, compound 518e (1.8 g, 89%) was obtained as a colorless oil. 1H-NMR (CDCl3, 400 MHz): δ=7.34-7.33 (m, 4H), 7.31-7.28 (m, 1H), 5.35-5.28 (m, 4H), 5.12 (s, 2H), 4.78-4.71 (m, 1H), 4.58-4.57 (m, 2H), 2.78-2.74 (m, 5H), 2.04-2.01 (m, 4H), 1.95-1.92 (m, 2H), 1.63 (m, 4H), 1.48 (m, 2H), 1.35-1.24 (br m, 24H), 0.89-0.84 (m, 6H). HPLC-90.98%.

Synthesis of 518f

Using a procedure analogous to that described for the synthesis of compound 505, compound 518f (1.9 g, 91%) was obtained as a colorless oil. 1H-NMR (CDCl3, 400 MHz): δ=7.34-7.33 (m, 4H), 7.31-7.27 (m, 1H), 5.37-5.28 (m, 4H), 5.12 (s, 2H), 4.78-4.71 (m, 1H), 4.58-4.57 (m, 2H), 2.78-2.75 (m, 5H), 2.04-2.02 (m, 4H), 1.95-1.92 (m, 2H), 1.62 (m, 4H), 1.48 (m, 2H), 1.35-1.24 (br m, 28H), 0.89-0.84 (m, 6H). HPLC-96.44%.

General Procedure for the Synthesis of Compounds 519a-g

A solution of compound 508a-g (1 eq) in hexane (15 mL) was added in a dropwise fashion to an ice-cold solution of LAH in THF (1 M, 2 eq). After complete addition, the mixture was heated at 40° C. over 0.5 h then cooled again on an ice bath. The mixture was carefully hydrolyzed with saturated aqueous $Na_2SO_4$ then filtered through celite and reduced to an oil. Column chromatography provided the pure 519a-g.

Preparation of Compound 519a (ALNY-100)

Using a procedure analogous to that described for the synthesis of compound 506, compound 519a (1.3 g, 68%) was obtained as a colorless oil. $^{13}$C NMR δ=130.2, 130.1 (×2), 127.9 (×3), 112.3, 79.3, 64.4, 44.7, 38.3, 35.4, 31.5, 29.9 (×2), 29.7, 29.6 (×2), 29.5 (×3), 29.3 (×2), 27.2 (×3), 25.6, 24.5, 23.3, 226, 14.1; Electrospray MS (+ve): Molecular weight for $C_{44}H_{80}NO_2$ (M+H)$^+$ Calc. 654.6. Found 654.6.

Preparation of Compound 519b (ALNY-189)

Using a procedure analogous to that described for the synthesis of compound 506, reduction of compound 518b (1.41 g, 1.83 mmol) provided compound 519b (1.2 g, 99%) as a colorless oil. $^1$H NMR (400 MHz, CDCl$_3$) δ 5.48-5.25 (m, 10H), 4.60 (d, J=4.0, 2H), 2.86-2.65 (m, 8H), 2.31-2.16 (m, 7H), 2.14-1.96 (m, 11H), 1.63 (dd, J=10.1, 5.9, 2H), 1.53-1.16 (m, 38H), 1.02-0.91 (m, 3H), 0.91 (s, 3H).

Preparation of Compound 519c (ALNY-107)

Using a procedure analogous to that described for the synthesis of compound 506, reduction of compound 518c (0.92 g, 1.19 mmol) provided compound 519c (0.7 g, 91%) as a colorless oil. $^1$H NMR (400 MHz, CDCl$_3$) δ 5.51-5.20 (m, 6H), 4.62 (d, J=4.7, 2H), 2.76 (dd, J=11.6, 5.4, 3H), 2.25 (s, 6H), 2.17-1.85 (m, 10H), 1.63 (dd, J=10.1, 5.9, 2H), 1.56-1.15 (m, 46H), 0.98-0.77 (m, 6H). $^{13}$C NMR (101 MHz, CDCl$_3$) δ 130.57, 130.51, 130.39, 130.35, 130.33, 130.11, 130.05, 130.03, 128.14, 128.11, 112.54, 79.51, 77.54, 77.22, 76.90, 64.65, 44.92, 38.53, 36.31, 35.59, 32.83, 32.11, 31.73, 30.16, 30.09, 29.98, 29.92, 29.87, 29.84, 29.76, 29.74, 29.68, 29.64, 29.56, 29.53, 29.51, 29.39, 29.35, 27.45, 27.41, 25.83, 24.75, 23.52, 22.90, 22.79, 14.35, 14.31. Calc. mass for the $C_{44}H_{81}NO_2$: 656.12. found 656.5.

Preparation of Compound 519d (ALNY-108)

Using a procedure analogous to that described for the synthesis of compound 506, reduction of compound 518d (1.58 g, 2.03 mmol) provided compound 519d (1.14 g, 86%) as a colorless oil. $^1$H NMR (400 MHz, CDCl$_3$) δ 5.50-5.20 (m, 4H), 4.61 (d, J=4.7, 2H), 2.75 (dt, J=11.7, 5.9, 3H), 2.24 (s, 6H), 2.08 (ddd, J=28.4, 13.7, 6.3, 6H), 1.63 (dd, J=10.1, 5.9, 2H), 1.54-1.14 (m, 54H), 0.95-0.77 (m, 6H). $^{13}$C NMR (101 MHz, cdcl$_3$) δ 130.39, 130.36, 130.33, 128.14, 128.12, 112.55, 79.52, 77.55, 77.23, 76.91, 64.65, 44.94, 38.55, 36.32, 35.60, 32.14, 31.74, 30.17, 30.10, 29.92, 29.88, 29.84, 29.79, 29.77, 29.75, 29.69, 29.59, 29.57, 29.51, 27.46, 27.44, 27.41, 25.83, 24.76, 23.53, 22.91, 22.80, 14.35, 14.31. Calc. mass for the $C_{44}H_{83}NO_2$: 658.14. found 658.5.

Preparation of Compound 519e (ALNY-110)

Using a procedure analogous to that described for the synthesis of compound 506, reduction of compound 518e (1.31 g, 1.98 mmol) provided compound 519e (0.73 g, 68%) as a colorless oil. $^1$H NMR (400 MHz, CDCl$_3$) δ 5.51-5.20 (m, 4H), 4.62 (d, J=4.8, 2H), 2.88-2.61 (m, 3H), 2.24 (s, 6H), 2.08 (ddd, J=20.5, 13.7, 6.3, 6H), 1.64 (dd, J=10.1, 5.9, 2H), 1.55-1.14 (m, 38H), 0.96-0.78 (m, 6H). $^{13}$C NMR (101 MHz, CDCl$_3$) δ 130.55, 130.51, 130.37, 130.33, 130.31, 130.11, 130.05, 130.02, 128.14, 128.11, 112.53, 79.51, 77.54, 77.23, 76.90, 64.65, 44.92, 38.53, 36.31, 35.57, 32.83, 32.11, 31.73, 30.16, 30.09, 29.98, 29.92, 29.87, 29.84, 29.77, 29.74, 29.68, 29.63, 29.56, 29.53, 29.51, 29.39, 29.35, 27.44, 27.40, 25.83, 24.75, 23.52, 22.90, 22.79, 14.34, 14.30. Calc. mass for the $C_{36}H_{67}NO_2$: 545.9. found 646.4.

Preparation of Compound 519f (ALNY-109)

Using a procedure analogous to that described for the synthesis of compound 506, reduction of compound 518f (1.5 g, 2.16 mmol) provided compound 519f (1.13 g, 92%) as a colorless oil. $^1$H NMR (400 MHz, CDCl$_3$) δ 5.47-5.19 (m, 4H), 4.62 (d, J=4.7, 2H), 2.88-2.62 (m, 3H), 2.25 (s, 6H), 2.08 (ddd, J=28.3, 13.7, 6.3, 6H), 1.64 (dd, J=10.1, 5.9, 2H), 1.56-1.14 (m, 42H), 0.94-0.78 (m, 6H). $^{13}$C NMR (101 MHz, CDCl$_3$) δ 130.18, 130.15, 130.12, 127.94, 127.91, 112.36, 79.31, 77.32, 77.01, 76.69, 64.44, 44.68, 38.30, 36.13, 35.38, 31.92, 31.52, 29.95, 29.88, 29.71, 29.65, 29.62, 29.56, 29.53, 29.47, 29.35, 29.29, 27.25, 27.22, 27.20, 25.62, 24.53, 23.32, 22.69, 22.58, 14.13, 14.08. Calc. mass for the $C_{38}H_{71}NO_2$: 573.9. found 574.5.

Preparation of Compound 519g

Using a procedure analogous to that described for the synthesis of compound 506, reduction of compound 518g (2 mmol) provided compound 519g (92%) as a colorless oil.

Example 12
Synthesis of Ketal 519

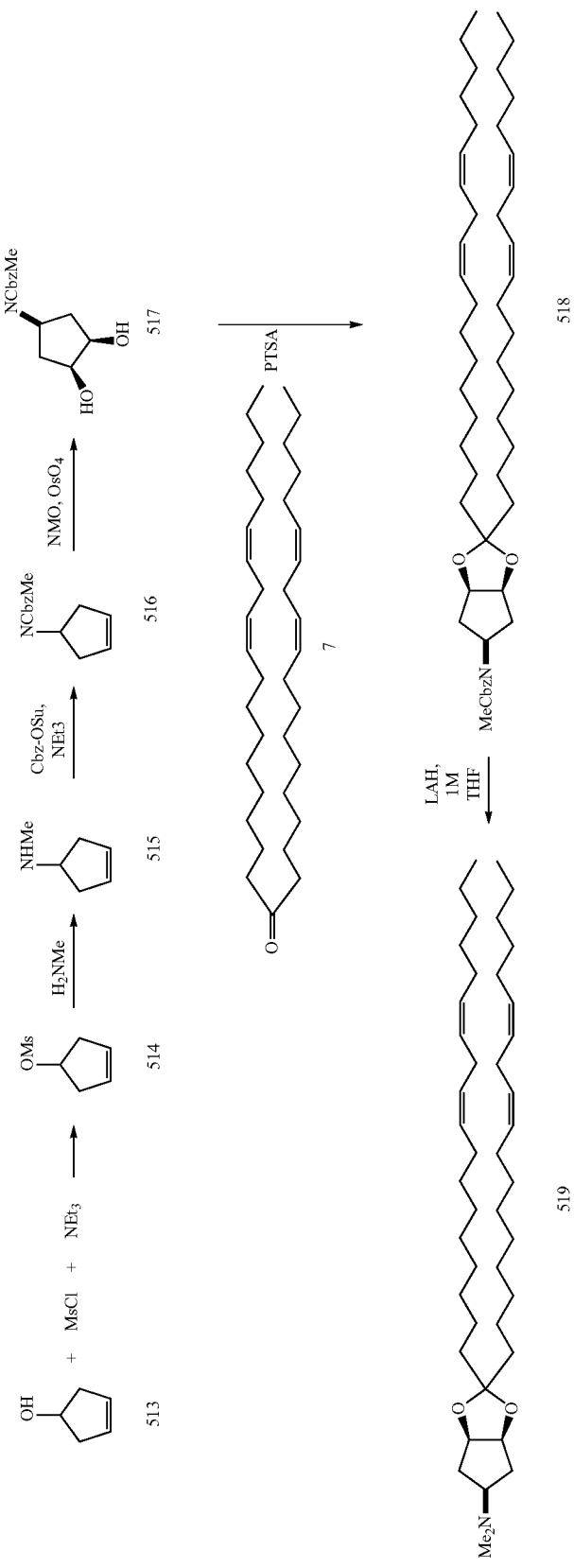

Preparation of Compound 516

An ice-cold solution of compound 513 (0.97 g, 11.5 mmol) and NEt$_3$ (1.2 eq) in DCM (50 mL) was treated in a dropwise fashion over 5 min with MsCl (1.1 eq). After 1 h at 0° C., aqueous workup gave crude compound 514 (pure by TLC) which was used without purification in the next step.

Compound 514 (11.5 mmol) was treated with 33% H$_2$NMe in EtOH (50 mL) over 72 h. Excess H$_2$NMe was removed by co-evaporation with Et$_2$O, then the ethanolic solution of compound 515 was treated with conc. HCl (2 eq). The EtOH was removed by evaporation and the residue was redissolved in DCM (100 mL). NEt$_3$ (6 eq) was added followed by Cbz-OSu (2.2 eq) and the mixture was stirred at r.t. for 3 h. Aqueous workup then column chromatography gave pure compound 516 as an oil (2.15 g, 81% from 513). $^1$H NMR (CDCl$_3$, 400 MHz) δ=7.40-7.28 (m, 5H), 5.70 (s, 2H), 5.14 (s, 2H), 5.1-4.9 (br, m, 1H), 2.75 (s, 3H), 2.7-2.54 (br, 2H), 2.29 (d, J=18.2 Hz, 2H); $^{13}$C NMR δ=156.2, 137.0, 129.3, 128.5, 127.9, 127.8, 67.0, 53.6, 36.5, 29.7; Electrospray MS (+ve): Molecular weight for C14H18NO2 (M+H)$^+$ Calc. 232.1. Found 232.0.

Preparation of Compound 517

Using a procedure analogous to that described for the synthesis of compound 502, compound 517 (1.75 g, 71%) was obtained as a colorless oil. $^{13}$C NMR δ=155.2, 137.1, 128.4, 127.8, 127.5, 127.4, 72.4, 66.1, 59.8, 52.8, 34.2, 28.8, 20.8, 14.1; Electrospray MS (+ve): Molecular weight for C14H20NO4 (M+H)$^+$ Calc. 266.1. Found 266.0.

Preparation of Compound 518

Using a procedure analogous to that described for the synthesis of compound 505, compound 518 (2.01 g, 63%) was obtained as a colorless oil. $^{13}$C NMR δ=156.2, 136.9, 130.2 (×2), 130.1, 128.4, 128.0, 127.9 (×2), 127.8, 127.7, 127.6 (×2), 112.6, 79.3, 67.0, 31.5, 29.6, 29.5 (×3), 29.3 (×2), 27.2 (×3), 25.6, 24.5, 22.6, 14.1; Electrospray MS (+ve): Molecular weight for C51H84NO4 (M+H)$^+$ Calc. 774.6. Found 774.6.

Preparation of Compound 519

Using a procedure analogous to that described for the synthesis of compound 506, compound 519 (1.3 g, 68%) was obtained as a colorless oil. $^{13}$C NMR δ=130.2, 130.1 (×2), 127.9 (×3), 112.3, 79.3, 64.4, 44.7, 38.3, 35.4, 31.5, 29.9 (×2), 29.7, 29.6 (×2), 29.5 (×3), 29.3 (×2), 27.2 (×3), 25.6, 24.5, 23.3, 226, 14.1; Electrospray MS (+ve): Molecular weight for C44H80NO2 (M+H)$^+$ Calc. 654.6. Found 654.6.

Example 13

Synthesis of Ketal ALNY-102 & 103

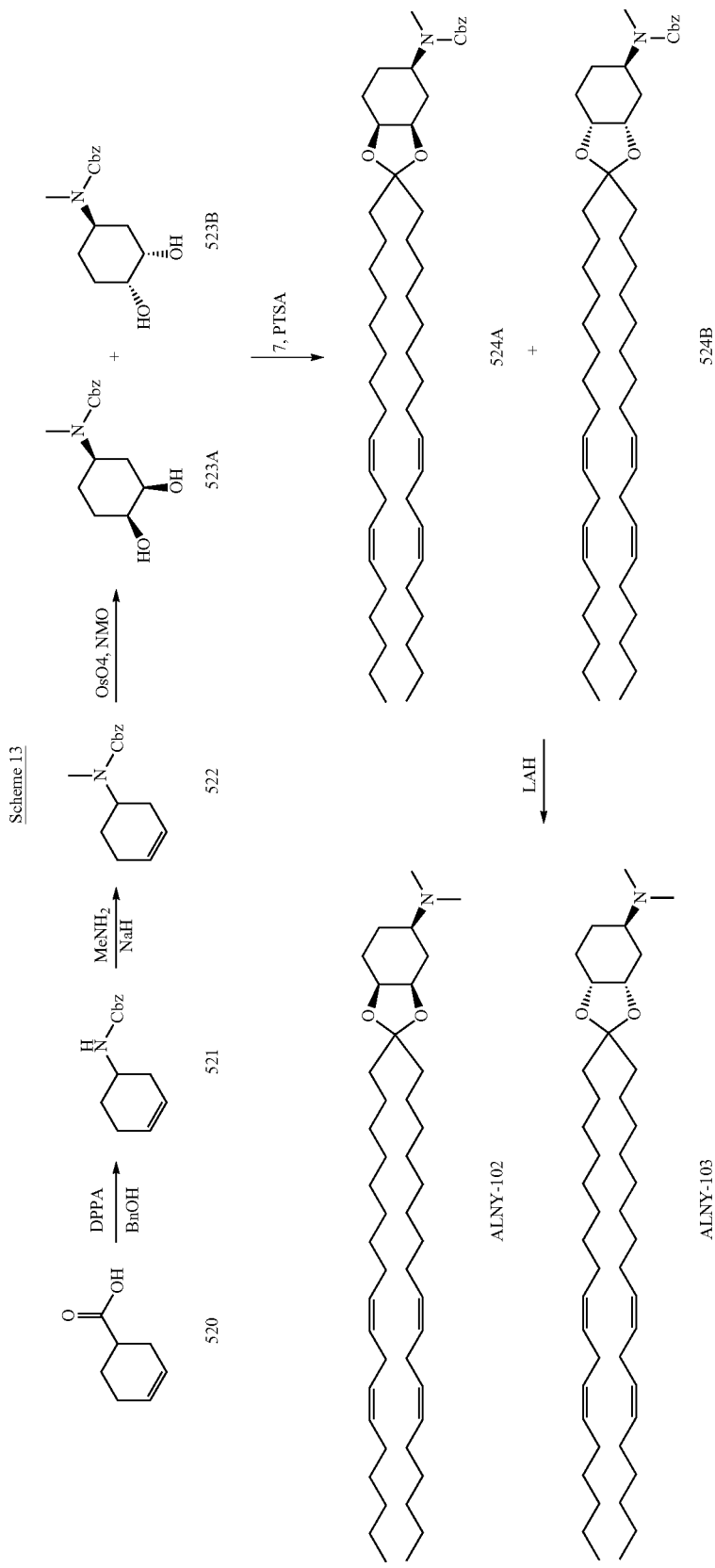

Synthesis of 521

To a solution of 520 (2.5 g, 0.0198 moles) in toluene (10 mL) in 50 mL two neck RBF, were added triethylamine (3 mL, 0.02178 moles) and DPAA (Diphenylphosphoryl azide) (5.08 mL, 0.0237 moles) was added at room temperature. After refluxing the mixture for 2 h, Benzyl alcohol (2.5 mL, 0.02376 moles) was added, and the mixture was refluxed for additional 10 h. The resulting mixture was concentrated under vacuum, diluted with ethyl acetate and washed with 1N HCl, NaHCO3 solution and brine respectively. The organic layer was dried over sodium sulphate and solvent was removed under vacuum. Crude material was purified by silica gel column chromatography using 0 to 3% ethyl acetate in hexane as eluting system. (3.2 g, 57%). 1H-NMR (CDCl3, 400 MHz): δ=7.37-7.28 (m, 5H), 5.67-5.64 (m, 1H), 5.59-5.55 (m, 1H), 5.08 (s, 2H), 4.77 (m, 1H), 3.86 (br, 1H), 2.40-2.36 (m, 1H), 2.11 (m, 2H), 1.91-1.84 (br m, 2H), 1.54 (br m, 1H).

Synthesis of 522

The compound 522 (2 g, 0.0865 moles) was dissolved in Dry DMF (20 mL) in 100 mL two neck RBF and cooled to 0° C. Sodium Hydride (60% in mineral oil) (0.83 g, 0.0173 moles) was added and the mixture was stirred for 30 mins under nitrogen atmosphere. Methyl iodide (4.27 g, 0.0303 moles) was then added slowly and the reaction mixture was then stirred at 60° C. for 4 h. The progress was monitored by TLC. After completion of reaction, it was cooled to 0° C. and quenched with ice water (100 mL) and extracted with ethyl acetate (3×50 mL). Organic layer was separated, dried over sodium sulfate and concentrated under vacuum. Crude product was purified by column chromatography; product was eluted with 0-10% ethyl acetate in hexane. Yield (1.8 gm, 92%). $^1$H-NMR (CDCl3, 400 MHz): δ=7.35-727 (m, 5H), 5.62-5.59 (s, 2H), 5.13-5.10 (s, 2H), 4.30-4.18 (br m, 1H), 2.80 (s, 3H), 2.17-2.11 (m, 4H), 1.72-1.61 (m, 2H).

Synthesis of 523A and 523B

To a stirred solution of 522 (6 g, 0.0244 mol) in 264 mL acetone:water (10:1) in a 500 mL single neck RBF was added NMO (8.5 g, 0.0732 mol) followed by 4.6 mL solution of 6.6% OsO4 (0.311 g, 0.001224 mol) in t-BuOH. Reaction was stirred for 2 hr and monitored by TLC. After completion of reaction, mixture was quenched with sat. aq. $Na_2SO_3$ solution stirred for 30 min and extracted with DCM (300 mL×3). Organic layer was dried over $Na_2SO_4$. Solvent was removed under vacuum to get crude mix of 523A and 523B. Crude mixture was purified on 60-120 silica gel using 0-5% ethyl acetate in hexane as eluent to give pure diastereomeric mixture which was separated by prep. HPLC. Peak-1 from prep HPLC was identified as 523A. Yield-6 g (87.84%) 523B (Peak-1), Yield 3 g (68%) (Colorless solid) 1H-NMR (DMSO, 400 MHz): δ=7.39-7.30 (m, 5H), 5.06 (s, 2H), 4.57-4.55 (d, 1H), 4.30-4.29 (m, 1H), 3.91-3.85 (m, 1H), 3.66 (br s, 1H), 3.43-3.40 (m, 1H), 2.73 (s, 3H), 1.77-1.67 (m, 3H), 1.39-1.33 (m, 2H), 1.22-1.17 (m, 1H). LC-MS:-[M+H]-280.2. HPLC:-99.85%. Stereochemistry confirmed by X-ray.

To a stirred mixture of 524A and 524B (1.2 g, 0.0043 mol) and dilinoleyl ketone (2.26 g, 0.0043 mol) in 150 mL toluene, p-TSA (0.073 g, 0.00043 mol) was added at room temperature. The reaction mixture was heated to reflux over Soxhlet Apparatus for 4 h. After completion of reaction (by TLC) toluene was removed on rotary evaporator and residual compound was dissolved in DCM (50 mL). Organic layer was washed with saturated NaHCO3 (1×10 ml), followed by water (1×15 mL). Organic layer was separated, dried over Na2SO4 and concentrated under vacuum. Crude product was purified on neutral Alumina using 0-5% ethyl acetate in hexane as eluent.

524A: Yield-1.2 g (36%) 1H-NMR (CDCl3, 400 MHz): δ=7.35-7.25 (m, 5H), 5.37-5.30 (m, 8H), 5.11 (s, 2H), 4.13 (m, 2H), 4.1-3.80 (m, 1H), 2.77 (m, 7H), 2.22 (m, 1H), 2.05-2.00 (m, 8H), 1.9 (m, 1H), 1.71-1.63 (m, 4H), 1.37-1.26 (br m, 40H), 0.89-0.85 (m, 6H). HPLC:-98.29%

524B: Yield-1.0 g (37%). 1H-NMR (CDCl3, 400 MHz): δ=7.34-7.27 (m, 5H), 5.35-5.28 (m, 8H), 5.12 (br s, 2H), 4.32-4.26 (m, 2H), 4.07-4.05 (m, 1H), 2.80 (s, 3H), 2.77-2.74 (m, 4H), 2.04-2.01 (m, 9H), 1.84-1.66 (m, 5H), 1.35-1.15 (br m, 40H), 0.89 (m, 6H). HPLC:-95.18%.

Synthesis of ALNY-102 & ALNY-103

Prepared the compound ALNY-102 and 103 by following similar procedure as compound 506.

The N-Cbz-compound 524B (0.9 g, 1.14 mmol) and 1M solution of LAH in THF (2.28 mL, 2.28 mmol, 2.0 eq), gave 0.65 g (85%) of the pure product ALNY-103. $^1$H NMR (400 MHz, CDCl$_3$) δ 5.48-5.22 (m, 8H), 4.33 (dd, J=9.5, 4.1, 1H), 4.23-4.00 (m, 1H), 2.77 (t, J=6.4, 4H), 2.65 (s, 1H), 2.34 (s, 6H), 2.18-1.95 (m, 9H), 1.86 (dd, J=11.7, 5.7, 3H), 1.78-1.59 (m, 4H), 1.54 (d, J=8.3, 2H), 1.45-1.16 (m, 37H), 0.98-0.79 (m, 6H). $^{13}$C NMR (101 MHz, CDCl$_3$) δ 130.40, 130.35, 128.16, 128.13, 111.45, 77.54, 77.23, 76.91, 73.11, 72.94, 57.93, 54.76, 41.69, 38.22, 36.23, 32.09, 31.74, 30.21, 29.91, 29.74, 29.71, 29.57, 29.54, 29.02, 27.45, 27.41, 26.89, 25.84, 24.71, 24.38, 23.34, 22.79, 21.42, 14.30. Calc. mass for the $C_{45}H_{81}NO_2$: 668.13. found 668.5.

Example 14

Synthesis of ALNY-169

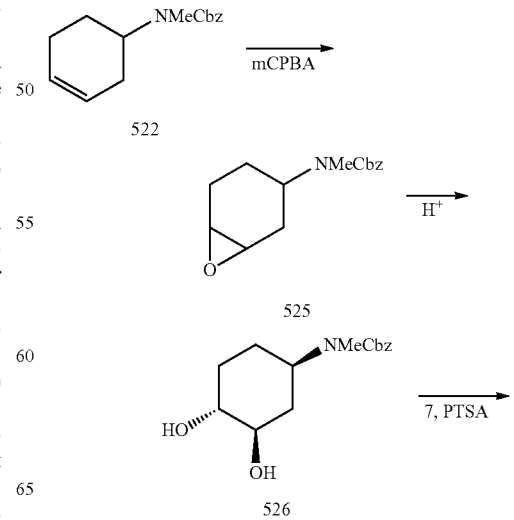

Scheme 14:

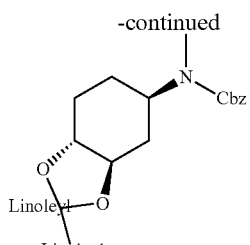

527

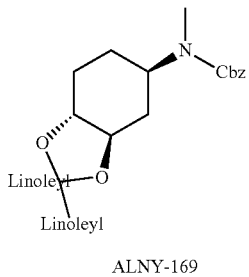

ALNY-169

Synthesis of 525

The compound 522 (7 g, 0.02857 moles) was dissolved in dry DCM (60 mL) in a 250 ml two neck RBF and cooled to 0° C. After stirring the mixture for 10 minutes (50-75%) m-CPBA (15.66 g, 0.04571 moles) was added in portions over a span of 30 minutes. Reaction mixture was then warmed to ambient temperature and stirred for 4 h. Progress of the reaction was monitored by TLC. After completion of the reaction, mixture was diluted with ethyl acetate (250 ml) and washed with sat. $Na_2SO_3$ solution (3×50 mL) followed by sat. $NaHCO_3$ solution (2×100 ml). Organic layer was then washed with brine (1×50 mL), dried over an. $Na_2SO_4$, and concentrated in vacuum. Crude mass thus obtained was purified by silica gel (60-120 mesh) column chromatography using 3% methanol in dichloromethane to give pure compound 525 as a thick liquid. Yield: 4.32 gm (58%). $^1H$ NMR (400 MHz, $CDCl_3$) δ=7.36-7.25 (s, 5H), 5.11 (s, 2H), 4.12-3.88 (m, 1H), 3.12 (br, 2H), 2.75 (s, 3H), 2.25-2.21 (m, 1H), 2.05 (m, 1H), 1.92-1.82 (m, 2H), 1.61-1.57 (m, 1H), 1.33-1.30 (m, 1H). LCMS [M$^+$H]: 279.3.

Synthesis of 526

A single neck 250 ml RBF charged with Compound 525 (4.32 g, 0.0165 moles) was cooled to 0° C., and then dissolved in 50 mL 2% aq. $H_2SO_4$. After stirring for 10 minutes, reaction mixture was warmed to room temperature and stirred for 1 h. Reaction was monitored by TLC. After completion of the reaction, mixture was cooled again and basified with 6N NaOH. Aqueous solution was then extracted with ethyl acetate (50 ml×3) and organic layer was separated, dried and evaporated on rotary evaporator. Crude compound thus obtained was purified by 230-400 mesh flash silica gel column chromatography using 0-2% methanol in dichloromethane as eluting system to afford the sticky mass as a diastereomeric mixture. Yield: $^1H$ NMR (400 MHz, DMSO) δ=7.38-7.28 (m, 5H), 5.06 (s, 2H), 4.75 (s, 1H), 4.62-4.61 (d, 1H), 4.24 (br, 1H), 3.71 (s, 1H), 3.48 (s, 1H), 2.71 (s, 3H), 1.84 (m, 1H), 1.76-1.74 (m, 2H), 1.52-1.50 (m, 1H), 1.37 (s, 1H), 1.21-1.18 (m, 1H). LCMS [M+H]: 280.3, [M+NH$_4$]: 297.3; HPLC shows a mixture of two diasteromers in 50:50 ratio.

Synthesis of 527

A 100 ml single neck RBF was charged with diastereomeric mixture of 526 (0.6 g, 0.00215 mol), dimethyl acetal of dilinoleyl ketone (1.23 g, 0.002150 mol) 50 ml toluene, catalytic amount of p-TSA. The resulting mixture was then stirred and heated to reflux vigorously over a Soxhlet apparatus containing 4A molecular sieves and 50 ml toluene. Progress of the reaction was monitored by TLC. After 6 h mixture was cooled to room temperature, volatilities were removed under vacuum and residual mass stirred in n-hexane for 10 minutes then decanted off. This procedure was repeated twice to remove the unreacted diol. All the hexane washings were combined and concentrated to give crude material which was purified by column chromatography on neutral alumina using 3% ethyl acetate in n-hexane as eluent to afford Alny-8-015 which was confirmed by $^1H$ NMR and MS. Yield: 0.6 g. (37.5%) $^1H$ NMR (400 MHz, $CDCl_3$) δ=7.35-7.30 (m, 5H), 5.40-5.29 (m, 8H), 5.15-5.07 (dd, 2H), 4.48 (m, 1H), 3.56-3.53 (m, 1H), 3.41-3.36 (m, 1H), 2.96 (s, 3H), 2.77-2.74 (m, 4H), 2.30-2.27 (m, 1H), 2.14 (m, 1H), 2.06-2.01 (m, 8H), 1.70 (m, 3H), 1.61 (m, 4H), 1.35-1.24 (m, aliphatic protons), 0.89-0.859 (m, 6H). Mass-[M+H]-788.8 & [M+Na]-811.8 HPLC purity-97.32%.

Synthesis of ALNY-169

Prepared the ALNY-169 by following similar procedure as compound 506, using N-Cbz-compound of 527 (0.52 g, 0.66 mmol) and 1M solution of LAH in THF (1.32 mL, 1.32 mmol), gave 0.4 g (91%) of the pure product ALNY-169. $^1H$ NMR (400 MHz, $CDCl_3$) δ 5.50-5.22 (m, 8H), 3.67 (ddd, J=12.1, 8.9, 3.3, 1H), 3.39-3.16 (m, 1H), 2.77 (t, J=6.4, 4H), 2.44 (dd, J=12.7, 2.2, 1H), 2.29 (s, 1H), 2.24 (s, 6H), 2.06 (dt, J=13.5, 10.9, 8H), 1.99-1.87 (m, 1H), 1.63 (dd, J=16.1, 9.8, 5H), 1.51-1.14 (m, 39H), 0.89 (t, J=6.7, 6H). $^{13}C$ NMR (101 MHz, $CDCl_3$) δ 130.40, 128.14, 112.25, 81.03, 77.54, 77.22, 76.91, 75.60, 61.55, 44.11, 38.19, 38.14, 31.74, 30.24, 30.21, 29.89, 29.80, 29.77, 29.74, 29.57, 29.54, 27.46, 27.41, 25.84, 24.86, 24.36, 24.23, 22.80, 14.31. Calc. mass for the $C_{45}H_{81}NO_2$: 668.1. found 668.5.

Example 15
Synthesis of Ketal ALNY-115 & 116

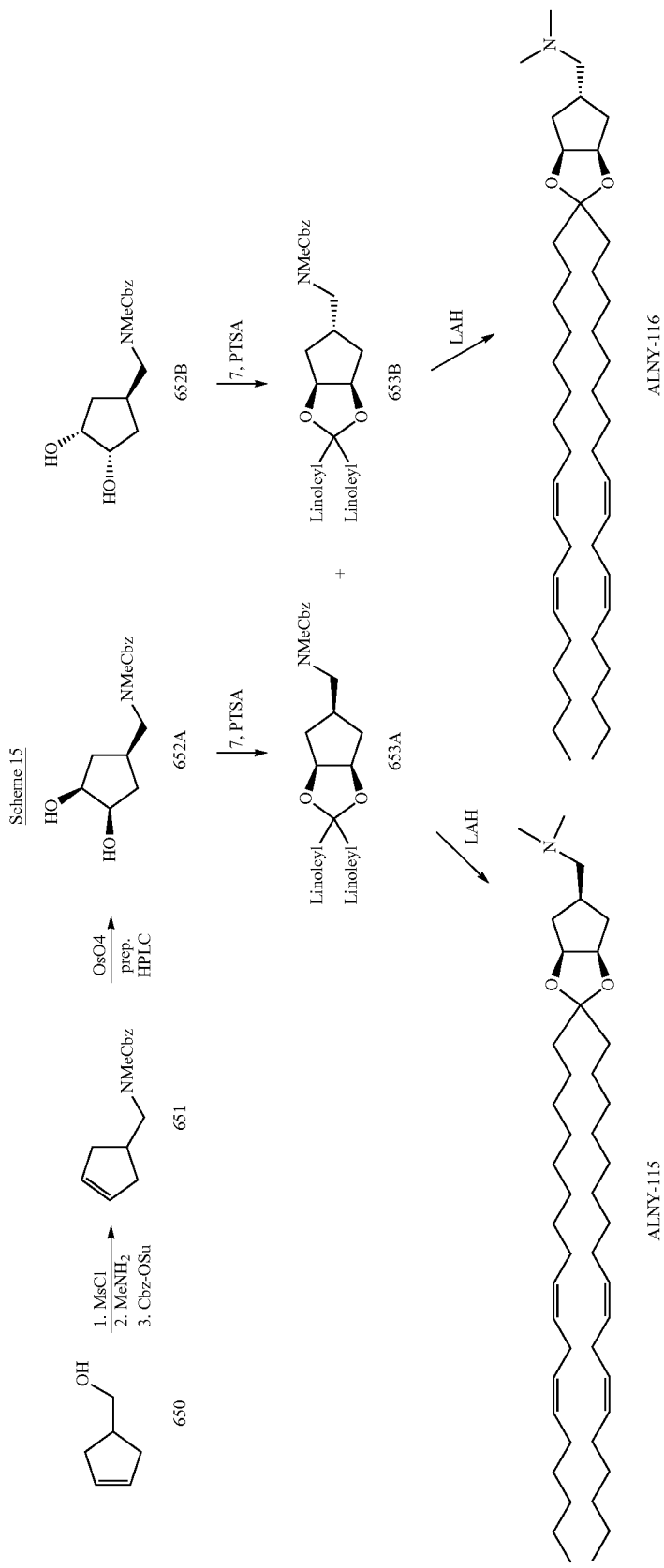

Preparation of Compound 651

An ice-cold solution of compound 650 (1.05 g, 10.7 mmol) and NEt$_3$ (1.2 eq) in DCM (50 mL) was treated in a dropwise fashion over 5 min with MsCl (1.1 eq). After 1 h at 0° C., aqueous workup gave crude mesylate (1.88 g, 99%, pure by TLC) which was used without purification in the next step. The mesylate (10.5 mmol) was treated with 33% H$_2$NMe in EtOH (100 mL) at 50° C. over 18 h. Excess H$_2$NMe was removed by co-evaporation with Et$_2$O, then the ethanolic solution of the product was treated with conc. HCl (2 eq). The EtOH was removed by evaporation and the residue was redissolved in DCM (100 mL). NEt$_3$ (4 eq) was added followed by Cbz-OSu (1.5 eq) and the mixture was stirred at r.t. for 3 h. Aqueous workup then column chromatography gave pure compound 651 as an oil (86% from 650). $^1$H NMR (400 MHz, CDCl$_3$) δ 7.54-7.04 (m, 5H), 5.65 (d, J=8.6, 2H), 5.13 (s, 2H), 3.27 (t, J=8.9, 2H), 2.94 (s, 3H), 2.60 (s, 1H), 2.51-2.28 (m, 2H), 2.04 (dd, J=22.1, 15.3, 2H); $^{13}$C NMR (101 MHz, CDCl$_3$) δ 129.47, 128.40, 127.83, 127.75, 66.92, 53.74, 53.13, 38.92, 36.34, 36.23, 36.06, 35.78; Electrospray MS (+ve): Molecular weight for C15H19NO2 (M+H)$^+$ Calc. 246.1. Found 246.0.

The diols 652A and 652B were synthesized using our standard reaction conditions starting from the commercially available cyclopentene alcohol 650.

Synthesis of Compounds 652A and 652B

Compound 652A and compound 652B were successfully separated from the diastereomeric mixture by preparative HPLC method. (the two isomers were in the ratio of 88:12) LC-MS-[M+H]-280.4 & [M+NH$_4$$^+$]-297.5.

652A: $^1$H-NMR (400 MHz, DMSO), δ=7.38-7.30 (m, 5H), 5.05 (s, 2H), 4.34 (d, 2H), 3.83 (br, 2H), 3.12-3.10 (m, 2H), 2.84-2.80 (m, 3H), 1.60-1.56 (m, 2H), 1.34-1.33 (m, 2H) HPLC purity-99.78%.

652B: $^1$H-NMR (400 MHz, DMSO), δ=7.36-7.31 (m, 5H), 5.05 (s, 2H), 4.33 (br, 2H), 3.73 (m, 2H), 3.25-3.20 (m, 2H), 2.85-2.82 (m, 3H), 2.07-2.03 (m, 1H), 1.82-1.73 (m, 2H), 1.28-1.25 (m, 2H) HPLC purity-98.76%.

Using a procedure analogous to that described for the synthesis of compound 505, compounds 653A and 653B were obtained as yellow oil.

653A:
Yield: 2.1 g (67.74%) colorless oil $^1$H-NMR (400 MHz, CDCl$_3$), δ=7.33-7.29 (m, 5H), 5.38-5.28 (m, 8H), 5.10 (s, 2H), 4.58-4.55 (m, 2H), 3.29-3.23 (m, 2H), 2.92 (m, 3H), 2.77-2.74 (m, 4H), 2.5 (m, 1H), 2.06-2.01 (m, 8H), 1.92-1.88 (m, 2H), 1.60 (m, 2H), 1.45 (m, 2H), 1.37-1.25 (m, aliphatic protons), 0.89-0.85 (m, 6H) HPLC purity:-98.95%

653B:
Yield 0.210 g, (62.00%) $^1$H-NMR (400 MHz, CDCl$_3$), δ=7.33 (m, 5H), 5.37-5.32 (m, 8H), 5.10 (s, 2H), 4.57 (br, 2H), 3.35-3.33 (m, 2H), 2.95 (s, 3H), 2.77-2.74 (m, 4H), 2.33 (m, 1H), 2.26 (m, 1H), 2.06-2.00 (m, 8H), 1.92 (m, 2H), 1.65 (m, 2H), 1.60 (m, 2H), 1.37-1.25 (m, aliphatic protons), 0.89-0.85 (m, 6H) HPLC purity:-98.84%

Preparation of ALNY-115

Prepared the compound ALNY-115 by following similar procedure as compound ALNY-100, using N-Cbz-compound 653A (0.21 g, 0.27 mmol, 1.0 eq) and 1M solution of LAH in THF (0.4 mL, 0.4 mmol, 1.5 eq), gave 0.09 g (50%) of the pure product ALNY-115. $^1$H NMR (400 MHz, CDCl$_3$) δ 5.53-5.16 (m, 8H), 4.68-4.46 (m, 2H), 2.79 (t, J=6.6, 4H), 2.37 (d, J=7.1, 2H), 2.24 (d, J=5.1, 6H), 2.16-1.94 (m, 11H), 1.73-1.64 (m, 2H), 1.58 (ddd, J=20.2, 10.4, 6.8, 4H), 1.48-1.21 (m, 37H), 0.91 (dd, J=8.8, 5.1, 6H). $^{13}$C NMR (101 MHz, CDCl$_3$) δ 130.19, 130.17, 130.15, 127.95, 127.94, 127.93, 115.27, 80.90, 77.34, 77.02, 76.70, 65.01, 45.83, 37.40, 37.10, 31.55, 31.54, 31.53, 29.99, 29.70, 29.68, 29.58, 29.56, 29.50, 29.36, 29.35, 29.32, 27.26, 27.24, 27.21, 25.64, 24.42, 23.83, 22.59, 14.10. Calc. mass for the C$_{45}$H$_{81}$NO$_2$: 668.1. found 668.5.

Preparation of ALNY-116

Prepared the compound ALNY-116 by following similar procedure as compound ALNY-100, using N-Cbz-compound of the corresponding product (2.1 g, 2.66 mmol, 1.0 eq) and 1M solution of LAH in THF (4.0 mL, 4.0 mmol, 1.5 eq), gave 1.2 g (68%) of the pure product ALNY-116.

$^1$H NMR (400 MHz, CDCl$_3$) δ 5.57-5.21 (m, 8H), 4.67-4.53 (m, 2H), 2.79 (t, J=6.5, 4H), 2.52-2.33 (m, 1H), 2.23 (m, 8H), 2.14-1.94 (m, 10H), 1.66 (dd, J=10.1, 6.1, 2H), 1.58-1.22 (m, 39H), 1.22-1.07 (m, 2H), 0.91 (t, J=6.9, 6H). $^{13}$C NMR (101 MHz, CDCl$_3$) δ 130.19, 130.17, 130.14, 127.96, 127.94, 127.93, 112.24, 80.36, 77.34, 77.02, 76.70, 64.27, 45.80, 38.75, 36.15, 35.85, 34.67, 31.54, 30.01, 29.88, 29.71, 29.69, 29.68, 29.58, 29.53, 29.49, 29.37, 29.36, 29.31, 27.27, 27.24, 27.21, 25.64, 24.63, 23.17, 22.59, 22.58, 14.10. Calc. mass for the C$_{45}$H$_{81}$NO$_2$: 668.1. found 668.5.

Example 16

Synthesis of ALNY-121 and ALNY-122

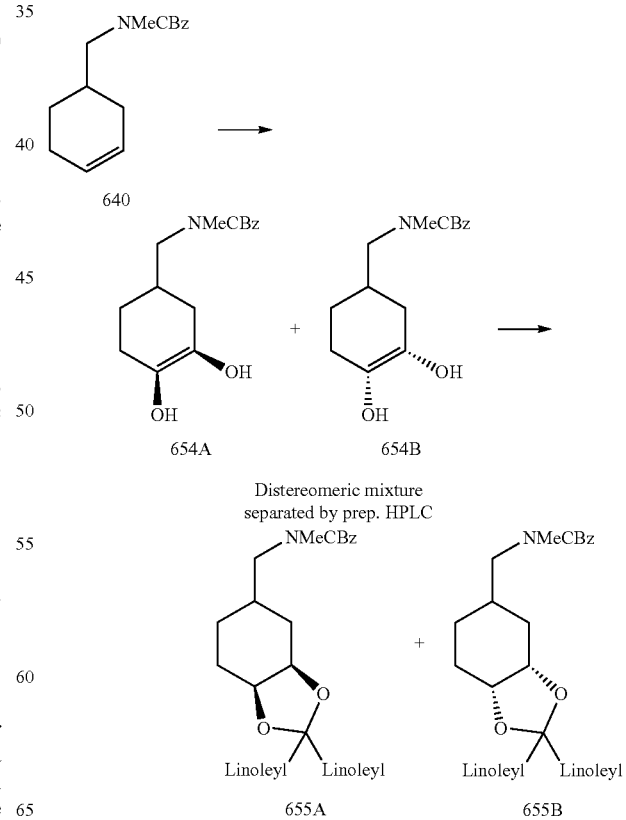

Synthesis of 654A and 654B

To a solution of compound 640 (5 g, 0.01930 mol) in a mixture of (10:1) mixture of acetone and water (220 ml) in a single neck 500 ml RBF was added NMO (6.784 g, 0.05791 mol) followed by a 6.25% solution of $OsO_4$ (0.245 g, 0.0009652 mol) in tert-butanol. The resulting solution was stirred at room temperature and progress of the reaction was monitored by TLC. After complete consumption of compound 640 (~2.0 h by TLC) reaction mixture was quenched with 100 ml aqueous $Na_2SO_3$ solution and the mixture was stirred at room temperature for 1.0 h. Aqueous phase was then extracted well with dichloromethane (2×250 ml) and separated out. Organic layer was washed with sat. $NaHCO_3$ (2×50 ml) followed by brine (1×50 ml). Organic phase was then dried over $Na_2SO_4$, filtered and concentrated in vacuum to give crude mass, which was subjected to column purification on 60-120 mesh silica gel and eluted with 6-10% methanol in dichloromethane system to afford pure diastereomeric mixture as thick yellow oil. Yield: 5.7 g, (100%) $^1$H-NMR (400 MHz, $CDCl^3$), δ=7.34-7.27 (m, 5H), 5.12 (s, 2H), 3.98-3.92 (m, 1H), 3.61-3.57 (m, 1H), 3.17-3.08 (m, 2H), 2.92-2.90 (m, 3H), 2.16-1.84 (m, 4H), 1.68 (m, 2H), 1.40-1.37 (m, 1H) LC-MS: [M+H]-294.3, HPLC purity: two peaks in a ratio (15:85).

Diastereomers were separated by preparative HPLC.
Peak-1:
$^1$H-NMR (400 MHz, $CDCl_3$), δ=7.35-7.28 (m, 5H), 5.10 (s, 2H), 3.98-3.94 (m, 1H), 3.63-3.55 (m, 1H), 3.19-3.06 (m, 2H), 2.90 (s, 3H), 2.00-1.99 (m, 1H), 1.90-1-59 (m, 4H), 1.23-1.17 (m, 1H), 1.12-0.86 (m, 2H), LC-MS: [M+H]-294.3 & [M+$NH_4^+$]-311.4, HPLC purity: 100%
Peak-2:
$^1$H-NMR (400 MHz, $CDCl_3$), δ=7.32-7.29 (m, 5H), 5.12 (s, 2H), 3.93 (br, 1H), 3.65-3.14 (m, 2H), 2.90 (s, 3H), 1.91 (m, 1H), 1.67-1.48 (m, 2H), 1.41-1.26 (m, 5H), LC-MS: [M+H]-294.4 & [M+Na]-316.4, HPLC purity: 99.36%

Synthesis of 655A and 655B

General Procedure:
A mixture of diol (1 eq), dilinoleyl ketone (3 eq), 50 ml toluene and catalytic amount of p-TSA (0.1 eq) in a 100 ml single neck RBF were stirred and heated to reflux vigorously over Soxhlet apparatus containing 4A molecular sieves and 50 ml toluene. Progress of the reaction was monitored by TLC. After completion of the reaction (~12-14 h), mixture was cooled to room temperature and then toluene was removed in vacuum to give crude mass which was purified by column chromatography on neutral alumina using 3-5% ethyl acetate in hexane as eluting system to afford pure product as yellow oil.
Peak-1 655A
Yield 0.3 g (38%) $^1$H-NMR (400 MHz, $CDCl_3$), δ=7.35-7.28 (m, 5H), 5.40-5.28 (m, 8H), 5.10 (s, 2H), 4.23-4.19 (m, 1H), 4.07-4.02 (m, 1H), 3.19-3.06 (m, 2H), 2.91-2.89 (m, 3H), 2.77-2.75 (m, 4H), 2.05-2.00 (m, 8H), 1.98 (m, 1H), 1.85 (m, 1H), 1.72-1.65 (m, 3H), 1.37-1.24 (m, aliphatic protons), 0.89-0.85 (m, 6H). HPLC purity: 90.88%
Peak-2 (655B)
Yield 0.225 g (38%) $^1$H-NMR (400 MHz, $CDCl_3$), δ=7.34-7.29 (m, 5H), 5.39-5.28 (m, 8H), 5.10 (s, 2H), 4.14 (br, 1H), 4.02 (m, 1H), 3.22-3.17 (m, 1H), 3.09-3.05 (m, 1H), 2.91 (1, 3H), 2.77-2.74 (m, 4H), 2.05-2.00 (m, 8H), 1.80 (m, 1H), 1.65 (m, 3H), 1.35-1.26 (m, aliphatic protons), 0.89-0.85 (m, 6H). HPLC purity: 92.83%

Preparation of Compound ALNY-121

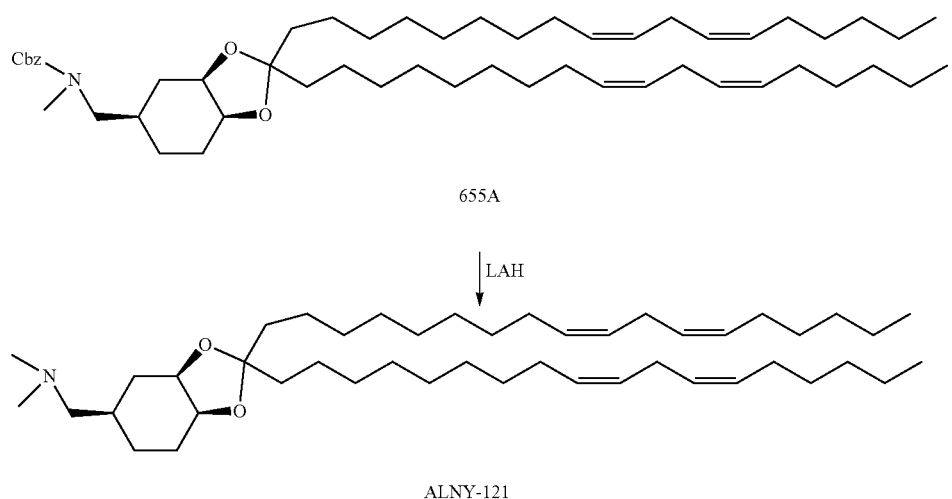

655A

↓ LAH

ALNY-121

Prepared the compound ALNY-121 by following similar procedure as compound ALNY-100, using N-Cbz-compound of the corresponding product (0.28 g, 0.35 mmol, 1.0 eq) and 1M solution of LAH in THF (0.52 mL, 0.52 mmol, 1.5 eq), gave 0.15 g (66%) of the pure product ALNY-121. $^1$H NMR (400 MHz, $CDCl_3$) δ 5.48-5.18 (m, 8H), 4.29-4.16 (m, 1H), 4.06 (dt, J=8.3, 5.6, 1H), 2.76 (t, J=6.4, 4H), 2.18 (s, 6H), 2.14-1.91 (m, 11H), 1.90-1.60 (m, 5H), 1.60-1.46 (m, 3H), 1.46-1.13 (m, 38H), 0.94-0.76 (m, 6H). $^{13}$C NMR (101 MHz, $cdcl_3$) δ 130.40, 130.38, 128.16, 111.29, 77.54, 77.23, 76.91, 74.02, 73.13, 66.44, 46.15, 38.44, 36.58, 32.07, 31.75, 30.25, 29.92, 29.90, 29.78, 29.75, 29.72, 29.57, 29.55, 29.54, 28.82, 28.52, 27.47, 27.43, 26.03, 25.86, 24.74, 24.42, 22.79, 14.29 Calc. mass for the $C_{46}H_{83}NO_2$: 682.1. found 682.5.

Preparation of ALNY-122

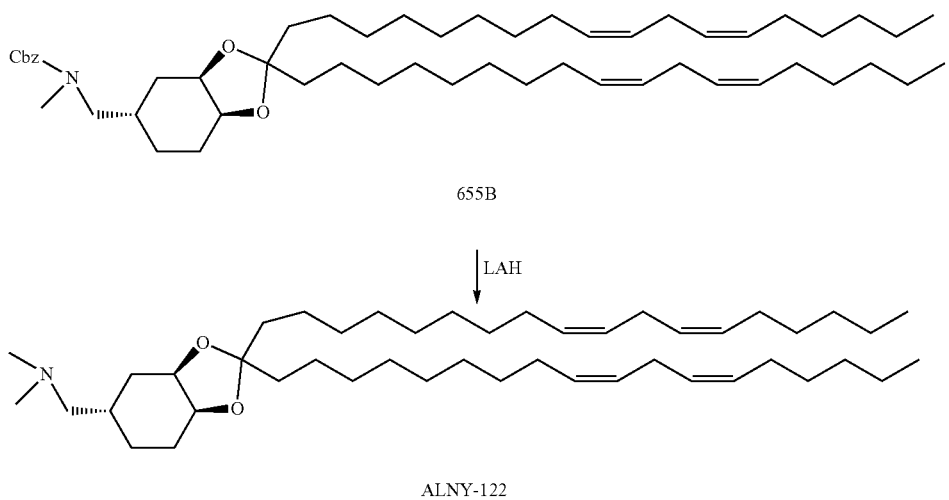

Using a similar procedure as described for the synthesis of 653B, the six membered analog 655B was synthesized and purified.

ALNY-122 was prepared by following similar procedure as compound ALNY-100, using N-Cbz-compound of the corresponding product (0.21 g, 0.26 mmol, 1.0 eq) and 1M solution of LAH in THF (0.4 mL, 0.4 mmol, 1.5 eq), gave 0.08 g (50%) of the pure product 11. $^1$H NMR (400 MHz, CDCl$_3$) δ 5.50-5.19 (m, 8H), 4.16 (dd, J=8.2, 4.2, 1H), 4.05 (dt, J=9.7, 6.1, 1H), 2.76 (t, J=6.4, 4H), 2.16 (d, J=10.3, 6H), 2.10-1.97 (m, 10H), 1.95-1.83 (m, 1H), 1.76-1.48 (m, 7H), 1.48-1.19 (m, 39H), 0.88 (t, J=6.8, 6H). $^{13}$C NMR (101 MHz, cdcl$_3$) δ 130.40, 130.38, 128.17, 111.50, 77.55, 77.23, 76.91, 74.33, 73.21, 66.44, 46.17, 38.75, 36.87, 34.64, 32.36, 31.75, 30.25, 29.92, 29.90, 29.77, 29.75, 29.72, 29.58, 29.54, 27.48, 27.47, 27.43, 26.70, 25.86, 25.12, 24.72, 24.54, 22.80, 14.29. Calc. mass for the C$_{46}$H$_{83}$NO$_2$: 682.1. found 682.5.

Example 17
Synthesis of ALNY-144

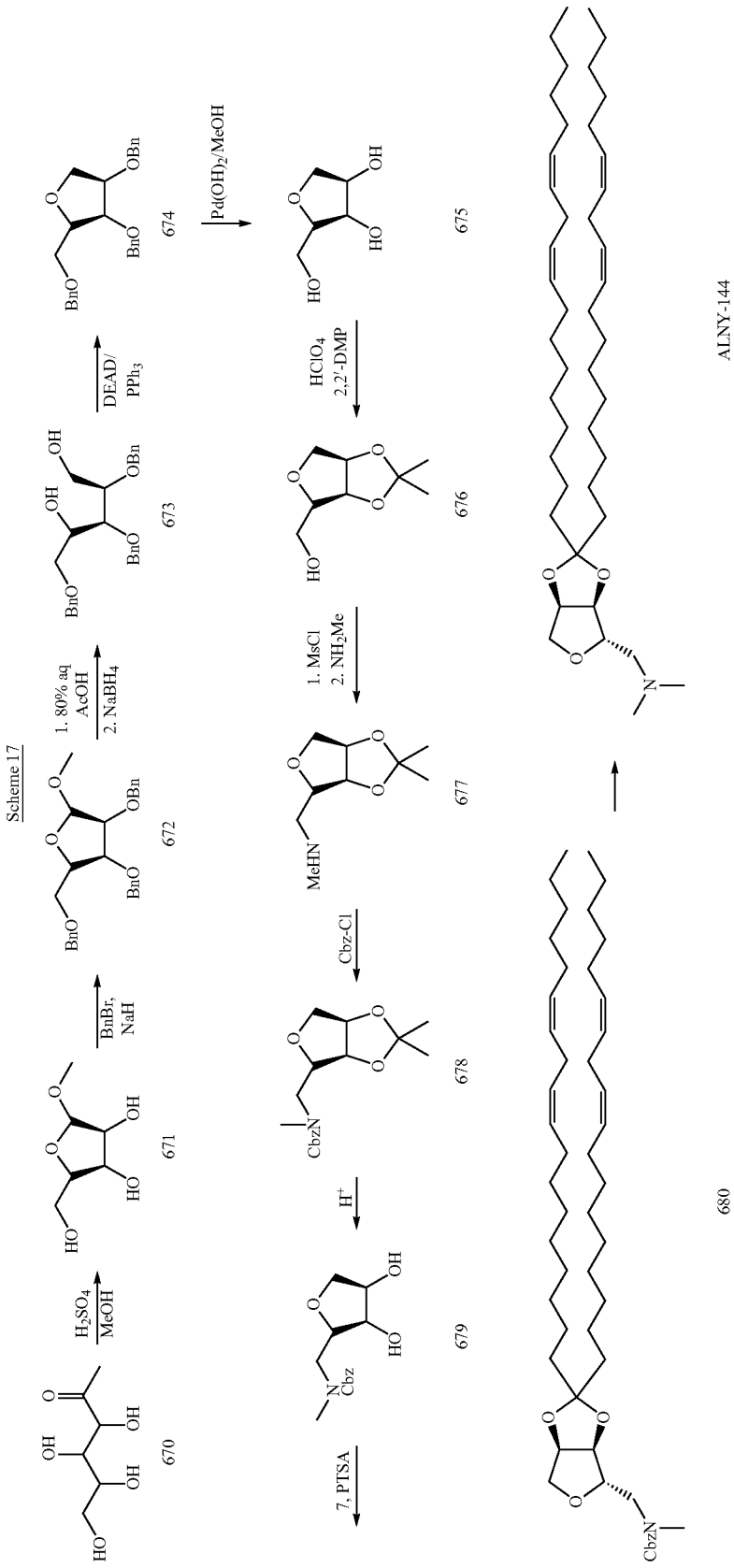

Synthesis of Compound 671

D (−) ribose (15 g, 0.1 mmol) was dissolved in 300 ml methanol in a 1 liter single neck RBF and cooled to 0° C. under nitrogen atmosphere. To this stirred solution was added conc. H2SO4 (2 mL) slowly and then reaction mixture was warmed to room temperature and stirred for 20 h. Progress of the reaction was monitored by TLC. After completion of reaction (~20 h), reaction mixture was concentrated under vacuum to half the original volume. Sodium carbonate (15 g) was then added into it and mixture was stirred for 2 h. Mixture was then filtered off and filtrate was concentrated to get compound 671 as pale yellow oil. Yield: 20 g crude (matched with authentic procured from Aldrich).

Synthesis of Compound 672

Compound 671 (2 g, 0.0121 mmol) was dissolved in 40 ml anhydrous DMF in a 100 mL two neck RBF and cooled to 0° C. To this stirred solution (60% as oil suspension) NaH (2.18 g, 0.0455 mmol) was added in portions under nitrogen atmosphere and mixture was stirred for 35 min. Benzyl bromide (5.32 mL, 0.0445 mmol) was then added slowly over a period of 30 min. Reaction mixture was then warmed to room temperature and stirring was continued for 16 h at room temperature. The progress was monitored by TLC. Upon completion, reaction mixture was poured onto crushed ice (~200 g). Aqueous phase was well extracted with Ethyl acetate (2×100 ml). Organic layer was then dried over $Na_2SO_4$, and ethyl acetate was stripped off to afford crude compound which was purified by column chromatography using 60-120 mesh silica gel with 0-30% EtOAc:Hexane as eluting system to get compound 2 as pale yellow liquid. Yield: 3 g (57%). 1H-NMR (CDCl3, 400 MHz): δ=7.36-7.24 (m, 15H), 4.9 (s, 1H), 4.67-4.51 (m, 5H), 4.45-4.42 (m, 1H), 4.34-4.32 (m, 1H), 4.01-3.98 (m, 1H), 3.81 (m, 1H), 3.61-3.59 (m, 1H), 3.58-3.47 (m, 1H), 3.3 (s, 3H). LC-MS: [M+H]-435.3 present.

Synthesis of Compound 673

A single neck 100 ml RBF was charged with Compound 672 (3 g, 0.0069 mmol) and 80% aq.AcOH solution. Resulting mixture was then heated at 90° C. for 9 h and monitored by TLC. Reaction mixture was cooled to room temperature and concentrated on rotatory evaporator. Residual mass was again co-evaporated with toluene and methanol to remove traces of AcOH. To this residue methanol (35.3 ml) was added and stirred for some time at 0° C. This was followed by addition of NaBH4 (0.277 g, 0.00734 mmol) in portions and mixture was stirred at 0° C. for 1 h. Solvent was evaporated off, residue was diluted with water (20 ml) and compound was extracted with DCM (2×20 ml). Organic layer was washed with 10% sodium carbonate, dried over Na2SO4 and concentrated in vacuum. Crude compound thus obtained was purified by silica gel (60-120 mesh) column chromatography using (0-50%) ethyl acetate & n-hexane as eluent to get compound 673 as a thick liquid. Yield: 1.7 g (59%). 1H-NMR (CDCl3, 400 MHz): δ=7.35-7.23 (m, 15H), 4.73 (m, 1H), 4.65-4.56 (m, 3H), 4.50 (m, 2H), 4.00-3.99 (m, 1H), 3.84-3.75 (m, 4H), 3.59-3.57 (m, 2H). LC-MS: [M+H]-423.2 present.

Synthesis of Compound 674

To a solution of Compound 673 (1.7 g, 0.00403 mmol) in 20 ml dioxane in 100 ml RBF, PPh3 (2.1 g, 0.00806 mmol) was added and reaction mixture was stirred for 5-10 minutes under nitrogen atmosphere. DEAD (1.24 ml,) was then added to this solution over a period of 1 h and reaction was continued at room temperature for 20 h. Progress of the reaction was monitored by TLC. After completion of the reaction, solvent was removed under vacuum and residue obtained was purified by (60-120 mesh) silica gel column chromatography using (0-30%) ethyl acetate in hexane as eluting system to get compound 674 in pure forms. Yield: 1.3 g (80%). 1H-NMR (CDCl3, 400 MHz): δ=7.34-7.19 (m, 15H), 4.63-4.53 (m, 4H), 4.50-4.46 (m, 2H), 4.16 (m, 1H), 4.02-3.90 (m, 4H), 3.63-3.59 (dd, 1H), 3.50-3.48 (dd, 1H). LC-MS: [M+H]-405.2, [M+NH4]-422.3

Synthesis of Compound 675

To a stirred solution of Compound 674 (1.3 g, 0.00321 mmol) in methanol (22 ml) and cyclohexene (7.5 ml) in a single neck RBF was added carefully Pd(OH)2/C (0.361 g) at once under nitrogen atmosphere and then reaction mixture was heated to reflux at 80° C. for 18 h. After completion of the reaction (by TLC) mixture was cooled to room temperature and the catalyst was removed by filtration, filtrate was concentrated to give crude compound which was purified by column chromatography using 60-120 mesh silica gel with (0-20%) ethyl acetate in hexane as eluting system to yield compound 675. Yield: 0.280 g (65%). $^1$H-NMR (DMSO, 400 MHz): δ=4.72-4.71 (m, 2H), 4.62-4.60 (m, 1H), 3.98-3.93 (m, 1H), 3.84-3.81 (m, 1H), 3.76-3.72 (q, 1H), 3.58-3.55 (m 1H), 3.50-3.46 (m, 2H), 3.37 (m, 1H).

Synthesis of Compound 676

Compound 675 (0.25 g, 0.00166 mmol) was dissolved in 2,2-dimethoxy propane (0.516 ml, 0.00365 mol) and acetone (2 ml) in a 25 ml single neck RBF and cooled to 0° C. To this stirred solution 70% aq.HClO4 (0.016 ml, 0.00166 mmol) solution was added slowly and after complete addition reaction mixture was warmed to ambient temperature and stirred for 4 h. After completion of the reaction by TLC, reaction mixture was neutralized by solid sodium carbonate and volatilities were removed on rota vapour. DCM (20 ml) was added to the residue and mixture was stirred for some time and DCM layer was washed with water (10 ml) followed by brine (5 ml). Organic layer was then dried over anhydrous Na2SO4 and concentrated in vacuum to give compound 676 as thick liquid. Yield: 0.270 g (94%). 1H-NMR (CDCl3, 400 MHz): δ=4.82-4.78 (m, 1H), 4.60-4.58 (m, 1H), 4.13-4.10 (m, 1H), 3.99-3.92 (m, 2H), 3.66-3.58 (m, 2H), 1.76-1.73 (m 1H), 1.51-(s, 3H), 1.33 (s, 3H).

Synthesis of Compound 677

Compound 676 (0.250 g, 0.001436 mmol) was dissolved in anhydrous DCM in a 25 ml single neck RBF and cooled to 0° C. To this mixture TEA (0.5 ml, 0.00359 mmol) was added under nitrogen atmosphere and mixture was stirred for 30 min. Ms-Cl (0.28 ml, 0.00359 mmol) was then added slowly at 0° C. and mixture was stirred at room temperature for 2 h. After completion of reaction (by TLC), reaction mixture quenched with water (20 ml) stirred for some time and DCM layer was separated out. Aqueous phase was further extracted with DCM (2×10 ml). Combined organic extracts was dried and concentrated in vacuum to give crude compound which was used as such for next step. Yield: 0.360 g crude. 1H-NMR (CDCl3, 400 MHz): δ=4.83-4.82 (m, 1H), 4.67-4.65 (m, 1H), 4.30-4.20 (m, 3H), 4.00-3.95 (m, 2H), 3.05 (s, 3H), 1.50 (s, 3H), 1.33 (s, 3H). LC-MS: [M+H]-253.0 & [M+NH4+]-

270.0 present. The crude compound (0.360 g) and 15 ml (25%) solution of methyl amine in ethanol were heated together in a 50 ml sealed tube at 50° C. for 18 h. Progress of the reaction was monitored by TLC. After completion of reaction, the mixture was concentrated under vacuum and co evaporated with diethyl ether to get compound 677 as gummy mass. Yield: 0.5 g crude. 1H-NMR (CDCl3, 400 MHz): δ=4.82-4.80 (m, 1H), 4.51-4.49 (m, 1H), 4.43-4.39 (m, 1H), 4.01 (d, 2H), 2.94 (s, 2H), 2.71 (s, 3H), 1.48 (s, 3H), 1.30 (s, 3H). LC-MS: [M+H]-188.2 present.

Synthesis of Compound 678

Crude compound 677 (0.5 g, 0.00267 mmol)) was dissolved in a mixture of (6 ml) dioxane: H2O (1:1) in a 50 ml single neck RBF and cooled to 0° C. Sodium bicarbonate (0.560 g, 0.00667 mmol) was then added in portions and resulting mixture was stirred for 30 min. To this cold solution, a solution of Cbz-Cl (50%) in toluene (1.2 ml, 0.0040 mmol) was added slowly. RM was then allowed to come to room temperature and stirred for 2-3 h. The progress was monitored by TLC. After completion of reaction, mixture was diluted with water (10 ml) and DCM (20 ml), stirred for 10 minutes and DCM layer was separated out. Aqueous phase was back extracted with DCM (1×10 ml). Organic phase was then dried over an. Na2SO4 and concentrated in vacuum to afford crude compound 678 which was purified by column chromatography using neutral alumina using 10% ethyl acetate in hexane as eluent to give pure compound 678. Yield: 0.3 g (35%). 1H-NMR (CDCl3, 400 MHz): δ=7.35-7.28 (m, 5H), 5.11 (m, 2H), 4.82-4.23 (m, 2H), 4.18 (m, 1H), 3.98-3.62 (m, 2H), 3.33-3.25 (m, 2H), 2.97 (s, 3H), 1.49 (m, 3H), 1.31 (m, 3H) (note: NMR reflects the presence of rotamers) LC-MS: [M+H]-322.4 present.

Synthesis of Compound 679

A single neck 25 ml RBF was charged with compound 678 (0.3 g, 0.000934 mmol) and 7 ml 70% aqueous acetic acid and the resulting mixture was heated to reflux for 3 h. After completion of reaction, solvent was stripped off and traces of AcOH were removed by co evaporation with toluene and methanol to get crude compound 679. Yield: 0.220 g (83%). 1H-NMR (DMSO, 400 MHz): δ=7.36-7.30 (m, 5H), 5.09 (m, 2H), 4.84-4.81 (m, 2H), 3.98-3.95 (m, 1H), 3.89-3.86 (m, 1H), 3.72 (m, 2H), 3.62 (m, 2H), 3.52-3.48 (m, 3H). LCMS: [M+H]-282.0 & [M+NH4+]-299.3 present.

Synthesis of 680

To a mixture of Compound 679 (0.21 g, 0.000747 mmol) in toluene (10 ml) was added dilinoleyl ketone (0.433 g, 0.000822 mmol) followed by catalytic amount of pTSA (0.014 g 0.1 eq,). Resulting mixture was then heated to reflux for 2-3 h over soxhlet apparatus containing 4A molecular sieves and 50 ml toluene. Progress of the reaction was monitored by TLC. After completion of reaction, toluene was removed on rotavapor and crude mass was dissolved in DCM (50 ml) and washed with aq. saturated bicarbonate solution (1×10 ml) followed by water (1×10 ml). Organic layer was dried over an. Na2SO4 and concentrated in vacuum. Crude compound thus obtained was purified by column chromatography using neutral alumina and eluted with 2% ethyl acetate in hexane system to yield the title compound 680. Yield: 0.34 g (60%). 1H-NMR (CDCl3, 400 MHz): δ=7.35-7.29 (m, 5H), 5.40-5.28 (m, 8H), 5.11 (s, 2H), 4.78-4.40 (m, 2H), 4.24-4.19 (m, 1H), 3.99-3.69 (m, 2H), 3.30-3.24 (m, 2H), 2.97 (s, 3H), 2.76 (m, 4H), 2.06-2.01 (m, 8H), 1.65 (m, 2H), 1.35-1.26 (m, aliphatic protons from linoleyl chain), 0.87 (t, 6H). LC-MS: [M+H]=790.4 & [M+Na]-812.4 present HPLC purity- 98.87%.

Synthesis of ALNY-144

Prepared the compound ALNY-144 by following similar procedure as compound ALNY-100, using N-Cbz-compound 680 of the corresponding product (0.3 g, 0.38 mmol, 1.0 eq) and 1M solution of LAH in THF (0.76 mL, 0.76 mmol, 1.5 eq), gave 0.17 g (69%) of the pure product ALNY-144. $^1$H NMR (400 MHz, CDCl$_3$) δ 5.54-5.22 (m, 8H), 4.76 (dd, J=7.5, 3.0, 1H), 4.50 (dd, J=6.4, 1.8, 1H), 4.18-4.08 (m, 1H), 3.95 (dd, J=10.6, 1.4, 1H), 3.84 (dd, J=10.6, 4.3, 1H), 2.77 (t, J=6.4, 4H), 2.27 (s, 6H), 2.04 (q, J=6.8, 8H), 1.68 (dd, J=9.9, 6.2, 2H), 1.53 (d, J=8.7, 2H), 1.49-1.17 (m, 38H), 0.89 (t, J=6.8, 6H). Calc. mass for the $C_{44}H_{79}NO_3$: 670.1. found 670.5.

Example 18

Synthesis of ALNY-151

Scheme 18:
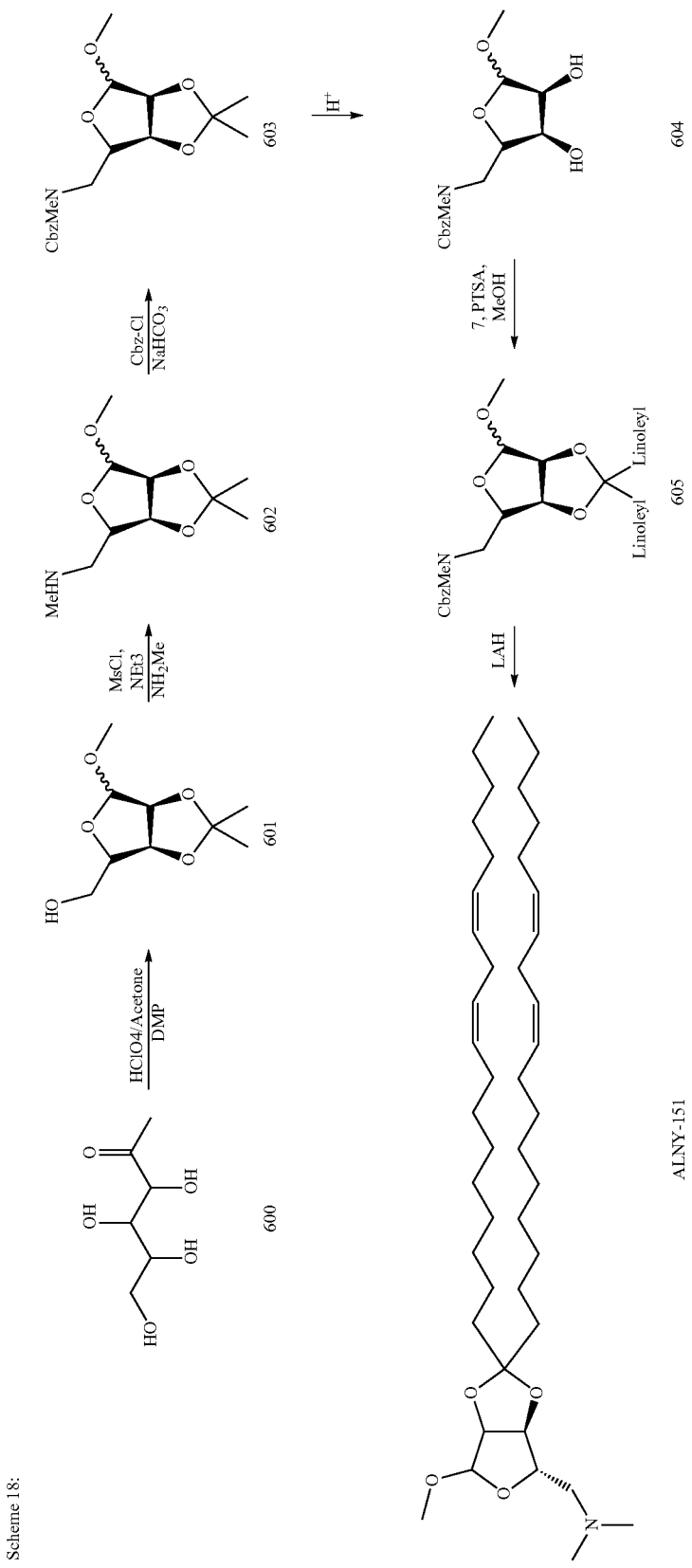

Synthesis of Compound 601

To suspension of compound 600 (10 gm, 0.0866 moles) in 2,2-dimethoxy propane (20.73 ml, 0.1399 moles) and dry acetone (140 ml) in a 500 ml two neck RBF was added 60% perchloric acid (4.5 ml, 0.066 moles) drop wise over 5 mins at 5° C. The reaction mixture was warmed to room temperature and stirred for 2 h. Methanol (14 ml) was then added and solution was stirred for an additional 2 h. Progress was monitored by TLC. The solution was then cooled at 5° C. and neutralized with aq. sodium carbonate solution (4 gm in 15 ml of water). Mixture was filtered off and filtrate was concentrated on rotary evaporator to give yellow solid that was dissolved in diethyl ether (200 ml), washed with water (150 ml) followed by brine (150 ml), dried over $Na_2SO_4$, and concentrated in vacuum to afford colorless oil. Crude oil was distilled under high vacuum (85-89° C., 0.25 mm of mercury) to give 601 as a colorless liquid.

Yield: (40%). $^1$H NMR (400 MHz, CDCl3) δ=4.95 (s, 1H), 4.81-83 (d, 1H), 4.56-4.58 (d, 1H), 4.42 (bs, 1H), 3.33-3.7 (m, 1H), 3.57-3.63 (m, 1H), 3.42 (s, 3H), 3.22-3.26 (m, 1H), 1.47 (s, 3H), 1.3 (s, 3H).

Synthesis of Compound 602

To a stirred solution of 601 (1 gm, 0.00490 moles) in dichloromethane (12 ml) and TEA (1.23 ml, 0.01225 moles) in a 50 ml two neck RBF at 0° C., was added methanesulfonyl chloride (0.95 ml, 0.01225 moles) drop wise over 5 min under nitrogen atmosphere. Reaction mixture was then warmed to room temperature and continued for 5 h. Progress was monitored by TLC. After completion of the reaction, mixture was washed with saturated sodium bicarbonate (2×7 ml) followed by water (2×7 ml). Organic layer was dried over $Na_2SO_4$ and solvent was evaporated off to give crude compound which was used for the next step without any purification. Yield: (1.05 gm, 85%). $^1$H NMR (400 MHz, $CDCl_3$) δ 4.97 (s1H), 4.67-4.69 (d, 1H), 4.58-4.59 (d, 1H), 4.37-4.41 (t, 1H), 4.19 (d, 2H), 3.32 (s, 3H), 3.11 (s, 1H), 3.05 (s, 3H), 1.46 (s, 3H), 1.30 (s, 3H). LCMS [M$^+$H]: 283.2. A solution of the crude product (1.05 g, 0.003723 moles) in 10 ml (25%) methylamine in ethanol was stirred at 50° C. in a 50 ml sealed tube overnight. After completion of reaction (by TLC) ethanol was concentrated on rota vapor and excess of methyl amine was removed by co evaporation with diethyl ether for three four times. Crude compound 602 thus obtained was used as such for the next reaction. Yield (1.20 gm, Crude). $^1$H NMR (400 MHz, $CDCl_3$) δ=4.68 (d, 1H), 4.58-0.46 (d, 1H), 4.47-4.5 (m, 1H), 3.43-3.47 (m, 1H), 3.39 (s, 3H), 2.81-2.94 (m, 2H), 2.66 (s, 3H), 1.47 (s, 3H), 1.29 (s, 3H). LCMS [M$^+$H]: 218.3

Synthesis of Compound 603

To a stirred solution of 602 (0.38 g, 0.00175 moles) was dissolved in a solution of 10 ml (1:1) Dioxane: water and cooled to 0° C. To this mixture was added solid $NaHCO_3$ (0.367 gm, 0.00143752 moles) in portions. After 30 min of interval 50% solution of Cbz-Cl in toluene (0.448 g, 0.002626 ml) was added slowly and resulting mixture was then stirred at room temperature for 3 h. After completion of the reaction (by TLC), volatilities were removed under vacuum. The residue thus obtained was dissolved in ethyl acetate (20 ml), washed with water (2×10 ml), dried over anhyd. $Na_2SO_4$ and concentrated under vacuum to give crude mass which was purified by column chromatography on neutral alumina using 3% ethyl acetate in hexane as eluent. Yield (0.5 gm, 75%). $^1$H NMR (400 MHz, $CDCl_3$) δ=7.24-7.35 (m, 5H), 5.24-5.04 (m, 2H), 4.94-4.91 (m, 1H), 4.74-4.46 (m, 2H) 4.31 (br, 1H), 3.84-3.65 (m, 1H), 3.31 (s, 3H), 3.16-3.02 (m, 1H), 2.98 (s, 3H), 1.46-1.43 (m, 3H), 1.29-1.20 (br., 3H). (note: NMR shows presence of rotamers). LCMS [M$^+$H]: 352.4, [M$^+$Na]: 374.2.

Synthesis of Compound 604

Compound 603 (1.5 gm, 0.00426 moles) was dissolved in 30 ml of 70% aq. Acetic acid in a 100 ml single neck RBF equipped with reflux condenser and mixture was heated to reflux for 2 h. After completion of reaction (by TLC) acetic acid was removed under reduced pressure and residue was directly subjected to column chromatography on 60-120 mesh silica gel using 0-5% of methanol in dichloromethane as eluent to give pure compound 604 as sticky mass. Yield (0.510 gm, 39.23%). $^1$H NMR (400 MHz, $CDCl_3$) δ=7.35 (m, 5H), 5.12-5.13 (m, 2H), 4.8 (m, 1H), 4.02-4.06 (m, 3H), 3.46-3.60 (m, 2H), 3.29-3.46 (m, 4H), 3.04 (s, 3H), 2.58 (br, 1H). LCMS: [M$^+$H]: 312.0, [M$^+$NH$_4$]: 328.9

Synthesis of Compound 605

A single neck 100 ml RBF was charged with Compound 6 (0.5 gm, 0.00160 moles), Dimethyl acetal of dilinoleyl ketone 7 (1.101 gm, 0.00192 mol) and 25 ml anhydrous toluene. To this catalytic amount of pTSA (5 mg) was added and reaction mixture was heated to reflux over soxhlet apparatus for 5 h. Progress of the reaction was monitored by TLC. After completion of reaction, toluene was evaporated off and residue obtained was purified by column chromatography on neutral alumina using 2% ethyl acetate in hexane as eluent. Yield (0.600 g, 45%). $^1$H NMR (400 MHz, $CDCl_3$) δ=7.35 (m, 5H), 5.37-5.30 (m, 8H), 5.20-5.08 (m, 2H), 4.94-4.91 (m, 1H), 4.91-5.05 (m, 1H), 4.72-4.45 (m, 2H), 4.33-4.30 (m, 1H), 3.77-3.62 (m, 1H), 3.30 (s, 3H), 3.17-3.08 (m, 1H) 2.98 (s, 3H), 2.77-2.74 (m, 4H), 2.06-2.01 (m, 8H), 1.61-1.60 (m, 2H), 1.49 (m, 2H), 1.35-1.26 (m, aliphatic protons), 0.89-0.85 (m, 6H). [M+H]=820 present. HPLC Purity:-95.78%.

Synthesis of ALNY-151

Prepared the compound ALNY-151 by following similar procedure as compound ALNY-100, using N-Cbz-compound of the corresponding product (0.5 g, 0.6 mmol, 1.0 eq) and 1M solution of LAH in THF (0.9 mL, 0.9 mmol, 1.5 eq), gave 0.32 g (76%) of the pure product ALNY-151. $^1$H NMR (400 MHz, $CDCl_3$) δ 5.51-5.19 (m, 8H), 4.95 (s, 1H), 4.60 (dd, J=29.4, 6.0, 2H), 4.25 (t, J=7.5, 1H), 3.33 (s, 3H), 2.77 (t, J=6.4, 4H), 2.38 (dd, J=7.5, 5.2, 2H), 2.27 (s, 6H), 2.05 (q, J=6.7, 8H), 1.65 (dd, J=10.1, 5.9, 2H), 1.50 (d, J=8.9, 2H), 1.33 (ddd, J=18.9, 12.2, 7.1, 36H), 0.89 (t, J=6.8, 6H). $^{13}$C NMR (101 MHz, cdcl$_3$) δ 130.40, 130.36, 128.17, 128.14, 116.25, 109.69, 85.68, 85.09, 83.54, 77.54, 77.23, 76.91, 63.06, 54.95, 46.17, 37.20, 36.95, 31.75, 30.11, 30.05, 29.91, 29.89, 29.78, 29.71, 29.58, 29.55, 29.53, 27.48, 27.46, 27.42, 25.85, 24.38, 23.33, 22.80, 14.30. Calc. mass for the $C_{45}H_{81}NO_4$: 700.1. found 700.5.

Example 19

Synthesis of ALNY-171

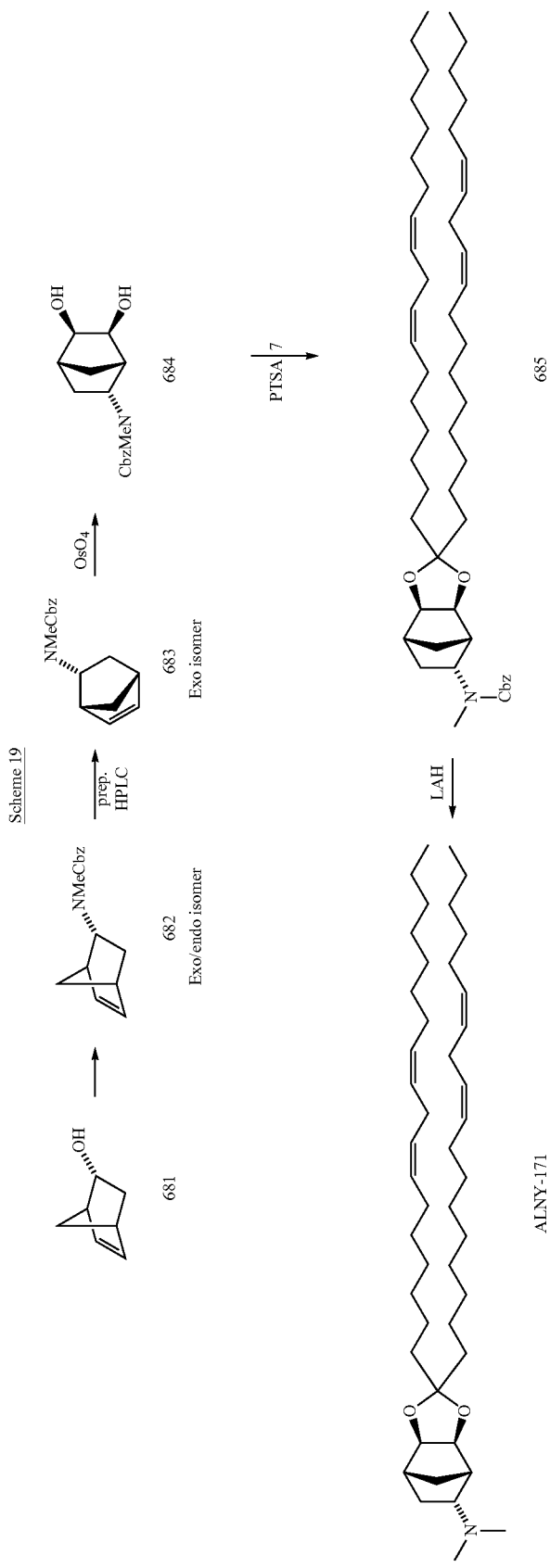

Synthesis of Compound 682

A procedure analogous to that described for the preparation of compound 651 was followed to give compound 682 in 26% yield. $^1$H NMR (400 MHz, CDCl$_3$) δ 7.61-7.14 (m, 5H), 6.13 (s, 1H), 5.29-5.01 (m, 2H), 3.97 (s, 0.5H), 3.67 (s, 0.5H), 2.95 (d, J=19.5, 2H), 2.83 (d, J=29.7, 1H), 1.71-1.52 (m, 2H), 1.52-1.38 (m, 1H), 1.31-1.08 (m, 2H); $^{13}$C NMR (101 MHz, CDCl$_3$) δ 156.81, 138.71, 137.10, 137.01, 135.77, 128.39, 127.80, 127.74, 127.67, 67.00, 66.72, 56.33, 46.77, 45.86, 40.72, 31.65, 29.75, 29.54, 12.64, 12.10, 11.57; Electrospray MS (+ve): Molecular weight for C16H20NO2 (M+H)$^+$ Calc. 258.1. Found 258.0.

Synthesis of Compound 683

Compound 683 (exo isomer) was successfully separated from exo/endo mixture of compound 682 by preparative HPLC. The exo isomer was confirmed by NOE experiments. $^1$H-NMR (400 MHz, CDCl$_3$) δ=7.35-7.28 (m, 5H), 6.11 (s, 2H), 5.16-5.08 (m, 2H), 3.96 (b, 1H), 2.91 (s, 3H), 2.85 (br, 1H), 2.78 (br, 1H), 1.46-1.24 (m, 4H). LCMS [M+H]: 258.2, [M+NH$_4$]:275.3, HPLC purity: 100%.

Synthesis of Compound 684

Compound 683 (1 g, 0.003891 mol) was dissolved in a mixture of 33 ml of (10:1) acetone and water in a 100 ml single neck RBF and to this were added NMO (1.36 g, 0.1167 mol) and 0.75 ml solution of 6.66% OsO$_4$ (0.05 g, 0.00014 mol) in tert-butyl alcohol successively at room temperature. Progress of the reaction was monitored by TLC. After completion of the reaction (2 h) reaction mixture was quenched with aqueous Na$_2$SO$_3$ solution (10 ml) and the mixture was stirred for 1.0 h. Aqueous phase was then extracted with dichloromethane (2×50 ml). Organic phase was washed once with sat. aq. NaHCO$_3$ (30 ml) solution followed by brine (1×25 ml). Organic layer was then dried over anhyd. Na$_2$SO$_4$ and concentrated in vacuum. Crude material thus obtained was subjected to (60-120 mesh) silica gel column chromatography using 3% methanol in dichloromethane as eluent which afforded the pure product as a thick liquid. Yield: 0.7 g (62%) $^1$H NMR (400 MHz, CDCl$_3$) δ=7.33-7.28 (m, 5H), 5.14-5.07 (dd, 2H), 3.87 (br, 1H), 3.76 (br, 1H), 3.72-3.69 (br, 1H), 2.91 (m, 1H), 2.85 (s, 3H), 2.75 (br, 1H), 2.19 (m, 2H), 1.82-1.79 (m, 1H), 1.68-1.66 (m, 1H), 1.44-1.40 (m, 2H). LC-MS: [M+H]-291.9 present. HPLC purity: 93% (chiral column) (Note: $^1$H NMR and HPLC confirmed the formation of only one diastereomer)

Synthesis of 685

A mixture of compound 684 (0.7 g, 0.002405 mol), dilinoleyl ketone (1.9 g, 0.003608 mol), 50 ml toluene and catalytic amount of p-TSA in a 100 ml single neck RBF were stirred and heated to reflux vigorously over Soxhlet apparatus containing 4A molecular sieves and 50 ml toluene. Progress of the reaction was monitored by TLC. After completion of the reaction (~8 h), mixture was cooled to room temperature and then toluene was removed in vacuum to give crude mass which was purified by column chromatography on neutral alumina using 1% ethyl acetate in hexane as eluting system to afford pure product 685 as pale yellow oil.

Yield: 1.5 g (78%) $^1$H NMR (400 MHz, CDCl$_3$) δ=7.26-7.20 (m, 5H), 5.29-5.19 (m, 8H), 5.06-4.97 (dd, 2H), 3.91-3.87 (m, 2H), 3.69 (m, 1H), 2.77 (s, 3H), 2.66 (m, 4H), 2.21-2.18 (m, 2H), 1.97-1.92 (m, 8H), 1.71-1.68 (m, 1H), 1.56-1.52 (m, 2H), 1.44 (m, 1H) 1.38 (m, 2H), 1.30-1.17 (m, aliphatic protons), 0.78 (t, 6H). MS—[M+H]-800.1, HPLC purity-90.91%.

Synthesis of ALNY-171

Prepared the compound ALNY-171 by following similar procedure as compound ALNY-100, using N-Cbz-compound 685 (1.4 g, 1.75 mmol, 1.0 eq) and 1M solution of LAH in THF (2.62 mL, 2.62 mmol, 1.5 eq), gave 1.0 g (84%) of the pure product 17. $^1$H NMR (400 MHz, CDCl$_3$) δ 5.50-5.20 (m, 8H), 3.91 (dd, J=15.3, 5.4, 2H), 2.77 (t, J=6.3, 4H), 2.43 (s, 1H), 2.29 (d, J=4.0, 1H), 2.18 (s, 6H), 2.04 (q, J=6.7, 8H), 1.64 (dd, J=10.4, 5.7, 4H), 1.50 (s, 2H), 1.45-1.13 (m, 39H), 0.89 (t, J=6.7, 6H). $^{13}$C NMR (101 MHz, cdcl$_3$) δ 130.41, 130.39, 130.38, 130.34, 128.19, 128.15, 113.17, 81.76, 81.21, 77.54, 77.22, 76.90, 65.76, 44.14, 43.40, 40.30, 36.17, 35.25, 32.05, 31.75, 30.21, 29.89, 29.77, 29.74, 29.71, 29.57, 29.52, 29.11, 27.46, 27.42, 25.85, 24.82, 24.08, 22.79, 14.29. Calc. mass for the C$_{46}$H$_{81}$NO$_2$: 680.1. found 680.5.

Example 20

Synthesis of ALNY-162, 163 and 164

Scheme 20

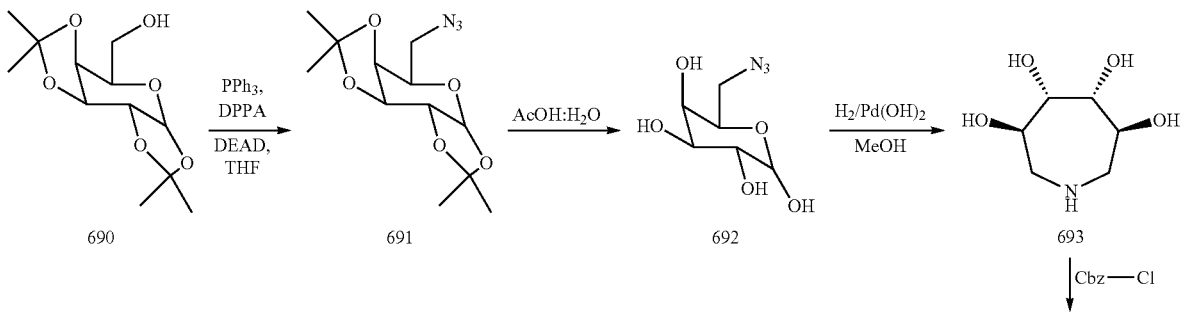

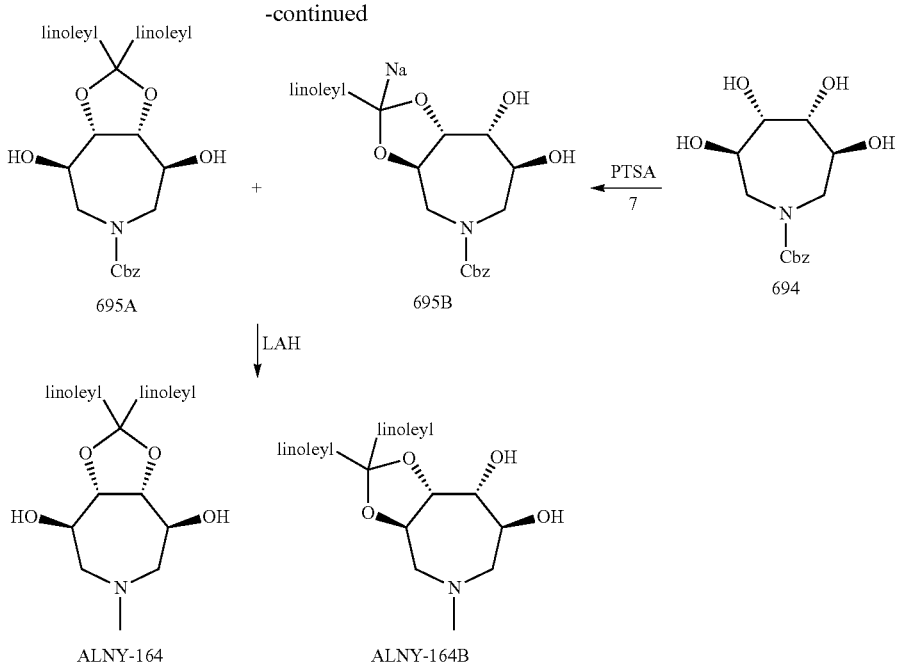

Synthesis of Compound 691

Compound 690 (25 gm, 0.09615 moles) was dissolved in 250 ml dry THF in a 500 ml two neck RBF and cooled to 0° C. To this solution was added $PPh_3$ (25.2 gm, 0.09615 moles) followed by DEAD (15.79 ml, 0.09615 moles) under nitrogen atmosphere and the resulting mixture was stirred for 15 min. Diphenyl phosphoryl azide (20.7 ml, 0.09615 moles) was then added into it drop wise at 0° C. Reaction mixture was then brought to room temperature slowly and stirred overnight. Upon completion of the reaction (by TLC) volatilities were removed under vacuum and crude mass was purified by silica gel (60-120 mesh) column chromatography using DCM as eluent to afford compound 691 as viscous liquid. Yield-19 gm (70.37%) 1H NMR (CDCl3, 400 MHz): δ=5.54-5.53 (d, 1H J=5.0 Hz), 4.63-4.60 (dd, 1H J=2.48 & 7.88 Hz), 4.33-4.31 (m, 1H), 4.19-4.17 (dd, 1H J=1.96 Hz & 7.92 Hz), 3.92-3.88 (m, 1H), 3.52-3.47 (dd, 1H J=7.92 & 12.68 Hz), 3.37-3.32 (dd, 1H J=5.4 & 12.72 Hz), 1.53 (s, 3H), 1.44 (s, 3H) 1.33 (s, 6H)

Synthesis of Compound 692

A 250 ml single neck RBF was charged with compound 691 (12 gm, 0.04195 moles) and 120 ml Acetic acid:water (1:1). The resulting solution was heated at 75° C. for 4 h. Reaction was monitored by TLC. Upon completion of the reaction, mixture was concentrated under vacuum and crude solid thus obtained was washed with DCM (3×50 ml) to yield pure compound 692 as an off white solid. Yield-6 gm 1H NMR (D2O, 400 MHz): δ=5.26-5.25 (d, 1H J=3.76 Hz), 4.20-4.16 (m, 1H), 3.94 (m, 1H), 3.86-3.76 (m, 2H), 3.54-3.43 (m, 2H)

Synthesis of Compound 693

Compound 692 (5.5 gm, 0.02669) was dissolved in (1:1) mixture of methanol: water (60 ml) in a 250 ml single neck RBF and degassed with nitrogen for 20 minutes. To this solution (20 wt %) Pd (OH)2/C (1.2 g, 20 wt % of compound 3) was added at once under nitrogen. Reaction mixture was then flushed with hydrogen gas and stirred under balloon pressure of hydrogen gas for 3 days. (Note: on second and third day 1g of (20 wt %) Pd (OH) 2/C was added into the reaction mixture and freshly filled hydrogen gas balloon was used for the reaction). After completion of the reaction, mixture was flushed with nitrogen and then filtered through celite bed. Filtrate and washings of (1:1) methanol and water were collectively evaporated under vacuum to yield crude compound 693 as off white solid. Yield-4.5 gm 1H NMR (D2O, 400 MHz): δ=4.02-4.00 (d, 2H, J=6.3 Hz), 3.88-3.84 (m, 2H), 3.08-3.03 (dd, 2H J=4.32 & 14.76 Hz), 2.88-2.83 (dd, 2H J=4.6 & 14.76 Hz).

Synthesis of 694

Compound 693 (4 gm, 0.0245 mol) and $NaHCO_3$ (5.14 gm, 0.06125 mol) were dissolved in (1:1) dioxan/water (30 ml) in a 100 ml single neck RBF and cooled to 0° C. After stirring the mixture for 10 minutes 50 wt % Cbz-Cl (8.25 g, 0.049 moles) in toluene (16.5 ml) was added slowly. Reaction mixture was then warmed to ambient temperature and monitored by TLC. After completion of the reaction (~2 h by TLC) reaction mixture was concentrated under vacuum. Crude material obtained was purified by silica gel (60-120 mesh) column chromatography using 0-20% methanol in DCM as eluent to afford the title compound Alny-13-001 as white solid. Yield-2.4 gm (33.33%) 1H NMR (400 MHz in MeOD): δ=7.38-7.25 (m, 5H), 5.11-5.09 (d, 2H, J=5.84 Hz), 3.97-3.80 (m, 6H), 3.33-3.25 (m, 2H) LC-MS-[M+H]-298 present.

Synthesis of 695A and 695B

A 250 ml single neck flask equipped with a magnetic stir bar and a Soxhlet apparatus containing 4A molecular sieves and 50 ml toluene, was charged with 694 (2.4 gm, 0.008081 mol), dilinoleyl ketone 7 (6.38 gm, 0.01212 mol) and p-TSA (catalytic). To this mixture was added 30 ml toluene followed by methanol 3 ml. Resulting solution was stirred and heated to reflux vigorously for 3 h. Progress of the reaction was monitored by TLC. After complete disappearance of the starting 694 on TLC, toluene was evaporated and residue obtained was purified by column chromatography on neutral alumina to get two different products as title compounds. 695A:— eluted with 12% ethyl acetate in hexane. Yield (900 mg) 1H NMR (400 MHz IN CDCl3): δ=7.34-7.31 (m, 5H), 5.40-5.16 (m, 8H), 5.15-5.14 (m, 2H), 4.13 (m, 1H), 4.03-3.98 (m, 4H), 3.66-3.62 (m, 1H), 3.21 (s, 1H), 3.14-3.10 (d, 1H, J=15.44 Hz), 2.77-2.74 (t, 4H), 2.26-2.22 (m, 1H), 2.06-2.01 (m, 8H), 1.63-1.59 (m, 4H), 1.35-1.26 (m, aliphatic protons from linoleyl group), 0.89-0.85 (m, 6H) LC-MS—[M+H]-806.30 HPLC-95.04%. 695B:—eluted with 9% ethyl acetate in hexane. Yield (500 mg) 1H NMR (400 MHz IN CDCl3): δ=7.38-7.25 (m, 5H), 5.40-5.28 (m, 8H), 5.16-5.12 (m, 2H), 4.43-4.36 (m, 2H), 4.12-4.11 (m, 1H), 4.03-3.99 (m, 3H), 3.62 (br s, 1H), 3.35-3.28 (m, 2H), 1.95 (br s, 1H), 2.77-2.74 (m, 4H), 2.06-2.01 (m, 8H), 1.58 (m, 4H), 1.35-1.26 (m, aliphatic protons from linoleyl group), 0.89-0.84 (m, 6H) LC-MS—[M+H]-806.40 HPLC-95.12%.

Synthesis of ALNY-164 and ALNY-164B

Prepared the compound ALNY-164 and ALNY-164B by following the similar procedure used for ALNY-100, using N-Cbz-compound 695A and 695B.

Example 21

Synthesis of ALNY-163 and ALNY-163B

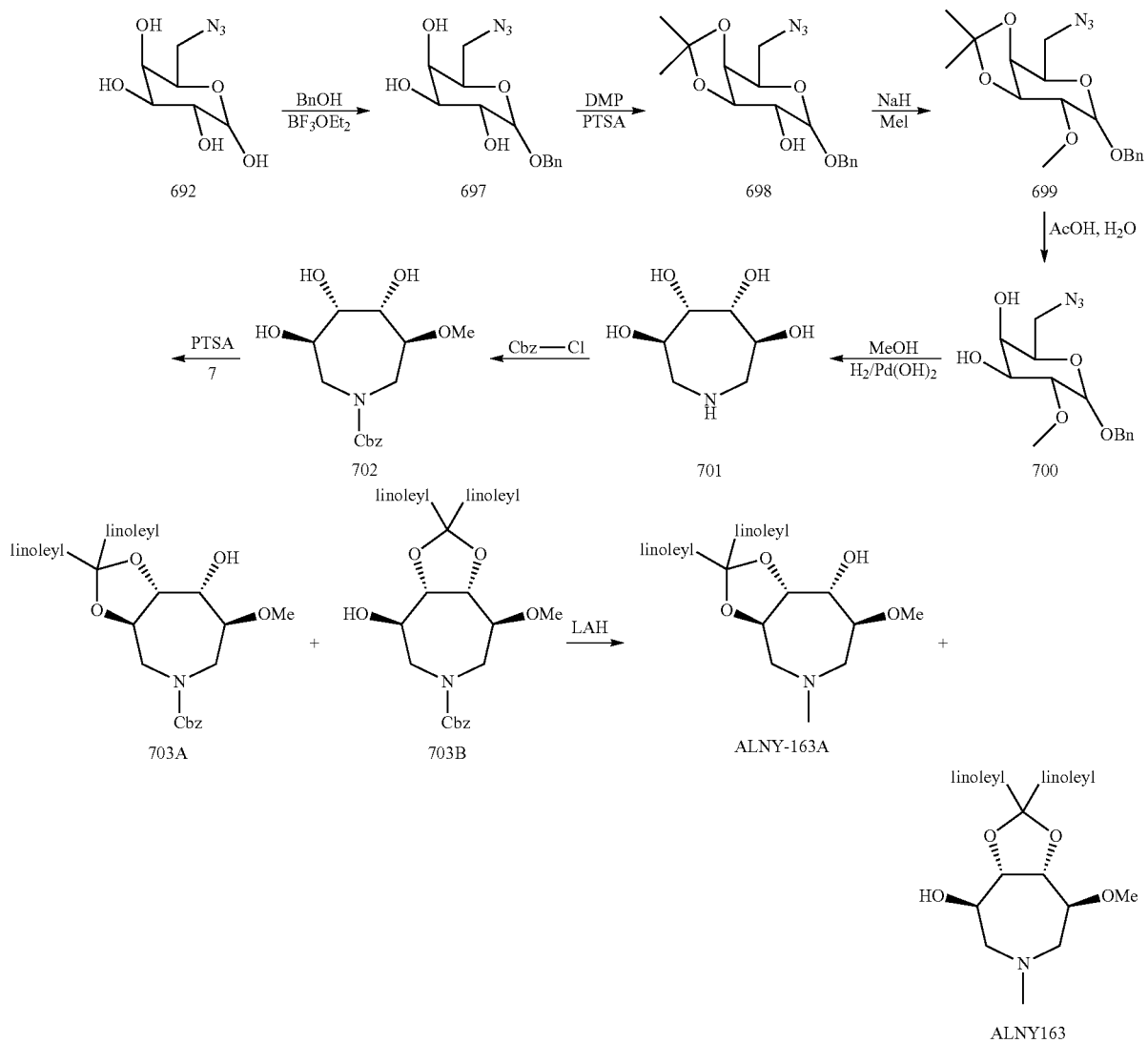

Scheme 21

Synthesis of Compound 697

Compound 692 (9.5 gm, 0.04611 μmol) was dissolved in 30 ml of benzyl alcohol in a 500 ml two neck RBF at 80° C. To this solution was added BF3.Et2O (6.54 gm, 0.04611 mol) slowly under nitrogen atmosphere. Reaction was continued for 1 h. Progress of the reaction was monitored by TLC. Upon completion of the reaction (~2 h) reaction mixture was directly chromatographed on 60-120 mesh silica gels. Benzyl alcohol was eluted with 20% EtOAc in hexane at first and pure compound was then eluted with ethyl acetate. Yield: (8.2 gm, 60.29%) 1H NMR (MeOD, 400 MHz): δ=7.40-7.21 (m, 5H), 4.77-4.56 (m, 2H), 4.09-4.08 (m, 1H), 3.98-3.95 (m, 1H), 3.80-3.77 (m, 2H), 3.72-3.68 (m, 1H), 3.57-3.51 (m, 1H), 3.27-3.23 (m, 1H)

Synthesis of Compound 698

To a stirred solution of 697 (8.2 gm, 0.0276 mol) in 80 ml anhydrous DMF contained in a 250 ml two neck RBF, was added PTSA (catalytic) and 2, 2-DMP (22 ml, Excess) under nitrogen atmosphere. Resulting mixture was stirred overnight at room temperature Reaction was monitored by TLC. After completion of the reaction, mixture was diluted with water (250 ml) was extracted well with diethyl ether (100 ml×3 ml). Organic layer was separated, dried over sodium sulphate and concentrated under vacuum to yield crude compound which was purified by (230-400 mesh) silica gel column chromatography using EtOAc in hexane as eluent. Fraction I was eluted with 12% ethyl acetate in hexane-Yield: (5 gm, 53.19%). 1H NMR (CDCl3, 400 MHz): δ=7.38-7.27 (m, 5H), 4.97-4.96 (d, 1H J=3.88 Hz), 4.86-4.83 (d, 1H J=11.56 hz), 4.62-4.59 (d, 1H J=11.64 Hz), 4.32-4.29 (m, 1H), 4.21-4.10 (m, 2H), 3.90-3.86 (m, 1H), 3.59-3.54 (dd, 1H J=8.48 & 12.84 Hz), 3.33-3.28 (dd, 1H J=4.36 & 12.88 Hz), 2.42-2.40 (d, 1H J=5.8 Hz) 1.58 (s, 3H), 1.48 (s, 3H). [Note: Fraction II was eluted with 20% ethyl acetate in hexane-yield: (1.4 gm, 15%,

Synthesis of Compound 699

To a stirred solution of compound 698 (5 gm, 0.01483 mol) in 50 ml Dry DMF in a 250 ml two neck RBF was added (60% suspension in mineral oil) sodium hydride (1.42 gm, 0.0296 mol) in portions for a period of 10 minute at 0° C. under nitrogen atmosphere. After stirring the mixture for 15 min at 0° C., MeI (1.1 ml, 0.0179 mol) was added slowly and reaction mixture was stirred additional for 1 h. Reaction was monitored by TLC. After completion, reaction mixture was quenched with crushed ice (~200 g) and aqueous phase was extracted with EtOAc (100 ml×3). Organic layer was then washed with water (100 ml×2) to remove traces of DMF, dried over Na2SO4, and then concentrated on rotary evaporator to get the title compound 699 as oily compound which was used directly without further purification. Yield (4.5 gm, 86.04%) 1H NMR (CDCl3, 400 MHz): δ=7.40-7.29 (m, 5H), 5.00-4.99 (d, 1H J=3.52 Hz), 4.77-4.74 (d, 1H J=12.16 Hz), 4.61-4.58 (d, 1H J=12.16 Hz), 4.31-4.28 (dd, 1H J=5.48 & 7.64 Hz), 4.15-4.11 (m, 2H), 3.60-3.55 (dd, 1H J=8.08 & 12.8 Hz), 3.42 (s, 3H), 3.38-3.34 (m, 2H), 1.51 (s, 3H), 1.32 (s, 3H).

Synthesis of Compound 700

A 100 ml single neck RBF was charged with compound 699 (4.4 gm, 0.12 mol), 44 ml of mixture of AcOH:water (8:2), and mixture was heated to 80° C. for 4 h. Reaction was monitored by TLC. After completion of the reaction, the mixture was extracted with DCM (3×40 ml). Organic layer was washed with water (2×25 ml) followed by saturated aq. NaHCO3 solution (2×30 ml). Organic layer was then dried over Na2SO4 and solvent was evaporated off in vacuum to yield compound 700 as white solid. Yield (3.7 gm, 95.60%) 1H NMR (MeOD, 400 MHz): δ=7.41-7.27 (m, 5H), 5.08-5.07 (d, 1H J=3.7 Hz), 4.77-4.74 (d, 1H J=11.88 Hz), 4.59-4.56 (d, 1H, J=11.88 Hz), 3.97-3.94 (dd, 1H J=4.0 & 8.44 Hz), 3.85-3.79 (m, 2H), 3.58-3.52 (m, 1H), 3.50-3.47 (m, 1H), 3.37 (s, 3H), 3.27-3.22 (m, 1H). 13C NMR (MeOD, 100 MHz) δ=137.24, 128.03, 127.99, 127.52, 94.84, 77.75, 70.02, 69.93, 68.82, 68, 73, 56.91, 51.24.

Synthesis of Compound 701

Compound 700 (3 gm, 0.0097 mol) was dissolved in (30 ml) methanol in a 250 ml single neck RBF and degassed with nitrogen for 20 minutes. To this solution (20 wt %) Pd (OH)2/C (0.8 gm, ~20 wt % of compound 7) was added at once under nitrogen. Reaction mixture was then flushed with hydrogen gas and stirred under balloon pressure of hydrogen gas for 3 days. (Note: on second and third day 0.8 g of (20 wt %) Pd (OH) 2/C was added into the reaction mixture and freshly filled hydrogen gas balloon was used for the reaction). After completion of the reaction, mixture was flushed with nitrogen and then filtered through celite bed. Filtrate and washings of (1:1) methanol and water were collectively evaporated under vacuum to yield crude compound 701 as sticky mass. Yield (1.8 gm, Crude) 1H NMR (D2O, 400 MHz): δ=4.13-4.11 (m, 1H), 3.96-3.94 (m, 1H), 3.84-3.80 (m, 1H), 3.44-3.43 (m, 1H), 3.33 (s, 3H), 3.03-2.98 (m, 2H), 2.95-2.90 (m, 1H), 2.86-2.81 (m, 1H). 13C NMR (D2O, 100 MHz): δ=82.84, 75.60, 73.79, 72.09, 57.78, 53.06, 49.98

Synthesis of Compound 702

Compound 701 (1.8 g, 0.0101 mol) and NaHCO3 (2.121 g, 0.02525 mol) were dissolved in (1:1) dioxan and water (50 ml) in a 100 ml single neck RBF and cooled to 0° C. After stirring the mixture for 10 minutes 50 wt % Cbz-Cl (6.9 ml, 0.0203 mol) in toluene was added slowly. Reaction mixture was then warmed to ambient temperature and monitored by TLC. After completion of the reaction (~2 h by TLC) reaction mixture was concentrated under vacuum. Residual part was diluted with water (20 ml) and extracted with DCM (3×30 ml) Organic layer was then separated, dried over anhydrous Na2SO4 and concentrated under vacuum to yield the Crude material which was purified by silica gel (60-120 mesh) column chromatography using 0-20% methanol in DCM as eluent to afford the title compound 702 as off white solid. Yield (0.9 gm, 29%) 1H NMR (MeOD, 400 MHz): δ=7.37-7.28 (m, 5H), 5.15-5.06 (m, 2H), 4.01-4.00 (m, 1H), 3.89-3.88 (m, 1H), 3.84-3.83 (m, 1H), 3.75-3.69 (m, 2H), 3.61-3.60 (m, 1H), 3.55-3.30 (m, 5H). (note: exists as rotamers). LC-MS [M+H]-312.30

Ketalization Products: 703A & 703B

A 100 ml single neck flask equipped with a magnetic stir bar and a Soxhlet apparatus containing 4A molecular sieves and 50 ml toluene, was charged with 702 (0.9 gm, 0.00289 mol), dilinoleyl ketone (3.04 gm, 0.005787 mol) and p-TSA (catalytic). To this mixture was added 30 ml toluene followed by methanol 3 ml. Resulting solution was stirred and heated to reflux vigorously for 3 h. Progress of the reaction was monitored by TLC. After complete disappearance of the starting 702 on TLC, toluene was evaporated off and residue obtained was purified by column chromatography on neutral alumina to get two different products as title compounds. 703A was Eluted with 7-9% Ethyl Acetate in Hexane System.
Yield: (0.500 gm) 1H NMR (CDCl3, 400 MHz): δ=7.38-7.28 (m, 5H), 5.40-5.28 (m, 8H), 5.20-5.15 (m, 2H), 4.42-4.33 (m, 2H), 4.23 (m, 1H), 4.00 (m, 1H), 3.88-3.87 (m, 1H), 3.73 (m, 1H), 3.61-3.59 (m, 1H), 3.50 (s, 3H), 3.40-3.20 (m, 3H), 2.77-2.74 (m, 4H), 2.06-2.01 (m, 8H), 1.68-1.56 (m, 2H), 1.35-1.29 (m, aliphatic protons), 0.89-0.85 (m, 6H) MASS [M+H]-820.6, HPLC (ELSD) purity-95.69%
703B was Eluted with 12-15% Ethyl Acetate in Hexane System.

Yield: (0.400 g) 1H NMR (CDCl3, 400 MHz): δ=7.36-7.30 (m, 5H), 5.38-5.30 (m, 8H), 5.15-5.13 (m, 2H), 4.21-4.10 (m, 3H), 4.09-4.00 (m, 1H), 3.91-3.80 (m, 2H), 3.47 (s, 3H), 3.39 (m, 1H), 3.30-3.10 (m, 3H), 2.77-2.74 (m, 4H), 2.36-2.33 (d, 1H, J=13.2 Hz), 2.06-2.01 (m, 8H), 1.63-1.59 (m, 2H), 1.37-1.23 (m, aliphatic protons), 0.89-0.86 (m, 6H) MASS [M+H]-820.5, HPLC (ELSD) purity-95.12%.

Synthesis of ALNY-163 and ALNY-163B

Prepared the compound ALNY-163 and ALNY-163B by following the similar procedure used for ALNY-100, using N-Cbz-compound 703A and 703B.

Example 22

Synthesis of ALNY-205, ALNY-209 and ALNY-209B

Synthesis of Compound 706

Benzyl mannopyranoside 705 (5 g, 0.0185 mol) was dissolved in dry pyridine (50 ml) in a 250 ml two neck RBF and cooled to 0° C. To this stirred was added slowly a 25 ml solution of p-tosyl chloride (3.7 g, 0.0194 mol) in anhydrous DCM under nitrogen atmosphere. Resulting mixture was allowed to warm to room temperature and progress of the reaction was monitored by TLC. After completion of the reaction (~4 h. by TLC), reaction mixture was diluted with DCM (250 ml) and washed with 1N HCl (2×100 ml) followed by saturated NaHCO3 (2×50 ml) and brine (50 ml) respectively. Organic layer was then separated, dried over anhydrous Na2SO4, filtered and then concentrated under vacuum to give crude material which was subjected to silica gel (60-120 mesh) column chromatography and eluted with ethyl acetate to afford pure compound 706 as off white solid. Yield: 4.9 g (62.5%) 1H NMR (DMSO, 400 MHz): δ ppm=7.80-7.76 (d, 2H J=8.24 Hz), 7.48-7.46 (d, 2H J=8.16 Hz), 7.43-7.29 (m, 5H), 5.06-5.04 (d, 1H J=5.8 Hz), 4.93-4.92 (d, 1H, J=4.24 Hz), 4.78-4.76 (d, 1H J=6 Hz), 4.65 (d, 1H J=0.72 Hz),

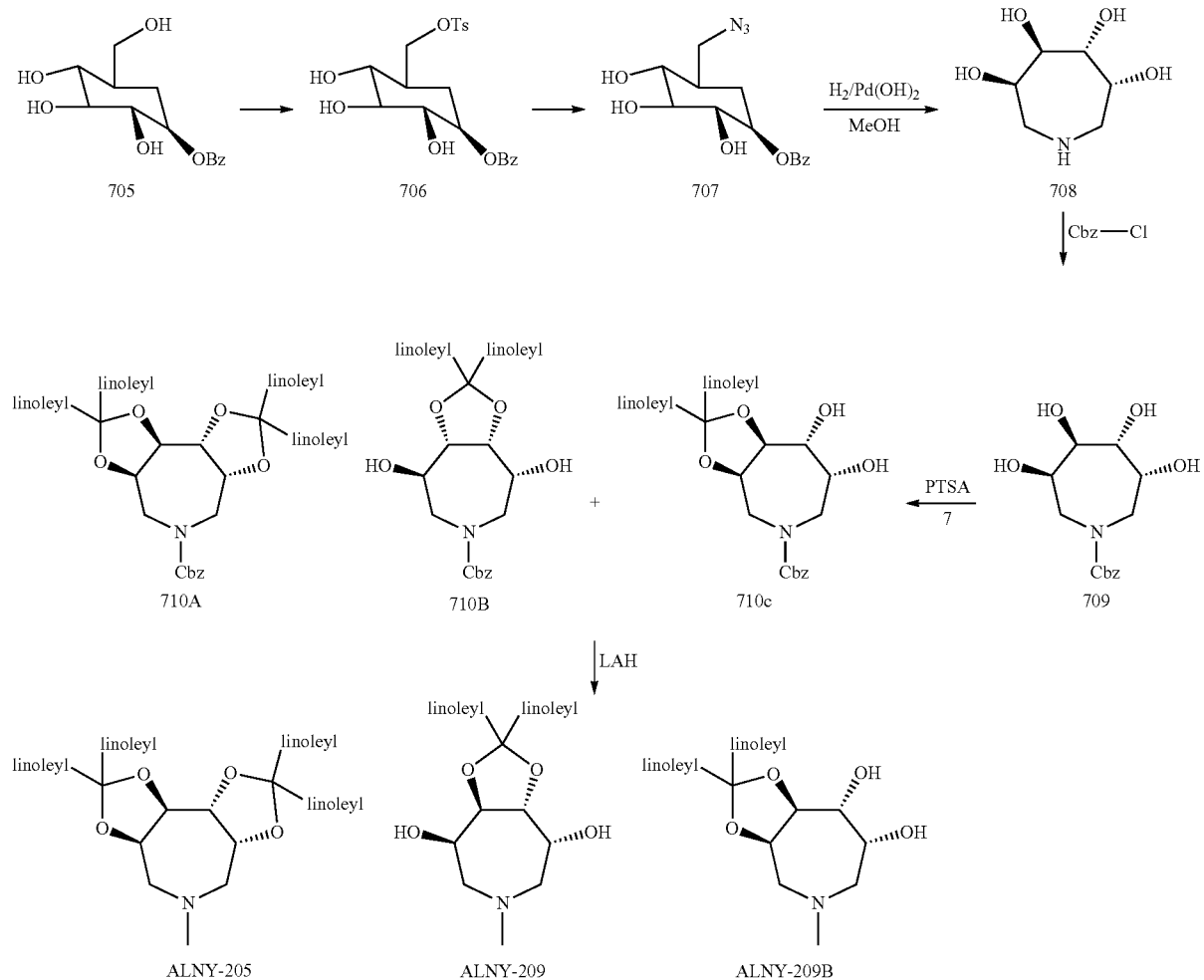

Scheme 22

4.55-4.52 (d, 1H J=11.8 Hz), 4.38-4.35 (d, 1H J=11.84 Hz), 4.23-4.05 (dd, 1H), 3.61 (m, 1H), 3.54 (m, 1H), 3.45-3.42 (m, 1H), 2.40 (s, 3H)

Synthesis of Compound 707

A 500 ml single neck RBF equipped with a magnetic bar and reflux condenser was charged with compound 706 (9.7 g, 0.02287 mol), sodium azide (10.4 g, 0.1600 mol), ammonium chloride (6.12 g, 0.1143 mol) and (9:1) Ethanol: water (150 ml). Resulting mixture was stirred and heated to reflux for 24 h. Upon completion of the reaction (monitored by TLC) solvent was removed on rotary evaporator and crude mass was chromatographed on silica gel (100-200 mesh) using ethyl acetate to give compound 707 as white solid. Yield: 4 g (59.2%) 1H NMR (DMSO, 400 MHz): δ ppm=7.43-7.28 (m, 5H), 5.01-5.00 (d, 1H, J=5.88 Hz), 4.93-4.92 (d, 1H, J=4.24 Hz), 4.74-4.72 (m, 2H), 4.68-4.65 (d, 1H J=11.88 Hz), 4.49-4.46 (d, 1H J=11.88 Hz), 3.65-3.64 (m, 1H), 3.60-3.54 (m, 1H), 3.52-3.47 (m, 1H), 3.46-3.38 (m, 3H).

Synthesis of Compound 708

Compound 707 (4 g, 0.01355 mol) was dissolved in (3:1) mixture of methanol and water (60 ml) in a 250 ml single neck RBF and degassed with nitrogen for 20 minutes. To this solution (20 wt %) Pd (OH)2/C (1 g, 25 wt % of compound 3) was added at once under nitrogen. Reaction mixture was then flushed with hydrogen gas and stirred under balloon pressure of hydrogen gas for 3 days. (Note: on second and third day 0.5 g of (20 wt %) Pd (OH) 2/C was added into the reaction mixture and freshly filled hydrogen gas balloon was used for the reaction). After completion of the reaction, mixture was flushed with nitrogen and then filtered through celite bed. Filtrate and washings of (3:1) methanol and water were collectively evaporated under vacuum to yield crude compound 708 as off white solid. Yield: 2 g (90%). 1H NMR (D2O, 400 MHz): δ ppm=4.09-4.07 (m, 2H), 3.91-3.89 (m, 2H), 2.98-2.86 (m, 4H).

Synthesis of 709

Compound 708 (2 g, 0.01225 mol) and NaHCO3 (2.57 g, 0.0306 mol) were dissolved in (1:1) dioxan:water (40 ml) in a 100 ml single neck RBF and cooled to 0° C. After stirring the mixture for 10 minutes 50 wt % Cbz-Cl (3.13 g, 0.01838 mol) in toluene (6.26 ml) was added slowly. Reaction mixture was then warmed to ambient temperature and monitored by TLC. After completion of the reaction (~3 h by TLC) reaction mixture was concentrated under vacuum. Residue thus obtained was stirred with 30 ml of 10% methanol in DCM solution and filtered. Filtrate was evaporated off and crude material obtained was purified by silica gel (60-120 mesh) column chromatography using 10% methanol in DCM as eluent to afford the title compound 709. Yield: 2 g (55%). 1H NMR (MeOD, 400 MHz): δ ppm=7.38-7.21 (m, 5H), 5.12 (s, 2H), 4.10-4.04 (m, 2H), 3.91 (s, 2H), 3.58-3.52 (m, 4H).

Ketalization: Synthesis of 710A, 710B and 710C

A 250 ml single neck flask equipped with a magnetic stir bar and a Soxhlet apparatus containing 4A molecular sieves and 50 ml toluene, was charged with 709 (2 g, 0.00673 mol), dilinoleyl ketone (10.64 g, 0.0204 mol) and p-TSA (0.129 g, 0.00067 mol). To this mixture was added 90 ml toluene followed by methanol 10 ml. Resulting solution was stirred and heated to reflux vigorously for 3 h. Progress of the reaction was monitored by TLC. After complete disappearance of the starting 709 on TLC, reaction was stopped, toluene was evaporated off and residue obtained was purified by column chromatography on neutral alumina to get three different products as title compounds.

710A: eluted with 1.5-2% ethyl acetate in hexane-1.5 g 1H NMR (CDCl3, 400 MHz): δ ppm=7.35-7.30 (m, 5H), 5.40-5.29 (m, 16H), 5.13-5.12 (m, 2H), 4.36-4.16 (m, 6H), 2.92-2.74 (m, 10H), 2.06-2.01 (m, 16H), 1.66-1.64 (m, 4H), 1.58-1.55 (m, 4H), 1.37-1.25 (m, aliphatic protons) 0.89-0.86 (m, 12H).

710B: eluted with 25-30% ethyl acetate in hexane—1 g 1H NMR (CDCl3, 400 MHz): ppm=7.36-7.30 (m, 5H), 5.38-5.30 (m, 8H), 5.14 (m, 2H), 4.35 (m, 2H), 4.13-4.11 (m, 2H), 3.85-3.83 (m, 1H), 3.72-3.71 (m, 1H), 3.55-3.54 (m, 1H), 3.33 (m, 1H), 2.77-2.74 (m, 4H), 2.46 (s, 1H) 2.36 (s, 1H), 2.06-2.01 (m, 8H), 1.63-1.61 (m, 4H), 1.37-1.25 (m, aliphatic protons) 0.89-0.85 (m, 6H). Mass [M+H]-806.30 present HPLC purity-94.85%

710C: eluted with 5% methanol in DCM—0.52 g. 1H NMR (CDCl3, 400 MHz): δ ppm=7.35-7.30 (m, 5H), 5.40-5.31 (m, 8H), 5.17-5.14 (m, 2H), 4.60 (m, 1H), 4.41-4.37 (m, 2H) 4.33-4.29 (m, 2H), 4.13 (m, 1H), 3.85-3.81 (m, 1H), 3.05-3.01 (m, 1H), 2.77-2.76 (m, 4H), 2.56 (m, 1H), 2.36-2.34 (m, 1H), 2.20 (m, 1H), 2.04-2.02 (m, 8H), 1.62-1.61 (m, 4H), 1.37-1.26 (m, aliphatic protons) 0.89-0.85 (m, 6H). Mass [M+H]-806.40 present HPLC purity-91.52%

Synthesis of ALNY-205 and ALNY-209 and ALNY-209B

Prepared the compound ALNY-205, ALNY-209 and ALNY-209B by following the similar procedure used for ALNY-100, using N-Cbz-compound 710A, 710B and 710C.

Synthesis of ALNY-148

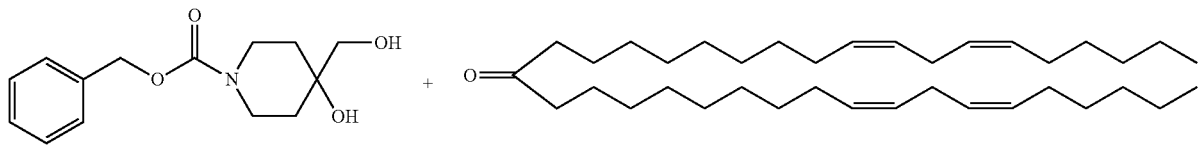

720          7

PTSA, toluene
reflux

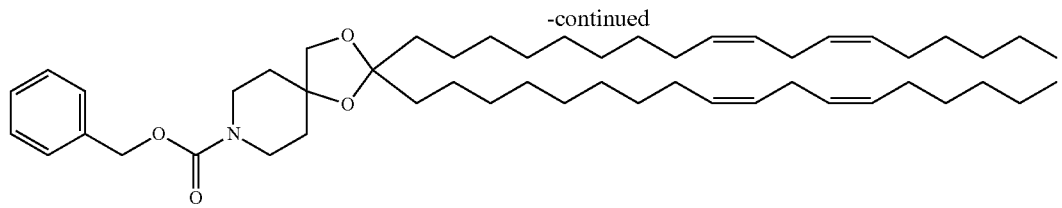

721

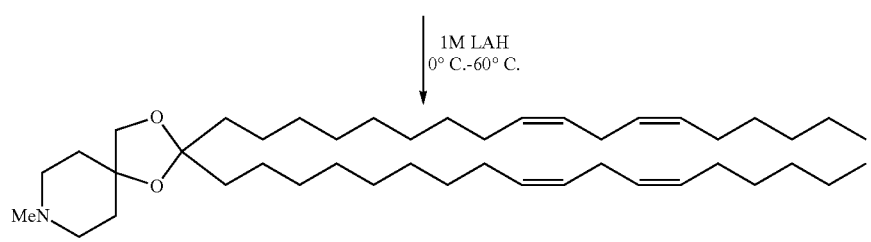

ALNY-148

Preparation of Compound 721: To a solution of dihydroxy-Cbz compound 720 (0.8 g, 3.0 mmol, 1.0 eq), dilinoleyl ketone 7 (1.58 g, 3.0 mmol, 1.0 eq) in toluene was added the PTSA (0.05 g, 0.3 mmol, 0.1 eq) and refluxed under Dean-Stock apparatus until there is no starting material left. Cooled the reaction mixture, evaporated, directly loaded on column chromatography and purified using hexane: ether (10%) as gradients to get 1.45 g of the pure compound 721 in 63% yields. $^1$H NMR (400 MHz, CDCl$_3$) δ 7.46-7.26 (m, 6H), 5.49-5.21 (m, 8H), 5.13 (s, 2H), 3.75 (s, 4H), 3.41 (t, J=10.4, 2H), 2.77 (t, J=6.4, 4H), 2.05 (q, J=6.7, 8H), 1.69 (s, 2H), 1.65-1.48 (m, 6H), 1.42-1.16 (m, 37H), 0.89 (t, J=6.8, 6H). Calc. mass for the C$_{51}$H$_{83}$NO$_4$: 773.6. found 796.5 (+Na).

Preparation of ALNY-148: Exactly repeated the experimental procedure as of the compound alny-100 using N-Cbz-compound 721 (1.44 g, 1.86 mmol, 1.0 eq), 1M LAH in THF (3.72 mL, 3.72 mmol, 2.0 eq), which gave 1.04 g (86%) of the pure product. $^1$H NMR (400 MHz, CDCl$_3$) δ 5.51-5.16 (m, 8H), 3.75 (s, 2H), 2.77 (t, J=6.4, 4H), 2.55 (s, 2H), 2.33 (s, 1H), 2.28 (s, 3H), 2.04 (q, J=6.8, 8H), 1.88-1.74 (m, 2H), 1.74-1.63 (m, 2H), 1.57 (dd, J=10.2, 5.4, 4H), 1.45-1.15 (m, 37H), 0.88 (t, J=6.8, 6H). $^{13}$C NMR (101 MHz, CDCl$_3$) δ 130.40, 130.36, 128.15, 128.13, 112.67, 78.12, 77.55, 77.23, 76.91, 73.59, 53.33, 46.31, 37.93, 36.66, 31.74, 30.17, 29.90, 29.79, 29.73, 29.57, 29.53, 27.45, 27.41, 25.84, 24.32, 22.80, 14.31. Calc. mass for the C44H79NO2: 653.6. found 654.5.

Example 23

Synthesis of Ketal 530

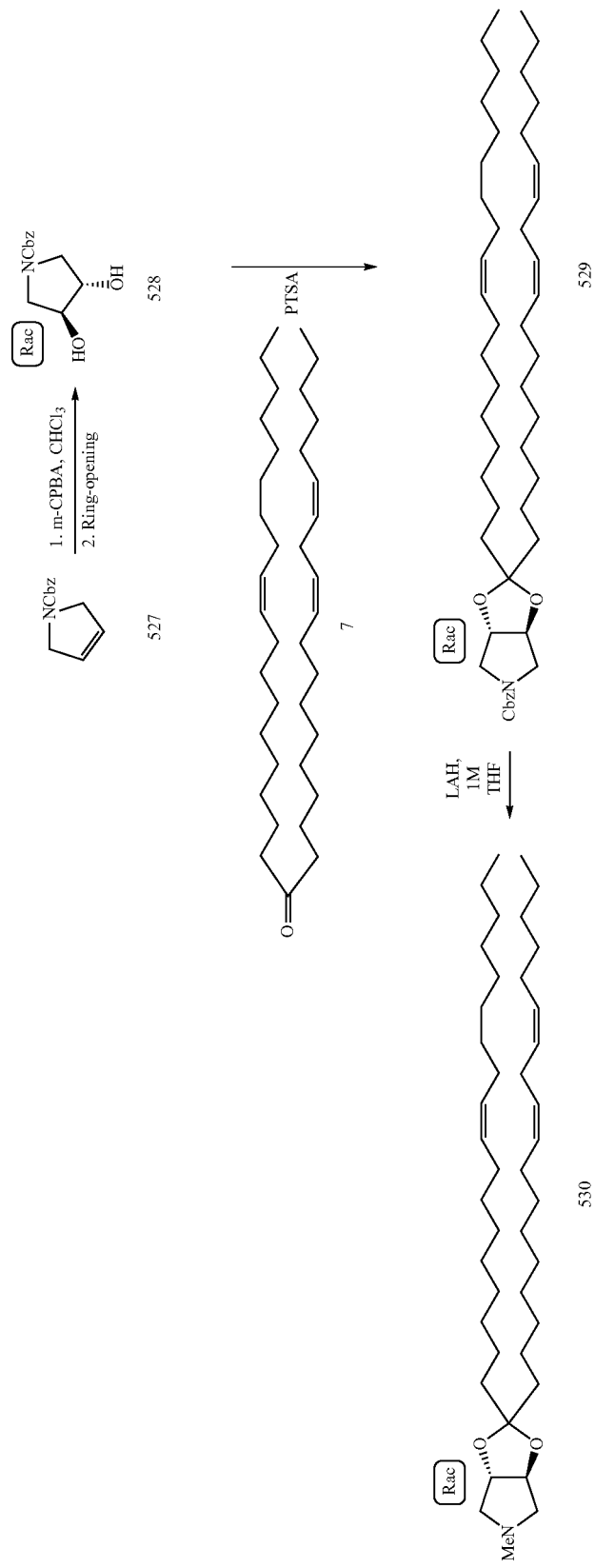

Preparation of Compound 528

An ice-cold solution of compound 527 (10 g) in CHCl$_3$ (500 mL) is treated all at once with m-chloroperbenzoic acid (1.1 eq), then warmed to r.t. and stirred for 18 h. Aqueous workup then column chromatography gives compound 528.

Preparation of 25 for ketone 7 and using a procedure analogous to that described for the synthesis of compound 505, compound 529 is obtained as a colorless oil.

Preparation of Compound 530

Using a procedure analogous to that described for the synthesis of compound 506, compound 530 is obtained as a colorless oil.

Example 24

Synthesis of Ketal 534

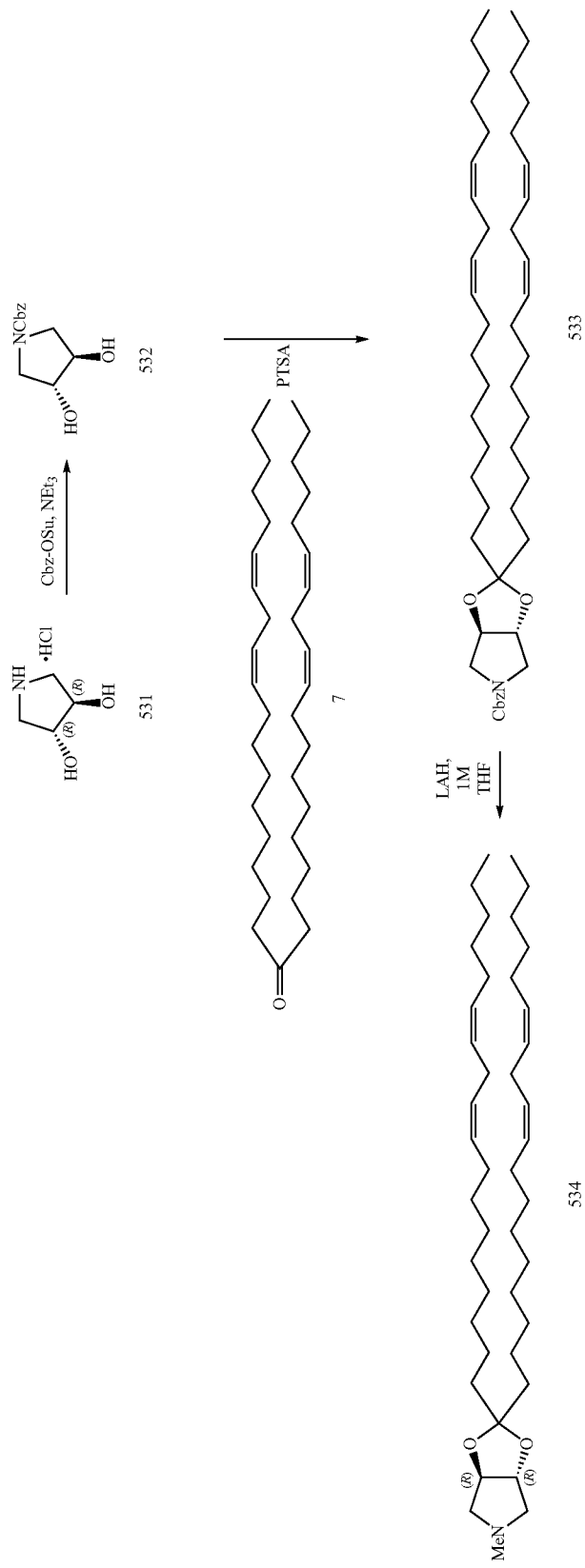
531 prepared according to *Tetrahedron* 2007, 63(5), 1243-1253

Preparation of Compound 532

Using a procedure analogous to that described for the synthesis of compound 504, compound 532 is obtained as a colorless oil.

Preparation of Compound 533

Using a procedure analogous to that described for the synthesis of compound 505, compound 533(%) is obtained as a colorless oil.

Preparation of Compound 534

Using a procedure analogous to that described for the synthesis of compound 506, compound 534 is obtained as a colorless oil.

Example 25

Synthesis of Ketal 538

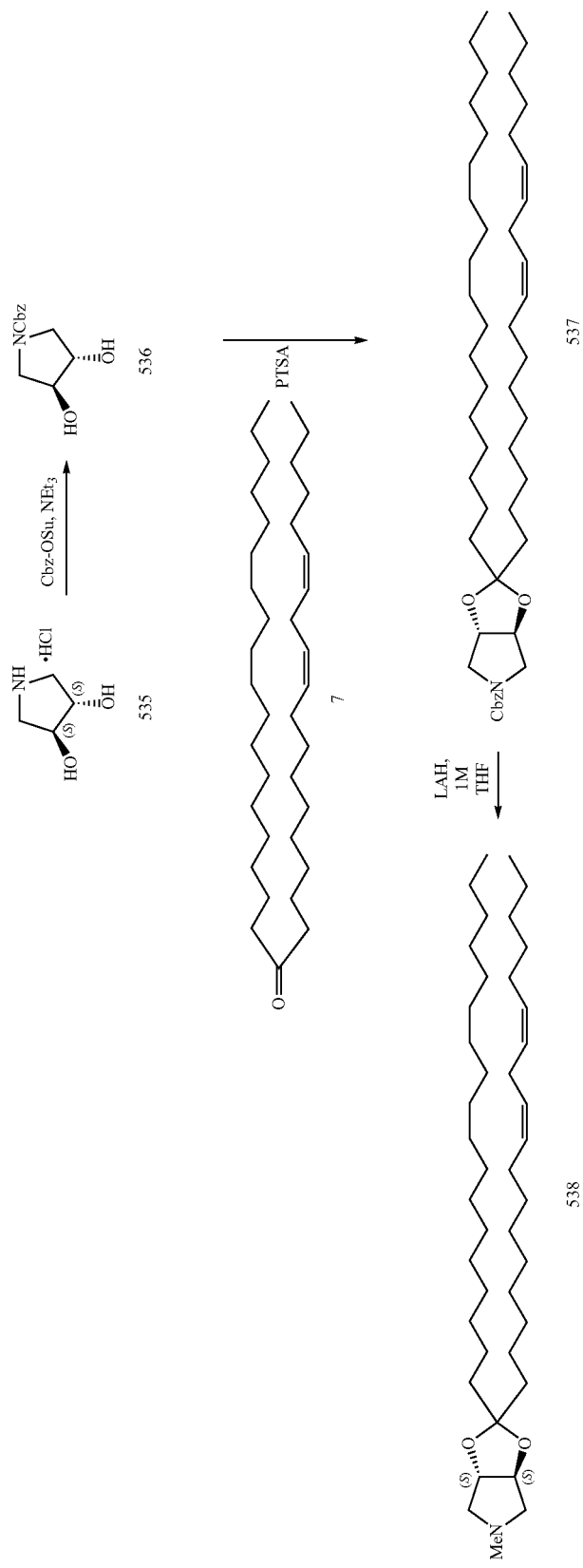
535 prepared according to *Tetrahedron* 2007, 63(5), 1243-1253

243

Preparation of Compound 536

Using a procedure analogous to that described for the synthesis of compound 504, compound 536 is obtained as a colorless oil.

Preparation of Compound 537

Substituting ketone 27 for ketone 7, and using a procedure analogous to that described for the synthesis of compound 505, compound 537 is obtained as a colorless oil.

244

Preparation of Compound 538

Using a procedure analogous to that described for the synthesis of compound 506, compound 538 is obtained as a colorless oil.

Example 26

Synthesis of Ketone 12

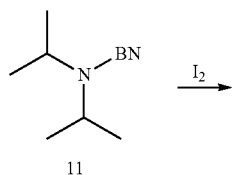

11

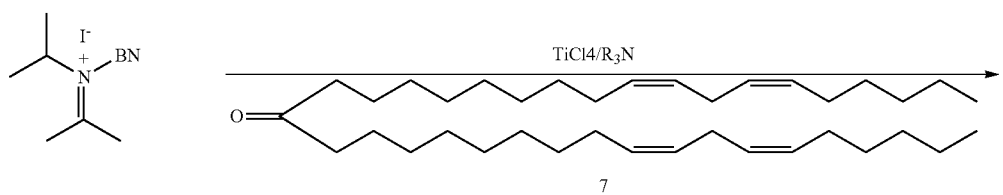

7

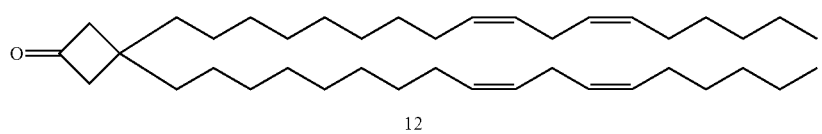

12

The cyclic ketone 12 is synthesized using a similar procedure to that reported in *J. Org. Chem.* 2005, 70, 5420-5425.

Example 27

Synthesis of Ketal 540

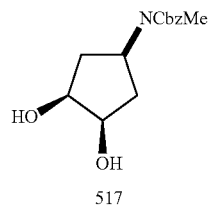

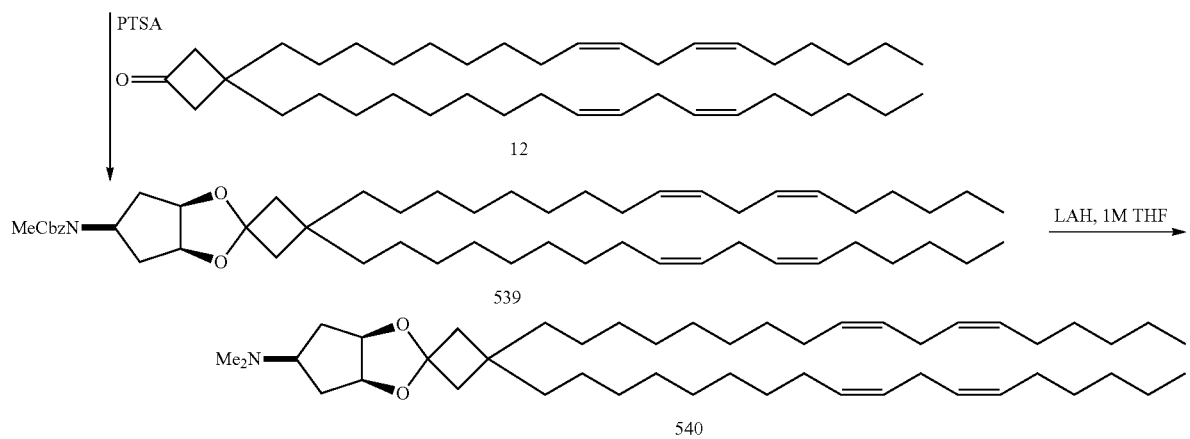

Preparation of Compound 539

Substituting ketone 12 for ketone 7, and using a procedure analogous to that described for the synthesis of compound 505, compound 539 is obtained as a colorless oil.

Preparation of Compound 540

Using a procedure analogous to that described for the synthesis of compound 506, compound 540 is obtained as a colorless oil.

Example 28

Synthesis of Ketone 15

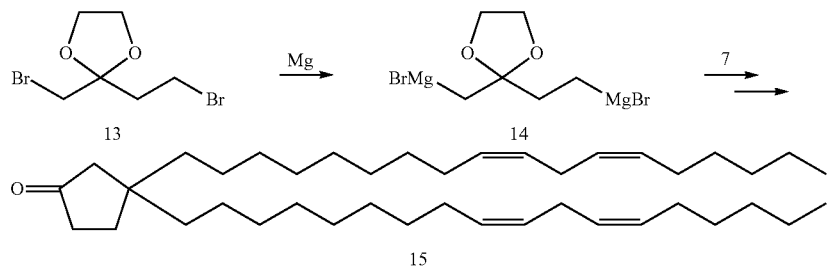

The ketone 15 is synthesized starting from the dibromo ketal 13 via the Grignard reagent 14 as shown in good yields.

Example 29

Synthesis of Ketal 542

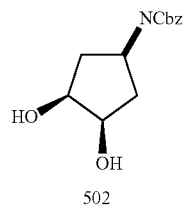
502

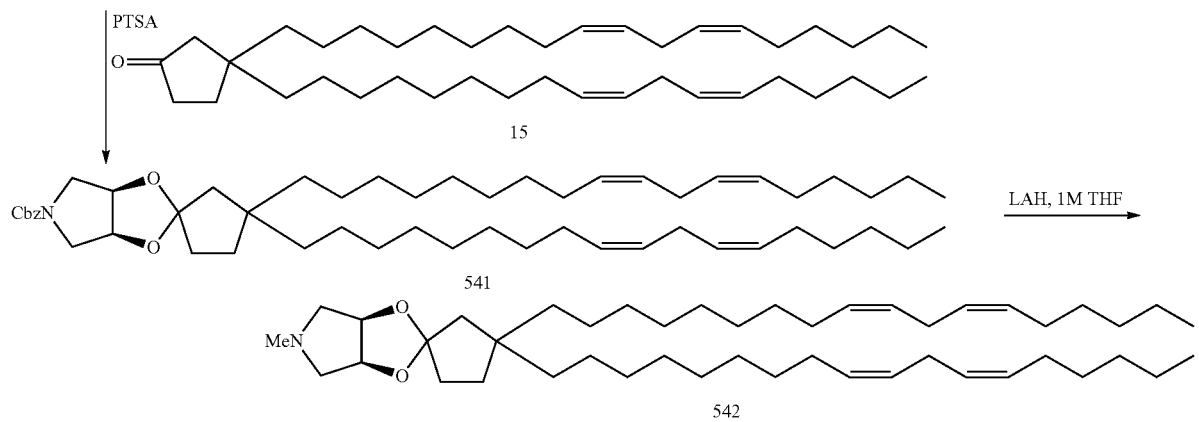

Preparation of Compound 541

Substituting ketone 15 for ketone 12, and using a procedure analogous to that described for the synthesis of compound 505, compound 541 is obtained as a colorless oil.

Preparation of Compound 542

Using a procedure analogous to that described for the synthesis of compound 506, compound 542 is obtained as a colorless oil.

Example 30

Synthesis of Ketone 18

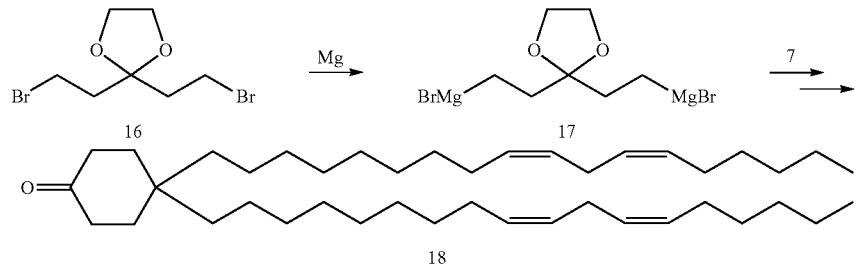

Using a similar procedure to that used for the synthesis of ketone 15, starting from dibromide 16 the six membered cyclic ketone 18 is synthesized as shown.

Example 31

Synthesis of Ketal 544

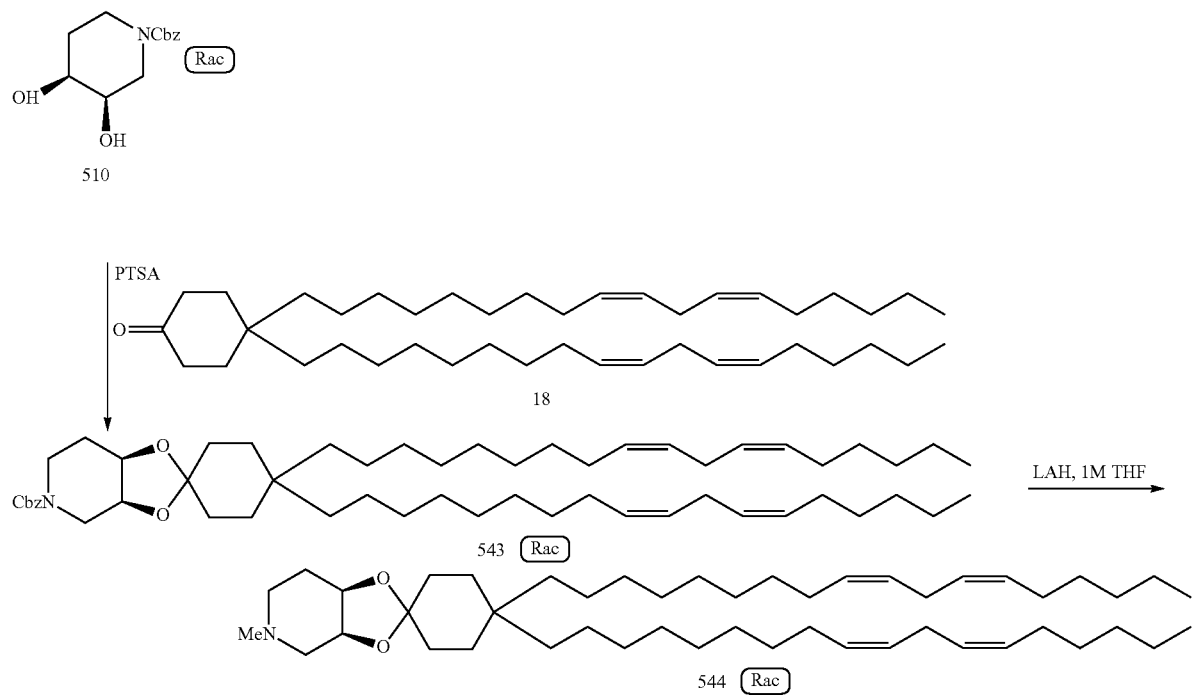

Preparation of Compound 543

Substituting ketone 18 for ketone 12, and using a procedure analogous to that described for the synthesis of compound 505, compound 541 is obtained as a colorless oil.

Preparation of Compound 544

Using a procedure analogous to that described for the synthesis of compound 506, compound 544 is obtained as a colorless oil.

Example 32

Preparation of Compounds 545-550

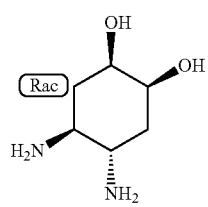

545

-continued

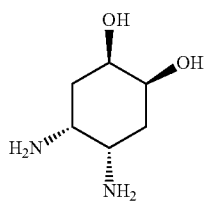

546

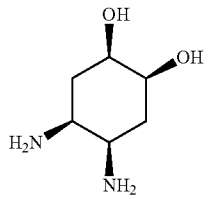

547

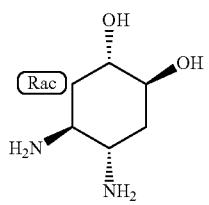

548

-continued
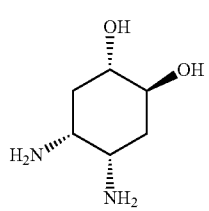
549
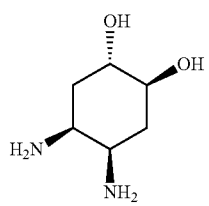
550
*Journal of Medicinal Chemistry, 30(8), 1327-36; 1987
The six diastereomers of 1,2-dihydroxy-4,5-diaminocyclohexane (compounds 545-550) are prepared according to the procedure described in *Journal of Medicinal Chemistry*, 30(8), 1327-36; 1987. Compounds 545 and 548 are obtained as racemates, compounds 546, 547, 549 and 550 are meso compounds.
Example 33
Preparation of Compound 553

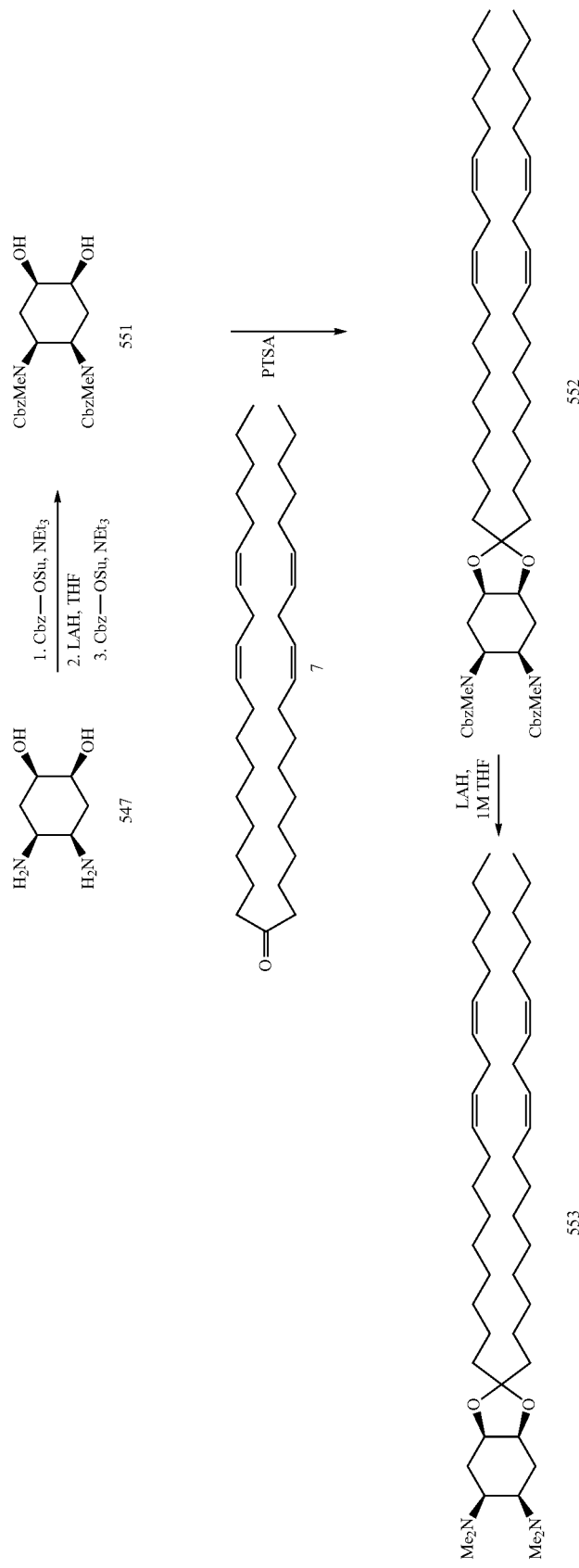

255

Preparation of Compound 551

Using procedures which are analogous to those described for the synthesis of compounds 504 and 506, compound 551 is obtained as a colorless oil.

Preparation of Compound 552

Using a procedure analogous to that described for the synthesis of compound 505, compound 552 is obtained as a colorless oil.

256

Preparation of Compound 553

Using a procedure analogous to that described for the synthesis of compound 506, compound 553 is obtained as a colorless oil.

Example 34

Preparation of Compound 556

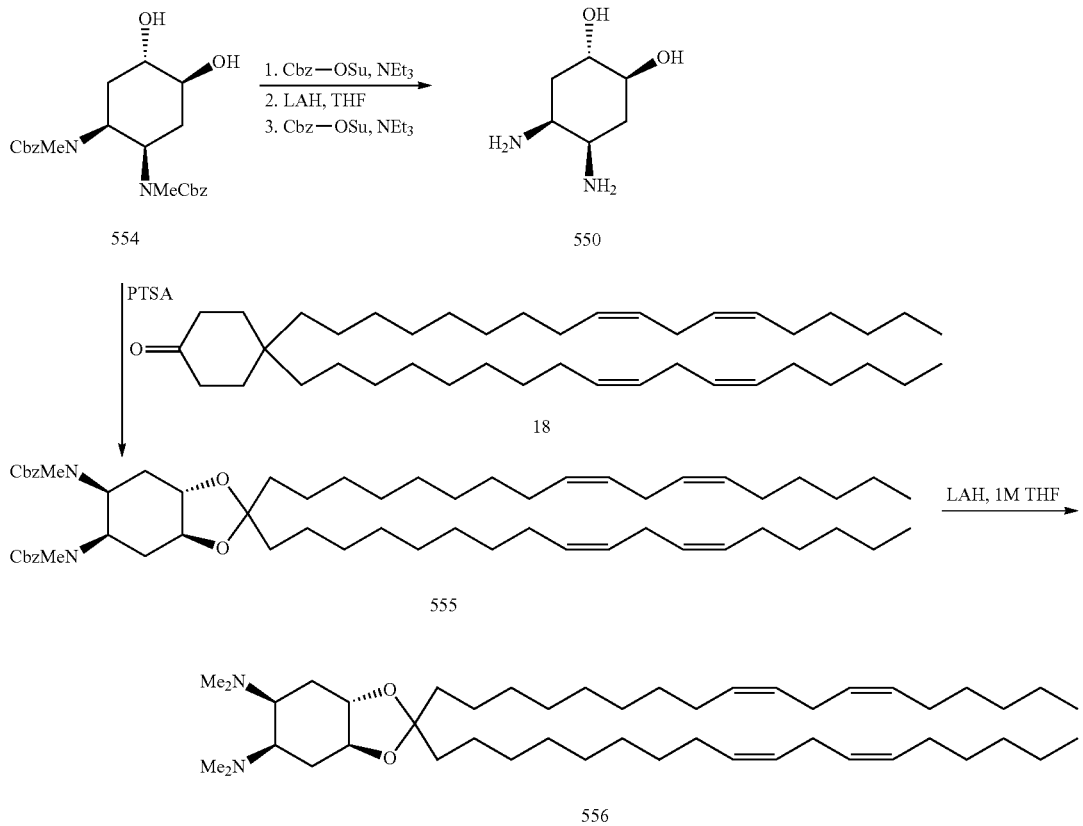

Preparation of Compound 556

Using procedures which are analogous to those described for the synthesis of compounds 551 to 506, compound 556 is obtained as a colorless oil.

Example 35

Synthesis of Optically Pure Cyclic Diol 25

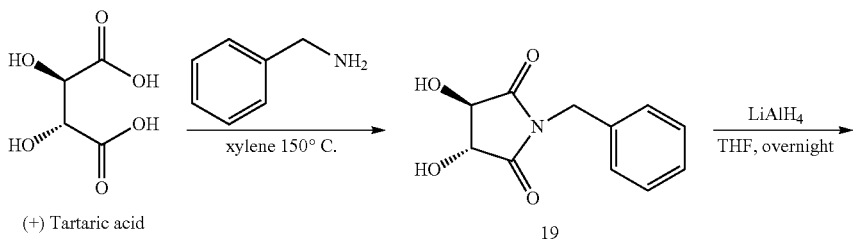

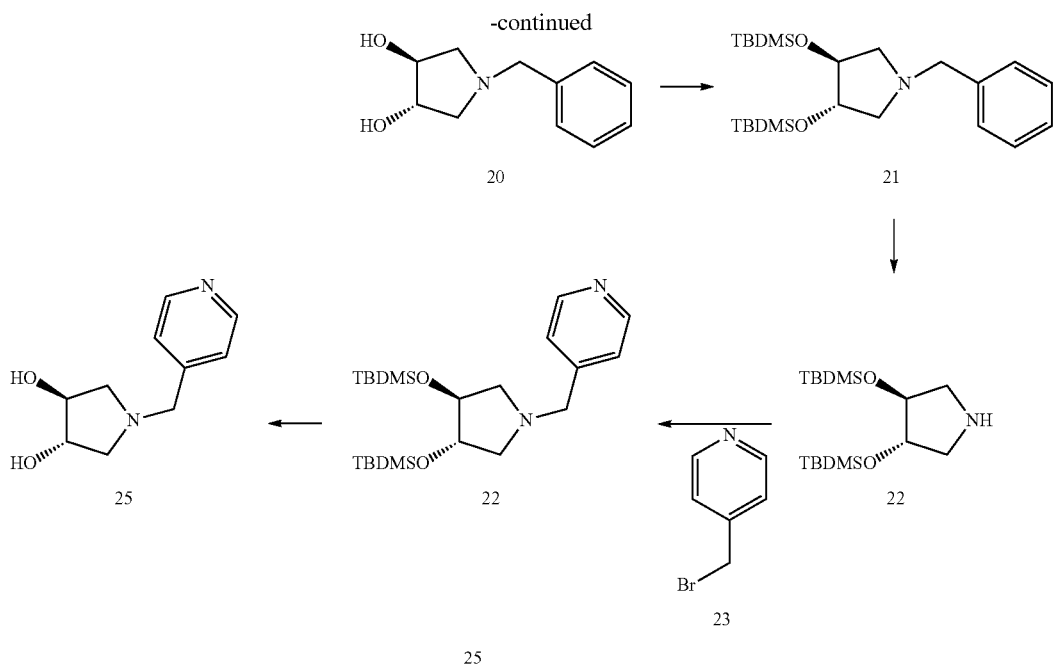

The optically pure diol 25 is synthesized as shown above starting from commercially available (+)-tartaric acid. Treatment of tartaric acid with benzylamine in refluxing xylene provided the imide 19 which on reduction with lithium aluminumhydride provided the pyrrolidine 20 in which the diol is protected with TBDMS and followed by alkylation with the bromide 23 to give product 24 which is deprotected to isolate the pure diol 25 in good yields.

Example 36

Synthesis of Ketal 26

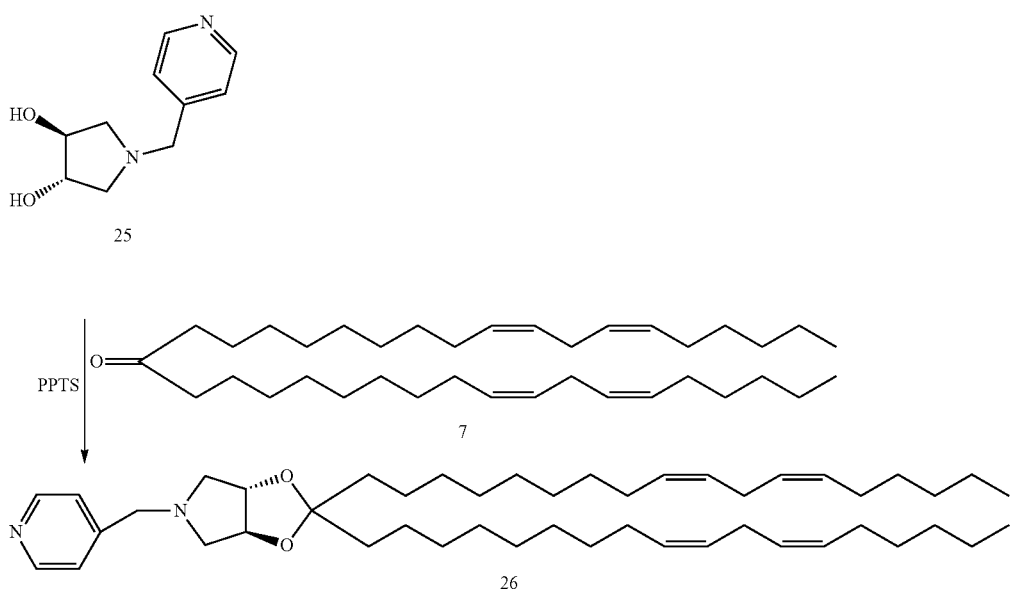

Using a procedure analogous to that described for the synthesis of compound 505, compound 26 is obtained as a colorless oil.

Example 37
Synthesis of Ketal 30
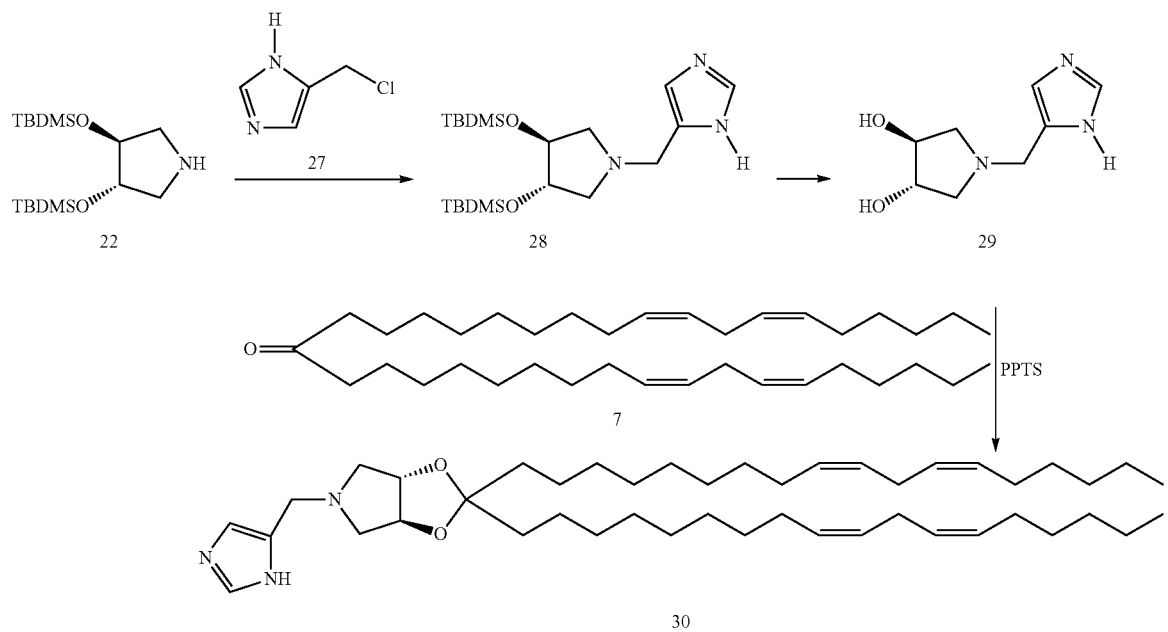
Using a procedure analogous to that described for the synthesis of compound 505, compound 30 is obtained as a colorless oil.
Example 38
Synthesis of Compound 406
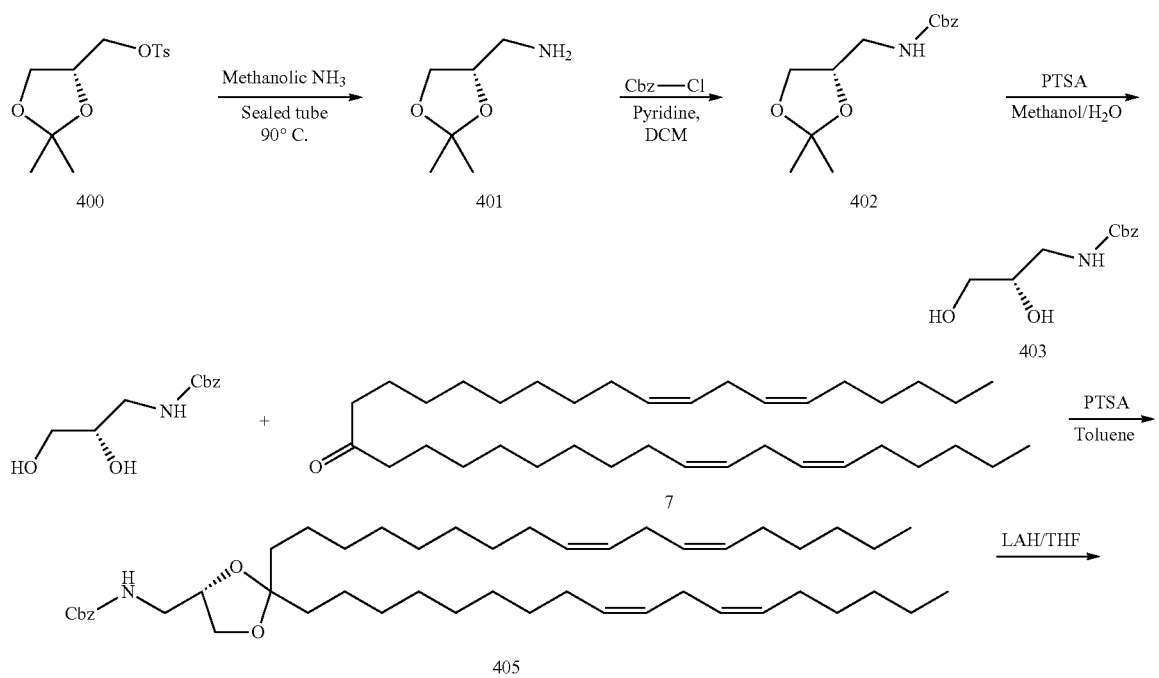

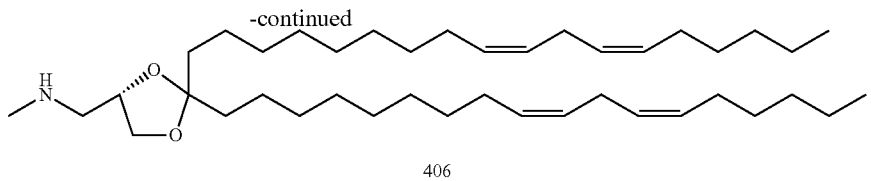

406

Preparation of 401

Tosylate (250 g, 0.873 mol) was charged in a 7.5 L auto clave followed by methanolic ammonia (60%) (3750 mL) at −20° C. The pressure vessel was closed and stirred while allowing the reaction mixture to warm to room temperature. It was then heated to 90° C. and continued for 5 hrs at 90° C. (TLC). Reaction mixture was cooled to room temperature and the internal pressure was released. It was then purged with nitrogen for 15 minutes to remove excess of ammonia, evaporated at reduced pressure at 30° C. to obtain crude residue. It was washed with diethyl ether (2×250 ml) to remove impurities and dried at reduced pressure at 30-34° C. to afford the desired product along with the by-product sulfonamide. This mixture has been taken as such for the next step (Yield 112 g, 95%). $^1$H NMR (400 MHz, DMSO-$d_6$): δ 1.29 (S, 3H), 1.38 (S, 3H), 2.83 (m, 1H), 3.02 (dd, 1H), 3.70 (m, 1H), 4.04 (t, 1H), 4.24 (m, 1H).

Preparation of 402

To a solution of 401 (112 g, 0.850 mol) in dichloromethane (560 mL) at 0° C., was added 2,6 Lutidine (182.2 g, 1.70 mol) drop-wise during 15 minutes. Then Cbz-Cl (147.50, 0.860 mol) was added drop-wise during 25 minutes at same temperature. It was then stirred for another 15 minutes at 0° C. (TLC). It was diluted with dichloromethane (300 ml), washed with 10% citric acid (3×250 ml) and brine (1×250 ml). The organic layer was separated, dried over sodium sulfate and evaporated at reduced pressure at 45° C. to obtain crude product, which was purified by silica gel chromatography using ethyl acetate/hexane as eluent to afford pure product (Yield 174, 77%). $^1$H NMR (400 MHz, CDCl$_3$): 1.33 (S, 3H), 1.40 (S, 3H), 3.23 (m, 1H), 3.43 (m, 1H), 3.64 (t, 1H), 4.01 (t, 1H), 4.2 (m, 1H), 5.60 (s, 2H), 5.24 (s, 1H), 7.31 (s, 5H).

Preparation of 403

To a solution of 402 (149 g, 0.5622 mol) in methanol and water (1:85, 800 mL) was added PTSA (214 g, 2 eq.) at room temperature and stirred for 15 minutes (TLC). It was then evaporated at reduced pressure to remove methanol and diluted with water (150 ml). Then pH of the aqueous solution was adjusted to 8.5-9 using solid sodium carbonate and extracted several times with ethyl acetate to ensure complete recovery of the product. The combined organic layer was dried over sodium sulfate and evaporated at reduced pressure to afford pure product (Yield, 118 g, 90%) as white solid. $^1$H NMR (CDCl$_3$, 400 MHz): δ 3.1 (s, 1H), 3.3 (m, 3H), 3.6 (m, 2H), 3.8 (s, 1H), 5.1 (s, 2H), 5.3 (s, 1H), 7.3 (m, 5H).

Preparation of 405

To stirred mixture of 403 (170 g, 0.755 mol) and ketone 7 (199 g, 0.377 mol) in anhydrous toluene (2 L), was added half of the quantity of PTSA (7.1 g, 0.1 eq) and heated to reflux at 130° C. bath using dean stark apparatus. After 6 hours second half of the quantity of PTSA (7.1 g, 0.1 eq.) was added and reaction was continued for another 12 hours (TLC). Reaction mass was allowed to cool to room temperature and filtered to remove precipitated solids. The filtrate was washed with saturated sodium bicarbonate solution, dried over sodium sulfate and evaporated at reduced pressure to obtain crude product, which was purified by silica gel chromatography using 5% ethyl acetate/hexane as eluent to afford pure product as color less liquid (153 g, 55%). $^1$H NMR (CDCl$_3$): δ value: 0.9 (t, 6H), 1.3 (m, 38H), 1.5 (m, 2H), 1.6 (s, 4H), 2.0 (m, 8H), 2.8 (t, 4H), 3.2 (m, 1H), 3.5 (m, 1H), 3.6 (t, 1H), 4.0 (t, 1H), 4.2 (s, 1H), 5.1 (s, 1H), 5.2 (s, 2H), 5.5 (m, 8H), 7.3 (m, 5H).

Preparation of 406

To LAH (16.6 g, 0.438 mol) under N$_2$ at 0° C. was added dry THF (1.3 L) and stirred for 30 minutes. To the suspension was added a solution of 405 (161 g, 0.219 mol) in THF (300 ml) slowly by maintaining the temperature at 0° C. After addition, the reaction mass was warmed to 40° C. During this period the inside temperature rose from 40 to 54° C. and after few minutes again decreased to 40° C. Reaction was continued for another 1 hr at 40° C. (TLC). It was then cooled to 0° C. and quenched with 100 ml of sat. sodium sulfate solution and diluted with ethyl acetate (1 L). The solid formed was filtered through a pad of celite bed. The residue was washed several times with ethyl acetate. The combined filtrate was evaporated at reduced pressure to obtain crude product, which was purified by silica gel chromatography using dichloromethane/15% ethyl acetate as eluent to obtain pure product as an yellow liquid (99 g, 74%). $^1$H NMR (CDCl$_3$): δ value: 0.96 (t, 6H), 1.3 (m, 38H), 1.6 (m, 4H), 2.1 (q, 8H), 2.53 (s, 3H), 2.76 (dd, 2H), 2.82 (q, 4H), 3.6 (t, 1H), 4.1 (t, 1H), 4.3 (m, 1H), 5.4 (m, 8H).

Example 39
Preparation of Compound 408
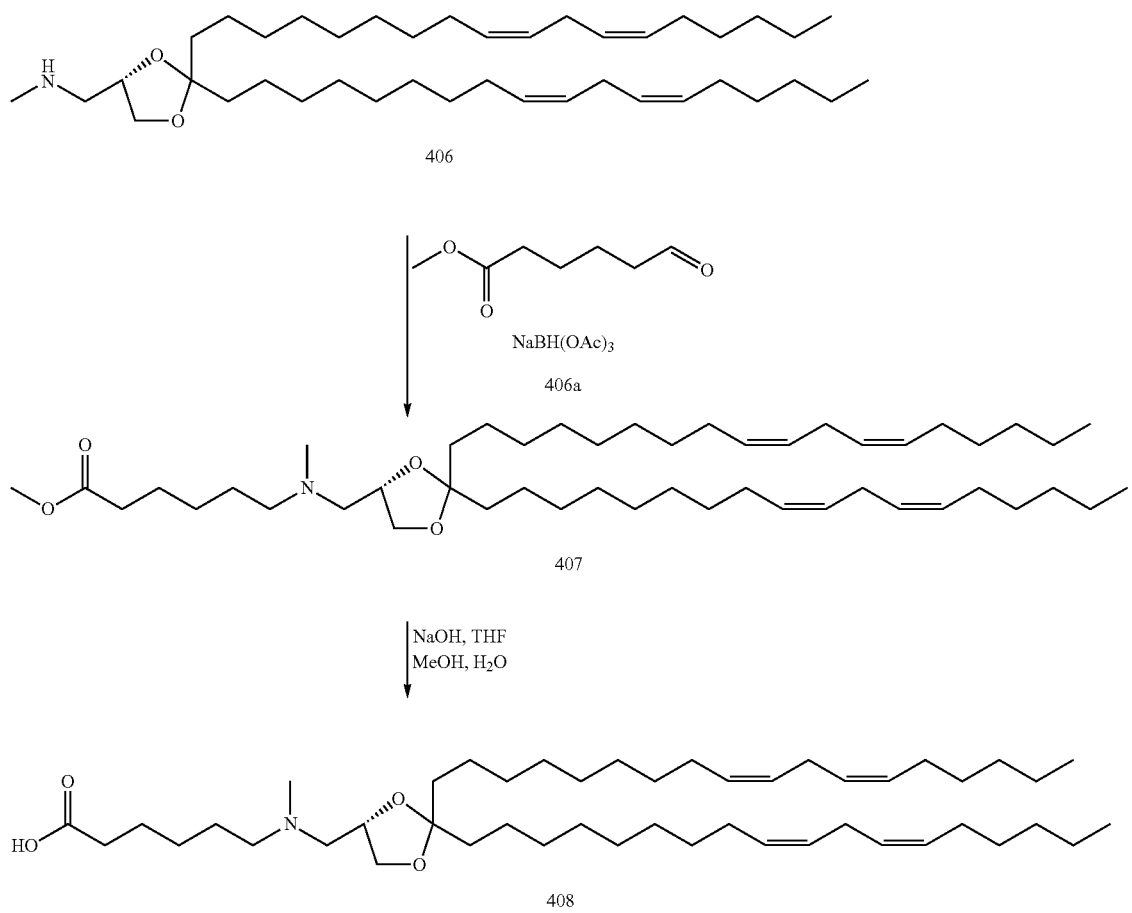
Compound 406 is treated with 406a under reductive amination conditions as shown above to get 407. It is then treated with Sodium hydroxide solution in Methanol/THF/Water to get 408.
Example 40
Preparation of Compound 410
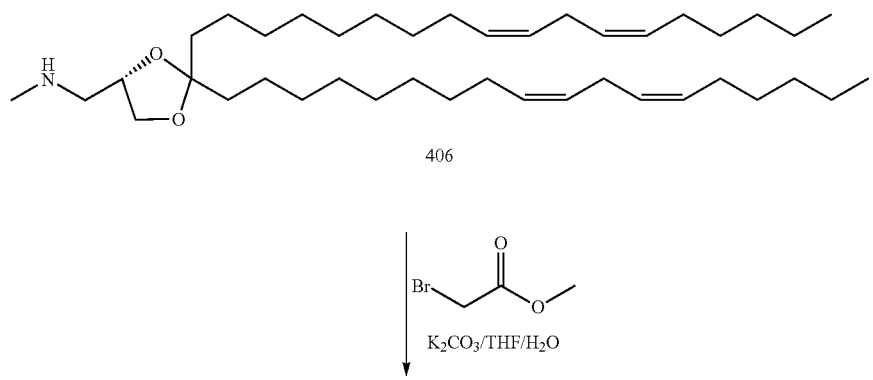

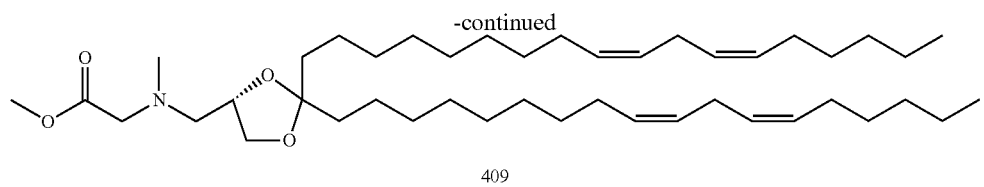
409
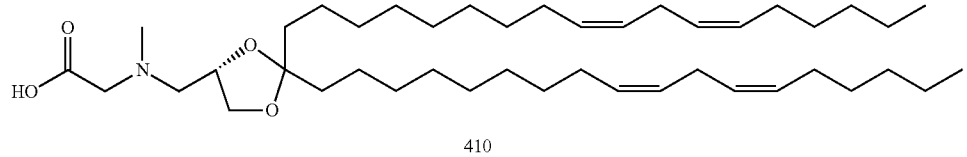
410
Compound 406 is alkylated with methyl bromo acetate using potassium carbonate in THF/Water as shown above to get 409. It is then treated with Sodium hydroxide solution in Methanol/THF/Water to get 410.
Example 41
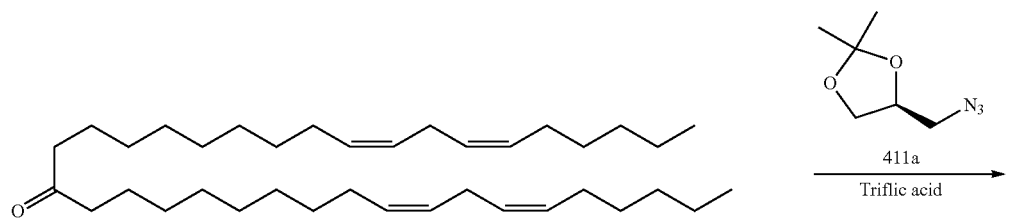
404
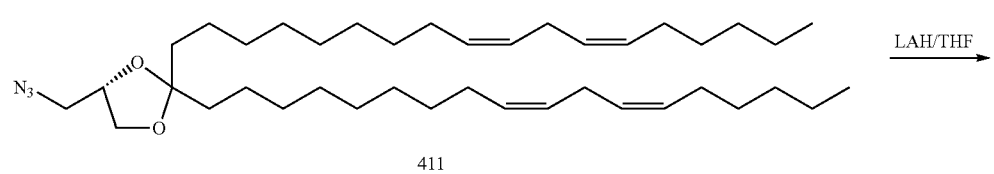
411
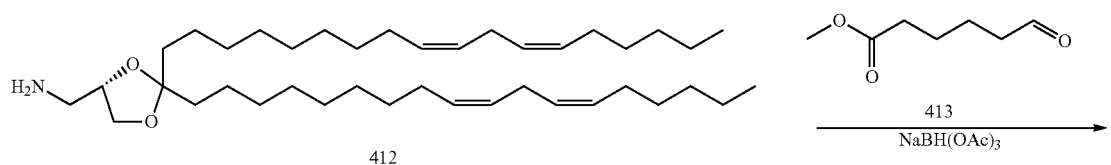
412
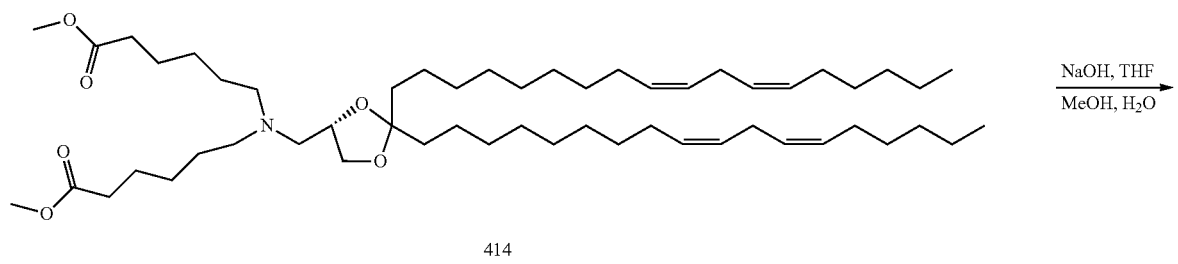
414

-continued
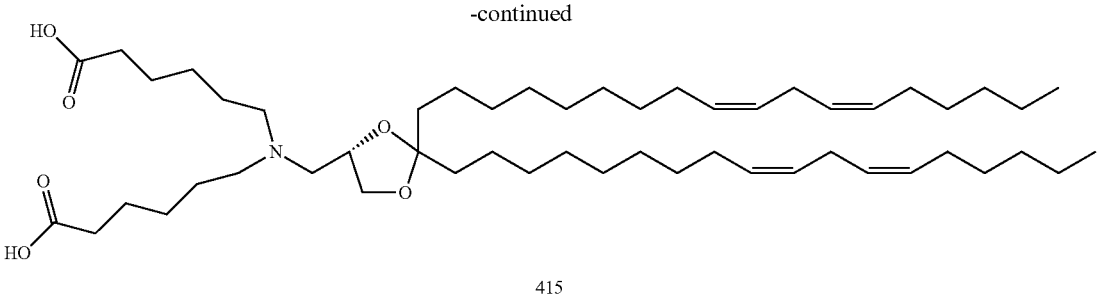
415
Compound 411 is prepared from the acetonide 411a using trans ketalysation. LAH reduction gives compound 412. It is then convert to the diester 414 by reductive amination. Deprotection of 414 using NaOH gives compound 415.
Example 42
Preparation of Compound 418

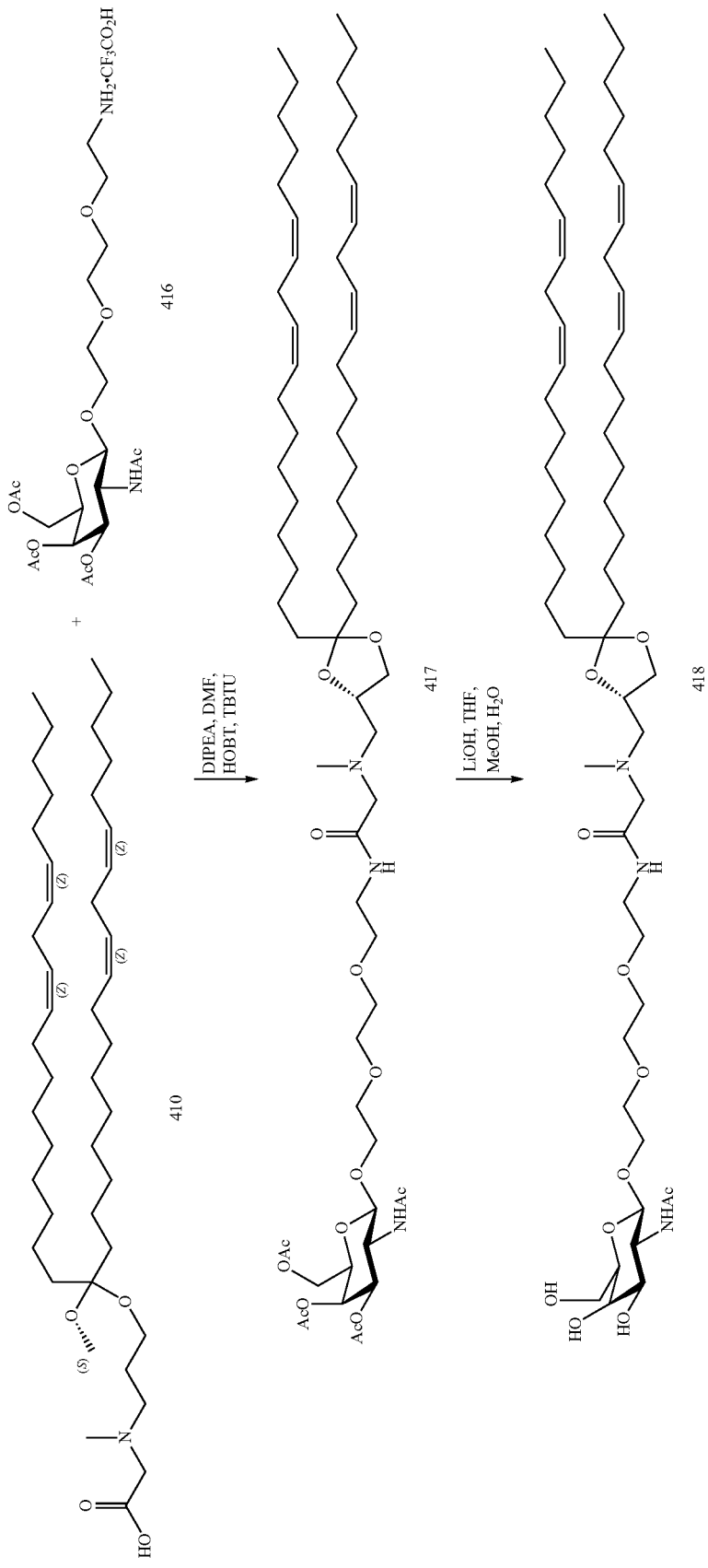

Lipid acid 410 is treated with GalNAc amine 416 under peptide coupling conditions to get 417. Deprotect the acetate groups using LiOH gives compound 418.

Example 43

Preparation of Compound 421

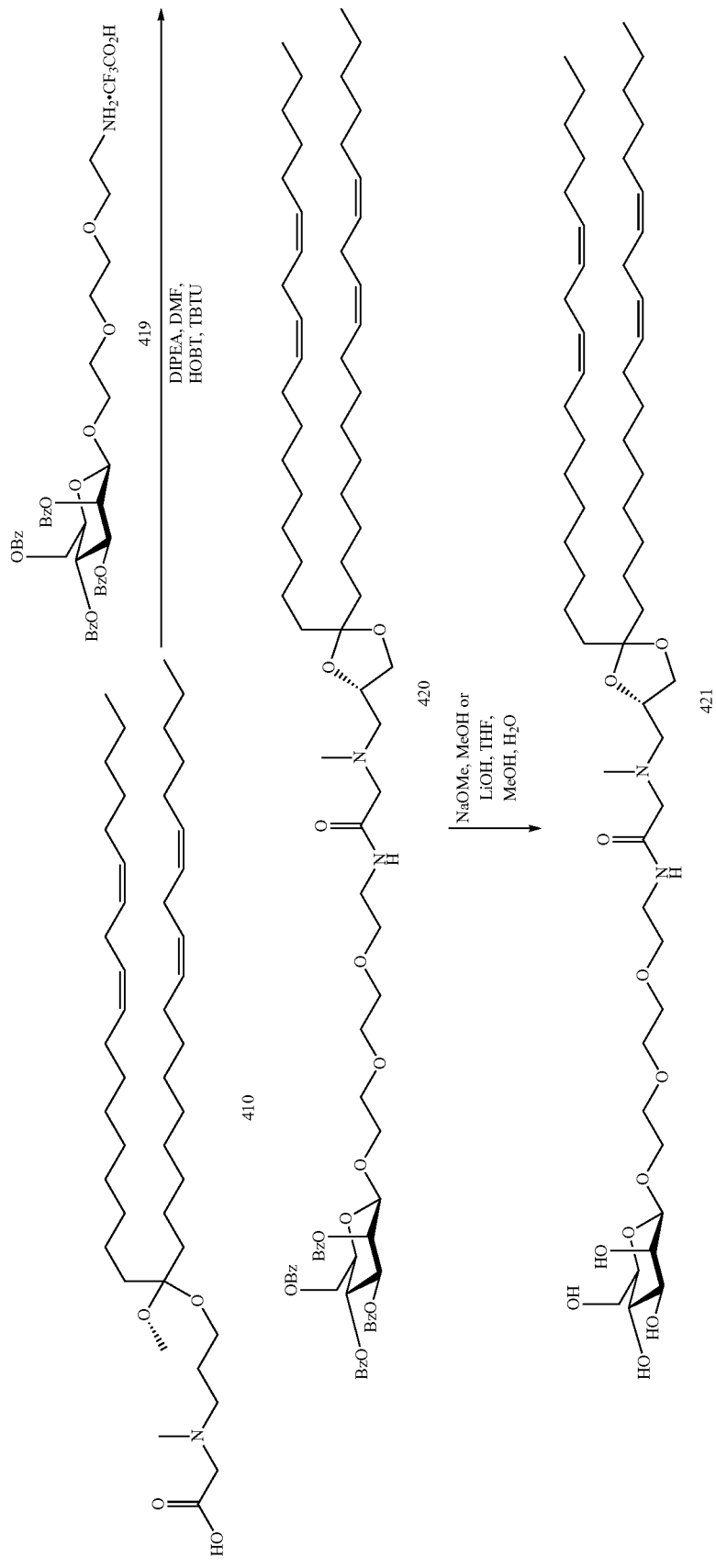

Lipid acid 410 is treated with Mannose amine 419 under peptide coupling conditions to get 420. Deprotect the benzoate groups using LiOH gives compound 421.

Example 44

Preparation of Compound 424

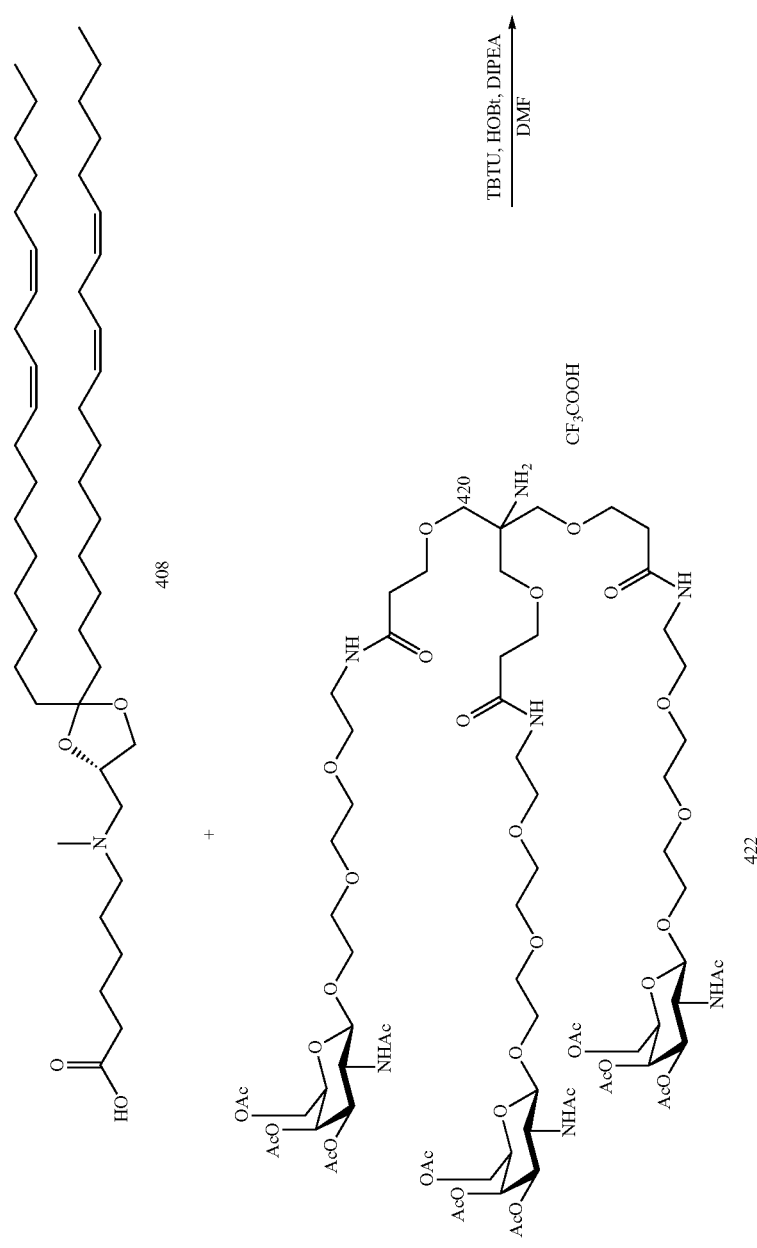

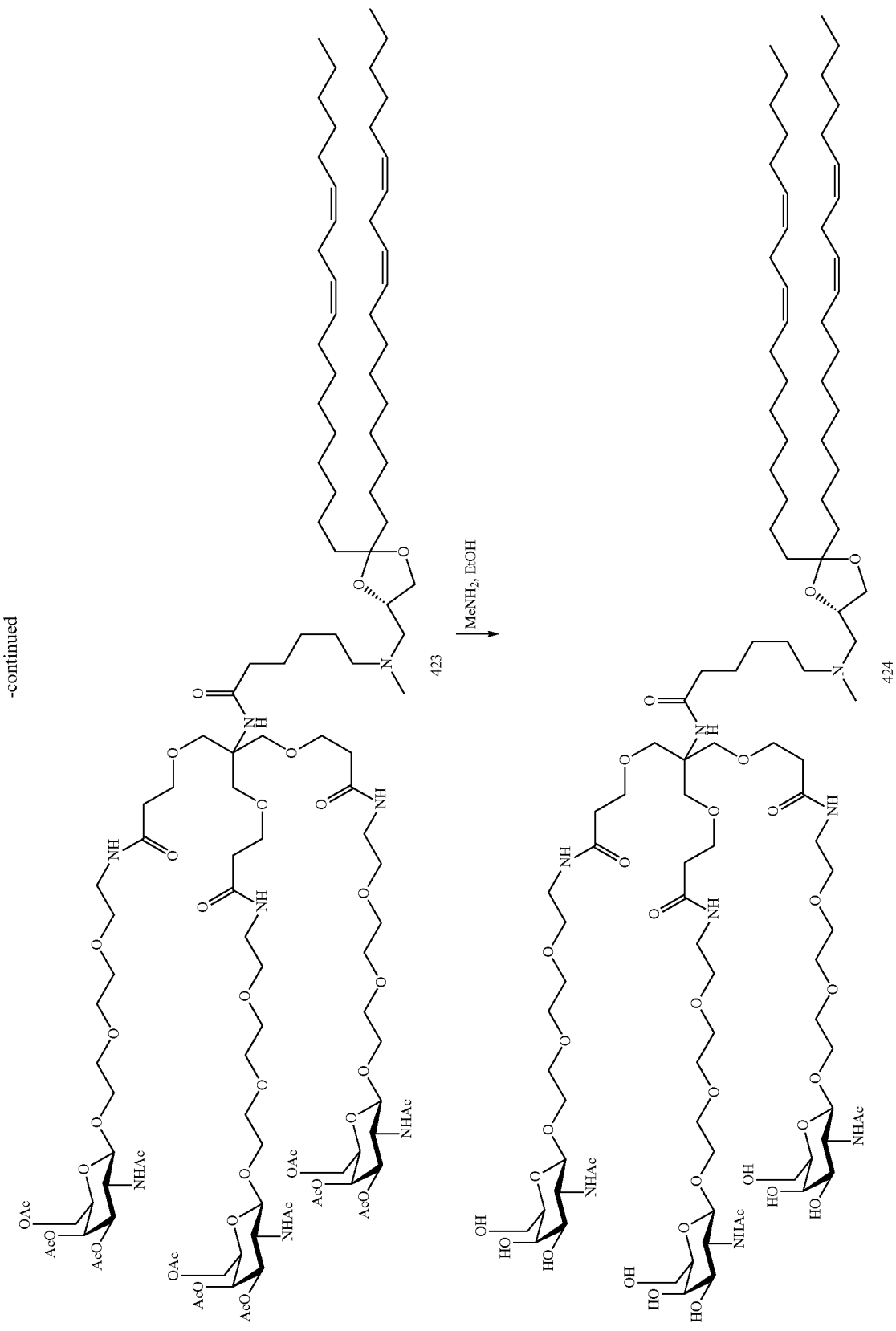

Lipid acid 408 is treated with triantineary GalNAc amine 422 under peptide coupling conditions to get 423. Deprotect the acetate groups using methyl amine at room temperature gives compound 424.

Example 45

Preparation of Compound 427

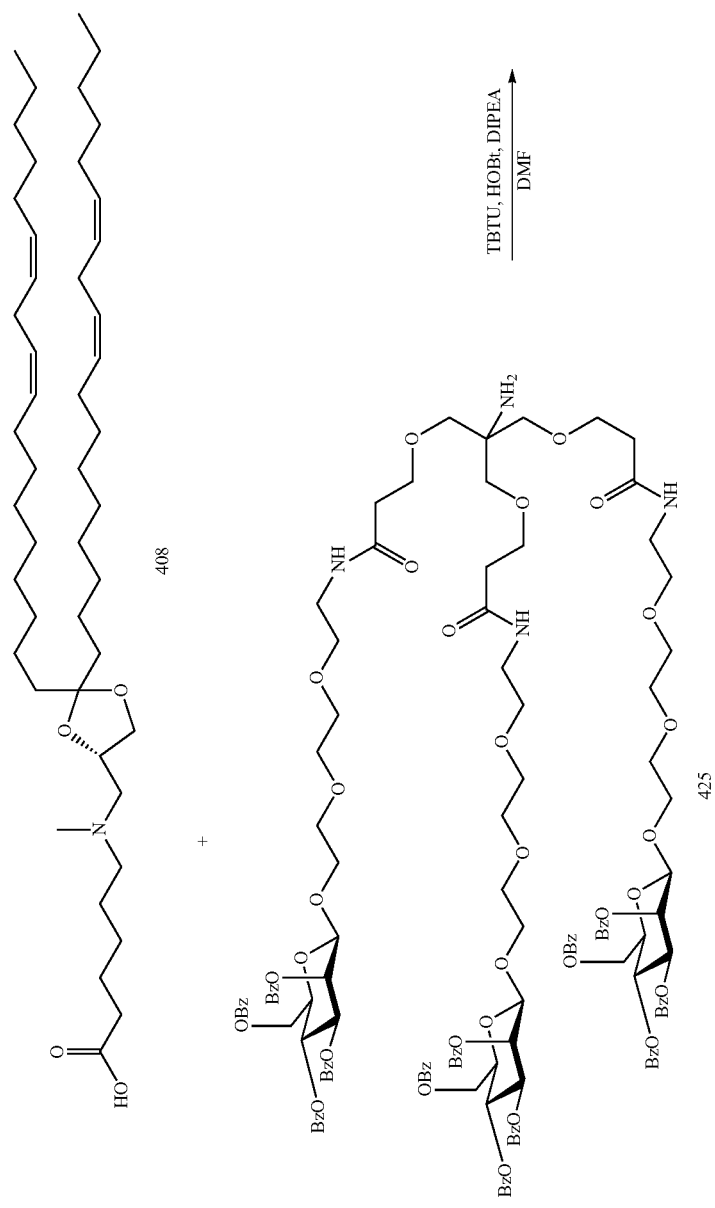

285 286
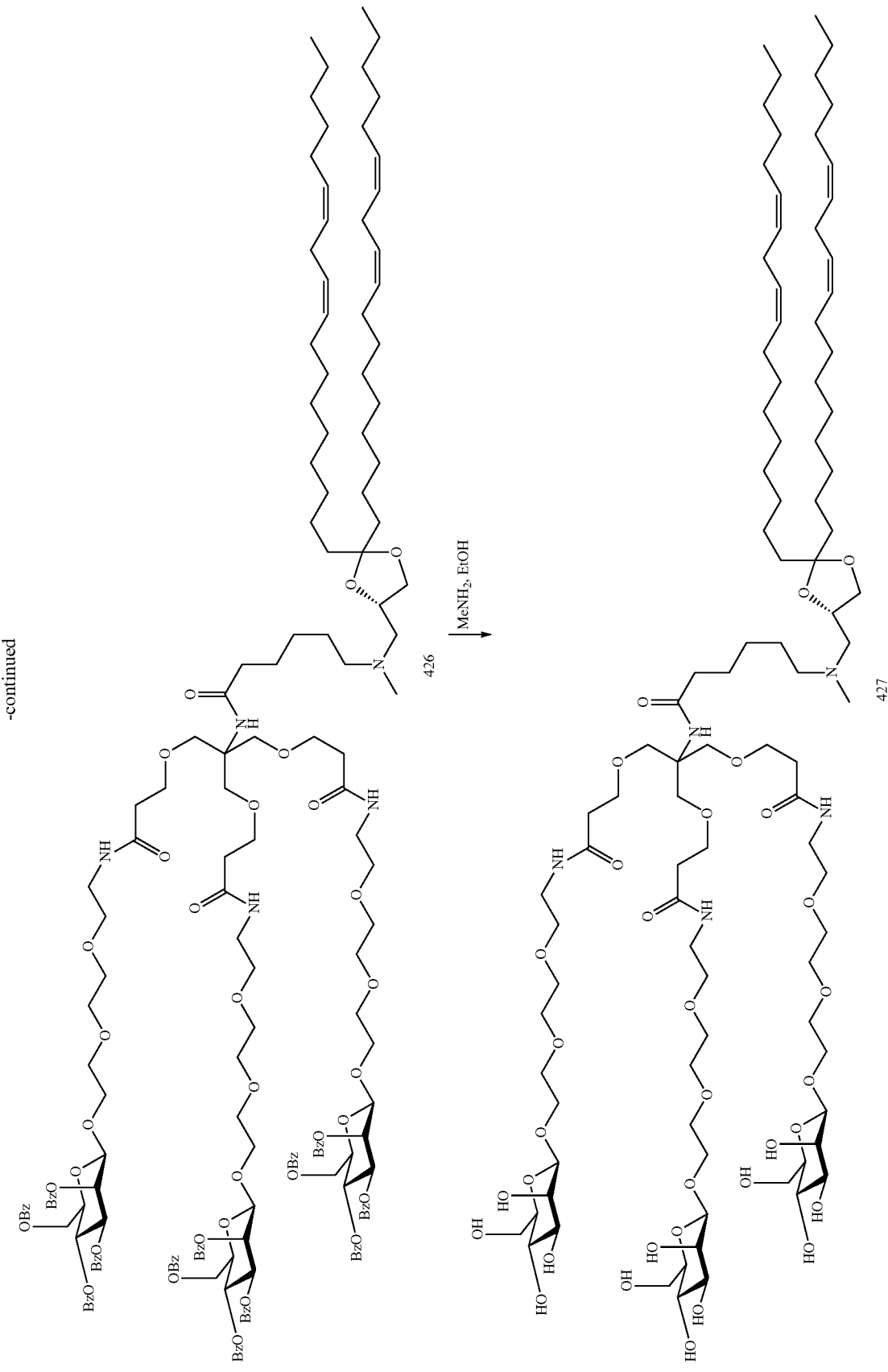

Lipid acid 408 is treated with triantineary mannose amine 425 under peptide coupling conditions to get 426. Deprotection of benzoate groups using methyl amine at room temperature gives compound 427.

Example 46

Preparation of Compound 430

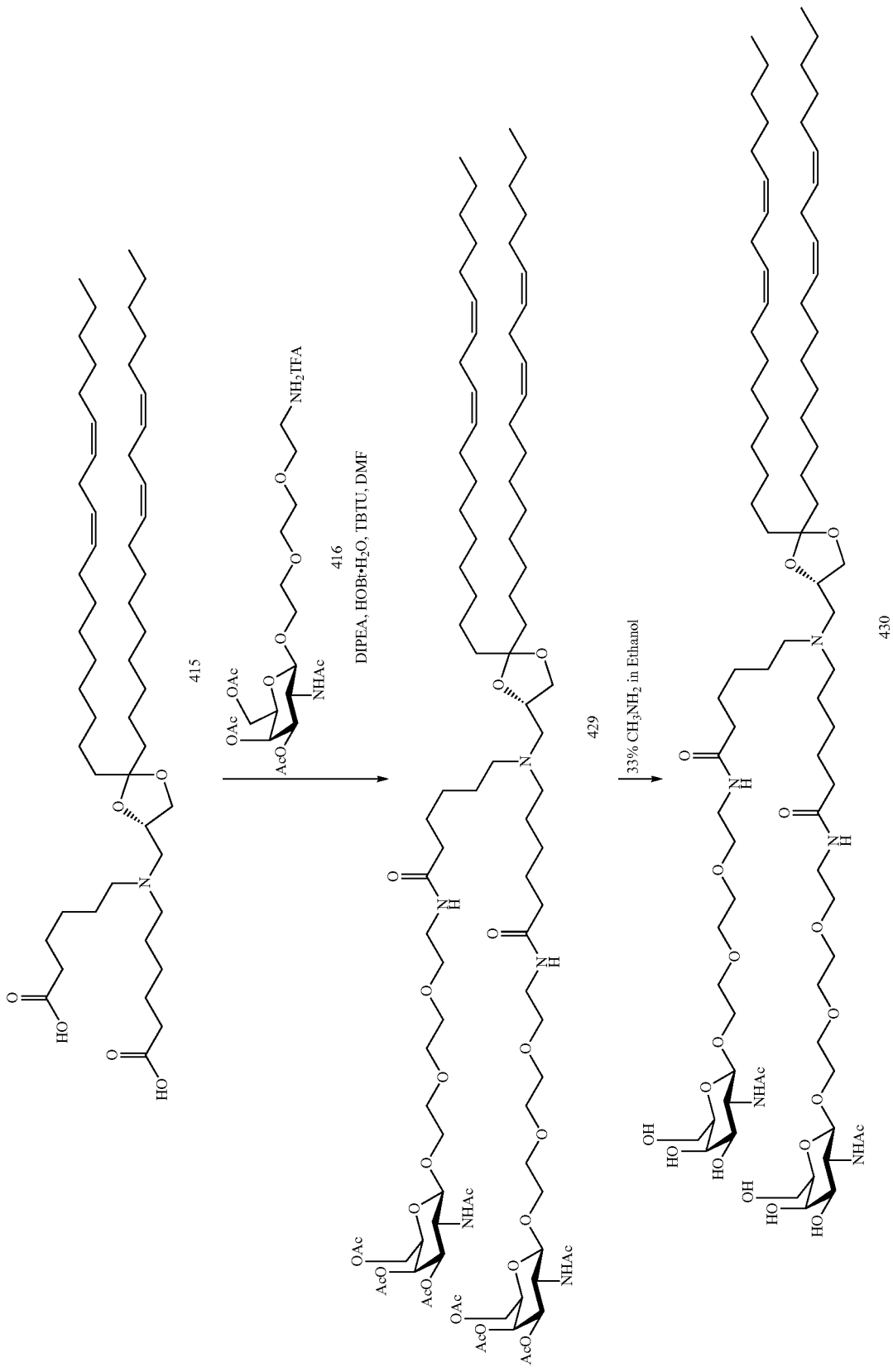

Lipid diacid 415 is treated with GalNAc amine 416 under peptide coupling conditions to get 429. Deprotection of acetate groups using methyl amine at room temperature gives compound 430.

Example 47

Preparation of Compound 432

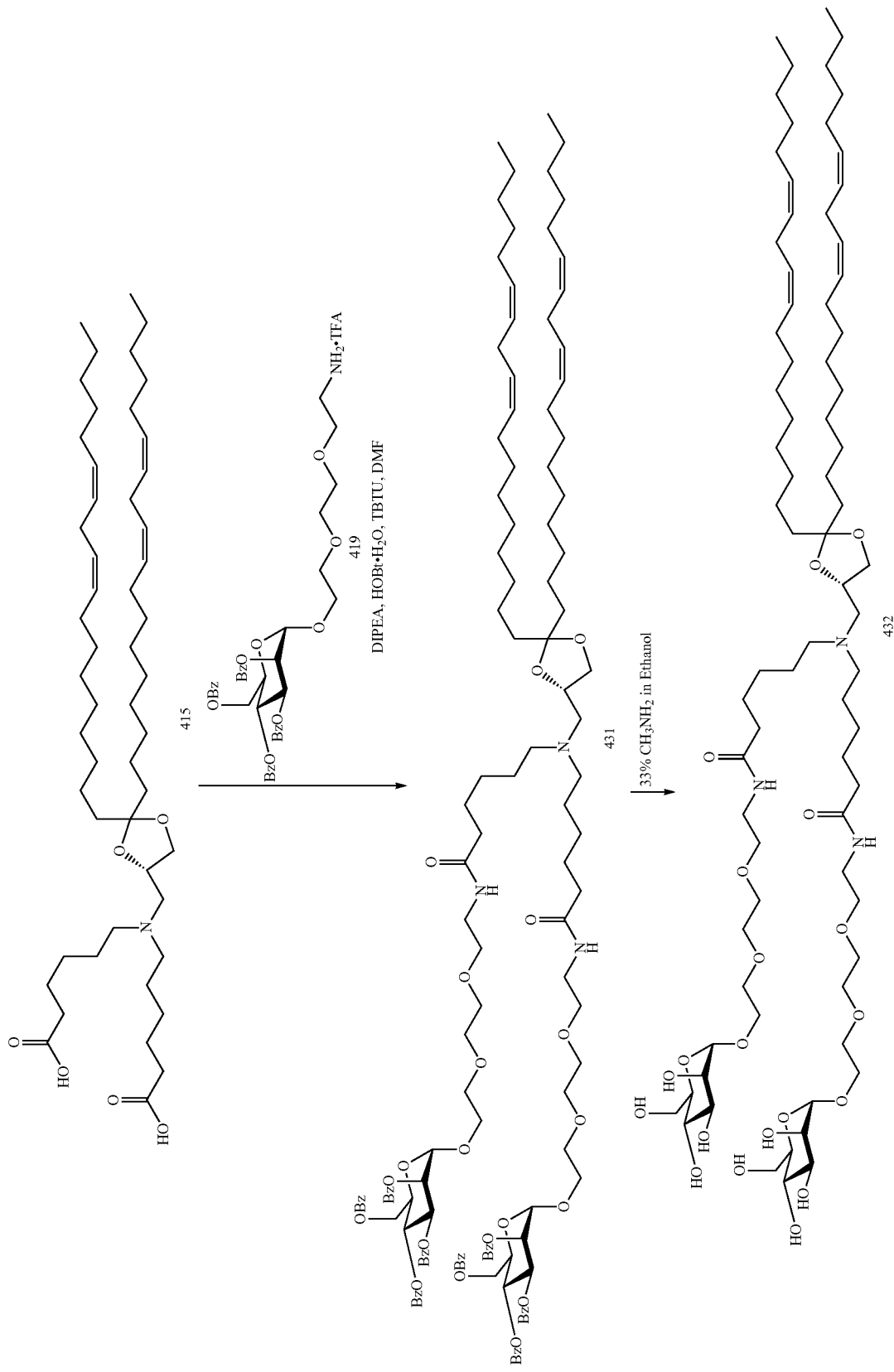

Lipid diacid 415 is treated with mannose amine 419 under peptide coupling conditions to get 431. Deprotection of acetate groups using methyl amine at room temperature gives compound 432.

Example 48

Preparation of Compound 438

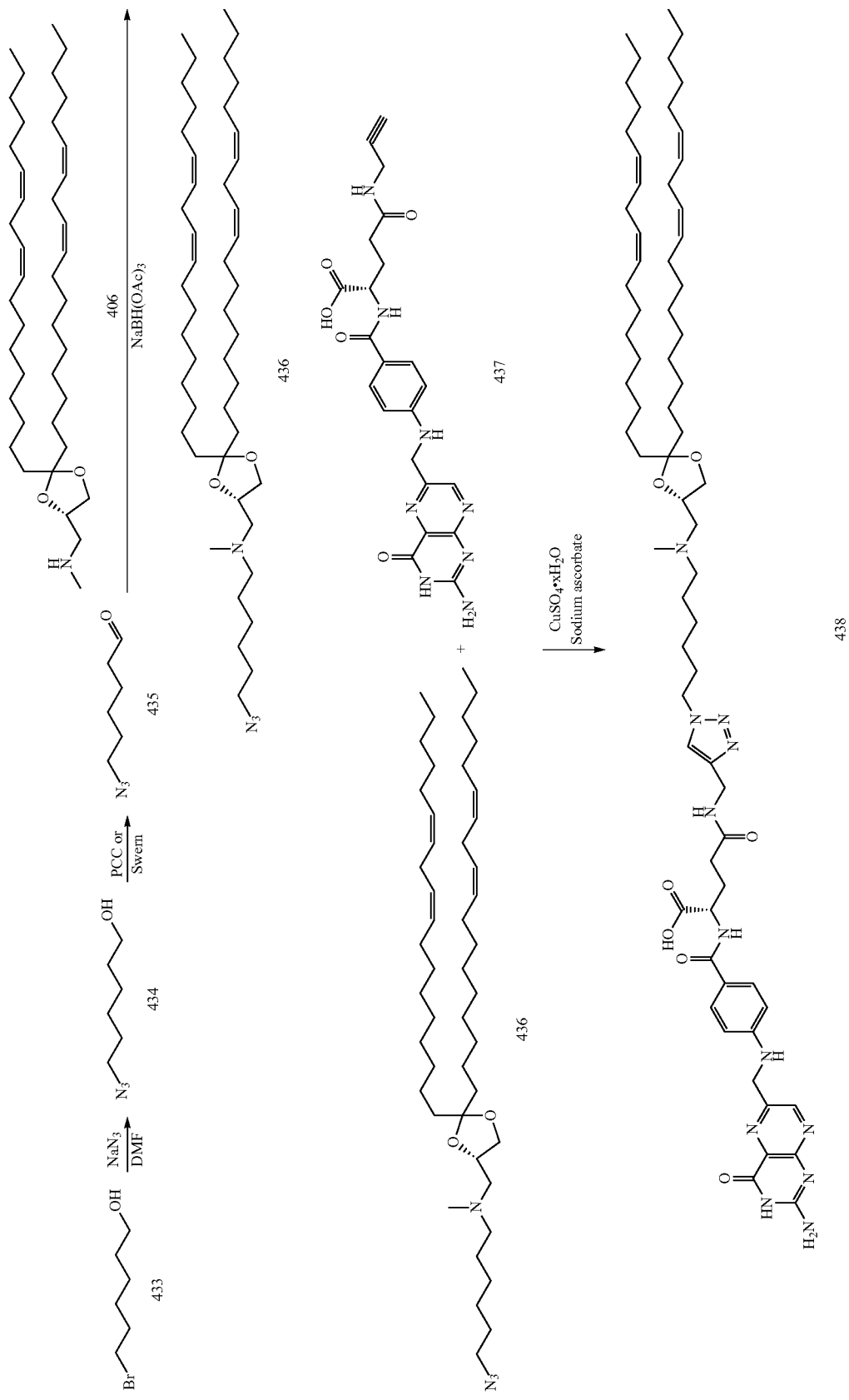

Compound 436 and 437 react to give compound 438 under click chemistry conditions.

Example 49

Preparation of Compound 442

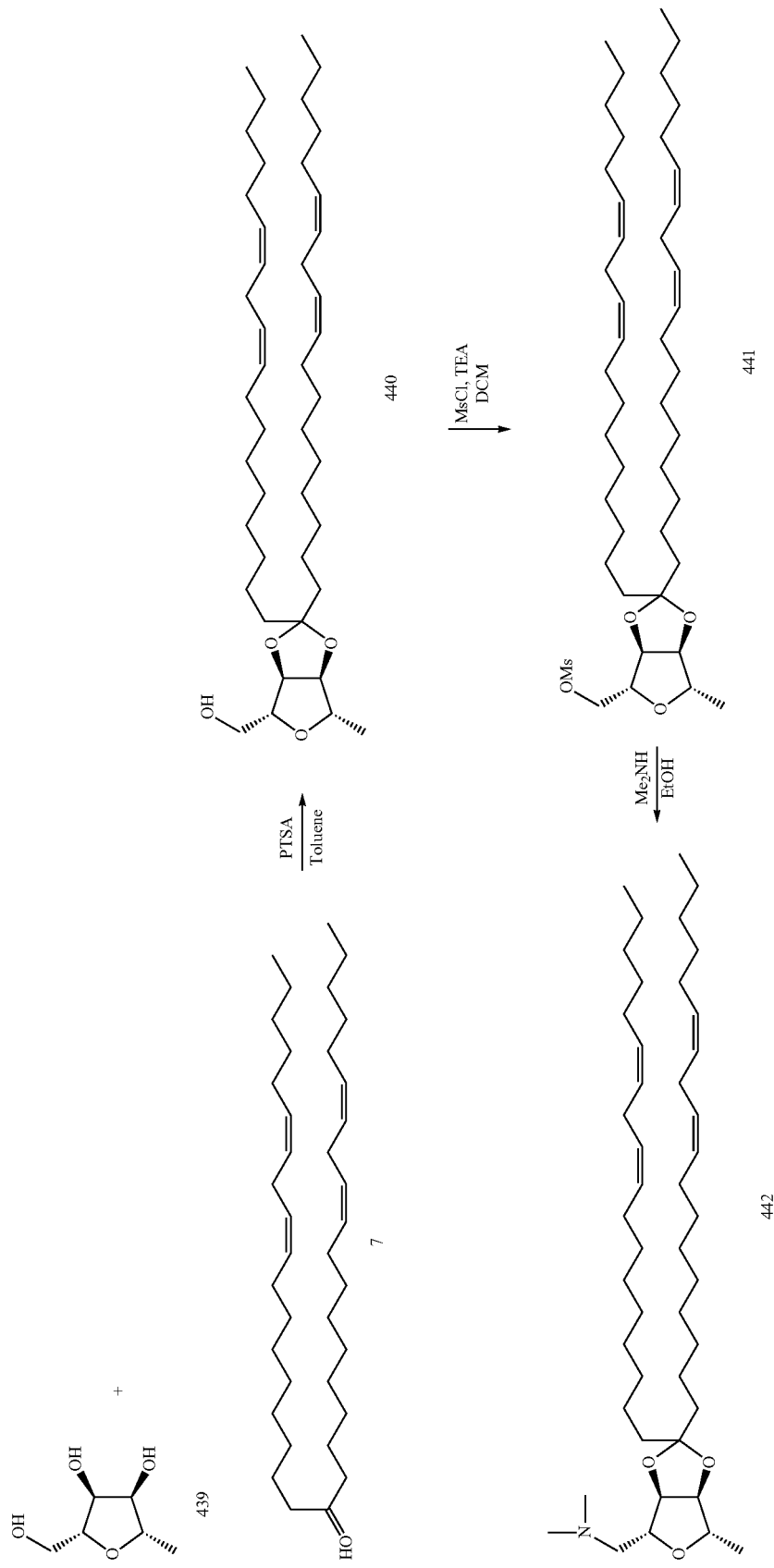

Preparation of 439

Compound 439 is prepared according to the procedure described in Dills, William L., Jr.; Covey, Thomas R.; Singer, Paul; Neal, Sharon; Rappaport, Mark S. "2,5-Anhydro-1-deoxy-D-lyxitol, 2,5-anhydro-1-deoxy-D-mannitol, and 2,5-anhydro-1-deoxy-D-talitol. Synthesis and enzymic studies" *Carbohydrate Research* (1982), 99(1), 23-31.

Preparation of 442

To a solution of 441 in EtOH, Dimethylamine in EtOH is added and heat the reaction mixture in a pressure reactor at 70° C. for overnight to get 442.

Example 50

Preparation of Compound 445

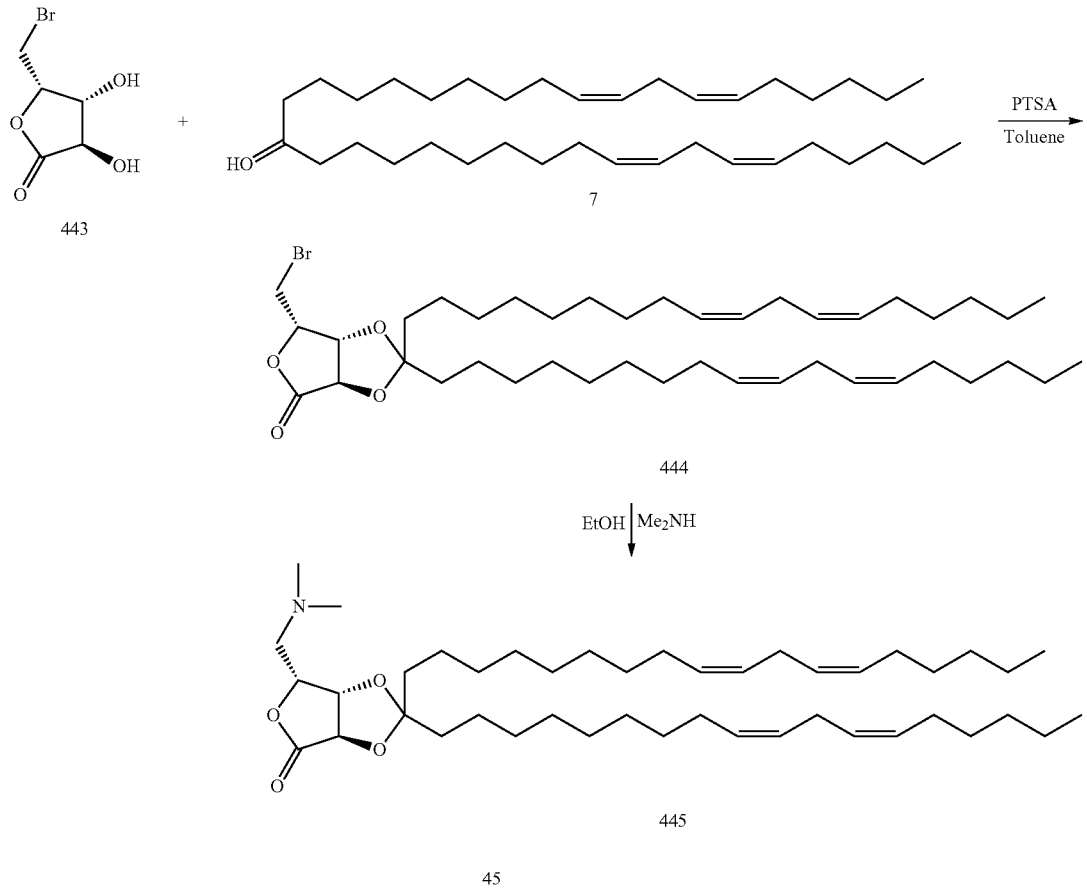

Preparation of 440

To a mixture of 439 (10 g, 67.53 mmol) and ketone 404 (18 g, 34 mmol) in anhydrous toluene (200 mL), is added PTSA (1.17 g, 0.2 eq) and heated to reflux at 130° C. bath using dean stark apparatus for 24 hr. Cool the reaction mixture to room temperature and wash with sodium bicarbonate solution. Crude product is purified by chromatography to get the product 440.

Preparation of 441

Compound 440 is treated with Methane sulfonylchloride in presence of triethylamine in dichloromethane to get 441.

Preparation of 443

Compound 443 is prepared according to the procedure described in Bouchez, Veronique; Stasik, Imane; Beaupere, Daniel; Uzan, Raoul; "Regioselective halogenation of pentono-1,4-lactones. Efficient synthesis of 5-chloro- and 5-bromo-5-deoxy derivatives", *Carbohydrate Research* (1997), 300(2), 139-142.

Preparation of 444

To a mixture of 443 (10 g, 47.39 mmol) and ketone 7 (13 g, 24 mmol) in anhydrous toluene (150 mL), is added PTSA (0.825 g, 0.2 eq) and heated to reflux at 130° C. bath using dean stark apparatus for 24 hr. Cool the reaction mixture to room temperature and wash with sodium bicarbonate solution. Crude product is purified by chromatography to get the product 444.

Preparation of 445

To a solution of 444 in EtOH, Dimethylamine in EtOH is added and heat the reaction mixture in a pressure reactor at 70° C. for overnight to get 445.

Example 51

Preparation of Compound 449

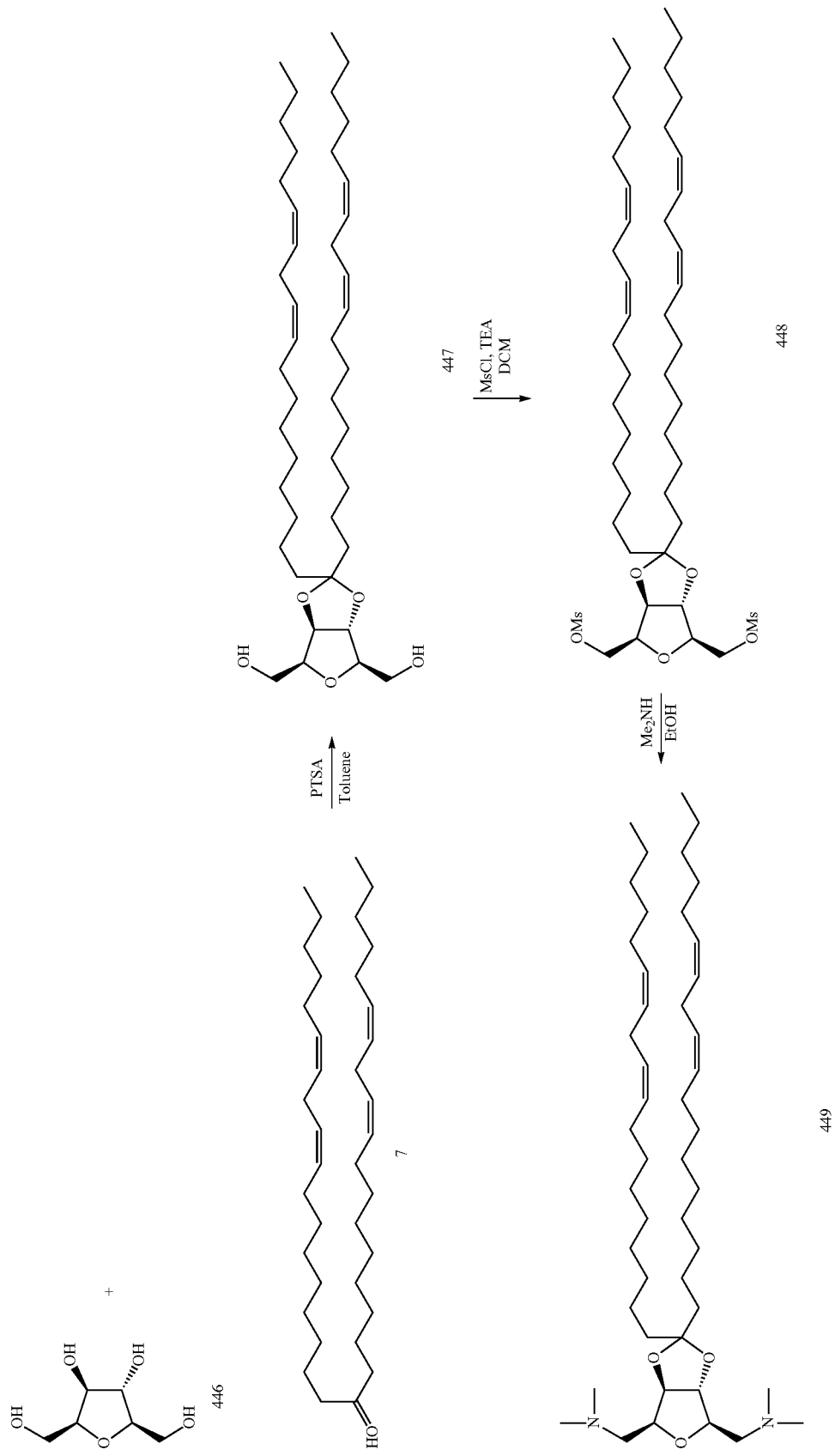

Preparation of 446

Compound 446 is prepared according to the procedure described in Persky, Rachel; Albeck, Amnon. "Synthesis of Selectively Labeled D-Fructose and D-Fructose Phosphate Analogues Locked in the Cyclic Furanose Form". *Journal of Organic Chemistry* (2000), 65(18), 5632-5638.

Preparation of 449

Compound 447 is prepared using the procedure described above. It is then convert to the corresponding dimesylate 448 using standard method. Diamination of the dimesylate is carried out using dimethylamine in EtOH to get the compound 449.

Example 52

Synthesis of Zwitterionic Lipids

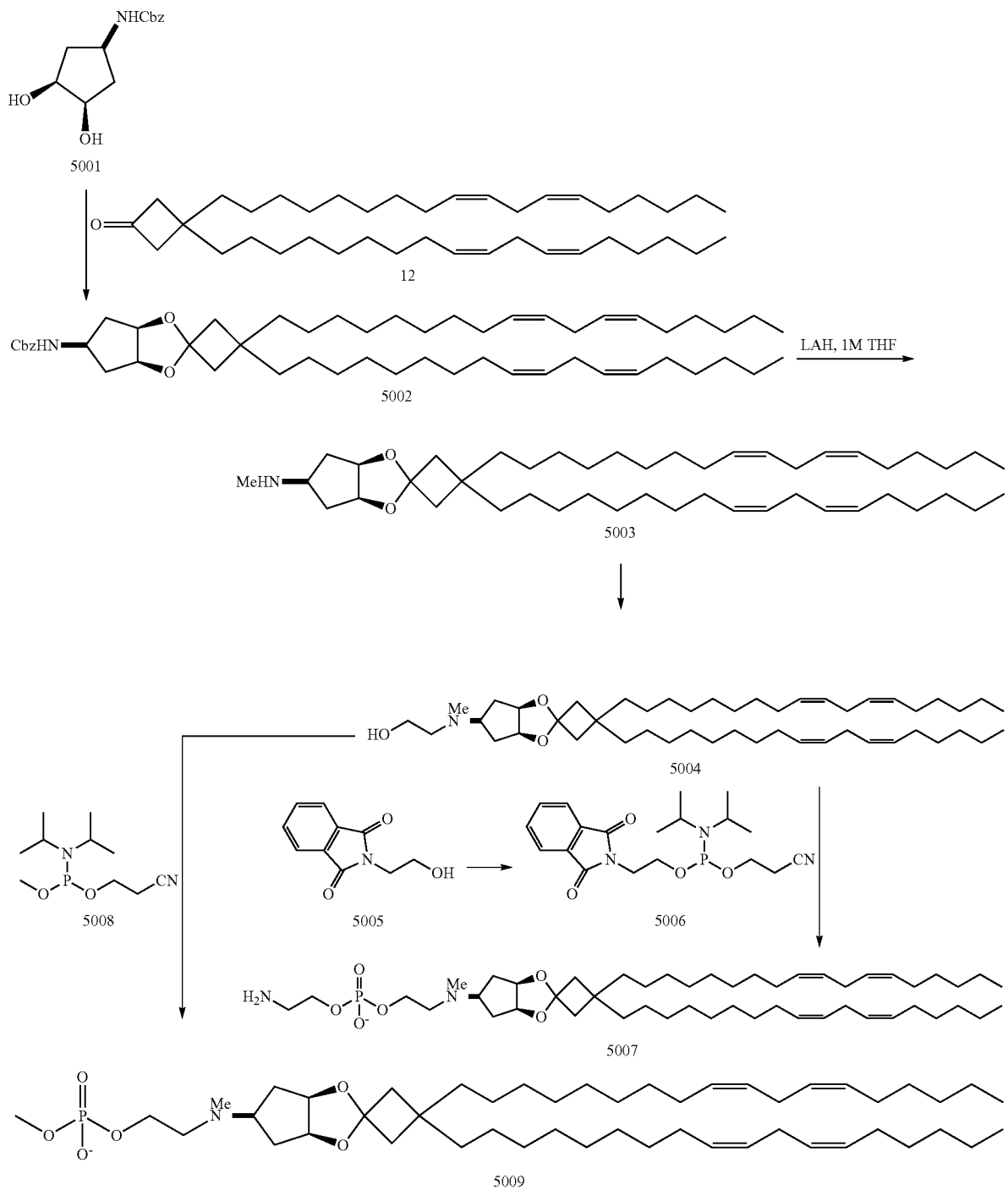

311
312
-continued
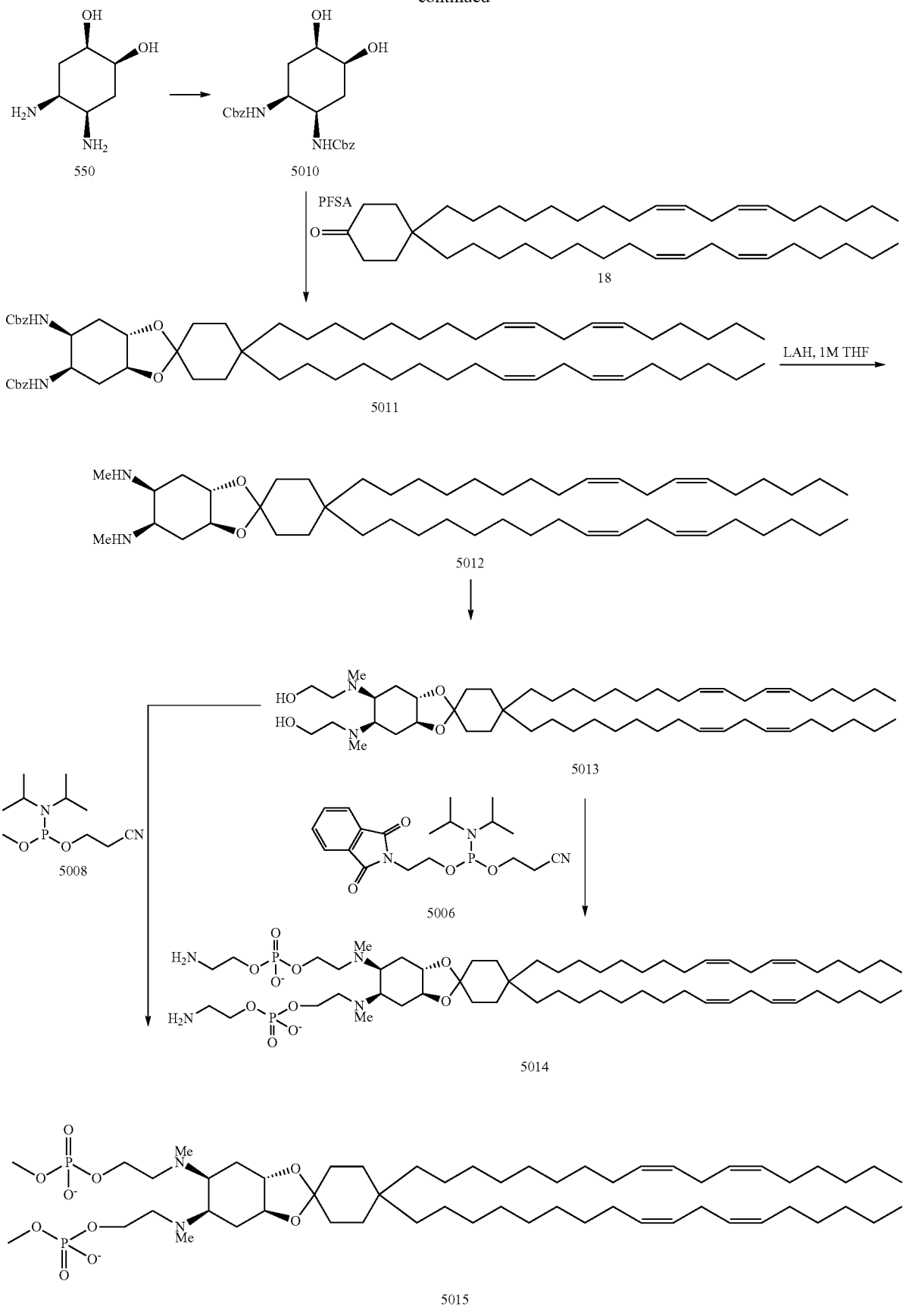

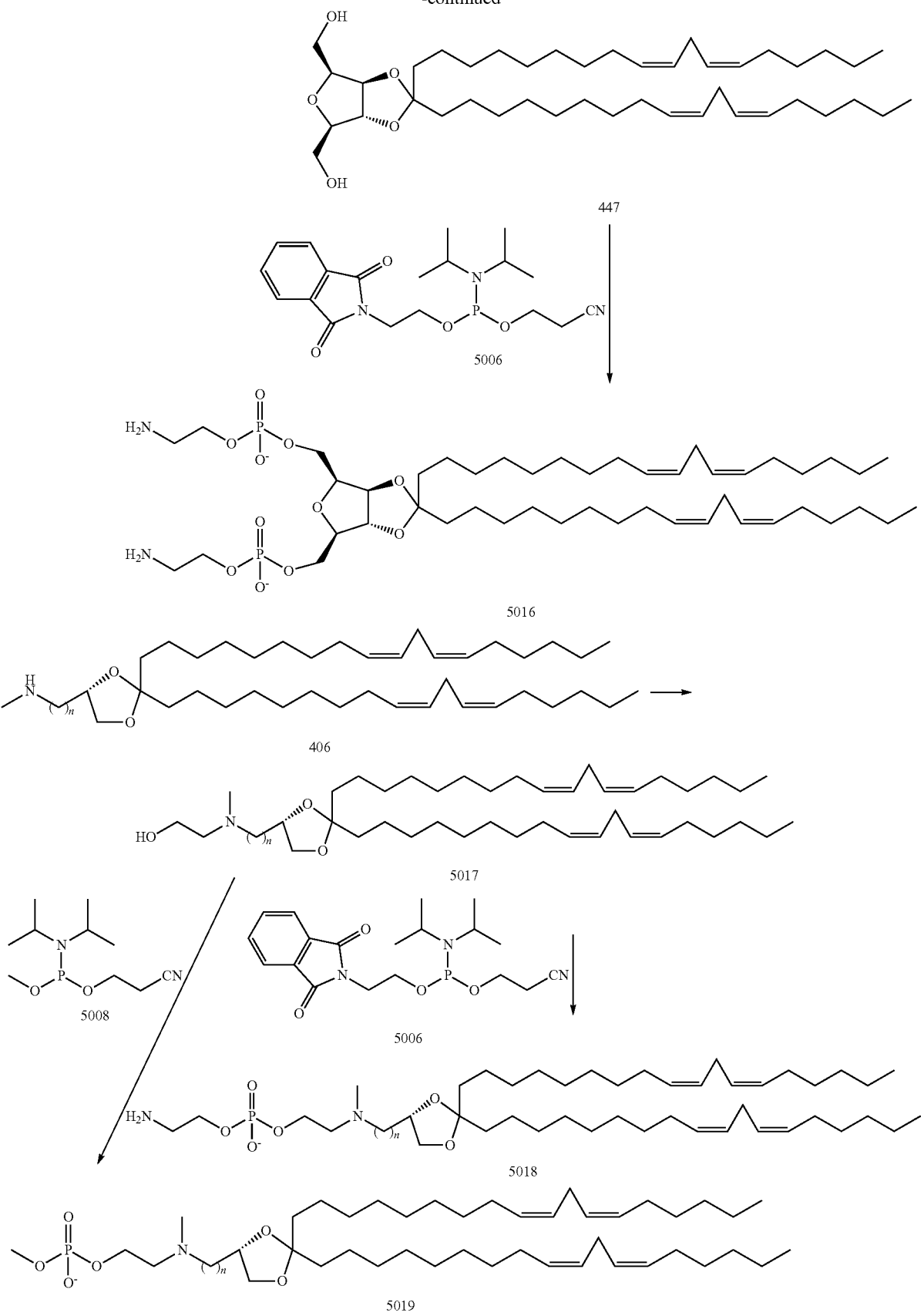

Example 53

Synthesis of Lipids Bearing Unsymmetric Lipid Anchors

Using a similar procedure used for the dilinoleyl ketone tail bearing cationic lipids, the unsymetric ketones 25, 27, 29, 31, 33 and 35 are all treated with the diols 517, 524, 528, 532, 536, 551, 554, 25 and 29 to isolate the product with the unsymmetrical chains are isolated.

Example 54

Oligonucleotide Synthesis

All oligonucleotides were synthesized on an AKTAoligopilot synthesizer. Commercially available controlled pore glass solid support (dT-CPG, 500 Å, Prime Synthesis) and RNA phosphoramidites with standard protecting groups, 5'-O-dimethoxytrityl N6-benzoyl-2'-t-butyldimethylsilyl-adenosine-3'-O—N,N'-diisopropyl-2-cyanoethylphosphoramidite, 5'-O-dimethoxytrityl-N4-acetyl-2'-t-butyldimethyl-silyl-cytidine-3'-O—N,N'-diisopropyl-2-cyanoethylphosphoramidite, 5'-O-dimethoxytrityl-N-2-isobutryl-2'-t-butyldimethylsilyl-guanosine-3'-O—N,N'-diisopropyl-2-cyanoethylphosphoramidite, and 5'-O-dimethoxytrityl-2'-t-butyldimethylsilyl-uridine-3'-O—N,N'-diisopropyl-2-cyanoethylphosphoramidite (Pierce Nucleic Acids Technologies) were used for the oligonucleotide synthesis. The 2'-F phosphoramidites, 5'-O-dimethoxytrityl-N4-acetyl-2'-fluoro-cytidine-3'-O—N,N'-diisopropyl-2-cyano-ethyl-phosphoramidite and 5'-O-dimethoxytrityl-2'-fluoro-uridine-3'-O—N,N'-diisopropyl-2-cyanoethyl-phosphoramidite were purchased from (Promega). All phosphoramidites were used at a concentration of 0.2M in acetonitrile ($CH_3CN$) except for guanosine which was used at 0.2M concentration in 10% THF/ANC (v/v). Coupling/recycling time of 16 minutes was used. The activator was 5-ethyl thiotetrazole (0.75M, American International Chemicals), for the PO-oxidation Iodine/Water/Pyridine was used and the PS-oxidation PADS (2%) in 2,6-lutidine/ACN (1:1 v/v) was used.

3'-ligand conjugated strands were synthesized using solid support containing the corresponding ligand. For example, the introduction of cholesterol unit in the sequence was performed from a hydroxyprolinol-cholesterol phosphoramidite. Cholesterol was tethered to trans-4-hydroxyprolinol via a 6-aminohexanoate linkage to obtain a hydroxyprolinol-cholesterol moiety. 5'-end Cy-3 and Cy-5.5 (fluorophore) labeled siRNAs were synthesized from the corresponding Quasar-570 (Cy-3) phosphoramidite were purchased from Biosearch Technologies. Conjugation of ligands to 5'-end and or internal position is achieved by using appropriately protected ligand-phosphoramidite building block An extended 15 min coupling of 0.1M solution of phosphoramidite in anhydrous $CH_3CN$ in the presence of 5-(ethylthio)-1H-tetrazole activator to a solid bound oligonucleotide. Oxidation of the internucleotide phosphite to the phosphate was carried out using standard iodine-water as reported (1) or by treatment with tert-butyl hydroperoxide/acetonitrile/water (10:87:3) with 10 min oxidation wait time conjugated oligonucleotide. Phosphorothioate was introduced by the oxidation of phosphite to phosphorothioate by using a sulfur transfer reagent such as DDTT (purchased from AM Chemicals), PADS and or Beaucage reagent The cholesterol phosphoramidite was synthesized in house, and used at a concentration of 0.1 M in dichloromethane. Coupling time for the cholesterol phosphoramidite was 16 minutes.

After completion of synthesis, the support was transferred to a 100 ml glass bottle (VWR). The oligonucleotide was cleaved from the support with simultaneous deprotection of base and phosphate groups with 80 mL of a mixture of ethanolic ammonia [ammonia:ethanol (3:1)] for 6.5 h at 55° C. The bottle was cooled briefly on ice and then the ethanolic ammonia mixture was filtered into a new 250 ml bottle. The CPG was washed with 2×40 mL portions of ethanol/water (1:1 v/v). The volume of the mixture was then reduced to ~30 ml by roto-vap. The mixture was then frozen on dyince and dried under vacuum on a speed vac.

The dried residue was resuspended in 26 ml of triethylamine, triethylamine trihydrofluoride (TEA.3HF) or pyridine-HF and DMSO (3:4:6) and heated at 60° C. for 90 minutes to remove the tert-butyldimethylsilyl (TBDMS) groups at the 2' position. The reaction was then quenched with 50 ml of 20 mM sodium acetate and pH adjusted to 6.5, and stored in freezer until purification.

The oligoncuelotides were analyzed by high-performance liquid chromatography (HPLC) prior to purification and selection of buffer and column depends on nature of the sequence and or conjugated ligand.

The ligand conjugated oligonucleotides were purified reverse phase preparative HPLC. The unconjugated oligonucleotides were purified by anion-exchange HPLC on a TSK gel column packed in house. The buffers were 20 mM sodium phosphate (pH 8.5) in 10% $CH_3CN$ (buffer A) and 20 mM sodium phosphate (pH 8.5) in 10% $CH_3CN$, 1M NaBr (buffer B). Fractions containing full-length oligonucleotides were pooled, desalted, and lyophilized. Approximately 0.15 OD of desalted oligonucleotidess were diluted in water to 150 μl and then pipetted in special vials for CGE and LC/MS analysis. Compounds were finally analyzed by LC-ESMS and CGE.

For the preparation of siRNA, equimolar amounts of sense and antisense strand were heated in 1×PBS at 95° C. for 5 min and slowly cooled to room temperature. Integrity of the duplex was confirmed by HPLC analysis

TABLE 7

| siRNA duplexes for Luc and FVII targeting. | | | | |
|---|---|---|---|---|
| Duplex | Sense/Antisense | Sequence 5'-3' | SEQ ID NO: | Target |
| | 1000/2434 | CUU ACG CUG AGU ACU UCG AdTdT<br>U*CG AAG fUAC UCA GCG fUAA GdT*dT | NO: 58.<br>NO: 59. | Luc |
| | 2433/1001 | C*UfU ACG CUG AGfU ACU UCG AdT*dT<br>UCG AAG UAC UCA GCG UAA GdTdT | NO: 60.<br>NO: 61. | Luc |
| | 2433/2434 | C*UfU ACG CUG AGfU ACU UCG AdT*dT<br>U*CG AAG fUAC UCA GCG fUAA GdT*dT | NO: 63<br>NO: 62 | Luc |

TABLE 7 -continued siRNA duplexes for Luc and FVII targeting.

| Duplex | Sense/Antisense | Sequence 5'-3' | SEQ ID NO: | Target |
|---|---|---|---|---|
|  | 1000/1001 | CUU ACG CUG AGU ACU UCG AdTdT | NO: 61 | Luc |
|  |  | UCG AAG UAC UCA GCG UAA GdTdT | NO: 64 |  |
| AD-1596 |  | GGAUCAUCUCAAGUCUUACdTdT | NO: 62 | FVII |
|  |  | GUAAGACUUGAGAUGAUCCdTdT | NO: 63. |  |
| AD-1661 |  | GGAfUfCAfUfCfUfCAAGfUfCfUfUAfCdTsdT | NO: 64. | FVII |
|  |  | GfUAAGAfCfUfUGAGAfUGAfUfCfCdT*dT | NO: 65. |  |

Note:
L8 is

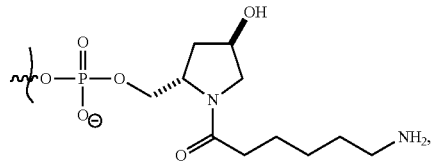

lowercase is 2'-O-methyl modified nucleotide,
* is phosphorothioate backbone linkages,
fN is a 2'-fluoro nucleotide,
dN is 2'-deoxy nucleotide.

Example 55

Serum Stability Assay for siRNA

A medium throughput assay for initial sequence-based stability selection was performed by the "stains all" approach. To perform the assay, an siRNA duplex was incubated in 90% human serum at 37° C. Samples of the reaction mix were quenched at various time points (at 0 min., 15, 30, 60, 120, and 240 min) and subjected to electrophoretic analysis (FIG. 1). Cleavage of the RNA over the time course provided information regarding the susceptibility of the siRNA duplex to serum nuclease degradation.

A radiolabeled dsRNA and serum stability assay was used to further characterize siRNA cleavage events. First, a siRNA duplex was 5' end-labeled with $^{32}P$ on either the sense or antisense strand. The labeled siRNA duplex was incubated with 90% human serum at 37° C., and a sample of the solution was removed and quenched at increasing time points. The samples were analyzed by electrophoresis.

Example 56

FVII In Vivo Evaluation Using the Cationic Lipid Derived Liposomes In Vivo Rodent Factor VII and ApoB Silencing Experiments C57BL/6 mice (Charles River Labs, MA) and Sprague-Dawley rats (Charles River Labs, MA) received either saline or siRNA in desired formulations via tail vein injection at a volume of 0.01 mL/g. At various time points post-administration, animals were anesthesized by isofluorane inhalation and blood was collected into serum separator tubes by retro orbital bleed. Serum levels of Factor VII protein were determined in samples using a chromogenic assay (Coaset Factor VII, DiaPharma Group, OH or Biophen FVII, Aniara Corporation, OH) according to manufacturer protocols. A standard curve was generated using serum collected from saline treated animals. In experiments where liver mRNA levels were assessed, at various time points post-administration, animals were sacrificed and livers were harvested and snap frozen in liquid nitrogen. Frozen liver tissue was ground into powder. Tissue lysates were prepared and liver mRNA levels of Factor VII and apoB were determined using a branched DNA assay (QuantiGene Assay, Panomics, Calif.).

Example 57

In Vivo Evaluation of FVII siRNA 1661 Using Cyclic Cationic Lipids, 506, 512 and 519 Based Formulation The cyclic cationic lipids 506, 512 and 519-based formulations as described below were prepared, characterized and evaluated in vivo by FVII assay. Results show that lipid particles formed with 519 showed almost complete knockdown of FVII protein levels in vivo.

|  | 519/Chol/PEG-C14/DSPC 52:30:5:13 | 506/Chol/PEG-C14/DSPC 52:30:5:13 | 512/Chol/PEG-C14/DSPC 52:30:5:13 |
|---|---|---|---|
| Particle size before siRNA conjugation(nm) | 87.4 | 96.5 | 102 |
| PDI | 0.155 | 0.164 | 0.183 |
| Particle size final (nm) | 81 | 88 | 95.8 |
| PDI | 0.105 | 0.1206 | 0.119 |
| % Encapsulation, Ribogreen | 91.5 | 64 | 87.5 |

| 519/Chol/PEG-C14/DSPC | 506/Chol/PEG-C14/DSPC | 512/Chol/PEG-C14/DSPC |
| --- | --- | --- |
| 52:30:5:13 | 52:30:5:13 | 52:30:5:13 |
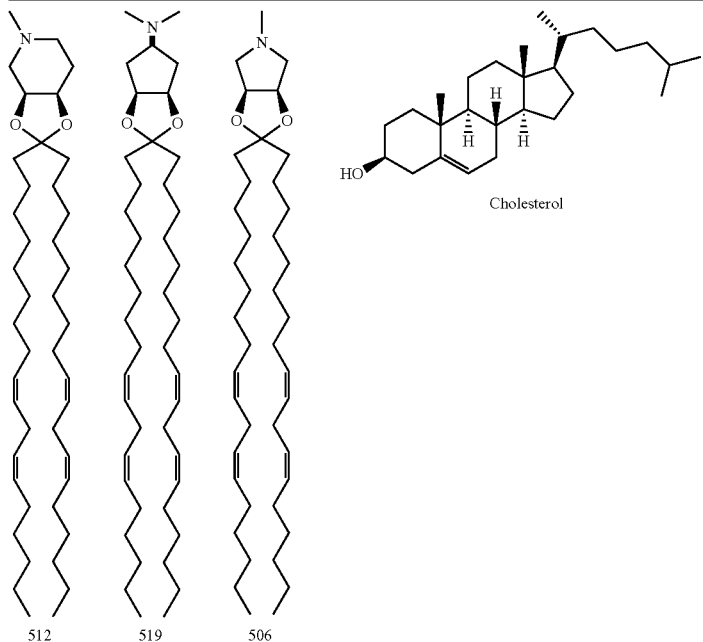
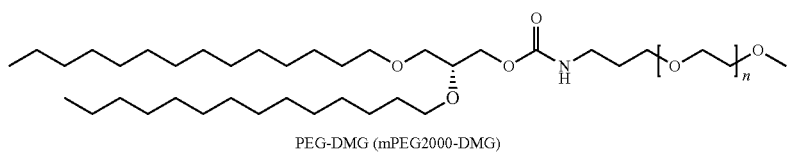
PEG-DMG (mPEG2000-DMG)
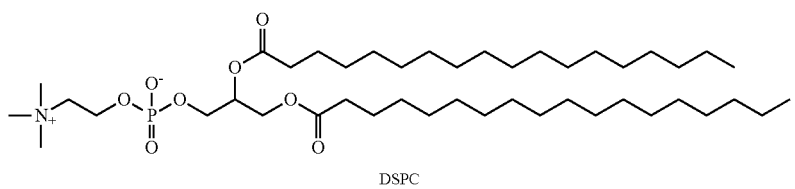
DSPC
Example 58
Liposome Formulations for FVII Targeting
The formulations shown above are made with DPPC in place of DSPC with varying amounts and the assays are repeated.
| 519/Chol/PEG-C14/DPPC | 512/Chol/PEG-C14/DPPC; | 506/Chol/PEG-14/DPPC; |
| --- | --- | --- |
| 52:30:5:13 | 52:30:5:13 | 52:30:5:13 |

-continued
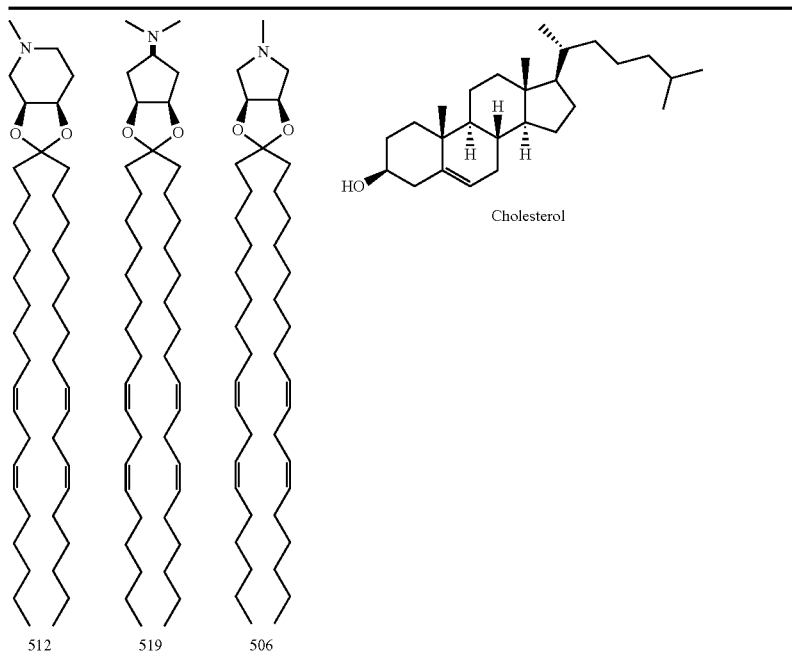
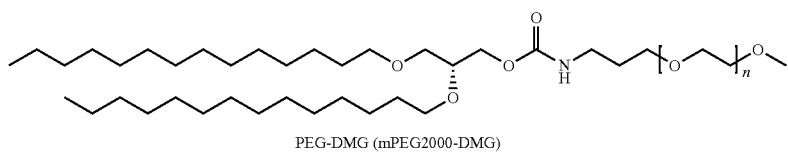
PEG-DMG (mPEG2000-DMG)
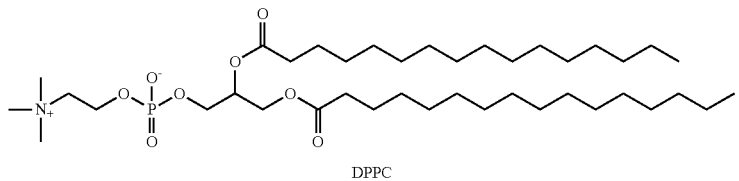
DPPC
Example 59
Preparation of 1,2-Di-O-alkyl-sn3-Carbomoylglyceride (PEG-DMG)
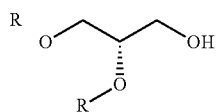
Ia R = $C_{14}H_{29}$
Ib R = $C_{16}H_{33}$
Ic R = $C_{18}H_{37}$
| DSC, TEA
| DCM
| 0° C.-RT
↓

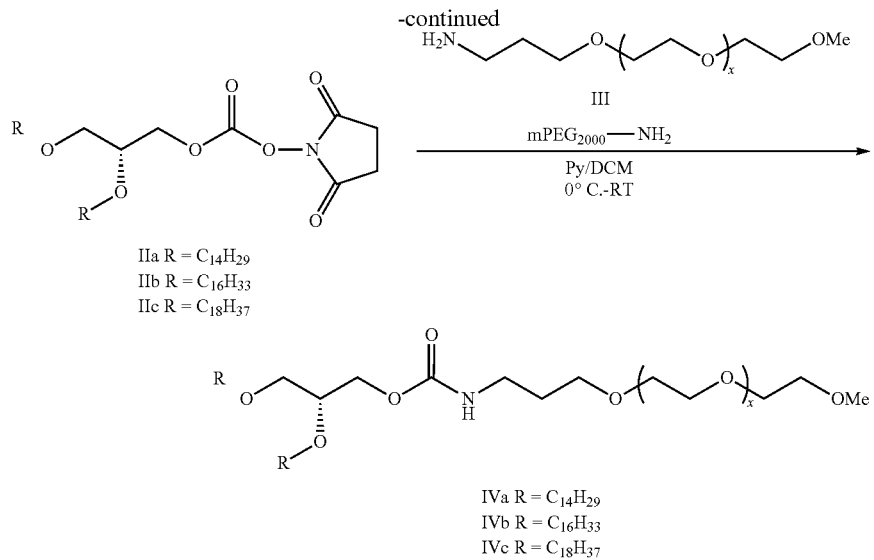

IIa R = C$_{14}$H$_{29}$
IIb R = C$_{16}$H$_{33}$
IIc R = C$_{18}$H$_{37}$

IVa R = C$_{14}$H$_{29}$
IVb R = C$_{16}$H$_{33}$
IVc R = C$_{18}$H$_{37}$

Preparation of IVa 1,2-Di-O-tetradecyl-sn-glyceride Ia (30 g, 61.80 mmol) and N,N'-succinimidylcarboante (DSC, 23.76 g, 1.5 eq) were taken in dichloromethane (DCM, 500 mL) and stirred over an ice water mixture. Triethylamine (TEA, 25.30 mL, 3 eq) was added to the stirring solution and subsequently the reaction mixture was allowed to stir overnight at ambient temperature. Progress of the reaction was monitored by TLC. The reaction mixture was diluted with DCM (400 mL) and the organic layer was washed with water (2×500 mL), aqueous NaHCO$_3$ solution (500 mL) followed by standard workup. The residue obtained was dried at ambient temperature under high vacuum overnight. After drying the crude carbonate IIa thus obtained was dissolved in dichloromethane (500 mL) and stirred over an ice bath. To the stirring solution mPEG$_{2000}$-NH$_2$ (III, 103.00 g, 47.20 mmol, purchased from NOF Corporation, Japan) and anhydrous pyridine (Py, 80 mL, excess) were added under argon. The reaction mixture was then allowed to stir at ambient temperature overnight. Solvents and volatiles were removed under vacuum and the residue was dissolved in DCM (200 mL) and charged on a column of silica gel packed in ethyl acetate. The column was initially eluted with ethyl acetate and subsequently with gradient of 5-10% methanol in dichloromethane to afford the desired PEG-Lipid IVa as a white solid (105.30 g, 83%). $^1$H NMR (CDCl$_3$, 400 MHz)=5.20-5.12 (m, 1H), 4.18-4.01 (m, 2H), 3.80-3.70 (m, 2H), 3.70-3.20 (m, —O—CH$_2$—CH$_2$—O—, PEG-CH$_2$), 2.10-2.01 (m, 2H), 1.70-1.60 (m, 2H), 1.56-1.45 (m, 4H), 1.31-1.15 (m, 48H), 0.84 (t, J=6.5 Hz, 6H). MS range found: 2660-2836.

Preparation of IVb 1,2-Di-O-hexadecyl-sn-glyceride Ib (1.00 g, 1.848 mmol) and DSC (0.710 g, 1.5 eq) were taken together in dichloromethane (20 mL) and cooled down to 0° C. in an ice water mixture. Triethylamine (1.00 mL, 3 eq) was added and the reaction was stirred overnight. The reaction was followed by TLC, diluted with DCM, washed with water (2 times), NaHCO$_3$ solution and dried over sodium sulfate. Solvents were removed under reduced pressure and the resulting residue of IIb was maintained under high vacuum overnight. This compound was directly used for the next reaction without further purification. MPEG$_{2000}$-NH$_2$ III (1.50 g, 0.687 mmol, purchased from NOF Corporation, Japan) and IIb (0.702 g, 1.5 eq) were dissolved in dichloromethane (20 mL) under argon. The reaction was cooled to 0° C. Pyridine (1 mL, excess) was added and the reaction stirred overnight. The reaction was monitored by TLC. Solvents and volatiles were removed under vacuum and the residue was purified by chromatography (first ethyl acetate followed by 5-10% MeOH/DCM as a gradient elution) to obtain the required compound IVb as a white solid (1.46 g, 76%). $^1$H NMR (CDCl$_3$, 400 MHz) δ=5.17 (t, J=5.5 Hz, 1H), 4.13 (dd, J=4.00 Hz, 11.00 Hz, 1H), 4.05 (dd, J=5.00 Hz, 11.00 Hz, 1H), 3.82-3.75 (m, 2H), 3.70-3.20 (m, —O—CH$_2$—CH$_2$—O—, PEG-CH$_2$), 2.05-1.90 (m, 2H), 1.80-1.70 (m, 2H), 1.61-1.45 (m, 6H), 1.35-1.17 (m, 56H), 0.85 (t, J=6.5 Hz, 6H). MS range found: 2716-2892.

Preparation of IVc 1,2-Di-O-octadecyl-sn-glyceride Ic (4.00 g, 6.70 mmol) and DSC (2.58 g, 1.5 eq) were taken together in dichloromethane (60 mL) and cooled down to 0° C. in an ice water mixture. Triethylamine (2.75 mL, 3 eq) was added and the reaction was stirred overnight. The reaction was followed by TLC, diluted with DCM, washed with water (2 times), NaHCO$_3$ solution, and dried over sodium sulfate. Solvents were removed under reduced pressure and the residue was maintained under high vacuum overnight. This compound was directly used for the next reaction without further purification. MPEG$_{2000}$-NH$_2$ III (1.50 g, 0.687 mmol, purchased from NOF Corporation, Japan) and IIc (0.760 g, 1.5 eq) were dissolved in dichloromethane (20 mL) under argon. The reaction was cooled to 0° C. Pyridine (1 mL, excess) was added and the reaction was stirred overnight. The reaction was monitored by TLC. Solvents and volatiles were removed under vacuum and the residue was purified by chromatography (ethyl acetate followed by 5-10% MeOH/DCM as a gradient elution) to obtain the desired compound IVc as a white solid (0.92 g, 48%). $^1$H NMR (CDCl$_3$, 400 MHz) δ=5.22-5.15 (m, 1H), 4.16 (dd, J=4.00 Hz, 11.00 Hz, 1H), 4.06 (dd, J=5.00 Hz, 11.00 Hz, 1H), 3.81-3.75 (m, 2H), 3.70-3.20 (m, —O—CH$_2$—CH$_2$—O—, PEG-CH$_2$), 1.80-1.70 (m, 2H), 1.60-1.48 (m, 4H), 1.31-1.15 (m, 64H), 0.85 (t, J=6.5 Hz, 6H). MS range found: 2774-2948.

Example 60

Preparation of Compound 563 (ALNY-106)

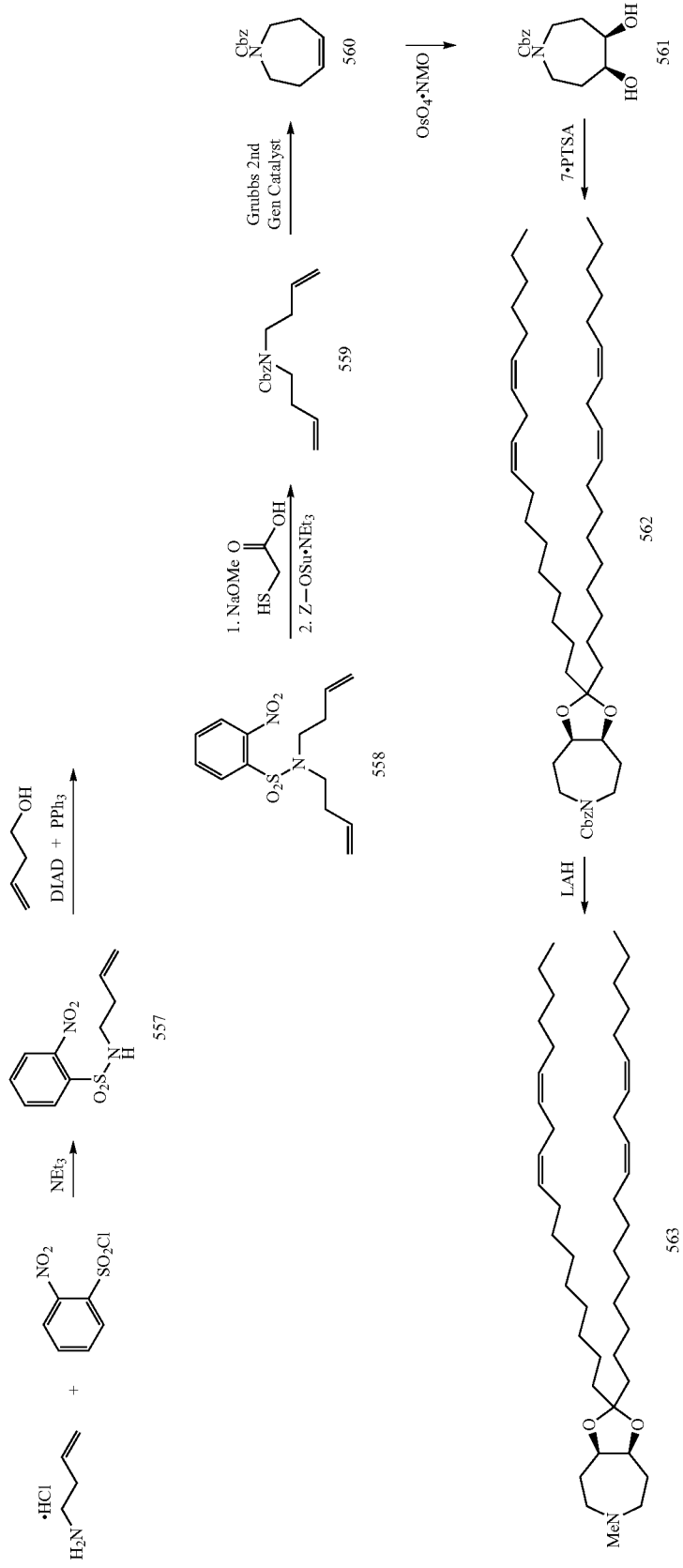

Preparation of Compound 557

An ice cold solution of but-3-en-1-amine hydrochloride (5 g, 46.5 mmol) and NEt$_3$ (2.4 eq) in DCM (300 mL) was treated dropwise with compound 2-Nos-Cl (1.1 eq) in DCM (120 mL) then warmed to r.t. After 2 h, aqueous workup then column chromatography gave compound 557 (11.6 g, 97%). $^1$H NMR (CDCl$_3$, 400 MHz) δ=8.22-8.06 (m, 1H), 7.87 (dt, J=6.5, 3.0, 1H), 7.81-7.64 (m, 2H), 5.65 (ddt, J=17.1, 10.3, 6.9, 1H), 5.32 (d, J=17.6, 1H), 5.13-4.96 (m, 2H), 3.19 (q, J=6.5, 2H), 2.28 (q, J=6.7, 2H); Electrospray MS (+ve): Molecular weight for C10H12N2O4S (M+H)$^+$ Calc. 257.1. Found 257.0.

Preparation of Compound 558

An ice-cold solution of but-3-en-1-ol (3.6 g, 50 mmol) and PPh$_3$ (1.2 eq) in DCM (400 mL) was treated dropwise over 15 min with DIAD (1.1 eq). After a further 5 min, a solution of compound 557 (11.6 g, mmol) in DCM (60 mL) was added dropwise over 10 min and the resulting solution was allowed to warm to r.t. The solvent was removed. Column chromatography gave pure compound 558 (13.1 g, 93%). $^1$H NMR (400 MHz, CDCl$_3$) δ 8.11-7.93 (m, 1H), 7.68 (pd, J=7.4, 3.8, 2H), 7.64-7.58 (m, 1H), 5.69 (ddt, J=17.1, 10.2, 6.8, 2H), 5.06 (dd, J=17.2, 1.5, 2H), 5.02 (d, J=10.2, 2H), 3.48-3.30 (m, 4H), 2.30 (dd, J=14.9, 7.1, 4H); Electrospray MS (+ve): Molecular weight for C14H18N2O4S (M+H)$^+$ Calc. 311.1. Found 311.0.

Preparation of Compound 559

A heated (50° C.) solution of 558 (3 g, 9.66 mmol) in ACN (100 mL) was treated successively with thioglycolic acid (3 eq) and NaOMe (25 w/w % solution in MeOH, 6 eq). Heating was continued for 1 h, then cooled to r.t. Aqueous workup gave the crude deprotected secondary amine which used without purification and subjected to Cbz protection by reaction with Cbz-OSu (1.5 eq) in the presence of NEt$_3$ (2 eq) at r.t. overnight. Aqueous workup then column chromatography gave compound 559 (1.65 g, 66%). $^1$H NMR (400 MHz, CDCl$_3$) δ $^1$H NMR (400 MHz, DMSO) δ 7.44-7.23 (m, 5H), 5.85-5.62 (m, 2H), 5.09-4.90 (m, 6H), 3.26 (t, J=7.2, 4H), 2.23 (q, J=6.6, 4H); Electrospray MS (+ve): Molecular weight for C16H21NO2 (M+H)$^+$ Calc. 260.2. Found 260.0.

Preparation of Compound 560

A DCM solution of compound 559 (1.65 g, 6.36 mmol) was treated with Grubbs second generation catalyst (1 mol %) at r.t. for 18 h. Column chromatography gave compound 560 (1.29 g, 88%). $^1$H NMR (400 MHz, CDCl$_3$) δ 7.44-7.13 (m, 5H), 5.73 (q, J=3.6, 2H), 5.15 (s, 2H), 3.63-3.43 (m, 4H), 2.31 (dd, J=19.2, 4.2, 4H); Electrospray MS (+ve): Molecular weight for C14H17NO2 (M+H)$^+$ Calc. 232.1. Found 232.0.

Preparation of Compound 561

A solution of compound 560 (1.29 g, 5.58 mmol) in acetone (10 mL) was added in a dropwise fashion to a stirring aqueous solution (10 mL) of NMO (1.5 eq) and OsO$_4$ (1 mol %). After 18 h at r.t., TLC indicated a complete reaction. The solvent was removed. Aqueous workup then column chromatography gave pure compound 561 (1.28 g, 86%). $^1$H NMR (400 MHz, DMSO) δ 7.48-7.25 (m, 5H), 5.09 (s, 2H), 4.56 (d, J=4.2, 2H), 3.67 (d, J=3.5, 2H), 3.45 (ddd, J=14.3, 7.4, 3.7, 2H), 3.40-3.18 (m, 2H), 1.86 (dtd, J=11.5, 7.4, 3.7, 2H), 1.70-1.49 (m, 2H); Electrospray MS (+ve): Molecular weight for C14H19NO4 (M+H)$^+$ Calc. 266.1. Found 266.0.

Preparation of Compound 562

A solution of dilinoleyl ketone (1.05 eq), PTSA (0.1 eq) and compound 561 (1.28 g, 4.82 mmol) in toluene (200 mL) was brought to reflux for 2 h. Removal of solvent then column chromatography gave pure compound 562 (1.44 g, 39%). $^1$H NMR (400 MHz, CDCl$_3$) δ 7.49-7.14 (m, 5H), 5.52-5.23 (m, 8H), 5.13 (s, 2H), 4.39 (s, 2H), 3.75-3.53 (m, 2H), 3.44 (dd, J=14.3, 9.3, 2H), 2.77 (t, J=6.4, 4H), 2.05 (dd, J=13.6, 6.7, 10H), 1.80 (s, 2H), 1.69 (dd, J=10.2, 6.1, 2H), 1.66-1.51 (m, 2H), 1.51-1.09 (m, 36H), 0.89 (t, J=6.8, 6H); $^{13}$C NMR (101 MHz, CDCl$_3$) δ 155.64, 136.89, 130.17, 130.16, 130.13, 130.09, 128.45, 127.96, 127.92, 127.89, 127.78, 110.14, 76.14, 67.08, 42.41, 41.99, 36.54, 34.95, 32.93, 32.48, 31.51, 29.97, 29.93, 29.65, 29.54, 29.46, 29.34, 29.29, 27.22, 27.21, 27.18, 25.61, 24.53, 23.64, 22.56, 14.07; Electrospray MS (+ve): Molecular weight for C51H83NO4 (M+Na)$^+$ Calc. 796.6. Found 796.4.

Preparation of Compound 563

A solution of compound 562 (1.4 g, 1.8 mmol) in hexane (20 mL) was added in a dropwise fashion over 10 min to an ice-cold solution of LAH in THF (1 M, 3.6 mL, 2 eq). On complete addition, the mixture was heated at 40° C. over 0.5 h then ice-cooled again. Aqueous workup then column chromatography gave compound 4 (1.04 g, 88%) as a colorless oil. $^1$H NMR (400 MHz, CDCl$_3$) δ 5.48-5.23 (m, 8H), 4.43-4.24 (m, 2H), 2.85-2.64 (m, 6H), 2.30 (s, 3H), 2.27-2.17 (m, 2H), 2.04 (q, J=6.6, 8H), 2.00-1.84 (m, 4H), 1.65 (dd, J=10.1, 6.0, 2H), 1.60-1.49 (m, 2H), 1.47-1.16 (m, 36H), 0.88 (t, J=6.8, 6H); $^{13}$C NMR (101 MHz, CDCl$_3$) δ 130.39, 130.34, 128.16, 128.12, 111.09, 53.90, 47.34, 36.84, 36.30, 31.74, 31.25, 30.23, 30.12, 29.90, 29.88, 29.86, 29.79, 29.74, 29.70, 29.57, 29.55, 29.52, 27.47, 27.44, 27.41, 25.84, 24.72, 23.63, 22.79, 14.30; Electrospray MS (+ve): Molecular weight for C44H79NO2 (M+Na)$^+$ Calc. 654.6. Found 654.4.

Example 61
Preparation of Compounds 571 and 573 (ALNY-121 and ALNY-122)

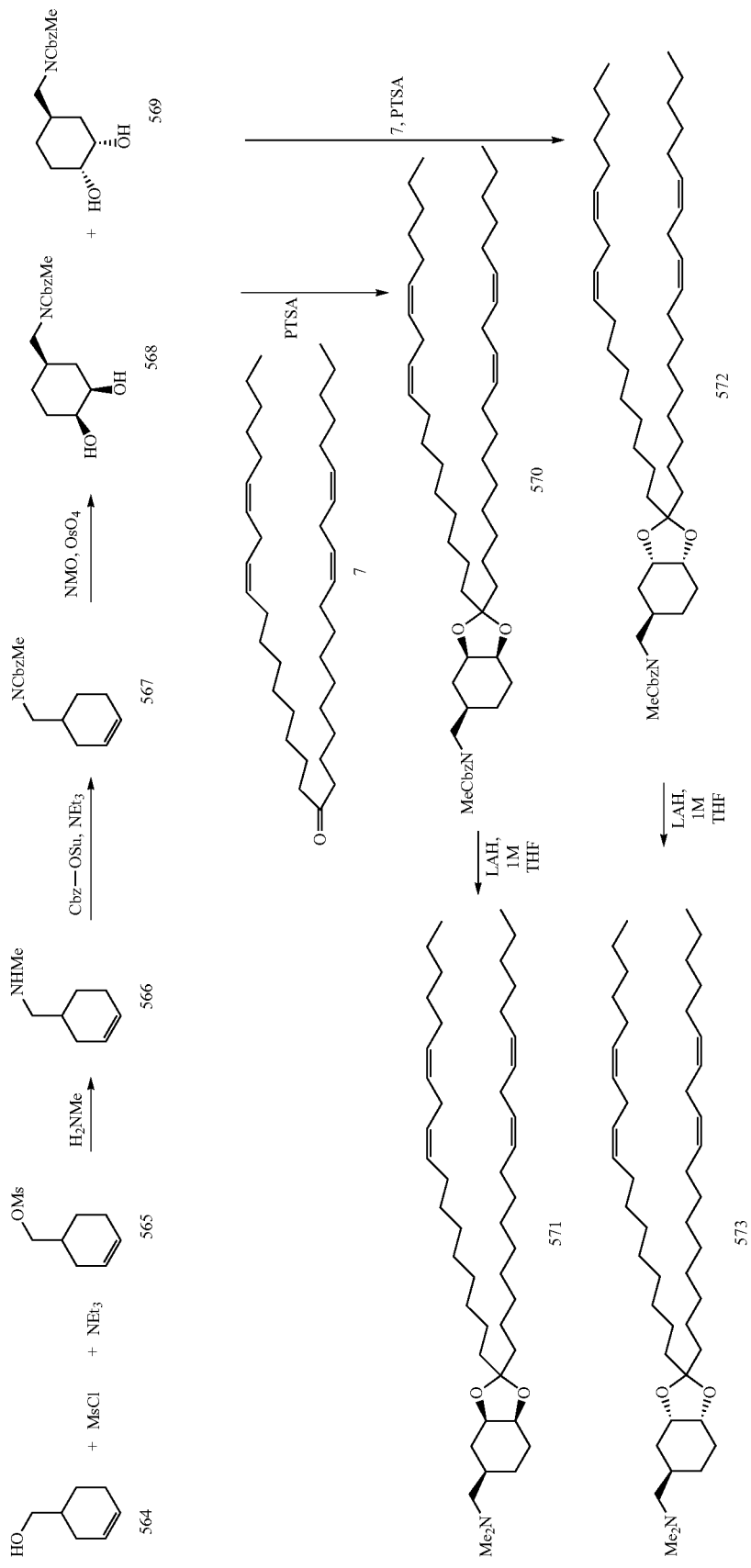

Preparation of Compound 567

An ice-cold solution of compound 564 (5.56 g, 49.6 mmol) and NEt$_3$ (1.2 eq) in DCM (300 mL) was treated in a dropwise fashion over 5 min with MsCl (1.1 eq). After 1 h at 0° C., aqueous workup gave crude compound 565 (pure by TLC) which was used without purification in the next step.

Compound 565 (49.6 mmol) was treated with 33% H$_2$NMe in EtOH (100 mL) over 72 h. Excess H$_2$NMe was removed by co-evaporation with Et$_2$O, then the ethanolic solution of compound 566 was treated with conc. HCl (2 eq). The EtOH was removed by evaporation and the residue was redissolved in DCM (100 mL). NEt$_3$ (6 eq) was added followed by Cbz-OSu (2 eq) and the mixture was stirred at r.t. for 3 h. Aqueous workup then column chromatography gave pure compound 568 as an oil (11.3 g, 88% from 564). $^1$H NMR (400 MHz, CDCl$_3$) δ 7.49-6.97 (m, 5H), 5.66 (s, 2H), 5.13 (s, 2H), 3.21 (t, J=8.1, 2H), 2.94 (d, J=2.8, 3H), 2.30-1.82 (m, 4H), 1.82-1.53 (m, 2H), 1.37-0.97 (m, 1H).

Preparation of Compound 568 and 569

Using a procedure which is analogous to those described for the synthesis of compounds 504, a mixture of 568 and 569 was obtained. This mixture was then separated by preparative HPLC to give both pure isomers.

Preparation of Compound 570 and 572

Using a procedure analogous to that described for the synthesis of compound 505, compounds 570 and 572 are obtained as colorless oils.

Preparation of Compound 571 and 573

Using a procedure analogous to that described for the synthesis of compound 506, compounds 571 and 573 are obtained as colorless oils.

Example 62

Preparation of Compound 581 and 583 (ALNY-115 & ALNY-116)

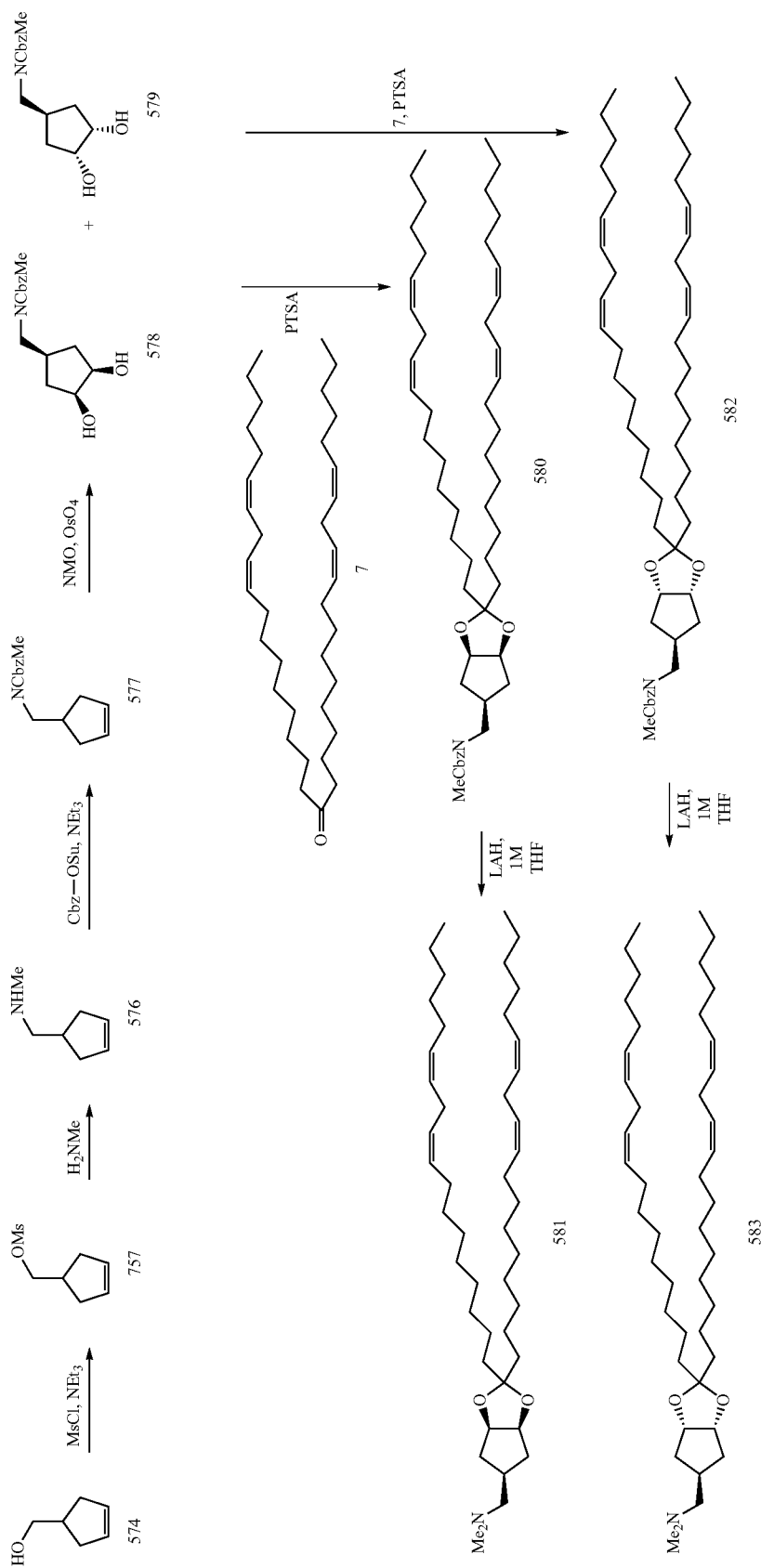

Preparation of Compound 577

An ice-cold solution of compound 574 (1.05 g, 10.7 mmol) and NEt$_3$ (1.2 eq) in DCM (50 mL) was treated in a dropwise fashion over 5 min with MsCl (1.1 eq). After 1 h at 0° C., aqueous workup gave crude compound 575 (1.88 g, 99%, pure by TLC) which was used without purification in the next step.

Compound 575 (10.5 mmol) was treated with 33% H$_2$NMe in EtOH (100 mL) at 50° C. over 18 h. Excess H$_2$NMe was removed by co-evaporation with Et$_2$O, then the ethanolic solution of compound 576 was treated with conc. HCl (2 eq). The EtOH was removed by evaporation and the residue was redissolved in DCM (100 mL). NEt$_3$ (4 eq) was added followed by Cbz-OSu (1.5 eq) and the mixture was stirred at r.t. for 3 h. Aqueous workup then column chromatography gave pure compound 577 as an oil (86% from 574). $^1$H NMR (400 MHz, CDCl$_3$) δ 7.54-7.04 (m, 5H), 5.65 (d, J=8.6, 2H), 5.13 (s, 2H), 3.27 (t, J=8.9, 2H), 2.94 (s, 3H), 2.60 (s, 1H), 2.51-2.28 (m, 2H), 2.04 (dd, J=22.1, 15.3, 2H); $^{13}$C NMR (101 MHz, CDCl$_3$) δ 129.47, 128.40, 127.83, 127.75, 66.92, 53.74, 53.13, 38.92, 36.34, 36.23, 36.06, 35.78; Electrospray MS (+ve): Molecular weight for C15H19NO2 (M+H)$^+$ Calc. 246.1. Found 246.0.

Preparation of Compound 578 and 579

Using a procedure which is analogous to those described for the synthesis of compounds 504, a mixture of 578 and 579 was obtained. This mixture was then separated by preparative HPLC to give both pure isomers.

Preparation of Compound 580 and 582

Using a procedure analogous to that described for the synthesis of compound 505, compounds 580 and 582 are obtained as colorless oils.

Preparation of Compound 581 and 583

Using a procedure analogous to that described for the synthesis of compound 506, compounds 581 and 583 are obtained as colorless oils.

Example 63

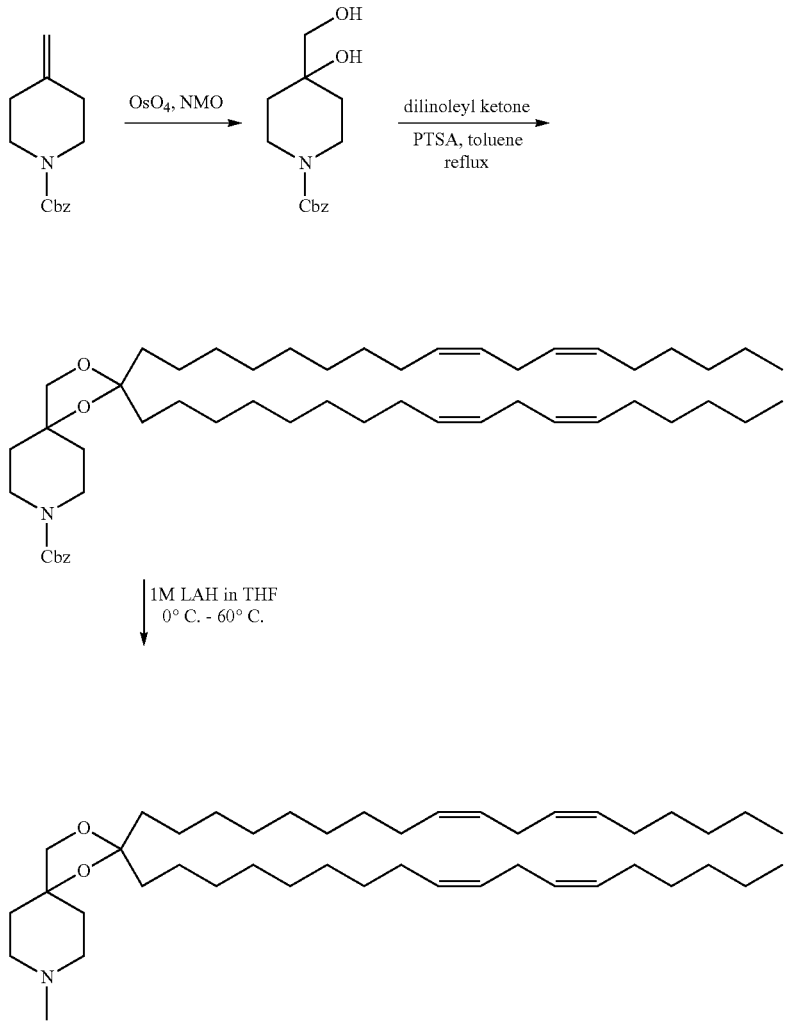

Example 64
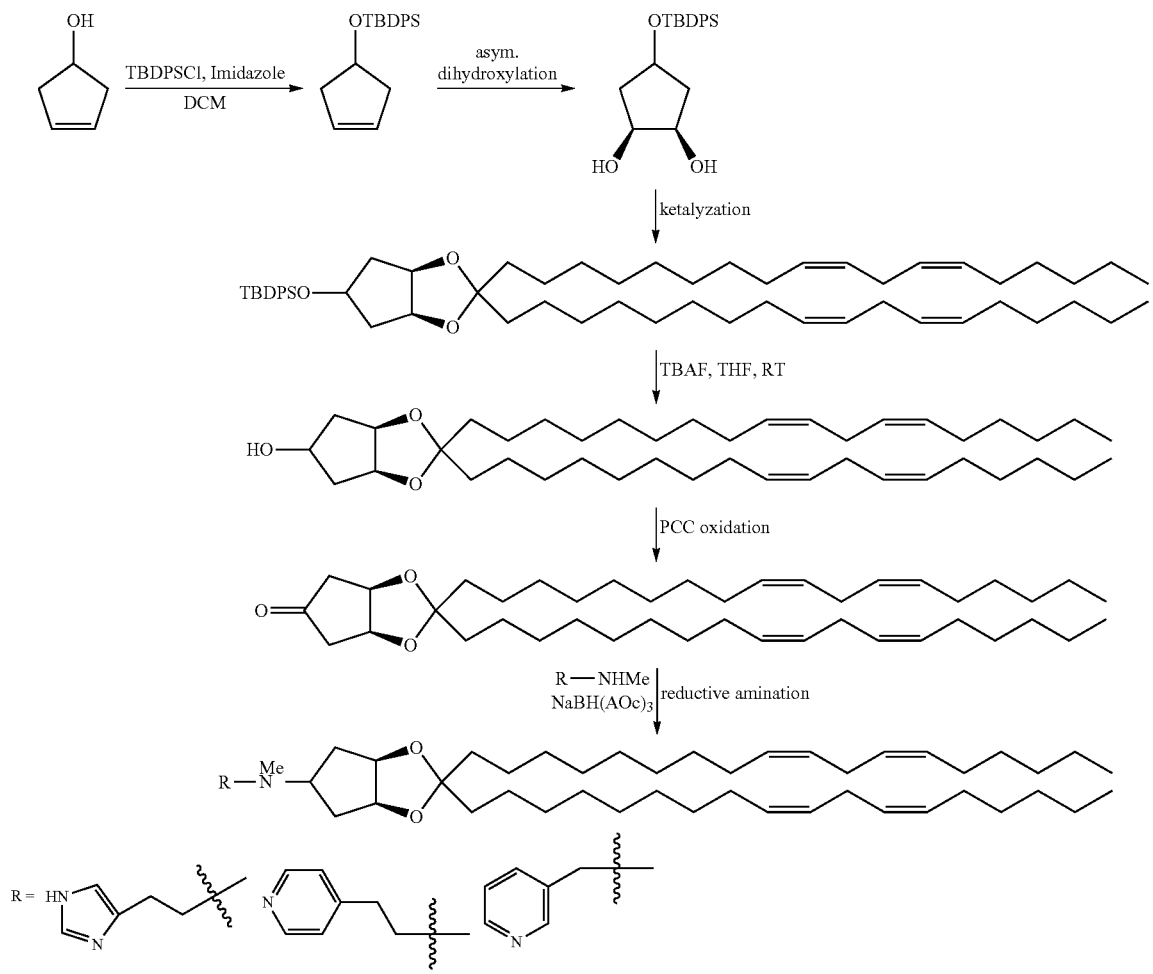
Example 65
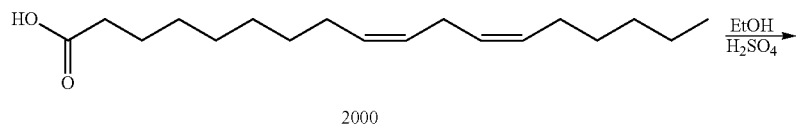
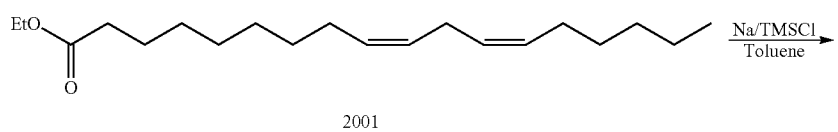
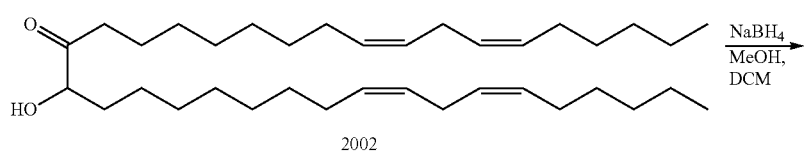

-continued

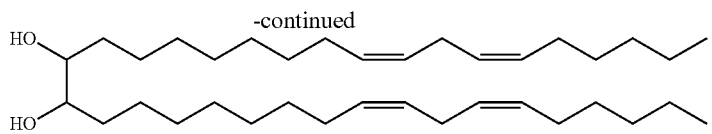

2003

Synthesis of 2001: To 500 ml of ethanol cooled below 0° C. using ice-salt mixture was added 10 ml of Conc. $H_2SO_4$ slowly. Linoleic acid (100 g, 357 mmol) in 500 ml of ethanol was added to the above solution slowly by maintaining the temperature below 0° C. After addition the reaction mass was warmed to RT and then refluxed for 5 hrs (TLC). It was then cooled to room temperature and neutralized by sat. $NaHCO_3$ solution. The resulting solution was concentrated to remove excess of solvent. The residue was diluted with water (1000 ml) and extracted with DCM (6×500 ml). The combined organic layer was washed with brine (1000 ml), and dried over sodium sulfate, filtered and evaporated at reduced pressure to obtain pure product (109.80 g, 99%) as a pale yellow liquid, which was taken as such for the next stage. $^1$H NMR ($CDCl_3$): δ 0.89 (t, 3H, J=6.8 Hz), 1.24-1.31 (m, 17H), 1.62 (m, 2H, J=10 Hz), 2.04 (q, 4H, $J_1$=6.8 Hz, $J_2$=6.8 Hz), 2.29 (t, 2H, J=7.6 Hz), 2.76 (t, 2H, J=6.4 Hz), 4.13 (q, 2H, $J_1$=7.2 Hz, $J_2$=7.2 Hz), 5.34 (m, 4H). $^{13}$C NMR ($CDCl_3$): δ 13.9, 14.1, 22.5, 24.9, 25.5, 27.1, 29.0, 29.1, 29.3, 29.5, 31.4, 34.2, 60.0, 127.8, 127.9, 129.9, 130.0, 173.6.

Synthesis of 2002: To 660 ml of freshly distilled toluene in a 2 L multineck RB flask fitted with reflux condenser under argon was added sodium pieces (41.1 g, 1.785 mol). To this was added TMSCl (192 mL, 1.499 mol) slowly and heated to 40° C. after addition. Then a solution of 2001 (110 g, 0.357 mol) in 275 ml of freshly distilled toluene was added slowly by maintaining the reaction temperature at 40° C. over a period of 1 hr. It was then refluxed for 2-3 hrs. After 3 hrs the reaction mass turned pale purple in color (TLC). Heating was stopped and the reaction mass was cooled to room temperature, filtered through a pad of celite and washed with toluene. (CAUTION: The reaction mixture contained unreacted sodium pieces). The filtrate obtained was stirred with 3 L of sat. $NH_4Cl$ solution for 15-20 minutes until the silyl ether converted to the required α-keto alcohol. The organic layer was separated and the aqueous layer was washed with ethyl acetate (3×1000 ml). The combined organic layer was washed with brine (1 L), dried over sodium sulfate, filtered and evaporated at reduced pressure to obtain the crude material, which was purified by silica gel chromatography using hexane/ethyl acetate as eluent. The product got eluted at 3% ethyl acetate in hexane to get 2002 (44 g, 47%) as a pale yellow liquid. $^1$H NMR (400 MHz, $CDCl_3$): δ 0.89 (t, 6H, J=7.2 Hz), 1.2-1.3 (m, 30H), 1.53 (m, 1H), 1.62 (m, 2H), 1.8 (m, 1H), 2.04 (q, 8H, $J_1$=6.8 Hz, $J_2$=6.8 Hz), 2.43 (m, 2H), 2.76 (t, 4H, J=6.4 Hz), 3.49 (d, 1H, J=4.8 Hz) 4.16 (m, 1H), 5.34 (m, 8H). $^{13}$C NMR (100 MHz, $CDCl_3$): δ 14.1, 22.6, 23.6, 24.8, 25.6, 27.2, 29.1, 29.2, 29.24, 29.3, 29.4, 29.56, 29.6, 31.5, 33.7, 37.8, 76.3, 127.8, 127.9, 129.9, 130.0, 212.4.

Synthesis of 2003: A solution of 2002 (44 g, 83 mol) in methanol/DCM mixture (490 mL, DCM was added to make the solution homogeneous) under argon was cooled below 0° C. using ice-salt mixture. Sodium borohydride (4.7 g, 125 mmol) was added in one lot to the reaction mass. The suspension was stirred for 2 hrs, and the mass temperature slowly raised to RT. After 2 hrs the reaction mass became homogeneous. TLC showed the absence of starting material. The reaction was quenched with 100 ml of water, and concentrated to remove excess solvent. The residue obtained was again diluted with water (500 ml), and extracted with DCM (4×500 ml). The combined organic layer was washed with brine (500 ml), dried over sodium sulfate, filtered and evaporated at reduced pressure to obtain the crude product, which was purified by silica gel chromatography using hexane/ethyl acetate as eluent. The product eluted from 4% to 20% of ethyl acetate in hexane to get 2003 (36 g, 82%) as a white semisolid. $^1$H NMR ($CDCl_3$): δ 0.89 (t, 6H, J=6.8 Hz), 1.2-1.5 (m, 36H), 1.78 (d, 1H, J=4 Hz), 1.95 (d, 1H, J=4 Hz), 2.04 (q, 8H, $J_1$=6.8 Hz, $J_2$=6.8 Hz), 2.77 (t, 4H, J=6.4 Hz), 3.40 (m, 1H), 3.61 (m, 1H), 5.34 (m, 8H). $^{13}$C NMR ($CDCl_3$): δ13.7, 22.2, 25.2, 25.3, 25.7, 26.8, 28.4, 28.9, 29.0, 29.1, 29.3, 30.8, 31.1, 33.2, 74.1, 74.3, 127.5, 127.6, 129.7, 129.8. MS: Molecular weight calculated for $C_{36}H_{66}O_2$ 530.51. Found: 531.52 (M+H).

Example 66

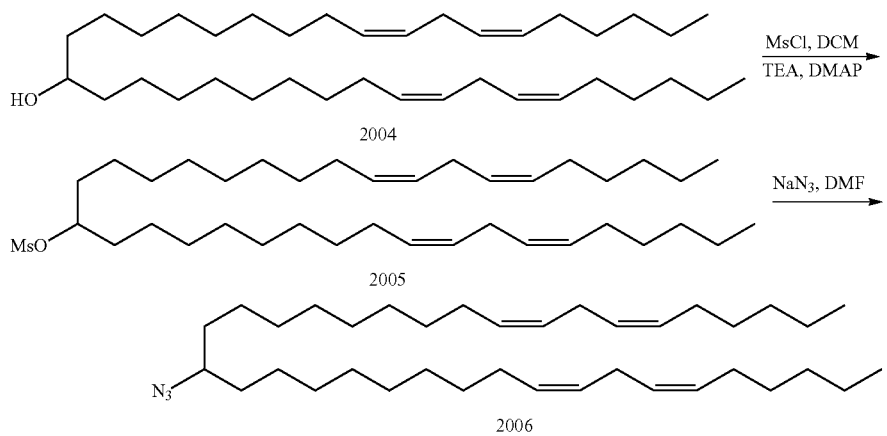

Synthesis of 2005: To a solution of 2004 (50 g, 95 mmol) in DCM (400 ml) under Ar atmosphere, was added TEA (53 mL, 378 mmol) and DMAP (1.2 g, 9.5 mmol) and stirred at room temperature under Ar atmosphere. Reaction mass was cooled to −5° C. and the solution of mesyl chloride (15 mL, 190 mmol) in DCM (100 ml) was added slowly at temperature below −5° C. and allowed to warm to RT after addition. After 30 minutes (TLC), reaction mass was quenched with ice cold water (20 ml). Organic layer was separated, washed with 1N HCl (30 ml), water, brine, dried over sodium sulfate and evaporated at reduced pressure to obtain pure product (55 g, 95.5%) as yellow liquid. 1H NMR (400 MHz, CDCl$_3$): δ 0.89 (t, 6H, J=6.8), 1.2-1.5 (m, 36H), 1.67 (m, 4H), 2.05 (q, 8H, J1=6.8, J2=6.8), 2.77 (t, 4H, J=6.4), 2.99 (s, 3H), 4.71 (m, 1H) and 5.36 (m, 8H).

Synthesis 2006: To a solution of 2005 (50 g, 82 mmol) in DMF (500 mL) under argon atmosphere, was added NaN$_3$ (27 g, 410 mmol) and heated to 70° C. and maintained the temperature for four hours (TLC). The mixture was diluted with water and extracted with ethyl acetate (3×250 ml). The organic layer was washed with water, brine, dried over Na$_2$SO$_4$ and evaporated at reduced pressure to give crude product, which was purified by silica gel chromatography using hexane/ether as eluent. The product was eluted at 2% ether hexane to get 2006 (36 g, 86%) as pale yellow liquid. $^1$H NMR (400 MHz, CDCl3): δ 0.90 (t, 8H), 1.30 (m, 36H), 1.49 (t, 4H, J=6.4 Hz) 2.04 (q, 8H, J1=7.6, J2=14 Hz), 2.77 (t, 4H, J=6.4 Hz), 3.22 (m, 1H), 5.34 (m, 8H). $^{13}$C NMR (400 MHz, CDCl$_3$): δ 14.1, 22.5, 25.6, 26.1, 27.2, 29.2, 29.3, 29.45, 29.65, 31.5, 34.1, 63.1, 127.9, and 130.1. IR (KBr): 2098.

Synthesis of 2007: To a solution of 2005 (76 g, 125 mmol) in dimethylformamide (500 mL), was added sodium hydrosulfide hydrate (35 g, 625 mmol) at room temperature. Reaction mixture was heated to 70° C. for 2 hrs (TLC). It was then cooled to room temperature and diluted with water (7V) and extracted with ether (3×5V). Combined ether layer was washed with water (2×3V), brine solution (2×3V), dried over sodium sulfate and evaporated at reduced pressure to obtain the crude product, which was purified by silica gel chromatography using a hexane as eluent to get the product 2007 (43.6 g, 64%). MS: Molecular weight calculated for C$_{37}$H$_{68}$S 544.50. Found: 545.51 (M+H).

Synthesis of 2008: To a solution of aldrithiol (20.2 g, 92 mmol) in dichloromethane (400 ml) was added benzyl bromide (11 mL, 92 mmol) at 0° C. After stirring at 0° C. for 15 min, it was warmed to room temperature and stirred for 15 minutes. Reaction mixture was cooled back to 0° C. and added a solution of 2007 (50 g, 92 mmol) in dichloromethane (100 ml) followed by diisopropylethylamine (16 mL, 92 mmol). After addition, it was heated to reflux for 2 hrs (TLC). It was then diluted with dichloromethane (10V), washed with water (2×10V), brine solution (2×10V), dried over sodium sulfate and evaporated at reduced pressure to obtain crude product, which was purified by silica gel chromatography using 3% ether/hexane to afford pure product as pale yellow liquid. (35 g, 58%) $^1$H NMR (400 MHz, CDCl$_3$): δ 0.89 (t, 6H, J1=6.4 Hz, J2=7.2 Hz), 1.25-1.42 (m, 38H), 1.56-1.63 (m, 2H), 2.05 (q, 8H, J1=6.4 Hz, J2=14 Hz), 2.78 (t, 5H, J1=6.4 Hz, J2=6 Hz), 5.30-5.42 (m, 8H), 7.06 (t, 1H, J1=5.2 Hz, J2=6.8 Hz), 7.62 (t, 1H, J1=7.6 Hz, J2=7.6 Hz), 7.76 (d, 1H, J=8 Hz), 8.42 (d, 1H, J=4.4 Hz). $^{13}$C NMR (100 MHz, CDCl$_3$): δ 22.6, 25.6, 26.7, 27.2, 29.2, 29.3, 29.5, 29.6, 31.5, Example 67

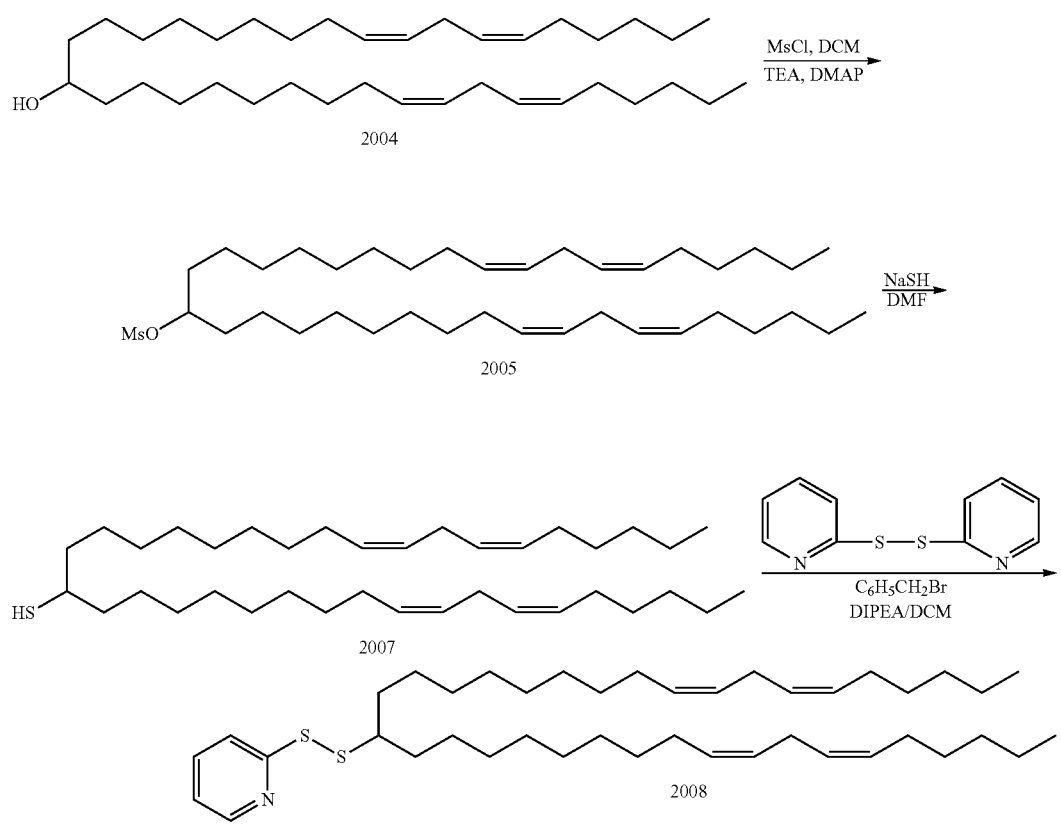

33.74, 52.9, 119.9, 120.4, 127.9, 128, 130.1, 130.2, 136.7, 149.3, 161.5. MS: Molecular weight calculated for $C_{42}H_{71}NS_2$ 653.50. Found: 654.49 (M+H).

Example 68

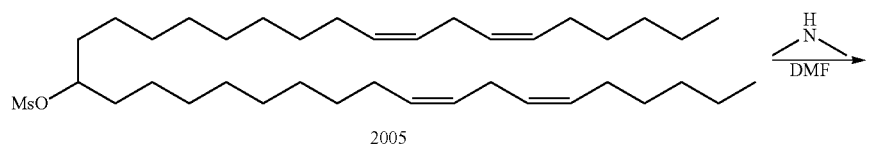

2005

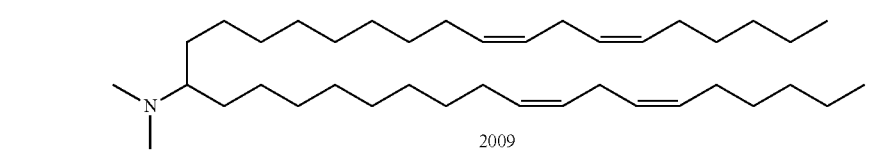

2009

Synthesis of 2009 (ALNY-138): A solution of 2005 (5 g, 8 mmol) in DMF and dimethylamine—40% aqueous solution was taken in a seal tube. The reaction mixture was heated at 90° C. for 20 hours (TLC). It was then cooled to room temperature, poured to water and extracted with ethyl acetate (3×50 ml). The organic layer was washed with water & brine, dried over $Na_2SO_4$ and evaporated to afford pure product as pale brown liquid (2.00 g, 45%) $^1$H NMR (400 MHz, CDCl$_3$): δ 0.89 (t, 6H, j=6.8), 1.2-1.4 (m, 40H), 2.05 (q, 8H, J$_1$=6.8 Hz, J$_2$=6.8 Hz), 2.2 (s, 6H), 2.77 (t, 4H, j=6.4 Hz), 5.35 (m, 8H). $^{13}$C NMR (400 MHz, CDCl$_3$): δ 14.1, 22.5, 22.6, 27.1, 27.2, 29.3, 29.5, 29.57, 29.63, 29.67, 30.0, 31.5, 32.5, 40.5, 64.0, 127.9 and 130.1 MS: Molecular weight calculated for $C_{39}H_{73}N$, 555.57. Found: 556.55 (M+H).

Example 69

Synthesis of 2010: To a solution of 2004 (30 g, 56.8 mmol) in toluene, was added N-Hydroxyphthalimide (13.9 g, 85 mmol) and TPP (22.30 g, 85 mmol) under argon. The reaction mass was cooled to −5° C., to this was added TEA (11.84 mL), followed by DEAD (13.14 ml). The reaction mass was allowed to stir for 12 hrs at room temperature (TLC). It was then filtered through celite pad. The filtrate was evaporated at reduced pressure to obtain crude product, which was purified by silica gel chromatography to afford pure product, which was eluted at 3% diethyl ether and hexane to get the product 2010 (22.90 g, 60.50%) as pale yellow liquid $^1$HNMR (400 MHz, CDCl$_3$,): δ 0.90 (6H, t, J=7.2 Hz), 1.2-1.4 (34H, m), 1.66-1.70 (4H, m), 2.03-2.08 (8H, m), 2.78 (4H, t, J=12.8 Hz), 4.22 (1H, m), 5.29-5.43 (8H, m), 7.74-7.76 (2H, m), 7.83-7.85 (2H, m). $^{13}$CNMR (100 MHz, CDCl$_3$,): δ 14.3, 22.5, 24.9, 25.6, 27.2, 27.20, 29.3, 29.3, 29.5, 29.5, 29.6, 29.7, 31.5, 32.4, 88.3, 123.3, 127.9, 129.0, 130.1, 134.3, 164.3. MS: Molecular weight calculated for $C_{45}H_{71}NO_3$ 673.54. Found: 674.55 (M+H).

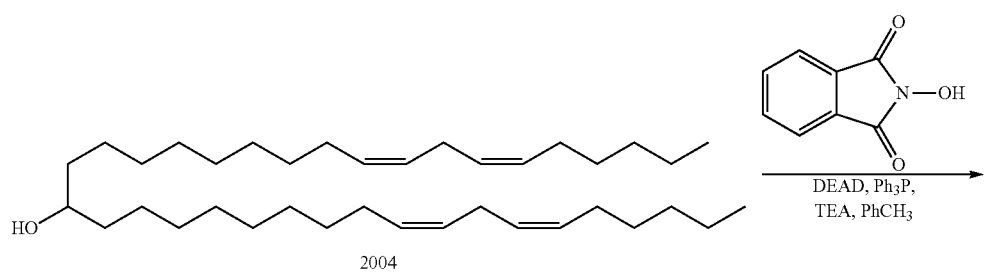

2004

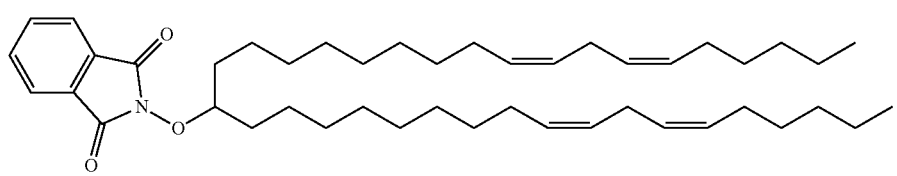

2010

Example 70
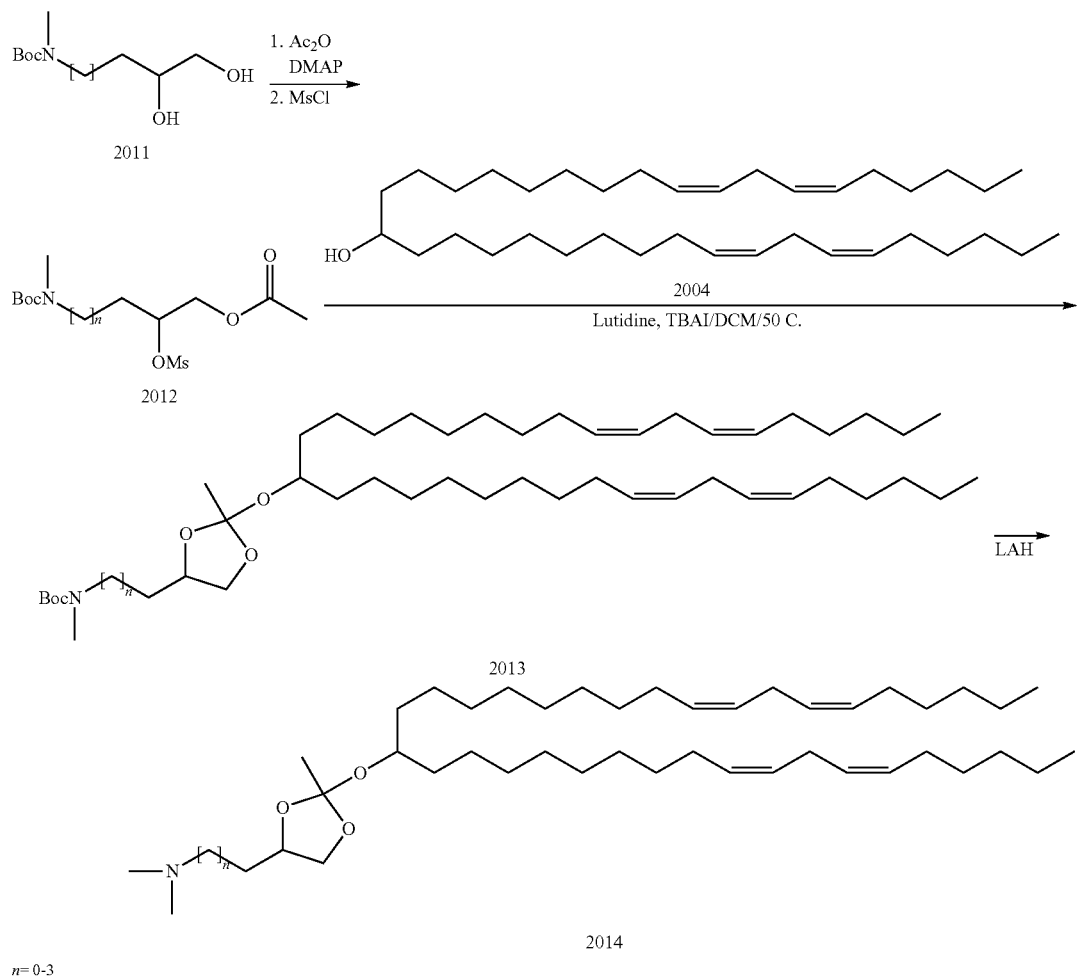
*n* = 0-3
Example 71
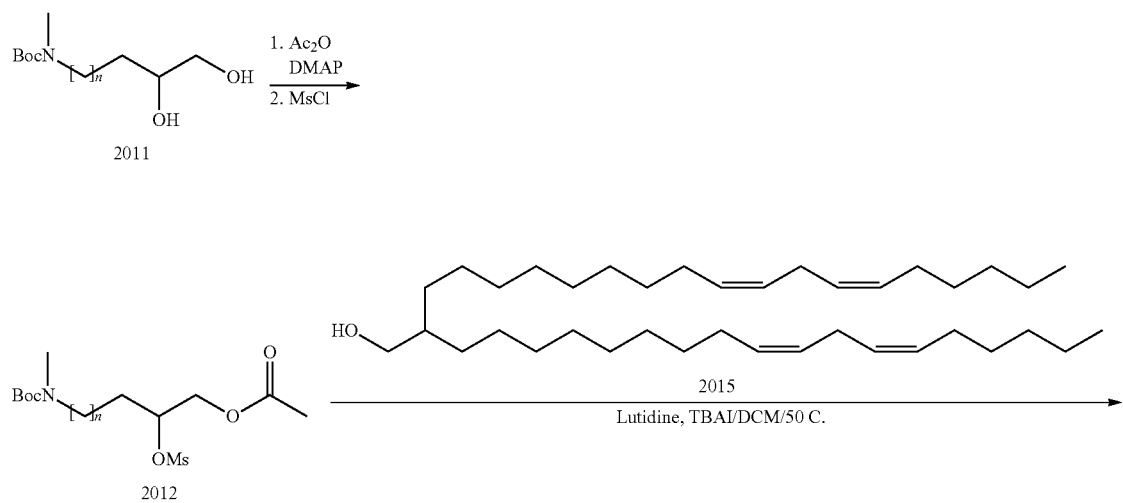

-continued
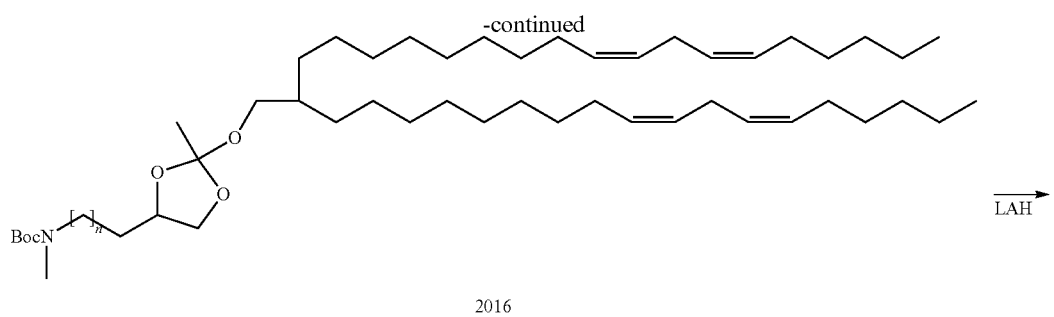
2016
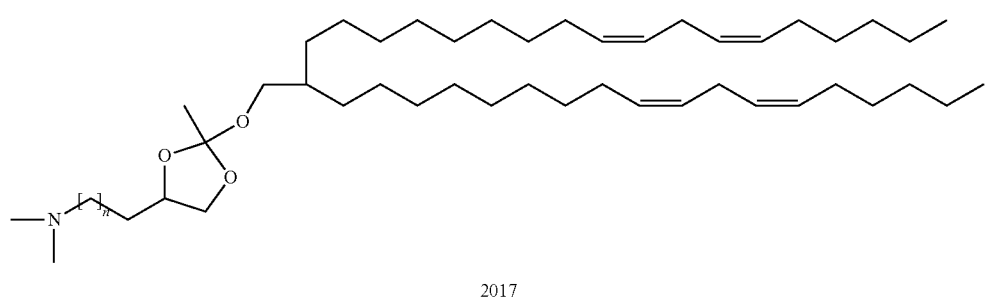
2017
n= 0-3
Example 72
Synthesis of 2019 (ALNY-152)
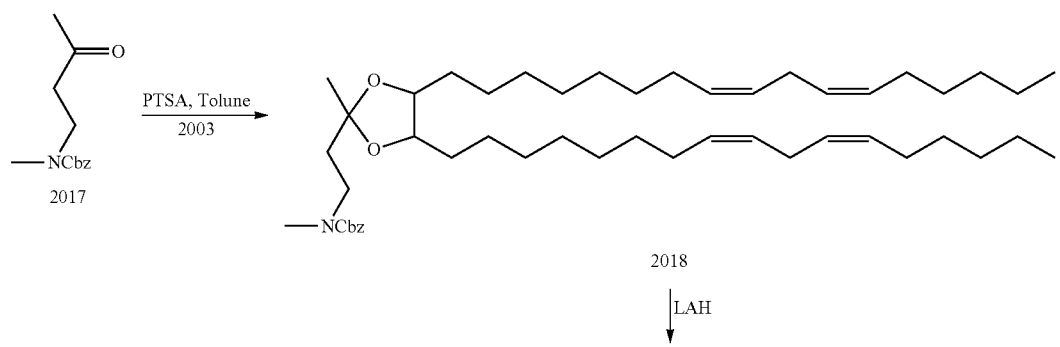
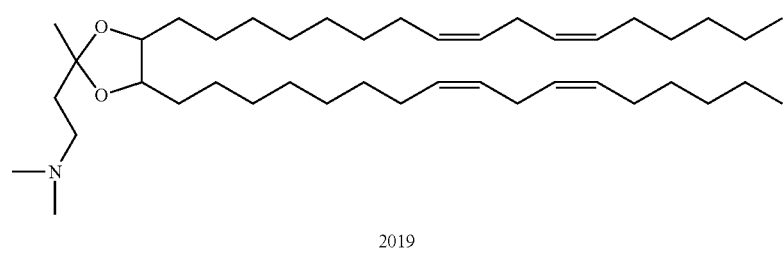
2019

Example 73
Synthesis of 2022 (ALNY-153)
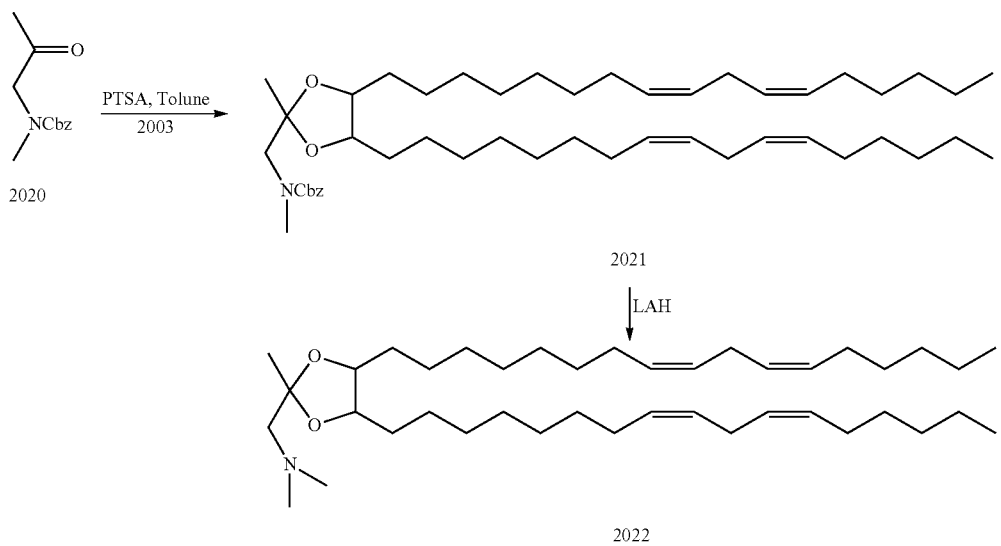
Example 74
Synthesis of 2025 (ALNY-158)
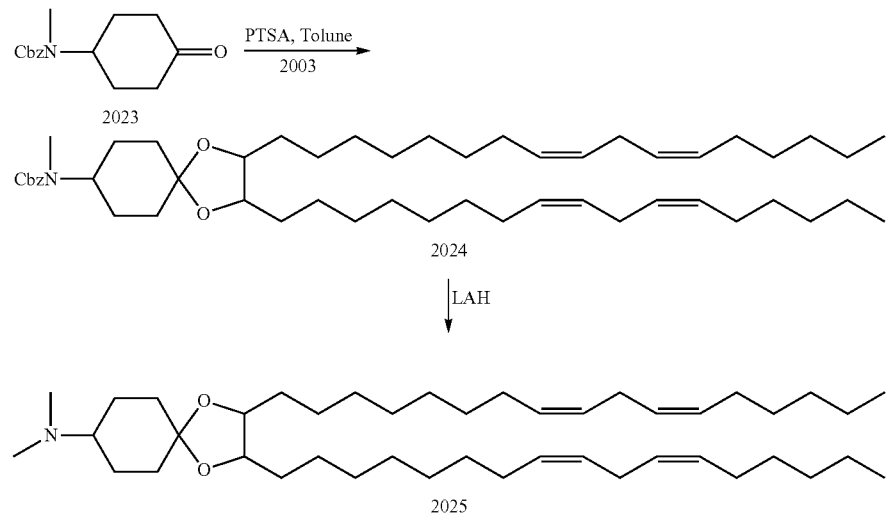
Example 75
Synthesis of 2028 (ALNY-156)
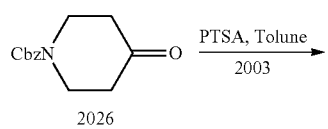

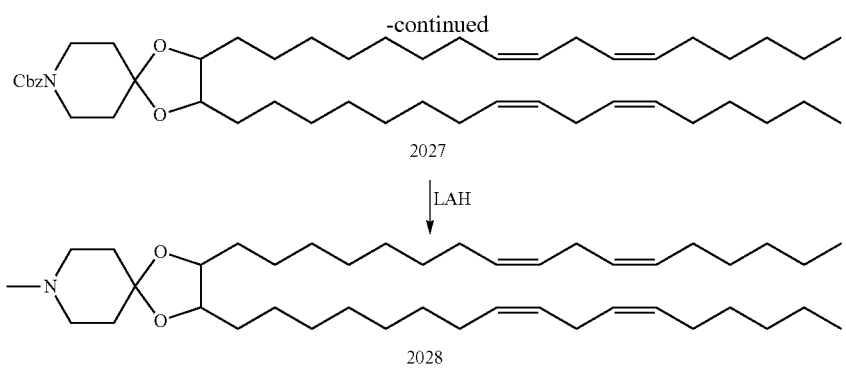
2027
↓ LAH
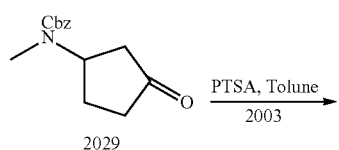
2028
Example 76
Synthesis of 2031 (ALNY-157)
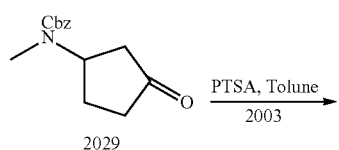
2029 →[PTSA, Tolune, 2003]
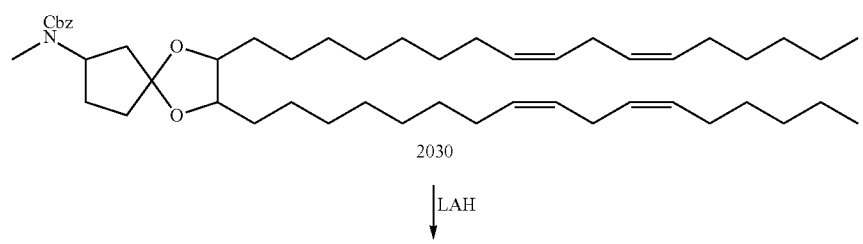
2030
↓ LAH
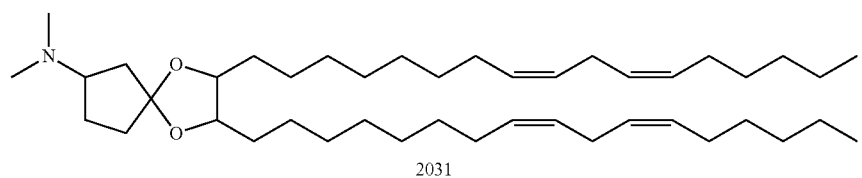
2031
Example 77
Synthesis of 2035
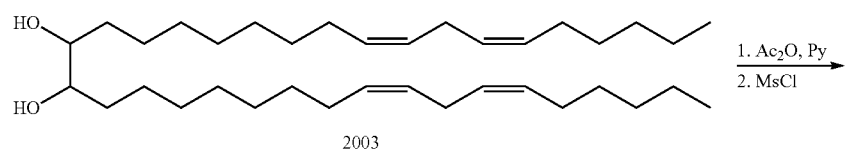
2003 →[1. Ac₂O, Py; 2. MsCl]

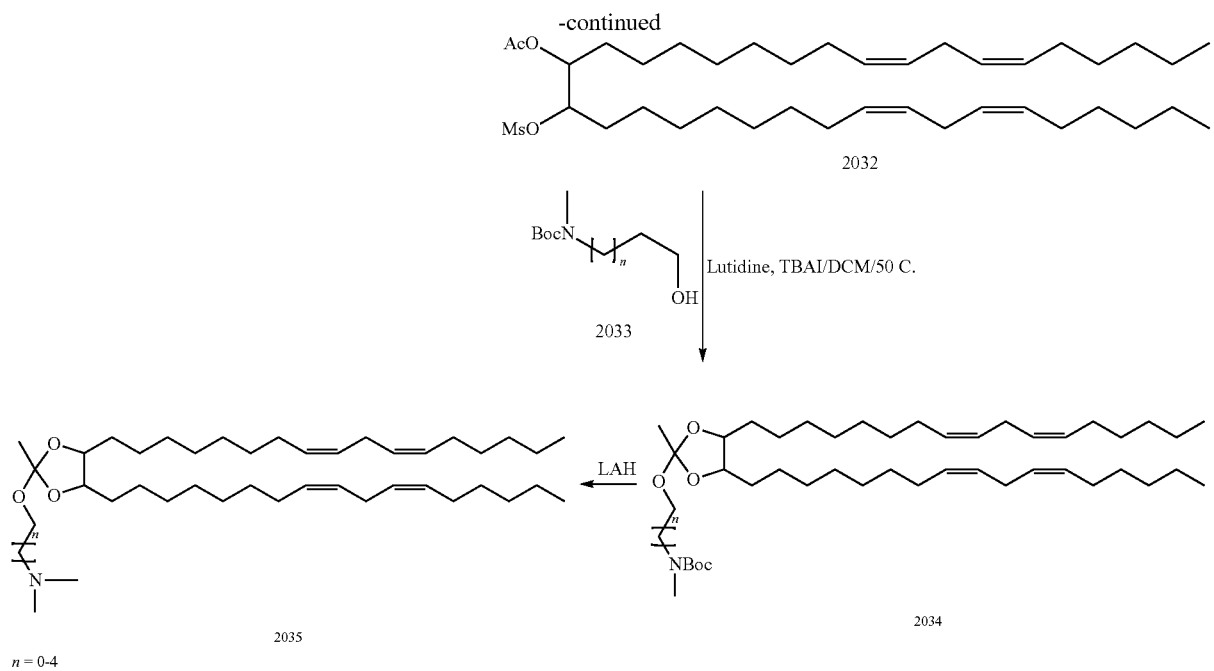

Example 78

Synthesis of 3-(dimethylamino)-N-((11Z,14Z)-2-((9Z,12Z)-octadeca-9,12-dienyl)icosa-11,14-dienyl)propanamide (ALNY-201)

Scheme 78

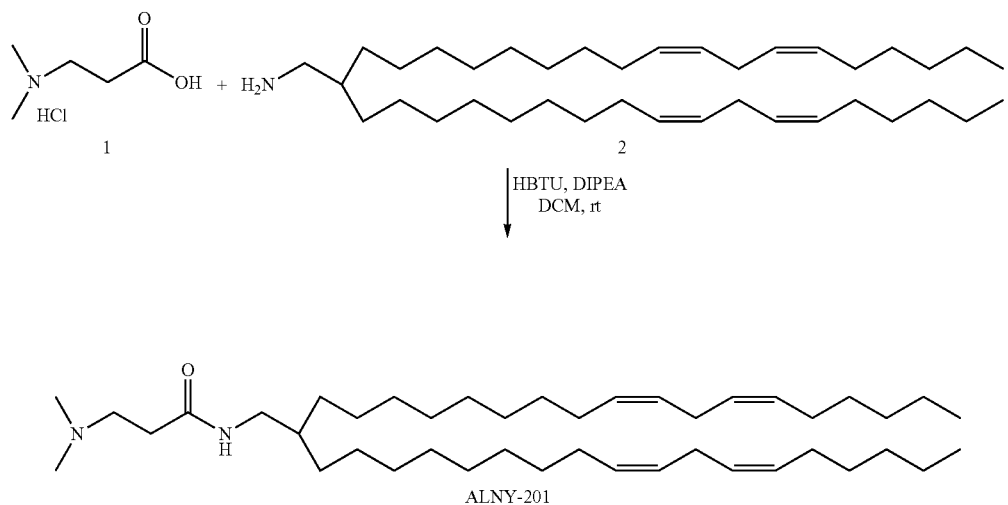

ALNY-201

To a stirred suspension of N,N-dimethylamino propionic acid hydrochloride (1, 0.198 g, 1.3 mmol, 1.0 eq) in DCM was added HBTU (0.59 g, 1.56 mmol, 1.2 eq) and DIPEA (0.71 mL, 3.9 mmol, 3.0 eq) at room temperature. After stirred for 10 minutes, a solution of amine (2, 0.7 g. 1.3 mmol, 1.0 eq) in DCM was added drop wise at room temperature and continued the stirring until completion of the reaction. Reaction mixture was diluted with DCM, washed with saturated NaHCO$_3$ solution followed by brine, organic layer was separated and dried over MgSO$_4$, concentrated and purified by the silica gel column chromatography using DCM:MeOH (5%) as gradients to get pure oily compound 3 in 70% yield. $^1$H NMR (400 MHz, CDCl$_3$) δ 7.18 (brs, 1H), 5.47-5.19 (m, 8H), 3.18-3.07 (m, 4H), 2.76 (t, J=6.5, 4H), 2.70 (s, 6H), 2.60 (t, J=6.0, 2H), 2.04 (q, J=6.8, 9H), 1.48 (brs, 1H), 1.40-1.14 (m, 43H), 0.88 (t, J=6.8, 6H). Calc. mass for the C43H80N2O: 640.6. found 641.5.

Synthesis of Novel Dilinoleyl Derivatives
| No | compound | Name |
|---|---|---|
| 1 | 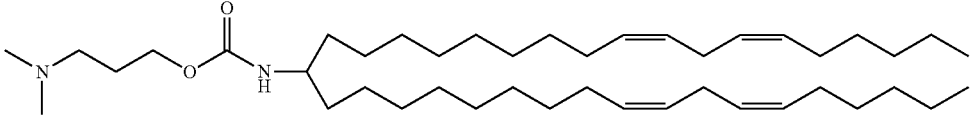 [SMILES: CCCCC/C=C\C/C=C\CCCCCCCCC(CCCCCCCC/C=C\C/C=C\CCCCC)NC(=O)OCCCN(C)C] | ALNY-192 |
| 2 | 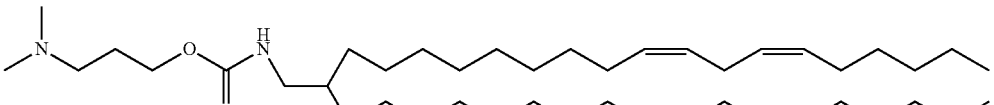 | ALNY-200 |
| 3 | 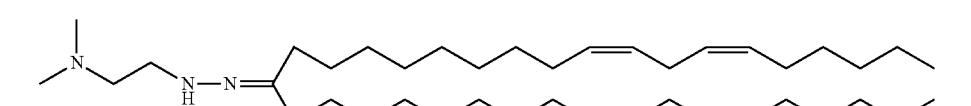 | ALNY-175 |
| 4 | 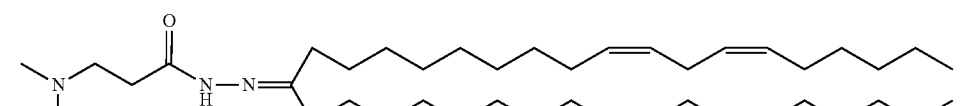 | ALNY-187 |
| 5 | 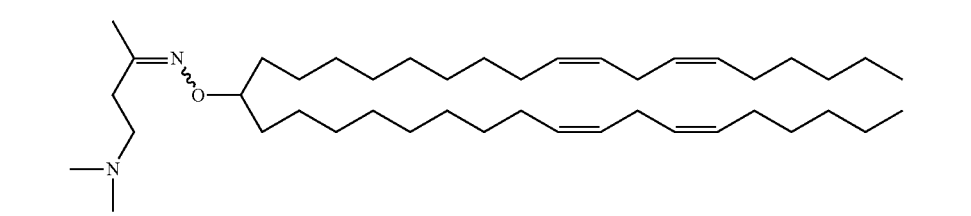 [SMILES: CCCCC/C=C\C/C=C\CCCCCCCCC(CCCCCCCC/C=C\C/C=C\CCCCC)ON=C(C)CCN(C)C] | ALNY-149 |
| 6 | 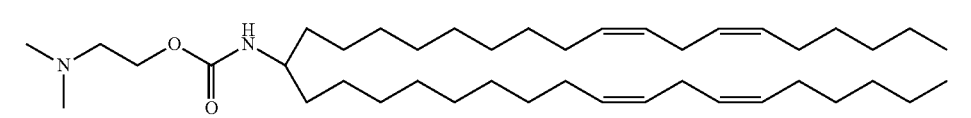 | ALNY-202 |
Compound 1
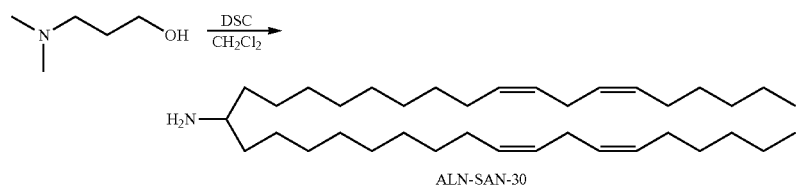
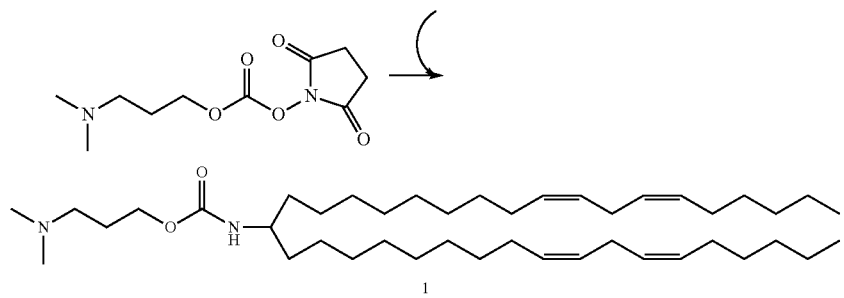
Compound 2
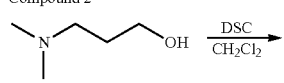

| No | compound | Name |
|---|---|---|
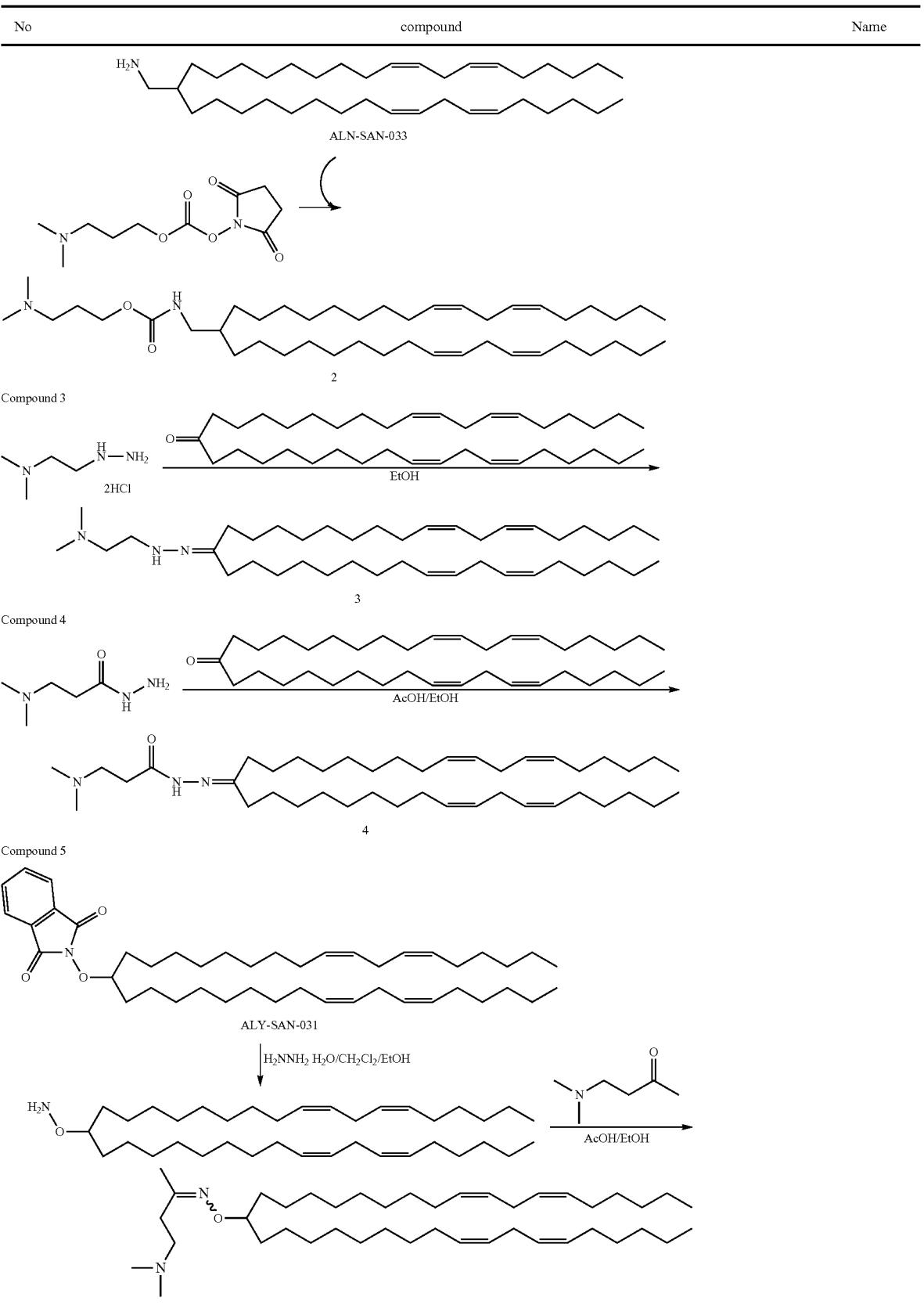

| No | compound | Name |
|---|---|---|
| Compound 6 | 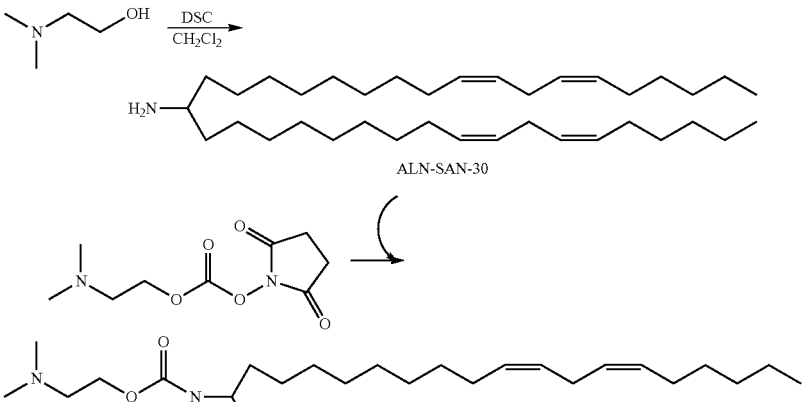 | |

Experimental Details

Compound 1 (ALNY-192)

To a solution of N,N'-disuccinimidyl carbonate (5.50 g, 21.5 mmol) in $CH_2Cl_2$ (200 mL), 3-dimethylamino-1-propanol (2.43 g, 23.6 mmol) was added dropwise. The resulting mixture was stirred at room temperature overnight. Taken up 50 mL of the solution, $Et_3N$ (0.822 mL, 5.90 mmol) and ALN-SAN-30 (2.08 g, 3.93 mmol) were added and the reaction mixture was stirred at room temperature overnight. The reaction mixture was diluted with $CH_2Cl_2$ and washed with saturated $NaHCO_3$ aq. The organic layer was dried over anhydrous $MgSO_4$, filtered and concentrated. The crude was purified by silica gel column chromatography (0-5% MeOH in $CH_2Cl_2$) to give compound 1 (1.66 g, 2.53 mmol, 64%, $R_f$=0.22 with 5% MeOH in $CH_2Cl_2$). $^1H$ NMR ($CDCl_3$, 400 MHz) δ 5.30-5.41 (m, 8H), 4.37 (d, J=8.0 Hz, 1H), 4.09 (t, J=6.0 Hz, 2H), 3.57 (brs, 1H), 2.78 (t, J=6.0 Hz, 4H), 2.33 (t, J=8.0 Hz, 2H), 2.23 (s, 6H), 2.02-2.06 (m, 8H), 1.76-1.80 (m, 2H), 1.27-1.45 (m, 40H), 0.89 (t, J=8.0 Hz, 6H). $^{13}C$ NMR ($CDCl_3$, 100 MHz) δ 156.5, 130.4, 130.3, 128.2, 128.1, 63.2, 56.6, 51.4, 45.7, 35.7, 31.7, 29.9, 29.8, 29.7, 29.6, 29.5, 27.7, 27.5, 27.4, 26.0, 25.8, 22.8, 14.3. Molecular weight for $C_{43}H_{81}N_2O_2$ $(M+H)^+$ Calc. 657.63. Found 657.5.

Compound 2 (ALNY-200)

To a solution of N,N'-disuccinimidyl carbonate (5.50 g, 21.5 mmol) in $CH_2Cl_2$ (200 mL), 3-dimethylamino-1-propanol (2.43 g, 23.6 mmol) was added dropwise. The resulting mixture was stirred at room temperature overnight. Taken up 50 mL of the solution, $Et_3N$ (0.697 mL, 5.00 mmol) and ALN-SAN-033 (1.71 g, 3.15 mmol) were added and the reaction mixture was stirred at room temperature overnight. The reaction mixture was diluted with $CH_2Cl_2$ and washed with saturated $NaHCO_3$ aq. The organic layer was dried over anhydrous $MgSO_4$, filtered and concentrated. The crude was purified by silica gel column chromatography (0-5% MeOH in $CH_2Cl_2$) to give compound 2 (1.14 g, 1.70 mmol, 54%, $R_f$=0.13 with 5% MeOH in $CH_2Cl_2$). Molecular weight for $C_{44}H_{83}N_2O_2$ $(M+H)^+$ Calc. 671.65. Found 671.5.

Compound 3 (ALNY-175)

To a flask containing EtOH (50 mL) was added dimethylaminoethyl hydrazine dihydrochloride (1.00 g, 5.70 mmol) and ALNY-SAN-003 (2.00 g, 3.80 mmol). The mixture was heated at 60° C. for 16 hours. After addition of $Et_3N$ (0.5 mL), the reaction mixture was evaporated. The residue was extracted with $Et_2O$ and saturated $NaHCO_3$ aq., and the organic layer was dried over $MgSO_4$, filtered and concentrated. The crude was purified by silica gel column chromatography ($CH_2Cl_2$:MeOH:$NH_3$ aq.=95:5:0.5, $R_f$=0.29) to give compound 3 (1.78 g, 2.91 mmol, 76%). Molecular weight for $C_{41}H_{78}N_3$ $(M+H)^+$ Calc. 612.62. Found 612.5.

Compound 4 (ALNY-187)

3-Dimethylamino-propionic acid hydrazide (Ryan Scientific, 500 mg, 3.89 mmol) in EtOH (10 mL) and the dilinoleyl ketone (1.74 g, 3.31 mmol) in EtOH (20 mL) were mixed together. To the solution was added acetic acid (0.038 mL, 0.662 mmol), and the reaction mixture was heated at 65° C. for 5 hours. After addition of $Et_3N$ (0.5 mL), the reaction mixture was evaporated. The residue was extracted with $CH_2Cl_2$ and saturated $NaHCO_3$ aq., and the organic layer was dried over $MgSO_4$, filtered and concentrated. The crude was purified by silica gel column chromatography ($CH_2Cl_2$: MeOH:$NH_3$ aq.=95:5:0.5, $R_f$=0.30) to give compound 4 (1.40 g, 2.19 mmol, 66%). Molecular weight for $C_{42}H_{78}N_3O$ $(M+H)^+$ Calc. 640.61. Found 640.5.

Compound 5 (ALNY-149)

ALY-SAN-031 (2.36 g, 3.50 mmol) was treated with hydrazine monohydrate (0.424 mL, 5.60 mmol) in $CH_2Cl_2$ (36 mL) and EtOH (4 mL) for 2 hours. After filtration of the resulting white precipitation, the filtrate was concentrated. The residue was extracted with $Et_2O$ and saturated $NaHCO_3$ aq., and the organic layer was dried over $MgSO_4$, filtered and concentrated. The crude material was used for next step without further purification. $R_f$: 0.44 (10% EtOAC in Hexane). Molecular weight for $C_{37}H_{70}NO$ $(M+H)^+$ Calc. 544.55. Found 544.2.

The aminooxy compound was dissolved in EtOH (30 mL), and 4-(dimethylamino)butan-2-one (Matrix Scientific, 500 mg, 4.34 mmol) and acetic acid (0.040 mL, 0.70 mmol) was added to the solution. The reaction mixture was stirred at room temperature for 14 hours. After addition of Et$_3$N (0.5 mL), the reaction mixture was evaporated. The residue was extracted with Et$_2$O and saturated NaHCO$_3$ aq., and the organic layer was dried over MgSO$_4$, filtered and concentrated. The crude was purified by silica gel column chromatography (Hexane:EtOAc=1:1) to give compound 5 as a mixture of E/Z-isomers (1.90 g, 2.96 mmol, 85%, 2 steps, R$_f$=0.39, 0.21 developed with Hexane:EtOAc=1:1). Molecular weight for C$_{43}$H$_{81}$N$_2$O (M+H)$^+$ Calc. 641.63. Found 641.5.

Compound 6 ALNY-202

To a solution of N,N'-disuccinimidyl carbonate (5.50 g, 21.5 mmol) in CH$_2$Cl$_2$ (200 mL), 3-dimethylamino-1-propanol (2.37 mL, 23.6 mmol) was added dropwise. The resulting mixture was stirred at room temperature overnight. Taken up 50 mL of the solution, Et$_3$N (0.822 mL, 5.90 mmol) and ALN-SAN-30 (2.07 g, 3.93 mmol) were added and the reaction mixture was stirred at room temperature overnight. The reaction mixture was diluted with CH$_2$Cl$_2$ and washed with saturated NaHCO$_3$ aq. The organic layer was dried over anhydrous MgSO$_4$, filtered and concentrated. The crude was purified by silica gel column chromatography (0-5% MeOH in CH$_2$Cl$_2$) to give compound 6. Molecular weight for C$_{42}$H$_{79}$N$_2$O$_2$ (M+H)$^+$ Calc. 643.61. Found 643.5.

Compounds of the present invention can be further synthesized by the procedures described in the following papers, which are hereby incorporated by their entirety:
1. Schlueter, Urs; Lu, Jun; Fraser-Reid, Bert. Synthetic Approaches To Heavily Lipidated Phosphoglyceroinositides. Organic Letters (2003), 5(3), 255-257
2. King, J. F.; Allbutt, A. D. Can. J. Chem. 1970, 48, 1754-1769
3. Mach, Mateusz; Schlueter, Urs; Mathew, Felix; Fraser-Reid, Bert; Hazen, Kevin C. Comparing n-pentenyl orthoesters and n-pentenyl glycosides as alternative glycosyl donors. Tetrahedron (2002), 58(36), 7345-7354.

Example 79

Determination of Efficacy of Lipid Particle Formulations Containing Various Cationic Lipids Using an In Vivo Rodent Factor VII Silencing Model Factor VII (FVII), a prominent protein in the coagulation cascade, is synthesized in the liver (hepatocytes) and secreted into the plasma. FVII levels in plasma can be determined by a simple, plate-based colorimetric assay. As such, FVII represents a convenient model for determining sirna-mediated downregulation of hepatocyte-derived proteins, as well as monitoring plasma concentrations and tissue distribution of the nucleic acid lipid particles and siRNA.

| Duplex | Sequence 5'-3' | SEQ ID NO: | Target |
|---|---|---|---|
| AD-1661 | GGAfUfCAfUfCfUfCAAGfUfCfUfU AfCdTsdT | NO:67. | FVII |
|  | GfUAAGAfCfUfUGAGAfUGAfUfCfC dTsdT | NO:68. |  |

Lower case is 2'OMe modification and Nf is a 2'F modified nucleobase, dT is deoxythymidine, s is phosphothioate The following cationic lipids were tested:

| Compound | Compound Structure | Molecular data |
|---|---|---|
| A | 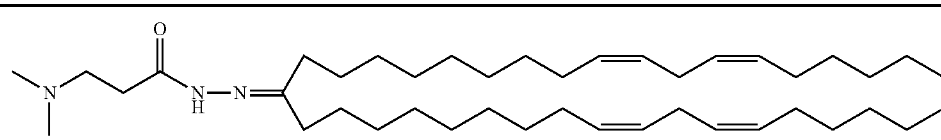 | C$_{42}$H$_{77}$N$_3$O Mol Wt: 640.08 |
| B | 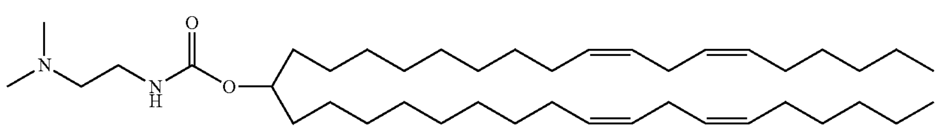 | C$_{42}$H$_{78}$N$_2$O$_2$ Mol Wt: 643.08 |
| C | 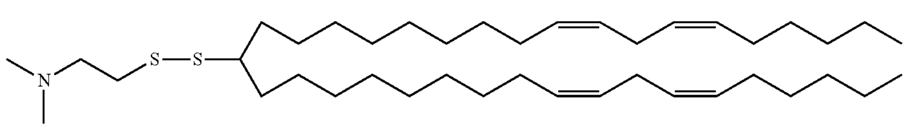 [SMILES: CCCCC/C=C\C/C=C\CCCCCCCCC(CCCCCCCC/C=C\C/C=C\CCCCC)SSCCN(C)C] | C$_{41}$H$_{77}$NS$_2$ Mol Wt: 648.19 |
| D | 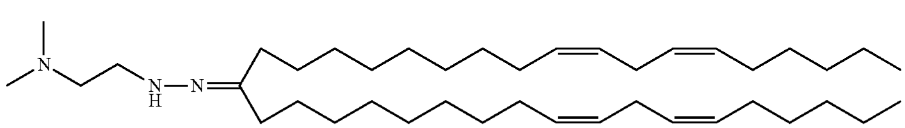 [SMILES: CCCCC/C=C\C/C=C\CCCCCCCCC(CCCCCCCC/C=C\C/C=C\CCCCC)=NNCCN(C)C] | C$_{41}$H$_{77}$N$_3$ Mol Wt: 612.07 |
| E | 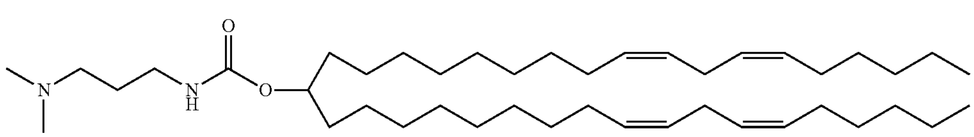 | C$_{43}$H$_{80}$N$_2$O$_2$ Mol Wt: 657.11 |

-continued

| Compound | Compound Structure | Molecular data |
|---|---|---|
| F | (structure) | $C_{43}H_{80}N_2O_2$ Mol Wt: 657.11 |
| G | (structure) | $C_{44}H_{82}N_2O_2$ Mol Wt: 671.134 |
| H | (structure) | $C_{43}H_{80}N_2O$ Mol Wt: 641.108 |
| I | (structure) | $C_{43}H_{80}N_2O$ Mol Wt: 641.11 |
| J | (structure) | $C_{42}H_{78}N_2O_2$ Mol Wt: 643.081 |
| K | (structure) | $C_{43}H_{80}N_2O_2$ Mol Wt: 657.107 |

The cationic lipids shown above were used to formulate liposomes containing the AD-1661 duplex using an in-line mixing method, as described in U.S. provisional patent application 61/228,373. Lipid particles were formulated using the following molar ratio: 50% Cationic lipid/10% distearoylphosphatidylcholine (DSPC)/38.5% Cholesterol/1.5% PEG-DMG (1-(monomethoxy-polyethyleneglycol)-2,3-dimyristoylglycerol, with an average PEG molecular weight of 2000).

C57BL/6 mice (Charles River Labs, MA) received either saline or formulated siRNA via tail vein injection. At various time points after administration, serum samples were collected by retroorbital bleed. Serum levels of Factor VII protein were determined in samples using a chromogenic assay (Biophen FVII, Aniara Corporation, OH). To determine liver mRNA levels of Factor VII, animals were sacrificed and livers were harvested and snap frozen in liquid nitrogen. Tissue lysates were prepared from the frozen tissues and liver mRNA levels of Factor VII were quantified using a branched DNA assay (QuantiGene Assay, Panomics, Calif.).

Figure 6:
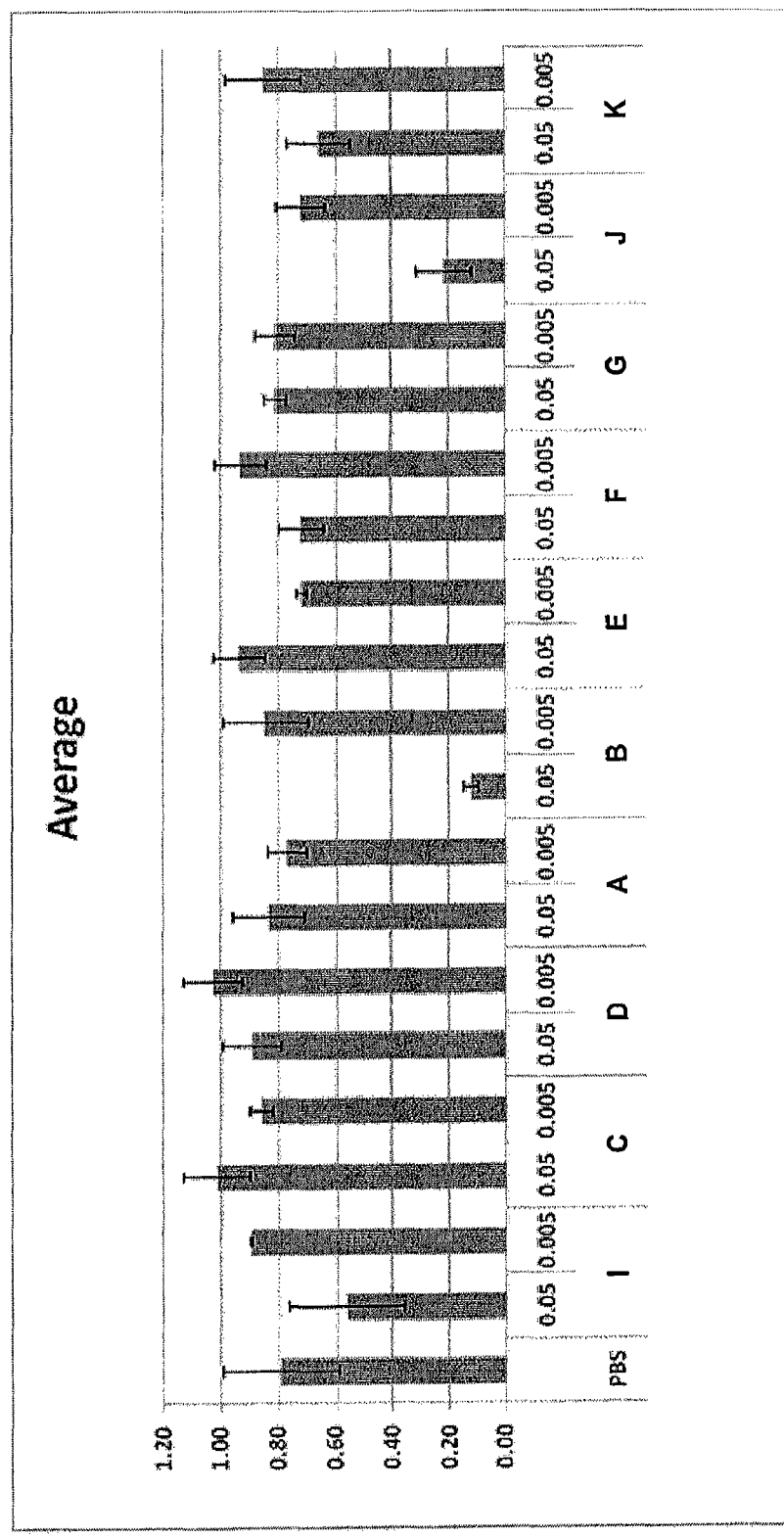
FIG. 6 shows a graph illustrating the relative FVII protein levels in animals administered with 0.05 or 0.005 mg/kg of lipid particles containing different cationic lipids.

FVII activity was evaluated in FVII siRNA-treated animals at 48 hours after intravenous (bolus) injection in C57BL/6 mice. FVII was measured using a commercially available kit for determining protein levels in serum or tissue, following the manufacturer's instructions at a microplate scale. FVII reduction was determined against untreated control mice, and the results were expressed as % Residual FVII. Two dose levels (0.05 and 0.005 mg/kg FVII siRNA) were used in the screen of each novel liposome composition. FIG. 6 shows a graph illustrating the relative FVII protein levels in animals administered with 0.05 or 0.005 mg/kg of lipid particles containing different cationic lipids.

Example 80 siRNA Formulation Using Preformed Vesicles

Cationic lipid containing particles were made using the preformed vesicle method. Cationic lipid, DSPC, cholesterol and PEG-lipid were solubilised in ethanol at a molar ratio of 40/10/40/10, respectively. The lipid mixture was added to an aqueous buffer (50 mM citrate, pH 4) with mixing to a final ethanol and lipid concentration of 30% (vol/vol) and 6.1 mg/mL respectively and allowed to equilibrate at room temperature for 2 min before extrusion. The hydrated lipids were extruded through two stacked 80 nm pore-sized filters (Nuclepore) at 22° C. using a Lipex Extruder (Northern Lipids, Vancouver, BC) until a vesicle diameter of 70-90 nm, as determined by Nicomp analysis, was obtained. This generally required 1-3 passes. For some cationic lipid mixtures which did not form small vesicles hydrating the lipid mixture with a lower pH buffer (50 mM citrate, pH 3) to protonate the phosphate group on the DSPC headgroup helped form stable 70-90 nm vesicles.

The FVII siRNA (solubilised in a 50 mM citrate, pH 4 aqueous solution containing 30% ethanol) was added to the vesicles, pre-equilibrated to 35° C., at a rate of ~5 mL/min with mixing. After a final target siRNA/lipid ratio of 0.06 (wt/wt) was achieved, the mixture was incubated for a further 30 min at 35° C. to allow vesicle re-organization and encapsulation of the FVII siRNA. The ethanol was then removed and the external buffer replaced with PBS (155 mM NaCl, 3 mM Na2HPO4, 1 mM KH2PO4, pH 7.5) by either dialysis or tangential flow diafiltration. The final encapsulated siRNA-to-lipid ratio was determined after removal of unencapsulated siRNA using size-exclusion spin columns or ion exchange spin columns Example 81

In Vivo Determination of Efficacy of Novel Lipid Formulations

Test formulations were initially assessed for their FVII knockdown in female 7-9 week old, 15-25 g, female C57B1/6 mice at 0.1, 0.3, 1.0 and 5.0 mg/kg with 3 mice per treatment group. All studies included animals receiving either phosphate-buffered saline (PBS, Control group) or a benchmark formulation. Formulations were diluted to the appropriate concentration in PBS immediately prior to testing. Mice were weighed and the appropriate dosing volumes calculated (10 µl/g body weight). Test and benchmark formulations as well as PBS (for Control animals) were administered intravenously via the lateral tail vein. Animals were anesthetised 24 h later with an intraperitoneal injection of Ketamine/Xylazine and 500-700 µl of blood was collected by cardiac puncture into serum separator tubes (BD Microtainer). Blood was centrifuged at 2,000×g for 10 min at 15° C. and serum was collected and stored at −70° C. until analysis. Serum samples were thawed at 37° C. for 30 min, diluted in PBS and aliquoted into 96-well assay plates. Factor VII levels were assessed using a chromogenic assay (Biophen FVII kit, Hyphen BioMed) according to manufacturer's instructions and absorbance measured in microplate reader equipped with a 405 nm wavelength filter. Plasma FVII levels were quantified and ED50s (dose resulting in a 50% reduction in plasma FVII levels compared to control animals) calculated using a standard curve generated from a pooled sample of serum from Control animals. Those formulations of interest showing high levels of FVII knockdown (ED50<<0.1 mg/kg) were re-tested in independent studies at a lower dose range to confirm potency and establish ED50. The ED50 values of a representative number of compounds is shown in Table 8

Example 82

Determination of pKa of Formulated Lipids

The pKa's of the different ionisable cationic lipids were determined essentially as described (Eastman et al 1992 Biochemistry 31:4262-4268) using the fluorescent probe 2-(p-toluidino)-6-naphthalenesulfonic acid (TNS), which is non-fluorescent in water but becomes appreciably fluorescent when bound to membranes. Vesicles composed of cationic lipid/DSPC/CH/PEG-c-DOMG (40:10:40:10 mole ratio) were diluted to 0.1 mM in buffers (130 mM NaCl, 10 mM $CH_3COONH_4$, 10 mM MES, 10 mM HEPES) of various pH's, ranging from 2 to 11. An aliquot of the TNS aqueous solution (1 µM final) was added to the diluted vesicles and after a 30 second equilibration period the fluorescent of the TNS-containing solution was measured at excitation and emission wavelengths of 321 nm and 445 nm, respectively. The pKa of the cationic lipid-containing vesicles was determined by plotting the measured fluorescence against the pH of the solutions and fitting the data to a Sigmodial curve using the commercial graphing program Igor Pro. The pKa values for a representative number of compounds is shown in Table 8

| Compound | Structure | ED50 | pKa |
|---|---|---|---|
| ALNY-104 | 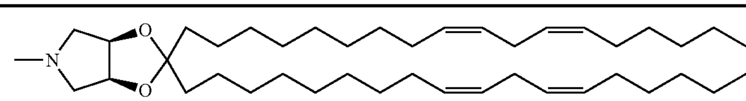 | 2.5 | 5.65 |
| ALNY-105 | 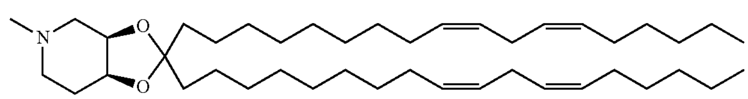 | 1.5 | 5.60 |
| ALNY-106 | 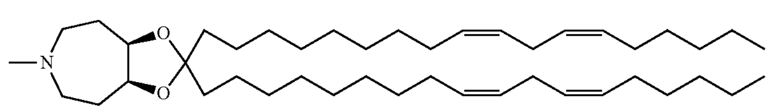 [SMILES: CCCCC/C=C\C/C=C\CCCCCCCCC1(CCCCCCCC/C=C\C/C=C\CCCCC)O[C@H]2CCN(C)CC[C@H]2O1] | 0.3 | 6.85 |
| ALNY-100 | 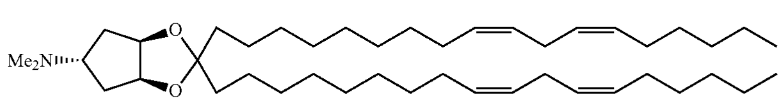 [SMILES: CCCCC/C=C\C/C=C\CCCCCCCCC1(CCCCCCCC/C=C\C/C=C\CCCCC)O[C@H]2C[C@H](N(C)C)C[C@H]2O1] | 0.3 | 6.4 |
| ALNY-101 | 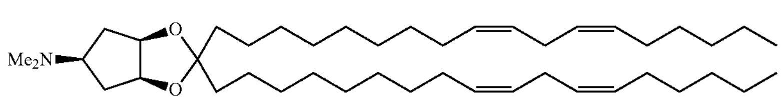 [SMILES: CCCCC/C=C\C/C=C\CCCCCCCCC1(CCCCCCCC/C=C\C/C=C\CCCCC)O[C@H]2C[C@@H](N(C)C)C[C@H]2O1] | 0.1 | 6.43 |
| ALNY-102 | 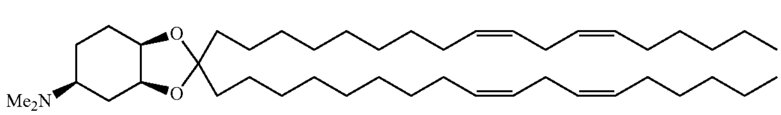 [SMILES: CCCCC/C=C\C/C=C\CCCCCCCCC1(CCCCCCCC/C=C\C/C=C\CCCCC)O[C@H]2C[C@@H](N(C)C)CC[C@H]2O1] | 2.0 | 7.3 |

| Compound | Structure | ED50 | pKa |
|---|---|---|---|
| ALNY-103 | 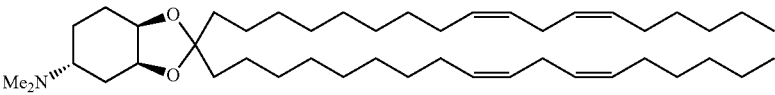 | 2.5 | 6.98 |
| ALNY-107 | 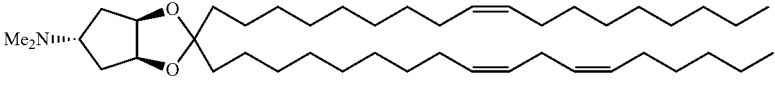 | 0.25 | 6.63 |
| ALNY-108 | 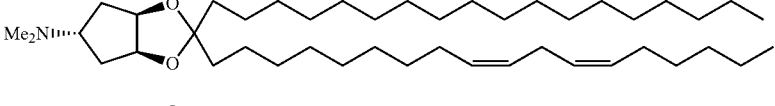 | 0.75 | 6.55 |
| ALNY-109 | 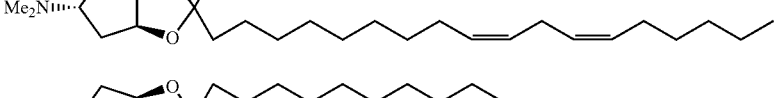 | 2.0 | 6.75 |
| ALNY-110 | 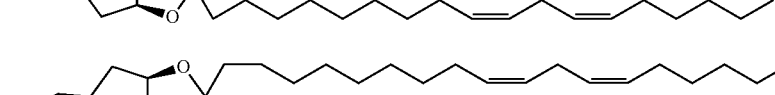 | 2.0 | 6.5 |
| ALNY-115 | 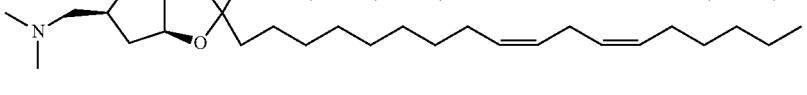 | 1.0 | |
| ALNY-116 | 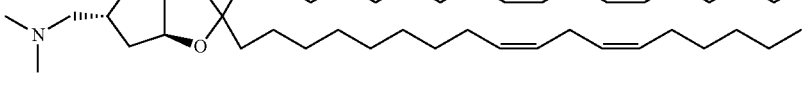 | 1.0 | |
| ALNY-121 | 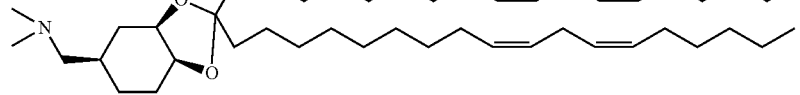 | 0.5 | 6.60 |
| ALNY-122 | 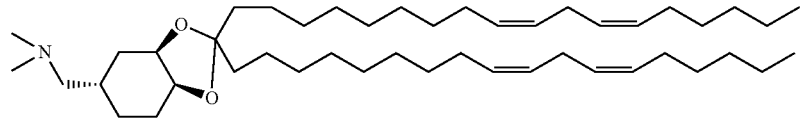 [SMILES: CCCCC/C=C\C/C=C\CCCCCCCCC1(CCCCCCCC/C=C\C/C=C\CCCCC)O[C@H]2CC[C@H](CN(C)C)C[C@H]2O1] | 0.55 | |
| ALNY-169 | 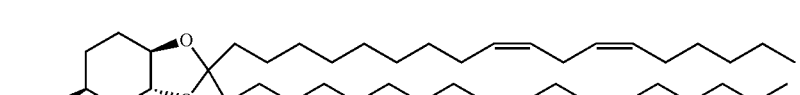 | 2.60 | |
| ALNY-144 | 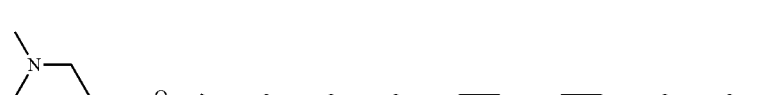 | 0.60 | |
| ALNY-151 | 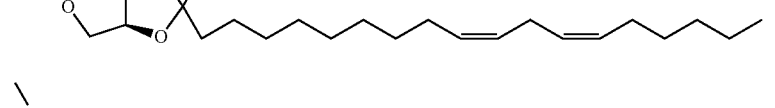 | >5.00 | 5.50 |

-continued

| Compound | Structure | ED50 | pKa |
|---|---|---|---|
| ALNY-152 | 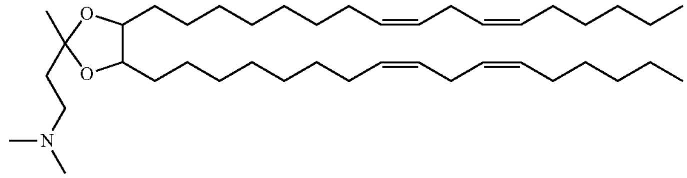 [SMILES: CCCCC/C=C\C/C=C\CCCCCCCC1OC(C)(CCN(C)C)OC1CCCCCCC/C=C\C/C=C\CCCCC] | 0.15 | 6.60 |
| ALNY-156 | 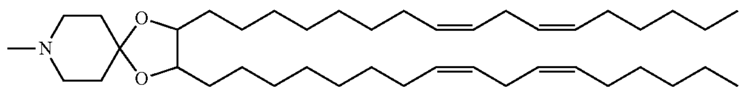 [SMILES: CCCCC/C=C\C/C=C\CCCCCCCC1OC2(CCN(C)CC2)OC1CCCCCCC/C=C\C/C=C\CCCCC] | <0.1 | 6.08 |
| ALNY-158 | 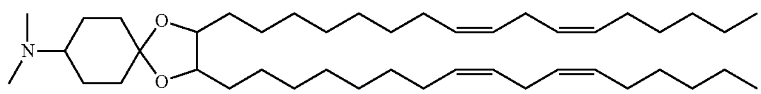 | 1.40 | |
| ALNY-190 | 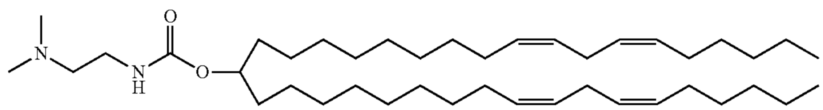 | 0.47 | 6.49 |
| ALNY-192 | 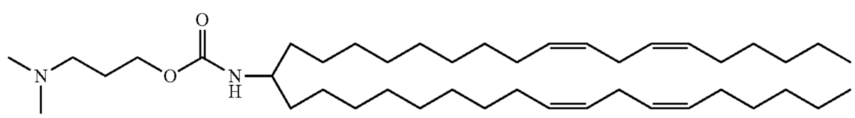 [SMILES: CCCCC/C=C\C/C=C\CCCCCCCCC(CCCCCCCC/C=C\C/C=C\CCCCC)NC(=O)OCCCN(C)C] | 2.1 | 7.21 |
| ALNY-200 | 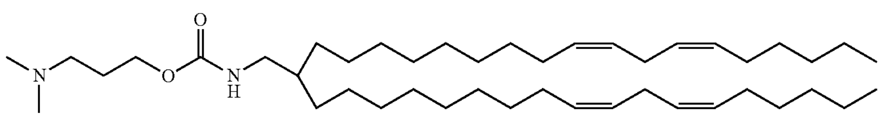 [SMILES: CCCCC/C=C\C/C=C\CCCCCCCCC(CCCCCCCC/C=C\C/C=C\CCCCC)CNC(=O)OCCCN(C)C] | >5.00 | 7.57 |
| ALNY-202 | 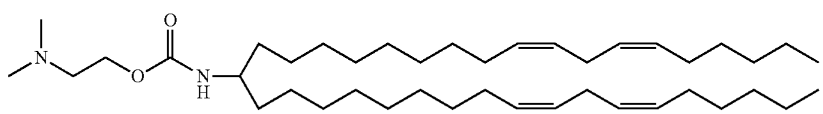 | 0.12 | 6.52 |
| ALNY-203 | 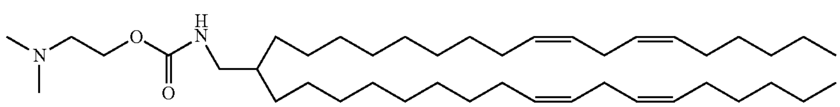 | 5.0 | 7.07 |
| ALNY-175 | 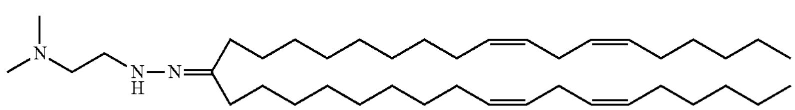 [SMILES: CCCCC/C=C\C/C=C\CCCCCCCCC(CCCCCCCC/C=C\C/C=C\CCCCC)=NNCCN(C)C] | 2.7 | |
| ALNY-149 | 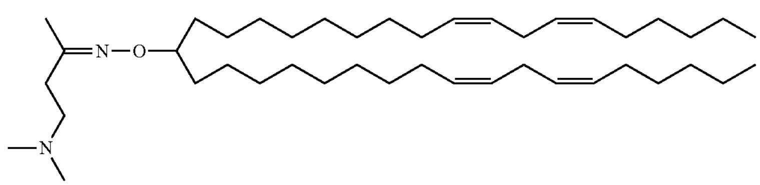 [SMILES: CCCCC/C=C\C/C=C\CCCCCCCCC(CCCCCCCC/C=C\C/C=C\CCCCC)ON=C(C)CCN(C)C] | 0.1 | 5.81 |
| ALNY-160 | 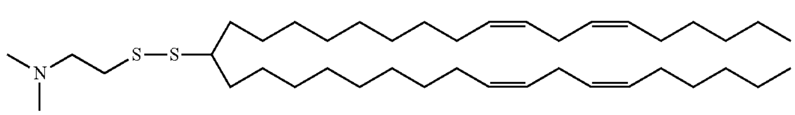 [SMILES: CCCCC/C=C\C/C=C\CCCCCCCCC(CCCCCCCC/C=C\C/C=C\CCCCC)SSCCN(C)C] | 2.00 | 5.18 |
| ALNY-201 | 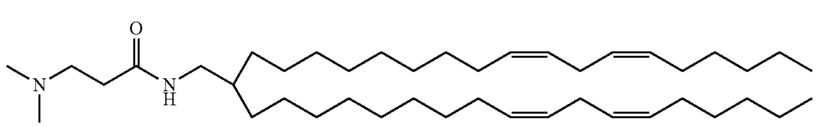 [SMILES: CCCCC/C=C\C/C=C\CCCCCCCCC(CCCCCCCC/C=C\C/C=C\CCCCC)CNC(=O)CCN(C)C] | >5.0 | 8.02 |

-continued
| Compound | Structure | ED50 | pKa |
|---|---|---|---|
| ALNY-141 | 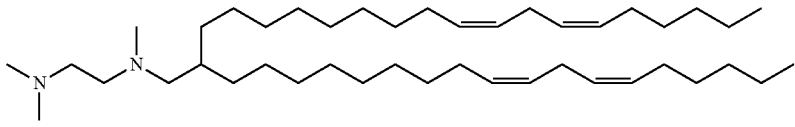 [SMILES: CCCCC/C=C\C/C=C\CCCCCCCCC(CCCCCCCC/C=C\C/C=C\CCCCC)CN(C)CCN(C)C] | 0.14 | 6.62 |
| ALNY-181 | 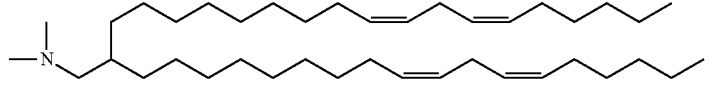 | 0.25 | |
| ALNY-140 | 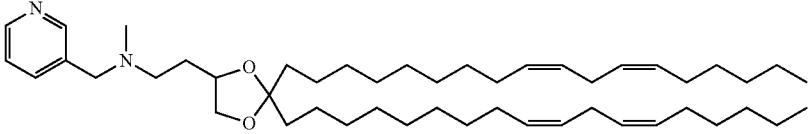 [SMILES: CCCCC/C=C\C/C=C\CCCCCCCCC1(CCCCCCCC/C=C\C/C=C\CCCCC)OCC(CCN(C)Cc2cccnc2)O1] | >5.0 | 4.95 |
| ALNY-148 | 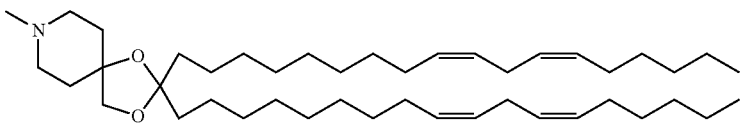 [SMILES: CCCCC/C=C\C/C=C\CCCCCCCCC1(CCCCCCCC/C=C\C/C=C\CCCCC)OCC2(CCN(C)CC2)O1] | 0.3 | 6.53 |
| ALNY-117 | 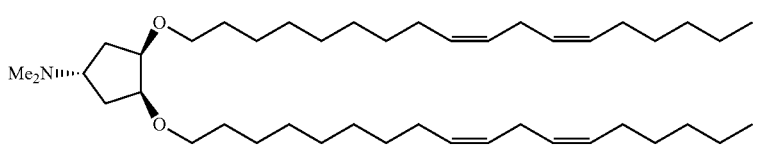 [SMILES: CCCCC/C=C\C/C=C\CCCCCCCCO[C@H]1C[C@H](N(C)C)C[C@H]1OCCCCCCCC/C=C\C/C=C\CCCCC] | >5.0 | |
Example 83
Synthesis of Pyridine Containing Lipids

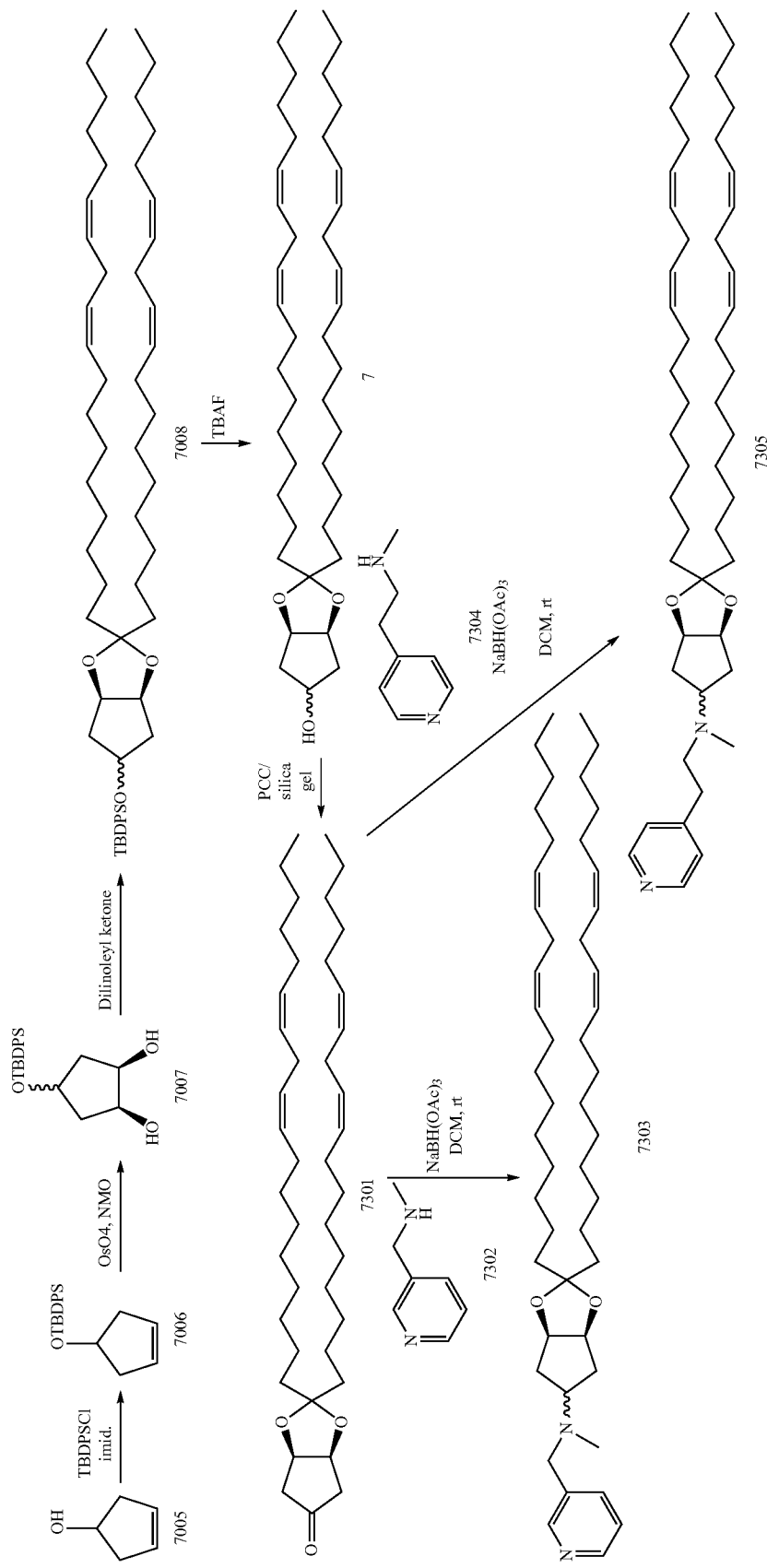

Compound 7006: To a stirred solution of 3-cyclopentene-1-ol (7005, 2.0 g, 23.77 mmol, 1.0 eq) in dichloromethane, was added imidazole (3.88 g, 57.08 mmol, 2.4 eq) portion wise, followed by TBDPSCl (6.1 mL, 23.77 mmol, 1.0 eq) drop wise at room temperature under argon atmosphere. The reaction was continued at room temperature for overnight. After completion of the reaction was washed with water, brine, combined organic layers were dried on $MgSO_4$, evaporated the solvent under reduced pressure and purified by column chromatography using 3% ether in hexane as a gradients to get pure TBDPS protected 3-cyclopentenol (7006) as oil an 87% yield. $^1$H NMR (400 MHz, $CDCl_3$) δ 7.67 (dd, J=7.8, 1.4, 4H), 7.53-7.31 (m, 6H), 5.60 (d, J=7.0, 2H), 4.55 (dq, J=6.6, 4.3, 1H), 2.57-2.24 (m, 4H), 1.05 (s, 9H). Calc. mass for $C_{21}H_{26}OSi$ is 322.0. found 322.5.

Compound 7007: To a cooled solution of $OsO_4$ (0.031 g, 0.12 mmol, 0.01 eq), NMO (50% in water, 5.14 mL, 24.84 mmol, 2.0 eq) in water was treated drop wise with a solution of compound 7006 (4.0 g, 12.42 mmol, 1.0 eq) in acetone. The reaction was continued at room temperature for overnight, after complete consumption of the starting material, solvent was evaporated and the reaction mixture was extracted into ethyl acetate (2×). Combined organics were dried over $Na_2SO_4$, solvent was evaporated, and the mixture was purified by column chromatography using hexane and ethyl acetate (50%) as gradients to get pure dihydroxylated compound (7007) as an oil in 92% yield. $^1$H NMR (400 MHz, $CDCl_3$) δ 7.70-7.53 (m, 4H), 7.49-7.28 (m, 6H), 4.53-4.37 (m, 1H), 4.29 (dd, J=8.0, 4.6, 2H), 2.08 (d, J=4.0, 1H), 1.99-1.78 (m, 4H), 1.58 (s, 1H), 1.04 (d, J=10.2, 9H). Calc. mass for $C_{21}H_{28}O_3Si$ is 356.5. found 379.0 (+Na).

Compound 7008: A mixture of dihydroxylated compound (7007, 4.0 g, 11.4 mmol, 1.0 eq), dilinoleyl ketone (6.0 g, 11.4 mmol, 1.0 eq) and p-toluenesulfonic acid (0.21 g, 1.14 mmol, 0.1 eq) in toluene was refluxed under Dean-stock conditions for 4 hours. TLC shows completion of the reaction, solvent was evaporated and directly purified on column chromatography using hexane and ethyl acetate (5%) as gradients to get 95% of the pure ketal (7008) as an oil. $^1$H NMR (400 MHz, $CDCl_3$) δ 7.75-7.57 (m, 4H), 7.49-7.28 (m, 6H), 5.48-5.16 (m, 8H), 4.62-4.35 (m, 3H), 2.77 (dd, J=14.0, 6.8, 4H), 2.12-1.94 (m, 10H), 1.59 (dd, J=15.4, 6.4, 2H), 1.48-1.15 (m, 35H), 1.07 (d, J=22.0, 14H), 0.88 (t, J=6.8, 6H). Calc. mass for $C_{58}H_{92}O_3Si$ is 864.5. found 887.5 (+Na).

Compound 7009: To a stirred solution of compound 7008 (3.94 g, 4.55 mmol, 1.0 eq) in dichloromethane was added drop wise a solution of 1M TBAF (22.8 mL, 22.79 mmol, 5.0 eq) in THF at 0° C., and the reaction was continued at room temperature until completion of the reaction. Concentrated the reaction, mixture was directly loaded onto the column and purified by column using hexane and ethyl acetate (20%) as gradients to get pure product (7009) as an oil in 87% yield. $^1$H NMR (400 MHz, $CDCl_3$) δ 5.53-5.23 (m, 8H), 4.71-4.61 (m, 2H), 4.56 (s, 1H), 2.80 (t, J=6.4, 4H), 2.41 (dd, J=8.5, 6.7, 2H), 2.23 (dd, J=13.9, 6.0, 2H), 2.07 (q, J=6.8, 8H), 1.70-1.48 (m, 6H), 1.39 (dddd, J=23.0, 20.3, 11.9, 6.6, 36H), 0.92 (q, J=7.2, 6H). Calc. mass for $C_{42}H_{74}O_3$ is 627.0. found 627.5.

Compound 7301: To a solution of the hydroxy compound (7009, 2.5 g, 4.0 mmol, 1.0 eq) in dichloromethane was added PCC (1.3 g, 6.0 mmol, 1.5 eq) adsorbed on silica gel portion wise at room temperature and continued the stirring until the completion of the reaction. Reaction mixture was filtered through the celite, washed with the dichloromethane, the combined organics were washed with water, separated the organic layer, dried, concentrated and purified the mixture using hexane and ethyl acetate (20%) as gradients to get pure oil material of the compound 7301 in 68% yield. $^1$H NMR (400 MHz, $CDCl_3$) δ 5.56-5.22 (m, 8H), 5.05-4.78 (m, 2H), 2.80 (t, J=6.4, 4H), 2.58-2.49 (m, 3H), 2.07 (q, J=6.8, 8H), 1.72-1.50 (m, 4H), 1.47-1.21 (m, 36H), 1.09 (s, 1H), 0.91 (t, J=6.8, 6H). Calc. mass for $C_{42}H_{72}O_3$ is 625.0. found 625.5.

Compound 7303 (ALNY-137): $NaBH(OAc)_3$ (0.16 g, 0.75 mmol, 1.5 eq) was added portion wise to a solution of N-methyl-3-pyridyl methylamine 7302 (0.06 g, 0.5 mmol, 1.0 eq) in dichloromethane at room temperature. After 10 minutes of stirring, a solution of ketone derivative (7301, 0.34 g, 0.55 mmol, 1.1 eq) in dichloromethane was added drop wise at room temperature and continued the reaction for overnight. After completion of the reaction, mixture was quenched with 1N $NaHCO_3$, extracted with dichloromethane; combined organic layers were washed with brine and dried on $MgSO_4$. The concentrated mixture was purified by column chromatography using dichloromethane, methanol (5%), triethylamine (0.3%) as gradients to get pure product (7303) in 0.18 g (51%) quantities. $^1$H NMR (400 MHz, $CDCl_3$) δ 8.63-8.32 (m, 2H), 7.66 (d, J=7.8, 1H), 7.24 (dd, J=7.3, 4.4, 1H), 5.48-5.17 (m, 8H), 4.53 (dd, J=10.0, 5.5, 2H), 3.51 (s, 2H), 2.93-2.61 (m, 5H), 2.24 (dt, J=12.6, 6.1, 2H), 2.13 (s, 3H), 2.04 (q, J=6.7, 8H), 1.71 (ddd, J=15.9, 10.2, 4.6, 4H), 1.52 (d, J=7.3, 2H), 1.46-1.16 (m, 36H), 0.88 (t, J=6.7, 6H). $^{13}$C NMR (101 MHz, $cdcl_3$) δ 150.47, 148.80, 136.76, 134.74, 130.39, 130.38, 130.35, 128.16, 128.14, 123.56, 116.10, 78.93, 77.54, 77.23, 76.91, 64.01, 57.35, 39.32, 37.24, 37.01, 35.85, 31.74, 30.18, 30.10, 29.91, 29.88, 29.82, 29.79, 29.70, 29.57, 29.55, 29.52, 27.46, 27.44, 27.41, 25.84, 24.58, 23.80, 22.80, 14.31. Calc. mass for the $C_{49}H_{82}N_2O_2$: 730.6. found 731.5.

Compound 7305 (ALNY-136): Prepared by similar experimental conditions used as for compound 7303, using $NaBH(OAc)_3$ (0.2 g, 0.98 mmol, 1.5 eq), N-methylpyridine derivative 7304 (0.09 g, 0.65 mmol, 1.0 eq) and ketone derivative (7301, 0.45 g, 0.72 mmol, 1.1 eq), this gave 0.3 g (62%) of the pure product 7305. $^1$H NMR (400 MHz, $CDCl_3$) δ 8.49 (dd, J=4.5, 1.5, 2H), 7.11 (d, J=5.9, 2H), 5.45-5.22 (m, 8H), 4.51 (t, J=4.5, 2H), 2.95-2.56 (m, 9H), 2.31 (s, 3H), 2.19 (dt, J=12.5, 6.2, 2H), 2.04 (q, J=6.7, 8H), 1.71-1.58 (m, 4H), 1.50 (d, J=6.9, 2H), 1.32 (ddd, J=22.2, 13.8, 7.6, 36H), 0.88 (t, J=6.8, 6H). $^{13}$C NMR (101 MHz, $CDCl_3$) δ 149.94, 149.58, 130.39, 130.34, 128.16, 128.13, 128.11, 124.31, 116.12, 78.84, 77.54, 77.22, 76.90, 63.88, 56.34, 39.43, 37.22, 37.04, 35.94, 33.10, 31.73, 30.17, 30.08, 29.91, 29.87, 29.81, 29.78, 29.69, 29.56, 29.54, 29.51, 27.46, 27.43, 27.41, 25.83, 24.55, 23.74, 22.79, 14.30. Calc. mass for the $C_{50}H_{84}N_2O_2$: 744.65. found 745.5.

Example 84

Synthesis of Amide Linked Lipid

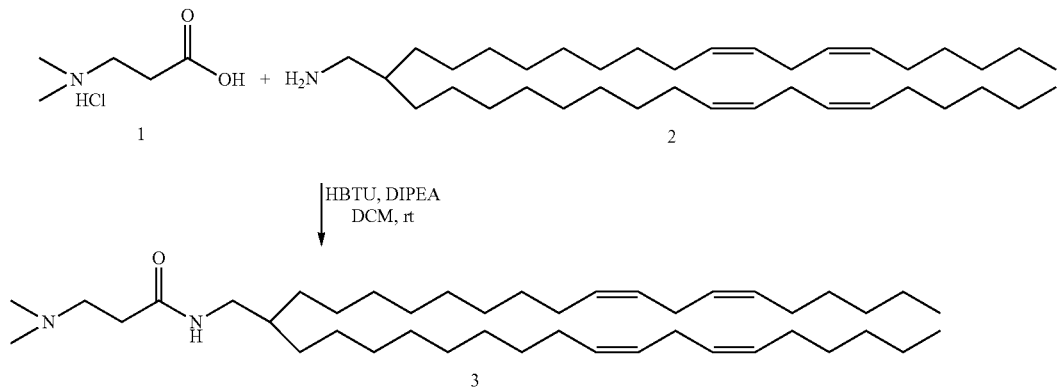

To a stirred suspension of N,N-dimethylamino propionic acid hydrochloride (1, 0.198 g, 1.3 mmol, 1.0 eq) in DCM was added HBTU (0.59 g, 1.56 mmol, 1.2 eq) and DIPEA (0.71 mL, 3.9 mmol, 3.0 eq) at room temperature. After stirred for 10 minutes, a solution of amine (2, 0.7 g. 1.3 mmol, 1.0 eq) in DCM was added drop wise at room temperature and continued the stirring until completion of the reaction. Reaction mixture was diluted with DCM, washed with saturated NaHCO$_3$ solution followed by brine, organic layer was separated and dried over MgSO$_4$, concentrated and purified by the silica gel column chromatography using DCM:MeOH (5%) as gradients to get pure oily compound 3 (ALNY-201) in 70% yield.

$^1$H NMR (400 MHz, CDCl$_3$) δ 7.18 (brs, 1H), 5.47-5.19 (m, 8H), 3.18-3.07 (m, 4H), 2.76 (t, J=6.5, 4H), 2.70 (s, 6H), 2.60 (t, J=6.0, 2H), 2.04 (q, J=6.8, 9H), 1.48 (brs, 1H), 1.40-1.14 (m, 43H), 0.88 (t, J=6.8, 6H). $^{13}$C NMR (101 MHz, CDCl$_3$) δ 172.26, 130.41, 130.36, 128.17, 128.15, 77.54, 77.22, 76.90, 55.70, 43.85, 43.02, 37.90, 31.99, 31.74, 30.25, 29.92, 29.86, 29.81, 29.57, 27.47, 27.42, 26.84, 25.85, 22.79, 14.29. Calc. mass for the C43H80N2O: 640.6. found 641.5.

Example 85

Synthesis of Carbamate and Urea Linked Lipids

Compound 1033

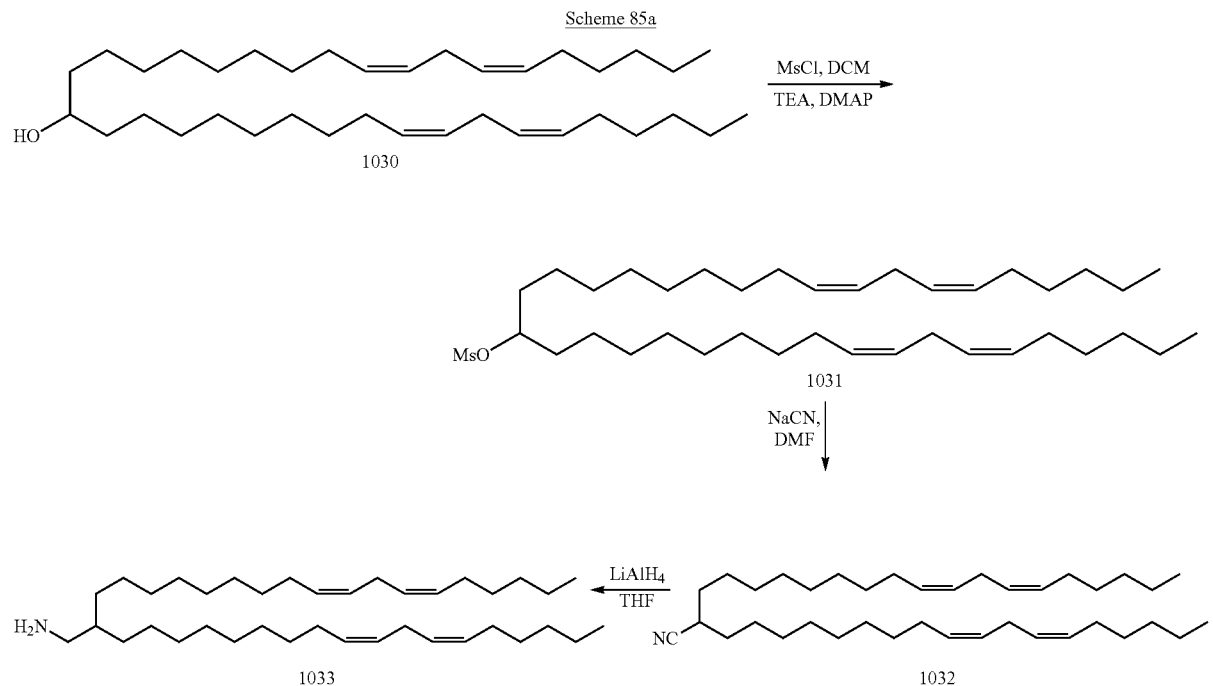

Stage-1:

| S. No | Chemicals/Reagents & solvents | M. Wt. | Mol | Eq. | Qty. |
|---|---|---|---|---|---|
| 1 | Alcohol 1030 | 528 | 0.095 | 1 | 50 g |
| 2 | DCM | | | | 500 ml |
| 3 | Triethylamine (TEA) | 101.2 | 0.378 | 4 | 53 ml |
| 4 | DMAP | 122.17 | 0.0095 | 0.1 | 1.2 g |
| 5 | Mesyl chloride | 114.55 | 0.19 | 2 | 15 ml |

To a solution of Alcohol 1030 in DCM (400 ml) under Ar atmosphere, was added TEA and DMAP and stirred at room temperature under Ar atmosphere. Reaction mass was cooled to −5° C. and the solution of mesyl chloride in DCM (100 ml) was added slowly at temperature below −5° C. and allowed to warm to RT after addition. After 30 minutes (TLC), reaction mass was quenched with ice cold water (20 ml). Organic layer was separated, washed with 1N HCl (30 ml), water, brine, dried over sodium sulfate and evaporated at reduced pressure to obtain pure product 1031 (55 g, yield 95.5%) as an yellow liquid. HPLC: 99.8%; $^1$H NMR (400 MHz, CDCl$_3$): δ 0.89 (t, 6H, J=6.8 Hz), 1.2-1.5 (m, 36H), 1.67 (m, 4H), 2.05 (q, 8H, J=6.8 Hz), 2.77 (t, 4H, J=6.4 Hz), 2.99 (s, 3H), 4.71 (m, 1H) and 5.36 (m, 8H). $^{13}$CNMR (100 MHz, CDCl$_3$): δ 14.0, 22.5, 24.9, 25.6, 27.2, 29.2, 29.3, 29.4, 29.5, 29.6, 31.5, 34.4, 38.6, 45.9, 84.3, 127.9, 128.0, 130.0, 130.1.

Stage-2:

| S. No | Chemicals/Reagents & solvents | M. Wt. | Mol | Eq. | Qty. |
|---|---|---|---|---|---|
| 1 | Mesylate 1031 | 606 | 0.0165 | 1 | 10 g |
| 2 | Dimethylformamide (DMF) | | | | 100 ml |
| 3 | Sodium cyanide | 49 | 0.0330 | 2 | 1.617 g |

To a solution of sodium cyanide in DMF under Ar atmosphere, was added stage-1 product in DMF slowly and then heated to 55° C. for 24 hrs (HPLC). It was then cooled to room temperature, diluted with water and extracted with ethyl acetate (several times). The combined organic layer was washed with water, brine, dried over sodium sulfate and evaporated at reduced pressure to obtain crude product, which was purified silica gel chromatography using 1% ether/hexane as eluent to afford pure product 1032 (5.8 g, yield: (62%) as a pale yellow liquid. $^1$H NMR (400 MHz, CDCl$_3$): δ 0.87 (t, 6H, J=6.8 Hz), 1.25 (m, 38H), 1.52 (m, 4H), 2.03 (q, 8H, J=6.8 Hz), 2.47 (m, 1H), 2.76 (t, 4H, J=6.4 Hz), 5.32 (m, 8H).

Stage-3:

| S. No | Chemicals/Reagents & solvents | M. Wt. | Mol. | Eq. | Qty. |
|---|---|---|---|---|---|
| 1 | Nitrile 1032 | 538 | 0.0097 | 1 | 5.2 g |
| 2 | Lithium aluminiumhydride | 38 | 0.0387 | 4 | 1.5 g |
| 3 | Tetrahydrofuran (THF) | | | | 52 ml |

To a suspension of lithium aluminiumhydride in dry THF at Ar atmosphere, was added stage-2 product in THF at 0° C. drop-wise. It was then allowed to warm to room temperature (RT) and stirred for 20 hrs at RT (TLC). It was cooled to 0° C. and quenched with saturated solution of sodium sulfate. The quenched mass was filtered through celite bed and washed with ethyl acetate. The combined filtrate was evaporated at reduced pressure to obtain crude product, which was purified by silica gel chromatography using 10% ethyl acetate in hexane to afford pure product 1033 (3.7 g, yield: 71%) as pale brown liquid, HPLC: 93.8%. $^1$H NMR (400 MHz, CDCl$_3$): δ 0.87 (t, 6H, J=6.8 Hz), 1.27 (m, 48H), 2.03 (q, 8H, J=6.8 Hz), 2.60 (d, 2H, J=4.0 Hz), 2.76 (t, 4H, J=6.4 Hz), 5.31 (m, 8H). $^{13}$CNMR (100 MHz, CDCl$_3$): δ 14.1, 22.6, 25.6, 26.8, 27.1, 27.2, 29.3, 29.5, 29.6, 30.1, 31.5, 40.9, 45.2, 128.0, 130.1. LC-MS: 543 (M+).

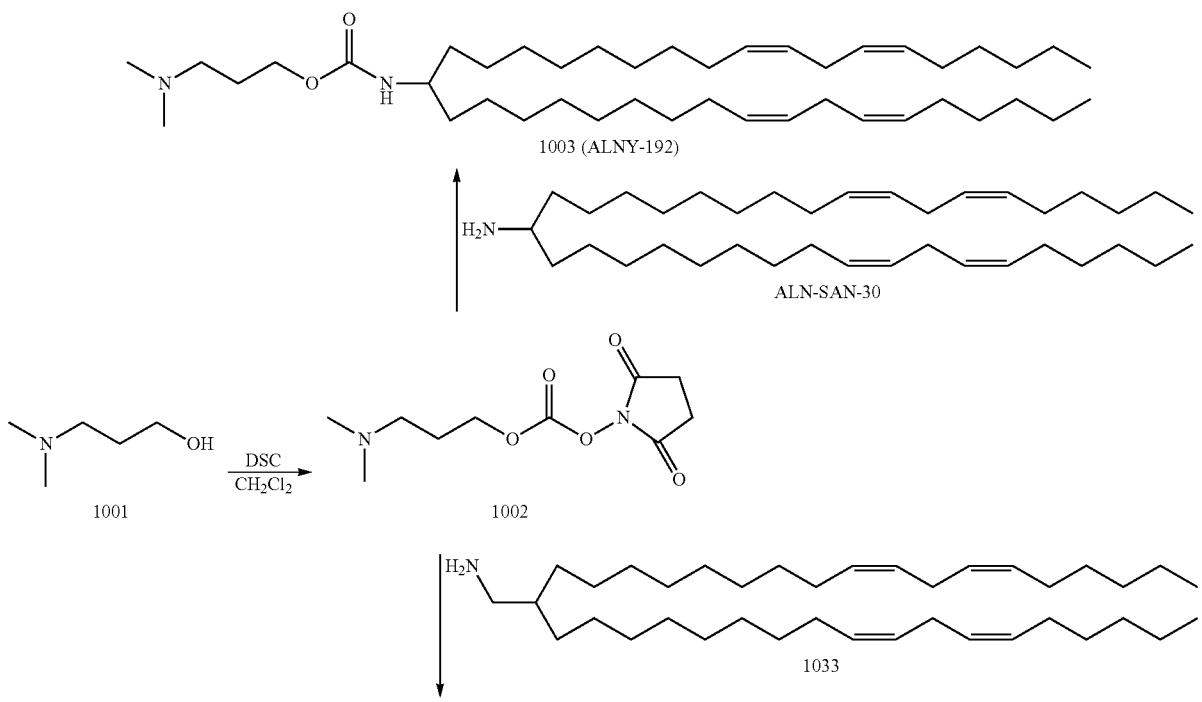

Scheme 85b

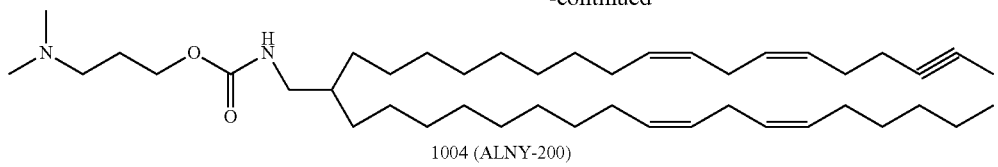

1004 (ALNY-200)

Compound 1003 (ALNY-192)

To a solution of N,N'-disuccinimidyl carbonate (5.50 g, 21.5 mmol) in CH$_2$Cl$_2$ (200 mL), 3-dimethylamino-1-propanol (1001, 2.43 g, 23.6 mmol) was added dropwise. The resulting mixture was stirred at room temperature overnight. Taken up 50 mL of the solution, Et$_3$N (0.822 mL, 5.90 mmol) and ALN-SAN-30 (2.08 g, 3.93 mmol) were added and the reaction mixture was stirred at room temperature overnight. The reaction mixture was diluted with CH$_2$Cl$_2$ and washed with saturated NaHCO$_3$ aq. The organic layer was dried over anhydrous MgSO$_4$, filtered and concentrated. The crude was purified by silica gel column chromatography (0-5% MeOH in CH$_2$Cl$_2$) to give compound 1003 (1.66 g, 2.53 mmol, 64%, R$_f$=0.22 with 5% MeOH in CH$_2$Cl$_2$). $^1$H NMR (CDCl$_3$, 400 MHz) 5.30-5.41 (m, 8H), 4.37 (d, J=8.0 Hz, 1H), 4.09 (t, J=6.0 Hz, 2H), 3.57 (brs, 1H), 2.78 (t, J=6.0 Hz, 4H), 2.33 (t, J=8.0 Hz, 2H), 2.23 (s, 6H), 2.02-2.06 (m, 8H), 1.76-1.80 (m, 2H), 1.27-1.45 (m, 40H), 0.89 (t, J=8.0 Hz, 6H). $^{13}$C NMR (CDCl$_3$, 100 MHz) 156.5, 130.4, 130.3, 128.2, 128.1, 63.2, 56.6, 51.4, 45.7, 35.7, 31.7, 29.9, 29.8, 29.7, 29.6, 29.5, 27.7, 27.5, 27.4, 26.0, 25.8, 22.8, 14.3. Molecular weight for C$_{43}$H$_{81}$N$_2$O$_2$ (M+H)$^+$ Calc. 657.63. Found 657.5.

Compound 1004 (ALNY-200)

To a solution of N,N'-disuccinimidyl carbonate (5.50 g, 21.5 mmol) in CH$_2$Cl$_2$ (200 mL), 3-dimethylamino-1-propanol (1001, 2.43 g, 23.6 mmol) was added dropwise. The resulting mixture was stirred at room temperature overnight. Taken up 50 mL of the solution, Et$_3$N (0.697 mL, 5.00 mmol) and amine 1033 (1.71 g, 3.15 mmol) were added and the reaction mixture was stirred at room temperature overnight. The reaction mixture was diluted with CH$_2$Cl$_2$ and washed with saturated NaHCO$_3$ aq. The organic layer was dried over anhydrous MgSO$_4$, filtered and concentrated. The crude was purified by silica gel column chromatography (0-5% MeOH in CH$_2$Cl$_2$) to give compound 1004 (1.14 g, 1.70 mmol, 54%, R$_f$=0.13 with 5% MeOH in CH$_2$Cl$_2$). Molecular weight for C$_{44}$H$_{83}$N$_2$O$_2$ (M+H)$^+$ Calc. 671.65. Found 671.5.

Scheme 85c

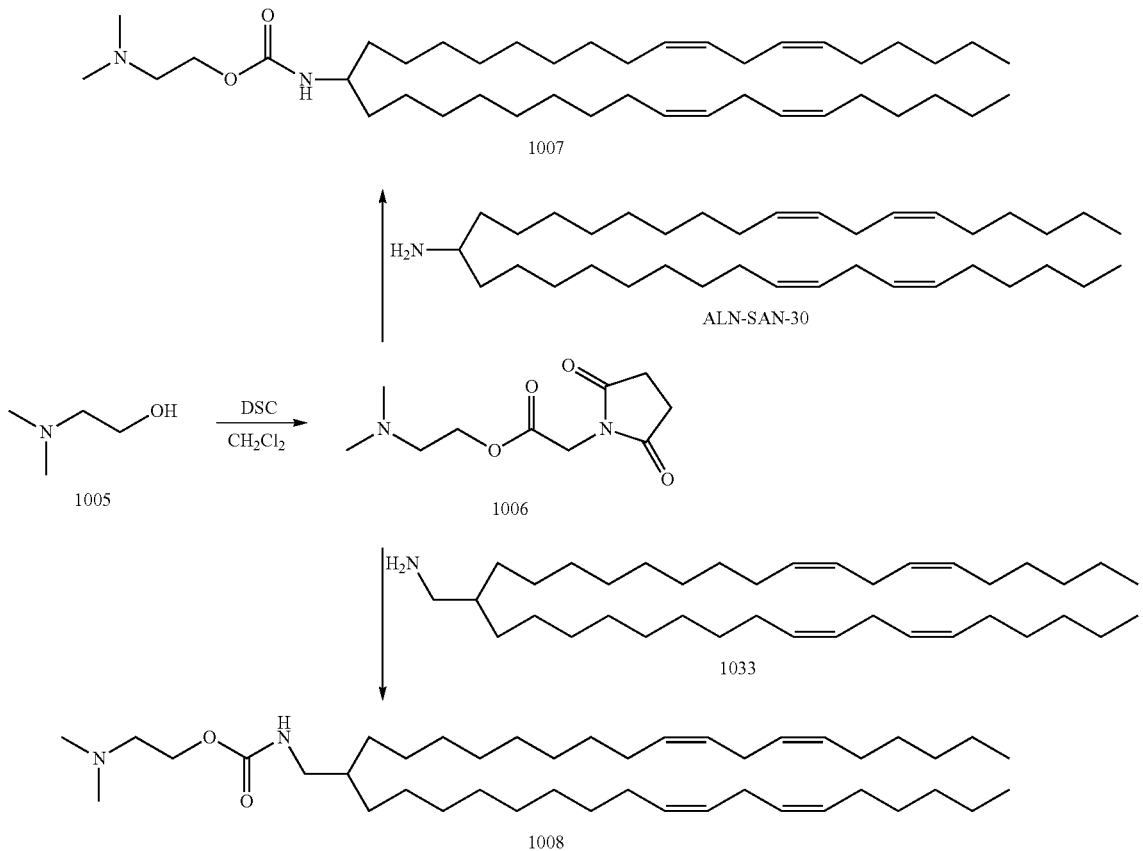

Compound 1007 (ALNY-202)

To a solution of N,N'-disuccinimidyl carbonate (5.50 g, 21.5 mmol) in $CH_2Cl_2$ (200 mL), 2-dimethylaminoethanol (1005, 2.37 mL, 23.6 mmol) was added dropwise. The resulting mixture was stirred at room temperature overnight. Taken up 50 mL of the solution, $Et_3N$ (0.822 mL, 5.90 mmol) and ALN-SAN-30 (2.07 g, 3.92 mmol) were added and the reaction mixture was stirred at room temperature overnight. The reaction mixture was diluted with $CH_2Cl_2$ and washed with saturated $NaHCO_3$ aq. The organic layer was dried over anhydrous $MgSO_4$, filtered and concentrated. The crude was purified by silica gel column chromatography (0-5% MeOH in $CH_2Cl_2$) to give compound 1007 (1.78 g, 2.77 mmol, 71%, 2 steps, $R_f$=0.26 developed with 5% MeOH in $CH_2Cl_2$). Molecular weight for $C_{42}H_{79}N_2O_2$ $(M+H)^+$ Calc. 643.61. Found 643.5.

Compound 1008 (ALNY-203)

To a solution of N,N'-disuccinimidyl carbonate (5.50 g, 21.5 mmol) in $CH_2Cl_2$ (200 mL), 2-dimethylaminoethanol (1005, 2.37 mL, 23.6 mmol) was added dropwise. The resulting mixture was stirred at room temperature overnight. Taken up 50 mL of the solution, $Et_3N$ (0.697 mL, 5.00 mmol) and 1033 (440 mg, 0.812 mmol) were added and the reaction mixture was stirred at room temperature overnight. The reaction mixture was diluted with $CH_2Cl_2$ and washed with saturated $NaHCO_3$ aq. The organic layer was dried over anhydrous $MgSO_4$, filtered and concentrated. The crude was purified by silica gel column chromatography (0-5% MeOH in $CH_2Cl_2$) to give compound 8 (332 mg, 0.505 mmol, 62%, $R_f$=0.30 with 5% MeOH in $CH_2Cl_2$). Molecular weight for $C_{43}H_{81}N_2O_2$ $(M+H)^+$ Calc. 657.63. Found 657.5.

Example 86

Synthesis of Guanidinium Linked Lipids

Guanidinium Analogs

Synthesis of 2064

Synthesis of 2063: To a solution of 2058 (6.7 g, 0.0112 mol) in DMF/Ethyl acetate mixture was added Bis-Boc-S-methylisothiourea (3.4 g, 0.0118 mol) and triethylamine (3.5 mL, 0.246 mol) at 0° C. To the homogeneous solution was added $HgCl_2$ (3.3 g, 0.0123 mol) at 0° C. and stirred at RT for 1 hr. TLC showed the absence of starting material. The reaction mass was then diluted with ethyl acetate (100 ml). Filtered through a pad of celite and washed with ethyl acetate. The filtrate was given water wash (2×150 ml) and brine wash (200 ml). The hazy organic layer was again filtered through a pad of celite/230-400 mesh silica gel/celite. The filtrate was evaporated at reduced pressure to obtain the crude product, which was purified by neutral alumina chromatography using and DCM/Hexane as eluent. The product got eluted at 40% DCM in Hexane as yellow liquid (Yield 5.2 g, 55%). $^1$H NMR (400 MHz, $CDCl_3$): 0.89 (t, 6H, J=6.8 Hz), 1.27-1.46 (m, 43H), 1.49 (s, 9H), 1.50 (s, 9H), 2.02 (q, 8H, $J_1$=6.8 Hz, $J_2$=6.8 Hz), 2.12 (d, 2H, J=7.2 Hz), 2.16 (s, 3H), 2.46 (t, 2H, J=5.6 Hz), 2.77 (t, 4H, J=6 Hz), 3.47 (m, 2H), 5.30 (m, 8H), 8.67 (s, 1H), 11.48 (9s, 1H).

Synthesis of 2064 (ALNY-139): To a solution of 2063 (5.2 g, 0.0062 mol) in 10 ml of DCM at 0° C., was added 10 ml of TFA in 60 ml of DCM slowly. After addition the reaction mass was stirred at RT for 3 hrs. The TLC showed the absence of starting material. Excess TFA was removed under vacuum, to obtain the required product as brown viscous liquid (5.3 g, 78%). $^1$H NMR (400 MHz, $CDCl_3$): 0.89 (t, 6H, J=6.8 Hz), 1.27-1.46 (m, 44H), 1.78 (s, 1H), 2.02 (q, 8H, $J_1$=6.4 Hz, $J_2$=6.8 Hz), 2.77 (t, 4H, J=6.4 Hz), 2.86 (s, 3H), 2.92-3.01 (m, 2H), 3.27-3.39 (m, 2H), 3.76-3.9 (m, 2H), 5.30 (m, 8H), 7.12 (m, 2H), 8.41 (m, 1H), 10.02 (m, 3H). $^{13}$C NMR (100 MHz, $CDCl_3$): 14.0, 22.5, 25.6, 25.8, 26.0, 27.17, 27.19, 27.6, 29.3, 29.33, 29.5, 29.6, 31.0, 31.5, 33.9, 36.3, 41.0, 54.1, 55.2, 62.0, 62.19, 111.4, 114.3, 117.1, 119.9, 127.9, 127.95, 130.1, 130.2, 152.1, 155.0, 157.4, 161.2, 161.6, 161.96, 162.3. MS: 1093 (tetra TFA salt).

Preparation of Compound 7204

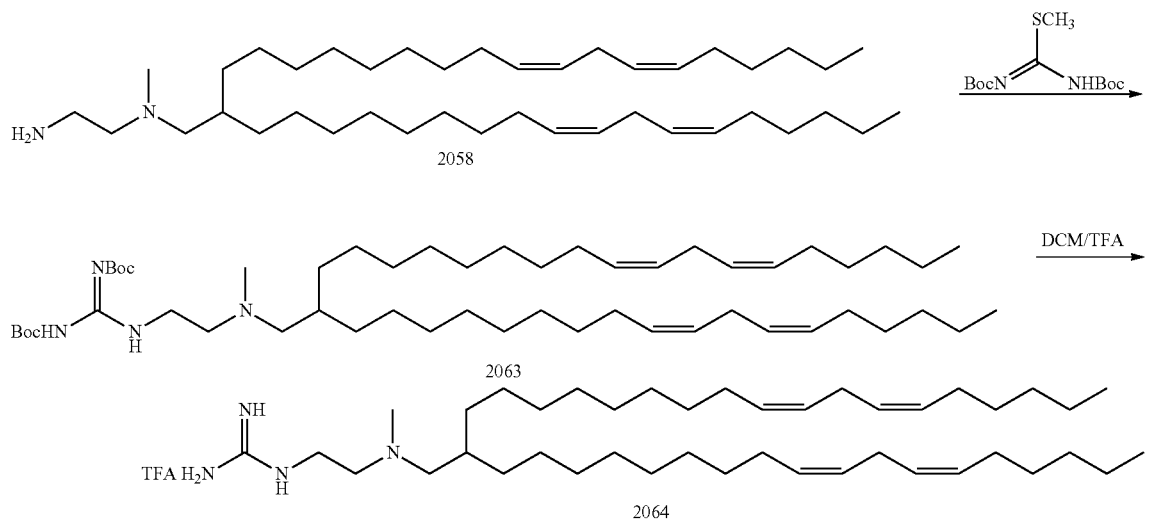

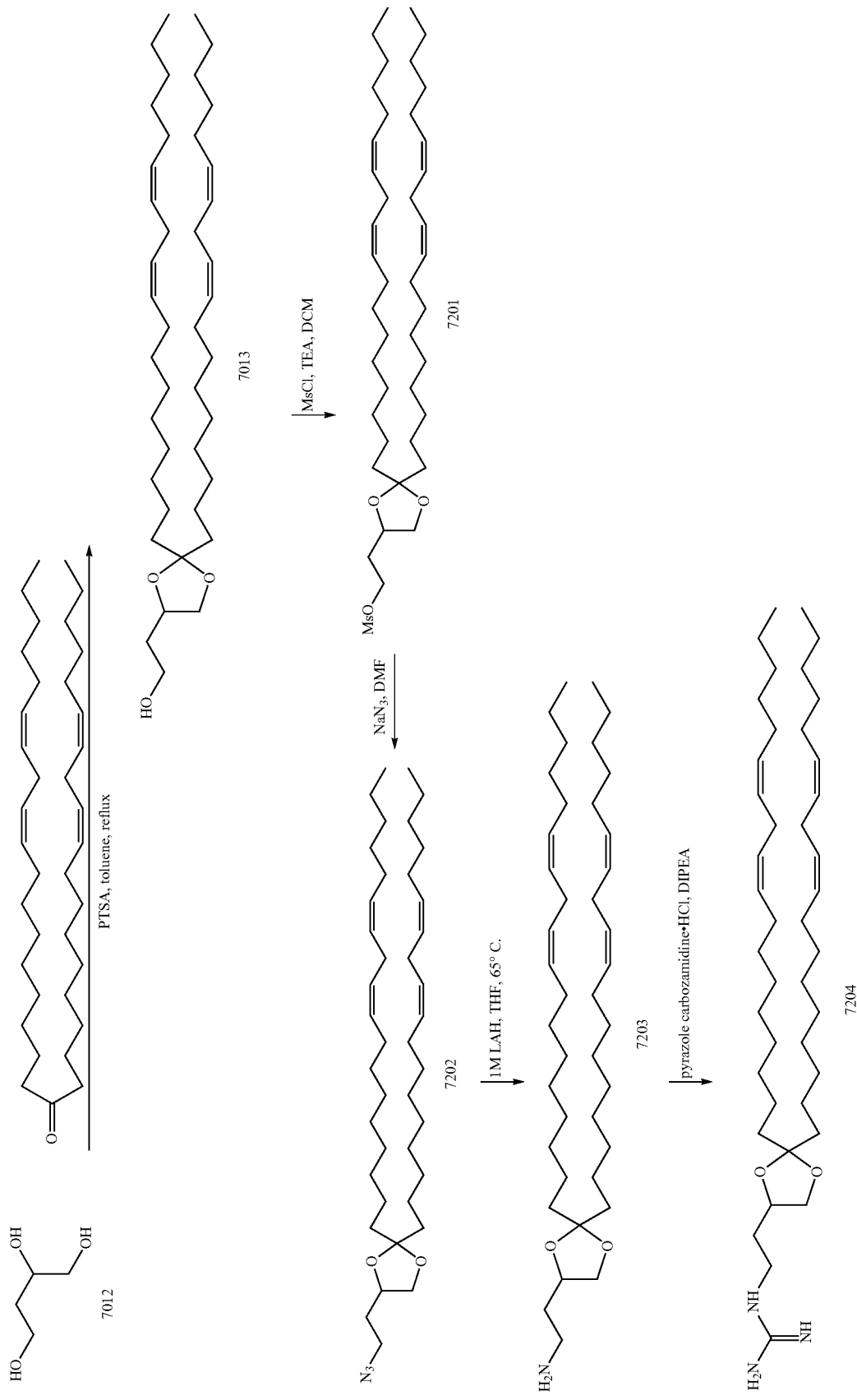

Preparation of Compound 7013: To a mixture of 1,2,4-butanetriol (7012, 21.2 g, 200 mmol, 5.0 eq), dilinoleyl ketone (21.0 g, 40.0 mmol, 1.0 eq) and p-toluenesulfonic acid (0.76 g, 4.0 mmol, 0.1 eq) in toluene was refluxed under Dean-stock conditions for overnight. After completion of the reaction, was cooled, evaporated the solvent and purified by column chromatography using hexane and ethyl acetate (15%) as gradients gave desired ketal (7013) in 47% yield as an oil. $^1$H NMR (400 MHz, CDCl$_3$) δ 5.48-5.24 (m, 8H), 4.32-4.17 (m, 1H), 4.08 (dd, J=7.8, 6.1, 1H), 3.86-3.74 (m, 2H), 3.53 (t, J=8.0, 1H), 2.77 (t, J=6.4, 4H), 2.30-2.19 (m, 1H), 2.05 (q, J=6.8, 8H), 1.88-1.75 (m, 2H), 1.69-1.51 (m, 4H), 1.42-1.19 (m, 36H), 0.89 (t, J=6.8, 6H). Calc. mass for C$_{41}$H$_{74}$O$_3$ is 614.5. found 637.3 (+Na).

Synthesis of compound 7201: To a solution of compound 7013 (11.6 g, 18.9 mmol, 1.0 eq) and triethyl amine (5.45 mL, 37.7 mmol, 2.0 eq) in dichloromethane at 0° C. was added drop wise a solution of methanesulfonyl chloride (1.74 mL, 22.67 mmol, 1.2 eq), and the reaction was continued at room temperature for 1 h. After completion of the reaction, was washed with water, brine, and combined organics were dried on MgSO$_4$. The concentrated mixture was purified on column chromatography using hexane and ethyl acetate (20%) as gradients to get pure mesylated derivative (7201) as an oil in 93% yield. $^1$H NMR (400 MHz, CDCl$_3$) δ 5.48-5.22 (m, 8H), 4.35 (qd, J=10.0, 4.9, 2H), 4.25-4.14 (m, 1H), 4.13-4.03 (m, 1H), 3.53 (t, J=7.6, 1H), 3.02 (s, 3H), 2.77 (t, J=6.4, 4H), 2.13-1.85 (m, 10H), 1.57 (dd, J=18.2, 9.2, 4H), 1.44-1.15 (m, 36H), 0.89 (t, J=6.7, 6H). Calc. mass for C$_{42}$H$_{76}$O$_5$S is 693.1. found 693.2.

Synthesis of compound 7202: To a solution of the compound 7201 (2.0 g, 3.0 mmol, 1.0 eq) in DMF was added solid NaN$_3$ (0.98 g, 15.0 mmol, 5.0 eq) at room temperature and the reaction was continued at 65° C. until the completion of the reaction. Reaction mixture was poured onto ice water, extracted into ethyl acetate, combined organics were dried on Na$_2$SO$_4$, concentrated, purified on column chromatography using hexane and ethyl acetate (5%) as gradients to get pure azido (7202) derivative in 89% yield. $^1$H NMR (400 MHz, CDCl$_3$) δ 5.53-5.19 (m, 8H), 4.21-3.97 (m, 2H), 3.57-3.29 (m, 3H), 2.76 (t, J=6.4, 4H), 2.04 (q, J=6.8, 8H), 1.80 (m, 2H), 1.66-1.43 (m, 4H), 1.40-1.07 (m, 36H), 0.88 (t, J=6.8, 6H). Calc. mass for C$_{41}$H$_{73}$N$_3$O$_2$ is 640.0. found 612.5 (—N$_2$).

Synthesis of compound 7203: To a solution of compound 7202 (1.7 g, 2.65 mmol, 1.0 eq) in anhydrous tetrahydrofuran, was added drop wise a 1M solution of LAH (3.98 mL, 3.98 mmol, 1.5 eq) at 0° C. Reaction was continued at room temperature, after completion of the reaction was quenched with saturated solution of Na$_2$SO$_4$ slowly at 0° C. Compound was extracted into excess amount of ethyl acetate, organic layer was washed with brine, dried over Na$_2$SO$_4$, concentrated and further dried on vacuum to get pure amine (7203) in 90% yield, and this has been used directly without further purification. $^1$H NMR (400 MHz, CDCl$_3$) δ 5.51-5.16 (m, 8H), 4.13 (dd, J=9.3, 3.6, 1H), 4.03 (dd, J=7.5, 6.1, 1H), 3.46 (t, J=7.8, 1H), 2.96-2.67 (m, 6H), 2.20-1.92 (m, 8H), 1.82-1.49 (m, 6H), 1.46-1.12 (m, 38H), 0.88 (t, J=6.8, 6H). Calc. mass for the C$_{41}$H$_{75}$NO$_2$ is 614.0. found 614.5.

Synthesis of compound 7204 (ALNY-232): To a solution of amine 7203 (0.61 g, 1.0 mmol, 1.0 eq) and DIPEA (1.84 mL, 10.0 mmol, 10.0 eq) in a solvent mixture (DCM:DMF) was added 1H-pyrazole-1-carboxamidine hydrochloride (1.46 g, 10.0 mmol, 10.0 eq) portion wise at room temperature, under argon atmosphere. The reaction was continued for overnight, after completion of the reaction, was poured onto ice, and extracted with the ethyl acetate. The combined organics were washed with water, brine, dried over Na$_2$SO$_4$ and purified by preparative chromatography to get pure 0.16 g (25%) of the guanidine derivative (7204). 1H NMR (400 MHz, CDCl3) δ 11.76 (s, 1H), 7.99 (t, J=6.3, 1H), 7.44 (s, 2H), 5.48-5.20 (m, 8H), 4.24-4.00 (m, 2H), 3.54 (dd, J=7.3, 6.2, 1H), 3.32 (d, J=3.0, 2H), 3.09 (dt, J=10.5, 5.3, 1H), 2.76 (t, J=6.5, 4H), 2.03 (q, J=6.8, 8H), 1.90-1.77 (m, 1H), 1.76-1.49 (m, 6H), 1.48-1.05 (m, 34H), 0.87 (dd, J=6.8, 6H). $^{13}$C NMR (101 MHz, cdcl$_3$) δ 158.96, 130.41, 130.36, 130.33, 128.18, 128.14, 113.52, 77.54, 77.22, 76.90, 76.60, 72.36, 69.54, 46.09, 38.39, 37.68, 37.01, 34.09, 31.74, 30.10, 29.92, 29.78, 29.76, 29.56, 29.55, 29.53, 27.47, 27.46, 27.41, 25.84, 24.37, 24.12, 22.79, 14.31, 8.86. Calc. mass for the C$_{42}$H$_{77}$N$_3$O$_2$ is 656.0. found 656.2.

Example 87

Synthesis of Ester Linked Lipids

Lipid Discovery
Ester Analogs

Scheme 87a

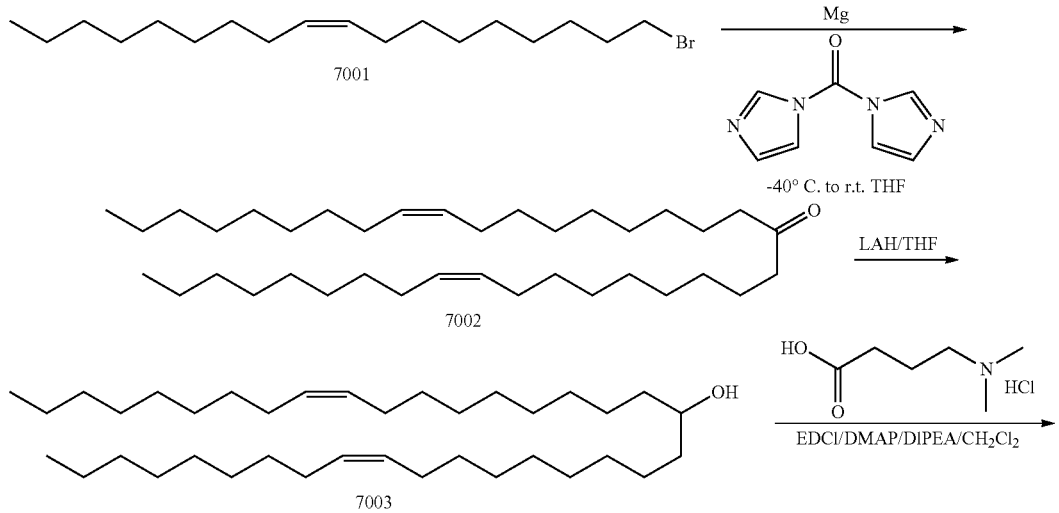

-continued

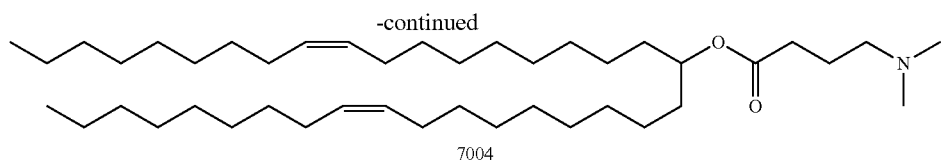

7004

Experimental

Compound 7002: Magnesium (711 mg, 29.25 mmol) was placed in a round bottle flask. THF (30 mL) and 2-3 mg of $I_2$ were added. The mixture was warmed at 50° C. and oleylbromide (7001, 6.46 g, 19.50 mmol) was added slowly. When ~1 mL of oleylbromide was added, formation of the Grignard reagent was initiated. After addition of the reast of oleylbromide, the Grignard reagent was stirred at room temperature for 60 min then slowly added to a solution of 1,1'-carbonyldiimidazole (1.54 g, 9.51 mmol) in THF (100 mL) at −50° C. The reaction mixture was kept stirring at −50° C. for 30 min then at room temperature for 60 min. The reaction was quenched with 40 mL of saturated $NH_4Cl$ aq. and the mixture was extracted with $Et_2O$ and $H_2O$. The organic layer was dried over $MgSO_4$, filtered and concentrated. The crude was purified by silica gel column chromatography (0-5% $Et_2O$ in Hexane) to give compound 7002 (2.70 g, 5.09 mmol, 53%, $R_f$=0.48 developed with 5% EtOAc in Hexane). Molecular weight for $C_{37}H_{71}O$ $(M+H)^+$ Calc. 531.55. Found 531.5.

Compound 7003: To a solution of compound 7002 (1.36 g, 2.56 mmol) in THF (25 mL), 1 M lithium aluminum hydride in THF (5.12 mL, 5.12 mmol) was added at 0° C. The reaction mixture was stirred at room temperature for 3 hours. The reaction was quenched with saturated $Na_2SO_4$ aq. (20 mL), then extracted with $Et_2O$ and $H_2O$. The organic layer was dried over $MgSO_4$, filtered and concentrated. The crude was purified by silica gel column chromatography (0-5% $Et_2O$ in Hexane) to give compound 7003 (942 mg, 1.77 mmol, 69%, $R_f$=0.26 developed with 5% EtOAc in Hexane).

Compound 7004: To a solution of compound 7003 (940 mg, 1.76 mmol) and 4-(dimethylamino)butyric acid hydrochloride (355 mg, 2.12 mmol) in $CH_2Cl_2$ (15 mL), diisopropylethylamine (0.920 mL, 5.28 mmol), N-(3-dimethylaminopropyl)-N'-ethylcarbodiimide hydrochloride (406 mg, 2.12 mmol) and DMAP (43 mg, 0.352 mmol) were added. The reaction mixture was stirred at room temperature for 14 hours. The reaction mixture was diluted with $CH_2Cl_2$ (100 mL) and washed with saturated $NaHCO_3$ aq. (50 mL). The organic layer was dried over $MgSO_4$, filtered and concentrated. The crude was purified by silica gel column chromatography (0-5% MeOH in $CH_2Cl_2$) to give compound 7004 (817 mg, 1.26 mmol, 72%, $R_f$=0.29 developed with 5% MeOH in $CH_2Cl_2$). Molecular weight for $C_{43}H_{84}NO_2$ $(M+H)^+$ Calc. 646.65. Found 646.5.

Scheme 87b

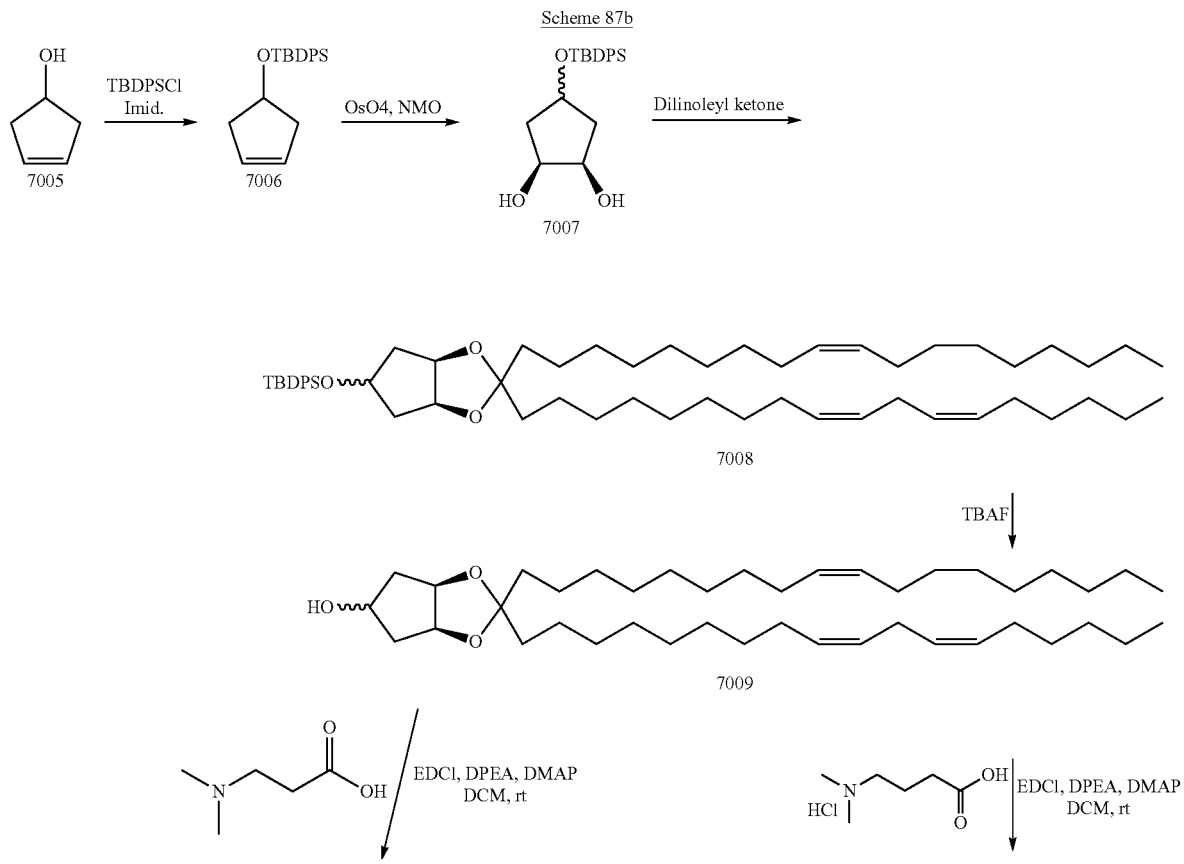

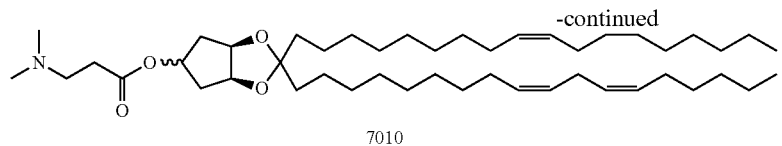

7010

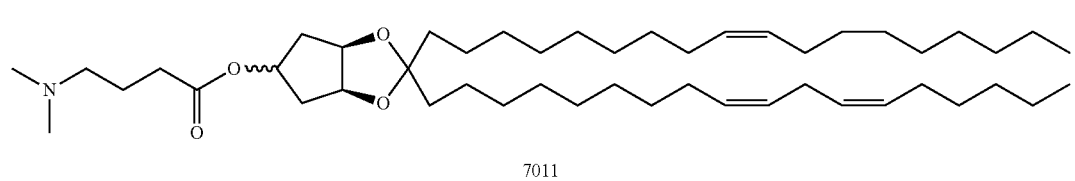

7011

Compound 7006: To a stirred solution of 3-cyclopentene-1-ol (7005, 2.0 g, 23.77 mmol, 1.0 eq) in dichloromethane, was added imidazole (3.88 g, 57.08 mmol, 2.4 eq) portion wise, followed by TBDPSCl (6.1 mL, 23.77 mmol, 1.0 eq) drop wise at room temperature under argon atmosphere. The reaction was continued at room temperature for overnight. After completion of the reaction was washed with water, brine, combined organic layers were dried on MgSO$_4$, evaporated the solvent under reduced pressure and purified by column chromatography using 3% ether in hexane as a gradients to get pure TBDPS protected 3-cyclopentenol (7006) as oil an 87% yield. $^1$H NMR (400 MHz, CDCl$_3$) δ 7.67 (dd, J=7.8, 1.4, 4H), 7.53-7.31 (m, 6H), 5.60 (d, J=7.0, 2H), 4.55 (dq, J=6.6, 4.3, 1H), 2.57-2.24 (m, 4H), 1.05 (s, 9H). Calc. mass for C$_{21}$H$_{26}$OSi is 322.0. found 322.5.

Compound 7007: To a cooled solution of OsO$_4$ (0.031 g, 0.12 mmol, 0.01 eq), NMO (50% in water, 5.14 mL, 24.84 mmol, 2.0 eq) in water was treated drop wise with a solution of compound 7006 (4.0 g, 12.42 mmol, 1.0 eq) in acetone. The reaction was continued at room temperature for overnight, after complete consumption of the starting material, solvent was evaporated and the reaction mixture was extracted into ethyl acetate (2×). Combined organics were dried over Na$_2$SO$_4$, solvent was evaporated, and the mixture was purified by column chromatography using hexane and ethyl acetate (50%) as gradients to get pure dihydroxylated compound (7007) as an oil in 92% yield. $^1$H NMR (400 MHz, CDCl$_3$) δ 7.70-7.53 (m, 4H), 7.49-7.28 (m, 6H), 4.53-4.37 (m, 1H), 4.29 (dd, J=8.0, 4.6, 2H), 2.08 (d, J=4.0, 1H), 1.99-1.78 (m, 4H), 1.58 (s, 1H), 1.04 (d, J=10.2, 9H). Calc. mass for C21H$_{28}$O$_3$Si is 356.5. found 379.0 (+Na).

Compound 7008: A mixture of dihydroxylated compound (7007, 4.0 g, 11.4 mmol, 1.0 eq), dilinoleyl ketone (6.0 g, 11.4 mmol, 1.0 eq) and p-toluenesulfonic acid (0.21 g, 1.14 mmol, 0.1 eq) in toluene was refluxed under Dean-stock conditions for 4 hours. TLC shows completion of the reaction, solvent was evaporated and directly purified on column chromatography using hexane and ethyl acetate (5%) as gradients to get 95% of the pure ketal (7008) as an oil. $^1$H NMR (400 MHz, CDCl$_3$) δ 7.75-7.57 (m, 4H), 7.49-7.28 (m, 6H), 5.48-5.16 (m, 8H), 4.62-4.35 (m, 3H), 2.77 (dd, J=14.0, 6.8, 4H), 2.12-1.94 (m, 10H), 1.59 (dd, J=15.4, 6.4, 2H), 1.48-1.15 (m, 35H), 1.07 (d, J=22.0, 14H), 0.88 (t, J=6.8, 6H). Calc. mass for C$_{58}$H$_{92}$O$_3$Si is 864.5. found 887.5 (+Na).

Compound 7009: To a stirred solution of compound 7008 (3.94 g, 4.55 mmol, 1.0 eq) in dichloromethane was added drop wise a solution of 1M TBAF (22.8 mL, 22.79 mmol, 5.0 eq) in THF at 0° C., and the reaction was continued at room temperature until completion of the reaction. Concentrated the reaction, mixture was directly loaded onto the column and purified by column using hexane and ethyl acetate (20%) as gradients to get pure product (7009) as an oil in 87% yield. $^1$H NMR (400 MHz, CDCl$_3$) δ 5.53-5.23 (m, 8H), 4.71-4.61 (m, 2H), 4.56 (s, 1H), 2.80 (t, J=6.4, 4H), 2.41 (dd, J=8.5, 6.7, 2H), 2.23 (dd, J=13.9, 6.0, 2H), 2.07 (q, J=6.8, 8H), 1.70-1.48 (m, 6H), 1.39 (dddd, J=23.0, 20.3, 11.9, 6.6, 36H), 0.92 (q, J=7.2, 6H). Calc. mass for C$_{42}$H$_{74}$O$_3$ is 627.0. found 627.5.

Compound 7010 (ALNY-236): To a stirred solution of alcohol 7009 (0.8 g, 1.27 mmol, 1.0 eq), N,N-dimethylamino propionic acid hydrochloride (0.23 g, 1.53 mmol, 1.2 eq), DIPEA (0.7 mL, 3.81 mmol, 3.0 eq) in dichloromethane at room temperature was added EDCI (0.26 g, 1.4 mmol, 1.1 eq) followed by DMAP (0.015 g, 0.12 mmol, 0.1 eq) portion wise under argon and continued the reaction for overnight at room temperature. After completion of the reaction was diluted with dichloromethane, washed with saturated solution of NaHCO$_3$, brine, combined organics were dried over MgSO$_4$, evaporated the solvent and purified by column chromatography using dichloromethane: methanol (5%) as gradients to get pure product 7010 in 79% (0.72 g) yields. $^1$H NMR (400 MHz, CDCl$_3$) δ 5.47-5.18 (m, 8H), 4.64 (d, J=5.3, 2H), 2.76 (t, J=6.3, 4H), 2.58 (t, J=7.3, 2H), 2.43 (dd, J=9.2, 5.3, 2H), 2.30 (dd, J=14.0, 6.3, 2H), 2.22 (s, 6H), 2.04 (q, J=6.7, 8H), 1.72-1.56 (m, 4H), 1.49 (s, 2H), 1.32 (ddd, J=22.1, 13.7, 7.6, 37H), 0.88 (t, J=6.8, 6H). $^{13}$C NMR (101 MHz, CDCl$_3$) δ 171.86, 130.20, 130.16, 130.13, 130.09, 127.95, 127.89, 127.87, 113.27, 78.29, 77.29, 76.97, 76.66, 73.95, 54.68, 45.24, 38.31, 36.25, 35.71, 32.91, 31.50, 29.93, 29.81, 29.66, 29.63, 29.52, 29.51, 29.44, 29.32, 29.30, 29.27, 27.24, 27.20, 27.17, 25.61, 24.46, 23.10, 22.54, 14.04. Calc. mass for the C$_{47}$H$_{83}$NO$_4$: 725.6. found 726.3.

Compound 7011 (ALNY-237): Prepared by similar experimental conditions used as for compound 7010, using alcohol 7009 (0.8 g, 1.27 mmol, 1.0 eq), N,N-dimethylamino butyric acid hydrochloride (0.25 g, 1.53 mmol, 1.2 eq), DIPEA (0.7 mL, 3.81 mmol, 3.0 eq), EDCI (0.26 g, 1.4 mmol, 1.1 eq), DMAP (0.015 g, 0.12 mmol, 0.1 eq) in DCM gave 0.8 g (85%) of the pure product 7011. $^1$H NMR (400 MHz, CDCl$_3$) δ 5.63-5.18 (m, 8H), 4.85-4.46 (m, 1H), 2.84-2.70 (m, 4H), 2.36-2.25 (m, 6H), 2.23 (s, 6H), 2.10-1.95 (m, 8H), 1.85-1.71 (m, 2H), 1.69-1.57 (m, 4H), 1.46 (d, J=21.4, 2H), 1.32 (ddd, J=21.9, 13.6, 7.7, 38H), 0.88 (t, J=6.8, 6H). $^{13}$C NMR (101 MHz, cdcl$_3$) δ 173.11, 130.44, 130.41, 130.39, 130.34, 128.19, 128.14, 128.12, 113.49, 78.53, 77.55, 77.23, 76.91, 74.06, 58.96, 45.48, 38.57, 36.50, 35.93, 32.28, 31.75, 30.18, 30.06, 29.91, 29.89, 29.77, 29.69, 29.57, 29.55, 29.52, 27.49, 27.45, 27.42, 25.86, 24.71, 23.36, 22.96, 22.79, 14.29. Calc. mass for the C$_{48}$H$_{85}$NO$_4$: 739.6. found 740.3.

Example 88

Synthesis of Oxime- and Hydrazone Linked Lipids

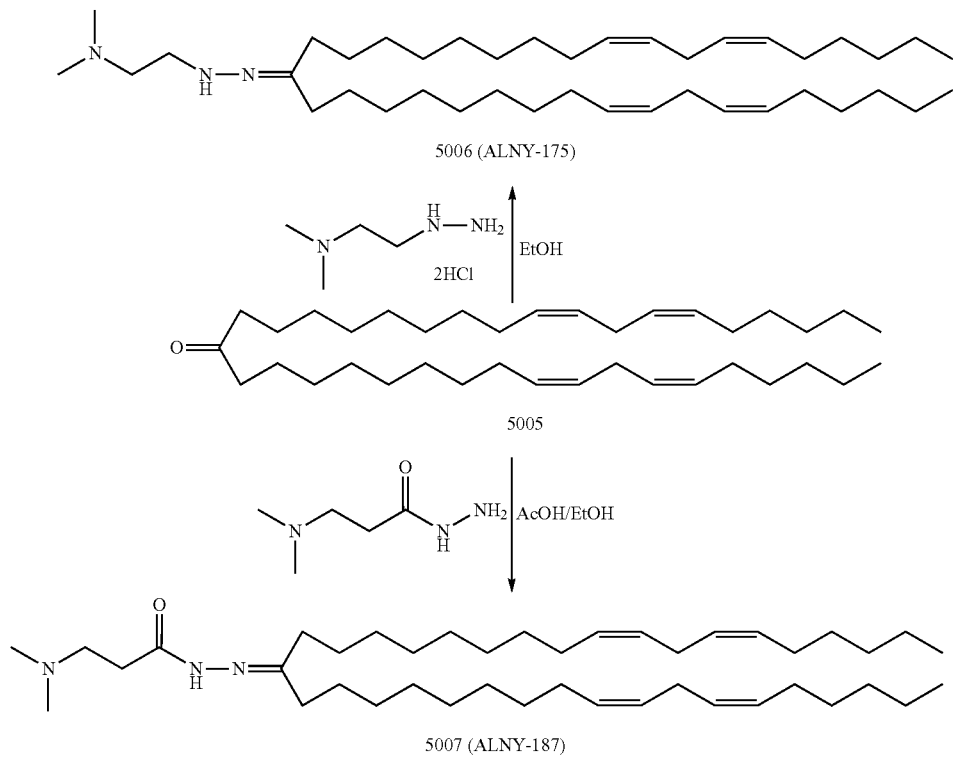

Experimental Details

Compound 5006 (ALNY-175): To a flask containing EtOH (50 mL) was added dimethylaminoethyl hydrazine dihydrochloride (1.00 g, 5.70 mmol) and the ketone 5005 (2.00 g, 3.80 mmol). The mixture was heated at 60° C. for 16 hours. After addition of Et$_3$N (0.5 mL), the reaction mixture was evaporated. The residue was extracted with Et$_2$O and saturated NaHCO$_3$ aq., and the organic layer was dried over MgSO$_4$, filtered and concentrated. The crude was purified by silica gel column chromatography (CH$_2$Cl$_2$:MeOH:NH$_3$ aq.=95:5:0.5, $R_f$=0.29) to give compound 3 (1.78 g, 2.91 mmol, 76%). Molecular weight for C$_{41}$H$_{78}$N$_3$ (M+H)$^+$ Calc. 612.62. Found 612.5.

Compound 5007 (ALNY-187): 3-Dimethylamino-propionic acid hydrazide (Ryan Scientific, 500 mg, 3.89 mmol) in EtOH (10 mL) and the dilinoleyl ketone 5005 (1.74 g, 3.31 mmol) in EtOH (20 mL) were mixed together. To the solution was added acetic acid (0.038 mL, 0.662 mmol), and the reaction mixture was heated at 65° C. for 5 hours. After addition of Et$_3$N (0.5 mL), the reaction mixture was evaporated. The residue was extracted with CH$_2$Cl$_2$ and saturated NaHCO$_3$ aq., and the organic layer was dried over MgSO$_4$, filtered and concentrated. The crude was purified by silica gel column chromatography (CH$_2$Cl$_2$:MeOH:NH$_3$aq.=95:5:0.5, $R_f$=0.30) to give compound 5007 (1.40 g, 2.19 mmol, 66%). Molecular weight for C$_{42}$H$_{78}$N$_3$O (M+H)$^+$ Calc. 640.61. Found 640.5.

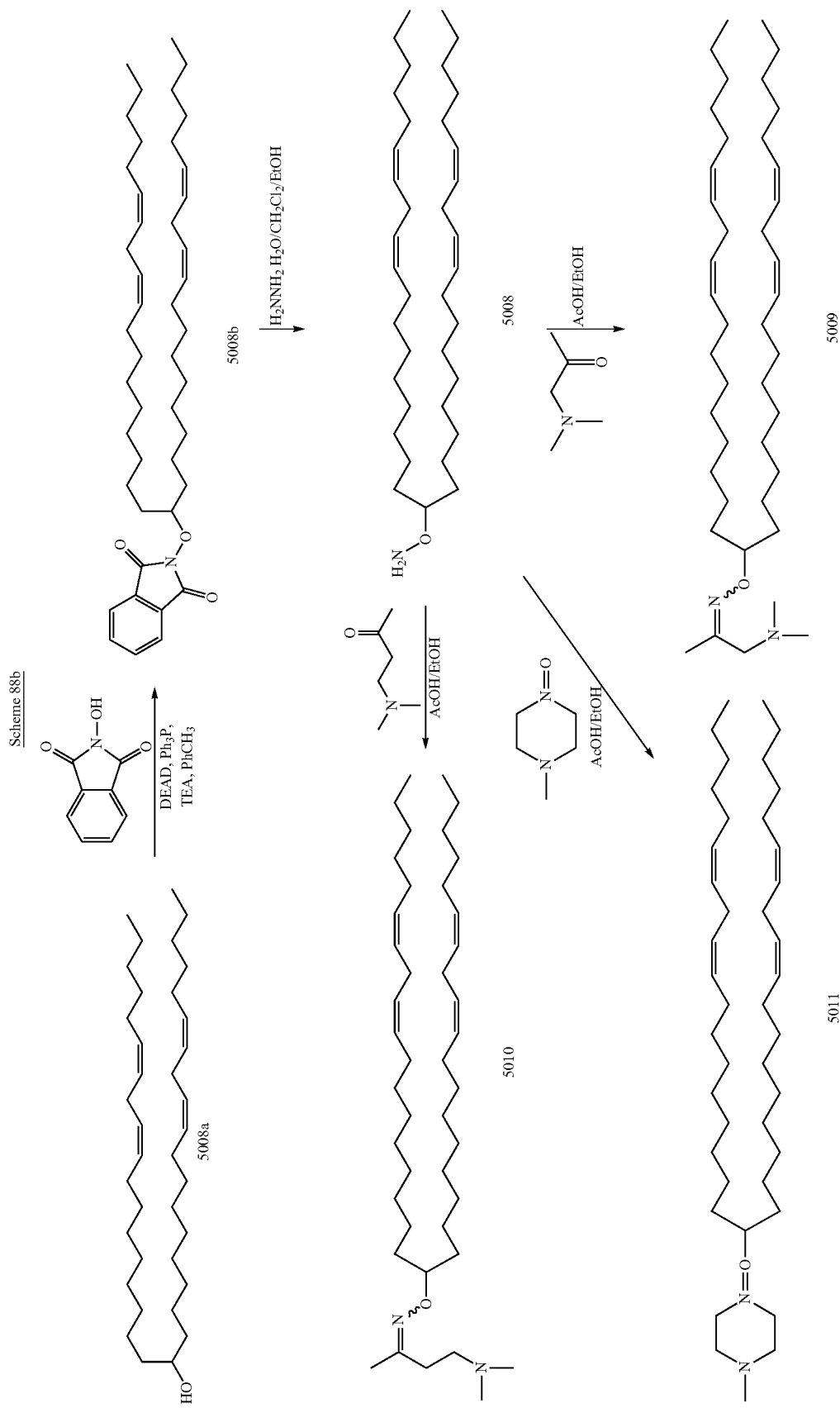

Compound 5008b: To a solution of 5008a (30 g, 56.8 mmol) in toluene, was added N-Hydroxyphthalimide (13.9 g, 85 mmol) and TPP (22.30 g, 85 mmol) under argon. The reaction mass was cooled to −5° C., to this was added TEA (11.84 mL), followed by DEAD (13.14 ml). The reaction mass was allowed to stir for 12 hrs at room temperature (TLC). It was then filtered through celite pad. The filtrate was evaporated at reduced pressure to obtain crude product, which was purified by silica gel chromatography to afford pure product, which was eluted at 3% diethyl ether and hexane to get the product 5008b (22.90 g, 60.50%) as pale yellow liquid $^1$HNMR (400 MHz, CDCl$_3$,): δ 0.90 (6H, t, J=7.2 Hz), 1.2-1.4 (34H, m), 1.66-1.70 (4H, m), 2.03-2.08 (8H, m), 2.78 (4H, t, J=12.8 Hz), 4.22 (1H, m), 5.29-5.43 (8H, m), 7.74-7.76 (2H, m), 7.83-7.85 (2H, m). $^{13}$CNMR (100 MHz, CDCl$_3$,): δ 14.3, 22.5, 24.9, 25.6, 27.2, 27.20, 29.3, 29.3, 29.5, 29.5, 29.6, 29.7, 31.5, 32.4, 88.3, 123.3, 127.9, 129.0, 130.1, 134.3, 164.3. MS: Molecular weight calculated for $C_{45}H_{71}NO_3$ 673.54. Found: 674.55 (M+H).

Compound 5010: ALY-SAN-031 (2.36 g, 3.50 mmol) was treated with hydrazine monohydrate (0.424 mL, 5.60 mmol) in CH$_2$Cl$_2$ (36 mL) and EtOH (4 mL) for 2 hours. After filtration of the resulting white precipitation, the filtrate was concentrated. The residue was extracted with Et$_2$O and saturated NaHCO$_3$ aq., and the organic layer was dried over MgSO$_4$, filtered and concentrated. The crude 5008 was used for next step without further purification. $R_f$=0.44 (10% EtOAC in Hexane). Molecular weight for $C_{37}H_{70}NO$ (M+H)$^+$ Calc. 544.55. Found 544.2.

The compound 5008 was dissolved in EtOH (30 mL), and 4-(dimethylamino)butan-2-one (Matrix Scientific, 500 mg, 4.34 mmol) and acetic acid (0.040 mL, 0.70 mmol) was added to the solution. The reaction mixture was stirred at room temperature for 14 hours. After addition of Et$_3$N (0.5 mL), the reaction mixture was evaporated. The residue was extracted with Et$_2$O and saturated NaHCO$_3$ aq., and the organic layer was dried over MgSO$_4$, filtered and concentrated. The crude was purified by silica gel column chromatography (Hexane:EtOAc=1:1) to give compound 5010 as a mixture of E/Z-isomers (1.90 g, 2.96 mmol, 85%, 2 steps, $R_f$=0.39, 0.21 developed with Hexane:EtOAc=1:1). Molecular weight for $C_{43}H_{81}N_2O$ (M+H)$^+$ Calc. 641.63. Found 641.5.

Compound 5009: Compound 5006 (800 mg, 1.47 mmol) was dissolved in EtOH (15 mL), (Dimethylamino)acetone (Aldrich, 0.220 mL, 1.91 mmol) and acetic acid (0.017 mL, 0.294 mmol) were added to the solution then the reaction mixture was stirred at room temperature for 14 hours. After addition of Et$_3$N (0.5 mL), the reaction mixture was evaporated. The residue was extracted with Et$_2$O and saturated NaHCO$_3$ aq., and the organic layer was dried over MgSO$_4$, filtered and concentrated. The crude was purified by silica gel column chromatography (Hexane:EtOAc=9:1) to give compound 5009 (868 mg, 1.38 mmol, 94%, $R_f$=0.22 developed with Hexane:EtOAc=9:1). Molecular weight for $C_{42}H_{79}N_2O$ (M+H)$^+$ Calc. 627.62. Found 627.5.

Compound 5011: Compound 5006 (1.09 g, 2.00 mmol) was dissolved in EtOH (20 mL). 1-Methyl-4-piperidone (Aldrich, 0.320 mL, 2.60 mmol) and acetic acid (0.40 mL, 0.400 mmol) were added to the solution then the reaction mixture was stirred at room temperature for 14 hours. After addition of Et$_3$N (0.5 mL), the reaction mixture was evaporated. The residue was extracted with Et$_2$O and saturated NaHCO$_3$ aq., and the organic layer was dried over MgSO$_4$, filtered and concentrated. The crude was purified by silica gel column chromatography (CH$_2$Cl$_2$:MeOH:NH$_4$OH=97:3:0.3) to give compound 5011 (1.11 g, 1.74 mmol, 87%, $R_f$=0.20 developed with CH$_2$Cl$_2$:MeOH:NH$_4$OH=97:3:0.3). Molecular weight for $C_{43}H_{79}N_2O$ (M+H)$^+$ Calc. 639.62. Found 639.5.

Example 89

Synthesis of Other Lipids

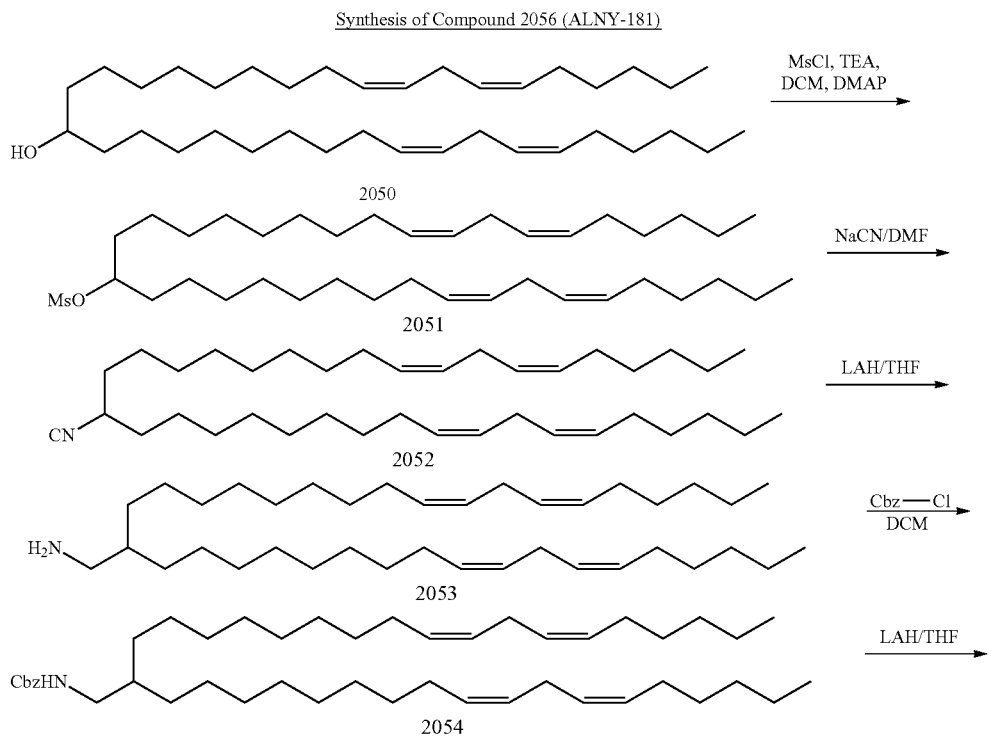

Synthesis of Compound 2056 (ALNY-181)

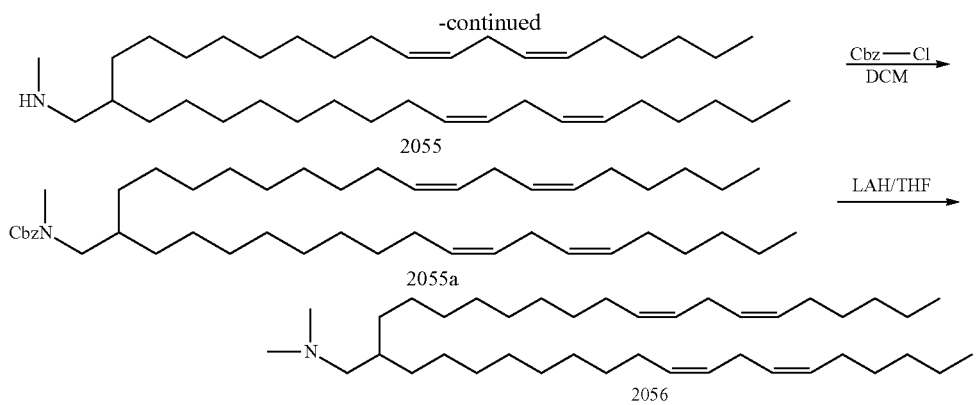

Synthesis of 2051: To a solution of 2004 (50 g, 95 mmol) in DCM (400 ml) under Ar atmosphere, was added TEA (53 mL, 378 mmol) and DMAP (1.2 g, 9.5 mmol) and stirred at room temperature under Ar atmosphere. Reaction mass was cooled to −5° C. and the solution of mesyl chloride (15 mL, 190 mmol) in DCM (100 ml) was added slowly at temperature below −5° C. and allowed to warm to RT after addition. After 30 minutes (TLC), reaction mass was quenched with ice cold water (20 ml). Organic layer was separated, washed with 1N HCl (30 ml), water, brine, dried over sodium sulfate and evaporated at reduced pressure to obtain pure product (55 g, 95.5%) as yellow liquid. 1H NMR (400 MHz, CDCl$_3$): δ 0.89 (t, 6H, J=6.8), 1.2-1.5 (m, 36H), 1.67 (m, 4H), 2.05 (q, 8H, J1=6.8, J2=6.8), 2.77 (t, 4H, J=6.4), 2.99 (s, 3H), 4.71 (m, 1H) and 5.36 (m, 8H).

Synthesis of 2052: To a stirred solution of sodium cyanide (1.70 g, 0.0330 mol) in DMF, was added compound 2051 (10 g, 0.0165 mol) in DMF (100 mL) slowly and heated to 55° C. for 24 hrs (TLC). It was then cooled to room temperature, diluted with water and extracted with ethyl acetate several times. The combined organic layers were washed with water, brine, dried over sodium sulfate and evaporated at reduced pressure to obtain crude product, which was purified silica gel chromatography using 1% ether/hexane to get the product as a pale yellow liquid (5.80 g, 62%). $^1$H NMR (400 MHz, CDCl$_3$): δ 0.87 (t, 6H, J=6.8 Hz), 1.25 (m, 38H), 1.52 (m, 4H), 2.03 (q, 8H, J=6.8 Hz, J=6.8 Hz), 2.47 (m, 1H), 2.76 (t, 4H, J=6.4 Hz), 5.32 (m, 8H).

Synthesis of 2053: To a cooled suspension of LAH (1.50 g, 0.0387 mol) in THF (52 ml) at 0° C. under argon atmosphere, was added compound 2052 (5.2 g, 0.0097 mol) in THF drop-wise. After addition, it was allowed to warm to RT and stirred for 20 hrs (TLC). It was cooled to 0° C. and quenched with saturated solution of sodium sulfate (10 ml) followed by ethyl acetate. It was filtered through celite bed and washed with ethyl acetate. The combined organic filtrate was evaporated at reduced pressure to obtain crude product, which was purified by silica gel chromatography using 10% ethyl acetate in hexane to get the product as pale brown liquid (3.70 g, 71%). $^1$H NMR (400 MHz, CDCl$_3$): δ 0.87 (t, 6H, J=6.8 Hz), 1.27 (m, 48H), 2.03 (q, 8H, 6.8 Hz, 6.8 Hz), 2.60 (d, 2H, J=4.0 Hz), 2.76 (t, 4H, J=6.4 Hz), 5.31 (m, 8H). $^{13}$C NMR (100 MHz, CDCl$_3$): δ 14.1, 22.6, 25.6, 26.8, 27.1, 27.2, 29.3, 29.5, 29.6, 30.1, 31.5, 40.9, 45.2, 128.0, 130.1. Mass 543 (M+).

Synthesis of 2054: To a solution of compound 2053 (45 g, 0.083 mol) in DCM (450 mL) under argon atmosphere at 0° C., was added 2,6-Lutidine (19.3 mL, 0.166 mol) followed by benzyl chloroformate (12.1 mL, 0.0847 mol) drop-wise. It was then warmed to 20° C. and stirred for one hour at that temperature (TLC). Then it was diluted with DCM (200 ml), washed with 10% citric acid (2×200 ml), water, brine and dried over anhydrous sodium sulfate, evaporated at reduced pressure to obtain crude product, which was purified by silica gel chromatography using 3% ether/hexane to get the final product as pale brown liquid (36 g, 64%). $^1$H NMR (400 MHz, CDCl$_3$): δ 0.87 (t, 6H, J=6 Hz), 1.28 (m, 44H), 2.02 (q, 8H, J$_1$=6.8 Hz, J$_2$=6.8 Hz), 2.76 (t, 4H, J=6.4 Hz), 3.11 (t, 2H, J=5.6 Hz), 4.67 (s, 1H), 5.18 (s, 2H), 5.30 (m, 8H), 7.31 (m, 4H).

Synthesis of 2055: To a suspension of lithium aluminium-hydride (4.05 g, 0.1066 mol) in THF (360 mL) under argon atmosphere at 0° C., was added a solution of 2054 (36 g, 0.0533 mol) in THF drop-wise. After addition, it was allowed to warm to room temperature and stirred for 15 hours (TLC). The reaction mass was cooled to 0° C. and quenched with saturated solution of sodium sulfate followed by ethyl acetate. It was filtered through celite bed and washed with ethyl acetate. Combined filtrates were evaporated and purified by silica gel using 100% methanol to get the final product 26 g, 87%). $^1$H NMR (400 MHz, CDCl$_3$): δ 0.87 (t, 6H, J=6.8 Hz), 1.27 (m, 42H), 2.03 (q, 8H, J$_1$=6.8 Hz, J$_2$=6.8 Hz), 2.45 (s, 3H), 2.49 (d, 2H, J=6 Hz), 2.76 (t, 4H, J=6.4 Hz), 5.30 (m, 8H).

Synthesis of 2055a: Compound 2055 (4 g, 0.0072 mol) was dissolved in DCM (40 mL) under argon atmosphere and cooled to 0° C. To this solution 2,6-Lutidine (1.7 mL, 0.0144 mol) was added drop-wise followed by benzyl chloroformate (1.0 mL, 0.0074 mol). It was then allowed to warm to 20° C. and stirred for one hour (TLC). Then it was diluted with DCM (200 ml), washed with 10% citric acid (2×200 mL), water and brine. The organic layer was dried over anhydrous sodium sulfate and evaporated at reduced pressure to obtain crude product, which was purified by silica gel using 3% ether/hexane to get the final product (3.80 g, 76%). $^1$H NMR (400 MHz, CDCl$_3$): δ 0.87 (t, 6H, J=6.8 Hz), 1.20 (m, 44H), 2.02 (q, 8H, J$_1$=6.8 Hz, J$_2$=6.8 Hz), 2.76 (t, 4H, J=6.4 Hz), 2.89 (d, 3H, J=6 Hz), 3.14 (m, 2H), 5.12 (s, 2H), 5.30 (m, 8H), 7.26 (m, 4H).

Synthesis of 2056: To a suspension of lithium aluminium-hydride (0.52 g, 0.0138 mol) in THF under argon atmosphere at 0° C., was added a solution of 2055a (3.80 g, 0.0055 mol) in THF (38 mL) dropwise. After addition, it was allowed to warm to room temperature and stirred for 15 hours (TLC). The reaction mass was cooled to 0° C. and quenched with saturated solution of sodium sulfate followed by ethyl acetate. Whole mass was filtered through celite bed and washed with ethyl acetate. Combined filtrates were evaporated at reduced pressure to obtain crude product, which was purified silica gel chromatography using 100% methanol to get the final product as colorless liquid (2.20 g, 70%) 1H NMR (400 MHz, CDCl$_3$): δ 0.87 (t, 6H, J=6.8 Hz), 1.21 (m, 44H), 2.03 (q, 8H, J=6.8 Hz, J=6.4 Hz), 2.18 (s, 6H), 2.76 (t, 4H, J=6.4 Hz), 5.30 (m, 8H). $^{13}$C NMR (100 MHz, CDCl$_3$): δ 14.0, 22.4, 25.5, 26.5, 27.0, 27.1, 29.2, 29.4, 29.6, 30.0, 31.4, 32.1, 35.6, 45.9, 64.8, 127.8, 130.0. ELSD: 99.0% Mass: 570.2 (M$^+$)

Synthesis of 2062 (ALNY-141)

product got eluted at 8% of ether in hexane as brown liquid (yield, 6.40 g, 96%). $^1$H NMR: (400 MHz, CDCl$_3$): 0.89 (t, 6H, J=7.2 Hz), 1.26-1.43 (m, 40H), 1.85 (m, 1H), 2.06 (q, 8H, J1=6.8 Hz, J2=6.8 Hz), 2.15 (s, 2H), 2.20 (s, 3H), 2.45 (m, 2H), 2.77 (t, 4H, J=6 Hz), 2.95 (s, 3H), 3.35 (m, 2H), 5.12 (s, 2H), 5.32 (m, 8H), 7.35 (m, 5H).

Synthesis of 2062: To a suspension of lithium aluminium-hydride (0.751 g, 0.0198 mol) in THF under argon atmosphere at 0° C., was added a solution of 2061 (5.7 g, 0.0076 mol) in THF drop-wise. After addition, it was allowed to warm to room temperature and stirred for 15 hours (TLC).

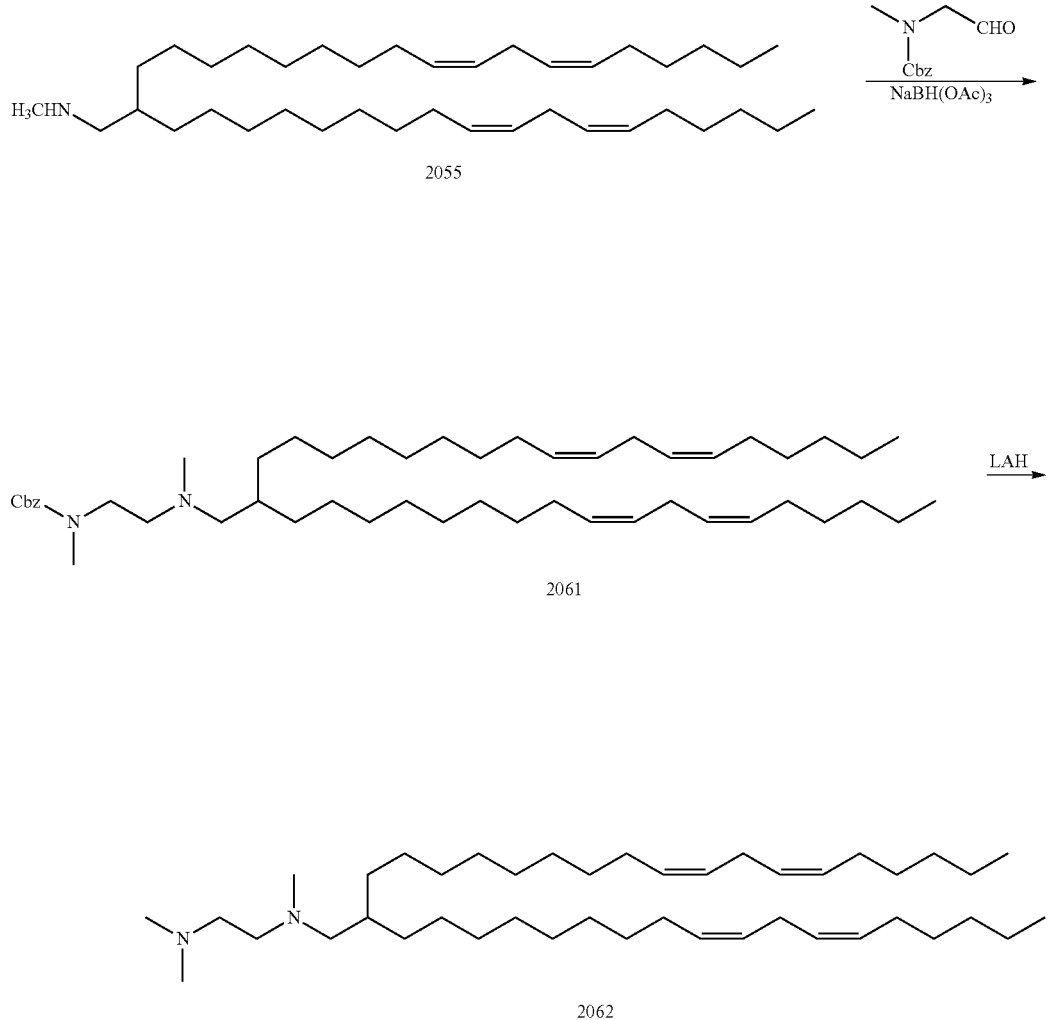

Synthesis of 2061: To a solution of 2055 (5 g, 0.0089 mol) in 100 ml of DCM under argon at 0° C. was added NaBH(OAc)$_3$ (2.30 g, 0.0106 mol) Stirred for 20 minutes. Aldehyde (1.70 g, 0.0082 mol) in 700 ml of DCM was added slowly to the reaction mass over a period of 45 minutes. After addition the reaction mass was allowed to stir at RT for 15-20 minutes. TLC showed the absence of starting material. The reaction mass was washed with sat. NaHCO$_3$ (2×500 ml) and water (500 ml). The aqueous layer was re-extracted with DCM (500 ml). The combined organic layer was washed with brine (500 ml). The organic layer was dried over Na$_2$SO$_4$, filtered and concentrated. The crude obtained was purified by silica gel chromatography and Hexane/Diethyl ether as eluent. The The reaction mass was cooled to 0° C. and quenched with saturated solution of sodium sulfate (50 ml) followed by ethyl acetate (100 ml). It was filtered through celite bed and washed with ethyl acetate. Combined filtrates were evaporated at reduced pressure to obtain crude product, which was purified silica gel chromatography using DCM/Ethylacetate/Chloroform/Methanol as eluent. The product eluted at 3% chloroform in methanol as brown liquid (3.80 g, 80%) $^1$H NMR: (400 MHz, CDCl$_3$): 0.89 (t, 6H, J=6.8 Hz), 1.26-1.37 (m, 40H), 1.42 (m, 1H), 2.06 (q, 8H, J1=6.8 Hz, J2=6.8 Hz), 2.15 (d, 2H, J=7.2 Hz), 2.20 (s, 3H), 2.29 (s, 6H), 2.45 (s, 4H), 2.78 (t, 4H, J=6.4 Hz), 5.36 (m, 8H). $^{13}$C NMR: (100 MHz, CDCl$_3$): 14.1, 22.6, 25.6, 26.6, 27.2, 27.22, 28.9, 29.3, 29.6, 29.7, 30.1, 31.5, 32.2, 35.8, 43.2, 45.7, 56.2, 57.2, 63.3, 127.9, 130.2. HPLC ELSD: 100% Mass: 627.53

Example 90

Synthesis of Reverse Ketals

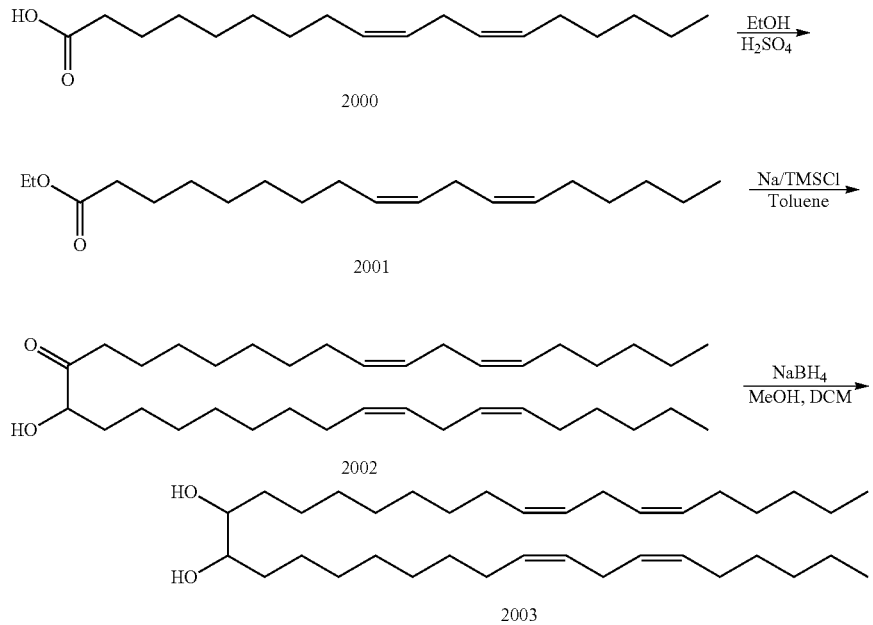

Synthesis of 2001: To 500 ml of ethanol cooled below 0° C. using ice-salt mixture was added 10 ml of Conc. H$_2$SO$_4$ slowly. Linoleic acid (100 g, 357 mmol) in 500 ml of ethanol was added to the above solution slowly by maintaining the temperature below 0° C. After addition the reaction mass was warmed to RT and then refluxed for 5 hrs (TLC). It was then cooled to room temperature and neutralized by sat. NaHCO$_3$ solution. The resulting solution was concentrated to remove excess of solvent. The residue was diluted with water (1000 ml) and extracted with DCM (6×500 ml). The combined organic layer was washed with brine (1000 ml), and dried over sodium sulfate, filtered and evaporated at reduced pressure to obtain pure product (109.80 g, 99%) as a pale yellow liquid, which was taken as such for the next stage. $^1$H NMR (CDCl$_3$): δ 0.89 (t, 3H, J=6.8 Hz), 1.24-1.31 (m, 17H), 1.62 (m, 2H, J=10 Hz), 2.04 (q, 4H, J$_1$=6.8 Hz, J$_2$=6.8 Hz), 2.29 (t, 2H, J=7.6 Hz), 2.76 (t, 2H, J=6.4 Hz), 4.13 (q, 2H, J$_1$=7.2 Hz, J$_2$=7.2 Hz), 5.34 (m, 4H). $^{13}$C NMR (CDCl$_3$): δ 13.9, 14.1, 22.5, 24.9, 25.5, 27.1, 29.0, 29.1, 29.3, 29.5, 31.4, 34.2, 60.0, 127.8, 127.9, 129.9, 130.0, 173.6.

Synthesis of 2002: To 660 ml of freshly distilled toluene in a 2 L multineck RB flask fitted with reflux condenser under argon was added sodium pieces (41.1 g, 1.785 mol). To this was added TMSCl (192 mL, 1.499 mol) slowly and heated to 40° C. after addition. Then a solution of 2001 (110 g, 0.357 mol) in 275 ml of freshly distilled toluene was added slowly by maintaining the reaction temperature at 40° C. over a period of 1 hr. It was then refluxed for 2-3 hrs. After 3 hrs the reaction mass turned pale purple in color (TLC). Heating was stopped and the reaction mass was cooled to room temperature, filtered through a pad of celite and washed with toluene. (CAUTION: The reaction mixture contained unreacted sodium pieces). The filtrate obtained was stirred with 3 L of sat. NH$_4$Cl solution for 15-20 minutes until the silyl ether converted to the required -keto alcohol. The organic layer was separated and the aqueous layer was washed with ethyl acetate (3×1000 ml). The combined organic layer was washed with brine (1 L), dried over sodium sulfate, filtered and evaporated at reduced pressure to obtain the crude material, which was purified by silica gel chromatography using hexane/ethyl acetate as eluent. The product got eluted at 3% ethyl acetate in hexane to get 2002 (44 g, 47%) as a pale yellow liquid. $^1$H NMR (400 MHz, CDCl$_3$): δ 0.89 (t, 6H, J=7.2 Hz), 1.2-1.3 (m, 30H), 1.53 (m, 1H), 1.62 (m, 2H), 1.8 (m, 1H), 2.04 (q, 8H, J$_1$=6.8 Hz, J$_2$=6.8 Hz), 2.43 (m, 2H), 2.76 (t, 4H, J=6.4 Hz), 3.49 (d, 1H, J=4.8 Hz) 4.16 (m, 1H), 5.34 (m, 8H). $^{13}$C NMR (100 MHz, CDCl$_3$): δ 14.1, 22.6, 23.6, 24.8, 25.6, 27.2, 29.1, 29.2, 29.24, 29.3, 29.4, 29.56, 29.6, 31.5, 33.7, 37.8, 76.3, 127.8, 127.9, 129.9, 130.0, 212.4.

Synthesis of 2003: A solution of 2002 (44 g, 83 mol) in methanol/DCM mixture (490 mL, DCM was added to make the solution homogeneous) under argon was cooled below 0° C. using ice-salt mixture. Sodium borohydride (4.7 g, 125 mmol) was added in one lot to the reaction mass. The suspension was stirred for 2 hrs, and the mass temperature slowly raised to RT. After 2 hrs the reaction mass became homogeneous. TLC showed the absence of starting material. The reaction was quenched with 100 ml of water, and concentrated to remove excess solvent. The residue obtained was again diluted with water (500 ml), and extracted with DCM (4×500 ml). The combined organic layer was washed with brine (500 ml), dried over sodium sulfate, filtered and evaporated at reduced pressure to obtain the crude product, which was purified by silica gel chromatography using hexane/ethyl acetate as eluent. The product eluted from 4% to 20% of ethyl acetate in hexane to get 2003 (36 g, 82%) as a white semisolid. $^1$H NMR (CDCl$_3$): δ 0.89 (t, 6H, J=6.8 Hz), 1.2-1.5 (m, 36H), 1.78 (d, 1H, J=4 Hz), 1.95 (d, 1H, J=4 Hz), 2.04 (q, 8H, J$_1$=6.8 Hz, J$_2$=6.8 Hz), 2.77 (t, 4H, J=6.4 Hz), 3.40 (m, 1H), 3.61 (m, 1H), 5.34 (m, 8H). $^{13}$C NMR (CDCl$_3$): δ13.7, 22.2, 25.2, 25.3, 25.7, 26.8, 28.4, 28.9, 29.0, 29.1, 29.3, 30.8, 31.1, 33.2, 74.1, 74.3, 127.5, 127.6, 129.7, 129.8. MS: Molecular weight calculated for C$_{36}$H$_{66}$O$_2$ 530.51. Found: 531.52 (M+H).

Example 91

Synthesis of ALNY-152

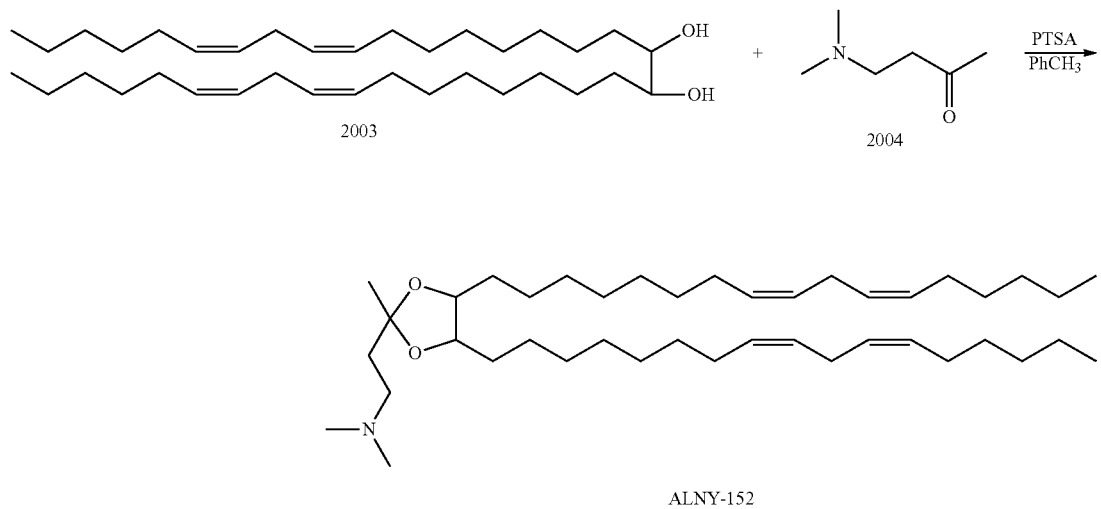

To a solution of diol 2003 (2.1 g, 4.0 mmol), ketone 2004 (0.50 g, 4.3 mmol) in toluene was added the PTSA (0.86 g, 5 mmol) and refluxed under Dean-Stock apparatus until there is no starting material left. Cooled the reaction mixture, evaporated, directly loaded on column chromatography and purified using 0-10% MeOH in CH$_2$Cl$_2$ to get 1.25 g of the pure compound ALNY-152 in 50% yields. $^1$H NMR (400 MHz, CDCl$_3$) δ 5.46-5.24 (m, 8H), 4.09-3.93 (m, 1H), 3.65-3.42 (m, 2H), 2.84-2.68 (m, 5H), 2.47-2.30 (m, 3H), 2.27-2.16 (m, 7H), 2.04 (q, J=6.8, 9H), 1.82 (qd, J=12.4, 7.8, 2H), 1.46 (t, J=19.0, 7H), 1.40 (s, 38H), 0.99-0.76 (m, 6H). Calc. mass for the C$_{42}$H$_{77}$NO$_2$: 628.07. found 628.5.

Example 92

Synthesis of ALNY-220

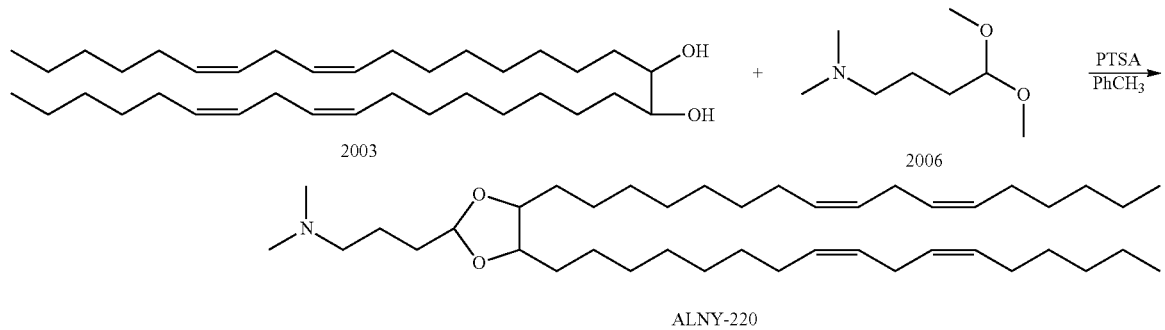

Using a similar procedure used for the synthesis of ALNY-152, using 1.06 g (2 mmol) of 2003 and 400 mg (2.5 mmol) of the amine 2006, 0.7 g (56%) the ketalized product ALNY-220 was isolated after column purification. $^1$H NMR (400 MHz, CDCl$_3$) δ 5.44-5.24 (m, 8H), 5.02-4.83 (m, 1H), 3.87 (dd, J=17.2, 14.0, 1H), 3.51 (dd, J=15.2, 8.5, 1H), 2.72 (dt, J=9.5, 5.0, 4H), 2.32-2.25 (m, 2H), 2.22 (s, 6H), 2.11-1.94 (m, 9H), 1.68-1.38 (m, 11H), 1.38-1.18 (m, 35H), 0.84 (dt, J=10.7, 5.9, 6H). Calc. mass for the C$_{42}$H$_{77}$NO$_2$: 628.07. found 628.5.

Preparation of Compound ALNY-158

4.63 (d, J=7.4, 1H), 3.97 (s, 1H), 3.55 (d, J=3.7, 2H), 2.76 (t, J=6.4, 4H), 2.04 (q, J=6.7, 8H), 1.91 (s, 2H), 1.81-1.59 (m, 3H), 1.56-1.42 (m, 8H), 1.42-1.15 (m, 31H), 0.88 (t, J=6.8, 6H). Calc. mass for the C$_{50}$H$_{81}$NO$_4$: 759.62. found 786 (+Na).

Preparation of Compound 2009: Used similar experimental procedure described earlier, using N-Cbz ketal 24 (2.42 g, 3.0 mmol, 1.0 eq), 1M LAH in THF (4.6 mL, 4.6 mmol, 1.5 eq), this gave 2.17 g of the compound 2009 in quantitative yields. $^1$H NMR (400 MHz, CDCl$_3$) δ 5.49-5.12 (m, 8H), 4.69 (s, 1H), 3.98 (d, J=5.9, 1H), 3.56 (d, J=3.7, 1H), 2.76 (t, J=6.2, 4H), 2.37 (s, 3H), 2.13-1.93 (m, 8H), 1.92-1.63 (m, 5H),

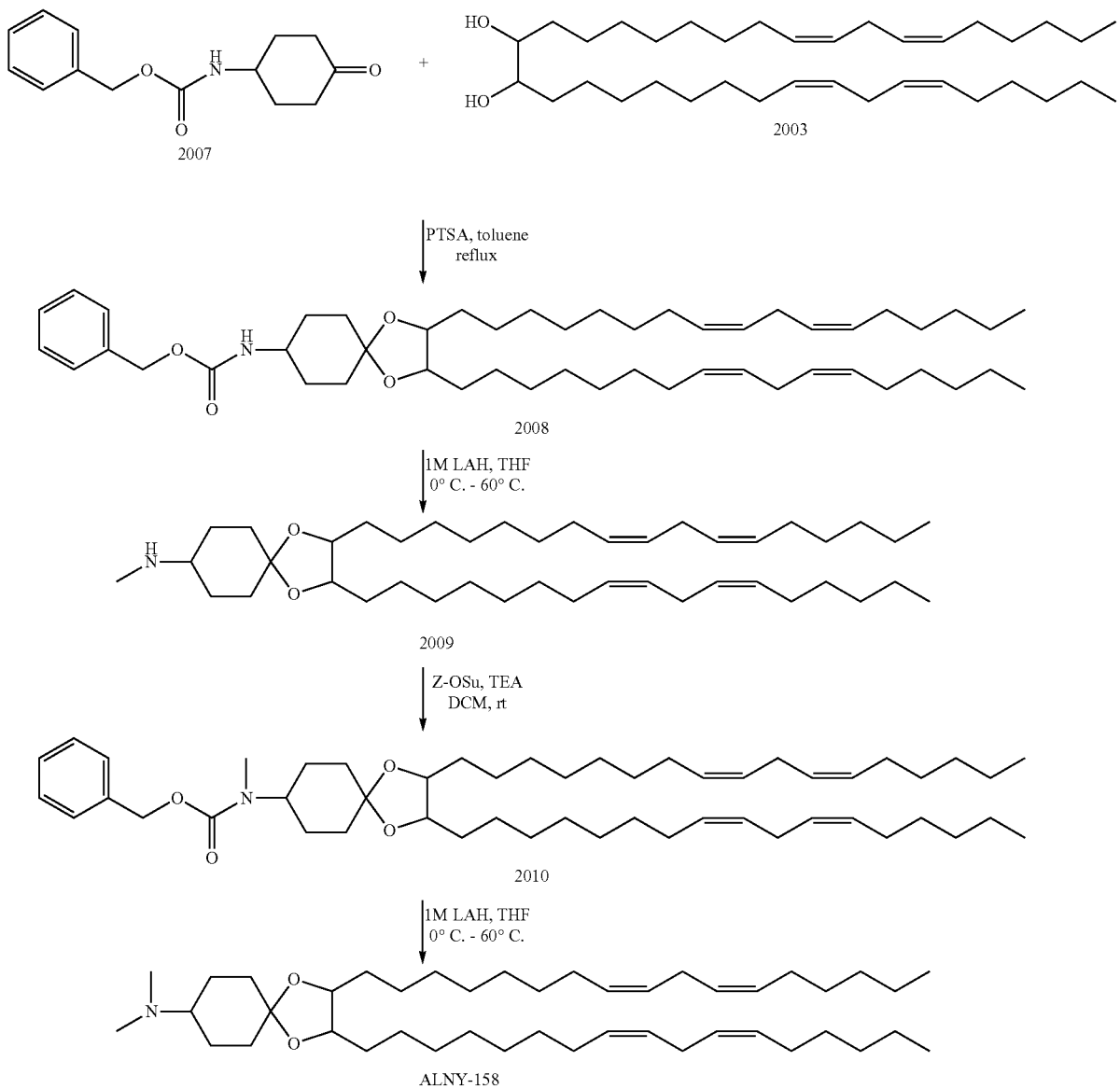

Preparation of Compound 2008: Using similar ketalyzation procedure as compound ALNY-220, using N-Cbz-4-amino cyclohexanone 2007 (1.5 g, 6.0 mmol, 1.0 eq), dilinoleyl diol 2003 (3.38 g, 6.0 mmol, 1.0 eq) and PTSA (0.11 g, 0.6 mmol, 0.1 eq), which gave 3.31 g (69%) of the pure corresponding ketal 2008. $^1$H NMR (400 MHz, CDCl$_3$) δ 7.45-7.24 (m, 5H), 5.47-5.24 (m, 8H), 5.06 (d, J=10.8, 1H), 1.60-1.40 (m, 8H), 1.40-1.14 (m, 34H), 0.88 (t, J=6.8, 6H). Calc. mass for the C$_{43}$H$_{77}$NO$_2$: 639.6. found 640.3.

Preparation of Compound 2010: To a stirred solution of N-methyl ketal 2009 (2.0 g, 3.0 mmol, 1.0 eq), triethyl amine (1.3 mL, 9.0 mmol, 3.0 eq) in dichloromethane at 0° C. was added solid Z-OSu portions wise and continued the reaction at room temperature under argon for overnight. After completion of the reaction, diluted with dichloromethane, washed with water, brine, dried on $MgSO_4$, concentrated and purified by column chromatography using hexane: ethylacetate (20%) as gradients to get 1.94 g (80%) of the pure Cbz-protected ketal 2009. $^1$H NMR (400 MHz, $CDCl_3$) δ 7.50-7.16 (m, 5H), 5.49-5.24 (m, 8H), 5.15 (d, J=15.4, 2H), 4.04 (dd, J=59.3, 9.4, 1H), 3.72-3.43 (m, 1H), 2.77 (dd, J=13.2, 6.5, 8H), 2.04 (q, J=6.7, 8H), 1.93-1.68 (m, 4H), 1.66-1.55 (m, 3H), 1.48 (d, J=5.1, 6H), 1.38-1.17 (m, 30H), 0.88 (t, J=6.7, 6H). Calc. mass for the $C_{51}H_{83}NO_4$: 773.6. found 774.3.

Preparation of Compound ALNY-158: Used similar experimental procedure as described earlier, using N-Cbz-ketal 2010 (1.48 g, 1.85 mmol, 1.0 eq), 1M LAH in THF (2.77 mL, 2.77 mmol, 1.5 eq), this gave 1.0 g of the compound ALNY-158 in 79% yield. $^1$H NMR (400 MHz, $CDCl_3$) δ 5.48-5.13 (m, 8H), 3.97 (d, J=5.8, 1H), 3.55 (d, J=4.2, 1H), 2.76 (t, J=6.3, 4H), 2.27 (s, 6H), 2.23-2.12 (m, 1H), 2.04 (q, J=6.7, 8H), 1.80 (dt, J=16.5, 10.8, 3H), 1.65 (t, J=10.2, 1H), 1.60-1.42 (m, 8H), 1.42-1.16 (m, 32H), 0.88 (t, J=6.8, 6H). $^{13}$C NMR (101 MHz, $cdcl_3$) δ 130.41, 130.32, 128.20, 128.13, 107.86, 107.39, 81.06, 80.95, 78.03, 77.98, 77.54, 77.22, 76.90, 62.74, 62.69, 42.07, 42.02, 37.20, 35.80, 35.18, 34.08, 33.59, 33.43, 31.74, 30.12, 29.98, 29.91, 29.87, 29.78, 29.69, 29.64, 29.57, 29.50, 29.47, 27.45, 27.42, 26.55, 26.43, 26.41, 26.37, 26.13, 25.85, 25.80, 22.79, 14.29. Calc. mass for the $C_{44}H_{79}NO_2$: 653.6. found 654.3.

Preparation of ALNY-155

Preparation of Compound 2012: Used similar ketalyzation procedure as compound ALNY-152, using 1-N-Cbz-pyrrolidinone 2011 (1.61 g, 7.37 mmol, 1.0 eq), dilinoleyl diol 2003 (4.16 g, 7.37 mmol, 1.0 eq) and PTSA (0.14 g, 0.73 mmol, 0.1 eq), which gave 3.2 g (57%) of the pure corresponding ketal 2012. $^1$H NMR (400 MHz, $CDCl_3$) δ 7.41-7.26 (m, 5H), 5.48-5.23 (m, 8H), 5.12 (s, 2H), 3.98 (m, 1H), 3.66-3.29 (m, 5H), 2.76 (t, J=6.4, 4H), 2.00 (dq, J=14.5, 6.9, 11H), 1.54-1.15 (m, 41H), 0.88 (t, J=6.8, 6H). Calc. mass for the $C_{48}H_{77}NO_4$: 731.5. found 732.0.

Preparation of ALNY-155: Used similar experimental procedure as described earlier, using N-Cbz-ketal 2012 (1.01 g, 1.33 mmol, 1.0 eq), 1M LAH in THF (2.0 mL, 2.0 mmol, 1.5 eq), this gave 0.61 g of the compound ALNY-155 in 72% yield. $^1$H NMR (400 MHz, $CDCl_3$) δ 5.47-5.16 (m, 8H), 4.00-3.77 (m, 1H), 2.76 (t, J=6.4, 4H), 2.62-2.37 (m, 3H), 2.30 (s, 3H), 2.15-1.90 (m, 11H), 1.57-1.15 (m, 42H), 0.88 (t, J=6.8, 6H). $^{13}$C NMR (101 MHz, $cdcl_3$) δ 130.41, 130.32, 128.21, 128.13, 115.42, 114.88, 114.78, 81.46, 81.22, 78.51, 78.21, 77.54, 77.22, 76.91, 66.74, 66.55, 66.34, 55.28, 55.00, 54.84, 42.70, 39.13, 38.78, 33.38, 33.20, 31.74, 29.88, 29.66, 29.64, 29.57, 29.51, 29.47, 29.41, 27.45, 27.42, 26.41, 26.25, 26.22, 25.85, 22.79, 14.29. Calc. mass for the $C_{41}H_{73}NO_2$: 611.5. found 612.3.

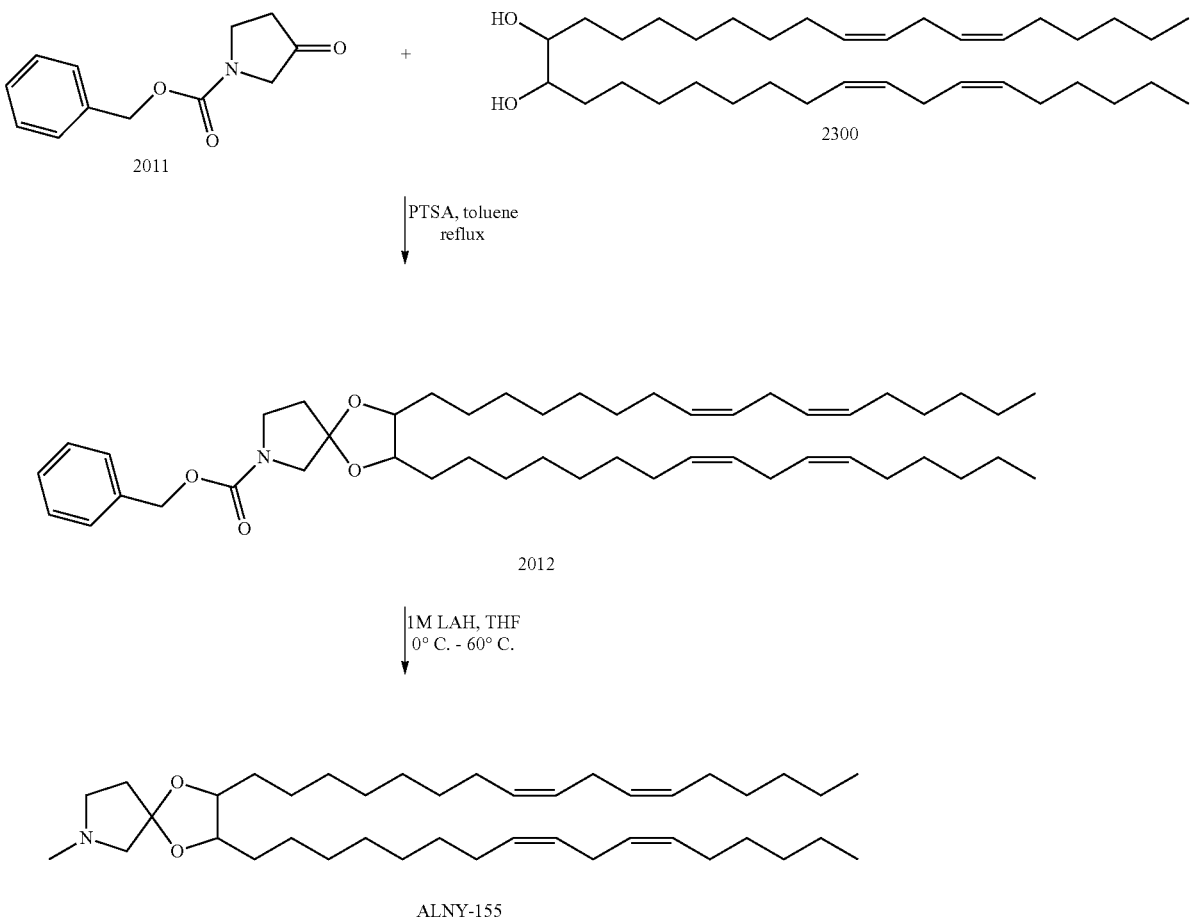

Preparation of ALNY-156

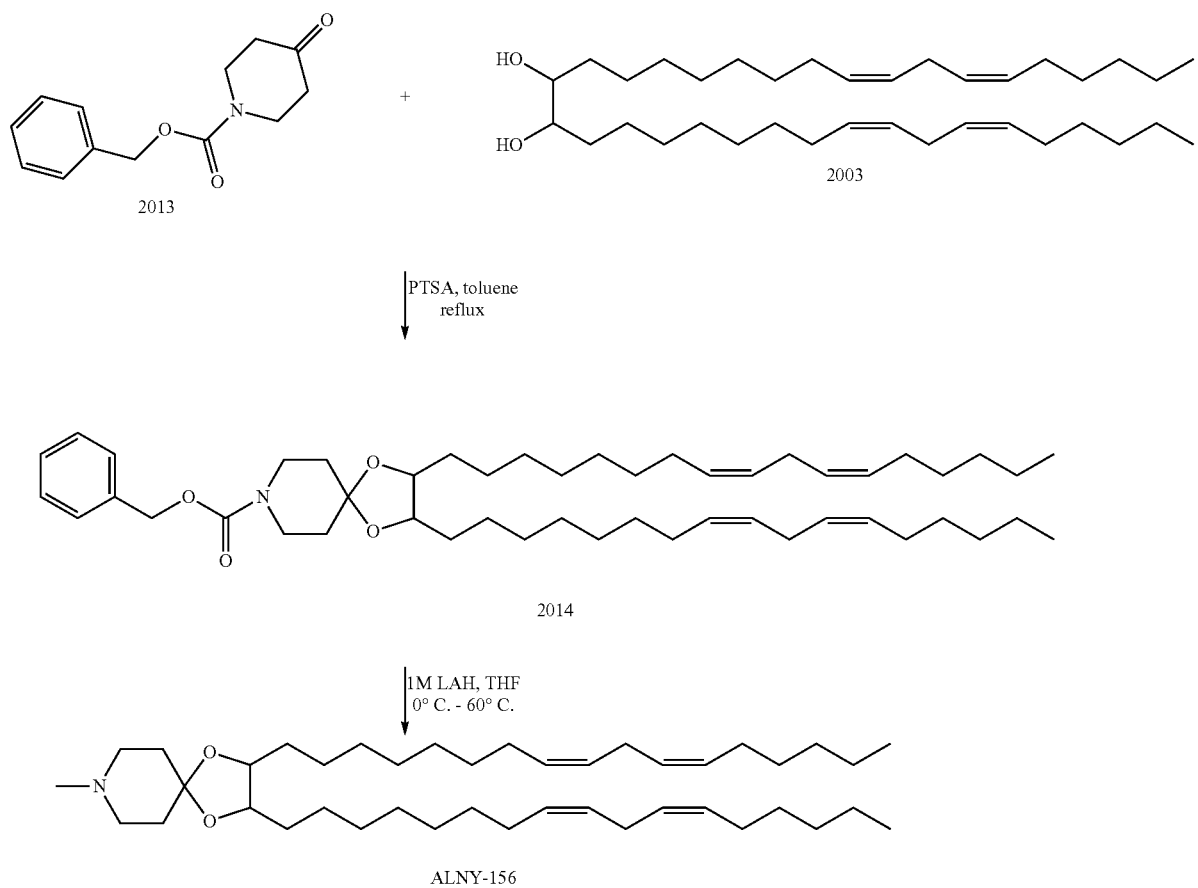

Preparation of Compound 2014: Used similar ketalyzation procedure as compound ALNY-152, using 1-N-Cbz-piperidone 2013 (1.0 g, 4.29 mmol, 1.0 eq), dilinoleyl diol 2003 (2.4 g, 4.29 mmol, 1.0 eq) and PTSA (0.08 g, 0.43 mmol, 0.1 eq), which gave 2.74 g (71%) of the pure corresponding ketal 2014. $^1$H NMR (400 MHz, CDCl$_3$) δ 7.42-7.21 (m, 5H), 5.46-5.22 (m, 8H), 5.11 (s, 2H), 4.01 (d, J=7.1, 1H), 3.68-3.43 (m, 5H), 2.81-2.66 (m, 4H), 2.04 (q, J=6.7, 8H), 1.76-1.40 (m, 9H), 1.40-1.15 (m, 32H), 0.88 (t, J=6.8, 6H). Calc. mass for the C$_{49}$H$_{79}$NO$_4$: 745.6. found 746.3.

Preparation of ALNY-156: Used similar experimental procedure as described earlier, using N-Cbz-ketal 2014 (2.72 g, 3.52 mmol, 1.0 eq), 1M LAH in THF (5.27 mL, 5.27 mmol, 1.5 eq), this gave 2.13 g of the compound ALNY-156 in 93% yield. $^1$H NMR (400 MHz, CDCl$_3$) δ 5.52-5.20 (m, 8H), 4.09-3.92 (m, 1H), 3.61 (s, 1H), 2.79 (t, J=6.5, 4H), 2.49 (s, 4H), 2.31 (s, 3H), 2.07 (q, J=6.8, 8H), 1.75 (dd, J=11.5, 5.8, 4H), 1.52 (m, 5H), 1.43-1.19 (m, 31H), 0.91 (t, J=6.9, 6H). $^{13}$C NMR (101 MHz, CDCl$_3$) δ 130.22, 130.12, 128.01, 127.92, 105.99, 105.51, 80.73, 77.82, 77.35, 77.23, 77.03, 76.71, 53.80, 53.61, 53.54, 45.98, 38.07, 36.53, 35.24, 33.27, 31.54, 29.74, 29.70, 29.66, 29.46, 29.45, 29.36, 29.27, 27.24, 27.21, 26.24, 26.14, 25.64, 22.59, 14.10. Calc. mass for the C$_{42}$H$_{75}$NO$_2$: 625.5. found 626.2.

Preparation of ALNY-227

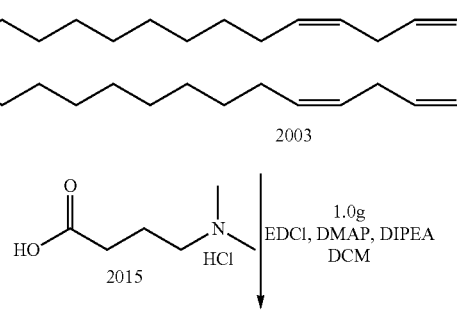

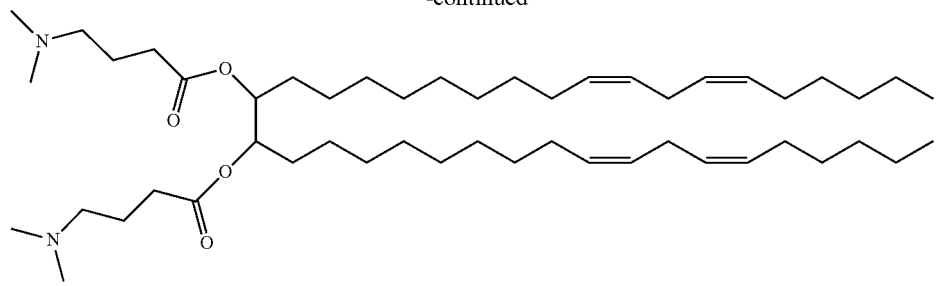

ALNY-227

To a stirred solution of dilinoleyl diol 2003 (1.0 g, 1.8 mmol, 1.0 eq), N,N-dimethyl butyric acid hydrochloride 2015 (0.89 g, 5.37 mmol, 3.0 eq), DIPEA (2.0 mL, 10.8 mmol, 6.0 eq) in dichloromethane was added solid EDCI (0.76 g, 3.96 mmol, 2.2 eq), DMAP (0.04 g, 0.36 mmol, 0.2 eq) portions wise and continued at room temperature. After completion of the reaction was diluted with dichloromethane, washed with saturated solution of NaHCO$_3$, brine and combined organics were dried over MgSO$_4$, evaporated the solvent, and the reaction mixture is purified by column chromatography using dichloromethane and methanol (5%) as gradients to get pure bis-ester ALNY-227.

Preparation of bis-MC2 derivative ALNY-239

The various embodiments described above can be combined to provide further embodiments. All of the U.S. patents, U.S. patent application publications, foreign patents, foreign patent applications and non-patent publications referred to in this specification and/or listed in the Application Data Sheet, U.S. Ser. No. 61/113,179, filed Nov. 10, 2008; U.S. Ser. No. 61/154,350, filed Feb. 20, 2009; U.S. Ser. No. 61/171,439, filed Apr. 21, 2009; U.S. Ser. No. 61/185,438, filed Jun. 9, 2009; U.S. Ser. No. 61/225,898, filed Jul. 15, 2009; and U.S. Ser. No. 61/234,098, filed Aug. 14, 2009 are incorporated herein by reference, in their entirety. Aspects of the embodiments can be modified, if necessary to employ concepts of the various patents, applications and publications to provide yet further embodiments.

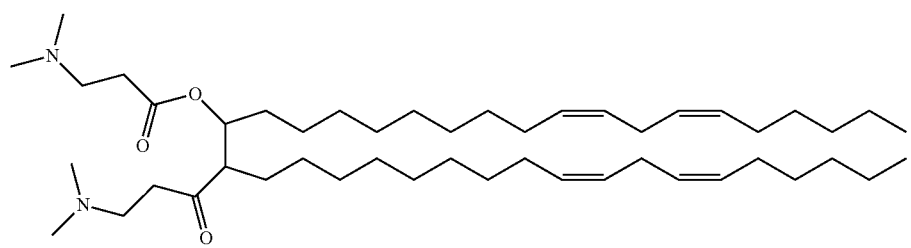

ALNY-239

Prepared the bis-MC2 analog (ALNY-239) by similar experimental conditions as compound ALNY-238, using dilinoleyl diol 2003 (1.0 g, 1.8 mmol, 1.0 eq), N,N-dimethyl propionic acid hydrochloride (0.82 g, 5.37 mmol, 3.0 eq), DIPEA (2.0 mL, 10.8 mmol, 6.0 eq) in dichloromethane was added solid EDCI (0.76 g, 3.96 mmol, 2.2 eq), DMAP (0.04 g, 0.36 mmol, 0.2 eq) to get pure bis ester of the MC2 derivative ALNY-239. Calc. mass for the $C_{46}H_{84}N_2O_4$: 729.1. found 729.5.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A lipid of formula I

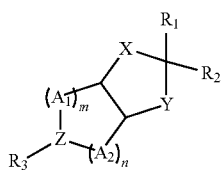

or a salt or isomer thereof, wherein $R_1$ and $R_2$ are each independently for each occurrence optionally substituted $C_{10}$-$C_{20}$ alkyl, optionally substituted $C_{10}$-$C_{20}$ alkenyl, or optionally substituted $C_{10}$-$C_{20}$ alkynyl;

$R_3$ is independently for each occurrence H, optionally substituted $C_1$-$C_{10}$ alkyl, optionally substituted alkylheterocycle, optionally substituted heterocyclealkyl, optionally substituted amino, optionally substituted alkylamino, optionally substituted di(alkyl)amino, optionally substituted aminoalkyl, optionally substituted alkylaminoalkyl, or optionally substituted di(alkyl)aminoalkyl;

X and Y are each independently —O— or alkylene;

$A_1$ and $A_2$ are each independently —O— or —$CH_2$—;

Z is N, or C($R_3$); and m and n are each independently 0 to 5, where m and n taken together result in a 5, 6, or 7 member ring.

2. A lipid selected from

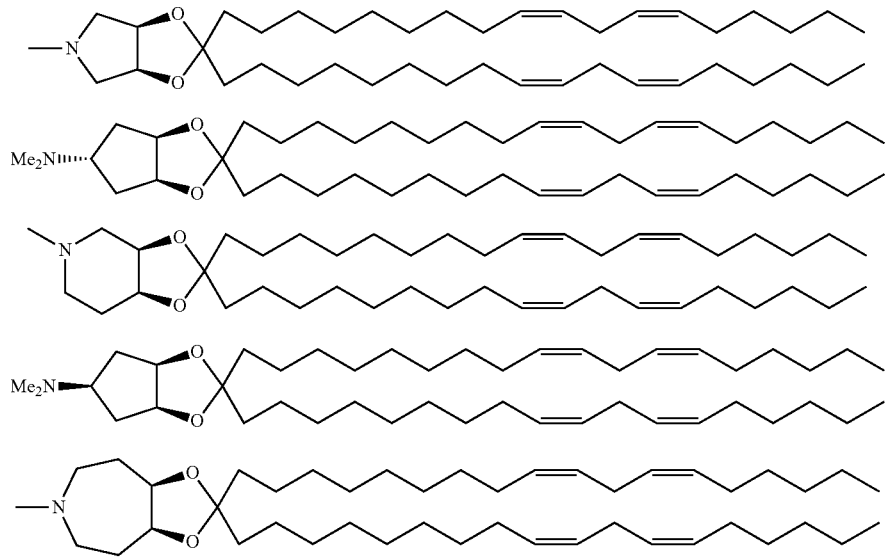

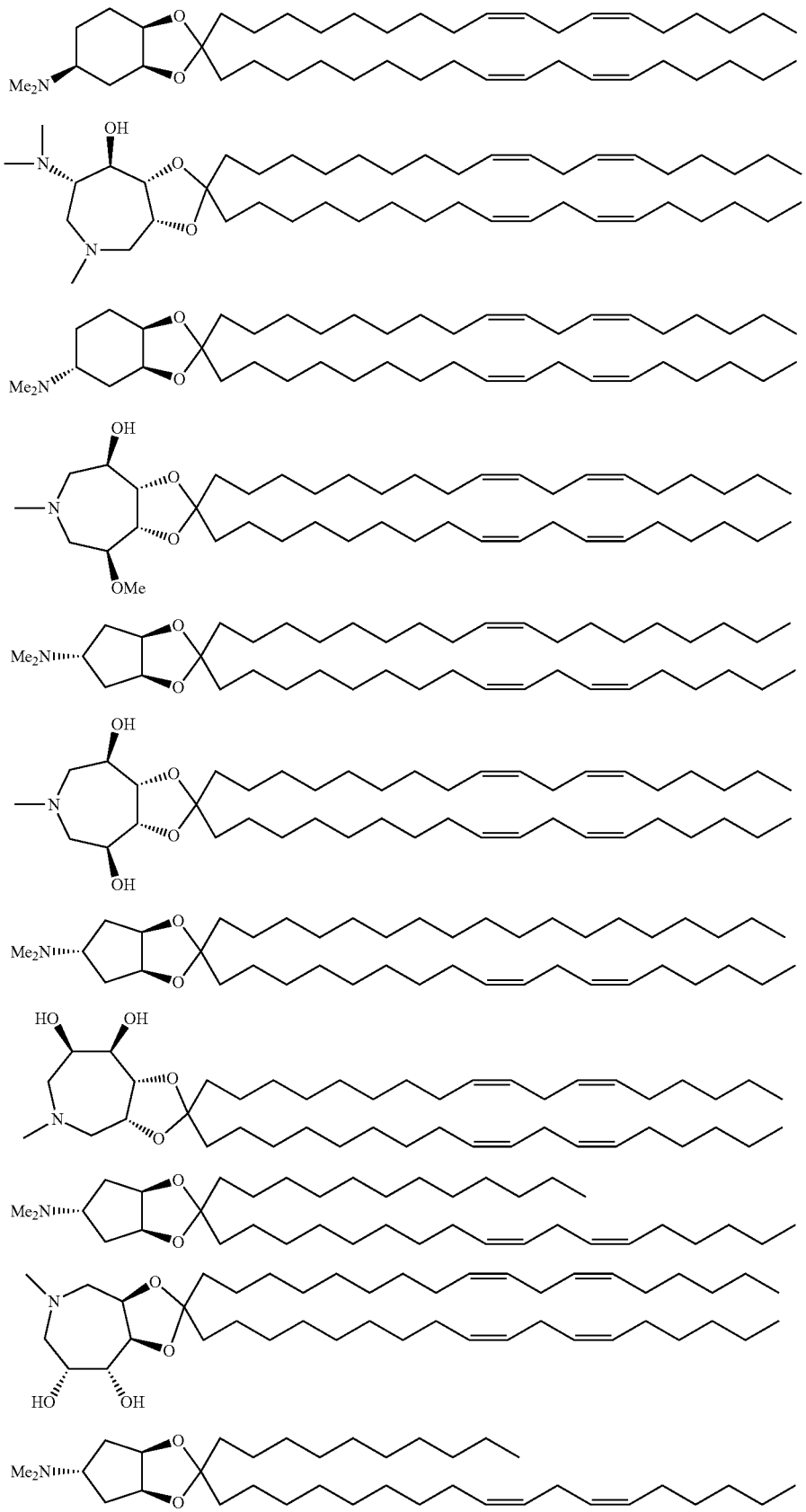

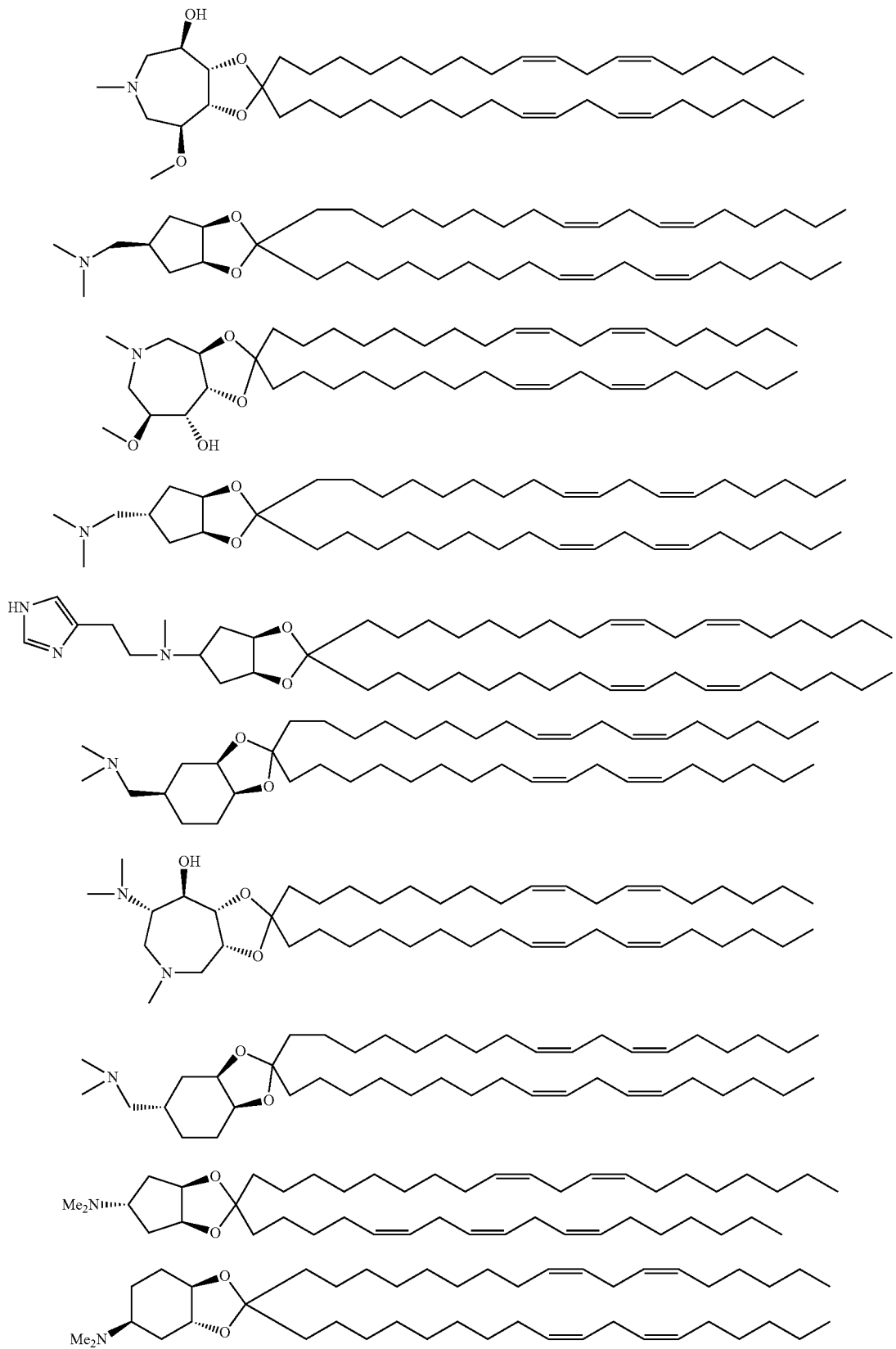

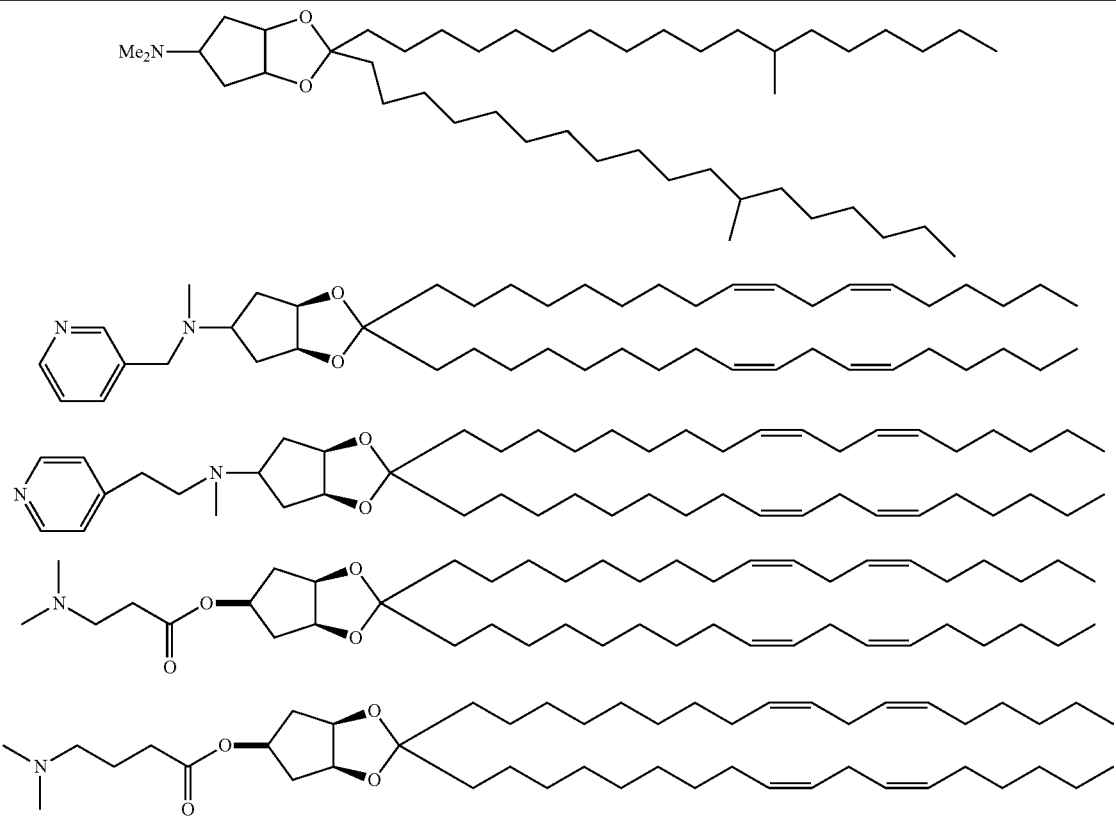

and salts thereof.

3. A lipid particle comprising a lipid of claim 2.

4. The lipid particle of claim 3, wherein the particle further comprises a neutral lipid and a lipid capable of reducing aggregation.

5. The lipid particle of claim 3, wherein the particle further comprising a therapeutic nucleic acid.

6. The lipid particle of claim 5, wherein the nucleic acid is an siRNA.

7. A pharmaceutical composition comprising a lipid particle of claim 5 and a pharmaceutically acceptable excipient, carrier, or diluent.

8. A method of modulating the expression of a target gene in a cell, comprising providing to a cell the lipid particle of claim 6.

9. The lipid of claim 1, wherein $R_1$ and $R_2$ are each independently for each occurrence optionally substituted $C_{10}$-$C_{20}$ alkyl.

10. The lipid of claim 1, wherein $R_1$ and $R_2$ are each independently for each occurrence optionally substituted $C_{10}$-$C_{20}$ alkenyl.

11. The lipid of claim 1, wherein $R_1$ and $R_2$ are each independently for each occurrence optionally substituted $C_{10}$-$C_{20}$ alkynyl.

12. The lipid of claim 1, wherein X and Y are each independently —O—.

13. The lipid of claim 1, wherein X and Y are each independently alkylene.

14. The lipid of claim 1, wherein $A_1$ and $A_2$ are each independently —O—.

15. The lipid of claim 1, wherein $A_1$ and $A_2$ are each independently —CH$_2$—.

16. The lipid of claim 1, wherein Z is N.

17. The lipid of claim 1, wherein Z is C(R$_3$).

* * * * *